(12) United States Patent
Chua et al.

(10) Patent No.: US 8,349,334 B2
(45) Date of Patent: Jan. 8, 2013

(54) MOLECULE

(75) Inventors: Kaw Yan Chua, Singapore (SG); See Voon Seow, Singapore (SG); Prasanna Ratnakar Kolatkar, Singapore (SG)

(73) Assignees: National University of Singapore, Singapore (SG); Agency for Science and Research, Singapore (SG)

( * ) Notice: Subject to any disclaimer, the term of this patent is extended or adjusted under 35 U.S.C. 154(b) by 0 days.

(21) Appl. No.: 13/172,909

(22) Filed: Jun. 30, 2011

(65) Prior Publication Data

US 2012/0003259 A1 Jan. 5, 2012

Related U.S. Application Data

(62) Division of application No. 10/553,674, filed as application No. PCT/SG2004/000098 on Apr. 16, 2004, now Pat. No. 7,998,701.

(30) Foreign Application Priority Data

Apr. 17, 2003 (GB) .................................. 0308988.5

(51) Int. Cl.
*A61K 39/00* (2006.01)
*A61K 38/00* (2006.01)
*C07K 1/00* (2006.01)
*C07K 14/00* (2006.01)
*C07K 17/00* (2006.01)

(52) U.S. Cl. .................. 424/185.1; 424/192.1; 514/1.1; 530/350

(58) Field of Classification Search ........................ None
See application file for complete search history.

(56) References Cited

U.S. PATENT DOCUMENTS 5,917,026 A 6/1999 Lowenadler et al.
2004/0071718 A1 4/2004 Tsai

FOREIGN PATENT DOCUMENTS

| WO | 98/32866 | 7/1998 |
| WO | 99/06544 | 2/1999 |
| WO | 02/22680 | 3/2002 |

OTHER PUBLICATIONS

Ngo et al. 'Computational Complexity, Protein Structure Prediction, and the Levinthal Paradox'. The Protein Folding Problem and Tertiary Structure Prediction. Ed° K. Merz and S. Le Grand. Boston: Birkhauser, 1994.491-495.*
Burgess et al. 'Possible Dissociation of the Heparin-binding and Mitogenis Activities of Heparin-binding (Acidis Fibroblast) Growth Factor-1 from Its Receptor-binding Activites by Site-directed Mutagenesis of a Single Lysine Residue.' J. Cell. Biol. 111:2129-2138, 1990.*
Lazar et al. 'Transforming Growth Factor alpha:Mutation of Aspartic Acid 47 and Leucine 48 Results in Different Biological Activities.' Mol. Cell. Biol. 8(3):1247-1252, 1988.*
Attwood et al., Science, 290(5491):471-473 (2000). "The Babel of bioinformatics."
Blumenthal et al., Allergens and Allergen Immunotherapy, New York: Marcel Decker, pp. 37-50 (2004). "Definition of an allergen."
Colman et al., Research in Immunology, 145(1):33-36 (1994). "Effects of amino acid sequence changes on antibody-antigen interactions."
Hsu et al., Biochem Journal, 323(2):557-565 (1997). "Fip-vvo, a new fungal immunomodulatory protein isolated from *Volvariella volvacea*."
Ko et al., European Journal of Biochemistry, 228(2):244-249 (1995). "A new fungal immunodulatory protein, FIP-fve isolated from the edible mushroom, *Flammulina velutipes* and its complete amino acid."
Ko et al., Journal of the Formosan Medical Association, 96(7):517-524 (1997). "Molecular cloning and expression of a fungal immunomodulary protein, FIP-fve, from *Flammulina velutipes*."
Murasugi et al., Journal of Biological Chemistry, 266(4):2486-2493 (1991). "Molecular cloning of cDNA and a gene encoding an immunomodulary protein, ling Zhi-8, from a fungus, gandodermalucidum."
Paaventhan et al., Journal of Molecular Biology, 332(2):461-470 (2003). "A 1.7 a structure of Fve, a member of the new fungal immunomodulatory protein family."
Skolnick et al., Trends in Biotech, 18:34-39 (2000). "From genes to protein structure and function: novel applications of computational approaches in the genomic era."
Tar (A).

(B).

(C).

(D).

(A).

(B).

(C).

(D).

*IFN-γ production at day 3*

(1a).  (1b).

GST 0.8%

(2a).  (2b).

GST-FveWT 12.3%

(3a).  (3b).

GST-FveR27A 14.3%

(4a).  (4b).

GST-FveG28A 1.8%

(5a).  (5b).

GST-FveT29A 17.6%

TNF-α PRODUCTION AT DAY 3

(1a). (1b).

GST 1.2%

(2a). (2b).

GST-FveWT 21.5%

(3a). (3b).

GST-FveR27A 18.7%

(4a).

(4b).

GST-FveG28A 1.5%

(5a).

(5b).

GST-FveT29A 14.4%

Mice received subcutaneous injection of a mixture of 10 ug of major mite allergen Der p 1 and 10 ug of Fve at days 0 and 14. Results showed that Der p1+ Fve induced higher Der p 1-specific IgG2a (pink) than Der p 1 alone (Blue).

| Blo t 5 | Fve | Bt5-Fve |

| Blo t 5 | FveR27A | Bt5-FveR27A |

| Blo t 5 | FveT29A | Bt5-FveT29A |

| Der p 2 | FveR27A | Dp2-FveR27A |

| Der p 2 | FveT29A | Dp2-FveT29A |

| Blo t 5 | Der p 2 | FveR27A | Bt5-Dp2-FveR27A |

| Blo t 5 | Der p 2 | FveT29A | Bt5-Dp2-FveT29A |

Control: Non-stimulated (10x10 magnification)

(1b)

Control : Non-stimulated (40x10 magnificat (2a)

20ug of GST  10x10

(2b)

20ug of GST  40x10

(3a)

20ug of Blo t 5  10x10

(3b)

20ug of Blo t 5  40x10

(4a)
20ug of native FIP-Fve 10x10

(4b)
20ug of native FIP-Fve 40x10

(5a)
20ug of Bt5-Fve 10x10

(5b)
20ug of Bt5-Fve 40x10

(6a)
40ug of Bt5-Fve 10x10

(6b)
40ug of Bt5-Fve 40x10

(7a)
40ug of Bt5-FveR27A  10x10
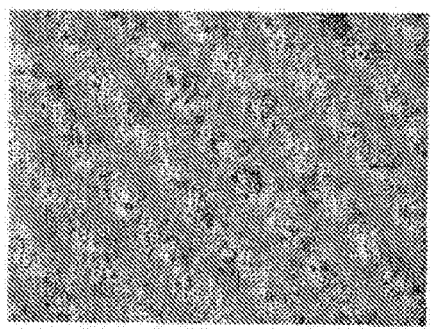
(7b)
40ug of B (a).

(d).

(b).

(e).

(c).

US 8,349,334 B2

MOLECULE

CROSS-REFERENCE TO RELATED APPLICATIONS

This application is a divisional application of U.S. patent application Ser. No. 10/553,674 filed Oct. 17, 2005, which claims priority under 35 U.S.C. §371 of International Application No. PCT/SG2004/000098 filed on Apr. 16, 2004, which claims priority to Great Britain Patent Application No. 0308988.5 filed on Apr. 17, 2003, the contents of which are incorporated herein by reference in their entireties.

FIELD

The present invention relates to the fields of microbiology. It also relates to the fields of medicine, especially therapy and diagnosis.

BACKGROUND

Some microorganisms are capable of acting as immunomodulating agents, such as *Mycobacterium smegmatis* used in Freund's complete adjuvant and OK432 from *Streptococcus pygens* as the anti-tumor potentiator. Many polysaccharide immunomodulating agents have also been detected and isolated from Basidiomycetes class of fungi, such as lentinan, schizophyllan, TML and SF AI. A novel family of fungal immunomodulatory proteins has been isolated from the edible mushrooms, such as Vvo from *Volvariella volvacea* (grass mushroom), LZ-S from *Ganoderma lucidum* (Ling-Zhi), Gts from *Ganoderma tsugae* (songshan lingzhi), and Fve from *Flammulina velutipes* (golden needle mushroom).

Although the therapeutic value of a number of mushrooms has been documented, the active components that confer such therapeutic effects are not well understood.

Ko et al (Eur. J. Biochem., 228, 244-2419) describes the isolation and purification of a protein known as FIP-fve from Golden Needle Mushroom extracts. The authors describe a method of extracting this protein, as well as some biochemical properties of FIP-fve. The amino acid sequence of FIP-fve is presented. FIP-fve is shown to cause proliferation of human peripheral blood lymphocytes, and mice sensitised to BSA are protected against anaphylactic shock by periodic injections of FIP-fve. A hind-paw edema test shows that FIP-fve inhibits antibody production against antigen 48/80. Finally, the authors show that FIP-fve induces expression of IL-2 and IFN-γ in spleen cells from mouse.

An amino acid sequence of FIP-fve is found as GenBank accession numbers: S69147 immunomodulatory protein FIP-fve-golden needle mushroom gi|7438667|pir||S69147 [7438667] and P80412 IMMUNOMODULATORY PROTEIN FIP-FVE gi|729544|sp|P80412|FVE_FLAVE [729544].

SUMMARY

According to a first aspect of the present invention, we provide an Fve polypeptide comprising at least one biological activity of native Fve protein, and being a fragment, homologue, variant or derivative thereof.

Preferably, the Fve polypeptide comprises an immunomodulatory activity. Preferably, the biological activity is selected from the group consisting of: up-regulation of expression of Th1/Tc1 cytokines, preferably IFN-γ and TNF-α, down-regulation of expression of Th2/Tc2 cytokines, preferably IL-4 and IL-13, up-regulation of expression of T regulatory (Tr) cytokines IL-10 and TGF-β, hemagglutination activity, cell aggregation activity, lymphocyte aggregation activity, lymphoproliferation activity, up-regulation of expression of IL-2, IFN-γ, TNF-α, but not IL-4 in CD3$^+$ T cells, interaction with T and NK cells, adjuvant activity, stimulation of CD3$^+$ CD16$^+$ CD56$^+$ natural killer (NK) T cells and CD3$^+$ CD8$^+$ CD18$^{+bright}$ T cells, and up-regulation of allergen specific Th1 immune responses.

Preferably, the polypeptide comprises between 2 to 20 residues of amino acid sequence flanking the glycine residue corresponding to position 28 of Fve.

Preferably, the polypeptide comprises the sequence RGT or the sequence RGD.

Preferably, the polypeptide has a sequence as set out in Appendix A or Appendix B.

There is provided, according to a second aspect of the present invention, a Fve polypeptide comprising an sequence selected from the group consisting of: Fve R27A, Fve T29A, GST-Fve (wild type), GST-Fve R27A, and GST-Fve T29A, and fragments, homologues, variants and derivatives thereof.

We provide, according to a third aspect of the present invention, a polypeptide comprising a first portion comprising at least a portion of Fve and a second portion comprising at least a portion of an allergen.

Preferably, the allergen comprises an allergen from a mite, preferably from Family Glycyphagidae or Family Pyroglyphidae, preferably a group 1 allergen (Der p 1, Der f 1, Blo t 1, Eur m1, Lep d 1), a group 2 allergen (Der p 2, Der f 2, Blo t 2, Eur m 2, Lep d 2), a group 5 allergen (Blo t 5, Der p 5, Der f 5, Eur m 5, Lep d 5) a group 15 allergen (Der p 15, Der f 15, Blot 15, Eur m 15, Lep d 15).

Preferably, the Fve polypeptide or a polypeptide is selected from the group consisting of: Blo t 5-Fve, Blo t 5-FveR27A, Blo t 5-FveT29A, GST-Der p 2-FveR27A, GST-Der p 2-FveT29A, Blo t 5-Der p 2-FveR27A, and Blo t 5-Der p 2-FveT29A. More preferably, it comprises Blo t 5-FveT29A, Der p 2-FveT29A, or Blo t 5-Der p 2-FveT29A.

Preferably, the allergen is selected from the group consisting of: tree pollen allergen, Bet v 1 and Bet v 2 from birch tree; grass pollen allergen, Phl p 1 and Phl p 2 from timothy grass; weed pollen allergen, antigen E from ragweed; major feline antigen, Fel d; major fungal allergen, Asp f1, Asp f2, and Asp f3 from *Aspergillus fumigatus*.

As a fourth aspect of the present invention, there is provided a polypeptide comprising a first portion comprising at least a portion of Fve and a second portion comprising at least a portion of a viral antigen selected from the group consisting of: E6 and E7 from HPV; core Ag and E2 from HCV; core and surface antigens from HBV; LMP-1, LMP-2, EBNA-2, EBNA-3 from EBV; and Tax from HTLV-1.

Preferably, it comprises HCV Core23-FveT29A, or HPV E7-FveT29A.

We also provide a polypeptide comprising a first portion comprising at least a portion of Fve and a second portion comprising at least a portion of a viral antigen selected from the group consisting of antigens from Adenovirus, Parainfluenza 3 virus, Human Immunodeficiency Virus (HIV), Herpes simplex virus, HSV, Respiratory syncytial virus, RSV, and Influenza A, Flu A.

We provide, according to a fifth aspect of the present invention, a polypeptide comprising a first portion comprising at least a portion of Fve and a second portion comprising at least a portion of a tumour-associated antigen selected from the group consisting of: MAGE-1, MAGE-2, MAGE-3, BAGE, GAGE, PRAME, SSX-2, Tyrosinase, MART-1, NY-ESO-1, gp100, TRP-1, TRP-2, A2 melanotope, BCR/ABL, Proteinase-3/Myeloblastin, HER2/neu, CEA, P1A, HK2, PAPA, PSA, PSCA, PSMA, pg75, MUM-1, MUC-1, BTA, GnT-V, β-catenin, CDK4, and P15.

Preferably, it comprises MAGE3-FveT29A, MART1-FveT29A or CEA-FveT29A.

The present invention, in a sixth aspect, provides a nucleic acid encoding a Fve polypeptide or a polypeptide according to any preceding statement of invention.

Preferably, the nucleic acid comprises CGT GGT ACC, or a sequence which differs from the above by virtue of the degeneracy of the genetic code and which encodes a sequence RGT.

In a seventh aspect of the present invention, there is provided a nucleic acid comprising a sequence encoding at least a portion of Fve and a sequence encoding at least a portion of an allergen.

Preferably, it comprises Blo t 5-FveT29A, Der p 2-FveT29A, or Blo t 5-Der p 2-FveT29A.

According to an eighth aspect of the present invention, we provide a nucleic acid comprising a sequence encoding at least a portion of Fve and a sequence encoding at least a portion of a viral antigen selected from the group consisting of: E6 and E7 from HPV; core Ag and E2 from HCV; core and surface antigens from HBV; LMP-1, LMP-2, EBNA-2, EBNA-3 from EBV; and Tax from HTLV-1.

Preferably, it comprises HCV Core23-FveT29A, or HPV E7-FveT29A.

We also provide a nucleic acid comprising a sequence encoding at least a portion of Fve and a sequence encoding at least a portion of a viral antigen selected from the group consisting of antigens from Adenovirus, Parainfluenza 3 virus, Human Immunodeficiency Virus (HIV), Herpes simplex virus, HSV, Respiratory syncytial virus, RSV, and Influenza A, Flu A.

We provide, according to a ninth aspect of the invention, a nucleic acid comprising a sequence encoding at least a portion of Fve and a sequence encoding at least a portion of a tumour associated antigen selected from the group consisting of: MAGE-1, MAGE-2, MAGE-3, BAGE, GAGE, PRAME, SSX-2, Tyrosinase, MART-1, NY-ESO-1, gp100, TRP-1, TRP-2, A2 melanotope, BCR/ABL, Proteinase-3/Myeloblastin, HER2/neu, CEA, P1A, HK2, PAPA, PSA, PSCA, PSMA, pg75, MUM-1, MUC-1, BTA, GnT-V, β-catenin, CDK4, and P15.

Preferably, it comprises MAGE3-FveT29A, MART1-FveT29A or CEA-FveT29A.

There is provided, in accordance with a tenth aspect of the present invention, a nucleic acid selected from the group consisting of: Fve R27A, Fve T29A, GST-Fve (wild type), GST-Fve R27A, GST-Fve T29A, Blo t 5-Fve, Blo t 5-FveR27A, Blo t 5-FveT29A, GST-Der p 2-FveR27A, GST-Der p 2-FveT29A, Blo t 5-Der p 2-FveR27A, Blo t 5-Der p 2-FveT29A, and fragments, homologues, variants and derivatives thereof.

As an eleventh aspect of the invention, we provide a vector, preferably an expression vector, comprising a nucleic acid sequence as set out above.

We provide, according to a twelfth aspect of the invention, there is provided DNA vaccine comprising a nucleic acid encoding Fve, a nucleic acid, or a vector as set out above.

According to a thirteenth aspect of the present invention, we provide host cell comprising a nucleic acid encoding Fve, a nucleic acid, or a vector as set out above.

There is provided, according to a fourteenth aspect of the present invention, transgenic non-human organism comprising a nucleic acid encoding Fve, a nucleic acid, or a vector as set out above.

Preferably, the transgenic non-human organism is a bacterium, a yeast, a fungus, a plant or an animal, preferably a mouse.

According to a sixteenth aspect of the present invention, we provide a pharmaceutical composition comprising a polypeptide, a nucleic acid, a vector, a DNA vaccine, or a host cell as set out above, together with a pharmaceutically acceptable carrier or diluent.

According to a seventeenth aspect of the present invention, we provide the use of a native Fve polypeptide, or an Fve polypeptide, nucleic acid, vector, DNA vaccine, host cell, transgenic organism, or a pharmaceutical composition as set out above as an immumodulator.

According to an eighteenth aspect of the present invention, we provide the use of a native Fve polypeptide, or an Fve polypeptide, nucleic acid, vector, DNA vaccine, host cell, transgenic organism, or a pharmaceutical composition as set out above to enhance an immune response in a mammal.

According to a nineteenth aspect of the present invention, we provide the use of a native Fve polypeptide, or an Fve polypeptide, nucleic acid, vector, DNA vaccine, host cell, transgenic organism, or a pharmaceutical composition as set out above to stimulate proliferation of $CD3^+$ $CD8^+$ $CD18^+_{bright}$ T cells.

According to a twentieth aspect of the present invention, we provide the use of a native Fve polypeptide, or an Fve polypeptide, nucleic acid, vector, DNA vaccine, host cell, transgenic organism, or a pharmaceutical composition as set out above to stimulate proliferation of $CD3^+$ $CD16^+$ $CD56^+$ natural killer (NK) T cells.

According to a twenty first aspect of the present invention, we provide the use of a native Fve polypeptide, or an Fve polypeptide, nucleic acid, vector, DNA vaccine, host cell, transgenic organism, or a pharmaceutical composition as set out above to stimulate production of IL-2, IL-10, TGF-β, IFN-γ or TNF-α in $CD3^+$ cells.

Preferably, production of IL-4 is not stimulated in the $CD3^+$ cells.

According to a twenty second aspect of the present invention, we provide the use of a native Fve polypeptide, or an Fve polypeptide, nucleic acid, vector, DNA vaccine, host cell, transgenic organism, or a pharmaceutical composition as set out above as an adjuvant for a vaccine.

According to a twenty third aspect of the present invention, we provide the use of a native Fve polypeptide, or an Fve polypeptide, nucleic acid, vector, DNA vaccine, host cell, transgenic organism, or a pharmaceutical composition as set out above in a method of treatment or prophylaxis of a disease.

According to a twenty fourth aspect of the present invention, we provide the use of a native Fve polypeptide, or an Fve polypeptide, nucleic acid, vector or host cell as set out above for the preparation of a pharmaceutical composition for the treatment of a disease.

According to a twenty fifth aspect of the present invention, we provide a method of treating an individual suffering from a disease or preventing the occurrence of a disease in an individual, the method comprising administering to the individual a therapeutically or prophylactically effective amount of a native Fve polypeptide, or an Fve polypeptide, nucleic acid, vector, DNA vaccine, host cell, transgenic organism, or a pharmaceutical composition as set out above.

Preferably, the use or method is such that disease comprises an atopic disease or allergy.

Preferably, the allergy is selected from the group consisting of: allergic asthma, a seasonal respiratory allergy, a perennial respiratory allergy, allergic rhinitis, hayfever, nonallergic rhinitis, vasomotor rhinitis, irritant rhinitis, an allergy against grass pollen, weed pollen, tree pollen or animal danders, an allergy associated with allergic asthma and a food allergy.

Preferably, the allergy is to a house dust mite from Family Glyphagidae, preferably *Blomia tropicalis* or from Family Pyroglyphidae, preferably *Dermatophagoides pteronyssinus* or *Dermatophagoides farinae*, or to fungi or fungal spores, preferably *Aspergillus fumigatus*.

In an alternative embodiment, the disease comprises a cancer.

According to a twenty seventh aspect of the present invention, we provide the use of a DNA vaccine as described, in a method of treatment or prevention of a cancer, or in a method of suppressing tumour progression.

Preferably, the cancer comprises a T cell lymphoma, melanoma, lung cancer, colon cancer, breast cancer or prostate cancer.

According to a twenty eighth aspect of the present invention, we provide a method of identifying a molecule capable of binding to Fve, the method comprising exposing a native Fve polypeptide, or an Fve polypeptide or nucleic acid, vector, host cell or transgenic organism according as set out above to a candidate molecule and detecting whether the candidate molecule binds to the native Fve polypeptide, or an Fve polypeptide or nucleic acid, vector, host cell or transgenic organism.

According to a twenty ninth aspect of the present invention, we provide a method of identifying an agonist or antagonist of an Fve polypeptide, the method comprising: (a) providing a cell or organism; (b) exposing the cell or organism to a native Fve polypeptide, or an Fve polypeptide or nucleic acid, vector, host cell or transgenic organism as set out above; (c) exposing the cell to a candidate molecule; and (d) detecting an Fve mediated effect.

Preferably, the Fve mediated effect is selected from the biological activities set out above.

Preferably, the method further comprises isolating or synthesising a selected or identified molecule.

According to a thirtieth aspect of the present invention, we provide a molecule identified or selected using such a method.

According to a thirty first aspect of the present invention, we provide a native Fve polypeptide, or an Fve polypeptide in crystalline form.

Preferably, the crystal has the structural coordinates shown in Appendix C.

According to a thirty second aspect of the present invention, we provide a model for at least part of Fve made using such a crystal.

According to a thirty third aspect of the present invention, we provide a method of screening for a receptor capable of binding to Fve, or designing a ligand capable of modulating the interaction between Fve and an Fve receptor, comprising the use of such a model.

According to a thirty fourth aspect of the present invention, we provide a computer readable medium having stored thereon the structure of such a crystal or such a model.

According to a thirty fifth aspect of the present invention, we provide a ligand identified by the method set out above.

According to a thirty sixth aspect of the present invention, we provide a use of such a molecule or such a ligand for the treatment or prevention of a disease in an individual.

According to a thirty seventh aspect of the present invention, we provide a pharmaceutical composition comprising such a molecule or such a ligand and optionally a pharmaceutically acceptable carrier, diluent, excipient or adjuvant or any combination thereof.

According to a thirty eighth aspect of the present invention, we provide a method of treating and/or preventing a disease comprising administering such a molecule or such a ligand and/or such a pharmaceutical composition to a mammalian patient.

According to a thirty ninth aspect of the present invention, we provide a method of amplifying a sub-population of cells, the method comprising: (a) obtaining a population of cells from an individual; (b) amplifying $CD3^+$ $CD8^+$ and $CD18^+_{bright}$ T cells by exposing the population of cells to a native Fve polypeptide, or an Fve polypeptide or nucleic acid, vector, host cell or transgenic organism as set out above.

Preferably, the method further comprises the step of: (c) isolating the $CD3^+$ $CD8^+$ and $CD18^{+bright}$ T cells.

According to a fortieth aspect of the present invention, we provide a method of treating an individual suffering from a disease or preventing the occurrence of a disease in an individual, the method comprising amplifying a $CD3^+$ $CD8^+$ and $CD18^{+bright}$ T cell by such a method, and administering the amplified $CD3^+$ $CD8^+$ and $CD18^{+bright}$ T cell to an individual.

According to a forty first aspect of the present invention, we provide a combination comprising a first component comprising an immunomodulator and a second component comprising at least a portion of an allergen, a viral antigen or a tumour associated antigen.

Preferably, the first component is separate from the second component. Alternatively, or in addition, the first component may be associated with the second component. Preferably, the combination comprises a fusion protein.

The first component may comprise a native Fve polypeptide, or a polypeptide as set out above. The second component may comprise an allergen selected from the group consisting of: a mite allergen, an mite allergen from Family Glycyphagidae or Family Pyroglyphidae, a group 1 allergen (Der p 1, Der f 1, Blo t 1, Eur m1, Lep d 1), a group 2 allergen (Der p 2, Der f 2, Blo t 2, Eur m 2, Lep d 2), a group 5 allergen (Blo t 5, Der p 5, Der f 5, Eur m 5, Lep d 5), a group 15 allergen (Der p 15, Der f 15, Blo t 15, Eur m 15, Lep d 15), a tree pollen allergen, Bet v 1 and Bet v 2 from birch tree; grass pollen allergen, Phl p 1 and Phl p 2 from timothy grass; weed pollen allergen, antigen E from ragweed; major feline antigen, Fel d; major fungal allergen, Asp f1, Asp f2, and Asp f3 from *Aspergillus fumigatus*.

In preferred embodiments, the second component comprises a viral antigen selected from the group consisting of: E6 and E7 from HPV; core Ag and E2 from HCV; core and surface antigens from HBV; LMP-1, LMP-2, EBNA-2, EBNA-3 from EBV; and Tax from HTLV-1. Alternatively, or in addition, the second component may comprise a tumour-associated antigen selected from the group consisting of: MAGE-1, MAGE-2, MAGE-3, BAGE, GAGE, PRAME, SSX-2, Tyrosinase, MART-1, NY-ESO-1, gp100, TRP-1, TRP-2, A2 melanotope, BCR/ABL, Proteinase-3/Myeloblastin, HER2/neu, CEA, P1A, HK2, PAPA, PSA, PSCA, PSMA, pg75, MUM-1, MUC-1, BTA, GnT-V, β-catenin, CDK4, and P15.

We further disclose an immunomodulator-antigen conjugate, preferably an immunomodulator-allergen conjugate, an immunomodulator-tumour associated antigen conjugate or a immunomodulator-viral antigen conjugate, in which the immunomodulator preferably comprises an Fve polypeptide.

BRIEF DESCRIPTION OF THE DRAWINGS

FIG. 16. A schematic representation of the seven fusion proteins of Bt5-Fve (wild type), Bt5-FveR27A, Bt5-FveT29A, Dp2-FveR27A, Dp2-FveT29A, Bt5-Dp2-FveR27A, and Bt5-Dp2-FveT29A.

Lane 1 and 10 are protein marker. Lane 2 to 9 are GST; Blo t 5; Fve; Bt5-Fve; Bt5-FveR27A; Der p 2; Fve; and GST-Bt5, respectively.

Figure 18:
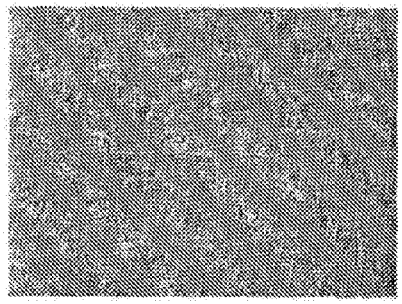
Figure 18:
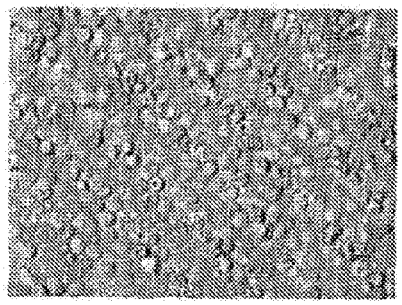
Figure 18:
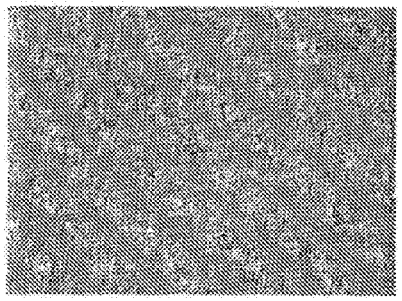
Figure 18:
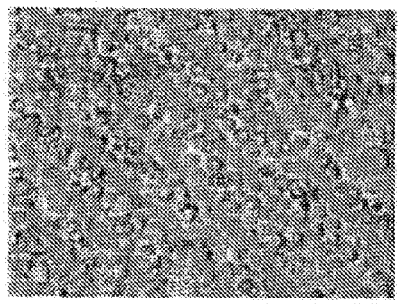
Figure 18:
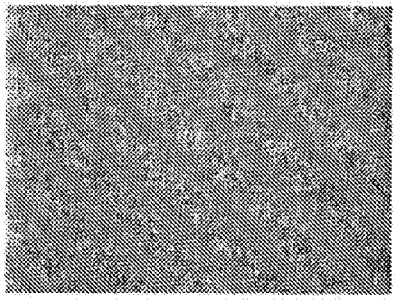
Figure 18:
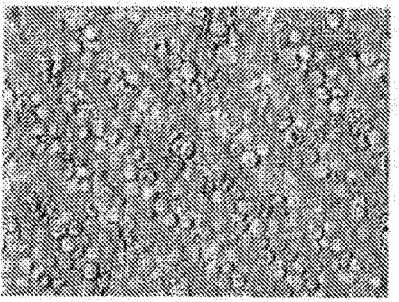
Figure 18:
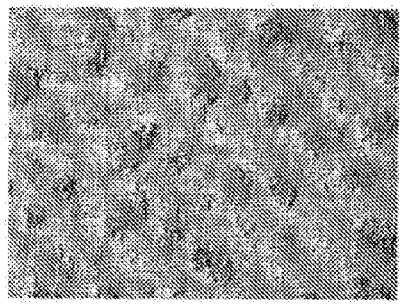
Figure 18:
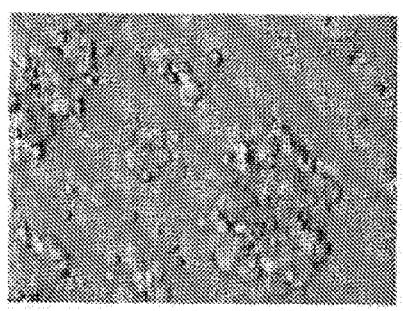
Figure 18:
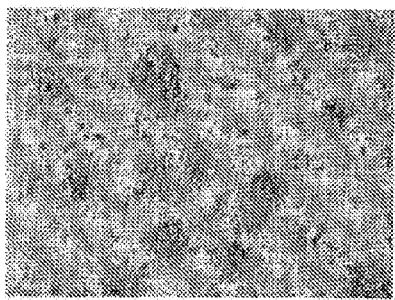
Figure 18:
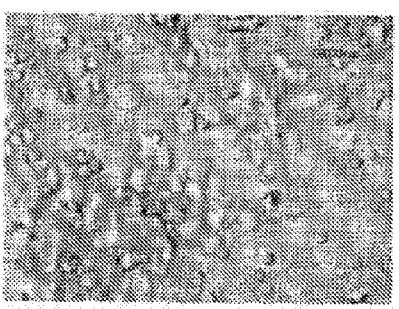
Figure 18:
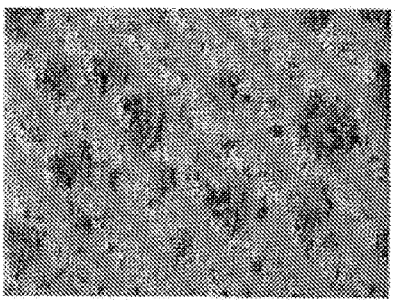
Figure 18:
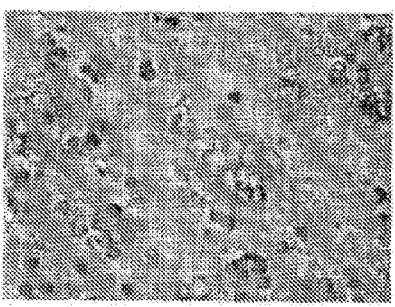

FIG. 18. Functional characterization of recombinant fusion proteins of Fve and allergen. The morphology of human lymphocytes upon stimulation with three different fusion proteins for three days. All photographs are taken at a magnification of ×10 and ×40 with a confocal microscope. 1(a) Control: Non-stimulated (10×10 magnification); 1(b) Control: Non-stimulated (40×10 magnification); 2(a): 20 μg of GST 10×10; 2(b): 20 μg of GST 40×10; 3(a): 20 μg of Blo t 5 10×10; 3(b): 20 μg of Blo t 5 40×10; 4(a): 20 μg of native Fve 10×10; 4(b): 20 μg of native Fve 40×10; 5(a): 20 μg of Bt5-Fve 10×10; 5(b): 20 μg of Bt5-Fve 40×10; 6(a): 40 μg of Bt5-Fve 10×10; 6(b): 40 μg of Bt5-Fve 40×10; 7(a) 40 μg of Bt5-FveR27A 10×10; 7(b): 40 μg of Bt5-FveR27A 40×10; 8(a): 20 μg of Der p 2 10×10; 8(b): 20 μg of Der p 2 40×10; 9(a): 40 μg of GST-Dp2-FveR27A 10×10; 9(b): 40 μg of GST-Dp2-FveR27A 40×10. Human lymphocytes maintained aggregation ability upon stimulation with Bt5-Fve (5a, 5b, 6a, 6b) and Bt5-FveR27A (7a, 7b) for 3 days. Native Fve (4a, 4b) is a positive control. Non-stimulated cells (1a, 1b), GST (2a, 2b), Blo t 5 (3a, 3b), and Der p 2 (8a, 8b) are negative controls. The aggregation ability of GST-Dp2-FveR27A is not apparent at day 3 (9a, 9b).

Figure 19A:
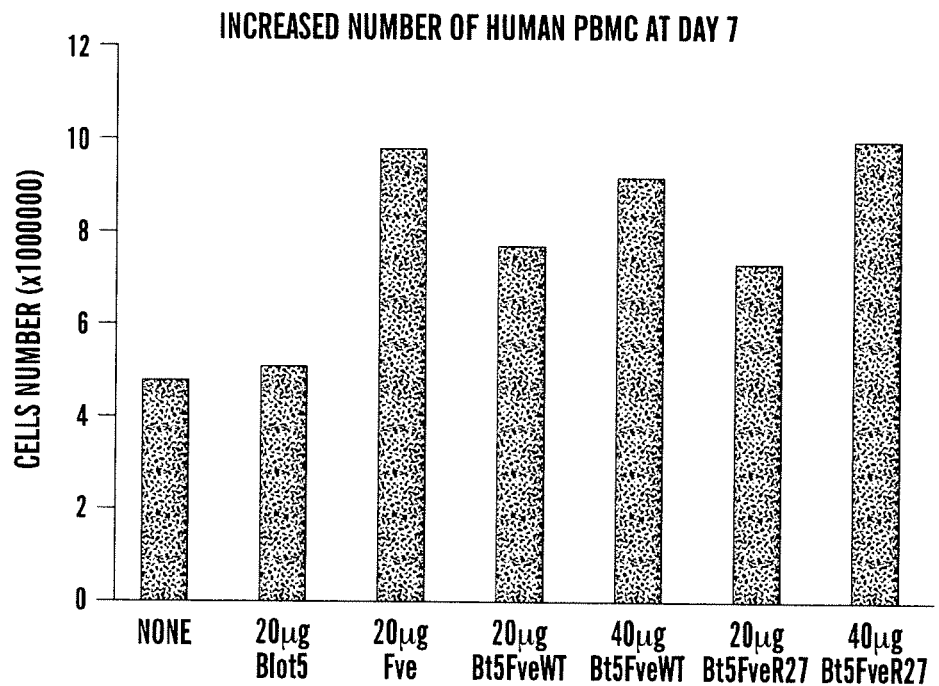
Figure 19B:
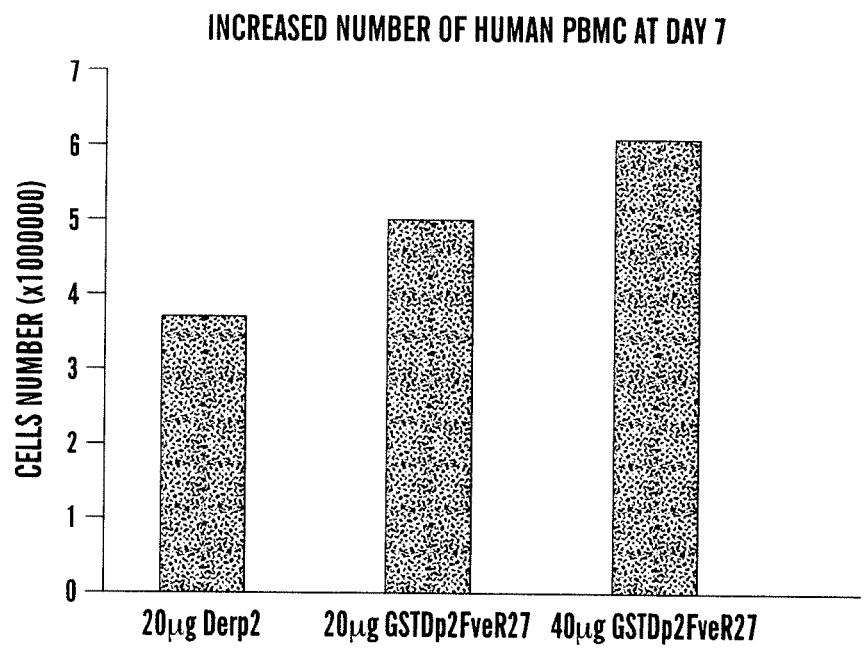

FIG. 19. Cell number comparison of human PBMC after 7 days cultured with tested antigens. Human PBMC are cultured with different doses of recombinant allergen and Fve fusion proteins. Non-stimulated cells and cells stimulated with either 20 μg of Blo t 5; 20 μg of Fve; 20 μg of Bt5-Fve; 40 μg of Bt5-Fve; 20 μg of Bt5-FveR27A; and 40 μg of Bt5-FveR27A are shown in FIG. 19A. Cells stimulated with 20 μg of Der p 2; 20 μg of GST-Dp2-FveR27A; and 40 μg of GST-Dp2-FveR27A are shown in FIG. 19B. The cells are collected and counted at day 7.

Figure 20:
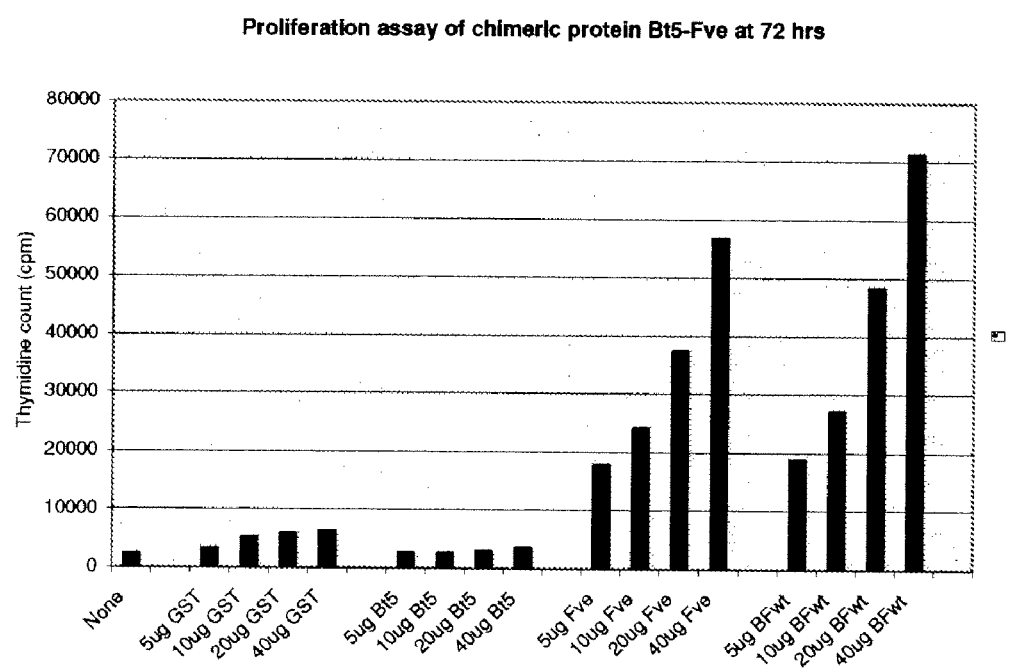
Figure 21A:
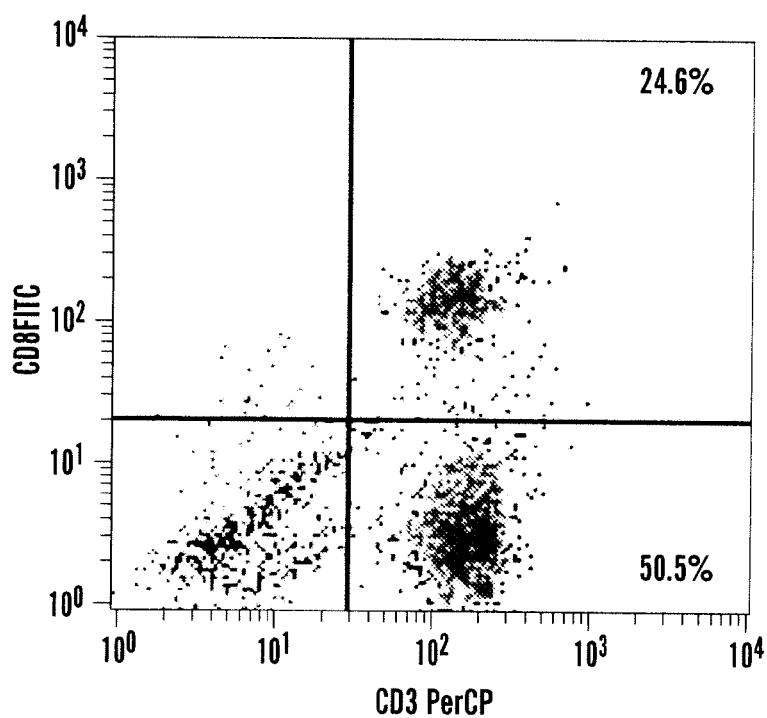
Figure 21B:
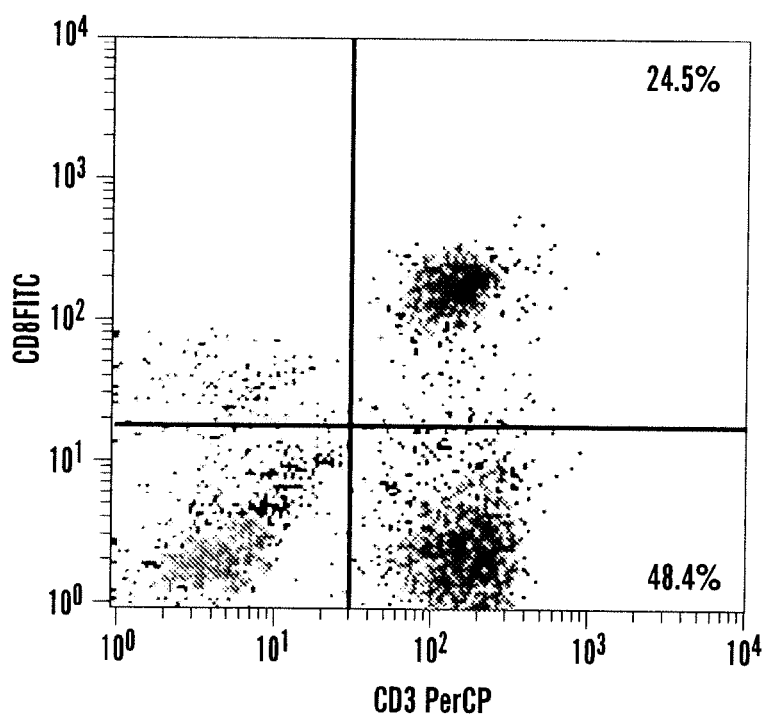
Figure 21C:
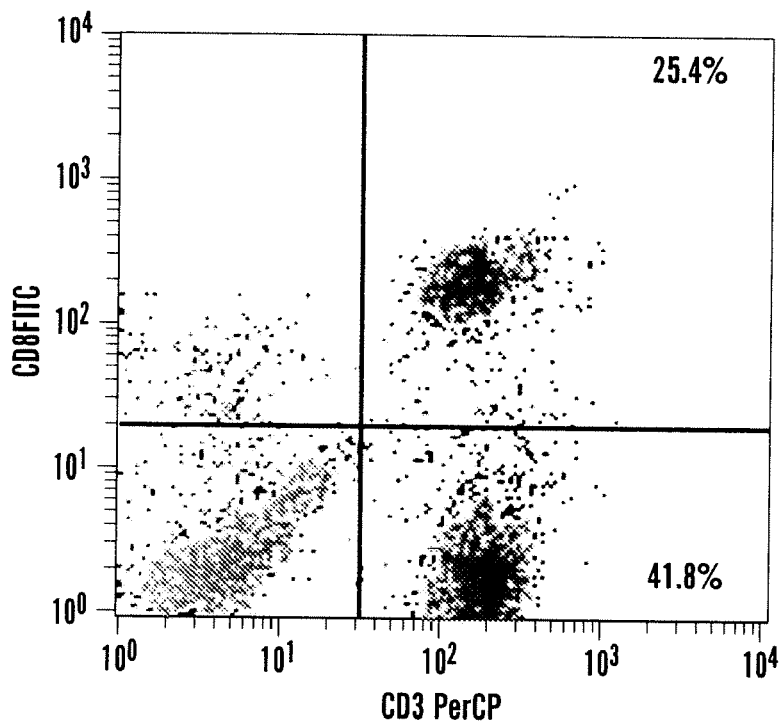
Figure 21D:
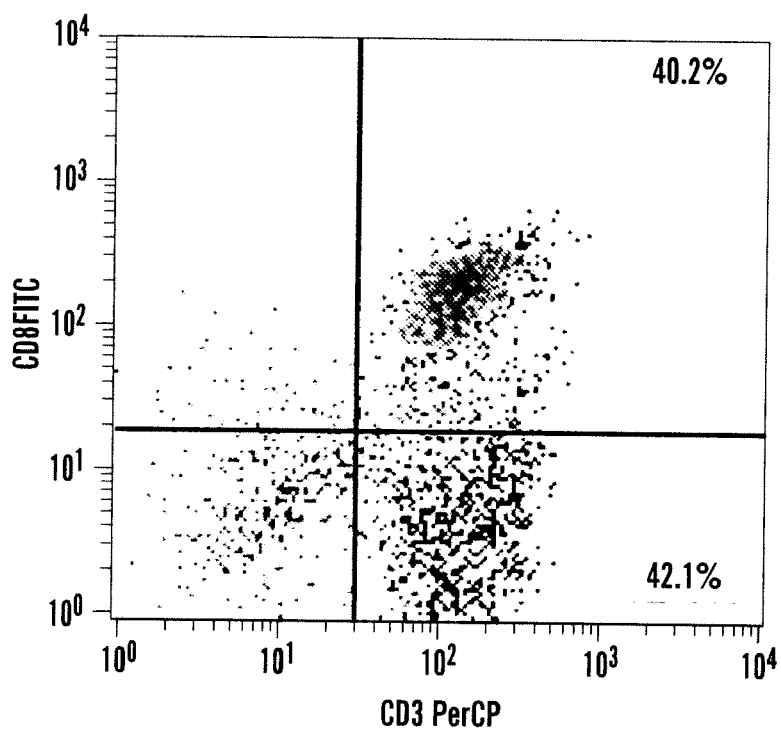
Figure 21E:
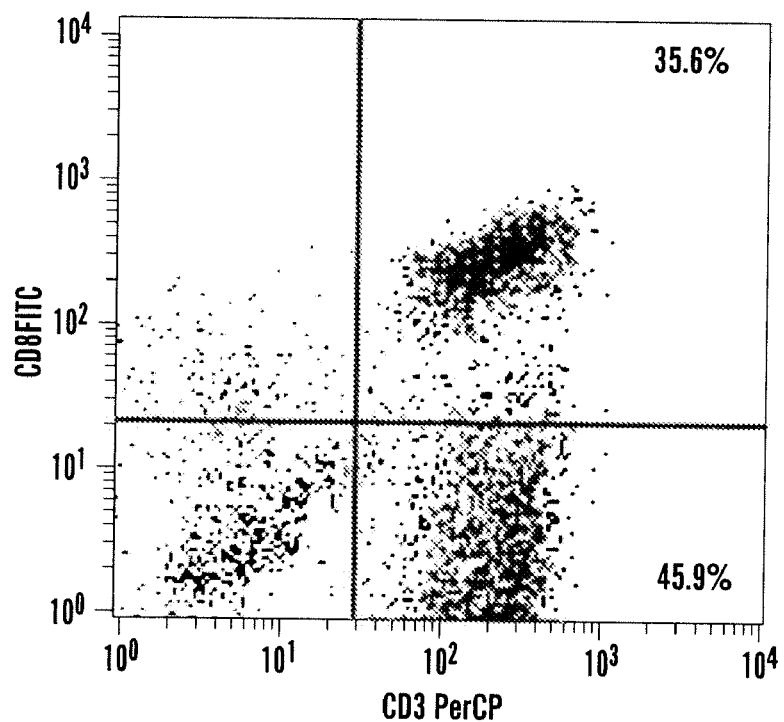
Figure 21F:
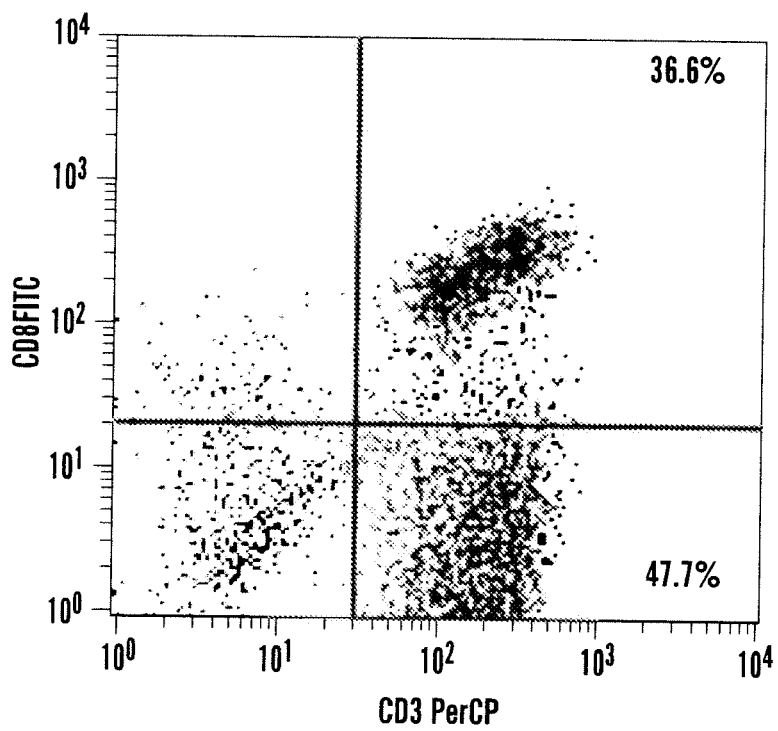
Figure 21G:
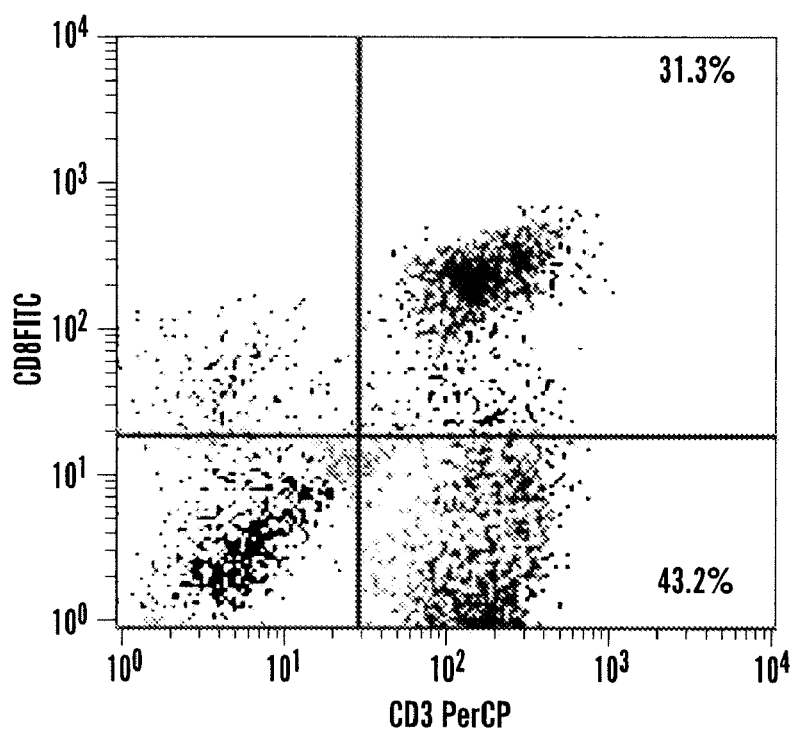
Figure 21H:
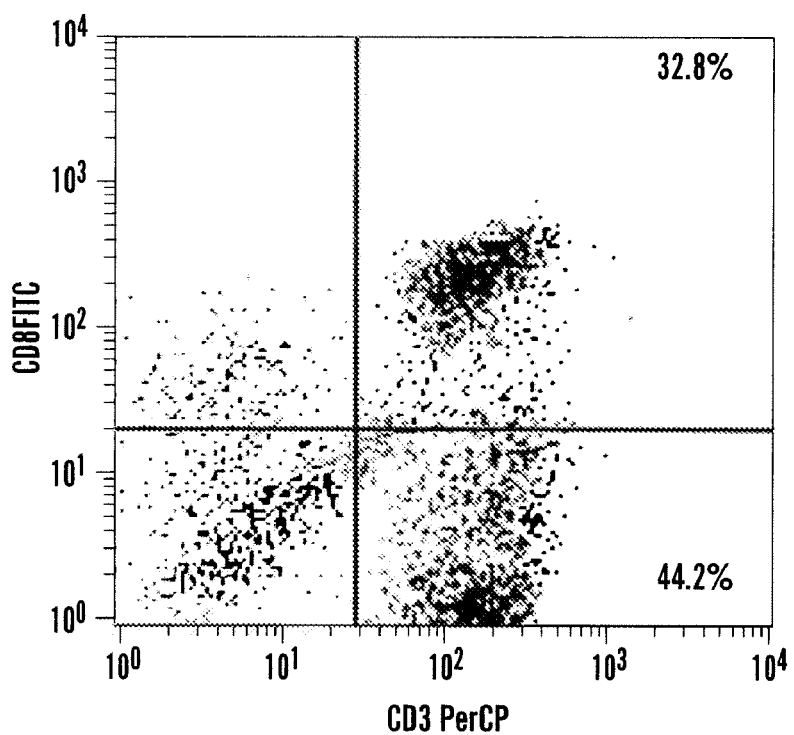

FIG. 20. The lymphoproliferation activity of human lymphocytes upon stimulation with recombinant fusion protein Bt5-Fve for 72 hours. Human PBMC from a healthy donor is co-cultured with 5 μg/ml, 10 μg/ml, 20 μg/ml, and 40 μg/ml, respectively, with fusion protein Bt5-Fve (BFwt). Recombinant GST and Blo t 5 are used as negative controls. Fve is used a positive control.

FIG. 21. Bt5Fve fusion protein maintained CD8 T cells polarization activity. Human PBMC are isolated from healthy donar and stimulated with 20 μg of GST (b), 20 μg of Blo t 5 allergen (c), 20 μg of Fve (d), 20 μg of Bt5Fve (e), 40 μg of Bt5Fve (f), 20 μg of Bt5FveR27 (g), and 40 μg of Bt5FveR27 (h) for 5 days. Cells without any stimulation served as negative control (a). Cultured cells are stained with CD3-PerCP and CD8-FITC monoclonal antibodies and analyzed with FACSCalibur cytometry.

Figure 22A:
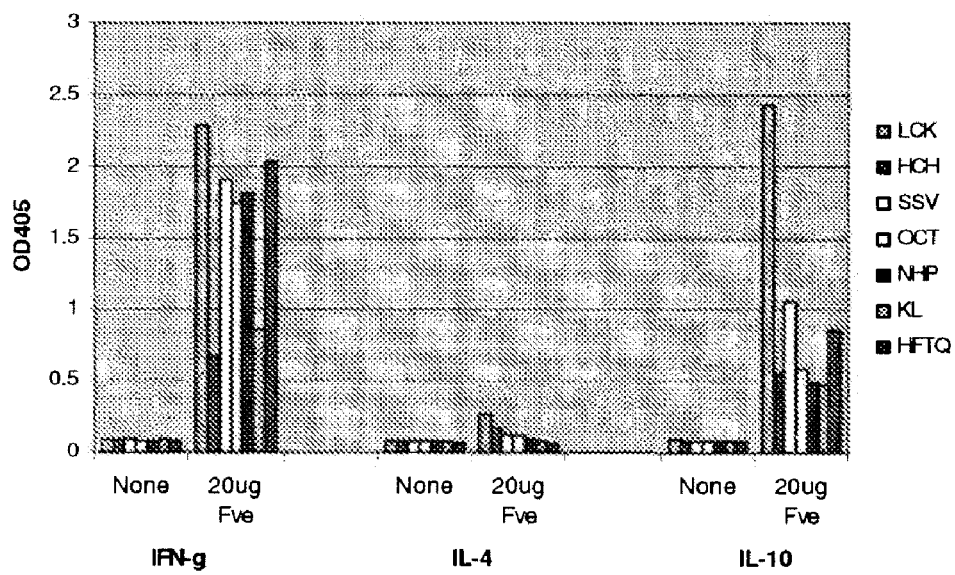
Figure 22B:
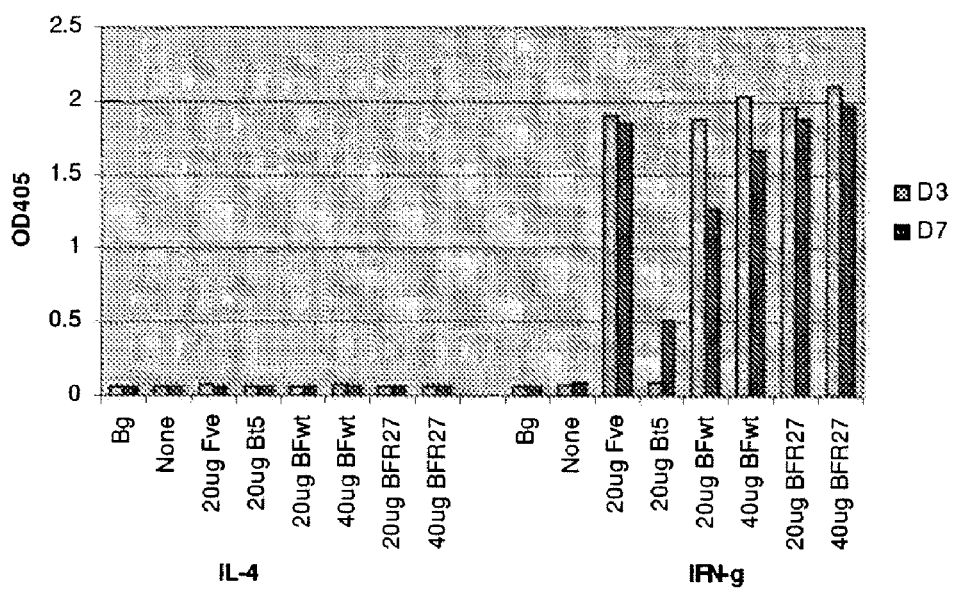

FIG. 22. Fve and allergen-Fve fusion protein are able to induce T helper type 1 and T regulatory immune responses. (A). Fve induced IFN-γ and IL-10 production. Human PBMC from seven individuals are cultured with 20 μg of Fve. The production of IFN-γ, IL-4 and IL-10 is assayed by ELISA at day 3. (B). Comparable levels of IFN-γ production are induced by Fve and allergen—Fve fusion protein. Human PBMC are stimulated with Fve, Blot5, Blot5-Fve (wild type) and Blot5-FveR27A (mutant), respectively. The production of IL-4 and IFN-γ is detected by ELISA at day 3 and day 7.

Figure 23:
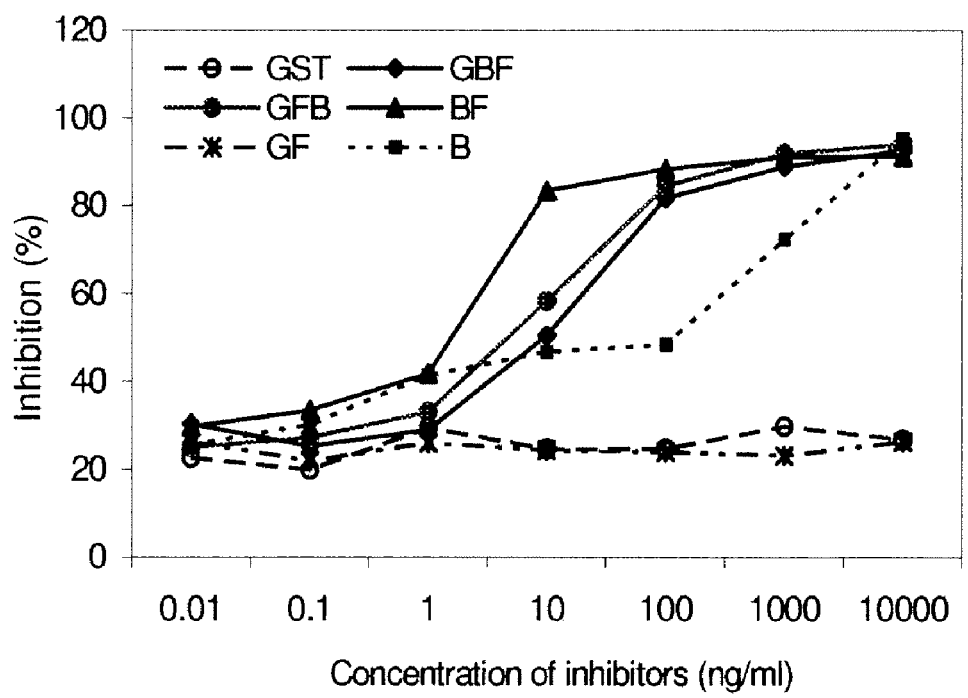

FIG. 23. Competitive inhibition assay. Varying concentrations of inhibitors are used to inhibit the binding of human IgE to GST-Blot5 bound to the Elisa plate. The concentration of different inhibitors ranged from 0.01 ng to 10000 ng/ml. Results are obtained from serum of a representative allergic subject with high IgE reactivity to house dust mite allergens. GST: Glutathione S-transferase. GF: GST-Fve. GFB: GST-Fve-Blot5. GBF: GST-Blot5-Fve. BF: Blot5-Fve. B: Blo t 5.

Figure 23B:
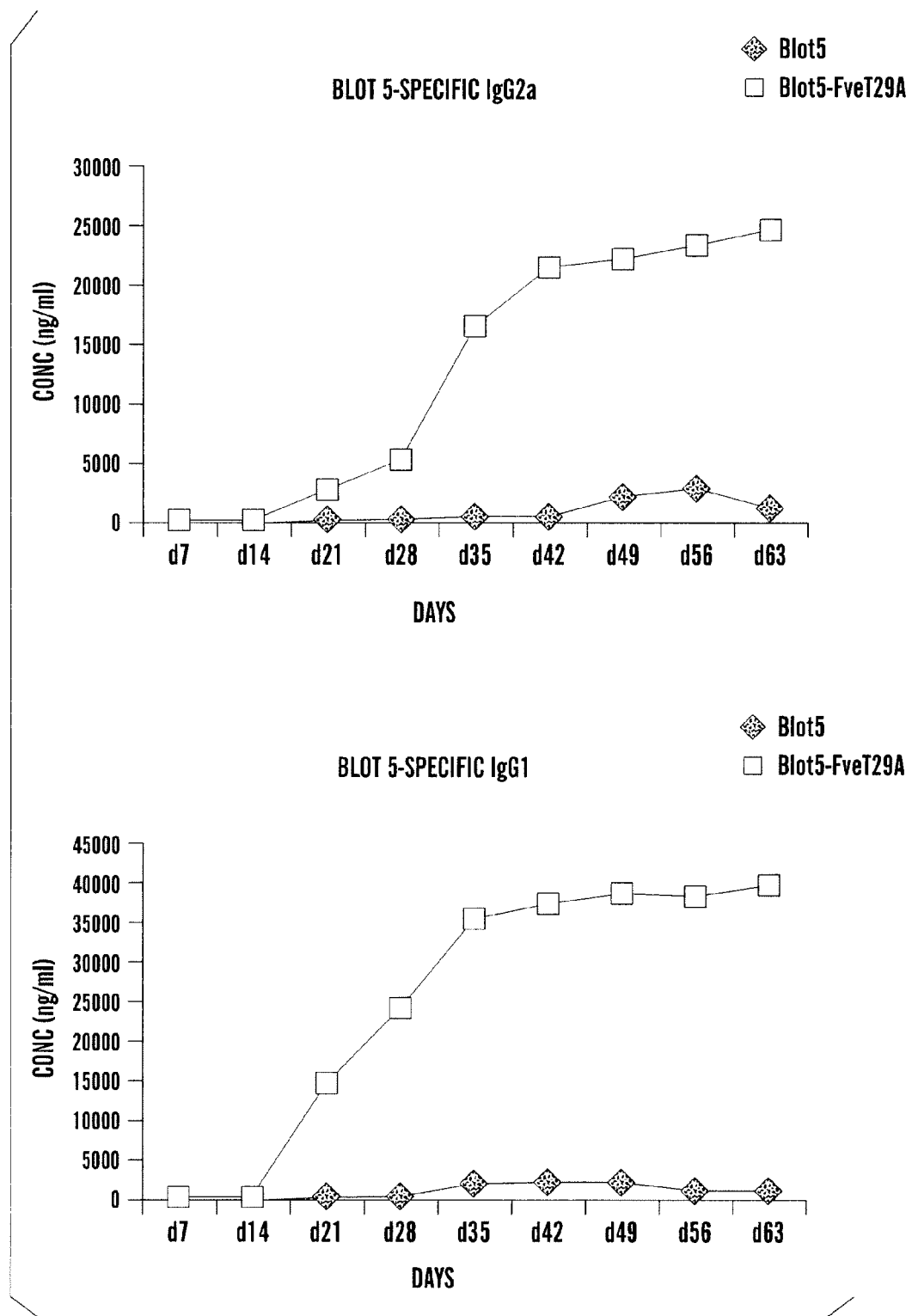
Figure 23B:
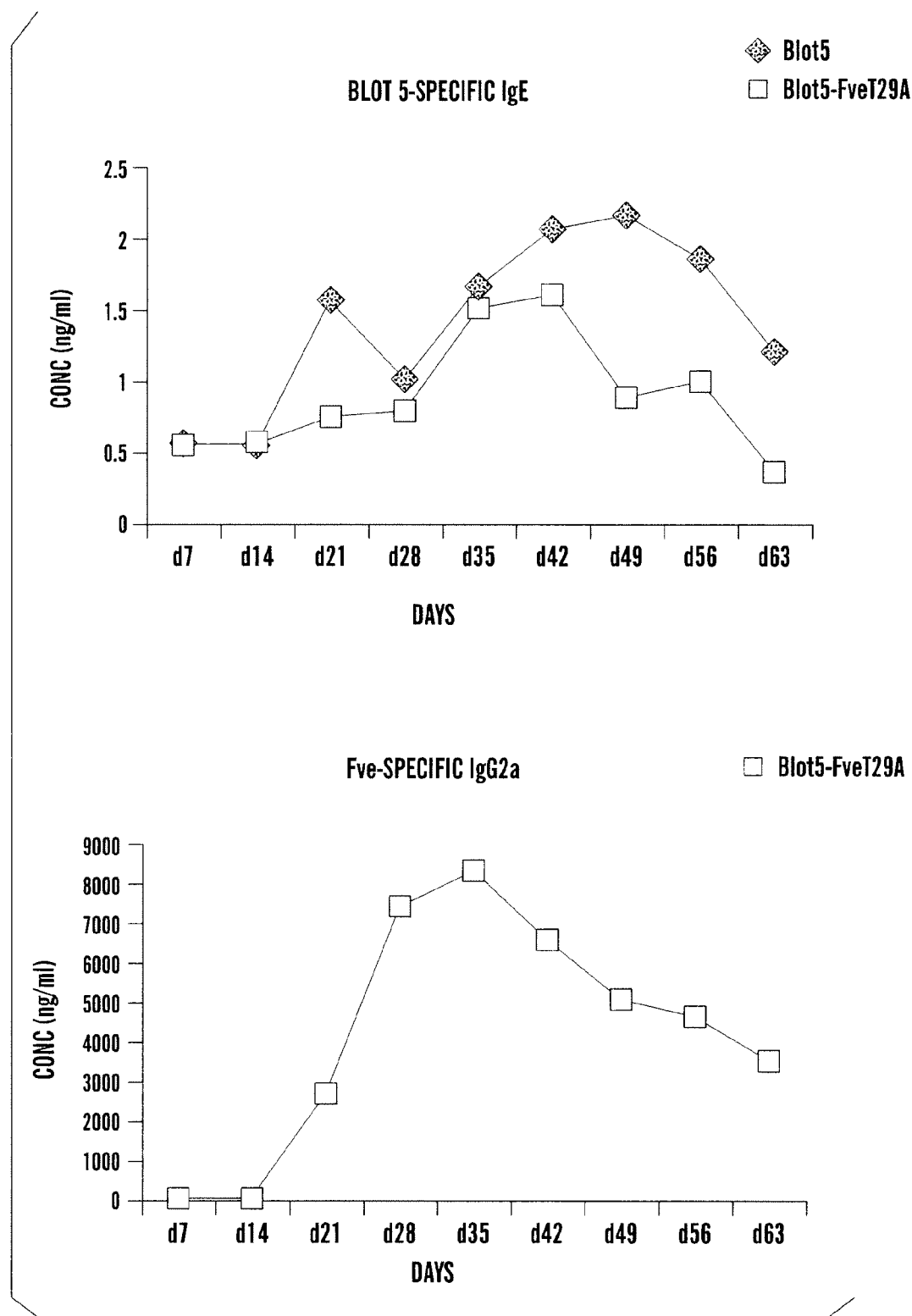
Figure 23B:
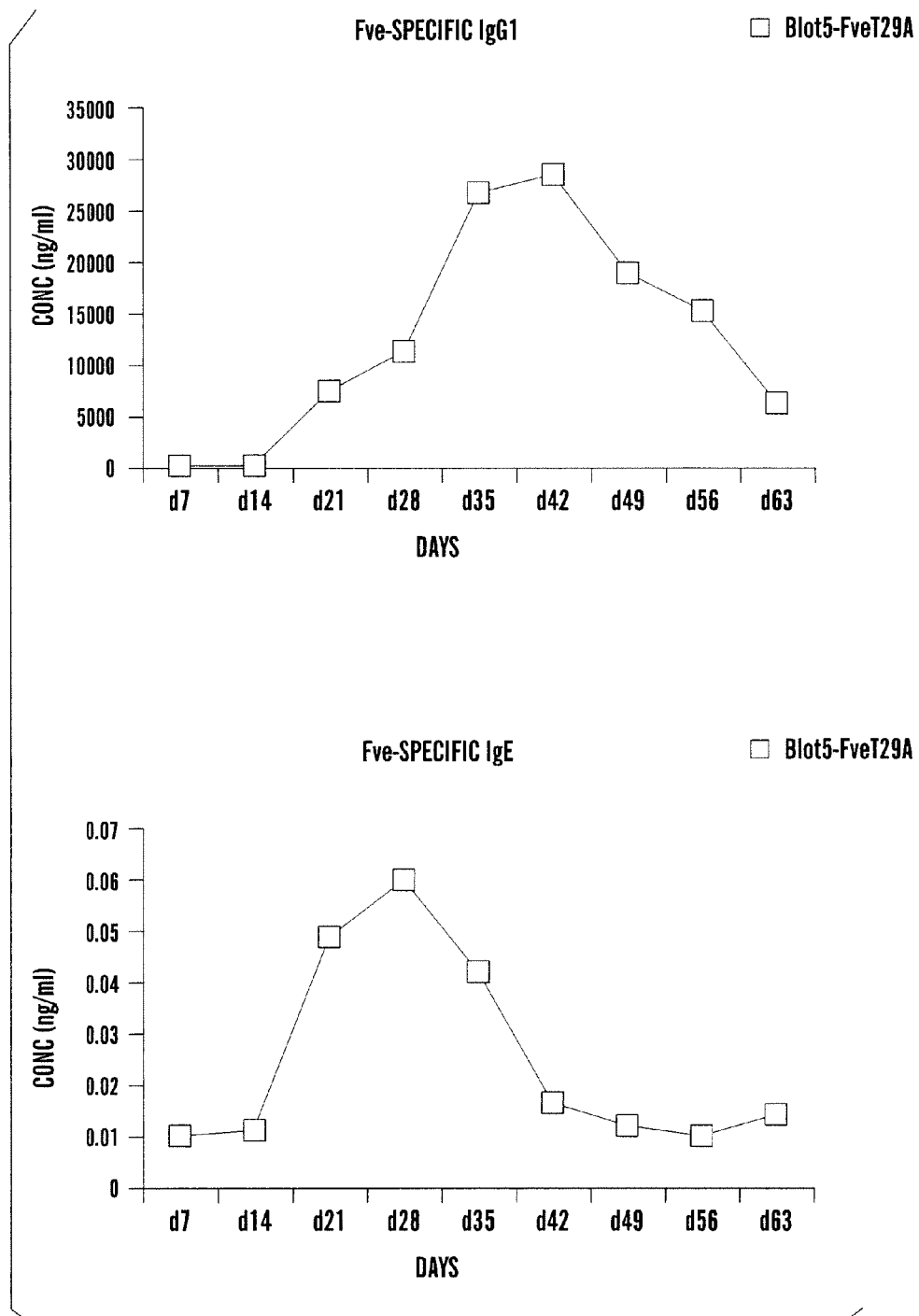

FIG. 23B. Polarized Th1 immune responses by recombinant fusion protein of allergen and fungal immunomodulatory protein Five mice per group of female BALB/cJ (6-8 weeks old) were subcutaneously immunized with 10 μg/ml of major house dust mite allergen Blo t 5 alone or fusion protein Blo t 5-FveT29A in tail at day 1. Mice were received similar antigen boosting in footpads at day 14 and day 28. All mice were bled weekly and sera were collected for analysis of Blo t 5 and Fve-specific IgG1, IgG2a and IgE by ELISA. Results show that recombinant fusion protein of allergen and fungal immunomodulatory protein has the ability to induce Blo t 5-specific IgG2a (2a) and down-regulate IgE production (2c). The overall of Fve-specific IgG1 and IgG2a antibodies are lower than Blo t 5 and decrease gradually after day 42 (2d and 2e), and the induction of Fve-specific IgE is less than 1 ng/ml (2f). Therefore, fungal immunomodulatory protein Fve has the potential to be developed for the immunotherapeutic vaccine of allergy.

Figure 23C:
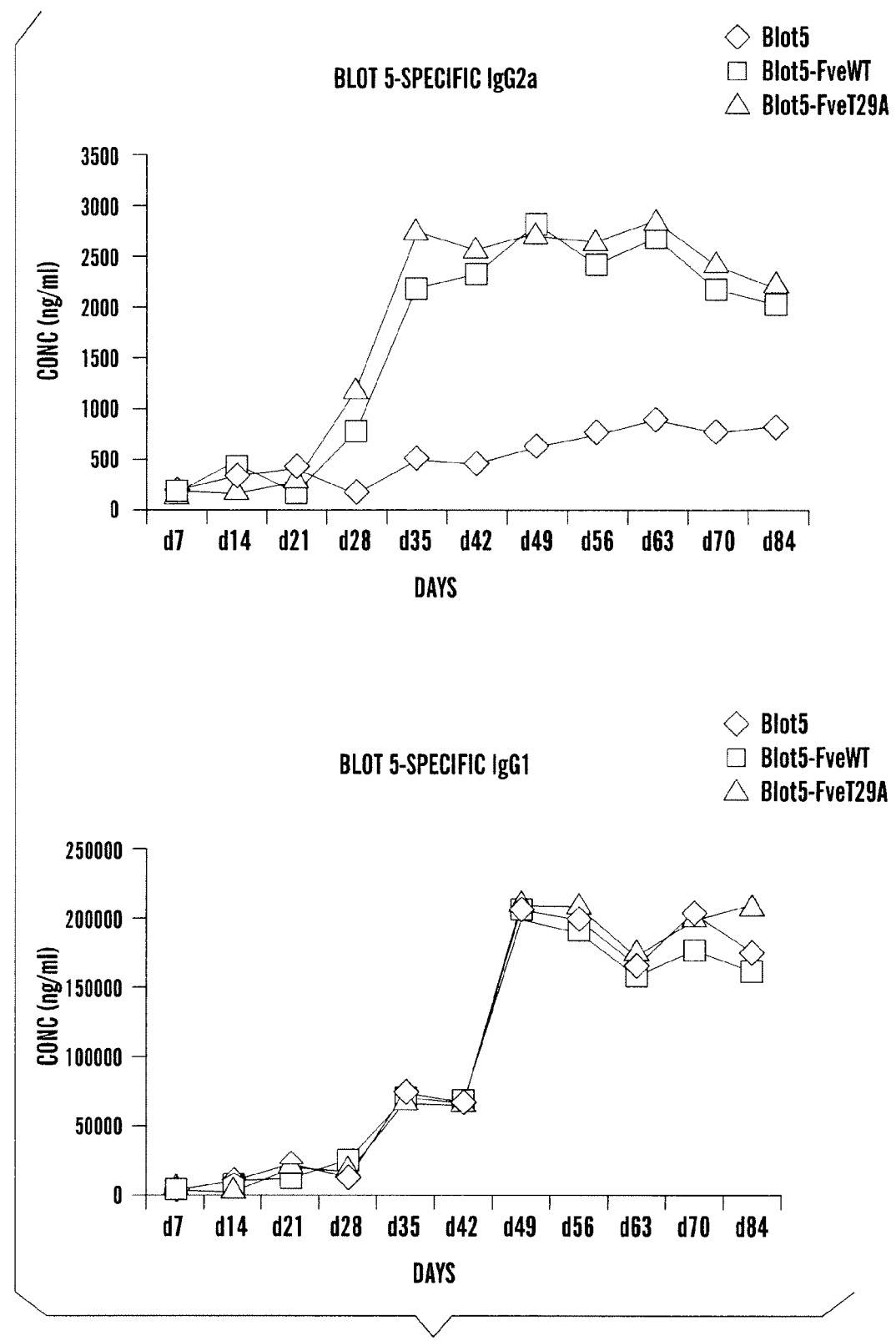
Figure 23C:
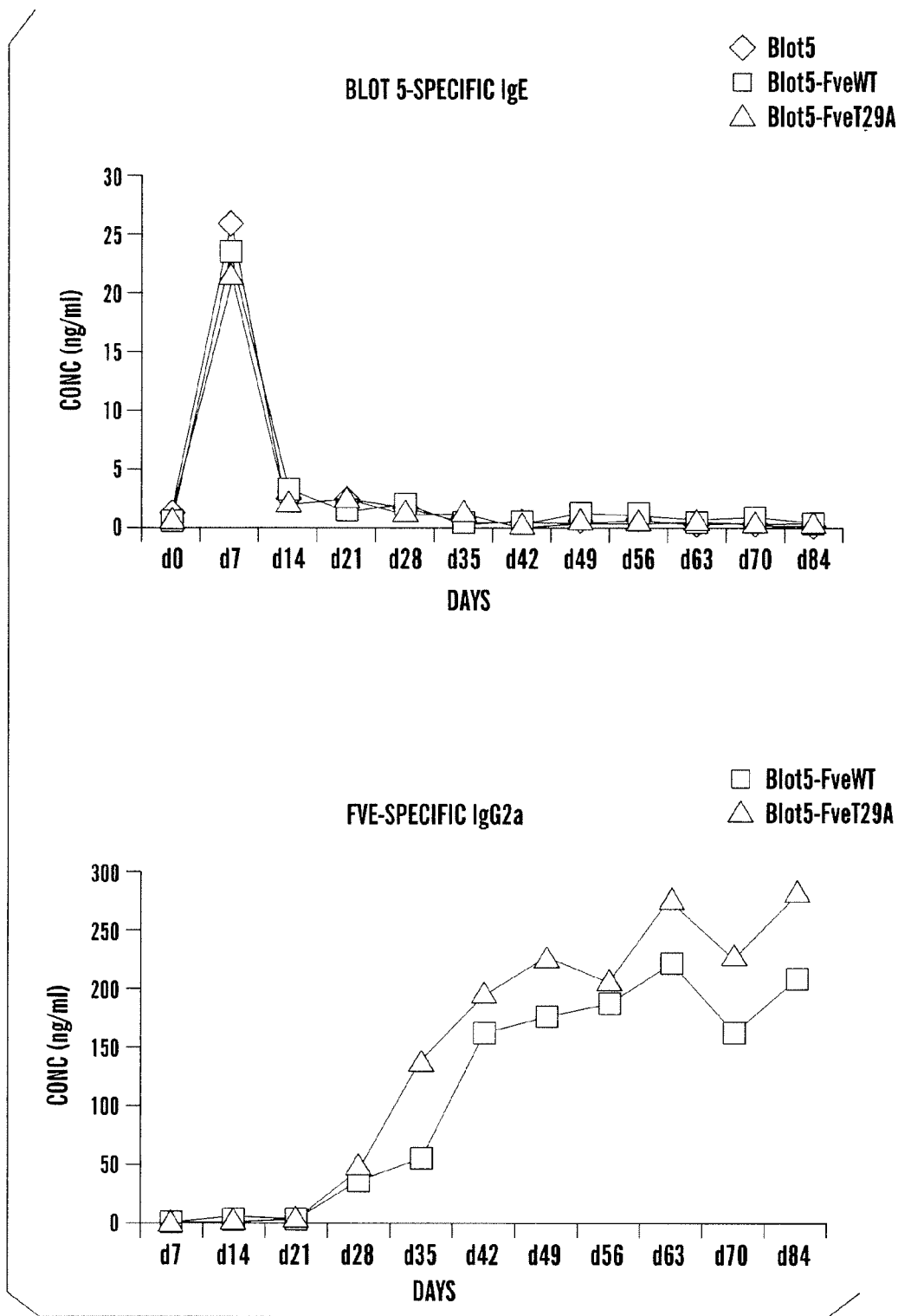
Figure 23C:
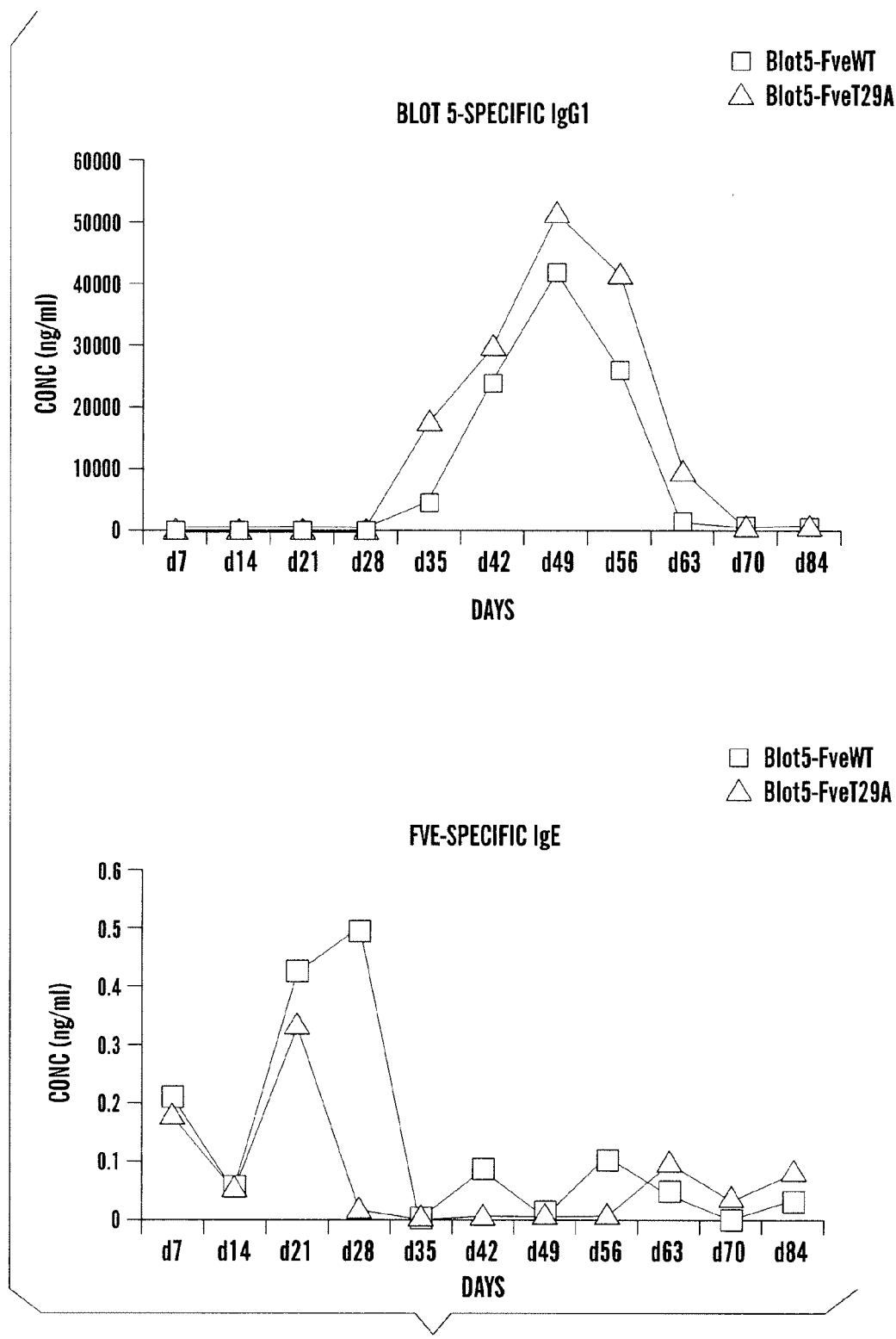

FIG. 23C. Efficient induction of Th 1-mediated immune responses in mite allergen induced mice by recombinant fusion protein Blo t 5-Fve All groups of female BALB/cJ (6-8 weeks old) were sensitized intraperitoneally on day 1 with 5 μg of recombinant mite allergen Blo t 5 and boosted at day 14 with 1 μg of Blo t 5 adsorbed to 64 μg/μl of aluminum hydroxide gel in a final volume of 200 μl. Mice treated with six subcutaneous injections of 20 μg of Blo t 5-FveWT or Blo t 5-FveT29A fusion protein in 200 μl of PBS at three days interval started from day 21-35. The negative control mice received six subcutaneous injections of 20 μg of Blo t 5 alone. All mice were bled weekly and sera were collected for analysis of Blo t 5 and Fve-specific IgG1, IgG2a, and IgE by ELISA. Result show that recombinant fusion protein Blo t 5-FveT29A has the ability to induce Blo t 5-specific IgG2a antibody (3a) in allergensensitized mice.

Figure 24:
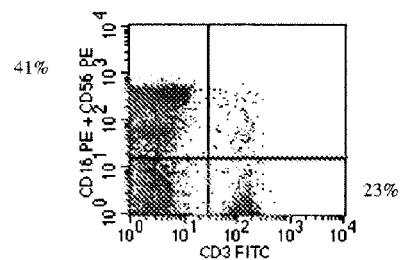
Figure 24:
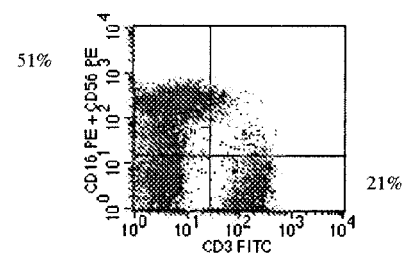
Figure 24:
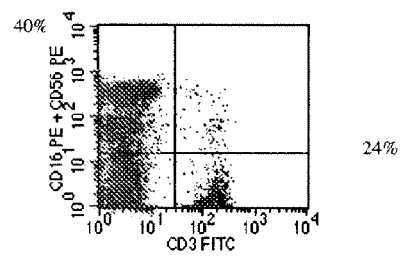
Figure 24:
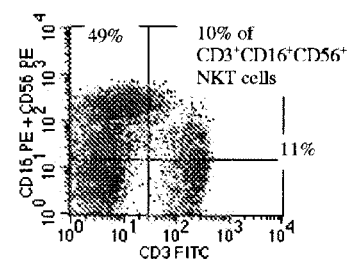
Figure 24:
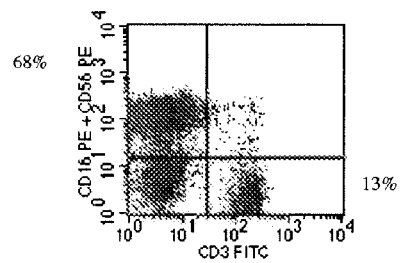
Figure 25A:
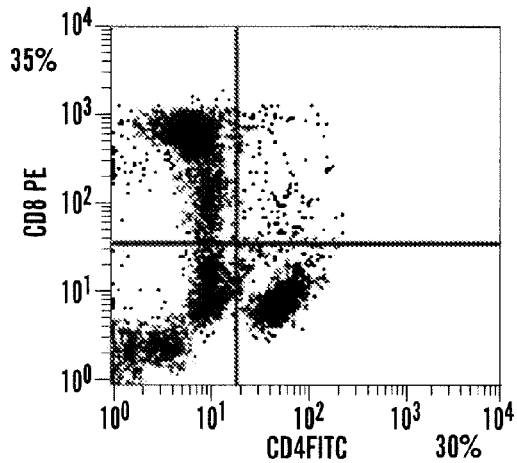
Figure 25D:
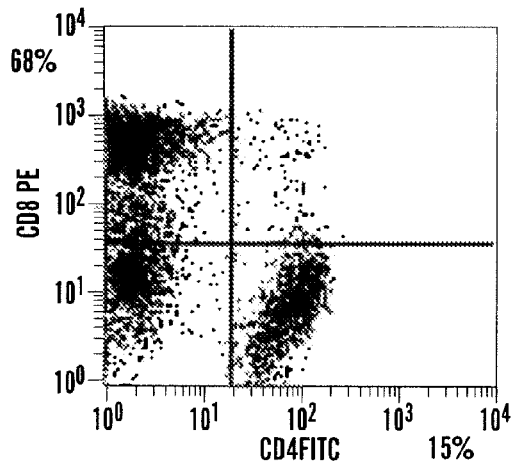
Figure 25B:
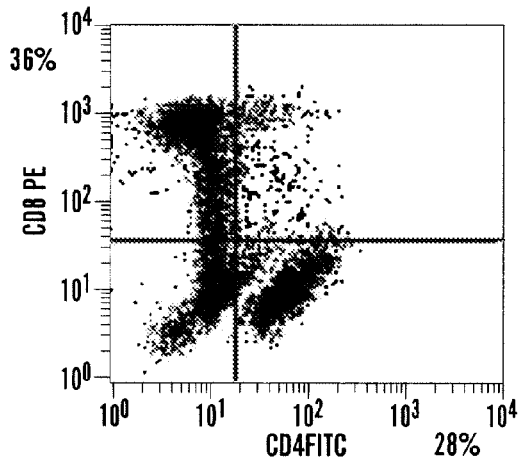
Figure 25E:
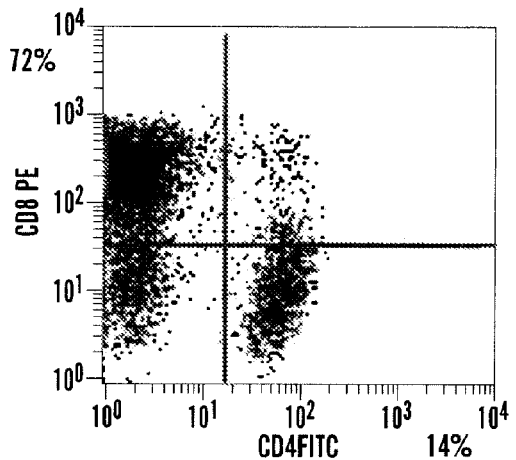
Figure 25C:
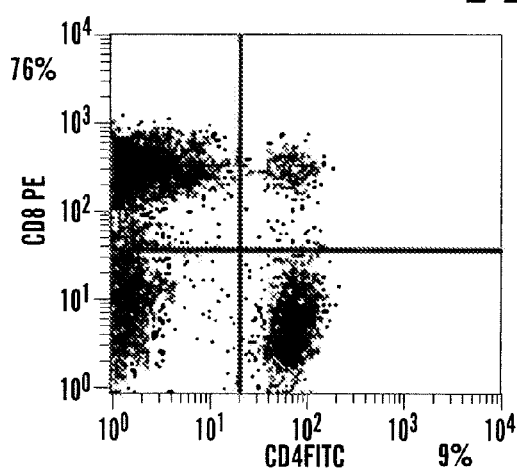
Figure 26A:
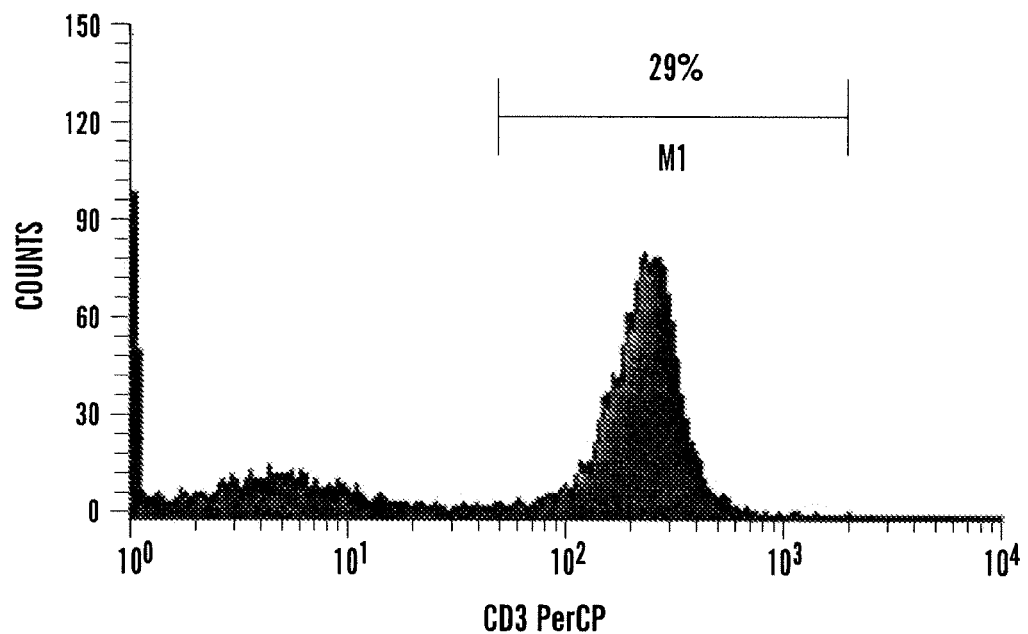
Figure 26B:
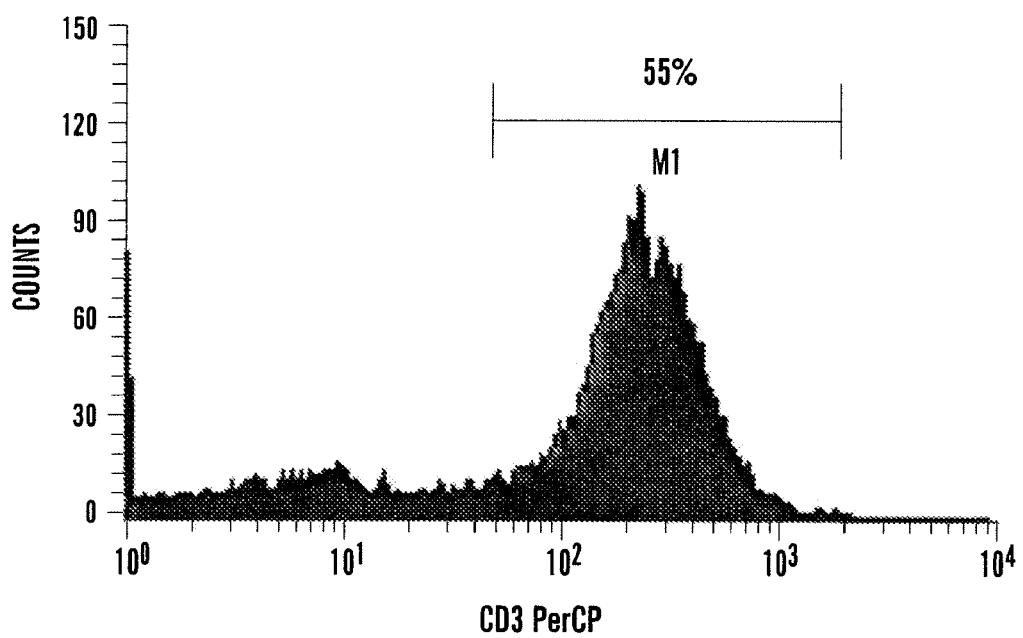
Figure 26C:
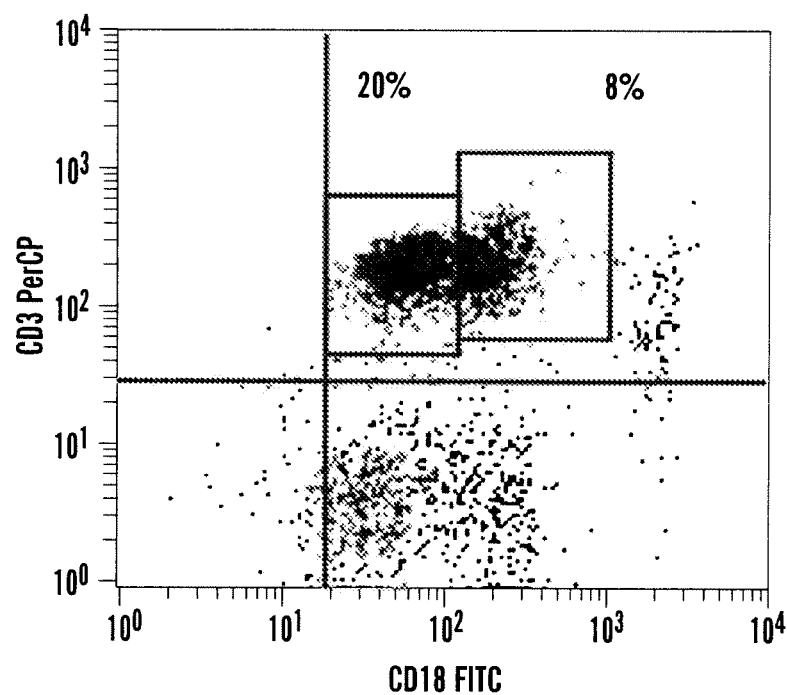
Figure 26D:
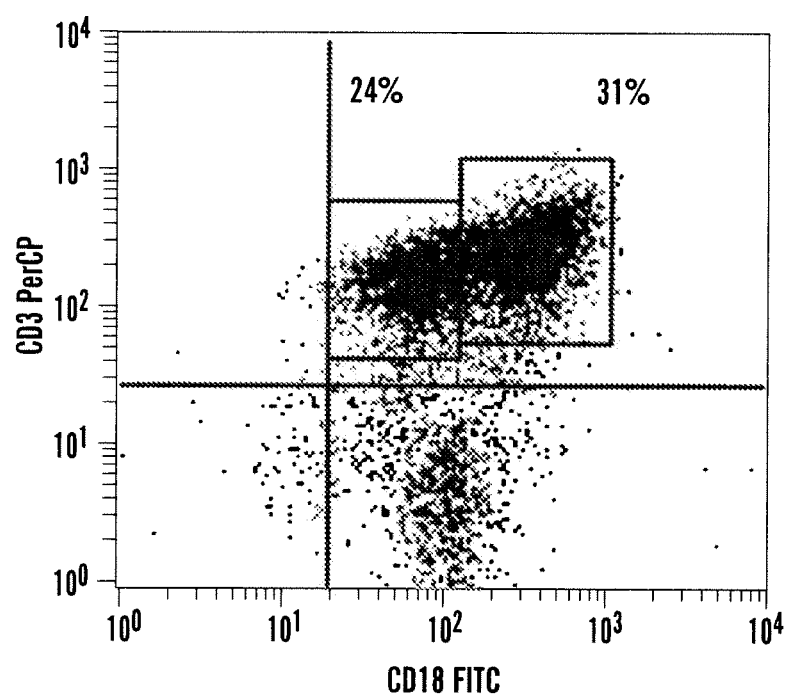

FIG. 24. Human PBMC stimulated with native Fve protein for five days showed a significant increase in $CD16^+$ and $CD56^+$ cells. The $CD3^+$ cells and $CD16^++CD56^+$ cells are analyzed by FACScan after staining with anti-CD3 FITC, anti-CD16 PE and anti-CD56 PE conjugated mouse anti-human specific monoclonal antibody. Cells stimulated with (a) no antigen; (b). 5 μg of Der p 2 house dust mite allergen as negative control; (c). 5 μg of PHA; (d). 5 μg of Fve; (e). 25 μg of Fve.

FIG. 25. Human PBMC stimulated with Fve protein for ten days showed a significant increase in $CD8^+$ cells. The proportion of $CD4^+$ and $CD8^+$ T cells are analyzed by FACScan after staining with anti-CD4 FITC and anti-CD8 PE conjugated mouse anti-human specific monoclonal antibody. Cells are stimulated with (a). no antigen; (b). 5 μg of Der p 2 house dust mite allergen as negative control; (c). 5 μg of PHA; (d). 5 μg of Fve; (e). 25 μg of Fve.

FIG. 26. Expanded human $CD3^+CD18^{+Bright}$ T cells subset in human PBMC after stimulation with Fve protein for five days. Human PBMC from healthy donor are cultured alone (a and c) or with 20 μg of native Fve protein (b and d) for 5 days. Cells are then analyzed by flow cytometry after staining with anti-CD3 PerCP, anti-CD8 PE and anti-CD18 FITC.

FIG. 27. Expanded $CD3^+CD8^{+Bright}CD18^{+Bright}$ T cells in human PBMC after cultured with Fve protein for five days. Human PBMC from healthy donor are cultured alone (a and c) or with 20 μg of native Fve protein (b and d) for five days. Cells are analyzed by flow cytometry after staining with anti-CD3 PerCP, anti-CD8 PE and anti-CD18 FITC.

FIG. 28. Proportion of in vivo BrdU incorporated natural killer (NK) cells from spleen of C57BL/6J naïve mice (a), or mouse received three consecutive subcutaneous injections with 10 μg of Fve (b), 50 μg of Fve (c), 250 μg of Fve (d). Splenocytes are stained with anti-Pan NK PE and anti-BrdU FITC monoclonal antibodies and then analyzed with flow cytometry.

FIG. 29. Proportion of in vivo BrdU incorporated CD8+ T cells from spleen of C57BL/6J naïve mice (a), or mouse received three consecutive subcutaneous injections with 10 μg of Fve (b), 50 μg of Fve (c), 250 μg of Fve (d). Splenocytes are stained with anti-CD8 PE and anti-BrdU FITC monoclonal antibodies and then analyzed with flow cytometry.

FIG. 30. Proportion of in vivo BrdU incorporated CD4+ T cells from spleen of C57BL/6J naïve mice (a), or mouse received three consecutive subcutaneous injections with 10 μg of Fve (b), 50 μg of Fve (c), 250 μg of Fve (d). Splenocytes are stained with anti-CD4 PE and anti-BrdU FITC monoclonal antibodies and then analyzed with flow cytometry.

FIG. 31. Proportion of in vivo BrdU incorporated CD19+ B cells from spleen of C57BL/6J naïve mice (a), or mouse received three consecutive subcutaneous injections with 10 μg of Fve (b), 50 μg of Fve (c), 250 μg of Fve (d). Splenocytes are stained with anti-CD19 PE and anti-BrdU FITC monoclonal antibodies and then analyzed with flow cytometry.

FIG. 32. Proportion of in vivo BrdU incorporated CD8+ T cells from lymph nodes of C57BL/6J naïve mice (a), or mouse received three consecutive subcutaneous injections with 10 μg of Fve (b), 50 μg of Fve (c), 250 μg of Fve (d). Lymph nodes are stained with anti-CD8 PE and anti-BrdU FITC monoclonal antibodies and then analyzed with flow cytometry.

FIG. 33. Proportion of CD4+ and CD8+ T cell subsets from mouse peripheral blood mononuclear cells of Balb/cJ naïve mouse (a), or mouse received seven consecutive subcutaneous injections with 125 μg of Fve. Panels (b), (c), (d) represent results for three respective individual mouse. Mouse peripheral blood mononuclear cells are collected in a tube with anti-coagulant. Cells are stained with anti-CD8 PE and anti-CD4 FITC monoclonal antibodies and then analyzed by flow cytometry.

FIG. 34. Schematic representative of two mammalian eukaryotic expression vectors. (A) pCI-neo can constitutively express high level of recombinant protein in mammalian cells (Picture adopted from Promega, USA). (B) pDisplay can display recombinant protein to the surface of mammalian cells (Picture adopted from Invitrogen life technologies, USA).

Figure 35:
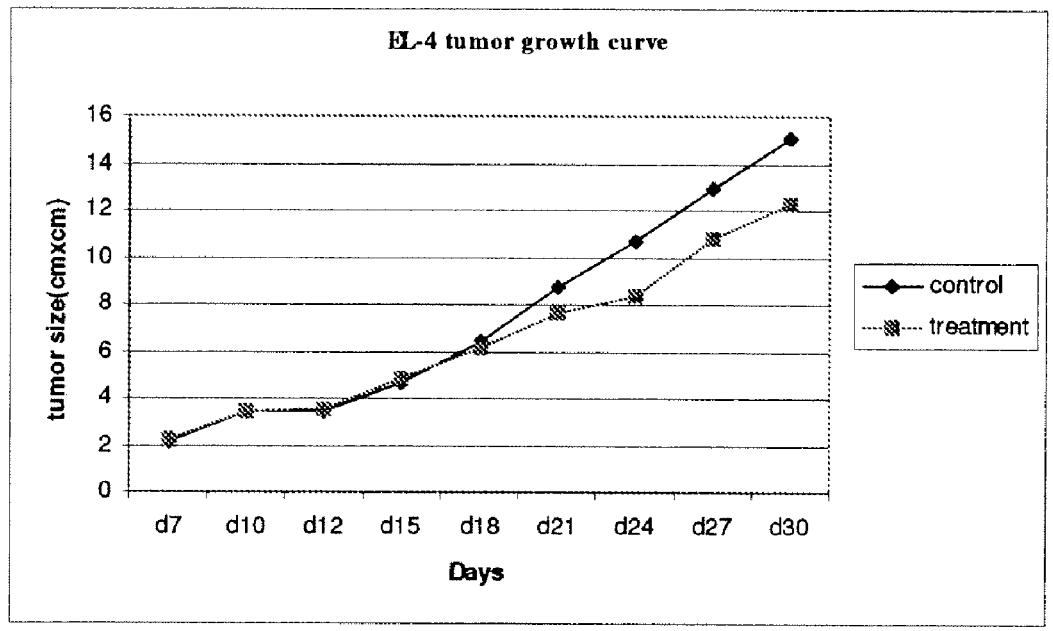

FIG. 35. Growth suppression of EL4 solid tumor. C57BL mice are inoculated with $8 \times 10^6$ EL4 cells have reduced tumor growing rate in the group treated with pCIneo-fve plasmid DNA and Fve protein (Square curve). The control group received pCIneo DNA vector alone and 1×PBS (Diamond curve). EL4 tumor formation is observed at day 3. 100 μg of pCIneo-fve DNA is intramuscularly injected into the tibialis muscle at days 0 and 7. 20 μg of Fve protein is given by subcutaneous injection at days 5, 7, 9, 11, 13, 15, and 18, respectively.

Figure 36:
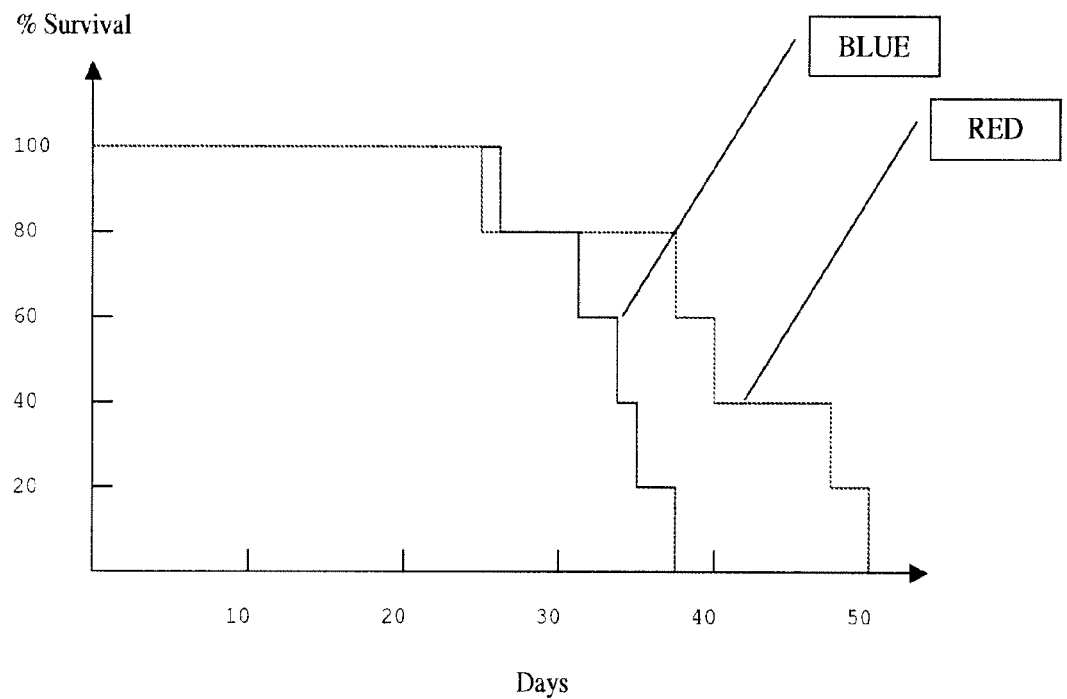

FIG. 36. C57BL/6J mice with EL4 solid tumor have extended mean survival time following treatment with the native Fve protein. Eight weeks old female C57BL mice are inoculated with EL4 tumor in the dorsal back. Tumor formation is observed 3 days after inoculation. Red line: 100 μg of pCIneo-fve plasmid DNA is intramuscularly injected at the tribilis muscle at days 0 and 7. Mice are received 20 μg of native Fve protein treatment by subcutaneous injection surrounding the tumor site at days 5, 7, 9, 11, 13, 15, and 18, respectively. Blue line: Mice received 100 μg of pCIneo vector alone and 1×PBS as control group.

Figure 37:
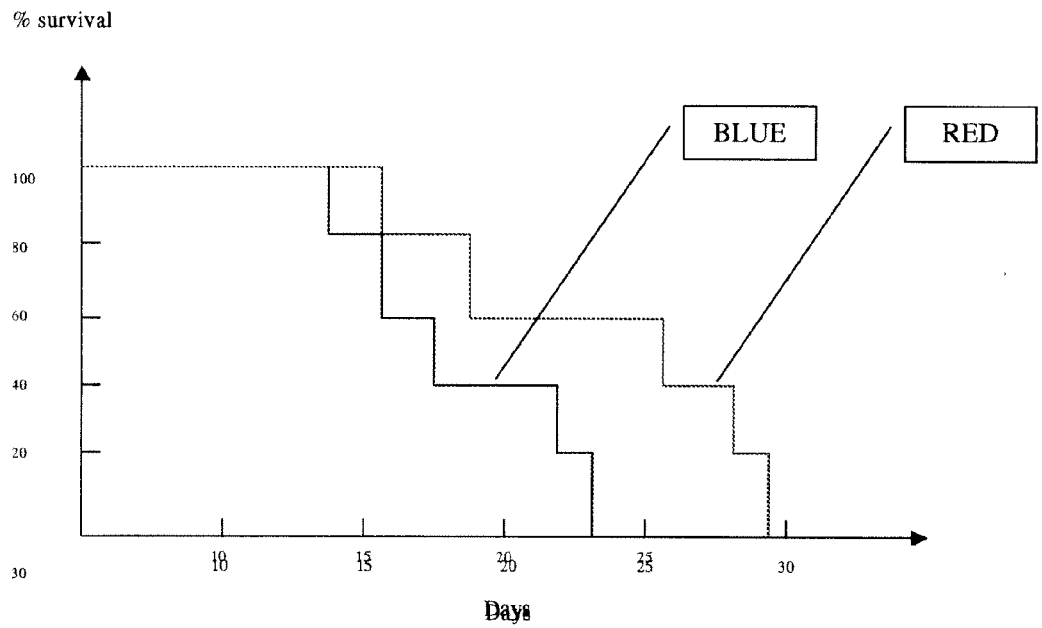

FIG. 37. C57BL/6J mice with B16-F1 melanoma have extended mean survival time following treatment with native Fve protein. Mice are inoculated with B16-F1 tumor cells in the dorsal back. Tumor formation is observed at day 3. Red line: 200 μg of pCIneo-fve plasmid DNA is intramuscularly injected at the tribilis muscle at days −30 and day −1. 50 μg of Fve protein is given by subcutaneous injection surrounding the tumor site at days 4, 7, 9, and 12, respectively. Blue line: Mice received 200 μg of pCIneo vector and 1×PBS as control group.

Figure 38:
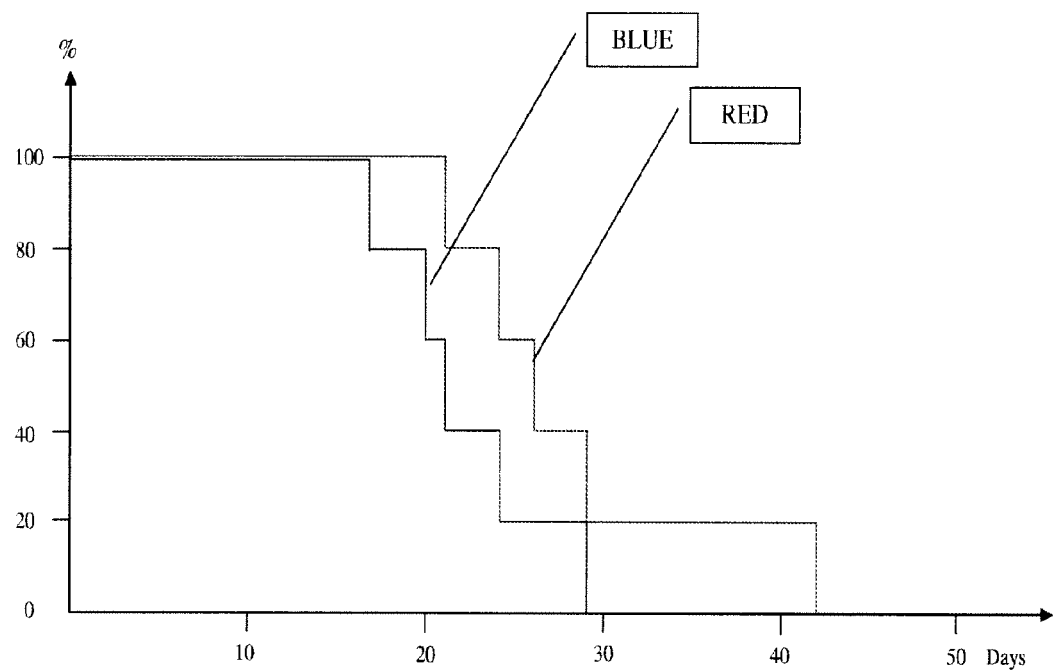

FIG. 38. B16-Fve transfectant has longer survival rate as comparing with B16-vec transfectant. Two groups of C56BL/6J female mice are inoculated either with $5 \times 10^4$ of B16-Fve (Red line) or $5 \times 10^4$ of B16-vec (Blue line) transfectants in the right flank. Transfectant melanoma solid tumor is established at days 5-7. The fatal rates of mice are recorded and presented as survival curve.

Figure 39:
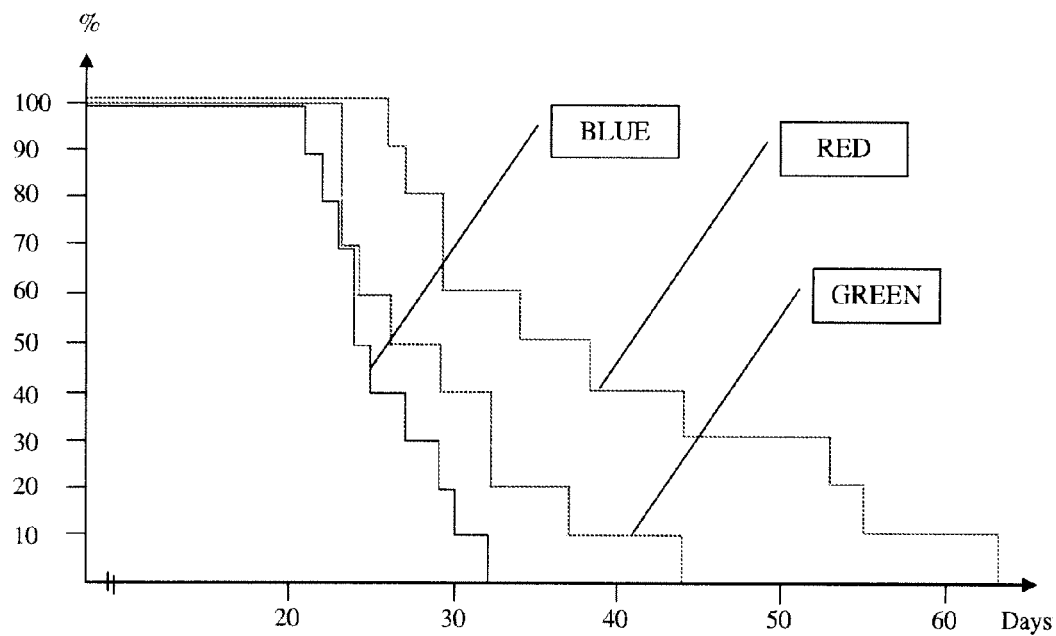

FIG. 39. Combined DNA vaccination and Fve gene-transduced melanoma cells synergizes the extension of life span in solid tumor-established mice. C57BL/6J mice are separated into three groups and each group consisted of ten mice. Mice are inoculated with $5 \times 10^4$ of B16-F1 tumor transfectants in the dorsal back. Tumor formation is observed at day 5-7. 100 μg of pCIneo-fve plasmid DNA is intramuscularly injected at the right and left tribilis muscle of C57BL/6J at day −77, day −35 and day −21. Mice are subcutaneously injected with $5 \times 10^4$ of B16-Fve transfectants (Red line) and B16-vec transfectant (Green Line) at day 0, respectively. 100 μg of pCIneo plasmid DNA is operated as same experimental procedure and mice are subcutaneously injected with $5 \times 10^4$ of B16-vec transfectants as negative control (Blue line).

Figure 40:
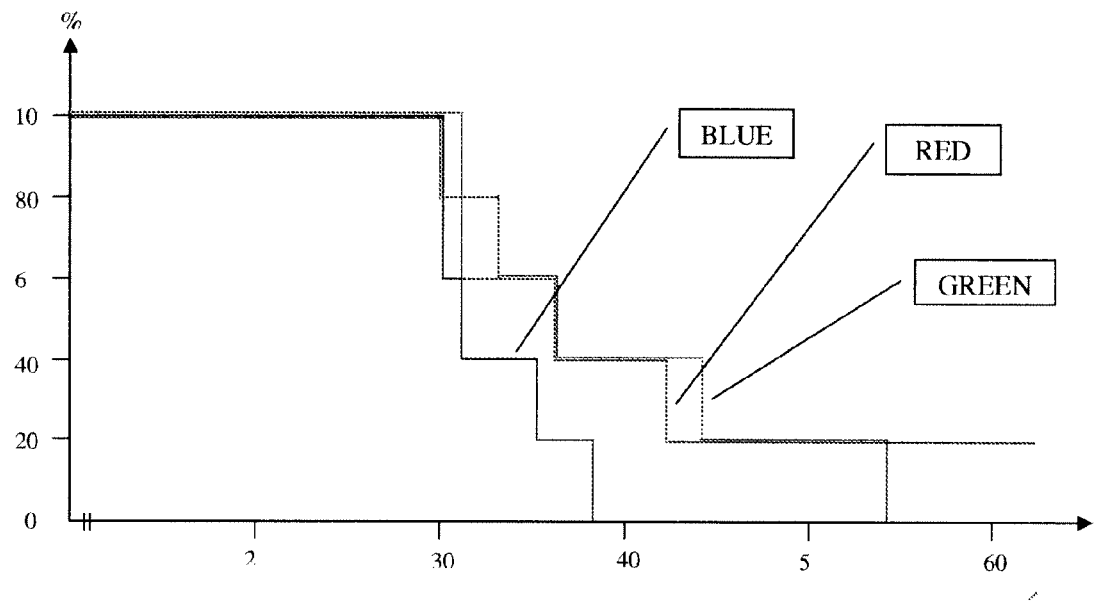

FIG. 40. Strategy of oral primed with Fve protein and intramuscular boosted with plasmid DNA could extend the survival rate of mice with lung metastasis. Two groups of five C57BL/6J mice are given with 10 mg/ml of Fve protein in the drinking water at day −35, −28 and −21, and each water providing is maintained consecutively for one week. Mice are intravenously injected with $2 \times 10^4$ of B16-F1 (wild type) melanoma cells at day 0. One week after, mice are intramuscularly injected with 100 μg of pCIneo-fve plasmid DNA into the right and left tribilis muscle, respectively. The mixture of $5 \times 10^4$ of B16-Fve cells lysate plus 10 μg of Fve protein (Red line) or 10 μg of Fve protein alone (Green line) are subcutaneously injected to mice at the following three weeks. Negative control group of mice received same amount of 1×PBS in the drinking water, intravenously injected with $2 \times 10^4$ of B16-F1 melanoma cells, followed by intramuscularly injected with plasmid DNA vector pCIneo, and finally subcutaneously injected with B16-vec cells lysate plus 1×PBS (Blue line).

Figure 40B:
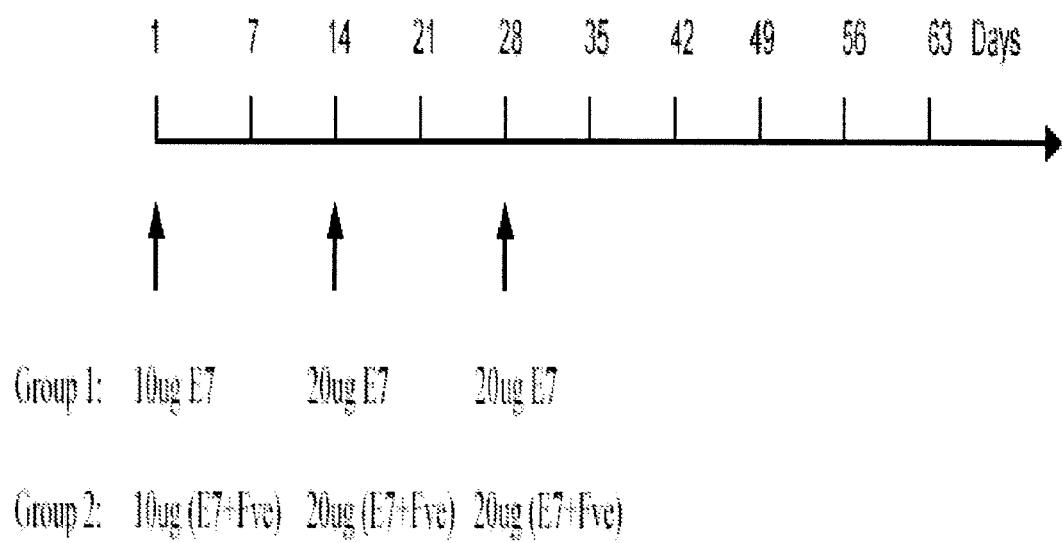

FIG. 40B is a schematic representation of the protocol used in the experiments described in Example 25A.

Figure 40C:
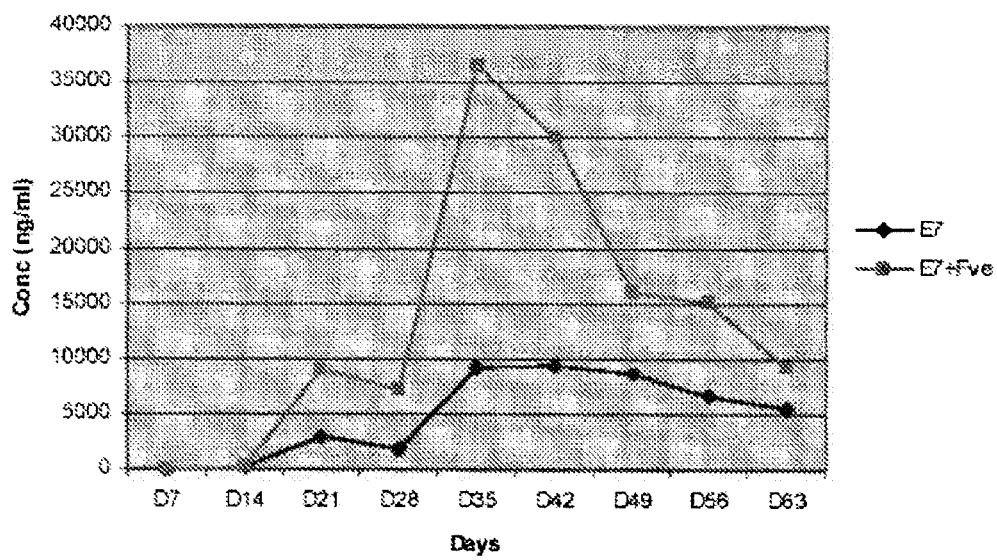
Figure 40C:
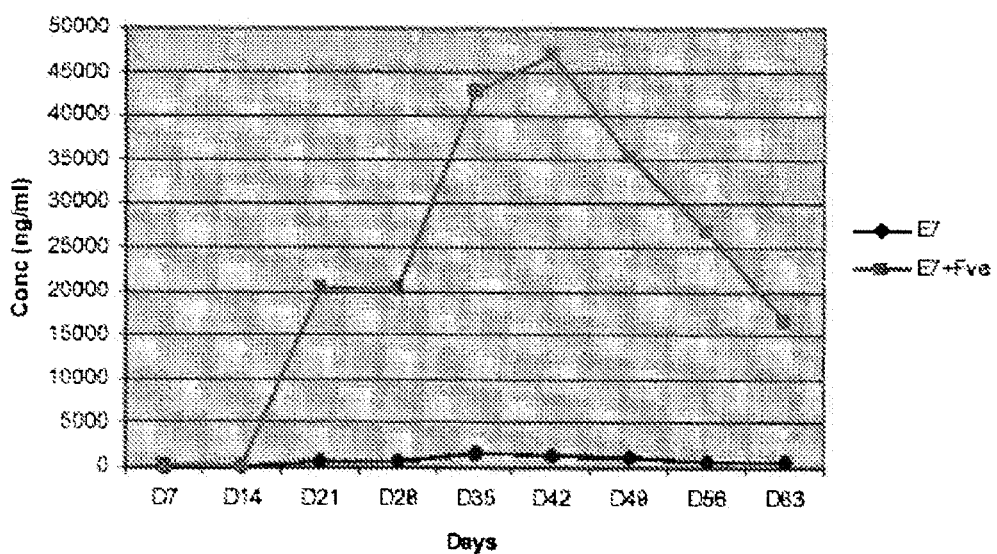

FIG. 40C is a graph showing the results of Example 25A.

Figure 41:
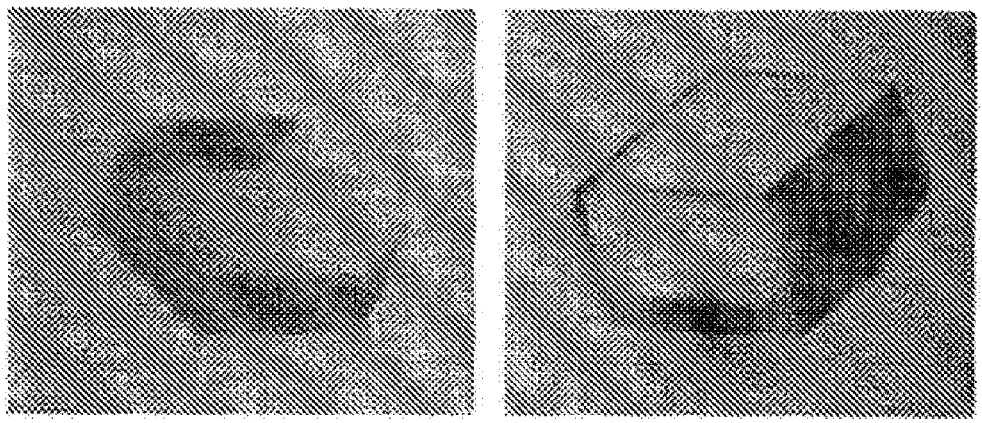

FIG. 41. Two representative crystals of Fve. Tetragonal crystal is grown in 2% PEG 400, 2.0 M Ammonium Sulfate; 0.1 M Tris-HCl pH 8.5. The crystal dimensions are approximately 1 mm×0.9 mm×0.5 mm.

Figure 42:
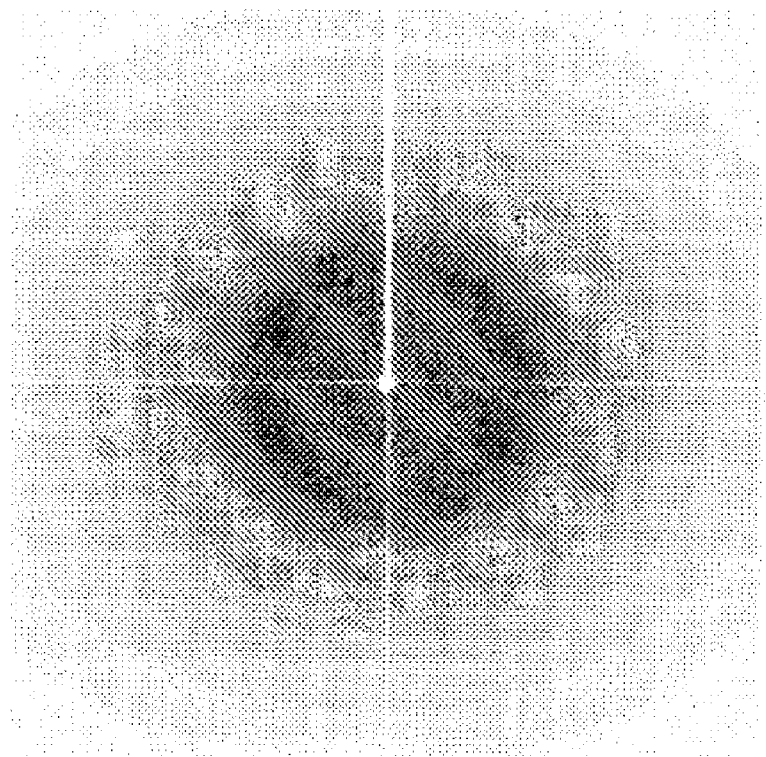
Figure 43:

FIG. 42. 1° oscillation image of Fve crystal. The edge of the image corresponds to a resolution of 1.4 Å. Image displayed with Mosflm/Scala.

FIGS. 43, 44A, 44B, 44C, 45A and 45B show structures of Fve.

SEQUENCES

Appendix A shows the nucleic acid and/or aminio acid sequences of the deletion mutants Fve D6-18, Fve D19-33, Fve D34-46, Fve D47-60, Fve D61-72, Fve D73-84, Fve D85-97, Fve D98-106, Fve D107-115, Fve D61-97, Fve p55-100.

Appendix A also shows the nucleic acid and/or aminio acid sequences of the substitution mutants Fve R27A, Fve G28A, Fve T29A, as well as the fusion proteins Blo t 5-Fve (two-in-one chimeric wild type), Blo t 5-Fve R27A (two-in-one chimeric mutant), Blo t 5-Fve T29A (two-in-one chimeric mutant), Der p 2-Fve R27A (two-in-one chimeric mutant), Der p 2-Fve T29A (two-in-one chimeric mutant), Blo t 5-Der p 2-Fve R27A (three-in-one chimeric mutant).

Appendix A also shows the nucleic acid and/or aminio acid sequences of the Fusion Proteins of Viral Antigen and Fve, HPV E7-FveT29A and HCV Core23-FveT29A, as well as the nucleic acid and/or aminio acid sequences of the Fusion Proteins of Tumor-Associated Antigen and Fve, MAGE3-FveT29A, MART1-FveT29A and CEA-FveT29A.

Appendix A also shows the sequences of the primers Fd6-18F (36 mer), Fd6-18R (36 mer), Fd19-33F (36 mer), Fd19-33R (36 mer), Fd34-46F (36 mer), Fd34-46R (36 mer), Fd47-60F (36 mer), Fd47-60R (36 mer), Fd61-72F (36 mer), Fd61-72R (36 mer), Fd73-84F (36 mer), Fd73-84R (36 mer), Fd85-97F (36 mer), Fd85-97R (36 mer), Fd98-106F (36 mer), Fd98-106R (36 mer), Fd107-115R (39 mer), d (61-97)-F (36mer), d (61-97)-R (36mer), [Fv55-100]-F (48mer), [Fv55-100]-R (42mer), F (R27A)-F (27 mer), F (R27A)-R (27 mer), F (G28A)-F (27 mer), F (G28A)-R (27 mer), F (T29A)-F (27 mer), F (T29A)-R (27 mer), Bt5Fv-F (36mer), Bt5Fv-R (36mer), Dp2Fv-F (36mer), Dp2Fv-R (36mer), Bt5Dp2-F (36mer), Bt5Dp2-R (36mer).

Appendix B shows the sequences of fragments of Fve, which comprise all or part of the RGT motif.

Appendix C shows the crystal coordinates of Fve protein.

The methods and compositions described here may suitably employ any one or more of the sequences shown in the Appendices.

DETAILED DESCRIPTION

We have identified an immunoregulatory protein, designated as native Fve, from *Flammulina velutipes*. The cDNA encoding Fve protein has been isolated and biologically active recombinant Fve has been successfully produced in *E. coli.*

Our studies show that native Fve is capable of inducing high levels of expression of 1FN-γ, TNF-αc and ICAM-I gene expression in activated human T- and NK cells. It also up-regulates transcription factors IRF-I and NF-κB (c-Rel), but down-regulates ll.-4. In allergic murine model, mice treated with Der p 2, a major house dust mite allergen from *Dermatophagoides pteronyssinus*, plus native Fve show a significant boost of Der p 2-specific IgG2a production. Native Fve also reduces wheel and erythematic flare formation on Der p 2 skin prick test-positive human subject. We also find that fragments, homologues, variants derivatives of native Fve disclosed here (termed "Fve polypeptides") as well as nucleic acids encoding these, also have such activities.

Furthermore, we show in the Examples that Fve polypeptide and native Fve polypeptide is a potent adjuvant that can be codelivered with specific allergens for desensitization of allergic disorders such as asthma, rhinitis and atopic dermatitis. In addition, Fve selectively induces polarization of NK (natural killer) cells and cytotoxic $CD8^+$ T cells in vitro and in vivo. We therefore disclose anti-cancer therapies and methods which employ these immunostimulatory or immunomodulatory effects. We disclose in vivo animal studies which show that this protein prolongs survival rate in solid tumor-transplanted mice.

Fve and its polypeptides may therefore be used for any application where up-regulation of a immune response is desired or necessary. Fve polypeptides may in particular be used in therapy, for example for the treatment of diseases such as infections, cancer, etc.

We further disclose a combination of Fve polypeptide or native Fve, with an allergen, for example in the form of a fusion protein. Such a combination is able to counteract an established allergic reaction. Combinations of Fve polypeptide or native Fve with a tumour associated protein or viral oncogenic protein may be used to prevent or treat cancer, or specifically for preventing tumour progression.

We disclose immunotherapeutic methods and reagents for allergy and virus infections, which take advantage of these immunomodulatory effects of native Fve and Fve polypeptides. We also disclose methods of treatment or prevention of a cancer, tumour, neoplasm or cancerous cell, by use of the Fve polypeptides and nucleic acids described here. DNA vaccines, expression vectors, host cells and transgenic organisms comprising such Fve nucleic acids, or a fragment, homologue, variant or derivative thereof, may also be used for such a purpose. In general, any use of a Fve polypeptide described here may employ a nucleic acid encoding such, or a DNA vaccine, expression vector, host cell and transgenic organism comprising such, and the disclosure should be read accordingly.

We also show that native Fve stimulates gene expression of human IFN-γ, TNF-α, IL-1β, IL-2, IRF-1, c-Rel, Bcl-$X_L$, ICAM-1 and iNOS. In addition, we show that Fve up-regulates a novel subset of $CD8^+$ T cells ($CD3^+$ $CD8^+$ $CD18^+_{bright}$) and induces NK cell and $CD8^+$ T cell proliferation in vivo. Animal studies show that Fve prolongs survival rate of tumor-inoculated mice treated with Fve gene and protein. We disclose methods and reagents for cancer therapy using the Fve gene, protein and products, for example in the form of cell-based vaccines for cancers.

Fve may be used in vitro to stimulate the proliferation of $CD3^+$ $CD8^{+bright}$ $CD18^{+bright}$ populations, and the amplified populations may then be administered to the individual in need of treatment. Thus, while it is possible to stimulate $CD3^+$ $CD8^{+bright}$ $CD18^{+bright}$ populations in the context of the body of the animal, it will be apparent that such amplification is also possible in vitro. We therefore disclose the use of Fve polypeptides to stimulate such cells in vitro. Such amplified populations may then be infused into or otherwise administered to the individual in need of treatment. The starting cell population may come from another individual, but preferably it is derived from the same individual who requires treatment.

We also disclose a crystal of FIP, which has been crystallised for the first time. Such a crystal may be used for modelling, or designing ligands which may interact with Fve. The crystal or model may be stored on a computer, or on a computer readable medium, and manipulated using methods known to the skilled person. A computer readable medium comprising a data representation of the crystal is therefore provided.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA* Methods in Enzymology, Academic Press. Each of these general texts is herein incorporated by reference.

Native Fve

The terms "native Fve polypeptide" or "native Fve protein", as used in this document, should be taken to refer to the immunoregulatory protein Fve from *Flammulina velutipes*, preferably in isolated form. The term "wild type Fve" should be understood to be synonymous with "native" Fve; furthermore, the term "nFve" is sometimes used to refer to native Fve.

Preferably, "native" Fve has an amino acid sequence set out as as GenBank accession numbers: 569147 immunomodulatory protein FIP-fve-golden needle mushroom gi|7438667|pir||S69147[7438667] and P80412 IMMUNOMODULATORY PROTEIN FIP-FVE gi|729544|sp|P80412|FVE_FLAVE[729544]. A polypeptide and nucleic acid sequence of "native" or "wild type" Fve is also shown in Appendix A, and the term "native FIP" preferably refers to a polypeptide or nucleic acid, as the case may be, having such sequence. Methods of isolating the "native" Fve gene and protein from *Flammulina velutipes* are known in the art, and are also set out in the Examples.

A "native" Fve may comprise a methionine residue at the N terminus; however, a native Fve may include versions which lack the initial methionine. The nucleic acid sequence which encodes such a native Fve may therefore comprise or not comprise an initial ATG codon.

As noted above, we have identified certain previously unknown properties of native Fve, including immunomodulatory and stimulatory properties, and one aspect of the invention is directed to such new uses of native Fve nucleic acid and native Fve polypeptide. These are disclosed in further detail below.

It should be understood, therefore, that the invention preferably does not include wild-type or native Fve protein; however, it does encompass the uses of this in immunomodulation, enhancing immune response and in allergy and cancer treatment. Furthermore, we disclose a fusion protein comprising gluthathione S transferase (GST) and native Fve; such a fusion protein is shown in the Examples to have the beneficial properties of native Fve itself. The sequence of GST-Fve is shown in Appendix A. Therefore, the invention includes this GST-Fve fusion protein (also referred to as rGST-Fve and GST-Fve (wild type)), and nucleic acids encoding it.

We further disclose a nucleic acid sequence encoding native Fve, termed here a "native Fve nucleic acid sequence". The Examples describe the cloning and isolation of a cDNA encoding native Fve protein. The sequence of this is set out as "Fve (Wild type)" in Appendix A. Preferably such a sequence is in isolated form.

Fve Polypeptides

Additionally, we have identified various fragments, homologues, variants and derivatives of "native Fve", which are previously unknown. Such fragments, homologues, variants and derivatives are referred to here as "Fve polypeptides" (as contrasted with "native Fve polypeptides"). We disclose such Fve polypeptides, and their uses.

It will be apparent that the terms "Fve" and "Fve polypeptide", as they is used in this document, preferably exclude the wild type or native Fve protein or gene encoding this, and includes only molecules derived from native Fve, being fragments, homologues, variants and derivatives of native Fve (i.e., Fve polypeptides).

The Fve polypeptides are preferably are at least as biologically active as native Fve. However, they may have 10%, 20%, 30%, 40%, 50%, 60%, 70%, 80%, 90%, 95% or more of the biological activity of native Fve, for example as assayed by any of the tests set out below. As used herein "biologically active" refers to a sequence having a similar structural function (but not necessarily to the same degree), and/or similar regulatory function (but not necessarily to the same degree), and/or similar biochemical function (but not necessarily to the same degree) of the naturally occurring sequence.

"Fve polypeptides" preferably comprise at least one biological activity of native Fve. By "biological activity" in relation to Fve, we refer to at least one of the following activities: up-regulation of expression of Th1 cytokines, preferably IFN-γ and TNF-α, down-regulation of expression of Th2 cytokines, preferably IL-4 and IL-13, hemagglutination activity, cell aggregation activity, lymphocyte aggregation activity, lymphoproliferation activity, up-regulation of expression of IL-2, IFN-γ, TNF-α, but not IL-4 in $CD3^+$ T cells, interaction with T and NK cells, adjuvant activity, stimulation of $CD3^+$ $CD16^+$ $CD56^+$ natural killer (NK) T cells, and up-regulation of expression of allergen specific IgG2a antibody. Further biological activities preferably comprised by Fve polypeptides as described here include prevention of systemic anaphylactic reactions and/or decreased footpad edema, preferably as assayed using the Arthus reaction (Ko et al, 1995). In particular, Fve polypeptides preferably comprise at least some of useful properties, preferably medically or therapeutically useful properties, of native Fve.

Assays for each of these activities are set out in the Examples, and preferably, whether a Fve polypeptide comprises a "biological activity" of Fve is to be assessed according to the relevant assay set out in the Examples.

Preferably, Fve polypeptides comprise at least one or more of the biological activities for the relevant use, preferably use as an immunomodulator, or for upregulating immune response. Preferably, they comprise at least one or more of the biological activities which enable use as a cancer therapy or allergy therapy.

Preferably, Fve polypeptides comprise two or more biological activities of native Fve, preferably substantially all the biological activities of native Fve.

We show in the Examples that the sequence RGT at positions 27-29 of the native Fve polypeptide sequence plays a crucial role in the biological activity of native Fve. In particular, the RGT is shown to mediate the ability of native Fve to cause lymphocyte aggregation and adhesion. This sequence is also shown to mediate lymphoproliferation, and stimulation of IL-2, IFN-γ and TNF-γ secretion in T cells, preferably $CD3^+$ T cells.

Accordingly, in preferred embodiments, the Fve polypeptides comprise at least one, two or all three of the RGT residues (or a functional variant such as RGD) at or about a position corresponding to position 28 of the native Fve polypeptide. By functional variant of RGT, we mean any change in the residues of RGT (or a sequence surrounding it) which does not substantially abolish its function, preferably its function in mediating the activities set out above. Preferably, the Fve polypeptide comprises between 2 to 50, more preferably between 2 to 40, more preferably between 2 to 30, most preferably between 2 to 20 residues of amino acid sequence flanking the glycine residue corresponding to position 28 of native Fve. More preferably, the Fve polypeptide comprises the sequence RGT or the sequence RGD.

However, we show that mutations of R at position 27, as well as mutations of T at position 29, have advantageous effects, in that they independently increase activity of a Fve polypeptide comprising either or both of these mutations. Furthermore, each of the mutations, or in combination, have the potential to increase the solubility of the Fve polypeptide comprising it or them. One, each or both of R27 and T29 may therefore be independently mutated advantageously, by substitution or deletion.

In preferred embodiments, the or each of R27 and T29 are mutated by substitution. The R27 and/or T29 may be substituted by any other residue, but preferably a neutral residue such as G or A. We therefore disclose Fve polypeptides in which R at position 27 is changed to another residue, for example, Fve polypeptides in which R27 is mutated to A, i.e., a Fve polypeptide comprising R27A. We therefore disclose Fve polypeptides in which T at position 29 is changed to another residue, for example, Fve polypeptides in which T29 is mutated to A, i.e., a Fve polypeptide comprising T29A.

Combinations are also possible; hence we disclose Fve polypeptides in which R at position 27 and T at position 29 are independently changed to one or more other residues. For example, we disclose Fve polypeptides in which R27 is mutated to A, and T29 is mutated to A, i.e., a Fve polypeptide comprising R27A and T29A. As noted above, the polypeptide may comprise between 2 to 50, 40, 30 or preferably 20 residues of amino acid flanking the glycine residue at position 28 of native Fve.

Fve polypeptides may comprise fragments of native Fve. For example, Fve D6-18, Fve D19-33, Fve D34-46, Fve D47-60, Fve D61-72, Fve D73-84, Fve D85-97, Fve D98-106, Fve D107-115, Fve D61-97, and Fvep55-100. Fusion proteins comprising these deletion fragments and GST are also disclosed. Fve polypeptides may comprise substitutions, including FveR27A, FveG28A and FveT29A. Further examples of Fve polypeptides are shown in Appendix B, each of which includes at least a portion of the RGT sequence (preferably the whole of the RGT sequence) discussed above. Preferably, the length of such a fragment is 9 amino acid residues or more, e.g., fragment numbers 34-403.

Fve polypeptides may comprise fusion proteins, particularly fusion proteins between an allergen and a Fve polypeptide as defined here. Such allergen-immunomodulator combinations include Blo t 5-Fve (two-in-one chimeric wild type), Blo t 5-FveR27A (two-in-one chimeric mutant), Blo t 5-FveT29A (two-in-one chimeric mutant), Der p 2-FveR27A (two-in-one chimeric mutant), Der p 2-FveT29A (two-in-one chimeric mutant) and Blo t 5-Der p 2-FveR27A (three-in-one chimeric mutant).

Fragments, homologues, variants and derivatives of each of these Fve polypeptides are also included.

The Fve polypeptides may be made by biochemical methods, for example, protein digestion of native Fve, or preferably by recombinant DNA methods as known in the art. Accordingly, it will be understood that Fve polypeptides specifically include recombinant Fve polypeptides. For example, we disclose in the Examples successful production in *E. coli* of biologically active recombinant Fve polypeptide.

The Fve polypeptides disclosed also include homologous sequences obtained from any source, for example related viral/bacterial proteins, cellular homologues and synthetic peptides, as well as variants or derivatives thereof. Thus polypeptides also include those encoding homologues of Fve from other species including other microorganisms. Furthermore, homologues from higher animals such as mammals (e.g. mice, rats or rabbits), especially primates, more especially humans are also included.

Homologues

In the context of this document, a "homologous" sequence is taken to include an amino acid sequence which is at least 15, 20, 25, 30, 40, 50, 60, 70, 80 or 90% identical, preferably at least 95 or 98% identical at the amino acid level over at least 10, 15, 20, 25, 30, 40, 50, 60, 70, 80, 90, 100, 110 or 114 amino acids with the sequence of native Fve shown as "Fve (Wild type)" in Appendix A. In particular, homology should typically be considered with respect to those regions of the sequence known to be essential for protein function rather than non-essential neighbouring sequences. This is especially important when considering homologous sequences from distantly related organisms.

Although homology can also be considered in terms of similarity (i.e. amino acid residues having similar chemical properties/functions), in the context of the present document it is preferred to express homology in terms of sequence identity.

Homology comparisons can be conducted by eye, or more usually, with the aid of readily available sequence comparison programs. These publicly and commercially available computer programs can calculate % homology between two or more sequences.

% homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A; Devereux et al., 1984, Nucleic Acids Research 12:387). Examples of other software than can perform sequence comparisons include, but are not limited to, the BLAST package (see Ausubel et al., 1999 *ibid*—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 *ibid*, pages 7-58 to 7-60). However it is preferred to use the GCG Bestfit program.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Advantageously, the BLAST algorithm is employed, with parameters set to default values. The BLAST algorithm is described in detail at http://www.ncbi.nih.gov/BLAST/blast_help.html, which is incorporated herein by reference. The search parameters are defined as follows, can be advantageously set to the defined default parameters.

Advantageously, "substantial identity" when assessed by BLAST equates to sequences which match with an EXPECT value of at least about 7, preferably at least about 9 and most preferably 10 or more. The default threshold for EXPECT in BLAST searching is usually 10.

BLAST (Basic Local Alignment Search Tool) is the heuristic search algorithm employed by the programs blastp, blastn, blastx, tblastn, and tblastx; these programs ascribe significance to their findings using the statistical methods of Karlin and Altschul (Karlin and Altschul 1990, *Proc. Natl. Acad. Sci. USA* 87:2264-68; Karlin and Altschul, 1993, *Proc. Natl. Acad. Sci. USA* 90:5873-7; see http://www.ncbi.nih.gov/BLAST/blast_help.html) with a few enhancements. The BLAST programs are tailored for sequence similarity searching, for example to identify homologues to a query sequence. For a discussion of basic issues in similarity searching of sequence databases, see Altschul et al (1994) Nature Genetics 6:119-129.

The five BLAST programs available at http://www.ncbi.nlm.nih.gov perform the following tasks: blastp—compares an amino acid query sequence against a protein sequence database; blastn—compares a nucleotide query sequence against a nucleotide sequence database; blastx—compares the six-frame conceptual translation products of a nucleotide query sequence (both strands) against a protein sequence database; tblastn—compares a protein query sequence against a nucleotide sequence database dynamically translated in all six reading frames (both strands); tblastx—compares the six-frame translations of a nucleotide query sequence against the six-frame translations of a nucleotide sequence database.

BLAST uses the following search parameters:

HISTOGRAM—Display a histogram of scores for each search; default is yes. (See parameter H in the BLAST Manual).

DESCRIPTIONS—Restricts the number of short descriptions of matching sequences reported to the number specified; default limit is 100 descriptions. (See parameter V in the manual page).

EXPECT—The statistical significance threshold for reporting matches against database sequences; the default value is 10, such that 10 matches are expected to be found merely by chance, according to the stochastic model of Karlin and Altschul (1990). If the statistical significance ascribed to a match is greater than the EXPECT threshold, the match will not be reported. Lower EXPECT thresholds are more stringent, leading to fewer chance matches being reported. Fractional values are acceptable. (See parameter E in the BLAST Manual).

CUTOFF—Cutoff score for reporting high-scoring segment pairs. The default value is calculated from the EXPECT value (see above). HSPs are reported for a database sequence only if the statistical significance ascribed to them is at least as high as would be ascribed to a lone HSP having a score equal to the CUTOFF value. Higher CUTOFF values are more stringent, leading to fewer chance matches being reported. (See parameter S in the BLAST Manual). Typically, significance thresholds can be more intuitively managed using EXPECT.

ALIGNMENTS—Restricts database sequences to the number specified for which high-scoring segment pairs (HSPs) are reported; the default limit is 50. If more database sequences than this happen to satisfy the statistical significance threshold for reporting (see EXPECT and CUTOFF below), only the matches ascribed the greatest statistical significance are reported. (See parameter B in the BLAST Manual).

MATRIX—Specify an alternate scoring matrix for BLASTP, BLASTX, TBLASTN and TBLASTX. The default matrix is BLOSUM62 (Henikoff & Henikoff, 1992). The valid alternative choices include: PAM40, PAM120, PAM250 and IDENTITY. No alternate scoring matrices are available for BLASTN; specifying the MATRIX directive in BLASTN requests returns an error response.

STRAND—Restrict a TBLASTN search to just the top or bottom strand of the database sequences; or restrict a BLASTN, BLASTX or TBLASTX search to just reading frames on the top or bottom strand of the query sequence.

FILTER—Mask off segments of the query sequence that have low compositional complexity, as determined by the SEG program of Wootton & Federhen (1993) Computers and Chemistry 17:149-163, or segments consisting of short-periodicity internal repeats, as determined by the XNU program of Clayerie & States (1993) Computers and Chemistry 17:191-201, or, for BLASTN, by the DUST program of Tatusov and Lipman (see http://www.ncbi.nlm.nih.gov). Filtering can eliminate statistically significant but biologically uninteresting reports from the blast output (e.g., hits against common acidic-, basic- or proline-rich regions), leaving the more biologically interesting regions of the query sequence available for specific matching against database sequences.

Filtering is only applied to the query sequence (or its translation products), not to database sequences. Default filtering is DUST for BLASTN, SEG for other programs.

It is not unusual for nothing at all to be masked by SEG, XNU, or both, when applied to sequences in SWISS-PROT, so filtering should not be expected to always yield an effect. Furthermore, in some cases, sequences are masked in their entirety, indicating that the statistical significance of any matches reported against the unfiltered query sequence should be suspect.

NCBI-gi—Causes NCBI gi identifiers to be shown in the output, in addition to the accession and/or locus name.

Most preferably, sequence comparisons are conducted using the simple BLAST search algorithm provided at http:// www.ncbi.nlm.nih.gov/BLAST. In some embodiments, no gap penalties are used when determining sequence identity.

Once the software has produced an optimal alignment, it is possible to calculate % homology, preferably % sequence identity. The software typically does this as part of the sequence comparison and generates a numerical result.

Variants and Derivatives

The terms "variant" or "derivative" in relation to the amino acid sequences disclosed here includes any substitution of, variation of, modification of, replacement of, deletion of or addition of one (or more) amino acids from or to the sequence providing the resultant amino acid sequence retains substantially the same activity as the unmodified sequence. Preferably, the modified sequence has at least one biological activity as the unmodified sequence, preferably all the biological activities of the unmodified sequence. Preferably, the "variant" or "derivative" has at least one biological activity of native Fve, as described above.

Polypeptides having the amino acid sequence shown in the description and Examples, or fragments or homologues thereof may be modified for use in the methods and compositions described here. Typically, modifications are made that maintain the biological activity of the sequence. Amino acid substitutions may be made, for example from 1, 2 or 3 to 10, 20 or 30 substitutions provided that the modified sequence retains the biological activity of the unmodified sequence. Alternatively, modifications may be made to deliberately inactivate one or more functional domains of the polypeptides described here. Functional domains of native Fve include the α helix at the N terminus, any of the six β helices, as well as the "loop-like" structures at the N and C termini. Preferably, the functional domain of native Fve comprises the N-terminus helix and the loop/strand, which are essential for protein dimerization.

Amino acid substitutions may include the use of non-naturally occurring analogues, for example to increase blood plasma half-life of a therapeutically administered polypeptide.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Polypeptides also include fragments of the full length sequence of native Fve, or any of the Fve polypeptides disclosed here. Preferably fragments comprise at least one epitope. Methods of identifying epitopes are well known in the art. Fragments will typically comprise at least 6 amino acids, more preferably at least 10, 20, 30, 50 or 100 amino acids.

Fve polypeptides, fragments, homologues, variants and derivatives, are typically made by recombinant means, for example as described below in the Examples. However they may also be made by synthetic means using techniques well known to skilled persons such as solid phase synthesis. The proteins may also be produced as fusion proteins, for example to aid in extraction and purification. Examples of fusion protein partners include glutathione-S-transferase (GST), 6×His (SEQ ID NO: 488), GAL4 (DNA binding and/or transcriptional activation domains) and β-galactosidase. It may also be convenient to include a proteolytic cleavage site between the fusion protein partner and the protein sequence of interest to allow removal of fusion protein sequences. Preferably the fusion protein will not hinder the function of the protein of interest sequence. Proteins may also be obtained by purification of cell extracts from animal cells.

The Fve polypeptides, variants, homologues, fragments and derivatives disclosed here may be in a substantially isolated form. It will be understood that such polypeptides may be mixed with carriers or diluents which will not interfere with the intended purpose of the protein and still be regarded as substantially isolated. A Fve variant, homologue, fragment or derivative may also be in a substantially purified form, in which case it will generally comprise the protein in a preparation in which more than 90%, e.g. 95%, 98% or 99% of the protein in the preparation is a protein.

The Fve polypeptides, variants, homologues, fragments and derivatives disclosed here may be labelled with a revealing label. The revealing label may be any suitable label which allows the polypeptide, etc to be detected. Suitable labels include radioisotopes, e.g. $^{125}$I, enzymes, antibodies, polynucleotides and linkers such as biotin. Labelled polypeptides may be used in diagnostic procedures such as immunoassays to determine the amount of a polypeptide in a sample. Polypeptides or labelled polypeptides may also be used in serological or cell-mediated immune assays for the detection of immune reactivity to said polypeptides in animals and humans using standard protocols.

A Fve polypeptide, variant, homologue, fragment or derivative disclosed here, optionally labelled, my also be fixed to a solid phase, for example the surface of an immunoassay well or dipstick. Such labelled and/or immobilised polypeptides may be packaged into kits in a suitable container along with suitable reagents, controls, instructions and the like. Such polypeptides and kits may be used in methods of detection of antibodies to the polypeptides or their allelic or species variants by immunoassay.

Immunoassay methods are well known in the art and will generally comprise: (a) providing a polypeptide comprising an epitope bindable by an antibody against said protein; (b) incubating a biological sample with said polypeptide under conditions which allow for the formation of an antibody-antigen complex; and (c) determining whether antibody-antigen complex comprising said polypeptide is formed.

The Fve polypeptides, variants, homologues, fragments and derivatives disclosed here may be used in in vitro or in vivo cell culture systems to study the role of their corresponding genes and homologues thereof in cell function, including their function in disease. For example, truncated or modified polypeptides may be introduced into a cell to disrupt the normal functions which occur in the cell. The polypeptides may be introduced into the cell by in situ expression of the polypeptide from a recombinant expression vector (see below). The expression vector optionally carries an inducible promoter to control the expression of the polypeptide.

The use of appropriate host cells, such as insect cells or mammalian cells, is expected to provide for such post-translational modifications (e.g. myristolation, glycosylation, truncation, lapidation and tyrosine, serine or threonine phosphorylation) as may be needed to confer optimal biological activity on recombinant expression products. Such cell culture systems in which the Fve polypeptides, variants, homologues, fragments and derivatives disclosed here are expressed may be used in assay systems to identify candidate substances which interfere with or enhance the functions of the polypeptides in the cell.

Immunomodulator-Antigen Combinations and Conjugates

We show throughout this document (for the first time) that Fve has immunomodulatory properties, and in particular can act to potentiate an immune response. The adjuvant property of Fve may be exploited by administering Fve polypeptide or nucleic acid (or a fragment, homologue, variant or derivative thereof, or a host cell or vector comprising such) as described below, along with a molecule to which an immune response is desired.

The Fve polypeptide, etc may be administered to an individual either in combination, sequentially or simultaneously or in succession with the molecule to which an immune response is desired. We therefore provide for the first time a combination of a Fve polypeptide, etc with an antigenic molecule.

Where the Fve polypeptide, etc and the molecule are administered in combination, this may be achieved by administering a mixture of the Fve polypeptide, etc and the molecule. We therefore provide a simple combination of the Fve polypeptide, etc and the molecule, preferably as a kit. The kit may comprise the Fve polypeptide, etc and the molecule to which an immune response is desired in separate containers, and may optionally comprise instructions to administer these simultaneously, sequentially, etc.

The molecule to which an immune response is desired may comprise an allergen. These are set out in further detail in the following section.

The molecule to which an immune response is desired may comprise a tumour associated antigen. In preferred embodiments, the tumour associated antigen comprises MAGE-1, MAGE-2, MAGE-3, BAGE, GAGE, PRAME, SSX-2, Tyrosinase, MART-1, NY-ESO-1, gp100, TRP-1, TRP-2, A2 melanotope, BCR/ABL, Proteinase-3/Myeloblastin, HER2/neu, CEA, P1A, HK2, PAPA, PSA, PSCA, PSMA, pg75, MUM-1, MUC-1, BTA, GnT-V, β-catenin, CDK4, or P15. Nucleic acid and amino acid sequences of these antigens are known in the art, and the skilled person will know how to produce tumour associated antigens, including those set out above. We therefore disclose combinations, preferably in the form of kits, comprising an Fve polypeptide or nucleic acid (or a fragment, homologue, variant or derivative thereof, or a host cell or vector comprising such), together with a tumour associated antigen, for example as set out above.

The molecule to which an immune response is desired may comprise a viral antigen. In preferred embodiments, the viral antigen comprises a protein from an oncogenic virus; such viruses are known in the art. Preferably the oncogenic viral antigen comprises E6 and E7 from HPV; core Ag and E2 from HCV; core and surface antigens from HBV; LMP-1, LMP-2, EBNA-2, EBNA-3 from EBV; or Tax from HTLV-1.

In a further embodiment, the viral antigen comprises an antigen, preferably a protein, more preferably an antigenic protein or fragment thereof from an infectious virus. Such immunomodulator-viral antigen conjugates may be used to treat or prevent a viral infectious disease, i.e., the cognate disease. For example, an immunomodulator-HSV antigen conjugate, for example, a Fve polypeptide-HSV antigen conjugate, may be used to treat or prevent Herpes Simplex Virus infection. Other preferred viral antigens include those from Adenovirus, Parainfluenza 3 virus, Human Immunodeficiency Virus (HIV), Herpes simplex virus, HSV, Respiratory syncytial virus, RSV, and Influenza A, Flu A. These viruses, and the diseases they cause, are well known in the art, and methods for making and purifying antigens from such viruses are also well known. For example, U.S. Pat. No. 4,313,927 (Fridlender) discloses detailed protocols for preparation of rubella and Cytomegalovirus (CMV) antigen.

Nucleic acid and amino acid sequences of these viral antigens are known in the art, and the skilled person will know how to produce viral antigen antigens, including these set out above. We therefore disclose combinations, preferably in the form of kits, comprising an Fve polypeptide or nucleic acid (or a fragment, homologue, variant or derivative thereof, or a host cell or vector comprising such), together with a viral antigen, for example as set out above.

In preferred embodiments, we provide administration of the Fve polypeptide, etc and the molecule to which an immune response is desired, in which there is some degree of association between the Fve polypeptide, etc and the molecule in question.

We therefore disclose for the first time an an agent which comprises an immunomodulator coupled, fused, mixed, combined, or otherwise joined to an allergen. Such a construct is referred to as a "immunomodulator-allergen conjugate" in this document. In particular, we disclose the use of Fve adjuvanted allergen vaccines, as explained in further detail in Examples 13 and 14.

The coupling, etc between the immunomodulator and the allergen may be permanent or transient, and may involve covalent or non-covalent interactions (including ionic interactions, hydrophobic forces, Van der Waals interactions, etc). The exact mode of coupling is not important, so long as the immunomodulator-allergen conjugate. Accordingly, where reference is made to "comprising", "conjugation", "coupling", etc, these references should be taken to include any form of interaction between the immunomodulator and the allergen.

Thus, the immunodulator may be a polypeptide which is provided as a fusion protein with the allergen, for example as shown in Example 13 for Fve/Allergen. An expression vector may be constructed by standard recombinant DNA technology to include a nucleotide sequence capable of expressing a immunodulator, such that a fusion protein is expressed comprising the allergen of interest fused to the immunodulator. The expression vector is transfected or transformed into a suitable host for large scale production of fusion protein, by means known in the art. Purification of the fusion protein may also be carried out by known means. Alternatively, or in addition, and as discussed above, the allergen may be physically associated with the immunomodulator, and attached to it by chemical conjugation. Thus, Example 14 below describes the use of allergen physically conjugated to Fve.

In preferred embodiments, the immunomodulator-allergen conjugate is capable of at least one of the following, preferably two or more, more preferably all: increase the number of human PBMC, to stimulate the proliferation of human lymphocytes, to polarize human $CD8^+$ T cells, and to increase the production of IFN-γ (Th1 response) and IL-10 (Tr response). Preferably, the immunomodulator-allergen conjugate is capable of inducing both Th1 and Tr immune responses. Preferably, the Th1 response inhibits the development of Th2 cells via IFN-γ, more preferably it is capable of inducing a life-long (or substantially long lasting) protective Th1 memory immune response. Allergen specific Tr cells may in turn dampen the anti-allergic Th1 immune response, ensuring a well-balanced protective but nonpathological Th1 response. Allergen-Fve fusion proteins meet these criteria since they induce cytokine IL-10, and these are therefore preferred.

Where the conjugate comprises Fve, the Fve portion of the conjugate may comprise the whole molecule, or fragments of it. It may for example comprise the native Fve, or any Fve polypeptide as disclosed above. The allergen portion may comprise any allergen, whether proteinaceous or not. Advantageously, proteinaceous allergens are conjugated to the immunomodulator portion by means of covalent bonds, for example, amide bonds (for example, as a fusion protein).

The allergen may comprise for example the whole or a portion of Blo t 5 or Der p 2 allergen. In highly preferred embodiments, the immunomodulator-allergen conjugate comprises Bt5-Fve, Bt5-FveR27 or GST-Dp2-FveR27. Examples of other allergens suitable for use in the immunomodulator-allergen conjugate described here are provided below.

Furthermore, protein-protein conjugation also provides a convenient and alternative choice to develop allergen vaccine. Any suitable means of conjugation, for example, chemical conjugation may be used to couple the immunomodulator and the allergen. Cross-linkers, for example, heterobifunctional cross linkers are known in the art, and may be used. Furthermore, other conjugation agents, for example, poly-lactic acid (PLA) and polyethylene glycol (PEG) may also be employed.

Allergens

In general, the allergen from which an immunomodulator-allergen conjugate may be constructed may come from any source, for example, a source known to induce allergenic responses in humans. For example, the allergen may comprise a tree pollen allergen, a grass pollen allergen, a weed pollen allergen, a feline antigen, or a fungal allergen. Thus, the allergen may comprise a tree pollen allergen, for example Bet v 1 and Bet v 2 from birch tree. It may comprise a grass pollen allergen, for example, Phl p 1 and Phl p 2 from timothy grass. It may comprise a weed pollen allergen, for example, antigen E from ragweed. It may comprise a major feline antigen, for example, Fel d 1. It may comprise a major fungal allergen, for example, Asp f1, Asp f2, and Asp f3 from *Aspergillus fumigatus*.

In preferred embodiments, the allergen comprises a dust mite allergen, preferably a house dust mite allergen. In particular, the allergen is preferably derived from a mite from Family Glycyphagidae or Family Pyroglyphidae. Dust mites of Family Glycyphagidae include those in the genera *Aeroglyphus, Austroglycyphagus, Blomia, Ctenoglyphus, Glycyphagus, Gohieria, Lepidoglyphus*. Dust mites of Family Pyroglyphidae include those in the genera *Dermatophagoides, Euroglyphus, Pyroglyphus*. In preferred embodiments, the allergen is preferably an allergen from a species in any of these genera.

In highly preferred embodiments, the allergen is a group 1 allergen (Der p 1, Der f 1, Blo t 1, Eur ml, Lep d 1), a group 2 allergen (Der p 2, Der f 2, Blo t 2, Eur m 2, Lep d 2), a group 5 allergen (Blo t 5, Der p 5, Der f 5, Eur m 5, Lep d 5) or a group 15 allergen (Der p 15, Der f 15, Blot 15, Eur m 15, Lep d 15) from dust mite. Nucleic acid and amino acid sequences of these allergens are known in the art, and the skilled person will know how to produce allergen-immunomodulator conjugates from any of these allergens using such sequences.

Other Immunomodulator Conjugates

Immunomodulator-Tumour Associated Antigen Conjugates

We also disclose for the first time an an agent which comprises an immunomodulator coupled, fused, mixed, combined, or otherwise joined to an tumour associated antigen. Such a construct is referred to as a "immunomodulator-tumour associated antigen conjugate" in this document.

As the term is used here, "tumour associated antigen" generally includes a cancer protein or a cancer antigen, i.e., a protein which is preferentially expressed in a tumour cell or a transformed cell, compared to a "normal" non-cancerous cell.

In highly preferred embodiments, the tumour associated antigen may comprise MAGE-1, MAGE-2, MAGE-3, BAGE, GAGE, PRAME, SSX-2, Tyrosinase, MART-1, NY-ESO-1, gp100, TRP-1, TRP-2, A2 melanotope, BCR/ABL, Proteinase-3/Myeloblastin, HER2/neu, CEA, P1A, HK2, PAPA, PSA, PSCA, PSMA, pg75, MUM-1, MUC-1, BTA, GnT-V, β-catenin, CDK4, or P15. Nucleic acid and amino acid sequences of these antigens are known in the art, and the skilled person will know how to produce tumour associated antigen-immunomodulator conjugates from any of these allergens using such sequences.

We present in Appendix A the sequences of MAGE3-FveT29A, MART1-FveT29A and CEA-FveT29A, which are preferred Immunomodulator-Tumour Associated Antigen Conjugates suitable for use in the methods and compositions described here.

Immunomodulator-Viral Antigen Conjugates

We further disclose an agent comprising an immunodulator coupled, etc to a viral antigen. In highly preferred embodiments, the viral antigen comprises a protein from an oncogenic virus; such viruses are known in the art. Preferably the oncogenic viral antigen comprises E6 and E7 from HPV; core Ag and E2 from HCV; core and surface antigens from HBV; LMP-1, LMP-2, EBNA-2, EBNA-3 from EBV; or Tax from HTLV-1. Nucleic acid and amino acid sequences of these viral antigens are known in the art, and the skilled person will know how to produce viral antigen-immunomodulator conjugates from any of these allergens using such sequences.

We also provide an agent (for example a polypeptide) comprising a first portion comprising at least a portion of Fve and a second portion comprising at least a portion of a viral antigen, preferably coupled together. The viral antigen may be selected from the group consisting of antigens from Adenovirus, Parainfluenza 3 virus, Herpes simplex virus, HSV, Respiratory syncytial virus, RSV, and Influenza A, Flu A.

The viral antigen may comprise any portion of the native viral antigen, for example, a portion of the HCV core antigen. We have established that a deletion of the HCV core antigen, particularly a deletion of 23 amino acids from residues 141 to 163 of the core antigen leads to an increase in efficiency of protein production. Accordingly, we provide an agent comprising an immunodulator coupled, etc to a viral antigen, which viral antigen comprises such a deleted core antigen (here referred to as "Core23"), e.g., the fusion protein HCV Core23-FveT29A.

In particular, we find that the polypeptides HCV Core23-FveT29A and HPV E7-FveT29A (the sequences of which are shown in Appendix A) are particularly useful as Immunomodulator-Viral Antigen conjugates.

The coupling, etc between the immunomodulator and the tumour associated antigen, and the viral antigen, may be as described above for the immunomodulator-allergen conjugate.

Fve Nucleic Acids

We provide for a nucleic acid encoding a Fve polypeptide, which we refer to as a "Fve nucleic acid". We also provide nucleic acids encoding variants, homologues, derivatives and fragments of native Fve, as well as fragments, homologues, derivatives and variants of Fve nucleic acids.

Preferably, the Fve nucleic acid is derived from a natural or native Fve sequence, for example, the nucleic sequence shown as "Fve (Wild type)" in Appendix A. In a preferred embodiment, the Fve nucleic acid is a recombinant fragment of native Fve nucleic acid, or any fragment, homologue, variant or derivative thereof. Fragments, homologues, variants and derivatives of each of the above sequences are also included.

"Fve nucleic acids" preferably encode polypeptides which have at least one biological activity of native Fve, as described above. Preferably, Fve nucleic acids encode polypeptides which comprise two or more biological activities of native Fve, preferably substantially all the biological activities of native Fve.

In preferred embodiments, the Fve nucleic acids encode polypeptides which comprise at least one, two or all three of the RGT residues (or a functional variant as defined above, such as RGD) at or about a position corresponding to position 28 of the native Fve polypeptide. In particular, the Fve nucleic acid may comprise the sequence CGTGGTACC. Alternatively, the Fve nucleic acid may comprise the sequence CGTGGTGAT or the sequence CGTGGTGAC. The Fve nucleic acid may comprise a nucleotide sequence which encodes the same amino acids as a result of the redundancy of the genetic code.

The Fve nucleic acid may comprise a sequence comprising three codons, with a first codon selected from the group consisting of: CGT, CGC, CGA, CGG, AGA and AGG, a second codon selected from the group consisting of: GGT, GGC, GGA and GGG, and a third codon selected from the group consisting of: ACT, ACC, ACA and ACG. Alternatively, the third codon may be selected from the group consisting of: GAT and GAC, Preferably, the Fve polypeptide comprises between 2 to 60 residues of nucleic acid sequence flanking the codon for the glycine residue corresponding to position 28 of native Fve.

In preferred embodiments, Fve nucleic acids may comprise nucleic acids encoding fragments of native Fve. For example, Fve nucleic acids may comprise the nucleic acid sequences depicted in Appendix A as Fve D6-18, Fve D19-33, Fve D34-46, Fve D47-60, Fve D61-72, Fve D73-84, Fve D85-97, Fve D98-106, Fve D107-115, Fve D61-97, and Fvep55-100. Nucleic acids encoding fusion proteins comprising these deletion fragments and GST are also disclosed. Fve nucleic acids may comprise those encoding substitutions, including FveR27A, FveG28A and FveT29A. Fve nucleic acids include those which encode the polypeptide sequences shown in Appendix A.

We also disclose Fve nucleic acids which encode Fve polypeptides comprising fusion proteins, particularly fusion proteins between an allergen and a Fve polypeptide as defined here. We disclose in particular nucleic acid sequences of Blo t 5-Fve (two-in-one chimeric wild type), Blo t 5-FveR27A (two-in-one chimeric mutant), Blo t 5-FveT29A (two-in-one chimeric mutant), Der p 2-FveR27A (two-in-one chimeric mutant), Der p 2-FveT29A (two-in-one chimeric mutant) and Blo t 5-Der p 2-FveR27A (three-in-one chimeric mutant), and shown in Appendix A.

As used here in this document, the terms "polynucleotide", "nucleotide", and nucleic acid are intended to be synonymous with each other. "Polynucleotide" generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Fve nucleic acids, variants, fragments, derivatives and homologues may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of this document, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence. Preferably said variant, homologues or derivatives code for a polypeptide having biological activity.

As indicated above, with respect to sequence homology, preferably there is at least 50 or 75%, more preferably at least 85%, more preferably at least 90% homology to the sequences shown in the sequence listing herein. More preferably there is at least 95%, more preferably at least 98%, homology. Nucleotide homology comparisons may be conducted as described above. A preferred sequence comparison program is the GCG Wisconsin Bestfit program described above. The default scoring matrix has a match value of 10 for each identical nucleotide and −9 for each mismatch. The default gap creation penalty is −50 and the default gap extension penalty is −3 for each nucleotide.

We further describe nucleotide sequences that are capable of hybridising selectively to the sequences presented herein, or any variant, fragment or derivative thereof, or to the complement of any of the above. Nucleotide sequences are preferably at least 15 nucleotides in length, more preferably at least 20, 30, 40 or 50 nucleotides in length.

The term "hybridization" as used herein shall include "the process by which a strand of nucleic acid joins with a complementary strand through base pairing" as well as the process of amplification as carried out in polymerase chain reaction technologies.

Polynucleotides capable of selectively hybridising to the nucleotide sequences presented herein, or to their complement, will be generally at least 70%, preferably at least 80 or 90% and more preferably at least 95% or 98% homologous to the corresponding nucleotide sequences presented herein over a region of at least 20, preferably at least 25 or 30, for instance at least 40, 60 or 100 or more contiguous nucleotides.

The term "selectively hybridizable" means that the polynucleotide used as a probe is used under conditions where a target polynucleotide is found to hybridize to the probe at a level significantly above background. The background hybridization may occur because of other polynucleotides present, for example, in the cDNA or genomic DNA library being screening. In this event, background implies a level of signal generated by interaction between the probe and a non-specific DNA member of the library which is less than 10 fold, preferably less than 100 fold as intense as the specific interaction observed with the target DNA. The intensity of interaction may be measured, for example, by radiolabelling the probe, e.g. with $^{32}P$.

Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences.

In a preferred aspect, we provide nucleotide sequences that can hybridise to the Fve nucleic acids, fragments, variants, homologues or derivatives disclosed here under stringent conditions (e.g. 65° C. and 0.1×SSC {1×SSC=0.15 M NaCl, 0.015 M $Na_3$ Citrate pH 7.0).

Where the polynucleotide is double-stranded, both strands of the duplex, either individually or in combination, are encompassed by the methods and compositions described here. Where the polynucleotide is single-stranded, it is to be understood that the complementary sequence of that polynucleotide is also included.

Polynucleotides which are not 100% homologous to the Fve sequences disclosed here but which are also included can be obtained in a number of ways. Other variants of the sequences may be obtained for example by probing DNA libraries made from a range of individuals, for example individuals from different populations. For example, Fve homologues may be identified from other individuals, or other species. Further recombinant Fve nucleic acids and polypeptides may be produced by identifying corresponding positions in the homologues, and synthesising or producing the molecule as described elsewhere in this document. Furthermore, the collagen region, neck region and carbohydrate binding domain in such homologues may be identified, for example, by sequence gazing or computer assisted comparisons, and selected for combination into or production of a recombinant Fve which has one or more biological activities of native Fve.

In addition, other viral/bacterial, or cellular homologues of Fve particularly cellular homologues found in mammalian cells (e.g. rat, mouse, bovine and primate cells), may be obtained and such homologues and fragments thereof in general will be capable of selectively hybridising to Fve. Such homologues may be used to design non-human Fve nucleic acids, fragments, variants and homologues. Mutagenesis may be carried out by means known in the art to produce further variety.

Sequences of Fve homologues may be obtained by probing cDNA libraries made from or genomic DNA libraries from other animal or non-animal species, particularly microbial or fungal species, and probing such libraries with probes comprising all or part of any of the Fve nucleic acids, fragments, variants and homologues, or other fragments of Fve under conditions of medium to high stringency.

Similar considerations apply to obtaining species homologues and allelic variants of the polypeptide or nucleotide sequences disclosed here.

Variants and strain/species homologues may also be obtained using degenerate PCR which will use primers designed to target sequences within the variants and homologues encoding conserved amino acid sequences within the sequences of the Fve nucleic acids. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences. It will be appreciated by the skilled person that overall nucleotide homology between sequences from distantly related organisms is likely to be very low and thus in these situations degenerate PCR may be the method of choice rather than screening libraries with labelled fragments the Fve sequences.

In addition, homologous sequences may be identified by searching nucleotide and/or protein databases using search algorithms such as the BLAST suite of programs.

Alternatively, such polynucleotides may be obtained by site directed mutagenesis of characterised sequences, for example, Fve nucleic acids, or variants, homologues, derivatives or fragments thereof. This may be useful where for example silent codon changes are required to sequences to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

The polynucleotides described here may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 8, 9, 10, or 15, preferably at least 20, for example at least 25, 30 or 40 nucleotides in length, and are also encompassed by the term "polynucleotides" as used herein.

Polynucleotides such as a DNA polynucleotides and probes may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15 to 30 nucleotides) flanking a region of the lipid targeting sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector Polynucleotides or primers may carry a revealing label. Suitable labels include radioisotopes such as $^{32}$P or $^{35}$S, enzyme labels, or other protein labels such as biotin. Such labels may be added to polynucleotides or primers and may be detected using by techniques known per se. Polynucleotides or primers or fragments thereof labelled or unlabeled may be used by a person skilled in the art in nucleic acid-based tests for detecting or sequencing polynucleotides in the human or animal body.

Such tests for detecting generally comprise bringing a biological sample containing DNA or RNA into contact with a probe comprising a polynucleotide or primer under hybridising conditions and detecting any duplex formed between the probe and nucleic acid in the sample. Such detection may be achieved using techniques such as PCR or by immobilising the probe on a solid support, removing nucleic acid in the sample which is not hybridised to the probe, and then detecting nucleic acid which has hybridised to the probe. Alternatively, the sample nucleic acid may be immobilised on a solid support, and the amount of probe bound to such a support can be detected. Suitable assay methods of this and other formats can be found in for example WO89/03891 and WO90/13667.

Tests for sequencing nucleotides, for example, the Fve nucleic acids, involve bringing a biological sample containing target DNA or RNA into contact with a probe comprising a polynucleotide or primer under hybridising conditions and determining the sequence by, for example the Sanger dideoxy chain termination method (see Sambrook et al.).

Such a method generally comprises elongating, in the presence of suitable reagents, the primer by synthesis of a strand complementary to the target DNA or RNA and selectively terminating the elongation reaction at one or more of an A, C, G or T/U residue; allowing strand elongation and termination reaction to occur; separating out according to size the elongated products to determine the sequence of the nucleotides at which selective termination has occurred. Suitable reagents include a DNA polymerase enzyme, the deoxynucleotides dATP, dCTP, dGTP and dTTP, a buffer and ATP. Dideoxynucleotides are used for selective termination.

Protein Expression and Purification

Host cells comprising polynucleotides may be used to express polypeptides, such as Fve polypeptides, fragments, homologues, variants or derivatives thereof. Host cells may be cultured under suitable conditions which allow expression of the proteins. Expression of the polypeptides may be constitutive such that they are continually produced, or inducible, requiring a stimulus to initiate expression. In the case of inducible expression, protein production can be initiated when required by, for example, addition of an inducer substance to the culture medium, for example dexamethasone or IPTG.

Polypeptides can be extracted from host cells by a variety of techniques known in the art, including enzymatic, chemical and/or osmotic lysis and physical disruption.

Polypeptides may also be produced recombinantly in an in vitro cell-free system, such as the Tnt™ (Promega) rabbit reticulocyte system.

Fve Nucleic Acid Molecules

We disclose a nucleic molecule that: a) has a strand that encodes an Fve polypeptide disclosed here, b) has a strand that is complementary with a strand as described in a) above; or c) has a strand that hybridises with a molecule as described in a) or b) above.

Unless the context indicates otherwise, such nucleic acid molecules, which are included within the term "Fve nucleic acid molecule" may have one or more of the following characteristics:

1) They may be DNA or RNA (including variants of naturally occurring DNA or RNA structures, which have non-naturally occurring bases and/or non-naturally occurring backbones).

2) They may be single-stranded or double-stranded (or in some cases higher stranded, e.g. triple-stranded).

3) They may be provided in recombinant form i.e. covalently linked to a heterologous 5' and/or 3' flanking sequence to provide a chimeric molecule (e.g. a vector) that does not occur in nature.

4) They may be provided with or without 5' and/or 3' flanking sequences that normally occur in nature.

5) They may be provided in substantially pure form, e.g. by using probes to isolate cloned molecules having a desired target sequence or by using chemical synthesis techniques. Thus they may be provided in a form that is substantially free from contaminating proteins and/or from other nucleic acids.

6) They may be provided with introns (e.g. as a full-length gene) or without introns (e.g. as DNA).

7) They may be provided in linear or non-linear (e.g. circular) form.

These Fve molecules include not only molecules with classical DNA or RNA structures, but also variants with modified (non-phosphodiester) backbones—e.g. morpholino derivatives and peptide nucleic acids (PNAs), which contain an N-(2-aminoethyl)glycine-based pseudopeptide backbone. (See Nielsen, P. E., Annual Review of Biophysics & Biomolecular Structure, 24:167-83 (1995)). Nucleic acid variants with modified backbones can have increased stability relative to unmodified nucleic acids and are particularly useful where hybridisation is desired over a relatively long period (e.g. in antisense therapy).

Nucleic acid molecules and uses thereof are discussed in further detail below:

a) Coding Nucleic Acid Molecules

The Fve polypeptides can be coded for by a large variety of nucleic acid molecules, taking into account the well-known degeneracy of the genetic code. All of these coding nucleic acid molecules are within the scope of the present document.

The Fve nucleic acids may be administered to an individual and used to express polypeptides disclosed here. Thus, they may be used for the same treatments as the Fve polypeptides.

The Fve nucleic acid molecules may be provided in the form of vectors, although this is not essential. Preferred vectors for use in treatment include replication-deficient adenoviruses, retroviruses and adeno-associated viruses.

Fve nucleic acid molecules may be administered to a patient by physical methods. These methods include topical application of the nucleic acid in an appropriate vehicle, for example in solution in a pharmaceutically acceptable excipient, such as phosphate buffered saline (PBS). They also include particle bombardment (which is sometimes known as "gene gun" technology and is described in U.S. Pat. No. 5,371,015). Here inert particles, such as gold beads coated with a nucleic acid, can be accelerated at speeds sufficient to enable them to penetrate cells. They can be used for example to penetrate the skin of a patient and may be administered by means of discharge under high pressure from a projecting device. Other physical methods of administering the Fve nucleic acid directly to a recipient include ultrasound, electrical stimulation (including iontophoresis) and microseeding (see e.g. U.S. Pat. No. 5,697,901). Alternatively, the Fve nucleic acid molecules may simply be injected at appropriate site (e.g. muscle). They may be incorporated in or on a carrier (which may be a lipid-based carrier, such as a liposome).

Fve nucleic acid molecules may be introduced into host cells (optionally in the form of vectors) to enable the expression of polypeptides. Alternatively, cell-free expression systems may be used. By using an appropriate expression system the Fve polypeptides can be produced in a desired form. For example, the Fve polypeptides can be produced by microorganisms such as bacteria or yeast, by cultured insect cells (which may be baculovirus-infected), by mammalian cells (such as CHO cells) or by transgenic animals that, for instance, secrete the Fve proteins in milk (see e.g. international patent application WO88/00239). Where glycosylation is desired, eukaryotic (e.g. mammalian or insect) expression systems are preferred.

Whatever means is used to obtain expression, transcriptional and translational control sequences will normally be present and will be operatively linked to a sequence encoding a polypeptide to be expressed. These control sequences may be heterologous to the sequence encoding the Fve polypeptide or may be found associated with it in vivo. Promoter, operator and/or enhancer sequences may, for example, be provided, as may polyadenylation sites, splice sites, stop and start codons, upstream and downstream regulatory regions, etc. If desired, a constitutive promoter may be provided. Alternatively, a regulatable promoter may be provided to enable transcription to be controlled by administration of a regulator. The promoter (if present) may be tissue-specific or non tissue-specific.

Polypeptides comprising N-terminal methionine may be produced using certain expression systems, whilst in others the mature polypeptide may lack this residue. Fve polypeptides may initially be expressed so as to include signal sequences. Different signal sequences may be provided for different expression systems. Alternatively, signal sequences may be absent, if not needed.

Once expressed, Fve polypeptides may be purified by a wide variety of techniques. Purification techniques may be used under reducing conditions (in order prevent disulphide bond formation) or non-reducing conditions. Available purification techniques include, for example, electrophoretic techniques, such as SDS PAGE (see e.g. Hunkapiller et al, *Methods Enzymol.* 91:227 (1983), which discloses "Isolation of microgram quantities of proteins from polyacrylamide gels for amino acid sequence analysis."); affinity techniques (e.g. immunoaffinity chromatography); HPLC; gel filtration; ion-exchange chromatography; isoelectric focussing; etc. If desired, combinations of different purification steps may be used and/or individual purification steps may be repeated.

In summary, techniques for cloning, expressing and purifying polypeptides are well known to the skilled person. Various such techniques are disclosed in standard text-books, such as in Sambrook et al [*Molecular Cloning* 2nd Edition, Cold Spring Harbor Laboratory Press (1989)]; in Old & Primrose [*Principles of Gene Manipulation* 5th Edition, Blackwell Scientific Publications (1994)]; and in Stryer [*Biochemistry* 4th Edition, W H Freeman and Company (1995)].

b) Complementary Nucleic Acid Molecules

We also describe nucleic acid strands complementary thereto, whether or not the coding and complementary strands are associated in a duplex. Thus, for example, mRNA and cDNA molecules are included.

c) Hybridising Nucleic Acid Molecules

Nucleic acid molecules that can hybridise to one or more of the Fve nucleic acid molecules discussed above are also disclosed. Such nucleic acid molecules are referred to herein as "hybridising" nucleic acid molecules. Desirably hybridising molecules are at least 10 nucleotides in length and preferably are at least 20, at least 50, at least 100, or at least 200 nucleotides in length.

A hybridising nucleic acid molecule may have a high degree of sequence identity along its length with a nucleic acid molecule within the scope of b) or a) above (e.g. at least 50%, at least 75% or at least 90% sequence identity), although this is not essential. The greater the degree of sequence identity that a given single stranded nucleic acid molecule has with a strand of a nucleic acid molecule, the greater the likelihood that it will hybridise to the complement of said strand.

Most preferably, hybridising nucleic acid molecules hybridise to either DNA strand of a Fve nucleic acid, for example a sequence shown in Appendix A, or to an RNA equivalent thereof, or to a strand that is complementary to either of the aforesaid strands.

Hybridising nucleic acid molecules can be useful as probes or primers, for example.

Probes can be used to purify and/or to identify Fve nucleic acids. They may be used in diagnosis. For example, probes may be used to determine whether or not an organism such as a fungus has a wild-type gene encoding a Fve polypeptide described here, or whether or not one or more deletions, insertions and/or replacements of bases relative to the wild-type sequence are present. It may therefore be used to identify organisms that do not express Fve polypeptides or that express Fve polypeptides having reduced activity (including inactive polypeptides).

Primers are useful in synthesising nucleic acids or parts thereof based upon a template to which a probe hybridises. They can be used in techniques such as PCR to provide large numbers of nucleic acid molecules.

Hybridising molecules also include antisense strands. These hybridise with "sense" strands so as to inhibit transcription and/or translation. An antisense strand can be synthesised based upon knowledge of a sense strand and base pairing rules. It may be exactly complementary with a sense strand, although it should be noted that exact complementarity is not always essential. It may also be produced by genetic engineering, whereby a part of a DNA molecule is provided in an antisense orientation relative to a promoter and is then used to transcribe RNA molecules. Large numbers of antisense molecules can be provided (e.g. by cloning, by transcription, by PCR, by reverse PCR, etc.

Hybridising molecules include ribozymes. Ribozymes can also be used to regulate expression by binding to and cleaving RNA molecules that include particular target sequences recognised by the ribozymes. Ribozymes can be regarded as special types of antisense molecule. They are discussed, for example, by Haselhoff and Gerlach (Nature (1988) 334:585-91).

Antisense molecules may be DNA or RNA molecules. They may be used in antisense therapy to prevent or reduce undesired expression or activity. Antisense molecules may be administered directly to a patient (e.g. by injection). Alternatively, they may be synthesised in situ via a vector that has been administered to a patient.

In addition to the uses described above, the Fve nucleic acid molecules disclosed here (of whatever nature) may be used in screening. Screening can be done to identify moieties that bind to said nucleic acid molecules (e.g. to identify hybridising molecules). It can also be done to identify moieties that affect transcription or translation from said nucleic acid molecules.

It can be used to analyse expression, including analysing expression levels or expression patterns (e.g. by analysing mRNA or cDNA), etc. It can be used to identify particular nucleic acid molecules in a sample. This is useful for in identifying biological material from a given source (e.g. from a human or non-human animal). For example, a reference nucleic acid molecule (or part of it) can be digested with restriction enzymes and the resultant nucleic acid fragments can be run on a gel. This can provide a restriction fragment pattern or "fingerprint" that can be compared with a sample. If the comparison provides a match that is unlikely to have occurred by chance, a conclusion can be reached that the sample and the reference molecule are likely to have originated from a common source. By performing statistical analysis a specific degree of confidence that such a conclusion is correct can be provided.

We also describe a library having a Fve nucleic acid molecule described here, as well as an array comprising such an Fve nucleic acid molecule (which may be a library). Preferably the array is a regular array. The array may have a predetermined pattern. It may have a grid-like pattern. The discussion provided herein in respect of libraries and arrays comprising a polypeptide described here applies mutatis mutandis to libraries and arrays comprising the corresponding nucleic acid molecule.

One or more Fve nucleic acid molecules may be immobilised upon a surface (e.g. the surface of a bead or a chip). The surface may, for example, be silicon surface, glass, quartz, a membrane, etc. Techniques for immobilising nucleic acid molecules upon a surface are known and are disclosed, for example, in EP-A-0487104, WO96/04404, WO90/02205, WO96/12014, WO98/44151. In some cases they may include a step of nucleic acid amplification, which may involve PCR. Immobilisation is not however essential. For example nucleic acids may be provided in wells or other containment means (e.g. in a fluid environment).

The Fve nucleic acids may be used in various ways. For example, sequence information can be used in predicting structure and/or function, in homology or identity studies, etc.

Vectors

As indicated above the nucleic acid molecules described here may be provided in the form of vectors.

Vectors comprising such nucleic acid include plasmids, phasmids, cosmids, viruses (including bacteriophages), YACs, PACs, etc. They will usually include an origin of replication and may include one or more selectable markers e.g. drug resistance markers and/or markers enabling growth on a particular medium. A vector may include a marker that is inactivated when a nucleic acid molecule, such as the ones described here, is inserted into the vector. Here a further marker may be provided that is different from the marker that is inactivated (e.g. it encodes a different type of drug resistance).

Vectors may include one or more regions necessary for transcription of RNA encoding a polypeptide. Such vectors are often referred to as expression vectors. They will usually contain a promoter and may contain additional regulatory regions—e.g. operator sequences, enhancer sequences, etc. Translation can be provided by a host cell or by a cell free expression system.

Vectors need not be used for expression. They may be provided for maintaining a given nucleic acid sequence, for replicating that sequence, for manipulating, it or for transferring it between different locations (e.g. between different organisms).

Large nucleic acid molecules may be incorporated into high capacity vectors (e.g. cosmids, phasmids, YACs or PACs). Smaller nucleic acid molecules may be incorporated into a wide variety of vectors.

Fve polynucleotides, for example those described here, can be incorporated into a recombinant replicable vector. The vector may be used to replicate the nucleic acid in a compatible host cell. Thus in a further embodiment, we provide a method of making polynucleotides by introducing a polynucleotide into a replicable vector, introducing the vector into a compatible host cell, and growing the host cell under conditions which bring about replication of the vector. The vector may be recovered from the host cell. Suitable host cells include bacteria such as *E. coli*, yeast, mammalian cell lines and other eukaryotic cell lines, for example insect Sf9 cells.

Preferably, a polynucleotide in a vector is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

The control sequences may be modified, for example by the addition of further transcriptional regulatory elements to make the level of transcription directed by the control sequences more responsive to transcriptional modulators.

Vectors may be transformed or transfected into a suitable host cell as described below to provide for expression of a protein. This process may comprise culturing a host cell transformed with an expression vector as described above under conditions to provide for expression by the vector of a coding sequence encoding the protein, and optionally recovering the expressed protein. Vectors will be chosen that are compatible with the host cell used.

The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used, for example, to transfect or transform a host cell.

Control sequences operably linked to sequences encoding the polypeptide include promoters/enhancers and other expression regulation signals. These control sequences may be selected to be compatible with the host cell for which the expression vector is designed to be used in. The term promoter is well-known in the art and encompasses nucleic acid regions ranging in size and complexity from minimal promoters to promoters including upstream elements and enhancers.

The promoter is typically selected from promoters which are functional in mammalian cells, although prokaryotic promoters and promoters functional in other eukaryotic cells, such as insect cells, may be used. The promoter is typically derived from promoter sequences of viral or eukaryotic genes. For example, it may be a promoter derived from the genome of a cell in which expression is to occur. With respect to eukaryotic promoters, they may be promoters that function in a ubiquitous manner (such as promoters of $\alpha$-actin, $\beta$-actin, tubulin) or, alternatively, a tissue-specific manner (such as promoters of the genes for pyruvate kinase). They may also be promoters that respond to specific stimuli, for example promoters that bind steroid hormone receptors. Viral promoters may also be used, for example the Moloney murine leukaemia virus long terminal repeat (MMLV LTR) promoter, the rous sarcoma virus (RSV) LTR promoter or the human cytomegalovirus (CMV) IE promoter.

It may also be advantageous for the promoters to be inducible so that the levels of expression of the heterologous gene can be regulated during the life-time of the cell. Inducible means that the levels of expression obtained using the promoter can be regulated.

In addition, any of these promoters may be modified by the addition of further regulatory sequences, for example enhancer sequences. Chimeric promoters may also be used comprising sequence elements from two or more different promoters described above.

Polynucleotides may also be inserted into the vectors described above in an antisense orientation to provide for the production of antisense RNA. Antisense RNA or other antisense polynucleotides may also be produced by synthetic means. Such antisense polynucleotides may be used in a method of controlling the levels of RNAs transcribed from genes comprising any one of the polynucleotides described here.

Host Cells

Vectors and polynucleotides or nucleic acids comprising or encoding mTOR nucleic acids, fragments, homologues, variants or derivatives thereof may be introduced into host cells for the purpose of replicating the vectors/polynucleotides and/or expressing the polypeptides encoded by the polynucleotides. Although the polypeptides may be produced using prokaryotic cells as host cells, it is preferred to use eukaryotic cells, for example yeast, insect or mammalian cells, in particular mammalian cells.

Vectors/polynucleotides may be introduced into suitable host cells using a variety of techniques known in the art, such as transfection, transformation and electroporation. Where vectors/polynucleotides are to be administered to animals, several techniques are known in the art, for example infection with recombinant viral vectors such as retroviruses, herpes simplex viruses and adenoviruses, direct injection of nucleic acids and biolistic transformation.

We therefore further disclose cells comprising mTOR nucleic acid molecules or vectors. These may for example be used for expression, as described herein.

A cell capable of expressing a mTOR polypeptide described here can be cultured and used to provide the mTOR polypeptide, which can then be purified.

Alternatively, the cell may be used in therapy for the same purposes as the mTOR polypeptide. For example, cells may be provided from a patient (e.g. via a biopsy), transfected with a nucleic acid molecule or vector and, if desired, cultured in vitro, prior to being returned to the patient (e.g. by injection). The cells can then produce the mTOR polypeptide in vivo. Preferably the cells comprise a regulatable promoter enabling transcription to be controlled via administration of one or more regulator molecules. If desired, the promoter may be tissue specific.

Expression is not however essential since the cells may be provided simply for maintaining a given nucleic acid sequence, for replicating the sequence, for manipulating it, etc.

Such cells may be provided in any appropriate form. For example, they may be provided in isolated form, in culture, in stored form, etc. Storage may, for example, involve cryopreservation, buffering, sterile conditions, etc. Such cells may be provided by gene cloning techniques, by stem cell technology or by any other means. They may be part of a tissue or an organ, which may itself be provided in any of the forms discussed above. The cell, tissue or organ may be stored and used later for implantation, if desired. Techniques for providing tissues or organs, include stem cell technology, the provision of cells tissues or organs from transgenic animals, retroviral and non-retroviral techniques for introducing nucleic acids, etc.

In some case cells may be provided together with other material to aid the structure or function or of an implant. For example scaffolds may be provided to hold cells in position, to provide mechanical strength, etc. These may be in the form of matrixes of biodegradable or non-biodegradable material. WO95/01810 describes various materials that can be used for this purpose.

Animals

We also disclose transgenic animals, preferably non-human transgenic animals. Such animals may be useful for producing the particular Fve polypeptides described here (e.g. via secretion in milk, as described herein). Alternatively, they may be useful as test animals for analysing the effect(s) of such Fve polypeptides.

Techniques for producing transgenic animals are well known and are described e.g. in U.S. Pat. Nos. 4,870,009 and 4,873,191. For example, a nucleic acid encoding a Fve polypeptide of interest may be microinjected into a pronucleus of a fertilised oocyte. The oocyte may then be allowed to develop in a pseudopregnant female foster animal. The animal resulting from development of the oocyte can be tested (e.g. with antibodies) to determine whether or not it expresses the particular polypeptide. Alternatively, it can be tested with a probe to determine if it has a transgene (even if there is no expression).

A transgenic animal can be used as a founder animal, which may be bred from in order to produce further transgenic animals. Two transgenic animals may be crossed. For example, in some cases transgenic animals may be haploid for a given gene and it may be desired to try to provide a diploid offspring via crossing.

A transgenic animal may be cloned, e.g. by using the procedures set out in WO97/07668 and WO97/07699 (see also Nature 385:810-813 (1997)). Thus a quiescent cell can be provided and combined with an oocyte from which the nucleus has been removed combined. This can be achieved using electrical discharges. The resultant cell can be allowed to develop in culture and can then be transferred to a pseudopregnant female.

Analytical Tools and Systems

We disclose a moiety comprising a Fve polypeptide, a Fve nucleic acid, a vector comprising Fve, a cell expressing Fve, an Fve binding agent, a moiety identified/identifiable by a screen as described here, when used as an analytical tool or when present in a system suitable for analysis, especially high throughput analysis.

Such an analytical tool or system is useful for a plethora of different purposes. These include diagnosis, forensic science, screening, the identification or characterisation of individuals or populations, preventative medicine, etc.

Libraries comprising such a Fve moiety may be used for the above purposes. A library will generally comprise a plurality of heterologous moieties. Preferred libraries comprise at least 100, at least 10,000, at least 1,000,000, or at least 1,000,000,000 heterologous moieties. Desirably a moiety is provided at a predetermined position within a library. In some cases a plurality of moieties may be present within a library at predetermined positions. A predetermined position may be assigned spatial co-ordinates. These may be stored or processed in a computer in order to assist in analysis.

We further disclose an array comprising such a Fve moiety (whether or not the array is also a library). Preferably the array is a regular array. The array may have a predetermined pattern. It may have a grid-like pattern. Preferred arrays comprise at least 100, at least 10,000, at least 1,000,000, or at least 1,000,000,000 components.

A library or array may include naturally occurring moieties, non-naturally occurring moieties, or a mixture of naturally occurring and non-naturally occurring moieties. The moieties may provided in solution, on beads, on chips (see e.g. Fodor (1993) Nature 364:555-556), on bacteria (see e.g. U.S. Pat. No. 5,223,409), on spores (see e.g. U.S. Pat. No. 5,223,409), on 'phage (see e.g. Scott and Smith (1990) Science 249:386-90 and U.S. Pat. No. 5,223,409), etc.

Such Fve moieties may be immobilised upon a surface, if desired. For example, one or more nucleic acid molecules may be immobilised upon a surface (e.g. the surface of a bead or a chip). The surface may, for example, be silicon, glass, quartz, a membrane, etc. Techniques for immobilising nucleic acid molecules upon a surface are known and are disclosed, for example, in EP-A-0487104, WO96/04404, WO90/02205, WO96/12014, WO98/44151. In some cases they may include a step of nucleic acid amplification, and may involve PCR.

Immobilisation is not however essential, even if moieties are to be used in high throughput analysis. For example, they may be provided in wells, channels, grooves or other containment means.

Whether or not present in a library, an array or in immobilised or non-immobilised form, it is often desirable to locate the position of one or more moieties being analysed or being used in analysis. This can be done by assigning it spatial co-ordinates, which may be provided, stored or processed or provided by a computer. In some cases the location may be determined by a sensor (e.g. a CCD device), which may be operatively linked with a computer.

DNA Vaccines

Any of the Fve nucleic acids disclosed here may be administered to an individual in the form of a DNA vaccine. DNA vaccines are known in the art, and are described in detail in, for example, WO03012117, WO03007986, etc.

The Fve may be administered to an individual in the form of a DNA vaccine. A DNA encoding the Fve, for example, a Fve nucleic acid as disclosed here, may be in any form, for example in the form of a cloned plasmid DNA or a synthetic oligonucleotide. The DNA may be delivered together with a cytokine, for example, IL-2, and/or other co-stimulatory molecules. The cytokines and/or co-stimulatory molecules may themselves be delivered in the form of plasmid or oligonucleotie DNA.

The response to a DNA vaccine has been shown to be increased by the presence of immunostimulatory DNA sequences (ISS). These can take the form of hexameric motifs containing methylated CpG, according to the formula: 5' purine-purine-CG-pyrimidine-pyrimidine-3'. The DNA vaccines may incorporate these or other ISSs, in the DNA encoding the Fve, in the DNA encoding the cytokine or other co-stimulatory molecules, or in both. A review of the advantages of DNA vaccination is provided by Tighe et al (1998, Immunology Today, 19(2), 89-97).

Antibodies

We also provide monoclonal or polyclonal antibodies to polypeptides or fragments thereof. Thus, we further provide a process for the production of monoclonal or polyclonal antibodies to an Fve polypeptide, fragment, homologue, variant or derivative thereof.

If polyclonal antibodies are desired, a selected mammal (e.g., mouse, rabbit, goat, horse, etc.) is immunised with an immunogenic polypeptide bearing an epitope(s) from a polypeptide. Serum from the immunised animal is collected and treated according to known procedures. If serum containing polyclonal antibodies to an epitope from a polypeptide contains antibodies to other antigens, the polyclonal antibodies can be purified by immunoaffinity chromatography. Techniques for producing and processing polyclonal antisera are known in the art. In order that such antibodies may be made, we also provide polypeptides or fragments thereof haptenised to another polypeptide for use as immunogens in animals or humans.

Monoclonal antibodies directed against epitopes in the polypeptides can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against epitopes in the polypeptides can be screened for various properties; i.e., for isotype and epitope affinity.

An alternative technique involves screening phage display libraries where, for example the phage express scFv fragments on the surface of their coat with a large variety of complementarity determining regions (CDRs). This technique is well known in the art.

Antibodies, both monoclonal and polyclonal, which are directed against epitopes from polypeptides are particularly useful in diagnosis, and those which are neutralising are useful in passive immunotherapy. Monoclonal antibodies, in particular, may be used to raise anti-idiotype antibodies. Anti-idiotype antibodies are immunoglobulins which carry an "internal image" of the antigen of the agent against which protection is desired.

Techniques for raising anti-idiotype antibodies are known in the art. These anti-idiotype antibodies may also be useful in therapy.

For the purposes of this document, the term "antibody", unless specified to the contrary, includes fragments of whole antibodies which retain their binding activity for a target antigen. Such fragments include Fv, F(ab') and F(ab')$_2$ fragments, as well as single chain antibodies (scFv). Furthermore, the antibodies and fragments thereof may be humanised antibodies, for example as described in EP-A-239400.

Antibodies may be used in method of detecting polypeptides present in biological samples by a method which comprises: (a) providing an antibody; (b) incubating a biological sample with said antibody under conditions which allow for the formation of an antibody-antigen complex; and (c) determining whether antibody-antigen complex comprising said antibody is formed.

Suitable samples include extracts tissues such as brain, breast, ovary, lung, colon, pancreas, testes, liver, muscle and bone tissues or from neoplastic growths derived from such tissues.

Antibodies may be bound to a solid support and/or packaged into kits in a suitable container along with suitable reagents, controls, instructions and the like.

Assays

We disclose assays that are suitable for identifying substances which bind to Fve polypeptides, or fragments, homologues, variants or derivatives thereof.

In general, such binding assays involve exposing a Fve polypeptide, nucleic acid, or a fragment, homologue, variant or derivative thereof to a candidate molecule and detecting an interaction or binding between the Fve polypeptide, nucleic acid, or a fragment, homologue, variant or derivative thereof and the candidate molecule. The binding assay may be conducted in vitro, or in vivo.

We disclose assays for identifying substances which are capable of potentiating the activities of Fve polypeptide. Activities of Fve have been described in detail above. Such compounds may be employed as agonists of Fve polypeptide, and may for example be co-administered to an individual to enhance any desired effect.

In general, an assay to identify such substances or compounds involves providing a cell or organism, exposing the cell or organism to a Fve polypeptide, nucleic acid, or a fragment, homologue, variant or derivative thereof, exposing the cell to a candidate molecule, and detecting an effect associated with Fve. Any Fve polypeptide mediated effect or function, as disclosed in this document, particularly the Examples, may be detected.

In particular, the Fve polypeptide mediated effect is preferably chosen from the group consisting of: up-regulation of expression of Th1 cytokines, preferably IFN-γ and TNF-α, down-regulation of expression of Th2 cytokines, preferably IL-4 and IL-13, hemagglutination activity, cell aggregation activity, lymphocyte aggregation activity, lymphoproliferation activity, up-regulation of expression of IL-2, IFN-γ, TNF-α, but not IL-4 in $CD3^+$ T cells, interaction with T and NK cells, adjuvant activity, stimulation of $CD3^+$ $CD16^+$ $CD56^+$ natural killer (NK) T cells, up-regulation of expression of allergen specific IgG2a antibody, prevention of systemic anaphylactic reactions and/or decreased footpad edema, preferably as assayed using the Arthus reaction (Ko et al, 1995).

In order to identify agonists, an additive or preferably synergistic effect is detected. Thus, while Fve polypeptide on its own is, for example, capable of reducing a level or number, or down-regulation of expression of a molecule, the assays identify molecules which further reduce the level, number or further down-regulate the expression of a molecule. Thus, preferably, the candidate molecule in conjunction with the Fve polypeptide, nucleic acid, or a fragment, homologue, variant or derivative thereof, down-regulates the expression of, or reduces the level or number, by more than 10%, more than 20%, more than 30%, more than 40%, more than 50%, more than 60%, more than 70%, more than 80%, more than 90%, or more compared to an Fve polypeptide on its own. Thus, for example, a candidate molecule suitable for use as an agonist is one which is capable of enhancing by 10% more the up-regulation of expression of Th1 cytokines, preferably IFN-γ and TNF-α, achieved by Fve polypeptide on its own.

Conversely, assays to identify antagonists involve the detection of a reduction in Fve polypeptide mediated effect. Preferably, the down-regulation of expression or reduction in number or level achieved by Fve polypeptide is reduced in the presence of a suitable candidate molecule. Preferably, the reduction is at least 10%, preferably at least 20%, preferably at least 30%, preferably at least 40%, preferably at least 50%, preferably at least 60%, preferably at least 70%, preferably at least 80%, preferably at least 90%, or more compared to an Fve polypeptide on its own. Thus, for example, a candidate molecule suitable for use as an antagonist is one which is capable of reducing by 10% more the up-regulation of expression of Th1 cytokines, preferably IFN-γ and TNF-α, achieved by Fve polypeptide on its own.

As an illustration, if N1 is the expression of Th1 cytokines, in an untreated organism or cell, and N2 the expression in an organism or cell exposed to Fve polypeptide, nucleic acid, or a fragment, homologue, variant or derivative thereof, the expression of Th1 cytokines is increased by $R=(N2-N1)/N1 \times 100\%$. Agonists increase R, by a factor x, where x is greater than 1 (e.g., x=1, 1.1, 1.2, 1.3, 1.4, 1.5, 2, 3, 4, 5, 10, 20, 50, 100 etc); while antagonists decrease R, by a factor x, where x is less than 1 (e.g., x=0.9, 0.9, 0.7, 0.6, 0.5, 0.4, 0.3, 0.2, 0.1 etc).

For example, an organism may be exposed to a Fve polypeptide, nucleic acid, or a fragment, homologue, variant or derivative thereof and a candidate molecule, and any of the biological activities as set out above, or any combination, detected. Preferred candidate molecules are those which provide an additive or synergistic effect in combination with Fve.

Also disclosed are assays to identify antagonists of Fve polypeptide. Such assays involve detecting a reduced effect on exposure of a cell or organism to an Fve polypeptide, nucleic acid, or a fragment, homologue, variant or derivative thereof in conjunction with a candidate molecule.

In a preferred embodiment, the assays are conducted on whole organisms rather than cells. Preferably, the organism is one which suffers from a disease as disclosed in this document, or exhibits one or more symptoms of such a disease.

Candidate Molecules

Suitable candidate molecules for use in the above assays include peptides, especially of from about 5 to 30 or 10 to 25 amino acids in size. Peptides from panels of peptides comprising random sequences or sequences which have been varied consistently to provide a maximally diverse panel of peptides may be used.

Suitable candidate molecules also include antibody products (for example, monoclonal and polyclonal antibodies, single chain antibodies, chimeric antibodies and CDR-grafted antibodies). Furthermore, combinatorial libraries, peptide and peptide mimetics, defined chemical entities, oligonucleotides, and natural product libraries may be screened for activity. The candidate molecules may be used in an initial screen in batches of, for example 10 types of molecules per reaction, and the molecules of those batches which show enhancement or reduction of a Fve polypeptide mediated effect tested individually.

Libraries

Libraries of candidate molecules, such as libraries of polypeptides or nucleic acids, may be employed in the methods and compositions described here. Such libraries are exposed a cell or organism in the presence of a Fve polypeptide, nucleic acid, or a fragment, homologue, variant or derivative thereof, and an Fve polypeptide mediated effect detected and assayed as described above.

Selection protocols for isolating desired members of large libraries are known in the art, as typified by phage display techniques. Such systems, in which diverse peptide sequences are displayed on the surface of filamentous bacteriophage (Scott and Smith (1990 supra), have proven useful for creating libraries of antibody fragments (and the nucleotide sequences that encoding them) for the in vitro selection and amplification of specific antibody fragments that bind a target antigen. The nucleotide sequences encoding the $V_H$ and $V_L$ regions are linked to gene fragments which encode leader signals that direct them to the periplasmic space of E. coli and as a result the resultant antibody fragments are displayed on the surface of the bacteriophage, typically as fusions to bacteriophage coat proteins (e.g., pIII or pVIII). Alternatively, antibody fragments are displayed externally on lambda phage capsids (phagebodies). An advantage of phage-based display systems is that, because they are biological systems, selected library members can be amplified simply by growing the phage containing the selected library member in bacterial cells. Furthermore, since the nucleotide sequence that encodes the polypeptide library member is contained on a phage or phagemid vector, sequencing, expression and subsequent genetic manipulation is relatively straightforward.

Methods for the construction of bacteriophage antibody display libraries and lambda phage expression libraries are well known in the art (McCafferty et al. (1990) supra; Kang et al. (1991) *Proc. Natl. Acad. Sci. U.S.A.*, 88: 4363; Clackson et al. (1991) *Nature*, 352: 624; Lowman et al. (1991) *Biochemistry*, 30: 10832; Burton et al. (1991) *Proc. Natl. Acad. Sci. U.S.A.*, 88: 10134; Hoogenboom et al. (1991) Nucleic Acids Res., 19: 4133; Chang et al. (1991) *J. Immunol.*, 147: 3610; Breitling et al. (1991) *Gene*, 104: 147; Marks et al. (1991) supra; Barbas et al. (1992) supra; Hawkins and Winter (1992) *J. Immunol.*, 22: 867; Marks et al., 1992, *J. Biol. Chem.*, 267: 16007; Lerner et al. (1992) *Science*, 258: 1313, incorporated herein by reference). Such techniques may be modified if necessary for the expression generally of polypeptide libraries.

One particularly advantageous approach has been the use of scFv phage-libraries (Bird, R. E., et al. (1988) *Science* 242: 423-6, Huston et al., 1988, Proc. Natl. Acad. Sci. U.S.A., 85: 5879-5883; Chaudhary et al. (1990) Proc. Natl. Acad. Sci. U.S.A., 87: 1066-1070; McCafferty et al. (1990) supra; Clackson et al. (1991) supra; Marks et al. (1991) supra; Chiswell et al. (1992) Trends Biotech., 10: 80; Marks et al. (1992) supra). Various embodiments of scFv libraries displayed on bacteriophage coat proteins have been described. Refinements of phage display approaches are also known, for example as described in WO96/06213 and WO92/01047 (Medical Research Council et al.) and WO97/08320 (Morphosys, supra), which are incorporated herein by reference.

Alternative library selection technologies include bacteriophage lambda expression systems, which may be screened directly as bacteriophage plaques or as colonies of lysogens, both as previously described (Huse et al. (1989) *Science*, 246: 1275; Caton and Koprowski (1990) *Proc. Natl. Acad. Sci. U.S.A.*, 87; Mullinax et al. (1990) *Proc. Natl. Acad. Sci. U.S.A.*, 87: 8095; Persson et al. (1991) *Proc. Natl. Acad. Sci. U.S.A.*, 88: 2432) and are of use. These expression systems may be used to screen a large number of different members of a library, in the order of about $10^6$ or even more. Other screening systems rely, for example, on direct chemical synthesis of library members. One early method involves the synthesis of peptides on a set of pins or rods, such as described in WO84/03564. A similar method involving peptide synthesis on beads, which forms a peptide library in which each bead is an individual library member, is described in U.S. Pat. No. 4,631,211 and a related method is described in WO92/00091. A significant improvement of the bead-based methods involves tagging each bead with a unique identifier tag, such as an oligonucleotide, so as to facilitate identification of the amino acid sequence of each library member. These improved bead-based methods are described in WO93/06121.

Another chemical synthesis method involves the synthesis of arrays of peptides (or peptidomimetics) on a surface in a manner that places each distinct library member (e.g., unique peptide sequence) at a discrete, predefined location in the array. The identity of each library member is determined by its spatial location in the array. The locations in the array where binding interactions between a predetermined molecule (e.g., a receptor) and reactive library members occur is determined, thereby identifying the sequences of the reactive library members on the basis of spatial location. These methods are described in U.S. Pat. No. 5,143,854; WO90/15070 and WO92/10092; Fodor et al. (1991) *Science*, 251: 767; Dower and Fodor (1991) *Ann. Rep. Med. Chem.*, 26: 271.

Other systems for generating libraries of polypeptides or nucleotides involve the use of cell-free enzymatic machinery for the in vitro synthesis of the library members. In one method, RNA molecules are selected by alternate rounds of selection against a target ligand and PCR amplification (Tuerk and Gold (1990) *Science*, 249: 505; Ellington and Szostak (1990) *Nature*, 346: 818). A similar technique may be used to identify DNA sequences which bind a predetermined human transcription factor (Thiesen and Bach (1990) *Nucleic Acids Res.*, 18: 3203; Beaudry and Joyce (1992) *Science*, 257: 635; WO92/05258 and WO92/14843). In a similar way, in vitro translation can be used to synthesise polypeptides as a method for generating large libraries. These methods which generally comprise stabilised polysome complexes, are described further in WO88/08453, WO90/05785, WO90/07003, WO91/02076, WO91/05058, and WO92/02536. Alternative display systems which are not phage-based, such as those disclosed in WO95/22625 and WO95/11922 (Affymax) use the polysomes to display polypeptides for selection. These and all the foregoing documents also are incorporated herein by reference.

Combinatorial Libraries

Libraries, in particular, libraries of candidate molecules, may suitably be in the form of combinatorial libraries (also known as combinatorial chemical libraries).

A "combinatorial library", as the term is used in this document, is a collection of multiple species of chemical compounds that consist of randomly selected subunits. Combinatorial libraries may be screened for molecules which are capable of potentiating, enhancing, reducing or minimising the a Fve polypeptide mediated effect when exposed to a cell or organism.

Various combinatorial libraries of chemical compounds are currently available, including libraries active against proteolytic and non-proteolytic enzymes, libraries of agonists and antagonists of G-protein coupled receptors (GPCRs), libraries active against non-GPCR targets (e.g., integrins, ion channels, domain interactions, nuclear receptors, and transcription factors) and libraries of whole-cell oncology and anti-infective targets, among others. A comprehensive review of combinatorial libraries, in particular their construction and uses is provided in Dolle and Nelson (1999), *Journal of Combinatorial Chemistry*, Vol 1 No 4, 235-282. Reference is also made to *Combinatorial peptide library protocols* (edited by Shmuel Cabilly, Totowa, N.J.: Humana Press, c1998. *Methods in Molecular Biology*; v. 87).

Further references describing chemical combinatorial libraries, their production and use include those available from the URL http://www.netsci.org/Science/Combichem/, including The Chemical Generation of Molecular Diversity. Michael R. Pavia, Sphinx Pharmaceuticals, A Division of Eli Lilly (Published July, 1995); Combinatorial Chemistry: A Strategy for the Future—MDL Information Systems discusses the role its Project Library plays in managing diversity libraries (Published July, 1995); Solid Support Combinatorial Chemistry in Lead Discovery and SAR Optimization, Adnan M. M. Mjalli and Barry E. Toyonaga, Ontogen Corporation (Published July, 1995); Non-Peptidic Bradykinin Receptor Antagonists From a Structurally Directed Non-Peptide Library. Sarvajit Chakravarty, Babu J. Mavunkel, Robin Andy, Donald J. Kyle*, Scios Nova Inc. (Published July, 1995); Combinatorial Chemistry Library Design using Pharmacophore Diversity Keith Davies and Clive Briant, Chemical Design Ltd. (Published July, 1995); A Database System for Combinatorial Synthesis Experiments—Craig James and David Weininger, Daylight Chemical Information Systems, Inc. (Published July, 1995); An Information Management Architecture for Combinatorial Chemistry, Keith Davies and Catherine White, Chemical Design Ltd. (Published July, 1995); Novel Software Tools for Addressing Chemical Diversity, R. S. Pearlman, Laboratory for Molecular Graphics and Theoretical Modeling, College of Pharmacy, University of Texas (Published June/July, 1996); Opportunities for Computational Chemists Afforded by the New Strategies in Drug Discovery: An Opinion, Yvonne Connolly Martin, Computer Assisted Molecular Design Project, Abbott Laboratories (Published June/July, 1996); Combinatorial Chemistry and Molecular Diversity Course at the University of Louisville: A Description, Arno F. Spatola, Department of Chemistry, University of Louisville (Published June/July, 1996); Chemically Generated Screening Libraries: Present and Future. Michael R. Pavia, Sphinx Pharmaceuticals, A Division of Eli Lilly (Published June/July, 1996); Chemical Strategies For Introducing Carbohydrate Molecular Diversity Into The Drug Discovery Process. Michael J. Sofia, Transcell Technologies Inc. (Published June/July, 1996); Data Management for Combinatorial Chemistry. Maryjo Zaborowski, Chiron Corporation and Sheila H. DeWitt, Parke-Davis Pharmaceutical Research, Division of Warner-Lambert Company (Published November, 1995); and The Impact of High Throughput Organic Synthesis on R&D in Bio-Based Industries, John P. Devlin (Published March, 1996).

Techniques in combinatorial chemistry are gaining wide acceptance among modern methods for the generation of new pharmaceutical leads (Gallop, M. A. et al., 1994, J. Med. Chem. 37:1233-1251; Gordon, E. M. et al., 1994, J. Med. Chem. 37:1385-1401.). One combinatorial approach in use is based on a strategy involving the synthesis of libraries containing a different structure on each particle of the solid phase support, interaction of the library with a soluble receptor, identification of the 'bead' which interacts with the macromolecular target, and determination of the structure carried by the identified 'bead' (Lam, K. S. et al., 1991, Nature 354:82-84). An alternative to this approach is the sequential release of defined aliquots of the compounds from the solid support, with subsequent determination of activity in solution, identification of the particle from which the active compound was released, and elucidation of its structure by direct sequencing (Salmon, S. E. et al., 1993, Proc. Natl. Acad. Sci. USA 90:11708-11712), or by reading its code (Kerr, J. M. et al., 1993, J. Am. Chem. Soc. 115:2529-2531; Nikolaiev, V. et al., 1993, Pept. Res. 6:161-170; Ohlmeyer, M. H. J. et al., 1993, Proc. Natl. Acad. Sci. USA 90:10922-10926).

Soluble random combinatorial libraries may be synthesized using a simple principle for the generation of equimolar mixtures of peptides which was first described by Furka (Furka, A. et al., 1988, Xth International Symposium on Medicinal Chemistry, Budapest 1988; Furka, A. et al., 1988, 14th International Congress of Biochemistry, Prague 1988; Furka, A. et al., 1991, Int. J. Peptide Protein Res. 37:487-493). The construction of soluble libraries for iterative screening has also been described (Houghten, R. A. et al. 1991, Nature 354:84-86). K. S. Lam disclosed the novel and unexpectedly powerful technique of using insoluble random combinatorial libraries. Lam synthesized random combinatorial libraries on solid phase supports, so that each support had a test compound of uniform molecular structure, and screened the libraries without prior removal of the test compounds from the support by solid phase binding protocols (Lam, K. S. et al., 1991, Nature 354:82-84).

Thus, a library of candidate molecules may be a synthetic combinatorial library (e.g., a combinatorial chemical library), a cellular extract, a bodily fluid (e.g., urine, blood, tears, sweat, or saliva), or other mixture of synthetic or natural products (e.g., a library of small molecules or a fermentation mixture).

A library of molecules may include, for example, amino acids, oligopeptides, polypeptides, proteins, or fragments of peptides or proteins; nucleic acids (e.g., antisense; DNA; RNA; or peptide nucleic acids, PNA); aptamers; or carbohydrates or polysaccharides. Each member of the library can be singular or can be a part of a mixture (e.g., a compressed library). The library may contain purified compounds or can be "dirty" (i.e., containing a significant quantity of impurities). Commercially available libraries (e.g., from Affymetrix, ArQule, Neose Technologies, Sarco, Ciddco, Oxford Asymmetry, Maybridge, Aldrich, Panlabs, Pharmacopoeia, Sigma, or Tripose) may also be used with the methods described here.

In addition to libraries as described above, special libraries called diversity files can be used to assess the specificity, reliability, or reproducibility of the new methods. Diversity files contain a large number of compounds (e.g., 1000 or more small molecules) representative of many classes of compounds that could potentially result in nonspecific detection in an assay. Diversity files are commercially available or can also be assembled from individual compounds commercially available from the vendors listed above.

Candidate Substances

Suitable candidate substances include peptides, especially of from about 5 to 30 or 10 to 25 amino acids in size, based on the sequence of the polypeptides described in the Examples, or variants of such peptides in which one or more residues have been substituted. Peptides from panels of peptides comprising random sequences or sequences which have been varied consistently to provide a maximally diverse panel of peptides may be used.

Suitable candidate substances also include antibody products (for example, monoclonal and polyclonal antibodies, single chain antibodies, chimeric antibodies and CDR-grafted antibodies) which are specific for a polypeptide. Furthermore, combinatorial libraries, peptide and peptide mimetics, defined chemical entities, oligonucleotides, and natural product libraries may be screened for activity as inhibitors of binding of a polypeptide to the cell division cycle machinery, for example mitotic/meiotic apparatus (such as microtubules). The candidate substances may be used in an initial screen in batches of, for example 10 substances per reaction, and the substances of those batches which show inhibition tested individually. Candidate substances which show activity in in vitro screens such as those described below can then be tested in whole cell systems, such as mammalian cells which will be exposed to the inhibitor and tested for inhibition of any of the stages of the cell cycle.

Polypeptide Binding Assays

One type of assay for identifying substances that bind to a polypeptide involves contacting a polypeptide, which is immobilised on a solid support, with a non-immobilised candidate substance determining whether and/or to what extent the polypeptide and candidate substance bind to each other. Alternatively, the candidate substance may be immobilised and the polypeptide non-immobilised. This may be used to detect substances capable of binding to Fve polypeptides, or fragments, homologues, variants or derivatives thereof.

In a preferred assay method, the polypeptide is immobilised on beads such as agarose beads. Typically this is achieved by expressing the Fve polypeptide, or a fragment, homologue, variant or derivative thereof as a GST-fusion protein in bacteria, yeast or higher eukaryotic cell lines and purifying the GST-fusion protein from crude cell extracts using glutathione-agarose beads (Smith and Johnson, 1988). As a control, binding of the candidate substance, which is not a GST-fusion protein, to the immobilised polypeptide is determined in the absence of the polypeptide. The binding of the candidate substance to the immobilised polypeptide is then determined. This type of assay is known in the art as a GST pulldown assay. Again, the candidate substance may be immobilised and the polypeptide non-immobilised.

It is also possible to perform this type of assay using different affinity purification systems for immobilising one of the components, for example Ni-NTA agarose and histidine-tagged components.

Binding of the Fve polypeptide, or a fragment, homologue, variant or derivative thereof to the candidate substance may be determined by a variety of methods well-known in the art. For example, the non-immobilised component may be labeled (with for example, a radioactive label, an epitope tag or an enzyme-antibody conjugate). Alternatively, binding may be determined by immunological detection techniques. For example, the reaction mixture can be Western blotted and the blot probed with an antibody that detects the non-immobilised component. ELISA techniques may also be used.

Candidate substances are typically added to a final concentration of from 1 to 1000 nmol/ml, more preferably from 1 to 100 nmol/ml. In the case of antibodies, the final concentration used is typically from 100 to 500 µg/ml, more preferably from 200 to 300 µg/ml.

Fve Diseases

As disclosed elsewhere in this document, Fve polypeptides, nucleic acids, and fragments, homologues, variants and derivatives thereof, host cells, vectors, DNA vaccines, etc, are suitable for treating or preventing various diseases (here referred to as "Fve diseases"). They may be be administered in an amount in the range of 1 microgram to 1 gramme to an average human patient or individual to be vaccinated. It is preferred to use a smaller dose in the range of 1 microgram to 1 milligram for each administration, however.

The Fve polypeptides, etc may be administered together, either simultaneously or separately with compounds such as cytokines and/or or growth factors, such as interleukin-2 (IL-2), Interleukin 12 (IL-12), GM-CSF or the like in order to strengthen the immune response. The Fve polypeptides, etc can be used in a vaccine or a therapeutic composition either alone or in combination with other materials, for example, in the form of a lipopeptide conjugate which is known to induce a high-affinity cytotoxic T cell responses (Deres, 1989, Nature 342).

In particular, Fve diseases include allergies and cancer, described in further detail below.

Cancer

Fve polypeptides, nucleic acids, and fragments, homologues, variants and derivatives thereof, are suitable for treating or preventing cancer.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer. Further examples are solid tumor cancer including colon cancer, breast cancer, lung cancer and prostrate cancer, hematopoietic malignancies including leukemias and lymphomas, Hodgkin's disease, aplastic anemia, skin cancer and familiar adenomatous polyposis. Further examples include brain neoplasms, colorectal neoplasms, breast neoplasms, cervix neoplasms, eye neoplasms, liver neoplasms, lung neoplasms, pancreatic neoplasms, ovarian neoplasms, prostatic neoplasms, skin neoplasms, testicular neoplasms, neoplasms, bone neoplasms, yellow fevertrophoblastic neoplasms, fallopian tube neoplasms, rectal neoplasms, colonic neoplasms, kidney neoplasms, stomach neoplasms, and parathyroid neoplasms. Breast cancer, prostate cancer, pancreatic cancer, colorectal cancer, lung cancer, malignant melanoma, leukaemia, lympyhoma, ovarian cancer, cervical cancer and biliary tract carcinoma are also included.

In preferred embodiments, Fve polypeptide, nucleic acid, and fragments, homologues, variants and derivatives thereof are used to treat T cell lymphoma, melanoma or lung cancer.

The Fve polypeptides and nucleic acids, etc, as described here, may also be used in combination with anticancer agents such as endostatin and angiostatin or cytotoxic agents or chemotherapeutic agent. For example, drugs such as such as adriamycin, daunomycin, cis-platinum, etoposide, taxol, taxotere and alkaloids, such as vincristine, and antimetabolites such as methotrexate. The term "cytotoxic agent" as used herein refers to a substance that inhibits or prevents the function of cells and/or causes destruction of cells. The term is intended to include radioactive isotopes (e.g. I, Y, Pr), chemotherapeutic agents, and toxins such as enzymatically active toxins of bacterial, fungal, plant or animal origin, or fragments thereof.

Also, the term includes oncogene product/tyrosine kinase inhibitors, such as the bicyclic ansamycins disclosed in WO 94/22867; 1,2-bis(arylamino) benzoic acid derivatives disclosed in EP 600832; 6,7-diamino-phthalazin-1-one derivatives disclosed in EP 600831; 4,5-bis(arylamino)-phthalimide derivatives as disclosed in EP 516598; or peptides which inhibit binding of a tyrosine kinase to a SH2-containing substrate protein (see WO 94/07913, for example). A "chemotherapeutic agent" is a chemical compound useful in the treatment of cancer. Examples of chemotherapeutic agents include Adriamycin, Doxorubicin, 5-Fluorouracil (5-FU), Cytosine arabinoside (Ara-C), Cyclophosphamide, Thiotepa, Busulfan, Cytoxin, Taxol, Methotrexate, Cisplatin, Melphalan, Vinblastine, Bleomycin, Etoposide, Ifosfamide, Mitomycin C, Mitoxantrone, Vincristine, VP-16, Vinorelbine, Carboplatin, Teniposide, Daunomycin, Caminomycin, Aminopterin, Dactinomycin, Mitomycins, Nicotinamide, Esperamicins (see U.S. Pat. No. 4,675,187), Melphalan and other related nitrogen mustards, and endocrine therapies (such as diethylstilbestrol (DES), Tamoxifen, LHRH antagonizing drugs, progestins, anti-progestins etc).

Allergies

Existing treatments for allergies typically involve the long-term use of steroids to depress the immune system. There are undesirable side effects with long-term steroid therapy. We demonstrate that Fve polypeptide, nucleic acid, or a fragment, homologue, variant or derivative thereof (as well as DNA vaccines, host cells and transgenic organisms comprising any of these) may be used to alleviate the symptoms of allergy, or to treat allergy. The term "allergy" as used here, refers to any allergic reactions such as allergic contact hypersensitivity.

In general, the allergy may be to an allergen from any source, for example, a source known to induce allergenic responses in humans. For example, the allergy may be to a tree pollen allergen, a grass pollen allergen, a weed pollen allergen, a feline antigen, or a fungal allergen. Thus, the allergy may be to a tree pollen allergen, for example Bet v 1 and Bet v 2 from birch tree. The allergy may be to a grass pollen allergen, for example, Phl p 1 and Phl p 2 from timothy grass. It may be to a weed pollen allergen, for example, antigen E from ragweed. It may be to an animal allergen, for example, a canine or feline antigen. Specifically, it may be to a major feline antigen, for example, Fel d 1. The allergy may be to a fungal allergen, for example a major fungal allergen, for example, Asp f1, Asp f2, and Asp f3 from *Aspergillus fumigatus*.

In preferred embodiments, the allergy is to a dust mite allergen, preferably a house dust mite allergen. In particular, the allergen is preferably derived from a mite from Family Glycyphagidae or Family Pyroglyphidae. Dust mites of Family Glycyphagidae include those in the genera *Aeroglyphus, Austroglycyphagus, Blomia, Ctenoglyphus, Glycyphagus, Gohieria, Lepidoglyphus*. Dust mites of Family Pyroglyphidae include those in the genera *Dermatophagoides, Euroglyphus, Pyroglyphus*. In preferred embodiments, the allergy is preferably to an allergen from a species in any of these genera.

In highly preferred embodiments, the allergy is to an allergen which is a group 1 allergen (Der p 1, Der f 1, Blo t 1, Eur m1, Lep d 1), a group 2 allergen (Der p 2, Der f 2, Blo t 2, Eur m 2, Lep d 2), a group 5 allergen (Blo t 5, Der p 5, Der f 5, Eur m 5, Lep d 5) or a group 15 allergen (Der p 15, Der f 15, Blo t 15, Eur m 15, Lep d 15) from dust mite.

Allergies suitable for treatment with Fve polypeptide, nucleic acid, or a fragment, homologue, variant or derivative thereof may therefore include a seasonal respiratory allergy, allergic rhinitis, hayfever, nonallergic rhinitis, vasomotor rhinitis, irritant rhinitis, an allergy against grass pollens, tree pollens or animal danders, an allergy associated with allergic asthma, and food allergies. In particular, and as described elsewhere, Fve polypeptide, nucleic acid, or a fragment, homologue, variant or derivative thereof may be used to treat allergies to house dust mite (*Dermatophagoides* spp), preferably *Dermatophagoides pteronyssinus* or *Dermatophagoides farinae*, or to fungi or fungal spores, preferably *Aspergillus fumigatus*. Preferably, the allergens are comprised in faeces of *Dermatophagoides* spp.

Viral Infections

The immunomodulator-viral infectious antigen combinations, preferably conjugates, may be used to treat or prevent any of a number of viral infectious diseases. The virus concerned may be an RNA virus or a DNA virus. Preferably, the virus is an integrating virus. Preferably, the virus is selected from a lentivirus and a herpesvirus. More preferably, the virus is an HIV virus or a HSV virus.

The methods described here can therefore be used to prevent the development and establishment of diseases caused by or associated with any of the above viruses, including human immunodeficiency virus, such as HIV-1 and HIV-2, and herpesvirus, for example HSV-1, HSV-2, HSV-7 and HSV-8, as well as human cytomegalovirus, varicella-zoster virus, Epstein-Barr virus and human herpesvirus 6. in humans. Human papillomavirus (HPV) is also included, and the immunomodulator as described may be administered in combination (simultaneously or sequentially, etc) together with a viral infectious antigen comprising for example E7 antigen from HPV, as shown in the Examples.

Examples of viruses which may be targeted using the methods and compositions described here are given in the tables below.

| | | DNA VIRUSES | |
|---|---|---|---|
| Family | Genus or [Subfamily] | Example | Diseases |
| Herpesviridae | [Alphaherpesvirinae] | Herpes simplex virus type 1 (aka HHV-1) | Encephalitis, cold sores, gingivostomatitis |
| | | Herpes simplex virus type 2 (aka HHV-2) | Genital herpes, encephalitis |
| | | Varicella zoster virus (aka HHV-3) | Chickenpox, shingles |
| | [Gammaherpesvirinae] | Epstein Barr virus (aka HHV-4) | Mononucleoisis, hepatitis, tumors (BL, NPC) |
| | | Kaposi's sarcoma associated herpesvirus, KSHV (aka Human herpesvirus 8) | ?Probably: tumors, inc. Kaposi's sarcoma (KS) and some B cell lymphomas |
| | [Betaherpesvirinae] | Human cytomegalovirus (aka HHV-5) | Mononucleosis, hepatitis, pneumonitis, congenital |
| | | Human herpesvirus 6 | Roseola (aka *E. subitum*), pneumonitis |
| Adenoviridae | | Human herpesvirus 7 | Some cases of roseola? |
| Papovaviridae | Mastadenovirus | Human adenoviruses | 50 serotypes (species); respiratory infections |
| | Papillomavirus | Human papillomaviruses | 80 species; warts and tumors |
| Hepadnaviridae | Polyomavirus | JC, BK viruses | Mild usually; JC causes PML in AIDS |
| Poxviridae | Orthohepadnavirus | Hepatitis B virus (HBV) | Hepatitis (chronic), cirrhosis, liver tumors |
| | | Hepatitis C virus (HCV) | Hepatitis (chronic), cirrhosis, liver tumors |
| | Orthopoxvirus | Vaccinia virus | Smallpox vaccine virus |
| | | Monkeypox virus | Smallpox-like disease; a rare zoonosis (recent outbreak in Congo; 92 cases from February 1996-February 1997) |
| Parvoviridae | Parapoxvirus | Orf virus | Skin lesions ("pocks") |
| | Erythrovirus | B19 parvovirus | E. infectiousum (aka Fifth disease), aplastic crisis, fetal loss |
| Circoviridae | Dependovirus | Adeno-associated virus | Useful for gene therapy; integrates into chromosome |
| | Circovirus | TT virus (TTV) | Linked to hepatitis of unknown etiology |

| | | RNA VIRUSES | |
|---|---|---|---|
| Family | Genus or [Subfamily] | Example | Diseases |
| Picornaviridae | Enterovirus | Polioviruses | 3 types; Aseptic meningitis, paralytic poliomyelitis |
| | | Echoviruses | 30 types; Aseptic meningitis, rashes |
| | | Coxsackieviruses | 30 types; Aseptic meningitis, myopericarditis |
| | Hepatovirus | Hepatitis A virus | Acute hepatitis (fecal-oral spread) |
| | Rhinovirus | Human rhinoviruses | 115 types; Common cold |
| Caliciviridae | Calicivirus | Norwalk virus | Gastrointestinal illness |
| Paramyxoviridae | Paramyxovirus | Parainfluenza viruses | 4 types; Common cold, bronchiolitis, pneumonia |
| | Rubulavirus | Mumps virus | Mumps: parotitis, aseptic meningitis (rare: orchitis, encephalitis) |
| | Morbillivirus | Measles virus | Measles: fever, rash (rare: encephalitis, SSPE) |
| | Pneumovirus | Respiratory syncytial virus | Common cold (adults), bronchiolitis, pneumonia (infants) |
| Orthomyxoviridae | Influenzavirus A | Influenza virus A | Flu: fever, myalgia, malaise, cough, pneumonia |
| | Influenzavirus B | Influenza virus B | Flu: fever, myalgia, malaise, cough, pneumonia |
| Rhabdoviridae | Lyssavirus | Rabies virus | Rabies: long incubation, then CNS disease, death |
| Filoviridae | Filovirus | Ebola and Marburg viruses | Hemorrhagic fever, death |
| Bornaviridae | Bornavirus | Borna disease virus | Uncertain; linked to schizophrenia-like disease in some animals |
| Retroviridae | Deltaretrovirus | Human T-lymphotropic virus type-1 | Adult T-cell leukemia (ATL), tropical spastic paraparesis (TSP) |
| | Spumavirus | Human foamy viruses | No disease known |
| | Lentivirus | Human immunodeficiency virus type-1 and -2 | AIDS, CNS disease |
| Togaviridae | Rubivirus | Rubella virus | Mild exanthem; congenital fetal defects |
| | Alphavirus | Equine encephalitis viruses (WEE, EEE, VEE) | Mosquito-born, encephalitis |
| Flaviviridae | Flavivirus | Yellow fever virus | Mosquito-born; fever, hepatitis (yellow fever!) |
| | | Dengue virus | Mosquito-born; hemorrhagic fever |
| | | St. Louis Encephalitis virus | Mosquito-born; encephalitis |
| | Hepacivirus | Hepatitis C virus | Hepatitis (often chronic), liver cancer |
| | | Hepatitis G virus | Hepatitis??? |
| Reoviridae | Rotavirus | Human rotaviruses | Numerous serotypes; Diarrhea |
| | Coltivirus | Colorado Tick Fever virus | Tick-born; fever |
| | Orthoreovirus | Human reoviruses | Minimal disease |
| Bunyaviridae | Hantavirus | Pulmonary Syndrome Hantavirus | Rodent spread; pulmonary illness (can be lethal, "Four Corners" outbreak) |
| | | Hantaan virus | Rodent spread; hemorrhagic fever with renal syndrome |
| | Phlebovirus | Rift Valley Fever virus | Mosquito-born; hemorrhagic fever |
| | Nairovirus | Crimean-Congo Hemorrhagic Fever virus | Mosquito-born; hemorrhagic fever |
| Arenaviridae | Arenavirus | Lymphocytic Choriomeningitis virus | Rodent-born; fever, aseptic meningitis |
| | | Lassa virus | Rodent-born; severe hemorrhagic fever (BL4 agents; also: Machupo, Junin) |
| | Deltavirus | Hepatitis Delta virus | Requires HBV to grow; hepatitis, liver cancer |
| Coronaviridae | Coronavirus | Human coronaviruses | Mild common cold-like illness |
| Astroviridae | Astrovirus | Human astroviruses | Gastroenteritis |
| Unclassified | "Hepatitis E-like viruses" | Hepatitis E virus | Hepatitis (acute); fecal-oral spread |

Human Immunodeficiency Virus-1 (HIV-1)

The combinations and conjugates described here, including Fve polypeptide combinations and conjugates, may be used to treat or prevent Human Immunodeficiency Virus (HIV) infection. The methods described here can therefore be used to prevent the development and establishment of diseases caused by or associated with human immunodeficiency virus, such as HIV-1 and HIV-2.

Human Immunodeficiency Virus (HIV) is a retrovirus which infects cells of the immune system, most importantly $CD4^+$ T lymphocytes. $CD4^+$ T lymphocytes are important, not only in terms of their direct role in immune function, but also in stimulating normal function in other components of the immune system, including $CD8^+$ T-lymphocytes. These HIV infected cells have their function disturbed by several mechanisms and/or are rapidly killed by viral replication. The end result of chronic HIV infection is gradual depletion of $CD4^+$ T lymphocytes, reduced immune capacity, and ultimately the development of AIDS, leading to death.

The regulation of HIV gene expression is accomplished by a combination of both cellular and viral factors. HIV gene expression is regulated at both the transcriptional and post-transcriptional levels. The HIV genes can be divided into the early genes and the late genes. The early genes, Tat, Rev, and Nef, are expressed in a Rev-independent manner. The mRNAs encoding the late genes, Gag, Pol, Env, Vpr, Vpu, and Vif require Rev to be cytoplasmically localized and expressed. HIV transcription is mediated by a single promoter in the 5' LTR. Expression from the 5' LTR generates a 9-kb primary transcript that has the potential to encode all nine HIV genes. The primary transcript is roughly 600 bases shorter than the provirus. The primary transcript can be spliced into one of more than 30 mRNA species or packaged without further modification into virion particles (to serve as the viral RNA genome).

Any of the HIV proteins disclosed here may be used as a viral infectious antigen for productions of conjugates and combinations as described above.

Herpes Virus

The combinations and conjugates described here, including Fve polypeptide combinations and conjugates, may be used to treat or prevent Herpesvirus infection. The methods described here can therefore be used to prevent the development and establishment of diseases caused by or associated with herpesvirus, for example HSV-1, HSV-2, HSV-7 and HSV-8.

Particular examples of herpesvirus include: herpes simplex virus 1 ("HSV-1"), herpes simplex virus 2 ("HSV-2"), human cytomegalovirus ("HCMV"), varicella-zoster virus ("VZV"), Epstein-Barr virus ("EBV"), human herpesvirus 6 ("HHV6"), herpes simplex virus 7 ("HSV-7") and herpes simplex virus 8 ("HSV-8").

Herpes viruses have also been isolated from horses, cattle, pigs (pseudorabies virus ("PSV") and porcine cytomegalovirus), chickens (infectious larygotracheitis), chimpanzees, birds (Marck's disease herpesvirus 1 and 2), turkeys and fish (see "Herpesviridae: A Brief Introduction", Virology, Second Edition, edited by B. N. Fields, Chapter 64, 1787 (1990)).

Herpes simplex viral ("HSV") infection is generally a recurrent viral infection characterized by the appearance on the skin or mucous membranes of single or multiple clusters of small vesicles, filled with clear fluid, on slightly raised inflammatory bases. The herpes simplex virus is a relatively large-sized virus. HSV-2 commonly causes herpes labialis. HSV-2 is usually, though not always, recoverable from genital lesions. Ordinarily, HSV-2 is transmitted venereally.

Diseases caused by varicella-zoster virus (human herpesvirus 3) include varicella (chickenpox) and zoster (shingles). Cytomegalovirus (human herpesvirus 5) is responsible for cytomegalic inclusion disease in infants. There is presently no specific treatment for treating patients infected with cytomegalovirus. Epstein-Barr virus (human herpesvirus 4) is the causative agent of infectious mononucleosis and has been associated with Burkitt's lymphoma and nasopharyngeal carcinoma. Animal herpesviruses which may pose a problem for humans include B virus (herpesvirus of Old World Monkeys) and Marmoset herpesvirus (herpesvirus of New World Monkeys).

Herpes simplex virus 1 (HSV-1) is a human pathogen capable of becoming latent in nerve cells. Like all the other members of Herpesviridae it has a complex architecture and double-stranded linear DNA genome which encodes for variety of viral proteins including DNA pol. and TK.

HSV gene expression proceeds in a sequential and strictly regulated manner and can be divided into at least three phases, termed immediate-early (IE or $\alpha$), early ($\beta$) and late ($\gamma$). The cascade of HSV-1 gene expression starts from IE genes, which are expressed immediately after lytic infection begins. The IE proteins regulate the expression of later classes of genes (early and late) as well as their own expression. The product of IE175k (ICP4) gene is critical for HSV-1 gene regulation and is mutants in this gene are blocked at IE stage of infection.

The IE genes themselves are activated by a virion structural protein VP16 (expressed late in the replicative cycle and incorporated into HSV particle). All 5 IE genes of HSV-1 (IE110k—2 copies/HSV genome, 1E175—2 copies/HSV genome, IE68k, IE63k and IE12k) have at least one copy of a conserved promoter/enhancer sequence—TAATGARAT. This sequence is recognized by the transactivation complex which consists of; Oct-1, HCF and VP16. The GARAT element is required for efficient transactivation by VP16. This mechanism of gene activation is unique for HSV and despite Oct-1 being a common transcription factor, the Oct-1/HCF/VP16 complex activates specifically only HSV IE genes.

Any of the herpesvirus proteins disclosed here may be used as a viral infectious antigen for productions of conjugates and combinations as described above.

Cytokines

In a further embodiment, the Fve polypeptide, nucleic acid, fragment, homologue, variant or derivative thereof is used to modulate cytokine levels in an individual. Preferably, the level of inflammatory cytokines is down-regulated. Examples of inflammatory cytokines include Granulocyte-Macrophage-Colony stimulating factor (GM-CSF), as well as any cytokine that mediates migration of alveolar macrophages into the lung and act to increase cell proliferation.

The term "cytokine" may be used to refer to any of a number of soluble molecules (e.g., glycoproteins) released by cells of the immune system, which act nonenzymatically through specific receptors to regulate immune responses. Cytokines resemble hormones in that they act at low concentrations bound with high affinity to a specific receptor. Preferably, the term "cytokine" refers to a diverse group of soluble proteins and peptides which act as humoral regulators at nano- to picomolar concentrations and which, either under normal or pathological conditions, modulate the functional activities of individual cells and tissues.

Particular examples of cytokines which are suitable for use in the methods and compositions described include interleukins, lymphokine, interferon, Colony Stimulating Factors (CSFs) such as Granulocyte-Colony Stimulating Factor (G-CSF), Macrophage-Colony stimulating factor (M-CSF) and Granulocyte-Macrophage-Colony stimulating factor (GM-CSF), GSF, Platelet-Activating Factors (PAF), Tumor Necrosis Factor (TNF).

Thus, interleukins such as IL1, IL2 and IL4, as well as interferons such as IFN-$\alpha$, IFN-$\beta$ and IFN-$\gamma$ are included. Tumour necrosis factors TNF-$\alpha$ (cachetin), TNF-$\beta$ (lymphotoxin) may also be suitably employed.

Preferred cytokines are those which are capable of recruiting immune responses, for example, stimulation of dendritic cell or cytotoxic T cell activity, or which are capable of recruiting macrophages to the target site. In a highly preferred embodiment, the cytokine comprises IL-2, GM-CSF or GSF.

Chemical Coupling

As noted above, the immunomodulator may be coupled to the allergen by a number of methods. Crosslinkers are divided into homobifunctional crosslinkers, containing two identical reactive groups, or heterobifunctional crosslinkers, with two different reactive groups. Heterobifunctional crosslinkers allow sequential conjugations, minimizing polymerization.

Any of the homobifunctional or heterobifunctional crosslinkers presented in the table below may be used to couple the allergen with the immunomodulator to produce an immunomodulator-allergen conjugate.

| Reagent | Cat. No. | Modified Group | Solubility | Comments | Refs |
|---|---|---|---|---|---|
| | | | Homobifunctional | | |
| BMME | 442635-Y | —SH | DMF, Acetone | Homobifunctional crosslinker useful for formation of conjugates via thiol groups. | Weston, P. D., et al. 1980. Biochem. Biophys Acta. 612, 40. |
| BSOCOES | 203851-Y | —NH2 | Water | Base cleavable crosslinker useful for studying receptors and mapping surface polypeptide antigens on lymphocytes. | Howard, A. D., et al. 1985. J. Biol. Chem.260, 10833. |
| DSP | 322133-Y | —NH2 | Water | Thiol cleavable crosslinker used to immobilize proteins on supports containing amino groups. | Lee, W. T., and Conrad, D. H. 1985. J. Immunol.134, 518. |
| DSS | 322131-Y | —NH2 | Water | Non-cleavable, membrane impermeable crosslinker widely used for conjugating radiolabeled ligands to cell surface receptors and for detecting conformational changes in membrane proteins. | D'Souza, S. E., et al. 1988. J. Biol. Chem.263, 3943. |
| EGS | 324550-Y | —NH2 | DMSO | Hydroxylamine cleavable reagent for crosslinking and reversible immobilization of proteins through their primary amine groups. Useful for studying structure-function relationships. | Geisler, N., et al. 1992. Eur. J. Biochem.206, 841.14. Moenner, M., et al. 1986. Proc. Natl. Acad. Sci. USA83, 5024. |
| EGS, Water Soluble | 324551-Y | —NH2 | Water | Water soluble version of EGS that reacts rapidly with dilute proteins at neutral pH. Crosslinked proteins are readily cleaved with hydroxylamine at pH 8.5 for 3-6 hours, 37° C. | Yanagi, T., et al. 1989. Agric. Biol. Chem.53, 525. |
| Glutaraldehyde | 354400-Y | —OH | Water | Used for crosslinking proteins and polyhydroxy materials. Conjugates haptens to carrier proteins; also used as a tissue fixative. | Harlow, E., and Lane, D. 1988. Antibodies: A Laboratory Manual, Cold Spring Harbor Publications, N.Y., p. 349. |
| SATA | 573100-Y | —NH2 | DMSO | Introduces protected thiols via primary amines. When treated with hydroxylamine, yields a free sulhydryl group that can be conjugated to maleimide-modified proteins. | Duncan, R. J. S., et al. 1983. Anal. Biochem.132, 68. |
| | | | Heterobifunctional | | |
| GMBS | 442630-Y | —NH2, —SH | DMSO | Heterobifunctional crosslinker useful for preparing enzyme-antibody conjugates (e.g. □-gal-IgG) and for immobilizing enzymes on solid supports. | Kitagwa, T., et al. 1983. J. Biochem.94, 1160.19. Rusin, K. M., et al. 1992. Biosens. Bioelectron.7, 367. |
| MBS | 442625-Y 442626-Y | —NH2, —SH —NH2, —SH | DMSO, Water | Thiol cleavable, heterobifunctional reagent especially useful for preparing peptide-carrier conjugates and conjugating toxins to antibodies. | Green, N., et al. 1982. Cell 28, 477. |
| PMPI | 528250-Y | —SH2, —OH | DMSO, DMF | Used in the preparation of alkaline phosphatase conjugates of estradiol, progesterone, serine-enriched peptides, and vitamin B12. | Aithal, H. N., et al. 1988. J. Immunol. Methods112, 63. |
| SMCC | 573114-Y 573115-Y | —NH2, —SH —NH2, —SH | DMF, AN Acetonitrile Water | Heterobifunctional reagent for enzyme labeling of antibodies and antibody fragments. The cyclohexane bridge provides extra stability to the maleimide group. Ideal reagent for preserving enzyme activity and antibody specificity after coupling. | Annunziato, M. E., et al. 1993. Bioconjugate Chem.4, 212. |
| SPDP | 573112-Y | —NH2, —SH | DMF, AN Acetonitrile | Introduces protected thiol groups to amine groups. Thiolated proteins can be coupled to a second molecule via an iodoacetamide or maleimide group, or to a | Caruelle, D., et al. 1988. Anal. Biochem.173, 328. |

| Reagent | Cat. No. | Modified Group | Solubility | Comments | Refs |
|---------|----------|----------------|------------|----------|------|
| | | | | second pyridyldisulfide containing molecule. | |

Each of these reagents may be obtained from a number of manufacturers, for example, from Calbiochem (catalogue number in column 2), or Piece Chemical Company.

Pharmaceutical Compositions

Fve polypeptides may be produced in large amounts at low cost in a bioactive form, allowing the development of Fve containing formulations by aerosolisation, nebulisation, intranasal or intratracheal administration.

While it is possible for the composition comprising the Fve polypeptide or nucleic acid to be administered alone, it is preferable to formulate the active ingredient as a pharmaceutical formulation. We therefore also disclose pharmaceutical compositions comprising Fve polypeptide or nucleic acid, or a fragment, homologue, variant or derivative thereof. Such pharmaceutical compositions are useful for delivery of Fve polypeptide, nucleic acid, fragment, homologue, variant or derivative thereof to an individual for the treatment or alleviation of symptoms as described.

The composition may include the Fve polypeptide, nucleic acid, fragment, homologue, variant or derivative thereof, a structurally related compound, or an acidic salt thereof. The pharmaceutical formulations comprise an effective amount of Fve polypeptide, nucleic acid, fragment, homologue, variant or derivative thereof, together with one or more pharmaceutically-acceptable carriers. An "effective amount" of an Fve polypeptide, nucleic acid fragment, homologue, variant or derivative thereof is the amount sufficient to alleviate at least one symptom of a disease as described.

The effective amount will vary depending upon the particular disease or syndrome to be treated or alleviated, as well as other factors including the age and weight of the patient, how advanced the disease etc state is, the general health of the patient, the severity of the symptoms, and whether the Fve polypeptide, nucleic acid, fragment, homologue, variant or derivative thereof is being administered alone or in combination with other therapies.

Suitable pharmaceutically acceptable carriers are well known in the art and vary with the desired form and mode of administration of the pharmaceutical formulation. For example, they can include diluents or excipients such as fillers, binders, wetting agents, disintegrators, surface-active agents, lubricants and the like. Typically, the carrier is a solid, a liquid or a vaporizable carrier, or a combination thereof. Each carrier should be "acceptable" in the sense of being compatible with the other ingredients in the formulation and not injurious to the patient. The carrier should be biologically acceptable without eliciting an adverse reaction (e.g. immune response) when administered to the host.

The pharmaceutical compositions disclosed here include those suitable for topical and oral administration, with topical formulations being preferred where the tissue affected is primarily the skin or epidermis (for example, psoriasis, eczema and other epidermal diseases). The topical formulations include those pharmaceutical forms in which the composition is applied externally by direct contact with the skin surface to be treated. A conventional pharmaceutical form for topical application includes a soak, an ointment, a cream, a lotion, a paste, a gel, a stick, a spray, an aerosol, a bath oil, a solution and the like. Topical therapy is delivered by various vehicles, the choice of vehicle can be important and generally is related to whether an acute or chronic disease is to be treated. Other formulations for topical application include shampoos, soaps, shake lotions, and the like, particularly those formulated to leave a residue on the underlying skin, such as the scalp (Arndt et al, in Dermatology In General Medicine 2:2838 (1993)).

In general, the concentration of the Fve polypeptide, nucleic acid, fragment, homologue, variant or derivative thereof composition in the topical formulation is in an amount of about 0.5 to 50% by weight of the composition, preferably about 1 to 30%, more preferably about 2-20%, and most preferably about 5-10%. The concentration used can be in the upper portion of the range initially, as treatment continues, the concentration can be lowered or the application of the formulation may be less frequent. Topical applications are often applied twice daily. However, once-daily application of a larger dose or more frequent applications of a smaller dose may be effective. The stratum corneum may act as a reservoir and allow gradual penetration of a drug into the viable skin layers over a prolonged period of time.

In a topical application, a sufficient amount of active ingredient must penetrate a patient's skin in order to obtain a desired pharmacological effect. It is generally understood that the absorption of drug into the skin is a function of the nature of the drug, the behaviour of the vehicle, and the skin. Three major variables account for differences in the rate of absorption or flux of different topical drugs or the same drug in different vehicles; the concentration of drug in the vehicle, the partition coefficient of drug between the stratum corneum and the vehicle and the diffusion coefficient of drug in the stratum corneum. To be effective for treatment, a drug must cross the stratum corneum which is responsible for the barrier function of the skin. In general, a topical formulation which exerts a high in vitro skin penetration is effective in vivo. Ostrenga et al (J. Pharm. Sci., 60:1175-1179 (1971) demonstrated that in vivo efficacy of topically applied steroids was proportional to the steroid penetration rate into dermatomed human skin in vitro.

A skin penetration enhancer which is dermatologically acceptable and compatible with the agent can be incorporated into the formulation to increase the penetration of the active compound(s) from the skin surface into epidermal keratinocytes. A skin enhancer which increases the absorption of the active compound(s) into the skin reduces the amount of agent needed for an effective treatment and provides for a longer lasting effect of the formulation. Skin penetration enhancers are well known in the art. For example, dimethyl sulfoxide (U.S. Pat. No. 3,711,602); oleic acid, 1,2-butanediol surfactant (Cooper, J. Pharm. Sci., 73:1153-1156 (1984)); a combination of ethanol and oleic acid or oleyl alcohol (EP 267,617), 2-ethyl-1,3-hexanediol (WO 87/03490); decyl methyl sulphoxide and Azone® (Hadgraft, Eur. J. Drug. Metab. Pharmacokinet, 21:165-173 (1996)); alcohols, sulphoxides, fatty acids, esters, Azone®, pyrrolidones, urea and polyoles (Kalbitz et al, Pharmazie, 51:619-637 (1996));

Terpenes such as 1,8-cineole, menthone, limonene and nerolidol (Yamane, J. Pharmacy & Pharmocology, 47:978-989 (1995)); Azone® and Transcutol (Harrison et al, Pharmaceutical Res. 13:542-546 (1996)); and oleic acid, polyethylene glycol and propylene glycol (Singh et al, Pharmazie, 51:741-744 (1996)) are known to improve skin penetration of an active ingredient.

Levels of penetration of an agent or composition can be determined by techniques known to those of skill in the art. For example, radiolabeling of the active compound, followed by measurement of the amount of radiolabeled compound absorbed by the skin enables one of skill in the art to determine levels of the composition absorbed using any of several methods of determining skin penetration of the test compound. Publications relating to skin penetration studies include Reinfenrath, W G and G S Hawkins. The Weaning Yorkshire Pig as an Animal Model for Measuring Percutaneous Penetration. In:Swine in Biomedical Research (M. E. Tumbleson, Ed.) Plenum, New York, 1986, and Hawkins, G. S. Methodology for the Execution of 1n Vitro Skin Penetration Determinations. In: Methods for Skin Absorption, B W Kemppainen and W G Reifenrath, Eds., CRC Press, Boca Raton, 1990, pp. 67-80; and W. G. Reifenrath, Cosmetics & Toiletries, 110:3-9 (1995).

For some applications, it is preferable to administer a long acting form of agent or composition using formulations known in the arts, such as polymers. The agent can be incorporated into a dermal patch (Junginger, H. E., in Acta Pharmaceutica Nordica 4:117 (1992); Thacharodi et al, in Biomaterials 16:145-148 (1995); Niedner R., in Hautarzt 39:761-766 (1988)) or a bandage according to methods known in the arts, to increase the efficiency of delivery of the drug to the areas to be treated.

Optionally, the topical formulations can have additional excipients for example; preservatives such as methylparaben, benzyl alcohol, sorbic acid or quaternary ammonium compound; stabilizers such as EDTA, antioxidants such as butylated hydroxytoluene or butylated hydroxanisole, and buffers such as citrate and phosphate.

The pharmaceutical composition can be administered in an oral formulation in the form of tablets, capsules or solutions. An effective amount of the oral formulation is administered to patients 1 to 3 times daily until the symptoms of the disease alleviated. The effective amount of agent depends on the age, weight and condition of a patient. In general, the daily oral dose of agent is less than 1200 mg, and more than 100 mg. The preferred daily oral dose is about 300-600 mg. Oral formulations are conveniently presented in a unit dosage form and may be prepared by any method known in the art of pharmacy. The composition may be formulated together with a suitable pharmaceutically acceptable carrier into any desired dosage form. Typical unit dosage forms include tablets, pills, powders, solutions, suspensions, emulsions, granules, capsules, suppositories. In general, the formulations are prepared by uniformly and intimately bringing into association the agent composition with liquid carriers or finely divided solid carriers or both, and as necessary, shaping the product. The active ingredient can be incorporated into a variety of basic materials in the form of a liquid, powder, tablets or capsules to give an effective amount of active ingredient to treat the disease.

Other therapeutic agents suitable for use herein are any compatible drugs that are effective for the intended purpose, or drugs that are complementary to the agent formulation. The formulation utilized in a combination therapy may be administered simultaneously, or sequentially with other treatment, such that a combined effect is achieved.

The invention is described further, for the purpose of illustration only, in the following examples.

EXAMPLES

In each of the Examples presented below, where an activity is described for a Fve polypeptide comprising a GST (glutathione S transferase) portion (for example, as a GST-FIP fusion protein), we find that the polypeptide itself, without the GST portion, has substantially the same activity. This is to be expected, as the GST domain does not have any relevant biological activity as far as FIP is concerned.

Example 1

Isolation and Purification of Native Fve Protein from Golden Needle Mushroom

Methods and Materials

Two kilograms of the fruit bodies of *Flammulina velutipes* are homogenized with 2 L ice-cold 5% acetic acid in the presence of 0.05 M 2-mercaptoethanol and 0.3 M sodium chloride. The proteins in the supernatant are precipitated by 95% saturated ammonium sulfate.

The precipitate is re-dissolved and dialyzed against 10 mM Tris-HCl pH 8.5 (buffer A) at 4° C. for 48 hours with six to eight changes of dialysis buffer. The protein solution is applied to the Q Sepharose FF column (2.6×10 cm, Pharmacia) that has been previously equilibrated with buffer A. The unbound fraction is collected and dialyzed against 10 mM sodium acetate pH 5.0 (buffer B) at 4° C. for 48 hours with six to eight changes of dialysis buffer and then further purified by applying to the SP Sepharose FF column (2.6×10 cm, Pharmacia) that has been previously equilibrated with buffer B.

The protein is eluted with a gradient of 0-0.5 M NaCl in buffer B. Fractions containing Fve protein are collected and analyzed by a 7.5% Tris-Tricine SDS-PAGE.

Results

High Yield of Native Fve Protein is Purified from *Flammulina velutipes*

Figure 1:
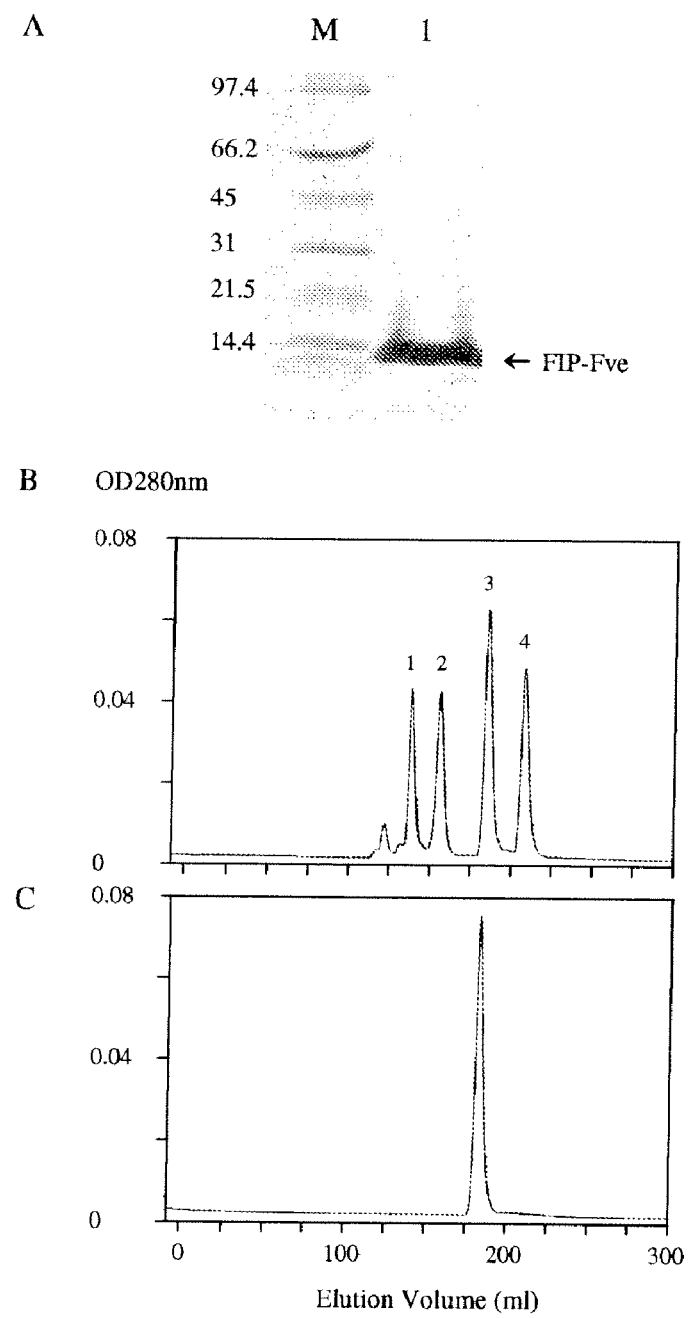
FIG. 1. Analysis of purified native Fve by SDS-PAGE and gel filtration chromatography. (a). The native Fve protein purified by cation and anion exchange chromatography is analyzed by Tricine SDS-PAGE. Fve protein gave a single band with an apparent molecular mass of 12.7 kDa. Lane M, molecular mass markers; lane 1, purified native Fve protein. (b) Elution profile of calibration proteins by Superdex 75 chromatography. Peaks, 1. bovine serum albumin (67 kDa); 2. ovalbumin (43 kDa); 3. chymotrypsinogen A (25 kDa); 4. ribonuclease A (13.7 kDa). (c) Purified native Fve formed homodimer at 25.5 kDa.

The native Fve protein has an apparent molecular weight of 12.7 kDa as determined by SDS-PAGE (FIG. 1A). However, it appears to be a homodimer with a molecular weight of 25.5 kDa as determined by Superdex 75 (26×60 cm, Pharmacia) gel filtration chromatography (FIGS. 1B and 1C). The running buffer for gel filtration is 10 mM Tris-HCl pH 7.5, 0.2 M sodium chloride.

Fve protein is the major component in the crude extract from the mushroom fruit bodies. By removing the cap of the mushroom, we managed to reduce the amount of polysaccharides that cause undesirable interference in the process of protein purification.

The yield of native Fve protein is 40 mg from 1 kg wet-weight of starting material.

Example 2

Measurement of Gene Expression Profile at mRNA Level after Fve Stimulation

Methods and Materials

Two subsets of effector Th cells have been defined on the basis of their distinct cytokine secretion patterns and immunomodulatory effects (Mosmann et al., 1989; Paul and seder, 1994; Abbas et al., 1996). Th1 cells produce inflammatory cytokines, such as IFN-γ, TNF-α, IL-12, IL-15 and IL-18, and enhance cellular immunity mediated by macrophages. In contrast, Th2 cells produce a different group of cytokines, such as IL-4, IL-5, IL-6 and IL-13. The differentiation of precursor T cells into Th1 or Th2 cells has important biologic implication in terms of susceptibility or resistance to a particular disease.

In order to characterize the cytokines expression pattern induced by Fve, human PBMC from healthy donor and splenocytes from 8 week-old BALB/cJ mice are collected and cultured with 20 µg of native Fve. The mRNA is extracted at 48 hours using RNeasy Mini mRNA Purification Kit (QIAGEN). First-strand cDNA is then generated from the mRNA template using oligo-dT primers and MMLV reverse transcriptase (Promega).

PCR reactions are performed with Taq polymerase (Promega) with standard conditions and optimized annealing temperatures. The amplified products are analysed by electrophoresis in 1.5% agarose gel containing ethidium bromide (0.5 µg/ml) and photographed with UV exposure. Messenger RNA for various cytokines and transcription factors are measured. House keeping genes mRNA for hypoxanthine ribosyl-transferase (HPRT) and cyclophilin are used as internal controls.

Results

Enhanced Expression of IFN-γ, TNF-α, IL-1β, IL-2, IRF-1, c-Rel, Bcl-$X_L$, ICAM-1, and iNOS mRNA Human PBMC and spleen cells from BALB/cJ mice are cultured with 20 µg of Fve and analyzed for cytokine mRNA expression at 48 hr. The results indicated that there is an increase in IFN-γ, TNF-α, iNOS mRNA production by spleen cells cultured with Fve protein. Mouse IL-12 remains unchanged. This phenomenon occurred in a dose dependent manner.

Figure 2:
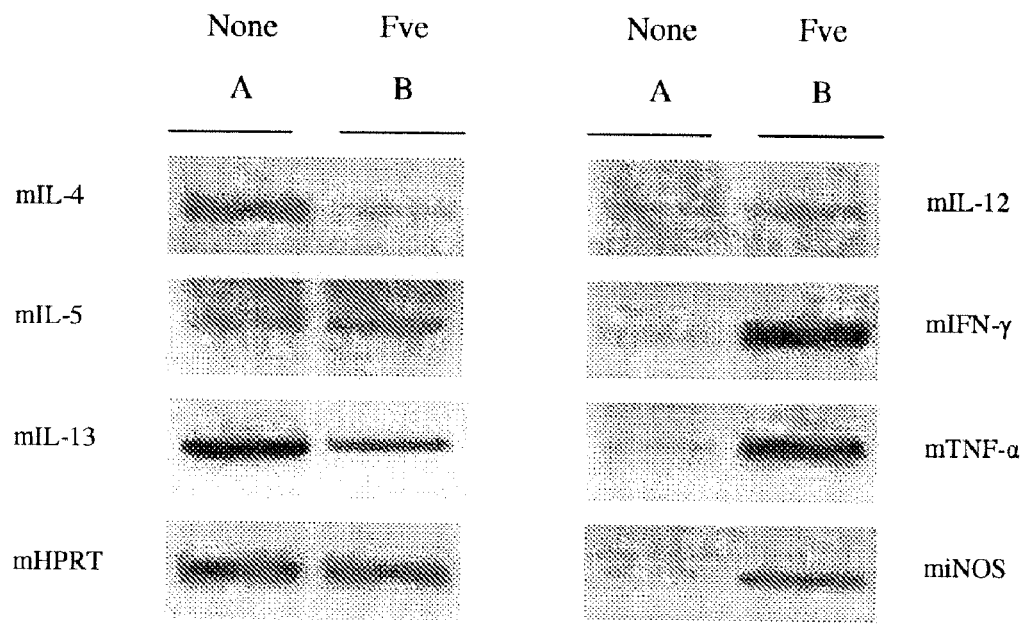
FIG. 2 shows a profile of cytokines and iNOS produced by mouse splenocytes upon stimulation with Fve protein. Mouse spleen cells from Balb/cJ mice are stimulated with 20 µg of Fve. The mRNAs of cytokines are analyzed by RT-PCR after culturing for 48 hours. A: A non-stimulated culture as negative controls, B: A culture stimulated with 20 µg of Fve.
Figure 3:
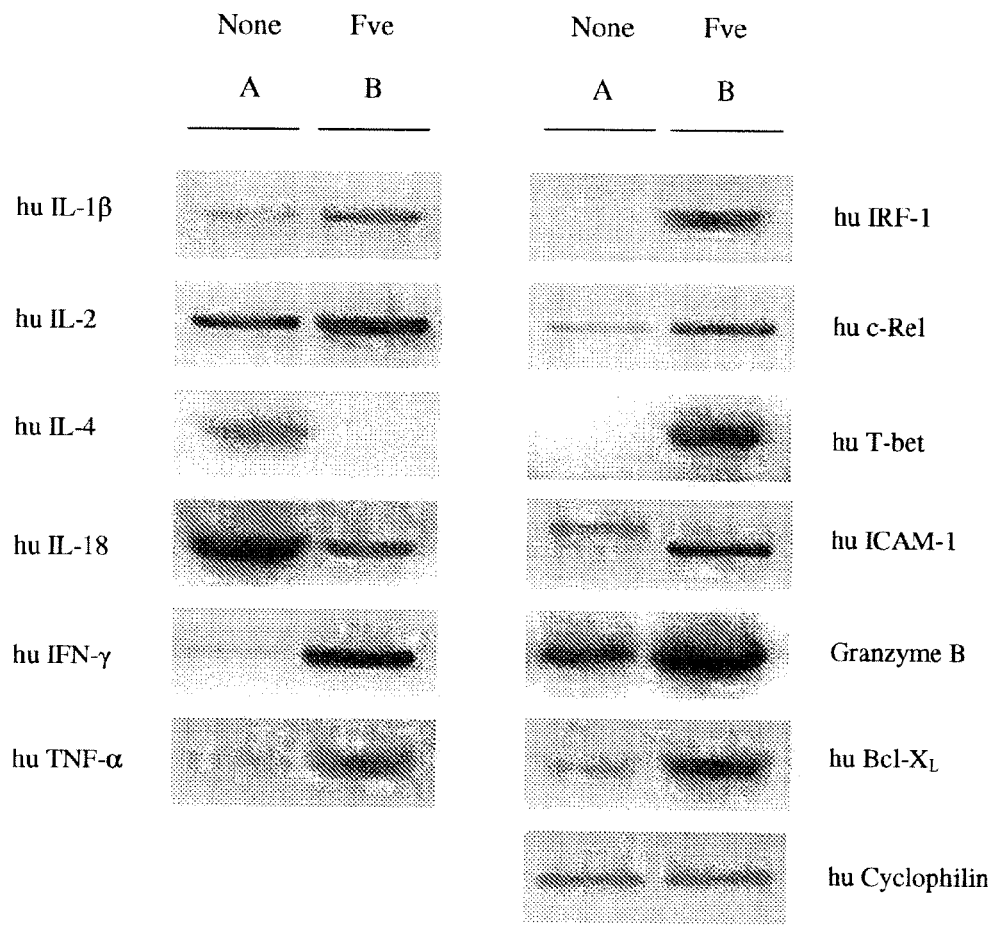
FIG. 3 shows a profile of human cytokines, transcriptional factors, adhesion molecule and anti-apoptotic protein produced by human PBMC upon stimulation with Fve protein. Human PBMC from healthy donor are stimulated with 20 µg of Fve. The mRNA expression is analyzed by RT-PCR after culturing for 48 hours. A: A non-stimulated culture as negative control, B: A culture stimulated with 20 µg of Fve.
Figure 4:
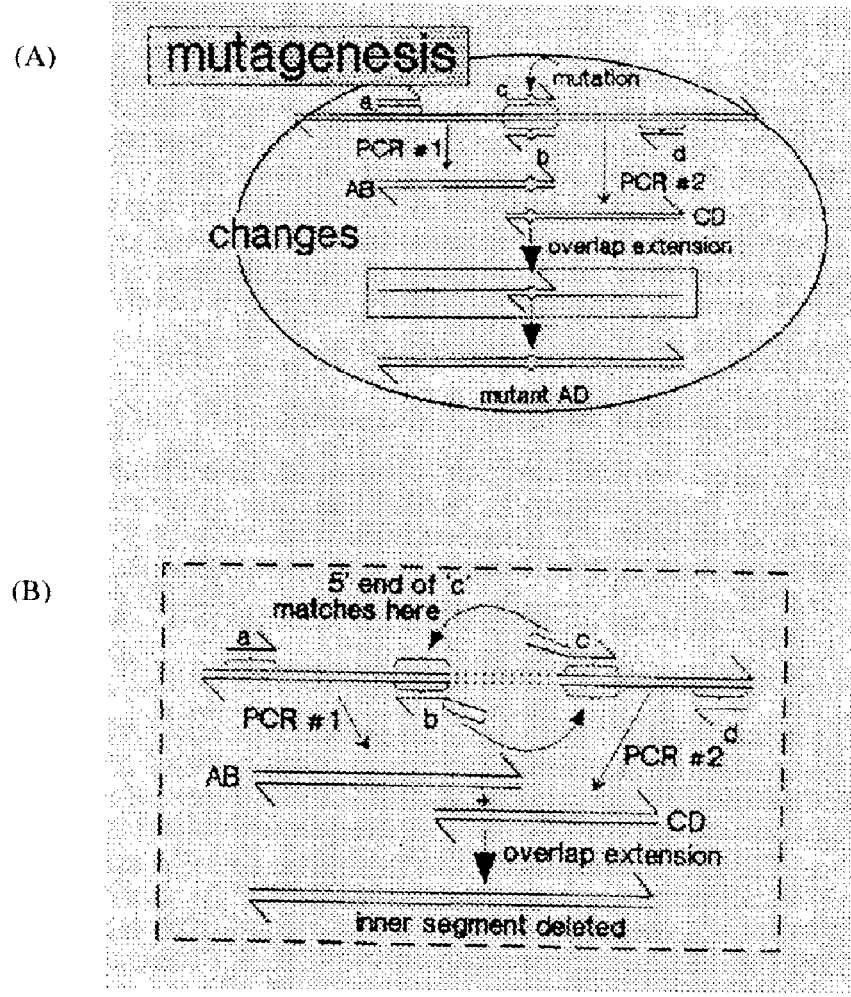
FIG. 4. A schematic representation showing the principle of overlap extension PCR for the generation of single amino acid residue substitution (A) and deletion mutagenesis of DNA (B).
Figure 5:
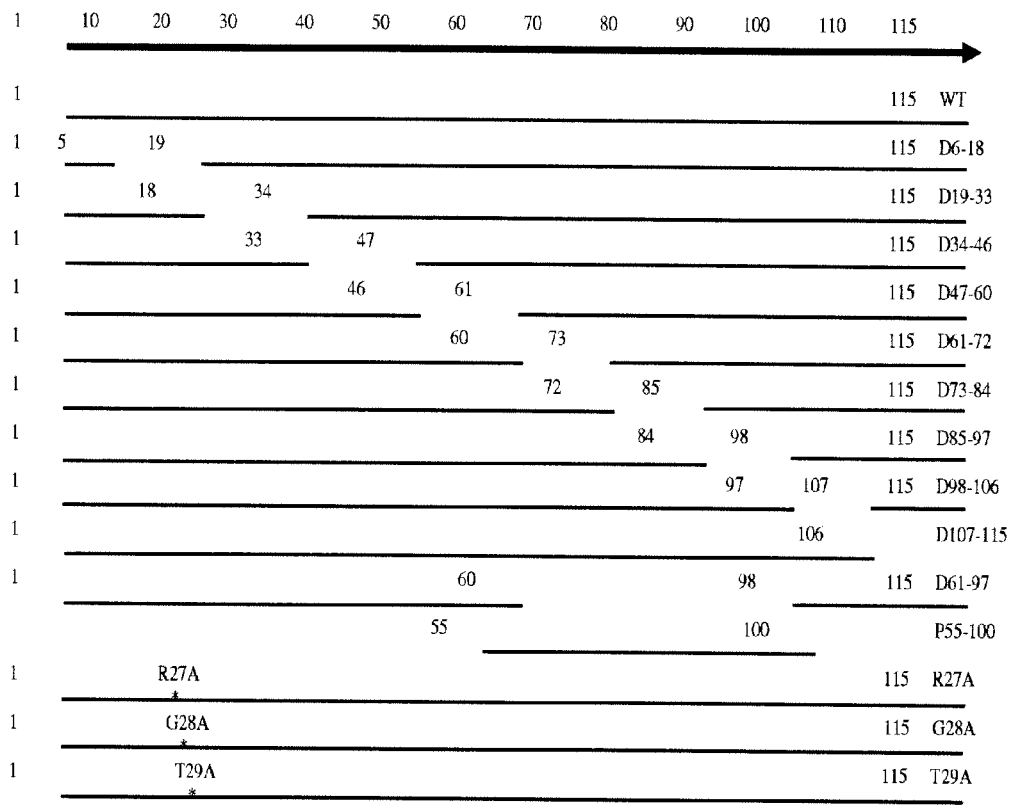
FIG. 5. A schematic representation of the strategy used to generate mutants. On the basis of the structures predicted by PHD prediction program, eleven deletion mutants and three point mutants of Fve plasmid DNA are generated by PCR-based mutagenesis.
Figure 6:
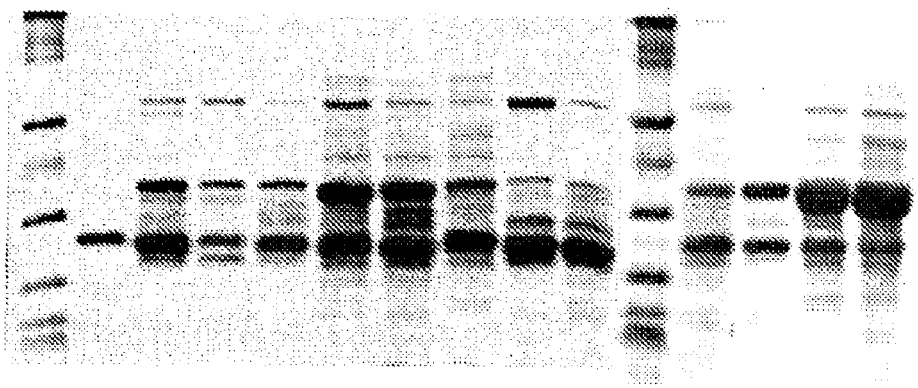
FIG. 6. SDS-PAGE analysis of recombinant Fve mutant proteins.

Similar results are seen in human PBMC. The mRNA for human cytokines IL-1β, IL-2, IFN-γ and TNF-α; transcription factor IRF-1 and c-Rel; adhesion molecule ICAM-1 and anti-apoptotic protein Bcl-$X_L$ is up regulated after Fve stimulation. FIG. 2 and FIG. 3 show the patterns of mRNA expression for transcription factors, cytokines and adhesion molecules of the splenocytes and PBMC stimulated by Fve.

Example 3

Generation of Fve Mutants By PCR-Based Mutagenesis

Materials and Methods

A cDNA encoding for the Fve protein is cloned into the BamHI and EcoRI site of pGEX-4T1. This DNA template is used to generate a panel of mutants by recombinant-PCR method (FIG. 4). A schematic representation of the strategy used to generate mutants is shown in FIG. 5.

As predicted by PHD prediction program, Fve contains one α-helix, six β-strands and two β-turns. Each of these predicted secondary structures is serially deleted by recombinant-PCR method. In addition, we also examined the potential function of the R27, G28, T29 residues, which resembles the cell aggregating RGD motif, located in the N-terminal β-turn of Fve protein by point mutation. Each of the amino acid residues of RGT is substituted by alanine residue.

A partial list of fragments of Fve is shown in Appendix B.

Example 4

Production of the Fve-Derived Mutant Proteins

Materials and Methods

Eleven deletion mutants and three point mutants of Fve DNA are generated. Each of the polypeptides is expressed in TG1 *E. coli* cells as fusion protein with GST carrier protein and purified by glutathione affinity column. All the mutants could express protein except insoluble mutant D6-18, in which α-helix has been deleted.

FIG. 6 shows the panel of the affinity purified mutant proteins on a SDS-PAGE. These purified proteins are used for the cell aggregation, hemagglutination and lymphocytes proliferation assay.

Example 5

Comparison of Hemagglutination Activity of Fve Mutants

Materials and Methods 5 ml of whole human blood obtained from a healthy volunteer is centrifuged at 2500×g for 10 min. The plasma is removed and 2 ml of packed red blood cells are collected from the bottom of the tube.

The red blood cells (RBC) are diluted 5× with 1×PBS buffer and centrifuged at 1200×g for 10 min. RBC pellet is resuspended in 1.5% (v/v) of 1×PBS. 50 ul of 2×serial dilutions (from 64 μg/ml to 0.25 μg/ml) of each Fve mutant protein is added into 50 ul of 0.2% gelatin in 1×PBS (pH 7.4) and then mixed with 100 ul of 1.5% RBC in each well of the 96-well round bottom microtiter plates. Cells are incubated at room temperature and examined for hemagglutination after 2 hours and over night, respectively (Table 1).

Example 6

Lymphocytes Aggregation Activity of Fve and its Mutants

Materials and Methods

Human peripheral blood mononuclear cells (PBMC) from a healthy donor are isolated and cells are then cultured with 20 μg/ml of various Fve mutants in 24-well plates. Cells aggregation is observed by inverted light microscopy after 24 hours (Table 1).

Results

Mutant GST-FveG28A Lost the Hemagglutination and Lymphocytes Aggregation Activity Native Fve, GST-Fve (wild type) and two point mutants, GST-FveR27A and GST-FveT29A, show positive aggregation and hemagglutination activity. These properties are not seen in all the deletion mutants and a point mutant GST-FveG28A. PHA and ConA are used as positive controls; GST and Blo t 5 are used as negative controls. These results are summarized in Table 1.

The Arg-Gly-Asp (RGD) tripeptide sequence is the most common molecular recognition site implicated in several immunological reactions. Normally RGD motif is located in the β-turn structure. According to the PHD prediction, residue 19 to 33 is a β-turn structure. Therefore, we propose that glycine residue of RGT (RGD-like motif) tripeptide sequence at position 28 plays an important role on lymphocyte aggregation/adhesion. The potentially interaction between Fve and the proteins of integrin family will be addressed.

TABLE 1

Lymphocytes aggregation and RBC hemagglutination activities of Fve mutants

|         | Cell aggregation | Hemagglutination |
|---------|------------------|------------------|
| D19-33  | −                | −                |
| D34-46  | −                | −                |
| D47-60  | −                | −                |
| D61-72  | −                | −                |
| D73-84  | −                | −                |
| D85-97  | −                | −                |
| D98-106 | −                | −                |
| D107-115| −                | −                |
| P55-100 | −                | −                |
| D61-97  | −                | −                |
| *R27A   | +                | +                |
| **G28A  | −                | −                |
| ***T29A | +                | +                |
| rGST-Fve| +                | +                |
| nFve    | +                | +                |
| GST     | −                | −                |
| Blo t 5 | −                | −                |
| ConA    | +                | +                |
| PHA     | +                | +                |

Example 7

Lymphoproliferation Activity of Fve Mutants

Materials and Methods

Splenocytes from Balb/cJ mice and peripheral blood mononuclear cells (PBMC) from a healthy donor are stimulated with 2.5 μg/ml, 5 μg/ml, 10 μg/ml or 20 μg/ml respectively of Fve mutant proteins for 24 hours. Then 1 μCi [$^3$H]-thymidine is added to the culture and further incubated for 18 hours. [$^3$H]-thymidine incorporation is measured in triplicates by a β counter (Beckman).

Results

Figure 7:
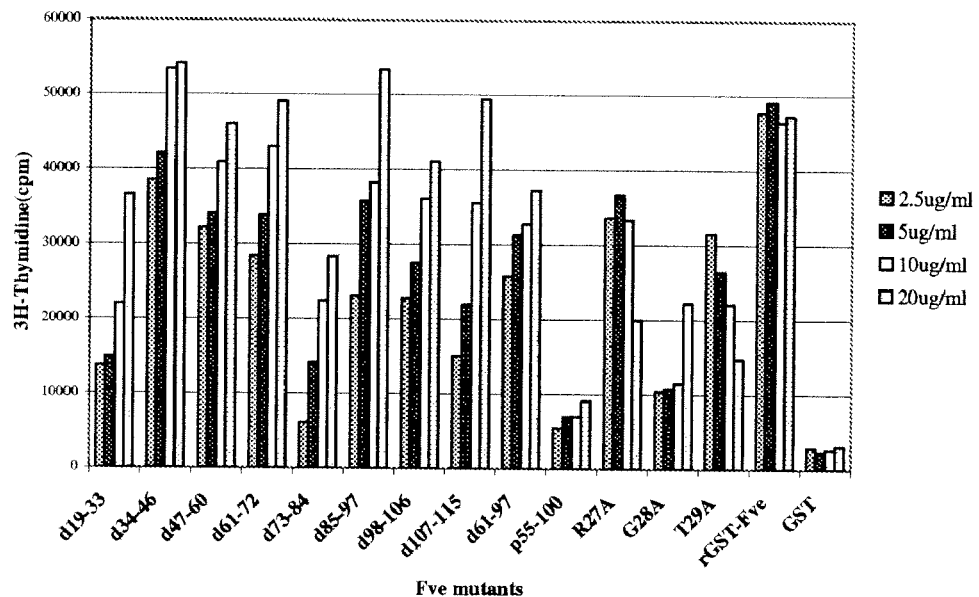
FIG. 7. In vitro proliferation assay of mouse splenocytes. Mouse splenocytes from Balb/cJ is stimulated with 2.5 µg/ml, 5 µg/ml, 10 µg/ml, and 20 µg/ml, respectively, with 13 of Fve mutant proteins for 48 hours. Recombinant GST-Fve is positive control. GST is negative control.
Figure 8:
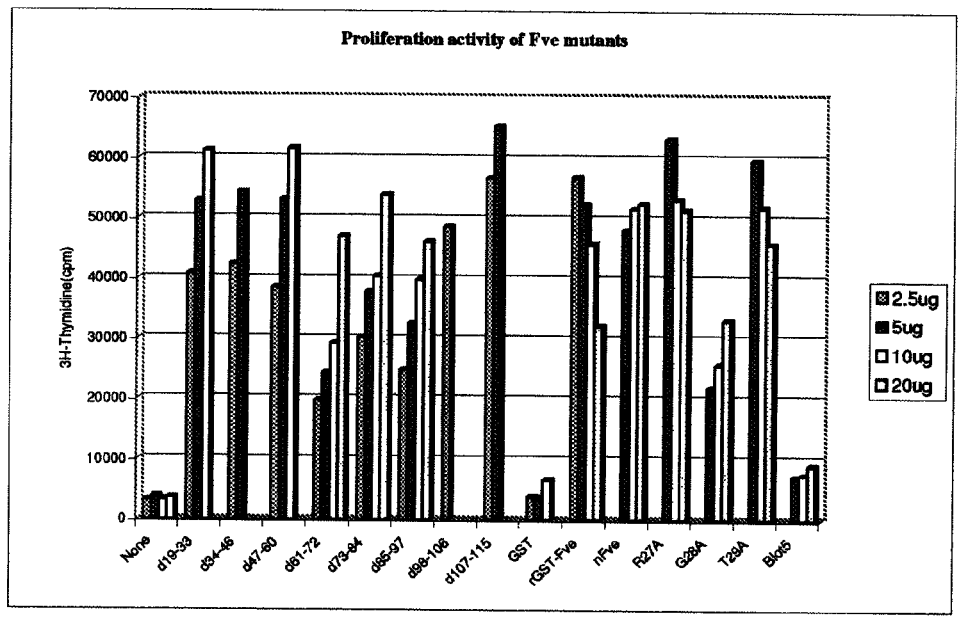
FIG. 8. Lymphoproliferation activity of human PBMC at 48 hours. Human PBMC from a healthy donor is stimulated with 2.5 µg/ml, 5 µg/ml, 10 µg/ml, and 20 µg/ml, respectively, with eleven of Fve mutant proteins for 48 hours. Recombinant GST-Fve and native Fve are positive control. GST and Blo t 5 are negative control.
Figure 9:
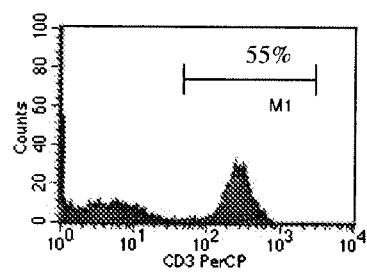
FIG. 9. Recombinant GST-Fve (wild type) and GST-FveT29 mutant protein showed strong lymphoproliferative activity. Human PBMC from healthy donor are cultured with: (A) no antigen, (B) GST, (C) wild type GST-Fve, (D) GST-FveT29, each protein is used at 20 µg/ml. The percentage of CD3$^+$ T lymphocytes is analyzed at day 5 by using flow cytometry.
Figure 9:
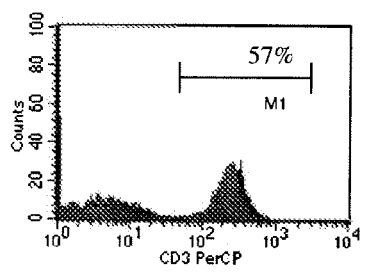
Figure 9:
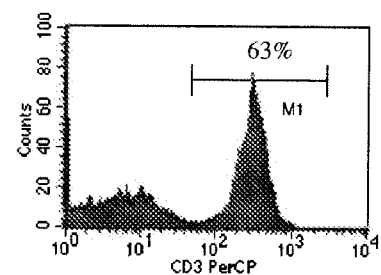
Figure 9:
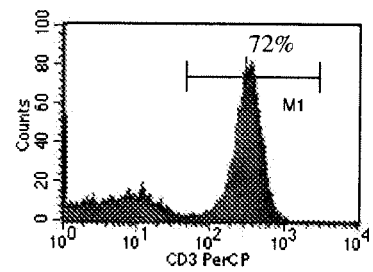
Figure 10:
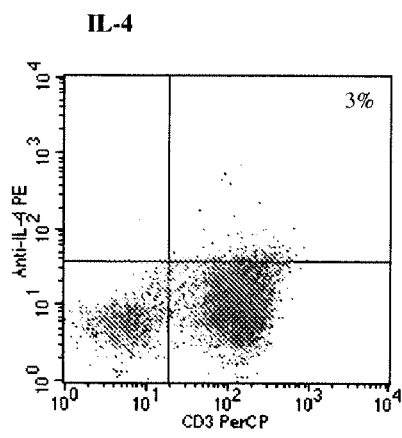
FIG. 10. Increased production of TNF-α, IFN-γ, IL-2 but not IL-4 in CD3$^+$ T lymphocytes after stimulation with native Fve protein. The production of (A) IL-4; (B) IL-2; (C) IFN-γ and (D) TNF-α by human PBMC after stimulation with 20 µg/ml of native Fve protein for three days. The data are analyzed by flow cytometry.
Figure 10:
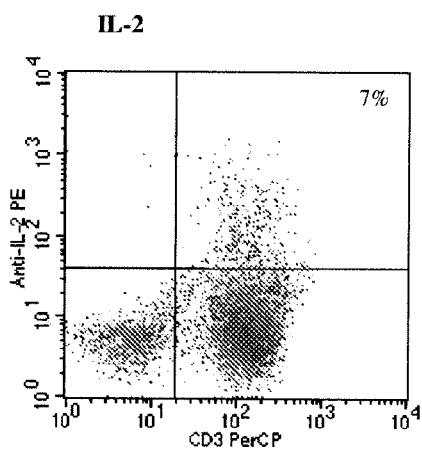
Figure 10:
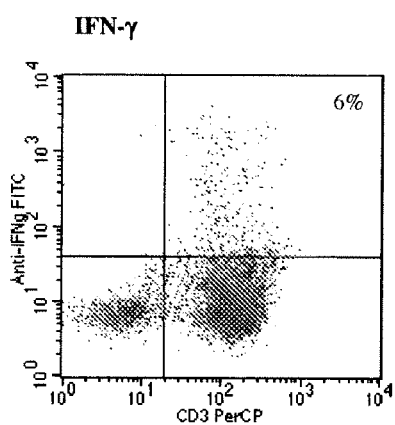
Figure 10:
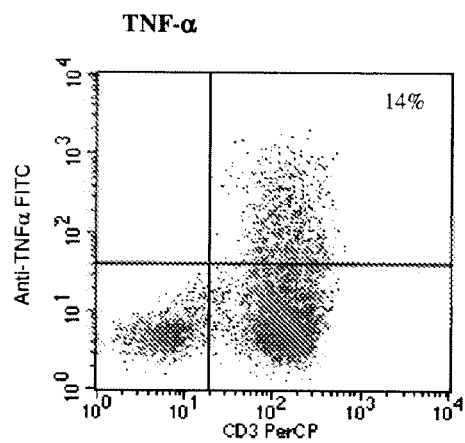
Figure 11:
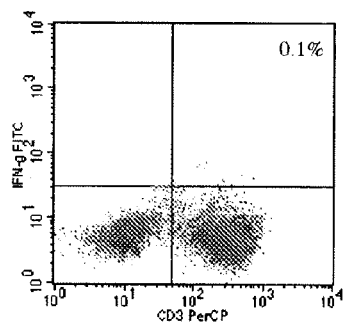
FIG. 11. Recombinant wild type GST-Fve and mutant GST-FveT29A, but not mutant GST-FveG28A, maintained IFN-γ cytokine production activity. Human PBMC from healthy donor are cultured with 20 µg of GST (1); GST-Fve (2); GST-FveR27A (3); GST-FveG28A (4); GST-FveT29A (5). IFN-γ cytokine by T cells is detected at day 3 by staining with anti-CD3 PerCP and anti-IFN-γ FITC specific monoclonal antibody. IFN-γ secretion by small granular lymphocytes and large granular lymphocytes are shown in (a) and (b), respectively. The total amount of IFN-γ production by T cells is the sum of (a) and (b).
Figure 11:
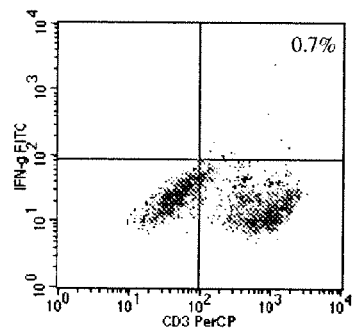
Figure 11:
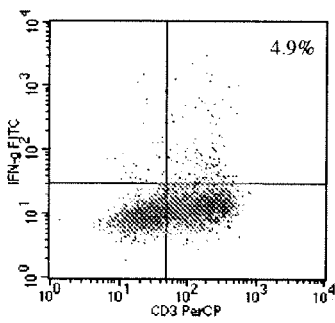
Figure 11:
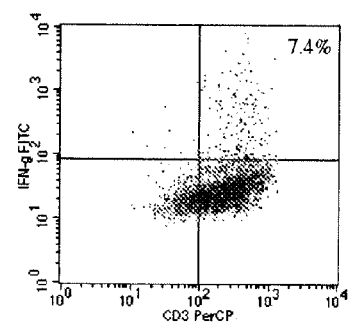
Figure 11:
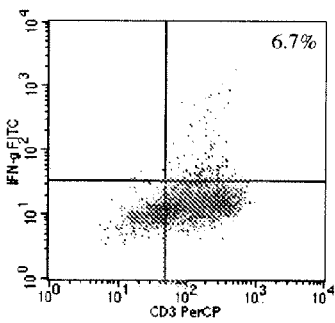
Figure 11:
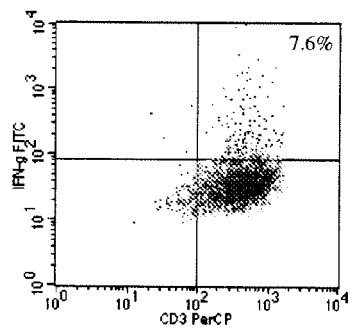
Figure 11:
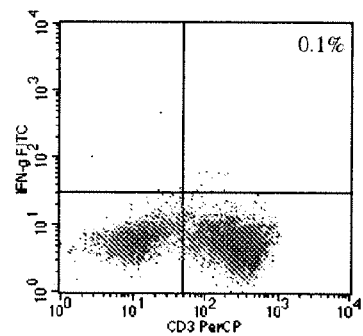
Figure 11:
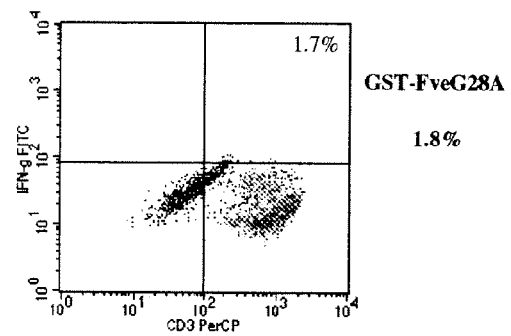
Figure 11:
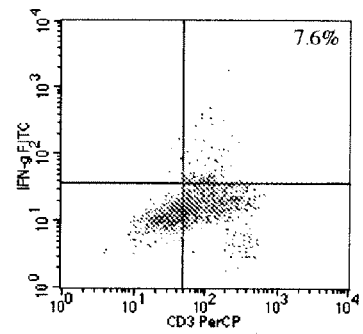
Figure 11:
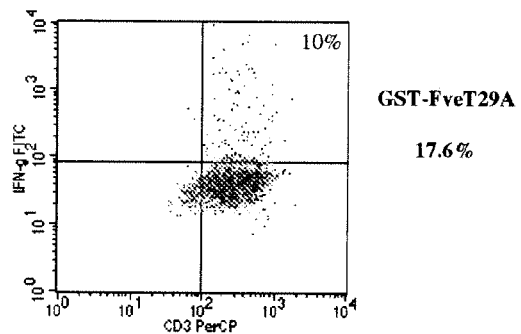
Figure 12:
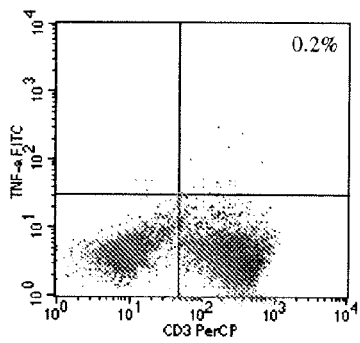
FIG. 12. Recombinant wild type GST-Fve and mutant GST-FveT29A, but not mutant GST-FveG28A, maintained TNF-α production activity. Human PBMC from healthy donor are cultured with 20 µg of GST (1); GST-Fve (2); GST-FveR27A (3); GST-FveG28A (4); GST-FveT29A (5). IFN-γ cytokine by T cells is detected at day 3 by staining with anti-CD3 PerCP and anti-TNF-α FITC specific monoclonal antibody. TNF-α secretion by small granular lymphocytes and large granular lymphocytes are shown in (a) and (b), respectively. The total amount of TNF-α production by T cells is the sum of (a) and (b).
Figure 12:
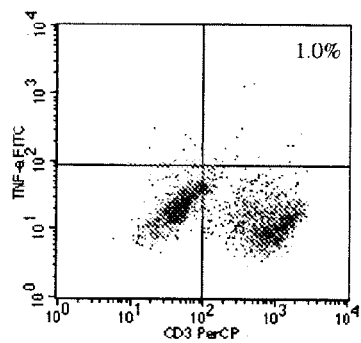
Figure 12:
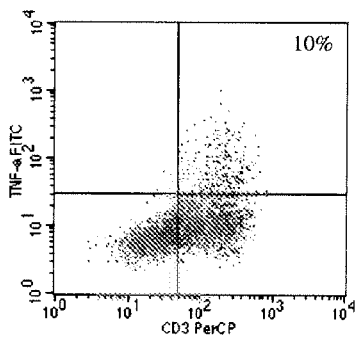
Figure 12:
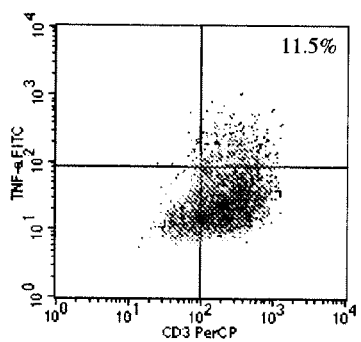
Figure 12:
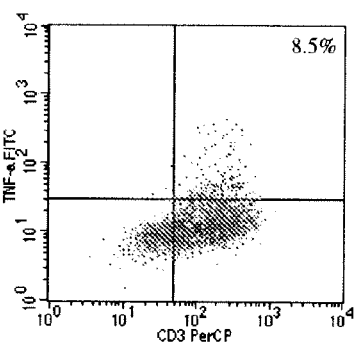
Figure 12:
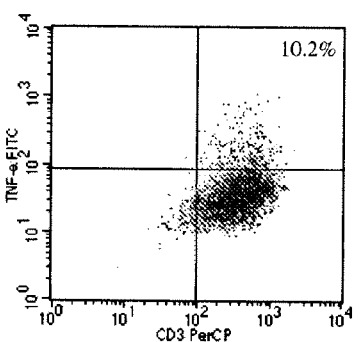
Figure 12:
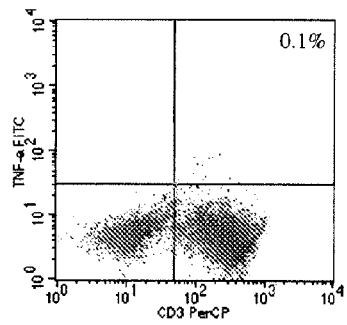
Figure 12:
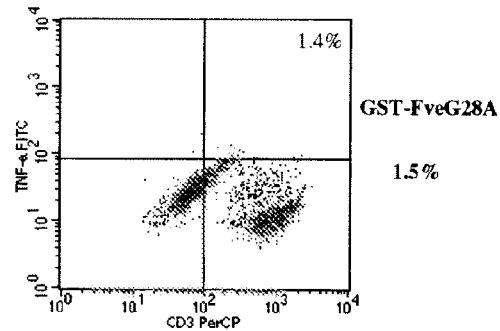
Figure 12:
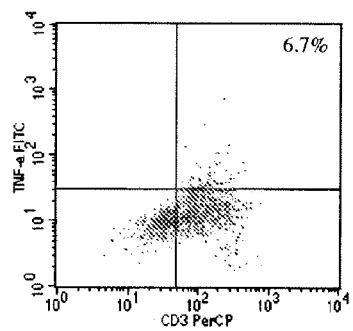
Figure 12:
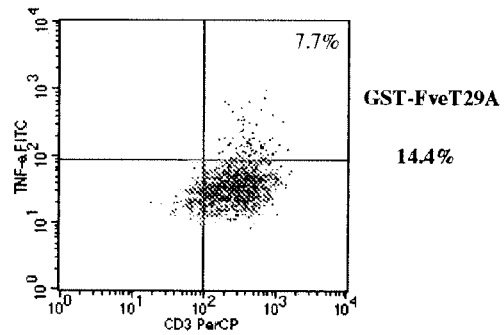

FIGS. 7 and 8 show the results of the proliferation assay for the panel of proteins tested. Deletion mutants D19-33, D73-84, P55-100, and mutant with single amino acid substitution G28A showed significant reduction in lymphoproliferation activity in mouse splenocytes, whereas, such reduction is less pronounced for the rest of the mutants tested (FIG. 7).

Interestingly, some mutants such as D34-46, D47-60 and D61-72, which show negative hemagglutination and cell aggregation, retain similar lypmphoproliferative activity as the wild type protein. For the result of human PBMC, deletion mutant D61-72 and mutant with single amino acid substitution G28A show more than 50% reduction in lymphoproliferation activity (FIG. 8). Taken together the proliferation results from mouse splenocytes and human PBMC demonstrate that glycine at position 28 plays an key role in lymphocyte proliferation.

Example 8

Recombinant GST-Fve (Wild Type) and GST-FveT29A (Mutant) Show Similar Proliferative Activity of CD3$^+$ T Cells as the Native Fve Materials and Methods Human peripheral blood mononuclear cells (PBMC) from a healthy donor are isolated according to the standard protocol (Coligan et al., 1998). The cells are then cultured with 20 μg/ml of recombinant wild type GST-Fve and mutant GST-FveT29A for 5 days. Cells are stained with anti-CD3$^+$ PerCP monoclonal antibody (Becton Dickinson), and analyzed by FACScan flow cytometry (Becton Dickinson).

Results

A histogram shows that 8% and 17% enrichment of T cells are detected after stimulation with recombinant wild type GST-Fve and mutant GST-FveT29A for 5 days (FIG. 9). Results showed that both recombinant wild type GST-Fve and mutant GST-FveT29A showed comparable lymphoproliferative activity of T lymphocytes as well as the native Fve protein.

These data suggest that Fve-mediated T cell polarization and enrichment is detectable at day 5.

Example 9

Detection of IFN-γ and TNF-α by Intracellular Cytokine Staining After Stimulation with Recombinant GST-Fve Protein Methods and Materials Intracellular cytokine staining is done by modification of a standard method from PharMingen. Briefly, human PBMC are stimulated in vitro with 20 μg of native Fve protein, GST, recombinant GST-Fve, GST-R27A, GST-G28A, or with GST-T29A. GlogiPlug™ (PharMingen) is added 48 hr after the cultures are initiated, cells are collected 14 hr later and then stained for T cells surface marker (CD3) in FACS buffer containing GlogiPlug™. Cells are then treated with Cytofix/Cytoperm (PharMingen) for 30 min. Cells are incubated with cytokine antibodies for 30 min after washing with Perm Wash buffer (PharMingen). Finally, cells are washed with PBS containing 1% paraformaldehyde and then analyzed by FACSCalibur flow cytometry (BD Biosciences). CellQuest software (BD Biosciences) is used for data analysis.

Results

The results show that native Fve protein is able to stimulate production of IL-2, IFN-γ, TNF-α, but not IL-4 in CD3$^+$ T cells (FIG. 10). Similar results are seen for the recombinant wild type GST-Fve and two mutants GST-FveR27A, GST-FveT29A. Strikingly, recombinant mutant GST-FveG28A failed to stimulate the production of such cytokines (FIGS. 11 and 12).

The percentages of IFN-γ production induced by GST, GST-Fve, GST-FveR27A, GST-FveG28A, GST-FveT29A are 0.8%, 12.3%, 14.3%, 1.8%, 17.6%, respectively. In contrast, the percentages of TNF-α production which induced by GST, GST-Fve, GST-FveR27A, GST-FveG28A, GST-FveT29A are 1.2%, 21.5%, 18.7%, 1.5%, 14.4%, respectively (Table 2). This data provides further evidence that the glycine residue at position 28 of Fve protein plays an important role in the biological function such as aggregation/adhesion, cytokines production, proliferation, and differentiation of lymphocytes. Further examination of the physiological role of RGT sequence in Fve protein by using blocking monoclonal antibodies and peptide inhibition assay are carried out to confirm this function. The possibility of integrin-mediated T/NK-cell adhesion is also investigated.

In summary, mutants FveR27A and FveT29A show enhanced mitogenic activities as compared to that of wild type Fve. In addition, the solubility of both mutant proteins is significantly increased in comparison with that of wild type Fve. This improved solubility will greatly facilitate the large scale production of such recombinant protein.

TABLE 2

The percentage of intracellular cytokines production in CD3+ T lymphocytes during stimulation with three different Fve mutants with single amino acid substitution

| Recombinant proteins | Intracellular IFN-γ | Intracellular TNF-α |
|---|---|---|
| GST | 0.8% | 1.2% |
| GST-FveWT | 12.3% | 21.5% |
| GST-FveR27A | 14.3% | 18.7% |
| GST-FveG28A | 1.8% | 1.5% |
| GST-FveT29A | 17.6% | 14.4% |

Example 10

Applications of Fve in Allergy

The increasing prevalence of atopic diseases such as hayfever or allergic asthma is a major problem in most developing and developed countries. Accumulating evidence indicates that appropriate immunotherapy prevents the onset of new sensitization and the progress of allergic rhinitis to asthma.

The central role of allergen-specific Th2 cells in the regulation of allergic inflammation has been highlighted. Exploration of novel and effective treatment for atopic diseases is active area of allergy research. Induction of allergen-specific T regulatory immune response, suppression of the effects of IL-4, IL-5 and IL-13 cytokines, and redirecting/balancing Th2 immune response in allergy is an attractive and promising approach to pursue (Akbari et al., 2002; Scanga and Le Gros, 2000; Zuany-Amorim et al., 2002).

Our in vitro and in vivo studies reveal that Fve interacts with T and NK cells.

Fve-activated T cells produce Th1-skewed cytokines in high levels, and suppress Th2 cytokines (IL-4 and IL-13) production. Thus these biological activities of Fve can be exploited to treat Th2-associated diseases such allergic asthma and rhinitis. The use of the immunomodulatory properties of Fve to treat allergic diseases is novel because there are a number of differences between Fve approach and other existing methods such as hexameric motifs, called CpG motifs or DNA immunostimulatory sequences (ISS).

The function of ISS is act as a danger signal to stimulate non-specific innate immune response (Krieg 2000). It is known that ISS is recognized by the toll-like receptor 9 on B cells and CD123+ dendritic cells. It is unexpected that TLR9 is also involved in autoimmunity (Leadbetter et al., 2002; Krieg 2002; Vinuesa and Goodnow, 2002). Upon the detection of CpG motifs or ISS element, B cells are induced to proliferate and secrete immunoglobulin (Ig), and dendritic cells (DCs) secrete a wide array of cytokines, interferons and chemokines that promote T helper type 1 (Th1) cells. Both B and DCs up-regulate costimulatory molecules and have enhanced abilities to induce Th1 cell immune responses. In contrast, Fve is directly target on T and NK cells to involve in the acquire immunity.

Example 11

Co-Administration of Fve with Allergens: In Vivo Study of the Adjuvant Effect of Fve Using a Murine Allergic Asthma Model Immunotherapy with recombinant allergen in combination with certain immunomodulator enhancing Th1 but suppressing Th2 immune response is a novel approach to achieve higher efficacies in immunotherapy. Since Fve protein is an activator of Th1/Tc1 immune response, it may be used as such an immunomodulator to provide the adjuvant effects to enhance Th1-skewed immunity.

We investigated the adjuvant effects of Fve for allergy immunotherapy with a combination of a recombinant house dust mite major allergen, Der p 2 and Fve using an animal model.

Methods and Materials

Figure 13:
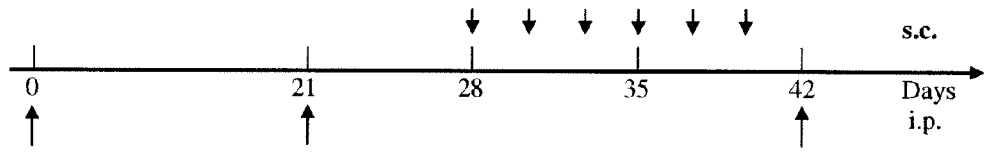
FIG. 13. Schematic representation of the experimental design of the in vivo study Balb/cJ mice are immunized with Der p 2 in aluminum hydroxide at day 0 and boosted at day 21 by intraperitoneal injection. Treatment with Der p 2 alone or Der p 2 plus Fve is started at day 28 by given 6 subcuteneous injections over 12 days. Mice are challenged with Der p 2 at day 42.

A schematic representation of the experimental design is shown in FIG. 13.

8 to 10 week old male BALB/cJ mice obtained from the Sembawang Laboratory Animal Center of Singapore are divided into two groups for each experiment. Mice are sensitized by intraperitoneal injection of 10 μg of recombinant Der p 2 in aluminum hydroxide at day 0 and day 21. Twenty-eight days after the sensitization, each group of mice is subcutaneously injected with 50 μg of Der p 2 and 50 μg of Der p 2 plus 40 μg of Fve, respectively. A total of six injections are performed at every alternative day over a period of 12 days. Mice are then challenged with the third intraperitoneal injection of 10 μg of Der p 2 plus aluminum hydroxide at day 42. Der p 2-specific IgG1 and IgG2a are determined weekly starting at day 14 by ELISA. Since IgG2a is the hallmark of Th1 immunity in mouse, titer of IgG2a is used a measure of Th1 immunity.

Results

Increased Allergen-Specific IgG2a Production in the Treatment Group with Combination of Fve and Allergen Der p 2

Figure 14:
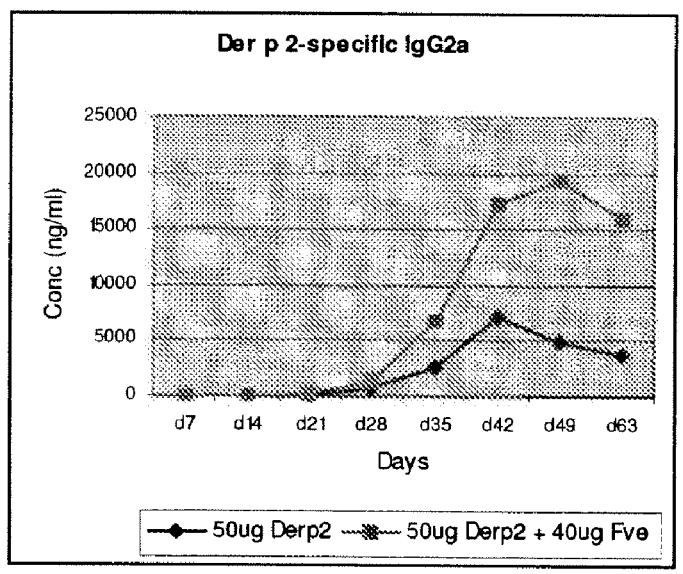
FIG. 14. Enhanced anti-Der p 2 IgG2a by adjuvanicity of Fve protein. IgG2a response in mice that are subcutaneously injected six times with Der p 2 alone (close circle), or Der p 2 plus Fve (close square) twenty-eight days after the initial sensitization with Der p 2 in alum. Mice received third intraperitoneal injection with Der p 2 in alum at day 42. Results are shown as mean titers and error bars indicate the standard deviations from the mean titers.
Figure 14:
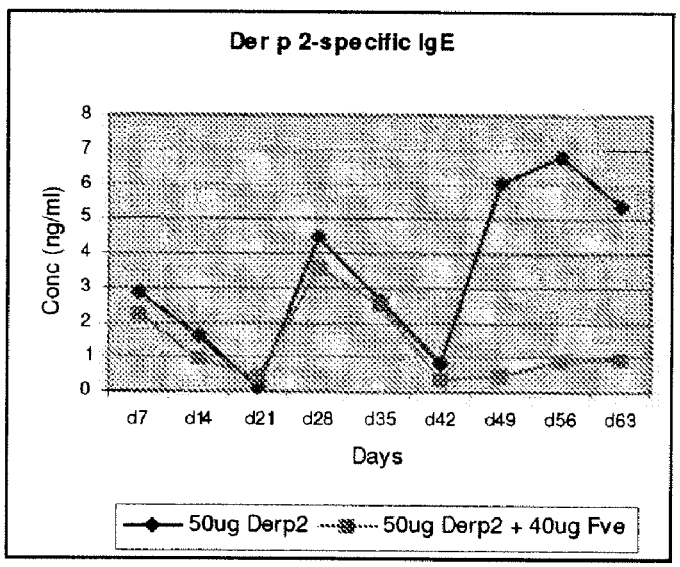

As shown in FIG. 13, mice that are subcutaneously treated with 50 μg of Der p 2 alone produced relatively lower titers of Der p 2-specific IgG2a, whereas mice treated with 50 μg of Der p 2 plus 40 μg of Fve showed a significant boost of Der p 2-specific IgG2a production (FIG. 14).

Upon challenge with intraperitoneal immunization of Der p 2 in alum at day 42, the Der p 2-specific IgG2a in Fve administered mice is further increased at day 49. It is interesting to note that the Fve-specific IgG1 and IgG2a remained low (data not shown).

Increased Allergen-Specific IgG2a Production in the Treatment Group with Combination of Fve and Allergen Blo t 5

Figure 14B:
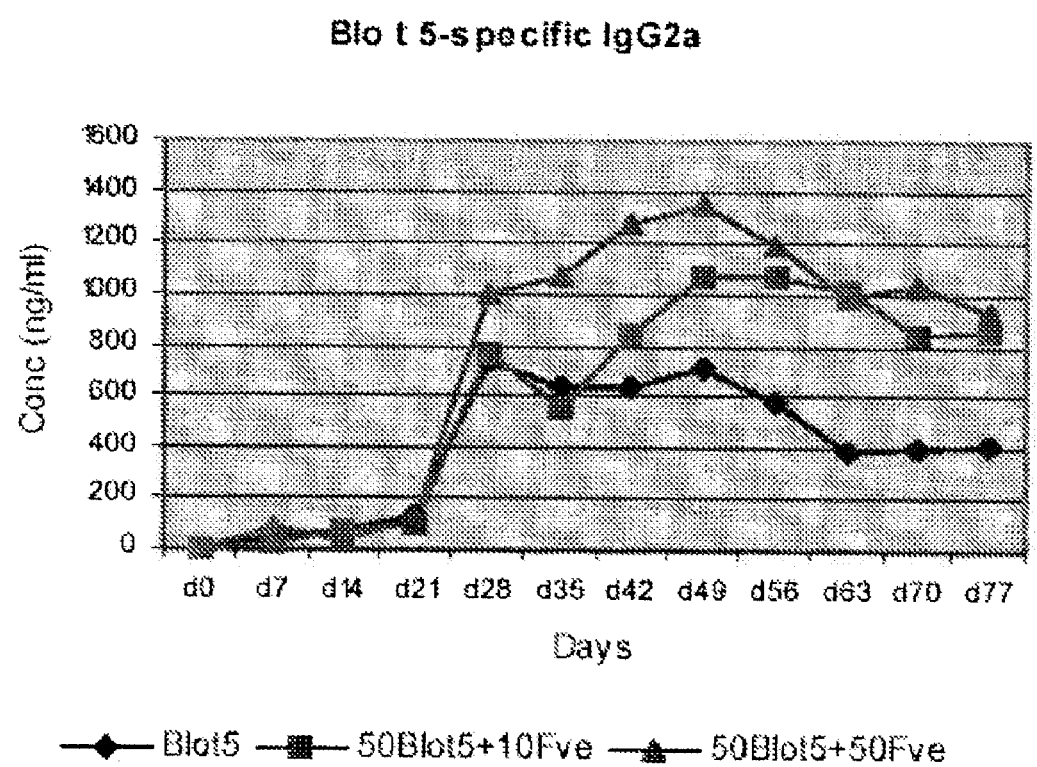
FIG. 14B. Fungal immunomodulatory protein Fve increases allergen-specific IgG2a production in mice sensitized to house dust mite major allergen. All groups of female BALB/cJ (6-8 weeks old) are sensitized intraperitoneally on day 1 with 20 µg of recombinant mite allergen Blo t 5 and boosted at day 14 with same dose of allergen adsorbed to 64 µg/µl of aluminum hydroxide gel in a final volume of 200 µl. Mice treated with six subcutaneous injections of 50 µg of Blo t 5 plus 10 µg of Fve or 50 µg of Blo t 5 plus 50 µg of Fve in 200 µl of PBS at three days interval starting from day 21-35. The negative control mice receive six subcutaneous injections of 50 µg of Blo t 5 alone. All mice are bled weekly and sera were collected for analysis of Blo t 5-specific IgG2a by ELISA. These results show that fungal immunomodulatory protein Fve has the ability to induce Blo t 5-specific IgG2a antibody in allergen-sensitized mice.
Figure 14C:
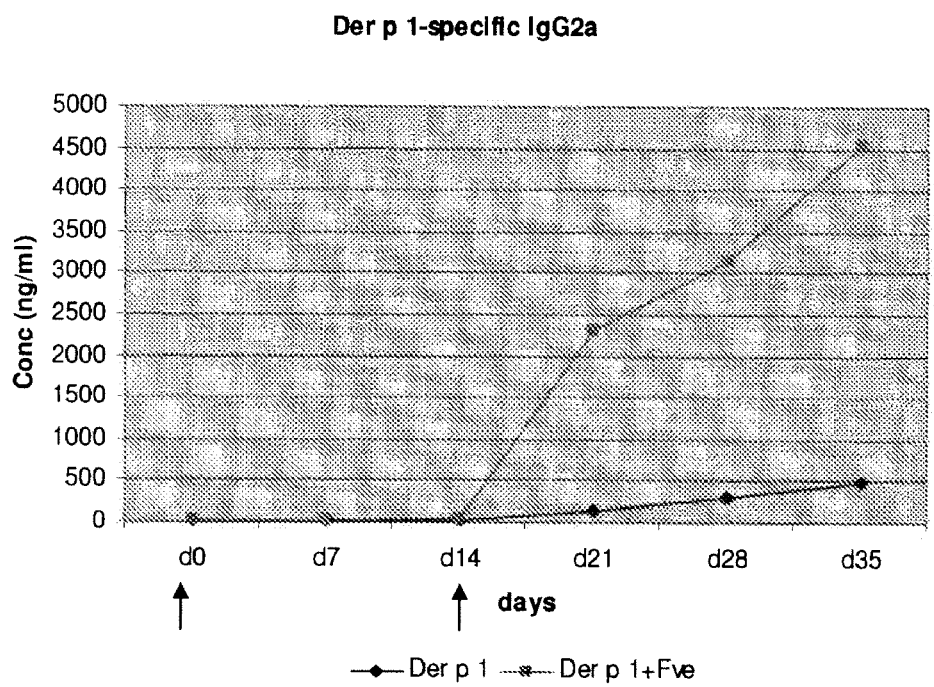

Similar results are observed in similar experiments performed with another house dust mite major allergen, Blo t 5, from *Bromia tropicalis*. These results are shown in FIG. 14B.

Thus we demonstrate mdulation of allergen-specific antibodies responses to the major house dust mite allergen, Blo t 5, by combining treatment with a fungal immunomodulatory protein, Taken together, the data suggested that Fve protein may act as a potent adjuvant/immunomodulator to boost antigen-specific Th1-skewed immune response, therefore it may serves as a useful reagent to improve the efficacies of immunotherapeutic treatment of allergy in humans. The adjuvanticity and immunomodulatory property of Fve protein may be improved by biomolecular engineering.

While not wishing to be bound by theory, it is postulated that this molecule may activate NK cells and CD8+ T cells and thus result in production of IFN-γ. These may induce a strong cellular-mediated immune response and promote isotype switching to specific IgG2a predominantly.

Example 12

Assessment of Erythema Flare and Wheal Diameter Formation Induced by Skin Prick Tests in Human Allergic Subject Materials and Methods The skin prick test is a convenient diagnostic method test for allergy in the clinics. The aim of this study is to evaluate the suppression effect of Fve protein to allergen hypersensitivity. As an in vivo topical challenge method, the skin prick test is administered to a human subject with history of sensitization to house dust mite *Dermatophagoides pteronyssinus*.

25 µg/ml of purified recombinant Der p 2 allergen mixed with same concentration of native Fve protein or Der p 2 allergen alone, is applied to the skin of left and right hand of human subject for 10 minutes. Histamine is used as a positive control. The size of the wheel and erythematic flare diameter is measured manually.

Results

Figure 15A:
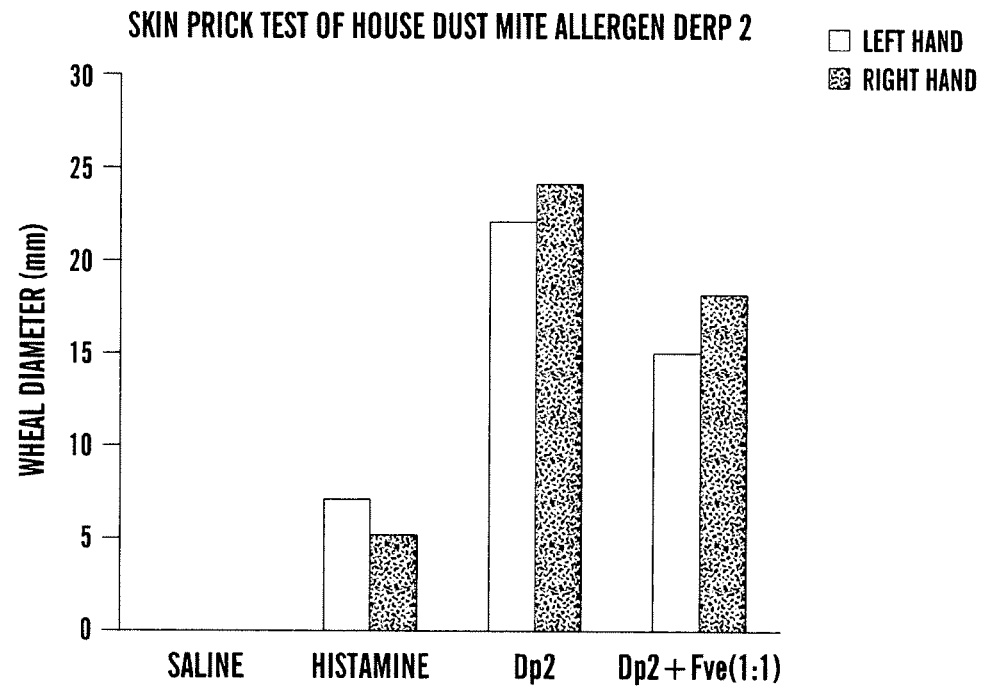
FIG. 15A and FIG. 15B. Fve could reduce wheal and erythematic flare formation on skin prick test-positive human subject. Both the left and right hands of the house dust mite allergen sensitized human subject are challenged with saline, histamine, Der p 2, and mixture of Der p 2 and Fve at the separated sites on hands. The diameter sizes of wheel (A) and erythematic flare (B) are measured after 10 minutes incubation time FIG. 15C. Demonstration of immunomodulatory activity of Fve in allergic subject. Quantitative skin-prick tests were performed to evaluate the immunomodulatory function of Fve by co-administration with Der p 2 mite allergen in vivo. A positive reaction (56-130 mm wheel diameter) was shown when Der p 2 alone (20 ug/ml) was applied onto the skin of the fore arm of *Dermatophagoides* mite allergic subject. There was a Fve-dose-dependent reduction of skin reaction when different amount of Fve was used in combination with Der p2 allergen for skin tests.
Figure 15B:
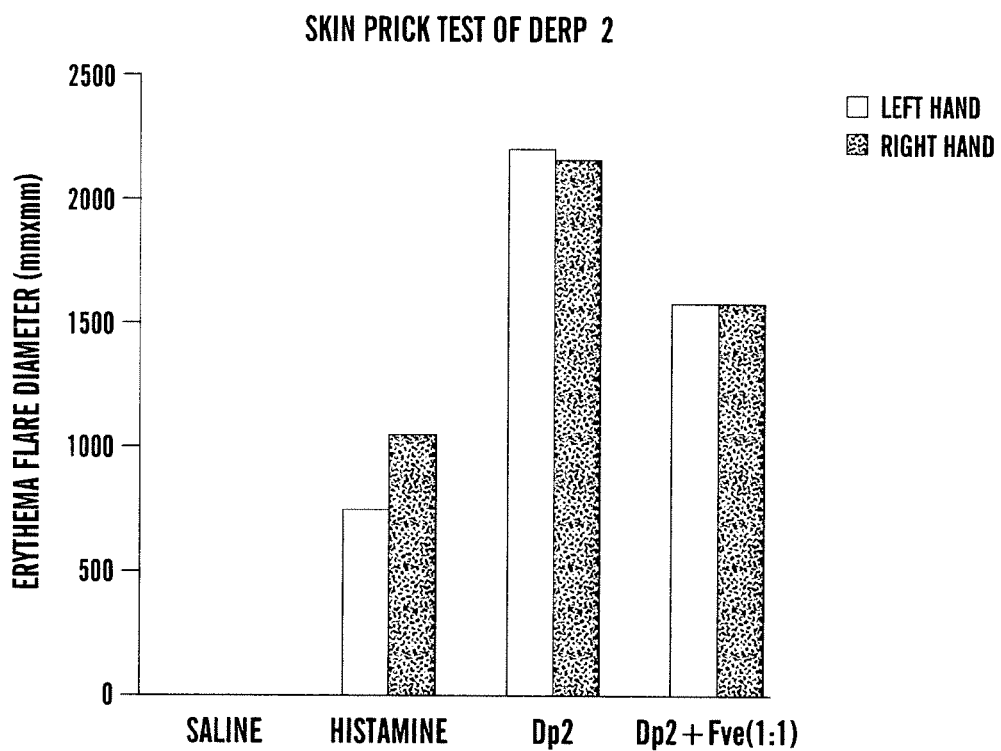

Fve Reduces Wheal and Erythematic Flare Formation on Der p 2 Skin Prick Test-Positive Human Subject The formation of wheal and erythematic flare could be detected in the challenged site of histamine, Der p 2, and Der p 2 combined with Fve. The diameter of the wheals in both left and right hand induced by Der p 2 is 22 mm and 24 mm, respectively. Interestingly, the mixture of Der p 2 and Fve reduces the wheal's diameter in both hands to 15 mm and 18 mm, respectively (FIG. 15A). A similar reduction is also seen in the size of erythematic flare (FIG. 15B, Table 3A and 3B).

The data indicates that there is a suppression of allergic reaction mediated by immunomodulatory effects of Fve protein. The results provide additional evidence that Fve could be used as an adjuvant for allergens immunotherapy.

Besides indoor allergens, outdoor allergens are also important triggering factors that lead to allergic diseases. Hay fever and allergic asthma triggered by grass pollen allergens affect approximately 20% of the population in cool temperate climates. Worldwide more than 200 million individuals are allergic to group 1 grass pollen allergens, and over 100 million individuals exhibit IgE-mediated allergic reactions against Phl p 2, a major allergen from timothy grass (*Phleum pratense*) pollen.

Therefore, we propose that recombinant Fve as well as the native Fve may also be applied in the treatment of other allergies that induced by tree pollen allergen (Bet v 1 and Bet v 2 from birch), grass pollen allergen (Phl p 1 and Phl p 2 from timothy grass), weed pollen allergen (antigen E from ragweed), major feline antigen (Fel d 1), major canine allergen (Der f 15), etc. Other allergens will be known to the person skilled in the art.

Another useful application of Fve protein in allergy is to conjugate or co-deliver with allergenic crude extracts such as mite extracts, pollen extracts, cat and dog extracts, cockroach extracts, fungal and mold extracts for desensitization by immunotherapy.

TABLE 3A

Wheal formation on skin after challenged with Der p 2

| | Wheal Diameter (mm) | |
|---|---|---|
| | Left hand | Right hand |
| Saline (negative control) | 0 | 0 |
| Histamine | 7 | 5 |
| Der p 2 | 22 | 24 |
| Der p 2 + Fve (1:1 w/w) | 15 | 18 |

TABLE 3B

Erythematic flare formation on skin after challenge with Der p 2

| | Erythematic Flare Diameter (mm) | |
|---|---|---|
| | Left hand | Right hand |
| Saline (negative control) | 0 | 0 |
| Histamine | 30 × 25 | 35 × 30 |
| Der p 2 | 55 × 40 | 50 × 43 |
| Der p 2 + Fve (1:1 w/w) | 45 × 35 | 45 × 35 |

Figure 15C:
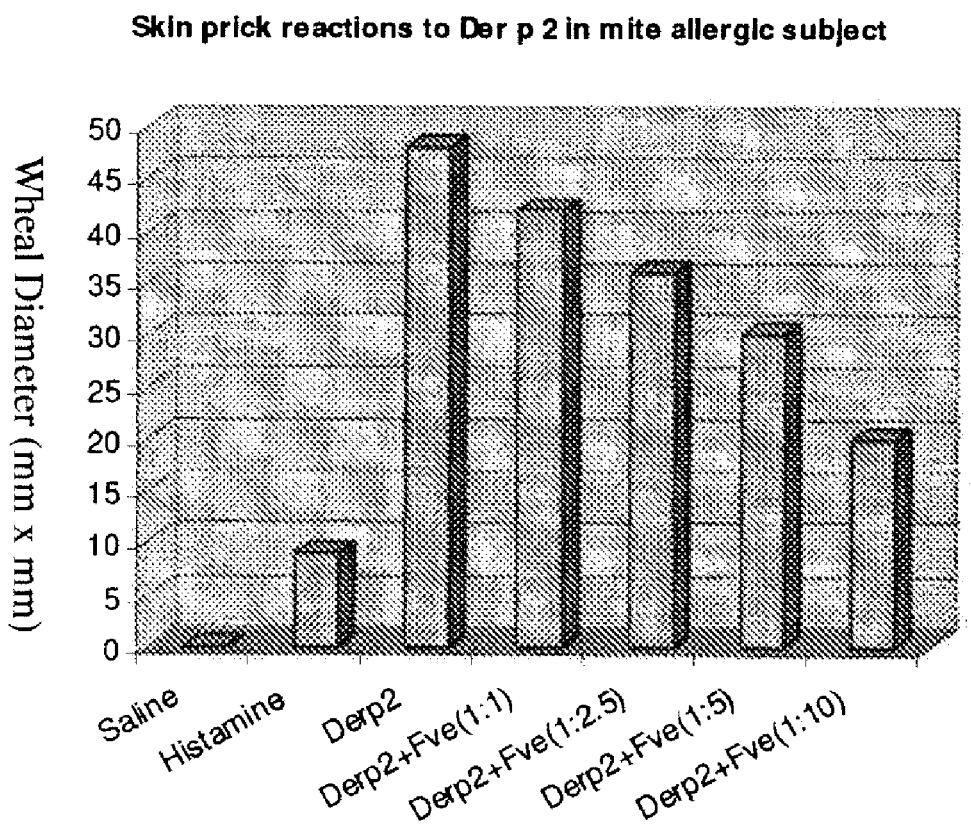

Reference is also made to FIG. 15C, which shows a demonstration of immomodulatory activity of Fve in an allergic subject. Thus, quantitative skin-prick tests are performed to evaluate the immunomodulatory function of Fve by co-administration with Der p 2 mite allergen in vivo.

A positive reaction (56-130 mm wheel diameter) is shown when Der p 2 alone (20 ug/ml) is applied onto the skin of the fore arm of *Dermatophagoides* mite allergic subject. There is a Fve-dose-dependent reduction of skin reaction when different amount of Fve are used in combination with Der p2 allergen for skin tests.

Fve Adjuvanted Allergen Vaccines

Example 13

Fusion Proteins of Fve and Allergen

Materials and Methods

Treatment of recombinant allergen or vaccination with naked DNA encoding a specific allergen has been shown previously to elevate allergen-specific Th1 immune response against Th2 immune reaction (Maecker et al., 2001). To enhance the effectiveness of immunotherapy or DNA vaccine therapy, we generate several fusion proteins consisting of the complete Fve molecule and the mature form of Blo t 5 or Der p 2 allergen.

FIG. 16 shows the construction of seven fusion proteins of Fve and major house dust mite allergen from *Dermatophagoides ptenyssinus* and *Blomia tropicalis*

Figure 17:
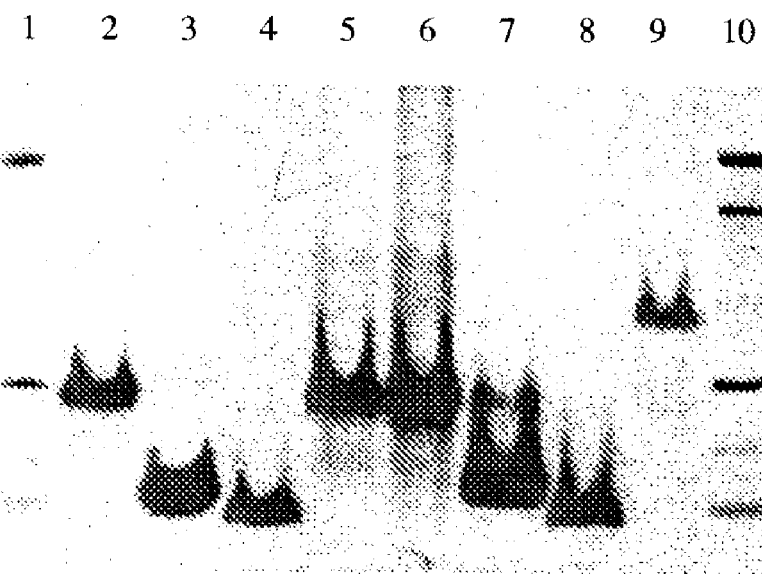
FIG. 17. Expression and purification of recombinant fusion protein Bt5-Fve, Bt5-FveR27A, and GST-Dp2-FveR27A.

The fused cDNAs are successfully expressed in *E. coli* (FIG. 17) and the biological properties of the recombinant proteins are examined.

Results

The morphology of lymphocyte culture upon stimulation with three recombinant fusion proteins is photographed with inverted microscope (FIG. 18A-C). Each of Bt5-Fve, Bt5-FveR27, GST-Dp2-FveR27 are able to increase the number of human PBMC (FIGS. 19A and 19B), to stimulate the proliferation of human lymphocytes (FIG. 20), to polarize human CD8+ T cells (FIG. 21), and to increase the production of IFN-γ (Th1 response) and IL-10 (Tr response) (FIG. 22).

A well-balanced vaccine that induces both Th1 and Tr immune response may be the most valuable and desirable. The Th1 response may very efficiently inhibit the development of Th2 cells via IFN-γ, leading to a life-long protective Th1 memory immune response. Allergen specific Tr cells may in turn dampen the anti-allergic Th1 immune response, ensuring a well-balanced protective but nonpathological Th1 response. Allergen-Fve fusion proteins meet these criteria since they induce cytokine IL-10.

Thus, combining Fve protein with allergen in the form of a fusion protein may be used effectively to induce antigen-specific adjuvant effect that augment the Th1 and Tr responses, which in turn down-regulate the Th2 allergic responses.

To test the antigenecity of a Blo t 5-Fve fusion protein, competitive inhibition ELISA is performed using varying concentrations of proteins (GST, GST-Blo t5, GST-Fve, GST-Blo t5-Fve, GST-Fve-Blo t5, Blo t5-Fve). The results show that fusion protein Blo t 5-Fve, un-cleaved GST-Blo t5-Fve and GST-Fve-Blo t5 have lower IgE binding affinity compared to Blo t5 alone and un-cleaved GST-Blo t5 (FIG. 23). The fusion protein Blo t5-Fve inhibited IgE binding to a maximum of 70% whereas Blo t5 is able to inhibit the binding of antibody to GST-Bt5 to 100% at inhibitor concentration of 10 µg/ml. Control GST and GST-Fve are not able to inhibit the binding of IgE to GST-Blo t5 (background levels). In summary, there is a reduction in the IgE binding affinity of Blo t5 when it is in the fusion forms of Blo t5-Fve, GST-Blo t5-Fve and GST-Fve-Blo t5 indicating that the antigenicity of Blo t5 with Fve in fusion forms is lowered.

Experiment B

Five mice per group of female BALB/cJ (6-8 weeks old) are subcutaneous immunized with 10 µg/ml of major house dust mite allergen Blo t 5 alone or fusion protein Blo t 5-FveT29A in tail at day 1. Mice are received similar antigen boosting in footpads at day 1-4 and day 28. All mice were bled weekly and sera were collected for analysis of Blo t 5 and Fve-specific IgG1, IgG2a and IgE by ELISA.

The results are presented in FIG. 23B, which shows the concentrations of Blo t 5-specific antibodies (left hand column: top Blo t 5-specific IgG2a, middle: Blo t 5-specific IgG1, bottom: Blo t 5-specific IgE) as well as Fve-specific antibodies (right hand column: top Fve-specific IgG2a, middle: Fve-specific IgG1, bottom: Fve-specific IgE).

The results show that recombinant fusion protein of allergen and fungal immunomodulatory protein has the ability to induce Blo t 5-specific IgG2a (2a) and down-regulate IgE production (2c). The overall of Fve-specific IgG1 and IgG2a antibodies are lower than Blo t 5 and decrease gradually after day 42 (2d and 2e), and the induction of Fve-specific IgE is less than 1 ng/ml (2f).

Therefore, fungal immunomodulatory protein Fve has the potential to be developed for the immunotherapeutic vaccine of allergy.

Experiment C

All groups of female BALB/cJ (6-8 weeks old) are sensitized intraperitoneally on day 1 with 5 µg of recombinant mite allergen Blo t 5 and boosted at day 14 with 1 µg of Blo t 5 adsorbed to 64 µg/µl of aluminum hydroxide gel in a final volume of 200 µl. Mice treated with six subcutaneous injections of 20 µg of Blo t 5-FveWT or Blo t 5-FveT29A fusion protein in 200 µl of PBS at three days interval started from day 21-35. The negative control mice receive six subcutaneous injections of 20 µg of Blo t 5 alone. All mice are bled weekly and sera were collected for analysis of Blo t 5 and Fve-specific IgG1, IgG2a, and IgE by ELISA.

The results are presented in FIG. 23C which shows the concentrations of Blo t 5-specific antibodies (left hand column: top Blo t 5-specific IgG2a, middle: Blo t 5-specific IgG1, bottom: Blo t 5-specific IgE) as well as Fve-specific antibodies (right hand column: top Fve-specific IgG2a, middle: Fve-specific IgG1, bottom: Fve-specific IgE).

These results show that recombinant fusion protein Blo t 5-FveT29A has the ability to induce Blo t 5-specific IgG2a antibody (3a) in allergensensitized mice.

Discussion

It is well recognized that a vaccine that induces both Th1 and Tr immune response is highly desirable for treatment of allergy, and the allergen-Fve fusion proteins seem to meet these criteria since it could induce both cytokines IFN-γ (Th1) and IL-10 (Tr). It is anticipated that Fve protein with allergen in the form of a fusion protein could be an effective way to induce antigen-specific adjuvant effect that augment the Th1 and Tr responses, which in turns can down-regulate the Th2 allergic responses. Besides, it is known that in the inductive phase of allergen sensitization, Th1 cytokines can inhibit the development of Th2 cells via IFN-γ, leading to a life-long protective Th1 memory immune response. Allergen specific Tr cells may in turn dampen the anti-allergic Th1 immune response, ensuring a well-balanced protective but nonpathological Th1 response.

Therefore, Fve-allergen fusion proteins can be exploited to develop vaccine for prophylactic of allergic disorders.

Example 14

Allergen Conjugated to Fve

Beside the use of gene fusions to produce fusion proteins, protein-protein conjugation also provides a convenient and alternative choice to develop allergen vaccine.

To date, allergen conjugated adjuvants which have been reported include crystalline bacteria cell surface layer (S-layers) (Jahn-Schmid et al., 1996), CpG oligodeoxynucleotides (CpG motifs) (Shirota et al., 2000), cholera toxin B subunit (CTB) (Rask et al., 2000), and Brucella abortus (Scharf et al., 2001).

Here we disclose Fve protein which is isolated from edible mushroom can also be an ideal adjuvant coupling to allergen vaccine. Poly-lactic acid (PLA) and polyethylene glycol (PEG) are two materials which may be used to couple Fve and house dust mite allergen (Der p 2 or Blo t 5), although other materials will be evident to the skilled reader.

Particular cross-linking reagents which may be used to conjugate an allergen and immumodulator, such as Fve, include N,N'-dicyclohexylcarbodiimide (DCC), N-succinimidyl-S-acetyl-thioacetate (SATA), N-succinimidyl-3-(2-pyridyldithio)propionate (SPDP), ortho-phenylenedimaleimide (o-PDM), and sulfosuccinimidyl 4-(N-maleimidomethyl)cyclohexane-1-carboxylate (sulfo-SMCC). A chemical conjugation protocol which may be used is that provided in the Protein-Protein Crosslinking Kit (P6305) from Molecular Probes, Eugene, USA. Protocols for conjugation using SPDP are disclosed in Clinical Experimental Allergy 30: 1024-1032, 2000 and European Journal of Immunology 28: 424-432, 1998.

For example, native Fve or recombinant Fve from E. coli is conjugated with N-succinimidyl 3-(2-pyridyldithio) propionate (SPDP, Molecular Probes) as a bifunctional coupling reagent. The resulting Allergen-Fve conjugates are purified by gel filtration and characterized for their allergenicity and adjuvanicity by in vitro and in vivo assays.

Example 15

Human Cytokine Assay in Purified $CD4^+$ and $CD8^+$ T Cell Subsets

Materials and Methods

To elucidate and identify subsets of human T lymphocytes responding to Fve stimulation, purified $CD4^+$ T cells and $CD8^+$ T cells from four human tonsillectomy patients (subject 1, 6 yrs-old Chinese; subject 2, 16 yrs-old Indian; subject 3, 17 yrs-old Malay; subject 4, 27 yrs-old Malay) are stimulated with 20 µg of Fve after AutoMACS seperation. AutoMACS is an automated magnetic cell sorter from Miltenyi-Biotec, Germany. The differential cytokine production profiles of these subsets are determined by intracellular cytokines staining after 48 hours in vitro culture.

Results

Fve Triggers Th1/Tc1 Cytokine Production in Human T Cells

The human cytokines induction studies show that Fve stimulates the production of IL-2, IFN-γ, TNF-α, whereas IL-4 and IL-10 are nearly undetectable. In addition, purified $CD4^+$ T cells produce higher levels of TNF-α than purified $CD8^+$ T cells ($CD4^+$ vs $CD8^+$: 11.4% vs 2.5%), whereas purified $CD8^+$ T cells produce higher levels of IFN-γ than purified $CD4^+$ T cells ($CD4^+$ vs $CD8^+$: 3.6% vs 8.5%) upon Fve stimulation (Table 4). Therefore, the enrichment of $CD8^+$ T cells seems to derive from a protein-cell direct interaction. Taken together, this data supported that Fve could trigger Th1/TC1 cytokines production in human T lymphocytes.

TABLE 4

Cytokines profile of purified human T cells subsets

| Intracellular Cytokines Scretion | Purified $CD8^+$ T cells from human tonsil | | Purified $CD4^+$ T cells from human tonsil | |
|---|---|---|---|---|
| | None | Fve | None | Fve |
| IL-2 | 0.1% | 0.6% | 0.2% | 6.8% |
| IL-4 | 0.1% | 0.3% | 0.1% | 0.9% |
| IL-10 | 0.6% | 0.5% | 2.3% | 0.9% |
| IFN-γ | 0.1% | 8.5% | 0.6% | 3.6% |
| TNF-α | 0.2% | 2.5% | 0.4% | 11.4% |

Example 16

Lymphocyte Aggregation Activity of Fve

Materials and Methods

Human $CD4^+$ and $CD8^+$ T cells subset are purified from AutoMACS (an automated magnetic cell sorter from Miltenyi-Biotec, Germany). The morphology of the cells is observed by light microscope at day 3.

Six human cell lines are also used for the cell aggregation study. Promyelocytic HL-60 cells, Jurkat-T cells, monocytic leukemia U937 cells, myeloid leukemia K562 cells, Raji B cells, natural killer NK-92 cells are cultured with native Fve protein with 2.5 µg/ml, 5 µg/ml, 10 µg/ml, 20 µg/ml and 40 µg/ml, respectively. Cells aggregation is observed by inverted light microscopy after 24 hours.

Results

Fve Induced Aggregation of Human CD4+ and CD8+ T Cells Subsets, HL-60, Jurkat-T Cells, and NK-92 Cells Human $CD4^+$ and $CD8^+$ T cells subset are purified from the tonsil of human subject. The aggregation of $CD4^+$ and $CD8^+$ T cells upon stimulation with 20 µg of Fve protein is observed by confocal microscope at day 3 (photographed data not shown).

From the human cell line study, we found that Fve could induce HL-60 aggregation at low concentration of 2.5 µg/ml. Jurkats-T cells and NK-92 also induced aggregation by Fve at concentration of 10 µg/ml and 20 µg/ml, respectively, where as U937, K562 and Raji didn't induce cell aggregation (Table 5). From the result, it seems that the level of cell aggregation correlates with the level of certain surface protein(s) expression in different cell lines. Promyelocytic cell line HL-60 seems to be an idea cell line to identify Fve receptor.

TABLE 5

Cell aggregation activity of human cell lines

| Human Cell Lines | Fve | | | | |
|---|---|---|---|---|---|
| | 2.5 µg/ml | 5 µg/ml | 10 µg/ml | 20 µg/ml | 40 µg/ml |
| HL-60 | + | + | + | + | + |
| Jurkat T | +/− | +/− | + | + | + |
| U937 | − | − | − | − | +/− |
| K562 | − | − | − | − | +/− |
| Raji | − | − | − | − | − |
| NK-92 | − | − | +/− | + | + |

Example 17

In Vitro Polarization of Human NK cells and $CD8^+$ T Cells

Materials and Methods

Human peripheral blood mononuclear cells (PBMC) from a healthy donor are isolated as standard protocol (Coligan et al., 1998). The cells are then cultured in 24-well plates with native Fve (5 µg/ml or 25 µg/ml). At days 5 and 10, cell culture are stained with anti-$CD4^+$ FITC, anti-$CD8^+$ PE, anti-$CD16^+$ PE plus anti-$CD56^+$ PE monoclonal antibodies (Becton Dickinson), and analyzed by FACScan flow cytometry (Becton Dickinson).

Results

Sequential Polarization of Cells by Fve, NK Cells and NKT Cells are Proportionally Increased at Day 5 Whereas $CD8^+$ T Cells are Increased at Day 10

The results show a 10% increase of $CD16^+$ and $CD56^+$ double positive cells (Natural Killer cells) after stimulation with Fve protein for 5 days (FIG. 24). In addition, $CD8^+$ T cells but not $CD4^+$ cells are increased up to 35% after culturing for 10 days (FIG. 25). This result showed that native Fve protein could stimulate both natural killer cells and $CD8^+$ T cells and the stimulation of these cells occurred sequentially with polarization of NK cells and $CD8^+$ T cells peaked at day 5 and day 10, respectively.

The data also showed that cell culture consisted of 10% of $CD3^+CD16^+CD56^+$ NKT cells after stimulation with 25 µg/ml of native Fve protein (FIG. 24E). This subset of cytotoxic NKT cells has a unique feature in that they mediate non-MHC-restricted cytotoxicity (Lanier et al., 1986).

Example 18

Up-Regulation of a Novel Subset of $CD8^+$ T Cells ($CD3^+$ $CD8^+$ $CD18^{+bright}$)

Materials and Methods

Repeated subcutaneous injection of IL-12 in patients with cancer resulted in the selective expansion of a unique subset of peripheral blood $CD8^+$ T cells. This subset expressed high levels of $CD18^+$ and up-regulated IL-12 receptor expression after IL-12 treatment in vivo. They appeared morphologically as large granular lymphocytes, increased high IFN-γ production and enhanced non-MHC-restricted cytolytic activity. Thus, these T cells may play an important role in innate as well as acquired immunity to tumors and infectious pathogens.

To determine whether CD3$^+$CD8$^+$CD18$^{+bright}$ T cells can be enriched by native Fve protein, human peripheral blood mononuclear cells (PBMC) from a healthy donor are isolated and cultured with 20 μg/ml of native Fve protein. Cell culture are stained with anti-CD18 FITC, anti-CD8 PE, anti-CD3 PerCP monoclonal antiboodies (Becton Dickinson) at day 5, and then analyzed by FACSCalibur flow cytometry (Becton Dickinson).

Results

Figure 27A:
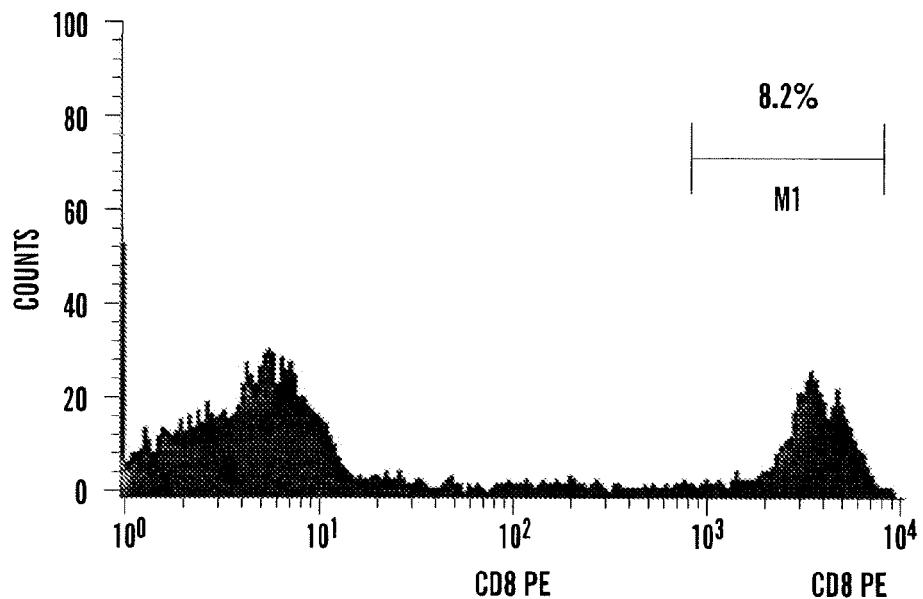
Figure 27B:
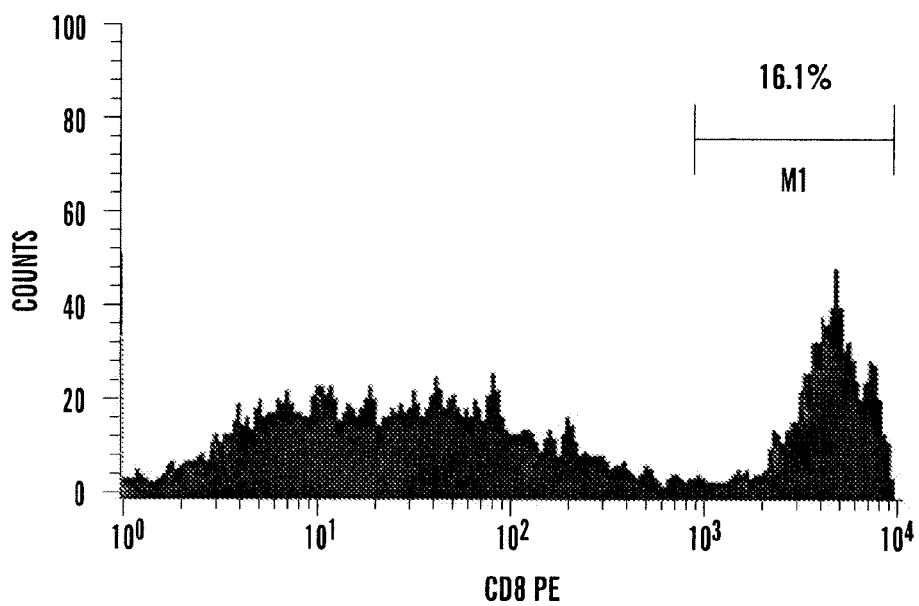
Figure 27C:
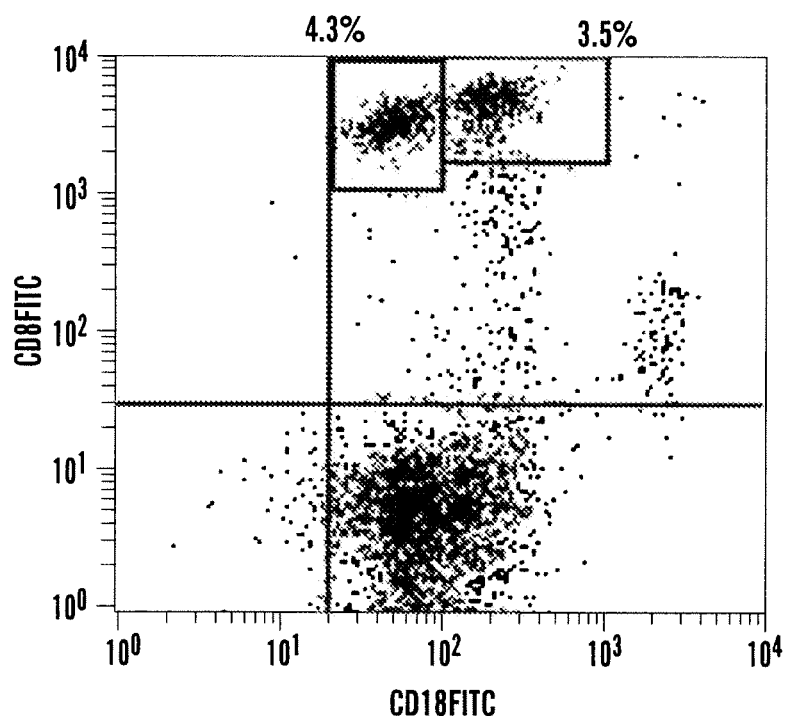
Figure 27D:
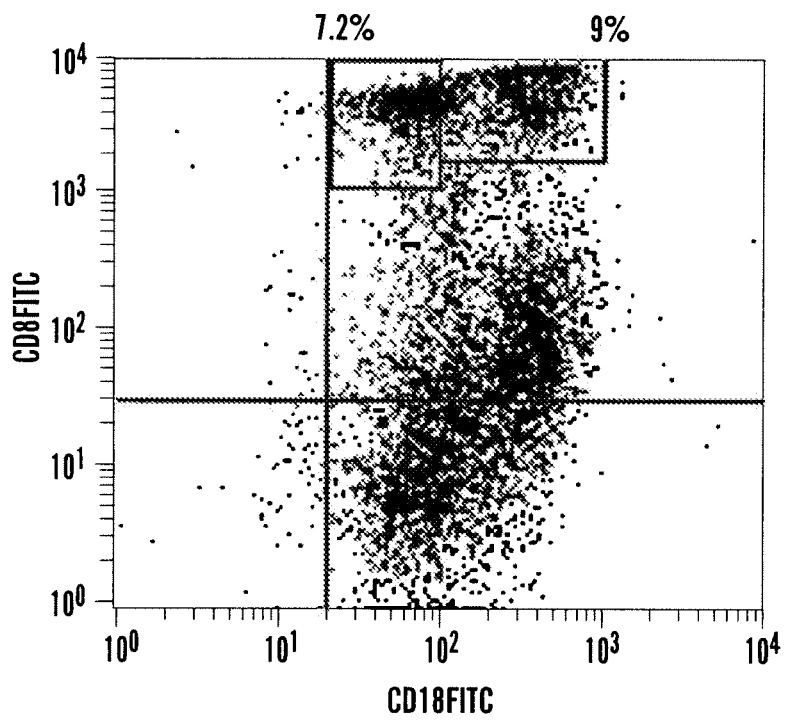
Figure 28A:
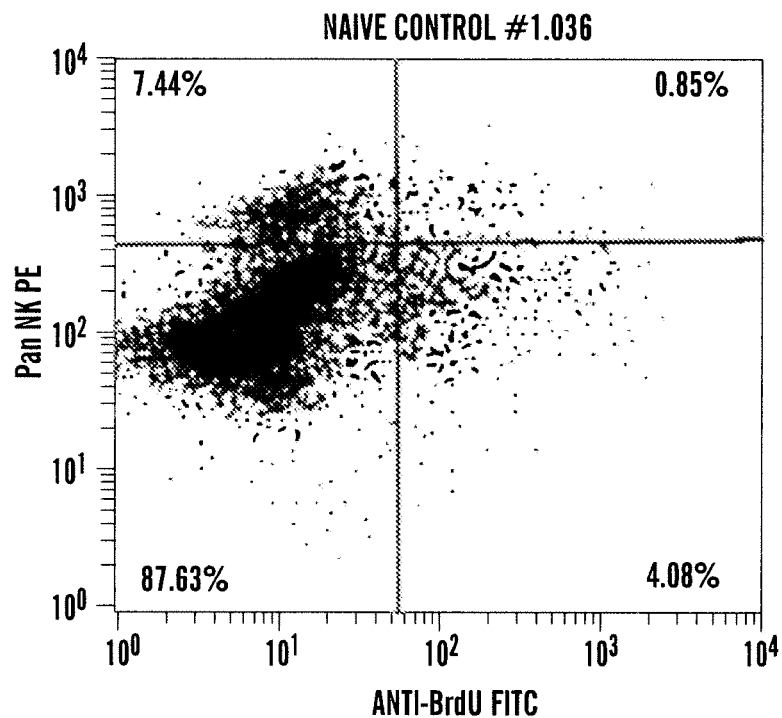
Figure 28B:
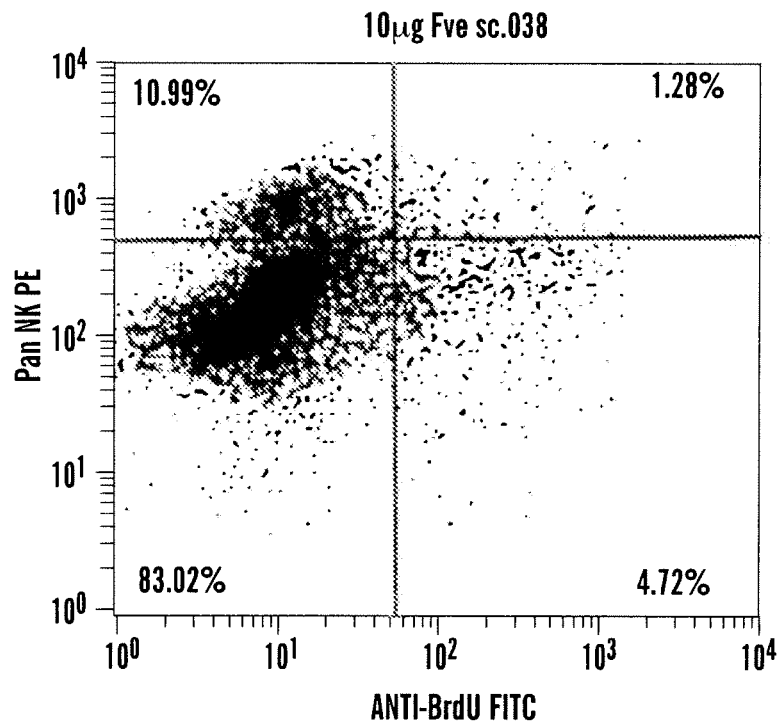
Figure 28C:
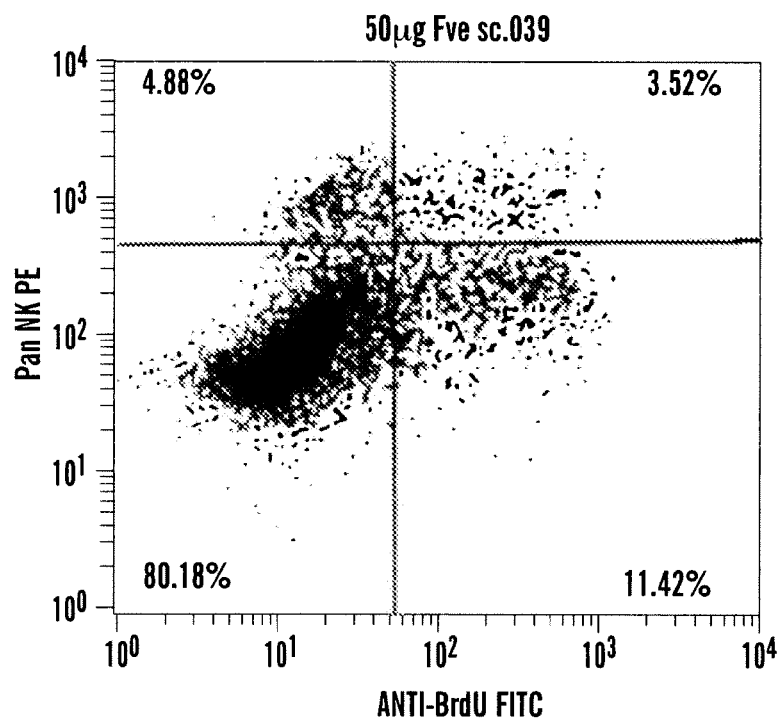
Figure 28D:
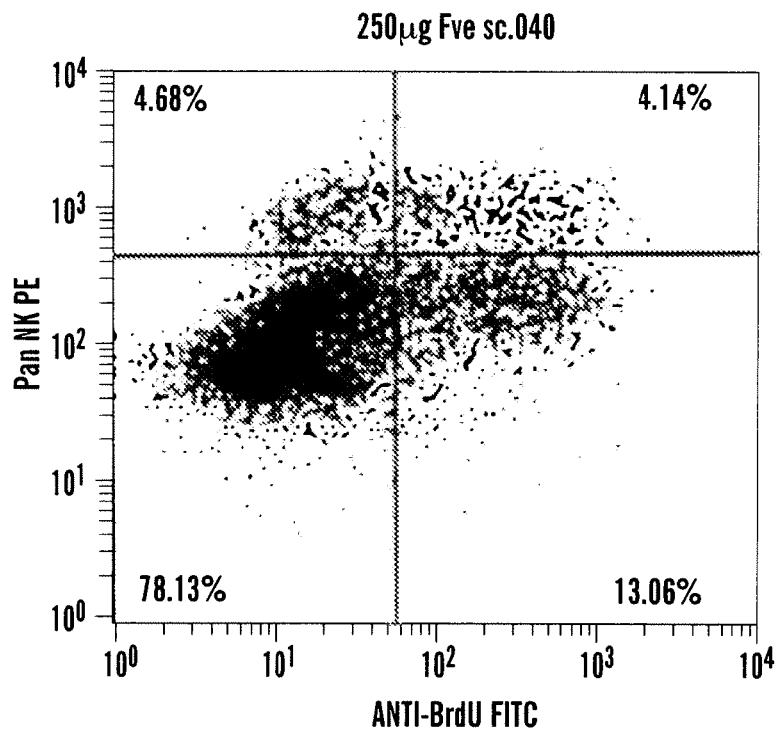
Figure 29A:
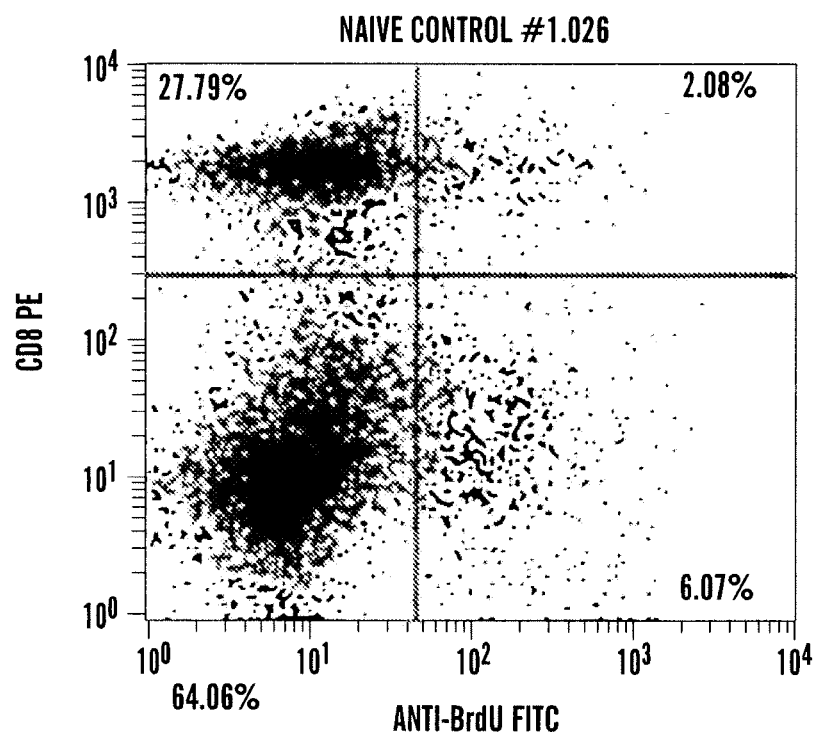
Figure 29B:
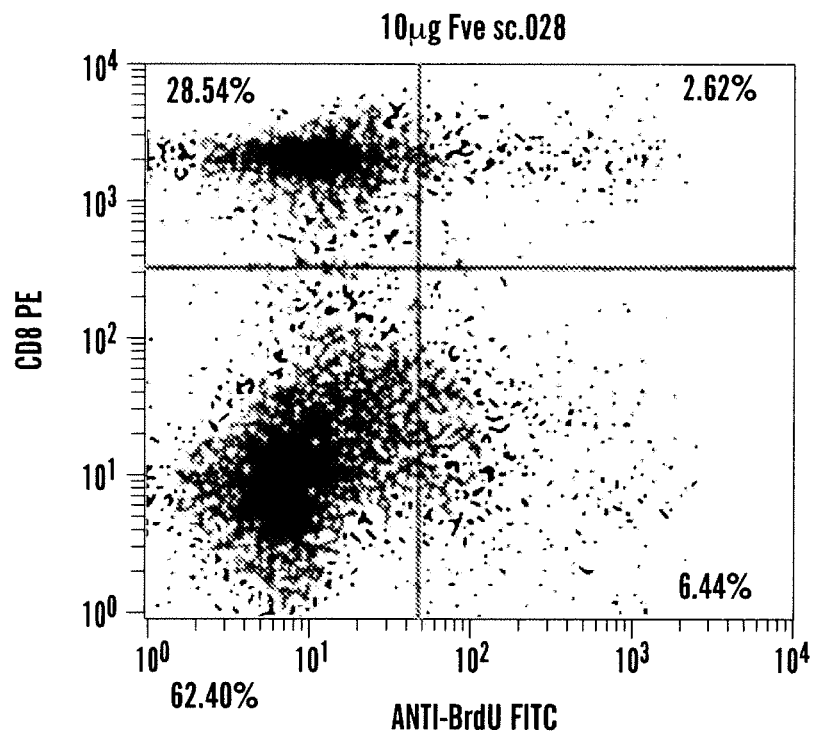
Figure 29C:
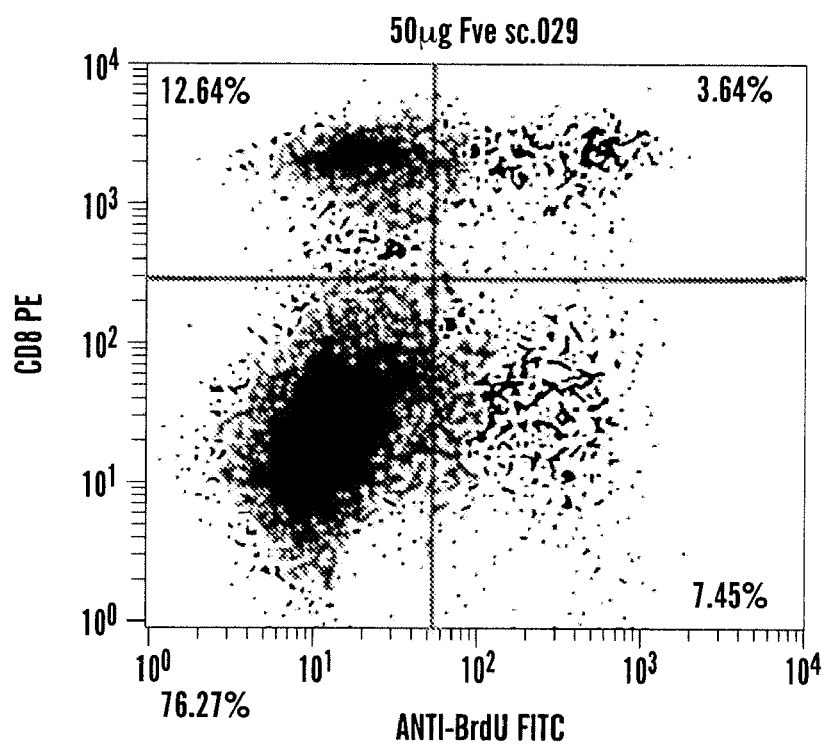
Figure 29D:
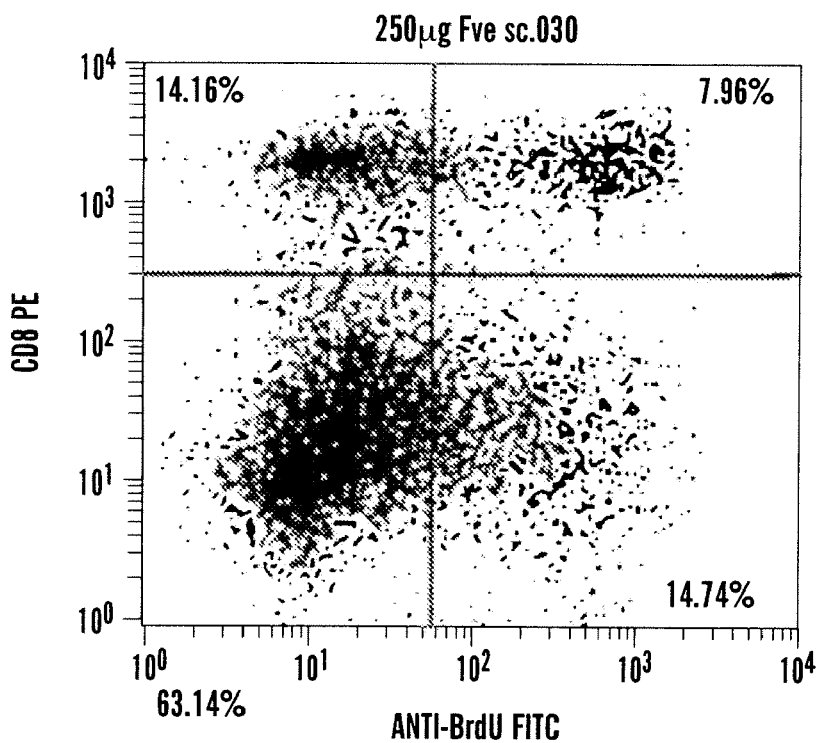
Figure 30A:
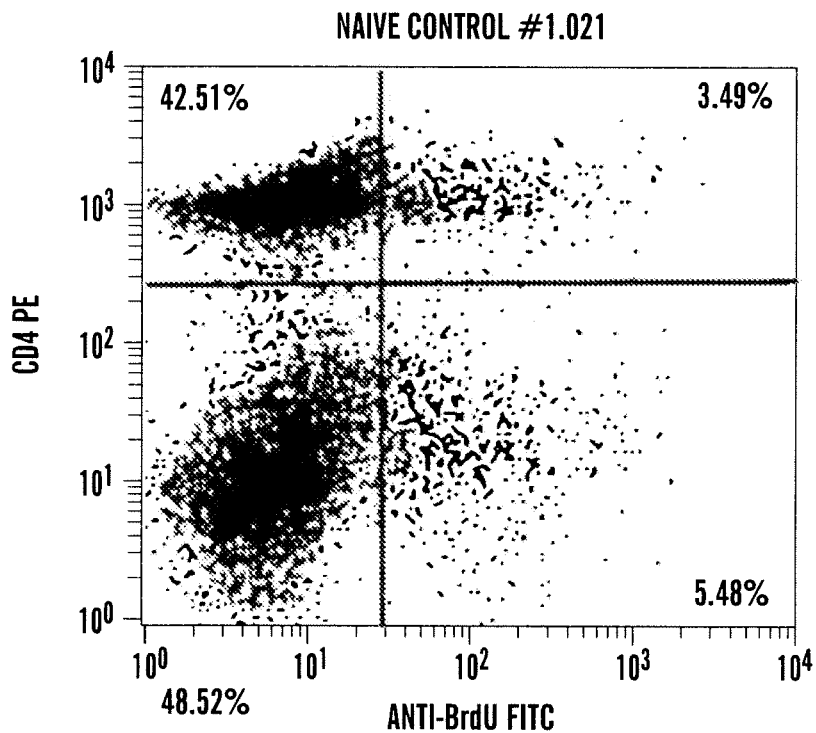
Figure 30B:
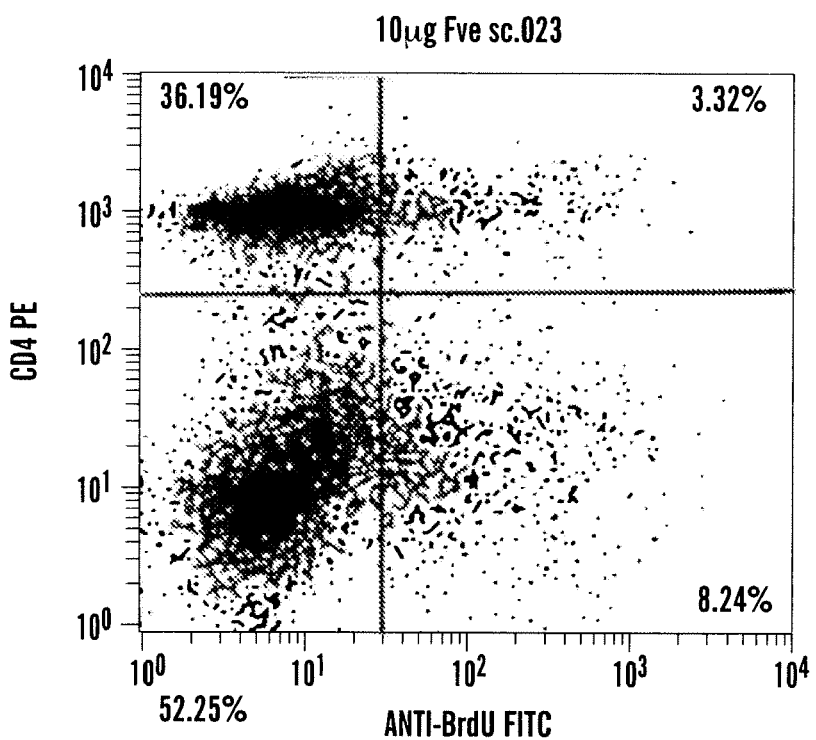
Figure 30C:
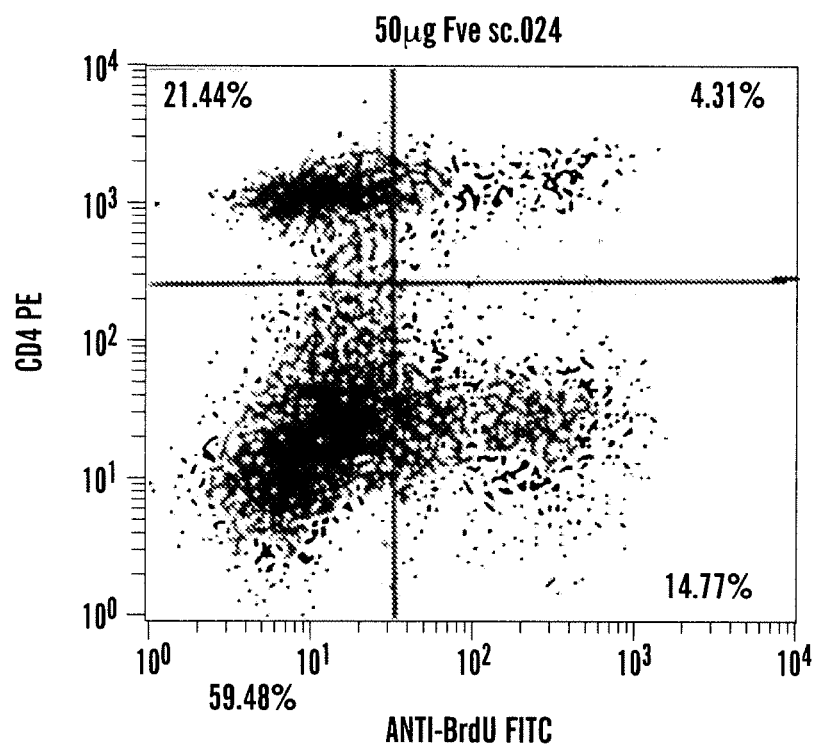
Figure 30D:
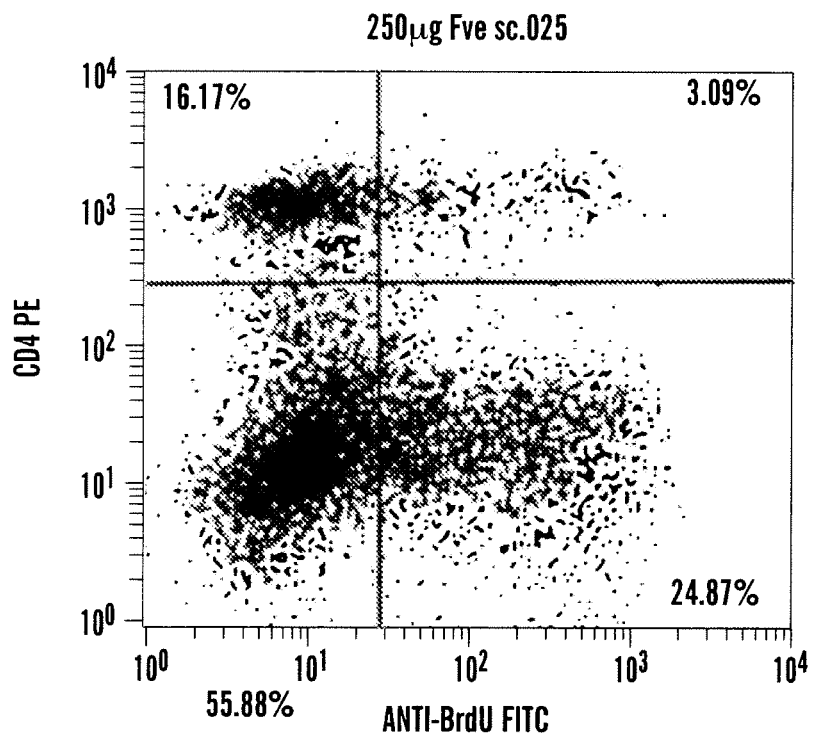
Figure 31A:
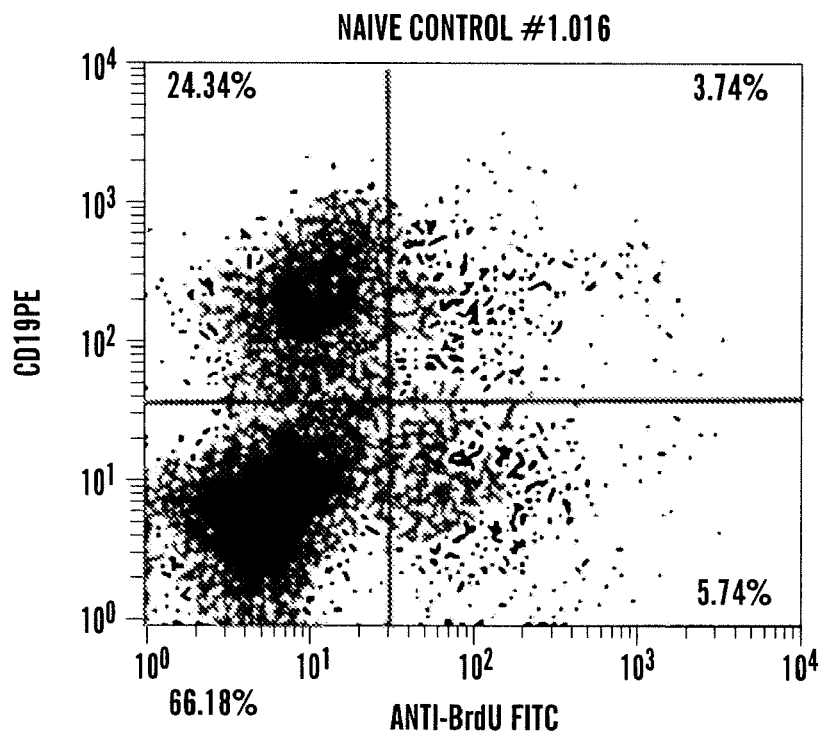
Figure 31B:
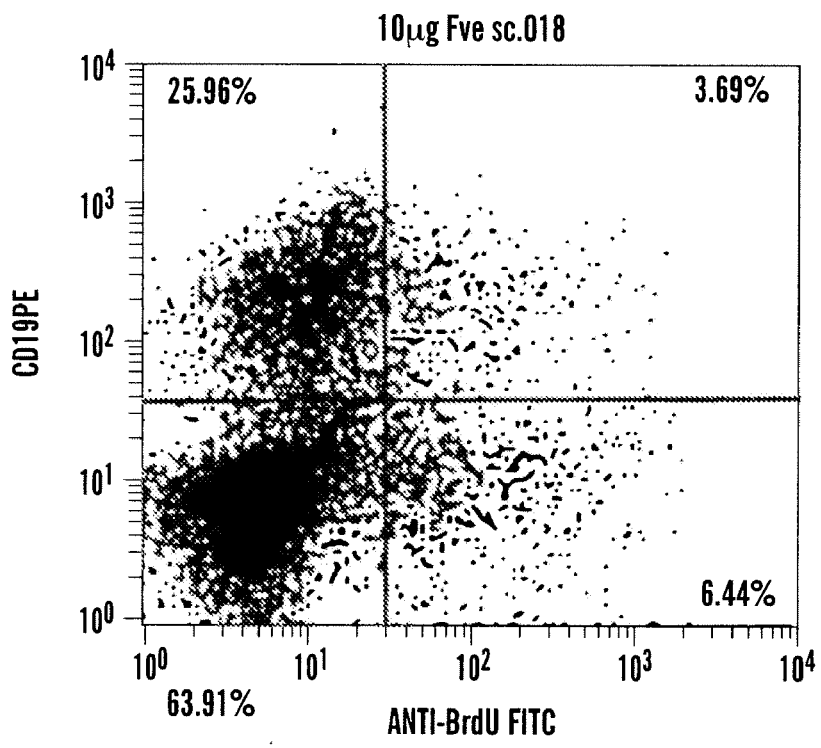
Figure 31C:
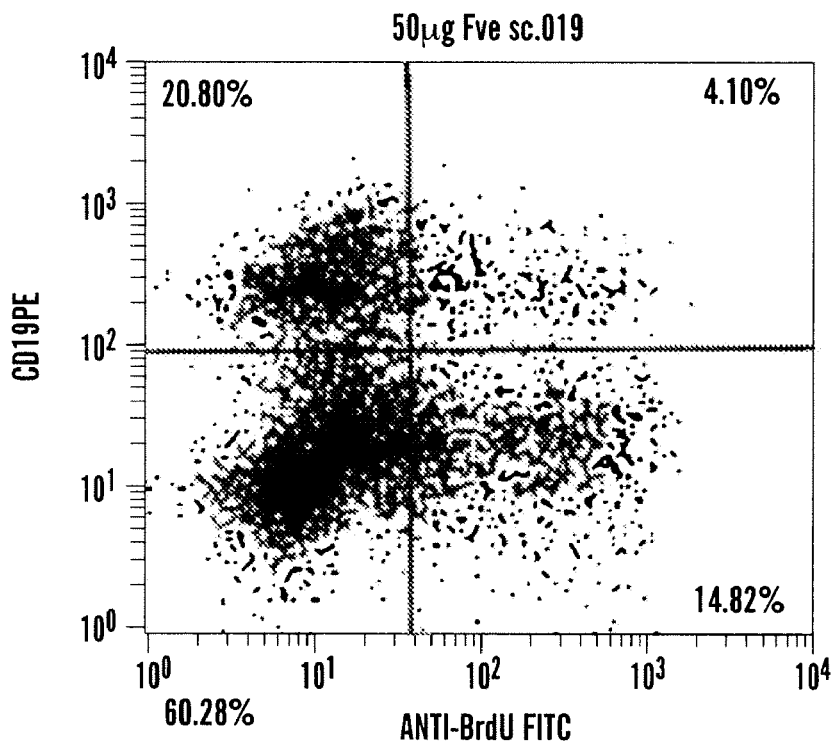
Figure 31D:
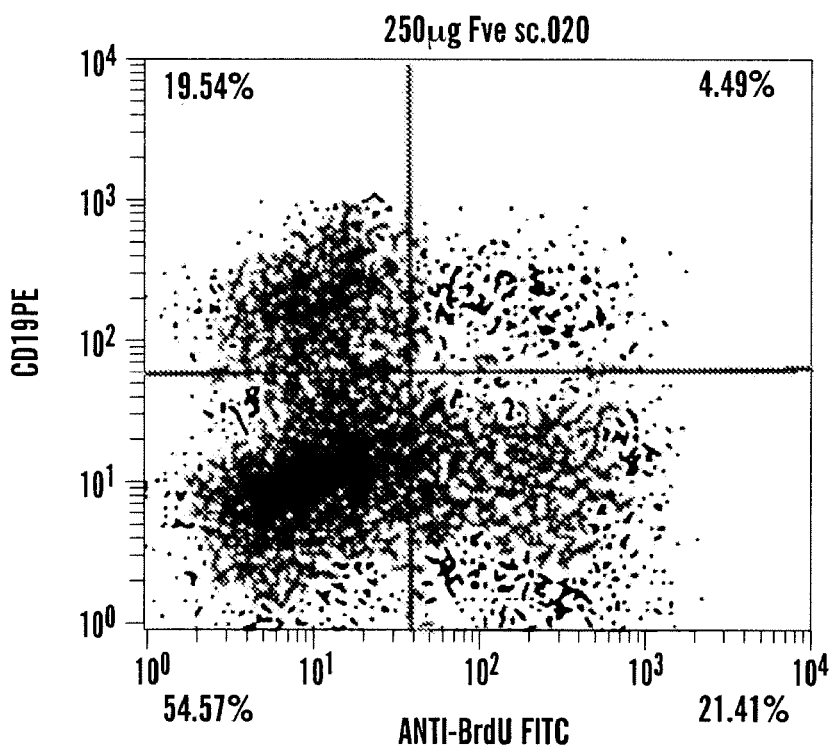
Figure 32A:
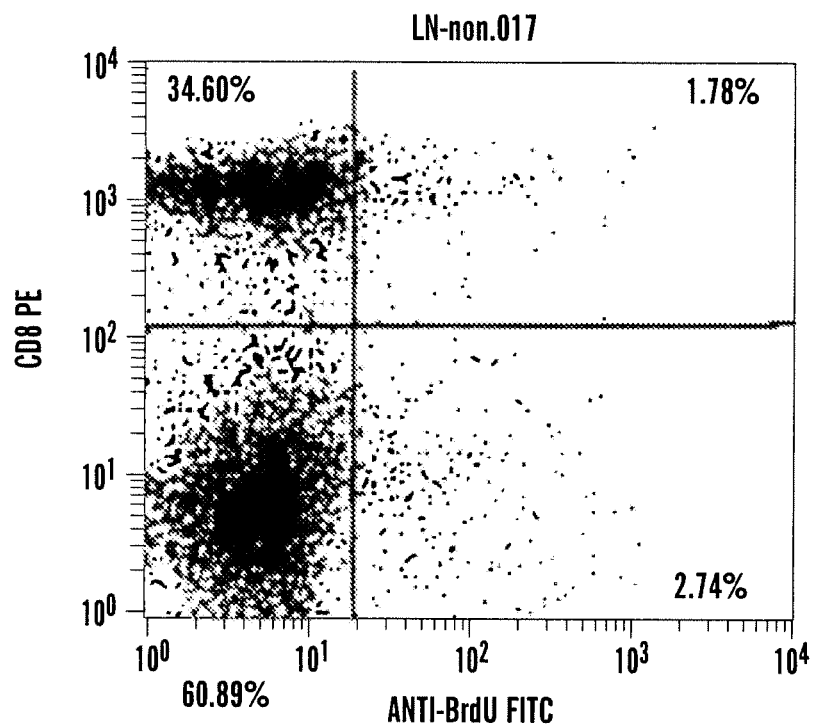
Figure 32B:
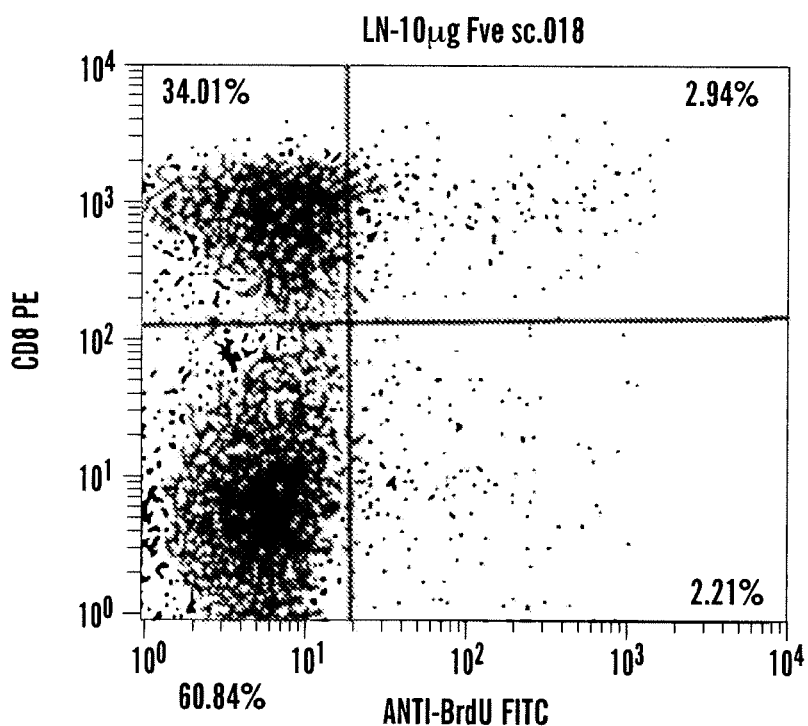
Figure 32C:
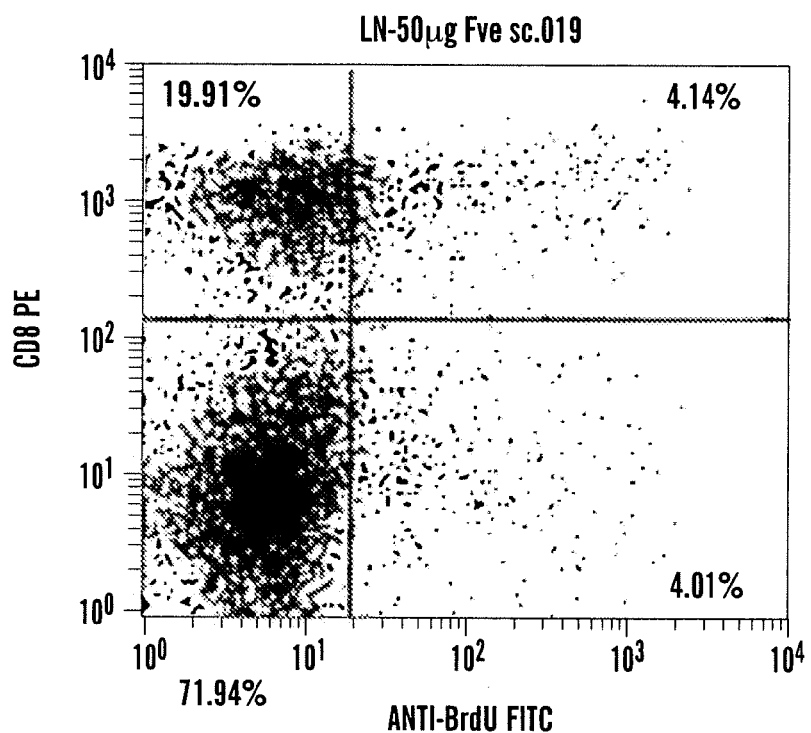
Figure 32D:
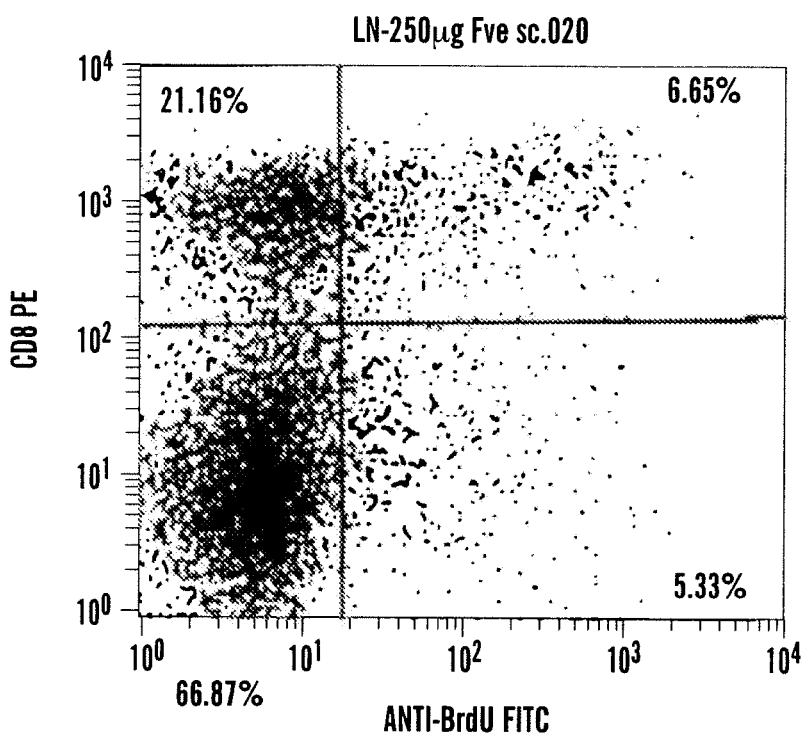
Figure 33A:
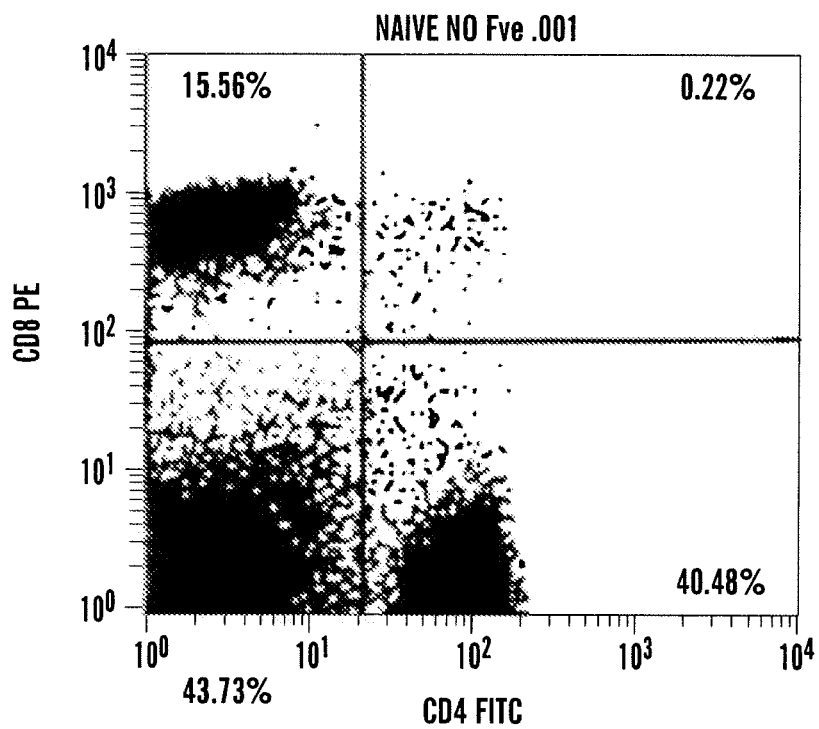
Figure 33B:
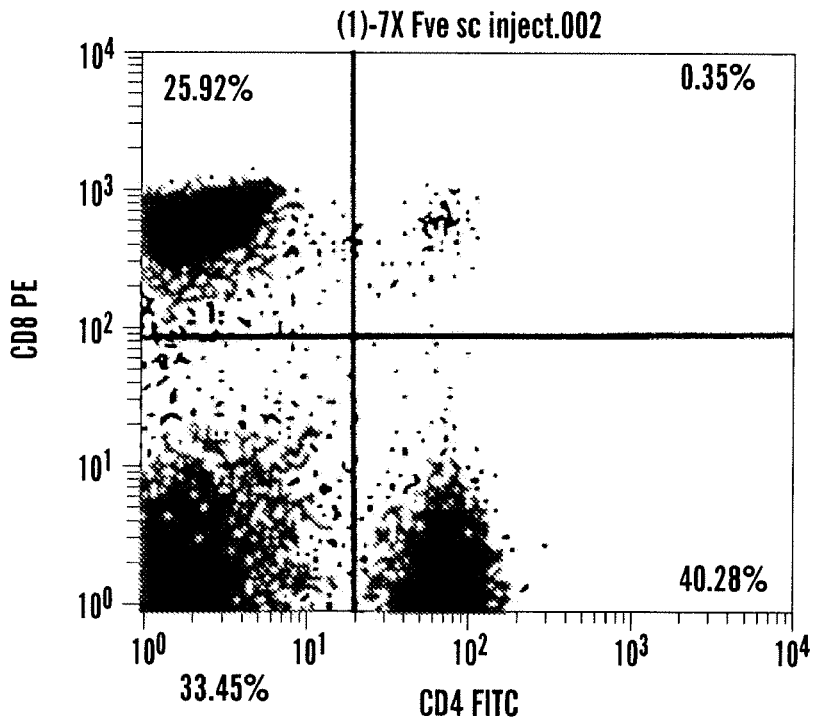
Figure 33C:
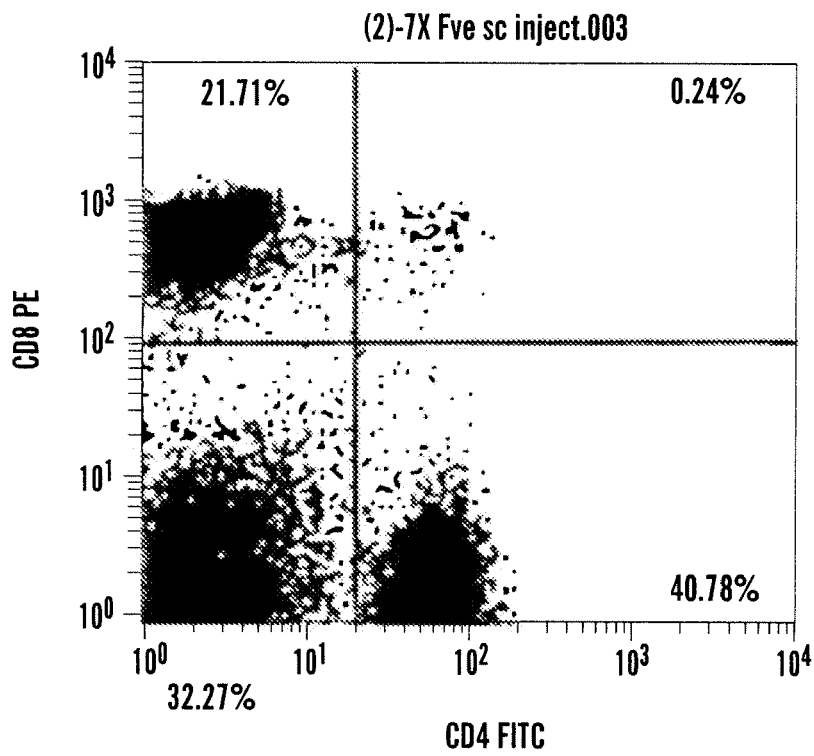
Figure 33D:
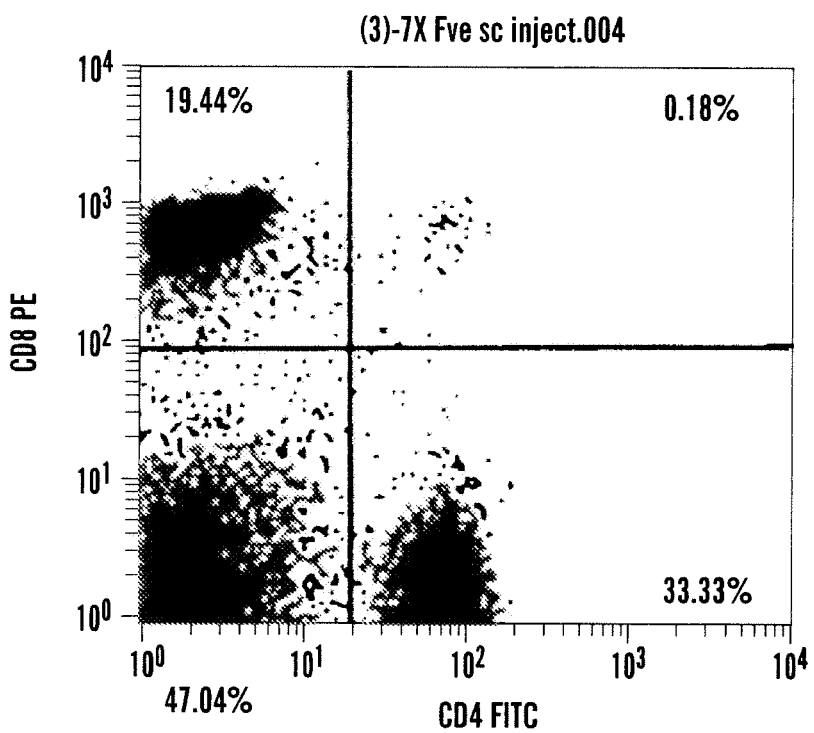

Result showed that CD3$^+$CD18$^{+bright}$ T cells are increased from 8% to 31% of total cell population (FIG. 26), and CD3$^+$CD8$^{+bright}$CD18$^{+bright}$ T cells are increased nearly three times, from 3.5% to 9% of the total cell population (FIG. 27) after stimulation with 20 μg/ml of native Fve protein. Furthermore, some CD18$^+$CD8$^-$ cells started to differentiate into CD18$^+$CD8$^{+dim}$ cells after stimulated with native Fve protein (FIG. 27B). This data suggested that Fve protein from the golden needle mushroom has a potential ability to stimulate cellular immune responses directed against malignancies in human.

Example 19

In Vivo Lymphocyte Proliferation Assays

Materials and Methods

Since Fve protein can activate human NK cells and CD8$^+$ T cells in vitro, we sought to determine whether Fve would enhance activation of these cells in vivo. Mouse provides a good model system for such a study.

A group of three C57BL/6J mice are subcutaneously injected with 10 μg, 50 μg or 250 μg Fve protein consecutively for three days, respectively. Another three BALB/cJ mice are treated with 125 μg of Fve protein each for seven days by subcutaneous injection. For continuous BrdU labeling, mice are given 0.5 mg/ml BrdU (Sigma) in the drinking water, which is changed every 3 days and then each mouse received one intraperitoneal injection of 1 mg of BrdU in PBS at 6 hours before being sacrificed. PBMC, lymph node and spleen are isolated and resuspended in 200 ul of washing buffer (1×PBS containing 1% bovine calf serum), then stained with anti CD4$^+$-FITC, anti CD8$^+$-PE, anti CD19$^+$-PE or anti PanNK-PE monoclonal antibody (Pharmingen) for 30 minutes on ice. After two washings with washing buffer, the samples are fixed with FACS Permeabilizing Solution (Becton Dickinson) for 16 hours. After that samples are treated with 50 U DNase I (Sigma) for 1 hr at room temperature. The cells are washed and stained with anti BrdU-FITC mAb (Becton Dickinson) in PBS for 30 minutes. 1–5×10$^5$ viable (forward and side scatter gated) PBMC, lymphocytes in lymph nodes or splenocytes per sample are analyzed with FACScan (Becton Dickinson) and data are processed using the CellQuest software (Becton Dickinson).

Results

Fve Induced NK Cells and CD8$^+$ T Cells Proliferation In Vivo

FACScan analysis data showed that Fve could induce increased proliferation of NK cells and CD8$^+$ T cells in a dose-dependent manner in C57BL/6J mice (FIG. 28 and FIG. 29). In contrast, CD4$^+$ T cells and CD19$^+$ B cells showed no significant increase (FIG. 30 and FIG. 31). Similar CD8$^+$ T cell polarization is also seen in lymph nodes of C57BL/6J mice (FIG. 32) and so the peripheral blood mononuclear cells (PBMC) of Balb/cJ mice that are subcutaneous injected for seven consecutive days with 125 μg of Fve protein. The CD8$^+$ versus CD4$^+$ T cells ratio is significantly increased in each of the Fve-treated BALB/cJ mouse as compared to the naïve control (FIG. 33). Data from the experiment are presented in Table 6 below.

TABLE 6

Data showing results of FIG. 33.

| Naïve Balb/cJ mouse | PBMC | | |
|---|---|---|---|
| | CD4$^+$ T cells | CD8$^+$ T cells | CD8$^+$/CD4$^+$ ratio |
| #1 None | 40.3% | 15.7% | 0.389 |
| #2 125 μg nFve | 40.2% | 26.2% | 0.651 |
| #3 125 μg nFve | 40.7% | 21.8% | 0.535 |
| #4 125 μg nFve | 33.3% | 19.6% | 0.588 |

In summary, for NK cells in spleen, 10 μg Fve caused one fold increase proliferation. The proliferation increased to 5-6 fold when 50 μg and 250 μg of Fve protein is added. Similar finding is observed in CD8 positive T cells in spleen and lymph nodes. 250 μg Fve protein caused 2-3 fold increase proliferation as compared to non-treated mouse. By contrast, Fve failed to stimulate CD4 positive T cells and has very mild stimulation to CD19 B cells (Table 7). Similar phenomenon is also seen in the peripheral blood mononuclear cells. The proportional of CD8 T cells increased up to 6-10% after 125 μg of Fve protein are subcutaneous injected to Balb/cJ mice for seven days (Table 8).

These in vivo data are in concordance with those derived from in vitro studies, which clearly indicate that Fve induces selective polarization of NK cells and CD8$^+$ T cells. Furthermore, these immunostimulatory effects of Fve are independent of the genetic background of mouse strains. Thus, Fve appears to be a potent immunostimulator for cellular mediated immune response. Purified NK cells and CD8$^+$ T cells will be used for future studies to examine the molecular and cellular basis for the polarization of cell subsets.

TABLE 7

In vivo stimulation of C57BL/6J mouse lymphocytes

| Naïve C57BL/6J mouse | Spleen | | | | Lymph nodes |
|---|---|---|---|---|---|
| | BrdU incorporated NK cells | BrdU incorporated CD4$^+$ T cells | BrdU incorporated CD8$^+$ T cells | BrdU incorporated CD19$^+$ B cells | BrdU incorporated CD8$^+$ T cells |
| #1 None | 0.63% | 3.49% | 2.22% | 3.48% | 5.83% |
| #2 10 μg Fve | 1.20% | 3.32% | 2.81% | 3.43% | 5.72% |
| #3 50 μg Fve | 3.53% | 3.47% | 3.34% | 4.11% | 9.19% |
| #4 250 μg Fve | 4.00% | 2.55% | 7.31% | 4.55% | 12.05% |

TABLE 7-continued

In vivo stimulation of C57BL/6J mouse lymphocytes

| Naïve C57BL/6J mouse | Spleen | | | | Lymph nodes BrdU incorporated CD8+ T cells |
|---|---|---|---|---|---|
| | BrdU incorporated NK cells | BrdU incorporated CD4+ T cells | BrdU incorporated CD8+ T cells | BrdU incorporated CD19+ B cells | |

TABLE 8

In vivo stimulation of Balb/cJ mouse lymphocytes

| Naïve Balb/cJ mouse | PBMC | | |
|---|---|---|---|
| | CD4+ T cells | CD8+ T cells | CD8+/CD4+ ratio |
| #1 None | 40.3% | 15.7% | 0.389 |
| #2 125 µg Fve | 40.2% | 26.2% | 0.651 |
| #3 125 µg Fve | 40.7% | 21.8% | 0.535 |
| #4 125 µg Fve | 33.3% | 19.6% | 0.588 |

Example 20

In Vivo Evaluation of the Potential Use of Fve for Immunotherapy of Solid Tumors There are several approaches to treat cancer such as surgery; radiation therapy; given tumor cell arrested drugs; induced apoptosis in cancerous cells; inhibited angiogenesis; elevated tumor recognition and specific killing ability of immune system to eliminate cancerous cells.

Previous data have indicated that Fve protein stimulate enhanced production of various cytokines, particularly IFN-γ, TNF-α and IL-2; induced polarization of natural killer cells and CD8+ T lymphocytes; and triggered a Th1/Tc1-like cellular-mediated immune response. Each of these biological properties may contribute to suppression of tumor growth and to prevent the risk of cancer recurrence by inducing various forms of nonspecific or even specific immunity after surgery.

Malignant melanoma is a very common cancer in the western world. A subset of patient with metastatic melanoma can be successfully treated by the administration of recombinant IL-2, sometimes given together with autologous melanoma-reactive lymphocytes that have been expanded ex vivo. Since melanocyte differentiation antigens, including MART-1/Melan-A, gp100, tyrosinase, TRP-1, and TRP-2, and cancer-testis antigens, including MAGE-3, BAGE, GAGE, NY-ESO-1, are recognized by human T lymphocytes, therefore they become the attractive targets for melanoma vaccines. However, from an immunological point of view, these melanocytes differentiation antigens and cancer-testis antigens are "self" antigens. It may induce central or peripheral tolerance, and thus potentially hampering the induction of powerful anti-melanoma immune responses. Therefore, induction of a strong tumor specific immunity with an immunopotentiator or novel adjuvant could be a useful treatment strategy to overcome immune ignorance and tolerance.

In order to investigate the anti-tumor effect of Fve, C57BL/6J mice are subcutaneously inoculated either with T cell lymphoma EL4 or melanoma B16-F1, the later is a well established and widely used tumor model for which treatment is notoriously difficult. The tumor growth and survival rate of mice are monitored.

Materials and Methods

Construction of pCIneo-fve and pDisplay-fve Recombinant Plasmid DNA

Figure 34A:
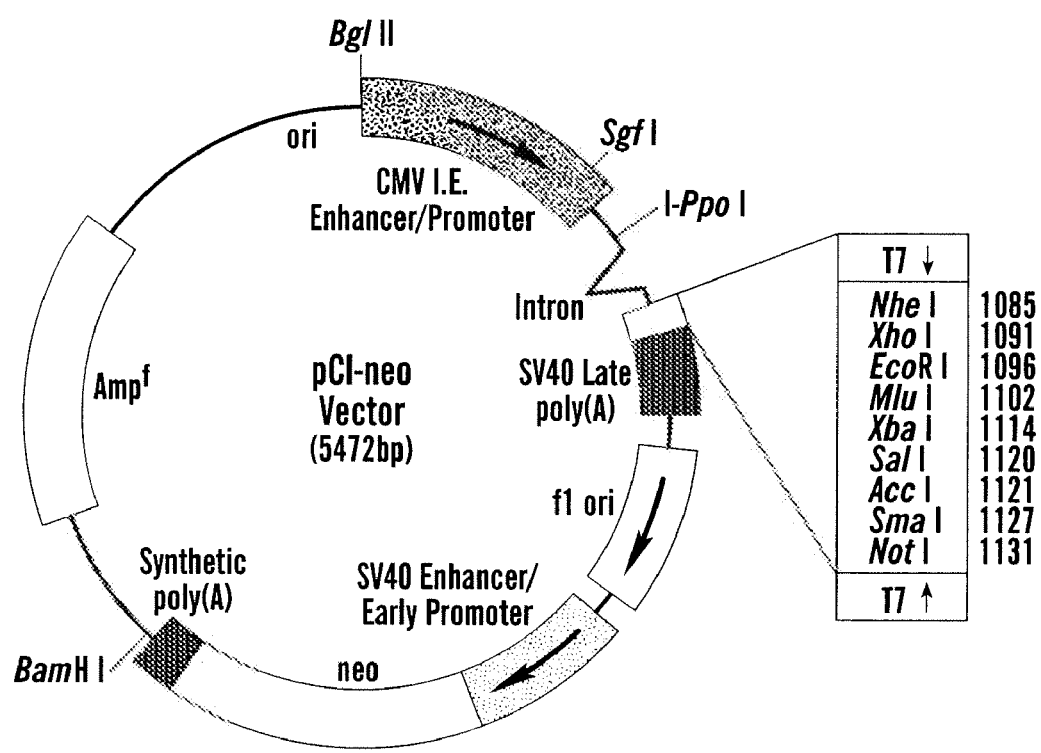

The pCIneo vector is designed for high level and constitutive expression of cloned DNA inserts in mammalian cells (FIG. 34A). Fve DNA is amplified from pGEX-fve and subcloned into the Xho I and EcoR I restriction enzyme cutting sites of pCIneo vector. The pCIneo-fve is used for priming the immune response by intramuscular injection.

Figure 34B:
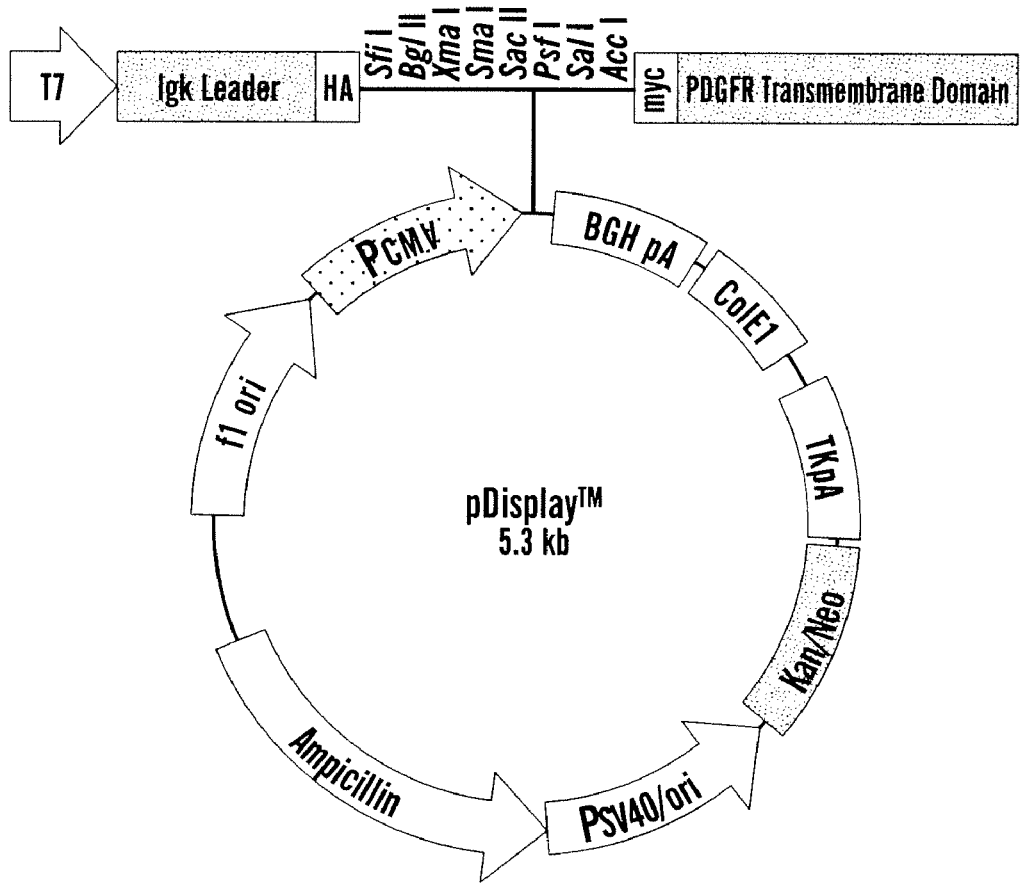

The pDisplay vector is a mammalian expression vector that is designed to target and to display recombinant proteins to the surface of mammalian cells (FIG. 34B). Fusion DNA of Fve and murine Ig kappa chain V-J2-C signal peptide without hemagglutinin A epitope is generated by recombinant PCR and subcloned into the EcoR I and Pst I restriction enzyme cutting sites of pDisplay vector. The Fve protein expressed from the pDisplay-fve acts as triggering signal for immune system and recruiting T lymphocytes to recognize tumor cells.

Transfection of B16-F1 Cells with pDisplay-fve

The murine melanoma cells B16-F1 is purchased from ATCC, USA. Tumor cells are grown in DMEM supplemented with 10% FBS in 5% $CO_2$. Cells in the exponential growth phase within four passages are used in this investigation. To obtain stable transfectants, endotoxin free plasmid pDisplay-fve is mixed with polyfect transfection reagent (QIAGEN, Germany) and transfected into B16-F1 cells. Colonies resistant to G418 (Geneticin, GIBCO BRL) at 1000 µg/ml for 25-30 days are isolated and designated as B16-Fve. The control B16-F1 cells which are transfected with pDisplay vector alone are designated as B16-vec.

EL4 Protection Assay

Six to eight weeks old C57BL/6J mice are inoculated with $8 \times 10^6$ EL4 cells. Tumor formation is observed at day 3. 100 µg of pCIneo-fve recombinant plasmid DNA is intramuscularly injected into the tibialis muscle at day 0 and day 7. 20 µg of Fve protein is given by subcutaneous injection surrounding the tumor site at day 5, 7, 9, 11, 13, 15, and 18, respectively. The diameters of tumors are measured with a caliper and tumor volume is calculated by long diameter time short diameter. Finally the survival rate is recorded.

DNA Vaccination and B16-F1 Tumor Protection Experiments

Endotoxin free pCIneo and pCIneo-fve are purified from the QIAGEN plasmid DNA extraction and purification kits. 100 µg of pCIneo-fve is intramuscularly injected into the tibialis muscle of C57BL/6 mice at day −30 and day −1. Muscles are pulsed with Electro Square Porator ECM830 (BTX, Genetronics, USA) equipped with a two needle array electrode after DNA injection. Mice are inoculated with $5 \times 10^5$ B16-F1 cells. Small tumor nodule developed at day 3. 50 µg of Fve protein is given by subcutaneous injection surrounding the tumor site at day 4, 7, 9, and 12, respectively.

Experimental Lung Metastasis

B16-F1 cells are trypsinized from monolayer cultures, counted and spun down at 1,200 rpm for 5 min and resuspended with DMEM. Five C57BL/6 syngenic 6-week-old female mice are intravenously injected with $2 \times 10^4$ of B16-F1 melanoma cells in a final volume of 120 µl. About 4 weeks after injection, tumor nodules are established in lung. Mice are kept until they died to assess survival.

Example 21

Prolonged Survival Rate of Tumor-Inoculated Mice Receiving with Fve Gene and Protein Our results show that tumor established mice that received pCIneo-fve DNA and Fve protein had shown a reduction of T cell lymphoma growth rate (FIG. 35) and an extension of survival time (FIG. 36). Similar results are also seen in melanoma B16-F1 inoculated C57BL/6J mice (FIG. 37).

These data indicate that Fve induces some protection against the solid EL4 tumor and B16-F1 melanoma, suggesting that Fve could be a potential candidate molecule for the development of the immunotherapeutic reagents for treatment of some cancers. The results also show that DNA vaccine-mediated treatment using the gene of Fve can be further exploited for effective cancer treatment. Nowadays, DNA vaccination is being explored as a potential strategy for combating cancer. However, tumor antigens are often weak and the immune system of patients may be compromised Like the concept of allergen-Fve fusion protein, fusion of Fve to specific tumor antigen may an effective way to activate protective anti-tumor immune response. Genetic immunization with chemeric gene encoding Fve and tumor antigen may augment and direct immune attack on a range of target tumor antigens.

Example 22

Life Span in Solid Tumor Model is Extended in Fve Transfectant

In previous study, we have proved that using Fve plasmid DNA primed in muscle and Fve protein boosted in tumor region could initiate anti-tumor immune response and thus prolong the survival time of tumor-inoculated mice. Instead of injection Fve surrounding the tumor, we specifically targeted Fve gene into tumor cells and tried to create an inducible-antigenic tumor for cancer therapy. This genetically modified tumor cells may provide signals for antigen presenting cells and both helper and cytotoxic T cells.

To determine whether introduction of the Fve gene into malignant cells would result in enhanced tumor recognition ability via Fve display and lead to extended survival rate in solid tumor experiment. Recombinant plasmid DNA pDisplay-fve is transfected into wild type B16-F1 mouse melanoma and then G418 resistant colonies are selected. Five female of C57BL/6J mice are inoculated with $5 \times 10^4$ of B16-Fve transfectant. The antigenicity of B16-vec and B16-Fve transfectants are compared through the life span of two groups of tumor-inoculated mice.

Result demonstrated that artificially expressed Fve on the surface of B16-F1 mouse melanoma extended survival rate as compared to B16-vec inoculated mice (FIG. 38). We propose that the characteristics of highly antigenecity and lymphocytes mitogenecity of Fve may elevate immune function to fight against tumor when it displayed on the surface of melanoma. Therefore, Fve may use as immune response activator and enhancer especially for those poorly recognized and low immunogenic tumor, which escaped from cancer surveillance and immune clearance by altering immune recognition and modulating cytotoxic response.

Example 23

Fve DNA Vaccination Retards Tumor Progression

Cancer vaccines are designed to prevent and treat cancer. In general, research has shown that the most effective anti-tumor immune responses are achieved by stimulating T cells, which can recognize and kill tumor cells directly. Most current cancer vaccines try to activate T cells directly, try to enlist APCs to activate T cells, or both. Some novel ways in which researchers are attempting to better activate T cells are: (1) Altering tumor cells so molecules that are normally only express on APCs are now express on the tumor cell. These molecules are capable of giving T cells a stronger activating signal than the original tumor cells. (2) Testing more cytokines and adjuvants to determine which are best candidates for recruiting APCs to areas where they are needed. (3) Using dendritic cells and other APCs fused with tumor cells as the cancer vaccines. These cells go into the body carrying tumor antigen and ready to activate T cells. Early cancer vaccine clinical trials involved mainly patients with melanoma. Currently, cancer vaccines are also being tested in the treatment of many other types of cancer, including prostate cancer, breast cancer, colon cancer, and lymphoma.

Here, we accessed tumor immunity that stimulated by recombinant Fve DNA vaccination alone and the combination of Fve DNA vaccination and Fve-transduced tumor cells. C57BL/6J mice are separated into three groups and each group consisted of ten mice. Mice are inoculated either with $5 \times 10^4$ of B16-Fve or B16-vec tumor transfectants in the dorsal back. Tumor formation is observed at day 5-7. 100 µg of pCIneo-fve plasmid DNA is intramuscularly injected at the right and left tribilis muscle of C57BL/6J at day −77, day −35 and day −21. Mice are subcutaneously injected with $5 \times 10^4$ of B16-Fve transfectant and B16-vec transfectant at day 0, respectively. 100 µg of pCIneo plasmid DNA is administered following similar experimental procedure and mice are subcutaneously injected with $5 \times 10^4$ of B16-vec transfectant as negative control. The fatal rate of mice are recorded and data are presented as survival curves.

Result showed that Fve DNA vaccination contained certain degree of tumor protection (Green line in FIG. 39) as compared with vector DNA vaccination (Blue line in FIG. 39). In addition, the combination of Fve DNA vaccination and B16-Fve transfectant exerted a stronger tumor protection effect (Red line in FIG. 39). Based on the result, we propose Fve is a novel protein to activate T cells directly. This protein is capable of giving T cells a strong activating signal when it is displayed on the surface of poorly immunogenic tumor cells. Therefore, the phenomenon of extended survival rate is observed in the experimental tumor-inoculated mice.

In future, the adjuvant effect of fusion proteins between Fve and tumor antigens to enhance tumor immunity will be determined. In particular, DNA fusion vaccine strategy, whereby target tumor antigen is genetically linked to immunostimulatory molecules such as Fve, is currently being explored. The introduction of fusion gene encoding tumor-associated antigen with Fve into antigen-presenting cells hold considerable promise for the treatment of patients with cancer. The ease of DNA manipulation has allowed incorporation of a wide variety of molecules able to promote antigen uptake, processing and presentation by professional antigen-presenting cells, to provide critical $CD4^+$ T-cell help and to activate more effective immune effector pathways (Zhu and Stevenson 2002). The concept of DNA fusion vaccine strategy is particularly important for cancer vaccines to increase their immunogenicity and to overcome tolerance.

Example 24

Fve Extends the Survival Rate of Lung Metastatic Mice $2\times10^4$ of B16-F1 melanoma cells is delivered to C57BL/6J via tail vein injection. The effect of combination of distill water and DNA vector pCIneo versus Fve protein and plasmid DNA pCIneo-fve administration on survival after the establishment of lung metastasis is determined. Survival extended in both metastatic experimental groups undergoing Fve protein orally primed and DNA intramuscularly boosted strategy.

Two groups of five C57BL/6J mice are given with 10 mg/ml of Fve protein in the drinking water at days −35, −28 and −21, and each water providing is maintained consecutively for one week. Mice are intravenously injected with $2\times10^4$ of B16-F1 (wild type) melanoma cells at day 0. One week after, mice are intramuscularly injected with 100 μg of pCIneo-fve plasmid DNA into the right and left tribilis muscle, respectively. The mixture of $5\times10^4$ of B16-Fve cells lysate plus 10 μg of Fve protein (Red line in FIG. 40) or 10 μg of Fve protein alone (Green line in FIG. 40) are subcutaneously injected into mice at the following three weeks. Negative control group of mice received same amount of 1×PBS in the drinking water, intravenously injected with $2\times10^4$ of B16-F1 melanoma cells, followed by intramuscularly injected with plasmid DNA vector pCIneo, and finally subcutaneously injected with B16-vec cells lysate plus 1×PBS (Blue line in FIG. 40).

Results showed that the strategy of orally primed with Fve protein before tumor introduced into the lung and intramuscularly boosted the immune response with the plasmid DNA pCIneo-fve after tumor established in lung could extend the survival rate of mice as compared with the control group (FIG. 40). This data provided another evidence suggesting Fve could augment anti-tumor immune response against developing or metastatic tumor cells. The inhibition of B16-F1 melanoma experimental lung metastasis by Fve may go through induction of IFN-γ, TNF-α and activation of anti-tumor host mechanisms. IFN-γ$^{-/-}$ and TNF-α$^{-/-}$ gene knock-out mice and in vivo depletions of CD4$^+$, CD8$^+$, or NK1.1$^+$ cells may provide supportive evidence to this phenomenon.

Example 25

Global Gene Expression Profiling of Human T Cells and NK Cells After Activation with Fve The invention of microarray technology allows the simultaneous monitoring of the transcriptional behavior of thousands of genes. This technology has been repeatedly shown to be useful in the analysis of the response of a variety of cellular systems to stimuli, in the classification of human cancer, and in the analysis of animal models of human disease (Churchill 2002; Slonim 2002; van Berkum and Holstege, 2001). To characterize the transcriptional profile of Fve, we analyzed gene expression patterns in T and NK cells from either healthy donor or human cell lines stimulation with Fve by using oligonucleotide microarrays and compared them with gene expression patterns in non-stimulation cells. In future, protein microarray assays would also be used to study protein-protein interactions on a genome-wide scale (Templin et al., 2002; Zhu et al., 2001).

Materials and Methods

Cells Collection and Total RNA Purification

Peripheral blood mononuclear cells (PBMC) are collected from healthy donors. CD8-positive T lymphocytes and natural killer cells isolation are performed by immunomagnetic bead selection with monoclonal mouse anti-human CD8 antibodies and monoclonal mouse anti-human CD56 antibodies using the AutoMACS automated separation system (Miltenyi-Biotec, Germany). CD8-positive T cells and CD56-positive natural killer cells purity of more than 94% and 88% homogeneity are confirmed by two-color flow cytometry using CD3$^+$/CD8$^+$ and CD56$^+$ criteria (Becton Dickinson, USA). Human T cell lines (Jurkat T cell, MOLT-4) and NK cell line (NK-92) are grown as recommended (ATCC, USA). Cells are stimulated with Fve and total RNA is isolated with RNeasy Mini Kit (Qiagen, Germany) after 2 and 48 hours, respectively.

Preparation of Labeled Complementary RNA and Hybridization to High-Density Microarray Double-stranded complementary DNA (cDNA) and biotinylated complementary RNA (cRNA) are synthesized from total RNA and hybridized to human GeneChip microarray (Affymetrix, USA), which are washed and scanned according to procedures developed by the manufacturer. The arrays are scanned using laser scanner and visualized using Affymetrix 3.3 software (Affymetrix).

GeneChip Data Analysis

Differentially expressed genes are analysed by functional assays

Example 25A

Th1 Adjuvant Effect of Fve on HPV E7 Antigen

Th1 adjuvant effect of Fve on HPV E7 antigen

Introduction

Fve protein, which is isolated from the fruit bodies of edible mushroom *Flammulina velutipes*, belongs to a new family of fungal immunomodulatory protein. Previous studies showed that Fve could stimulate gene expression of human IFN-γ, TNF-α, IL-10, IL-2. In allergic murine model, mice treated with Der p 2 plus Fve showed a significant Der p 2-specific IgG2a production. Taken together, Fve may act as a strong adjuvant to drive immune responses toward Th1-type responses. Human papillomavirus (HPV) infection is a major cause of cervical cancer worldwide. The HPV oncogenic proteins, E6 and E7 are required for tumorigenesis and maintenance of tumor state. Clinical study found that E7-specific immune responses are detected in cervical cancer patient, suggesting that E7 could be a specific target for immunotherapy against HPV-derived cervical cancer. In this animal study, we demonstrated that the production of HPV E7-specific IgG1 and IgG2a is greatly enhanced when E7 is co-administrated injection with the fungal immunomoodulatory protein Fve. Result suggests that Fve can be used as a potent adjuvant for viral vaccines development Materials And Methods 1. Construction of Plasmid DNA pGEX-4T1-E7

The DNA fragment encoding E7 of HPV type 16 is subcloned into pGEX-4T1 protein expression vector. E7 DNA fragment is amplified by polymerase chain reaction (PCR) using a set of primers: 5'-TTGTTGGATCCCATGGAGATA- CACCTACATTG-3' (SEQ ID NO: 3) and 5'-TTACTGAAT-TCTTATGGTTTCTGAGAACAGATG-3' (SEQ ID NO: 4). The amplified DNA is digested with BamH1 and EcoR1, and the resulting fragment is then cloned into the BamH1 and EcoR1 sites of pGEX-4T1 vector. The presence of the inserted E7 is confirmed by and restriction enzyme digestion and gel electrophoresis. The accuracy of the constructs is further confirmed by DNA sequencing. The plasmid construct is transformed into Escherichia coli TG-1 for protein expression.

2. Expression and Purification of Recombinant GST-E7 Protein

E7 is expressed as GST-fusions protein from pEGX-4T1 (Invitrogen, CA, USA). Small scale of pGEX-4T1-E7 transformed TG1 bacteria is seeded in LB medium. The overnight culture is transferred to 1 L of LB medium containing ampicillin (100 µg/ml) in 1 in 40 proportion and grown at 37.0 with 250 rpm vigorous shaking until the OD600 reach to 0.6-0.8 (approximately 2-3 hours). The recombinant protein is induced by 0.1 mM isopropyl-β-D-thiogalactopyranoside (Gold Biotechnology, MO, USA) at final concentration and further incubation of 4-6 hours at 35.0 with 200 rpm shaking. Cells are harvested by centrifugation at 6000 rpm for 10 minutes and the pellets are used for protein extraction. The pellets of E7 transformed bacteria are resuspended in 250 ml ice-cold lysis buffer (1×TBS pH 7.5, 1 mM PMSF (Sigma, Mo., USA), 20 µg/ml DNase 1 and 1% Tween 20). The cell suspension is then sonicated at 4.0 for 50 seconds, 18 cycles with 30 seconds intervals. Total cell lysate is centrifuged at 16 000 rpm for 25 min, 4.0 and the supernatant is collected for further affinity purification on glutathione agarose beads. Glutathione agarose beads (Sigma, Mo., USA) is dispensed into a chromatography column and then washed with 1×TBS (pH 7.5). Supernatant from the total cell lysate is then loaded onto the column and subsequently washed with 1×TBS. GST-E7 is eluted with elution buffer (Glutathione 0.15 g, Tris-base in a total volume of 50 ml dH2O) and then analyzed by SDS-PAGE. Pure fractions of GST-E7 protein are pooled together and cleaved with thrombin. Purified E7 is dialyzed against 1×PBS (pH 7.4) and used in further studies.

3. Isolation and Purification of Fve Protein from *Flammulina velutipes*

Two kilo grams of *Flammulina velutipes* (Golden needle mushroom) is purchased from Taiwan. The fresh fruit bodies of mushroom are homogenized with 2 L 5% acetic acid (v/v) in the presence of 0.1% (v/v) 2-mercaptoetheanol. The homogenate are centrifuged for 20 min and soluble proteins in the supernatant are precipitated by addition of ammonium sulphate to 95% saturation. After stirring for an overnight, the precipitates are collected by centrifuge for 20 min again. The pellets are dialyzed against 4.5 L of 10 mM Tris/HCl (PH 8.0) at 4° C. for 4 days with 9 changes of dialysis solution. The dialysate is firstly applied to Q column which is previously equilibrated with 10 mM Tris/HCl (PH 8.0). The flowthrough factions are then further purified by application to SP column which is previously equilibrated with 10 mM sodium acetate (PH 5.0). The column is first washed with 10 mM equilibration buffer and then eluted with a linear gradient of 0-1M NaCl in 10 mM sodium acetate (PH 5.0). The fractions are then further purified on a Q column (PH 8.0) and SP column (PH5.0). After purification, we combined them and dialyzed with 2 L 10 mM PBS (PH 7.4), then stores Fve protein at −20° C.

4. SDS-PAGE and Western Blot

Purified Fve and E7 are run in a 7.5% Tricine SDS-PAGE. After electrophoresis has completed, the proteins in the gel are stained with Coomassie plus Reagent (Pierce, Ill., USA). For western blotting, the proteins are transfer from the gel to a bio-blot nitrocellulose membrane and probed with either Fve polyclonal antibody or E7 monoclonal antibody (Southern Biotechnology, USA).

5. Mice

Female C57BL/6 mice are purchased from the Laboratory Animal Center (Sembawang, Singapore) and kept in the National University of Singapore (NUS) Animal Holding Unit. All animal procedures are performed according to approved protocols and in accordance with the Institutional Guidelines for Animal Care and Handling, NUS.

6. Protein Immunization of Mice

Two groups of eight- to ten-week-old female C57BL/6 mice (5 mice per group) are injected subcutaneously at the tail base with 10 µg of E7 alone or combination with 10 µg of Fve in a final volume of 100 µl of PBS at day 1. Mice are boosted with 20 µg of E7 alone or mixture with 20 µg of Fve at day 14 and day 28. Blood are collected weekly from the orbital sinus of the immunized mice and the collect sera are used for antibodies analysis using ELISA.

7. ELISA

In all ELISA experiments, samples are assayed in duplicates and 50 µl per well of reagents and samples are used. 96-well plates (Costar 9018, Corning, N.Y., USA) are incubated overnight at 4° C. with 5 µg/ml of purified E7 proteins in 0.1 M $NaHCO_3$, pH 8.3 coating buffer. Wells are washed three times with washing buffer TBST (0.05% Tween 20 (Sigma) in 1×(0.01 M) TBS, pH 7.4) using the automated Columbus washer (TECAN, Austria) and blocked with 100 µl/well of blocking buffer (1% BSA; bovine serum albumin in TBST) for 2 hours at room temperature. Plates are washed three times and diluted sera appropriately and incubated overnight at 4° C. For quantification and internal control purposes, known serial dilutions of purified mouse IgG1, IgG2a and ê light chain isotype standard (Pharmingen, CA, USA) is used on wells coated with anti-mouse ê light chain (Pharmingen, CA, USA).

Plates are again washed 6 times before adding biotin-conjugated anti-mouse isotypic antibodies IgG1, IgG2a (Southern Biotech, AL, USA) at 1:1000 dilution are added. The plates are then incubated for 1 hour at room temperature, followed by 6 times washing and 1 hour incubation at room temperature with ExtrAvidin alkaline-phosphatase conjugate (Sigma, Mo., USA). The plates are then washed 6 times and developed in paranitrophenyl phosphate (pNPP) substrate (Sigma, Mo., USA) at room temperature in the dark. The binding of specific antibodies is measured as absorbance at 405 nm with the Sectra (Shell) reader (TECAN, Austria). The antibody production units of antigen-specific antibodies are determined from the $OD_{405}$ using the plot of absorbance versus concentration of the standard.

Two groups of female BALB/cJ mice aged 6 to 8 weeks are given subcutenous injection of either 10 µg of HPV E7 antigen alone (group 1) or mixture of 10 µg of E7 with 10 µg of Fve (group 2) at day 1. Mice are boosted with 20 µg of same antigen at day 14 and 28. Sera are collected weekly and E7-specific IgG1 and IgG2a antibodies are analyzed using Elisa.

A schematic protocol of the animal study is shown in FIG. 40B.

Results

Combinations of E7 and Fve Enhance E7-Specific Immune Response

The results are shown in FIG. 40C. These results show that the production of E7-specific IgG1 and IgG2a are dramatically increased when E7 is co-administrated injection with Fve, as compared with E7 alone. The induction of IgG2a is 17-fold higher in the experimental mice as compare with the control group. This demonstrates that Fve displays an adjuvant effect and therefore enhance specific immune response to viral antigen. Co-administration of fungal immunomodulatory protein Fve and viral antigen HPV E7 increases the production of neutralizing antibodies.

Example 26

X-Ray Crystallographic Study of Fve: Materials and Methods

The three dimensional structural of Fve provides a good basis for the understanding of protein functions, immunomodulations and therapeutic applications in allergy and other diseases. We have crystallized the well-diffracting crystals of Fve and show that it diffracts to 1.4 Å resolution when exposed to synchrotron radiation.

This and the following Examples describe a 1.6 A° x-ray structure of Fve, determined by Single Anomalous Diffraction (SAD) using the anomalous signal of bromide ions present in the crystal for phasing. Fve represents a novel structure, wherein each monomer consists of an N-terminal α-helix followed by an immunoglobulin fold (beta-sandwich). The structure strongly suggests that dimerization, critical for the activity of FIP proteins, occurs by 3-D domain swapping of these helices and is stabilized predominantly by strong hydrophobic interactions between them.

Crystallization

Fve protein is obtained as described above. It is concentrated to 4 mg/ml in 10 mM Tris-HCl pH 7.5. Initial crystallization screening is done by the sparse matrix crystallization screening kit 1 & 2 from Hampton Research (Jancarik and Kim, 1991; Cudney, et al., 1994). All the screening and crystals growth are accomplished by hanging drops vapor diffusion method at 21° C. in VDX multi-well plates with 650 µl reservoir solutions. Drops consisting of 4 µl precipitant buffer from reservoirs and 4 µl protein sample (4 mg/ml) are equilibrated over the well solution for one week.

After extensive screening, plates-like crystals are obtained at two different low salt conditions: (1) 30% PEG 4000, 0.1 M Tris-HCl pH 8.5, 0.2 M $MgCl_2$; (2) 30% PEG 4000, 0.1 M Tris-HCl pH 8.5, 0.2 M NaOAc. 3D cubic-shaped and octahedral crystals also appeared after 3 days at two different high salt conditions: (1) 2.0 M $(NH_4)_2SO_4$, 0.1 M Tris-HCl pH 8.5; (2) 2% PEG 400; 0.1 M Na Hepes pH 7.5, 2.0 M $(NH_4)_2SO_4$. To optimize the crystallization condition, combinations of varied protein and salt concentrations, different molecular weights of PEG, and different pH are screened.

The best crystals formed at the high salt condition is optimized to 2.5% PEG 400, 2.0 M $(NH_4)_2SO_4$, 0.1 M Tris-HCl pH 8.5 at 21° C. They grew to the approximate dimensions of 1.0×0.9×0.5 mm within five days. The micrographs of Fve crystals are captured by inverted light microscope (FIG. 41).

High resolution protein crystals are therefore grown by vapor diffusion from hanging drop at 2.0% PEG 400, 2.0 M $(NH_4)_2SO_4$, 0.1 M Tris-Base, pH 8.5 for 1-2 weeks. Heavy atom derivatives are prepared by soaking the crystals in mother liquor containing 25% glycerol and 1M NaBr. The crystals are flash-frozen at 100 K after a 1-min soak in the heavy atom (Br) solution. SAD data from a derivatized crystal are collected at the National Synchrotron Light Source (NSLS) beam line X12C at one wavelength (***) around the Br absorption edge. The crystal diffracted to 1.7 Å.

X-Ray Analysis

The X-ray diffraction intensities from Fve crystals are measured at 100 K on beamline BL9-2 from the Stanford Synchrotron Radiation Laboratory facility with ADSC Quantum-315 CCD detector. Data are collected at a wavelength of 1.07 Å. All the data are processed by MOSFLM (Leslie, 1992) and X-ray intensities are scaled with SCALA (CCP4, 1994). Well-ordered diffraction data at 1.4 Å resolution are collected from larger crystals (FIG. 42).

Analysis of the collected data (Table 9) indicated that Fve crystals belong to the tetragonal space group $P4_32_12$ with unit cell dimensions of a=b=96.92 Å, c=61.42 Å. The Matthews parameter ($V_M$) of these crystals is 2.84 Å$^3$ per Da and thus the solvent content is 56.37% assuming two molecules of Fve per asymmetric unit (Matthews, 1968). A total of 344079 observations are obtained at 1.4 Å resolution giving approximate 56993 unique reflections (99.7% complete, $R_{merge}$=0.047).

TABLE 9

Data Collection and Statistics of Fve Crystal

| | |
|---|---|
| X-ray source, beamline | SSRL, BL9-2 |
| Wavelength | 1.07 Å |
| Detector distance | 99.97 mm, Q-315 CCD Detector |
| Cell angles (°) | 90.00, 90.00, 90.00 |
| Unit cell dimensions (Å) | 96.92, 96.92, 61.42 |
| Space group | $P4_32_12$ |
| Number of molecules per ASU | 2 |
| Number of observed reflections | 344079 |
| Number of unique reflections | 56993 |
| Solvent (%) | 56.37 |
| $V_M$ (Å$^3$Da$^{-1}$) | 2.84 |
| Resolution range (Å) | 33.5-1.4 |
| Average I/σ(I) | 10.1 |
| $R_{merge}$$^a$ | 0.047 |
| Completeness (%) | 99.7 |

$^a R_{merge} = \Sigma |I_i - <I>|/\Sigma I_i$, where $I_i$ is the mean intensity of symmetry-related measurements of this reflection.

Data Processing

The SAD data are processed and scaled using DENZO and SCALEPACK from the HKL2000 suite of programs (Otwinowski and Minor, 1997).

The crystal of Fve belongs to the tetragonal space group P43212 and has unit cell dimensions a=b=97.12, c=61.41 and α=β=β=90.0. All of the bromine heavy atom positions are located and refined by the program SOLVE at 1.7 Å (Terwilliger and Berendzen, 1999) and solvent flattened map is calculated using RESOLVE (Terwilliger, 2001). The resulting electron density map reveals secondary structure elements and side chains. In principle, it is possible to build an initial model by standard protein map-tracing methods. However, the phases obtained from RESOLVE are directly used in ARP/wARP (Morris et al., 2001) for automated main chains tracing, result in 4 continuous fragments that contained 97% of model. The rest of the model and side chains are fitted manually using XtalView (McRee, 1999). The refinement is carried out in REFMAC 5 (Murshudov et al., 1999) using resolution range 30.02-1.7 and water molecules are picked up by ARP/WARP later in the refinement.

In chain A, C-terminal residue 114 is modeled as Ala residue, whereas in chain B, C-terminal residue 113 and 114 are omitted from the final model, due to the poor interpretable density. The quality of the final model is verified with PROCHECK (Laskowski et al., 1993). However, the Ramachandran plot shows that Lys 14 in both A and B chains is in the disallowed region, although this residue fits very well in the 2fo-fc map.

Example 27

X-Ray Crystallographic Study of Fve: Results

The crystal structure is solved by single anomalous scattering using Br as the heavy-atom, and is refined to a resolution of 1.7 Å. The atomic coordinates are presented in Appendix C.

In total, two chains with a total of 226 residues, 16 bromine atoms and 136 solvent molecules are built into a high quality electron density map. Fve comprises almost exclusively of β-sheet structure with an Ig-like fold, which is formed by seven major antiparallel β-strands arranged into two sheets of four (D, E, H and I) and three (B, C and F) strands packed again each other. The N-terminal domain is composed of a α-helix which spans a length of 12 residues from Ala2 to Val13 and a β-sheet (A). The N-terminal serine residue is blocked by an acetyl group the density of which is also observed. Six loops connect the two main β-sheets and one loop connects the N-terminal domain with β-sheet structure. The loop between the β-sheets F and H contains a short β-strand and a $3_{10}$ helix.

The structure of Fve (FIG. 43) reveals that exists as a dimer. This is corroborated experimentally by running Fve on a gel filtration column against standard molecular weight markers (data not shown). From the structure, there are two extended regions of subunit-subunit interactions: between the two N-terminal α-helical regions (residues 2 to 13) and the β-stranded region (A and A').

Figure 44A:
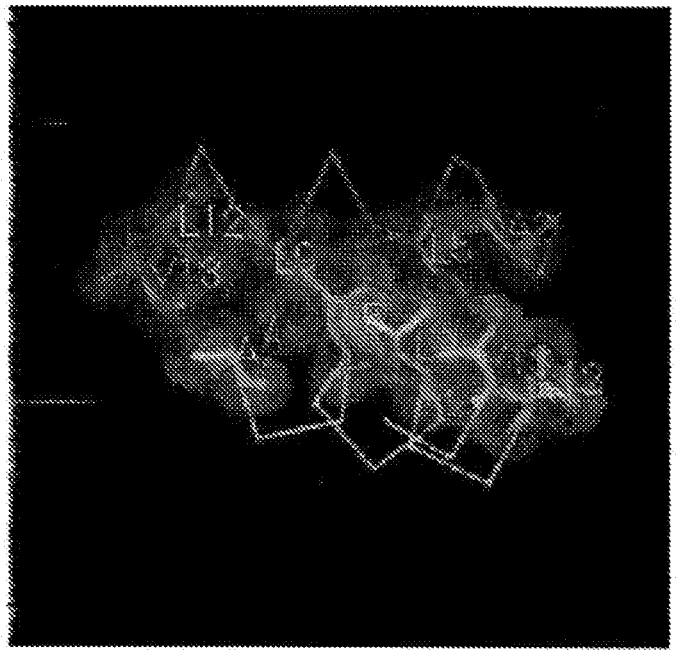
Figure 44B:
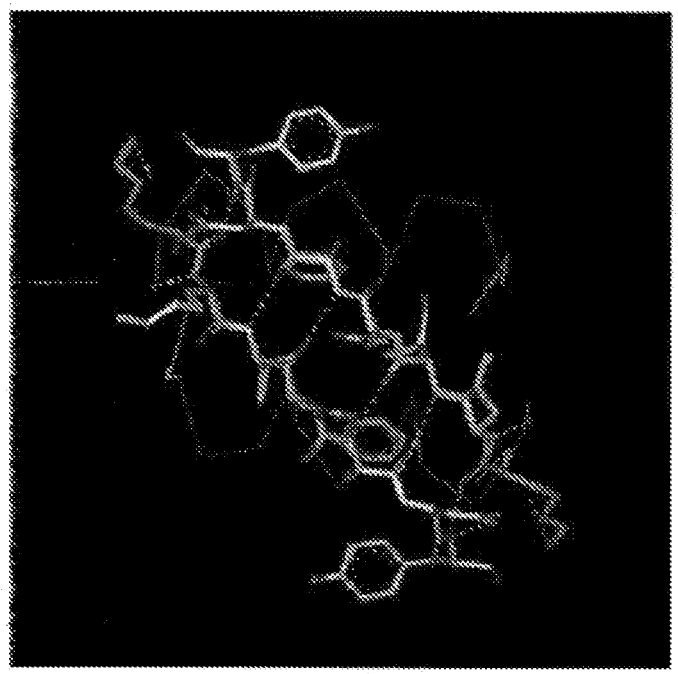
Figure 44C:
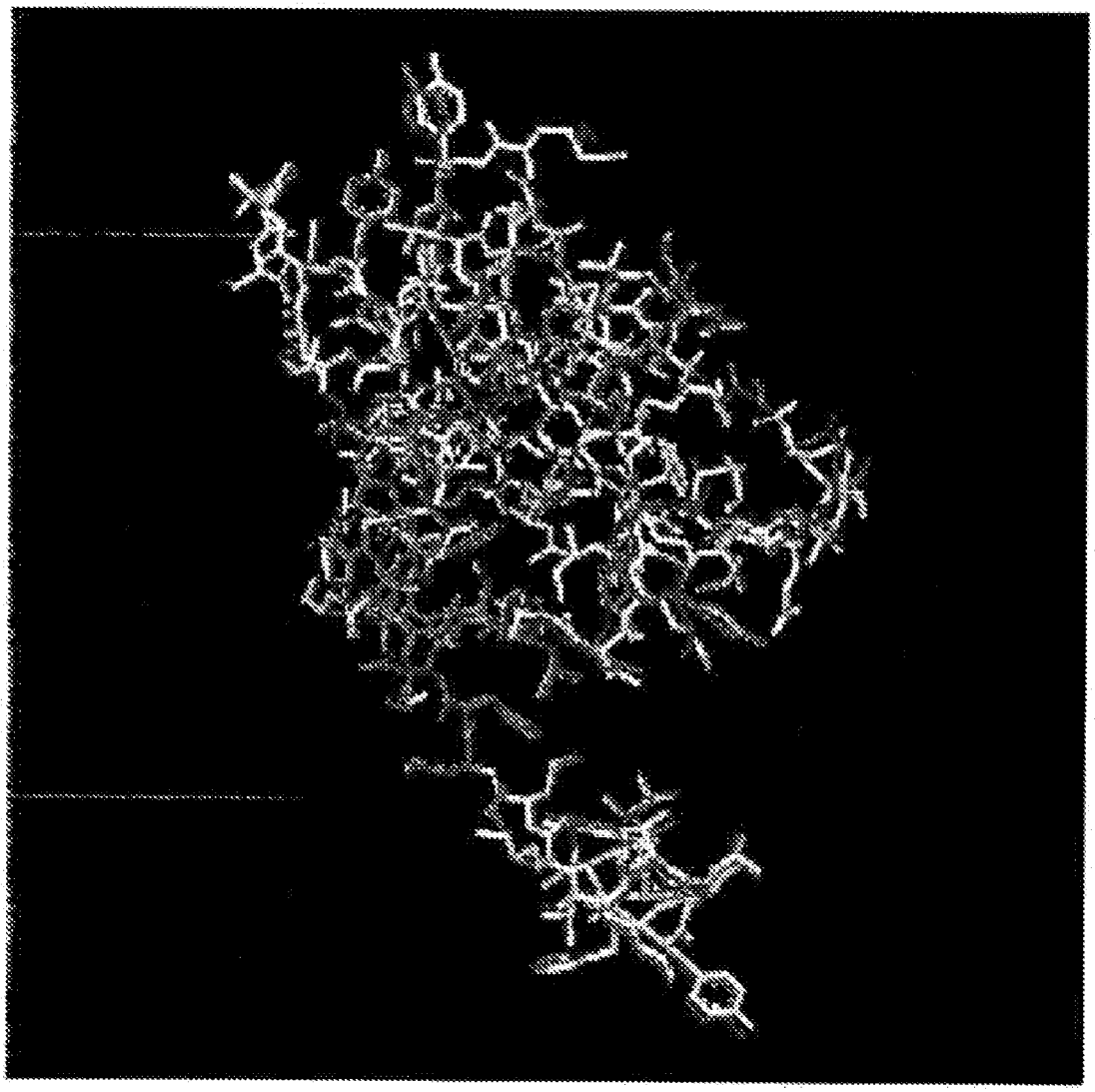

The buried side chains of the α-helical regions form a hydrophobic core (FIG. 44A), containing residues Ala 2, Leu 5, Leu 9 and Val 13 whereas the side chains of β-strand (A and A') make inter-subunit hydrogen bonds (FIG. 44B). These hydrophobic interactions and hydrogen bonds are responsible for dimer formation. The two monomers, A and B chains, of Fve can be closely superimposed: the RMSD between corresponding $C_\alpha$ positions of 112 residues is 0.29 Å (FIG. 44C).

Domain Swapping

Domain swapping is a very efficient method of forming oligomers since the interactions within the monomer are reused in the dimer. There is thus no need to evolve a new site on the surface which in one monomer mutually recognizes the corresponding site on the other monomer, since in the domain swapped dimer the recognition requirement has already largely been accounted for (Bennett et al., 1995).

Domain-swapped proteins have a C-interface generally with many specifics interaction, formed between domains linked by a hinge loop (Bennett et al., 1995). In p13suc1, two proline residues, located in the hinge region, have been shown to be essential and control the domain-swapping process (Rousseau et al., 2001).

Figures 45A, 45B:

As shown in FIG. 45A, half of the dimer of Fve contains one N-terminal helix, forming a C-interface with hydrophobic core, which is linked to rest of its subunit by a hinge loop, stretching from residue Val 13 to Pro 22. Furthermore, Fve contains a proline residue at the end of the hinge region, which could adopt alternative conformation in the dimer by releasing the tension in the monomer. These observations suggest that domain-swapping could be the mechanism for forming dimer protein from its monomer. The monomer is modeled (FIG. 45B).

Structural Similarity with Other Proteins

Fve has no sequence homology to any other non-FIP proteins. However, a search for similar structure in the DALI database (Holm and Sander, 1993) reveals that the protein has a significantly similar fold to 140 proteins but none with the significant sequence similarity to Fve. Among 140 similar fold protein, fibronectin type III family emerged with less topology diversity to Fve β-sandwich fold: the heparin and integrin binding segment of human fibronectin (FN12-15; PDB entry 1FNH), the fragment of human fibronectin type III repeat (FN7-10; 1FNF), The p40 domain of human interlukin-12 (p40; 1F42) and the antibody a6 fragment interferon-gamma receptor alpha chain (IFNγR1-108; 1JRH). An alignment of FN12-15, FN7-10, p40, IFNγR1-108 and Fve on the basis of structural similarity shows topology diversity in the range 11-17, calculated by Topp program (Lu, 1996) (Table 10).

TABLE 10

| | Name | PDB ID | Z-Score | RMSD | Length of aligned segment | Topological Diversity | Superfamily (Family) | Species |
|---|---|---|---|---|---|---|---|---|
| 1 | interleukin-4 receptor alpha chain fragment: b: 1-96 | 1iar-B | 5.8 | 3 | 78 | 8.5 | Fn III (FNIII) | Homo sapiens |
| 2 | mhc class ii i-ak: a: 82-181 | 1iak-A | 5.8 | 4.7 | 83 | 18.6 | Ig (C1) | Mus musculus |
| 3 | mhc class ii i-ak: b: 93-190 | 1iak-B | 5.6 | 3.5 | 74 | 17.8 | Ig (C1) | Mus musculus |
| 4 | igg2a intact antibody - mab23, kappa L chain: a: 1-108 | 1igt-B | 5.5 | 3.8 | 86 | 18.4 | Ig (V) | Mus musculus |
| 5 | class ii histocompatibility antigen, HLA-DM: a: 94-196 | 1hdm-B | 5.3 | 4.7 | 82 | 18.4 | Ig (C1) | Homo sapiens |
| 6 | fibronectin fragment, heparin & integrin binding segment: a: 93-182 | 1fnh-A | 5.3 | 3 | 73 | 11.1 | Fn III (FNIII) | Homo sapiens |
| 7 | ch3 domain of mak33 antibody fragment: chain a | 1cqk-A | 5.3 | 3.3 | 76 | 18.5 | Ig (C1) | Mus musculus |
| 8 | CD1, beta2-microglobulin and alpha-3 domain: d | 1cid | 5.3 | 2.8 | 76 | 17.8 | Ig (V) | Rattus rattus |
| 9 | fibronectin fragment, ED-B domain: chain a | 2fnb-A | 5.2 | 3.9 | 72 | 17 | Fn III (FNIII) | Homo sapiens |
| 10 | hiv-1 gag peptide: a: 182-276 | 1agd-A | 5.2 | 3.8 | 84 | 20.1 | Ig (C1) | Homo sapiens |
| 11 | igg1 antibody 32c2 fragment: a: 1-110 | 32c2-A | 5.1 | 5.6 | 80 | 19.4 | Ig (V) | Mus musculus |
| 12 | fibronectin repeat 7: 1142-1235 | 1fnf | 5.1 | 2.7 | 71 | 10.8 | Fn III (FNIII) | Homo sapiens |
| 13 | interleukin-12 beta chain | 1f42-A | 5.1 | 2.8 | 70 | 12.8 | Fn III | Homo |

TABLE 10-continued

| Name | PDB ID | Z-Score | RMSD | Length of aligned segment | Topological Diversity | Superfamily (Family) | Species |
|---|---|---|---|---|---|---|---|
| fragment: a: 88-211 | | | | | | (FNIII) | sapiens |
| 14 Mutant growth hormone receptor fragment: b: 131-236 | 1axi-B | 5.1 | 3.2 | 72 | 14.7 | Fn III (FNIII) | Homo sapiens |

REFERENCES

Akbari O, Freeman G J, Meyer E H, Greenfield E A, Chang T T, Sharpe A H, Berry G, DeKruyff R H, and Umetsu D T. (2002) Antigen-specific regulatory T cells develop via the ICOS-ICOS-ligand pathway and inhibit allergen-induced airway hyperreactivity. Nat. Med. 8:1024-1032.

Arkwright P D and David T J. (2001) Intradermal administration of a killed *Mycobacterium vaccae* suspension (SRL 172) is associated with improvement in atopic dermatitis in children with moderate-to-severe disease. J. Allergy Clin. Immunol. 107:531-534.

Banos, V., Gomez, J., Garcia, A., Ruiz, J., Alvarez, R., Lorenzo, M., Canteras, M., and Valdes, M. (1997) Effectiveness of immunomodulating treatment (thymostimulin) in chronic obstructive pulmonary disease. Respiration. 64, 220-223.

Bennett, M. J., Schlunegger, M. P. & Eisenberg, D. 3D domain swapping—a mechanism for oligomer assembly, Protein Science, 4, 2455-2468, (1995).

Bonde, J., Dahl, R., Edelstein, R., Kok-Jensen, A., Lazer, L., Punakivi, L., Seppala, A., Soes-Petersen, U., and Viskum, K. (1986) The effect of RU 41.740, an immune modulating compound, in the prevention of acute exacerbations in patients with chronic bronchitis. Eur. J. Respir. Dis. 69, 235-241.

Braga, P. C., Dal Sasso, M., Maci, S., Piatti, G., Palmieri, R., Bruno, L., and Albanese, C. (1994) Restoration of polymorphonuclear leukocyte function in elderly subjects by thymomodulin. J. Chemother. 6, 354-359.

Chihara, G., Maeda, Y., Hamuro, J., Sasaki, T., and Fukuoka, F. (1969) Inhibition of mouse sarcoma 180 by polysaccharide from *Lentinus edodes*(Berk) sing. Nature. 222, 687-688.

Churchill G A. (2002) Fundamentals of experimental design for cDNA microarrays. Nat. Genet. 32 Suppl 2:490-495. Collaborative Computational Computor Project 4. (1994) The CCP4 suite: programs for protein crystallography. Acta Crystallogr. D50, 760-763.

Cross M L and Gill H S. (2001) Can immunoregulatory Lactic acid bacteria be used as dietary supplements to Limit Allergies? Int. Arch. Allergy Immunol. 125:112-119.

Cudney, B., Patel, S., Weisgraber, K., and Newhouse, Y. (1994) Screening and optimization strategies for macromolecular crystal growth. Acta Crystallogr. D50, 414-423.

Daniell H, Streatfield S J, and Wycoff K. (2001) Medical molecular farming: production of antibodies, biopharmaceuticals and edible vaccines in plants. Trends Plant Sci. 6:219-226.

Darji A, Guzman C A, Gerstel B, Wachholz P, Timmis K N, Wehland J, Chakraborty T, and Weiss S. (1997) Oral somatic transgene vaccination using attenuated *S. typhimurium*. Cell 91:765-775.

Donnelly J J, Ulmer J B, Shiver J W, and Liu M A. (1997) DNA vaccines. Annu. Rev. Immunol. 15:617-648.

During M J, Symes C W, Lawlor P A, Lin J, Dunning J, Fitzsimons H L, Poulsen D, Leone P, Xu R, Dicker B L, Lipski J, and Young D. (2000) An oral vaccine against NMDAR1 with efficacy in experimental stroke and epilepsy. Science 287:1453-1460.

Erbacher, P., Zou, S., Bettinger, T., Steffan, A. M. & Remy, J. S. Chitosan-based vector/DNA complexes for gene delivery: biophysical characteristics and transfection ability. Pharm. Res. 15: 1332-1339, 1998.

Eriksson K and Holmgren J. (2002) Recent advances in mucosal vaccines and adjuvants. Curr. Opin. Immunol. 14:666-672.

Federico, M., Gobbi, P. G., Moretti, G., Avanzini, P., Di Renzo, N., Cavanna, L., Ascari, E., and Silingardi, V. (1995) Effects of thymostimulin with combination chemotherapy in patients with aggressive non-Hodgkin's lymphoma. A report from the Italian Lymphoma Study Group (GISL). Am. J. Clin. Oncol. 18, 8-14.

Fenske D B, MacLachlan I, and Cullis P R. (2002) Stabilized plasmid-lipid particles: a systemic gene therapy vector. Methods Enzymol. 346:36-71.

Fischer R and Emans N. (2000) Molecular farming of pharmaceutical proteins. Transgenic Res. 9:279-99.

Fisher, M., and Yang, L. X. (2002) Anticancer effects and mechanisms of polysaccharide-K (PSK): implications of cancer immunotherapy. Anticancer Res. 22, 1737-1754.

Fujimiya, Y., Suzuki, Y., Katakura, R., and Ebina, T. (1999) Tumor-specific cytocidal and immunopotentiating effects of relatively low molecular weight products derived from the basidiomycete, *Agaricus blazei* Murill. Anticancer Res. 19, 113-118.

Giddings G, Allison G, Brooks D, and Carter A. (2000) Transgenic plants as factories for biopharmaceuticals. Nat. Biotechnol. 18:1151-1155.

Hirasawa, M., Shouji, N., Neta, T., Fukushima, K., and Takada, K. (1999) Three kinds of antibacterial substances from *Lentinus edodes* (Berk.) Sing. (Shiitake, an edible mushroom). Int. J. Antimicrobial Agents. 11, 151-157.

Holm, L & Sander, C. Protein structure comparison by alignment of distance matrices. J. Mol. Biol. 233, 123-138 (1993).

Holm, L & Sander, C. Protein structure comparison by alignment of distance matrices. J. Mol. Biol. 233, 123-138 (1993).

Hsu C H, Chua K Y, Tao M H, Lai Y L, Wu H D, Huang S K, and Hsieh K H. (1996) Immunoprophylaxis of allergen-induced immunoglobulin E synthesis and airway hyperresponsiveness in vivo by genetic immunization. Nat. Med. 2:540-544.

Hsu, H. C., Hsu, C. I., Lin, R. H., Kao, C. L., and Lin, J. Y. (1997) Fip-vvo, a new fungal immunomodulatory protein isolated from *Volvariella volvacea*. Biochem. J. 323, 557-565.

Iguchi, C., Nio, Y., Takeda, H., Yamasawa, K., Hirahara, N., Toga, T., Itakura, M., and Tamura, K. (2001) Plant polysaccharide PSK: cytostatic effects on growth and invasion; modulating effect on the expression of HLA and adhesion molecules on human gastric and colonic tumor cell surface. Anticancer Res. 21, 1007-1013.

Illum L, Jabbal-Gill I, Hinchcliffe M, Fisher A N, and Davis SS. (2001) Chitosan as a novel nasal delivery system for vaccines. Adv. Drug Deliv. Rev. 51:81-96.

Jahn-Schmid B, Graninger M, Glozik M, Kupcu S, Ebner C, Unger F M, Sleytr U B, and Messner P. (1996) Immunoreactivity of allergen (Bet v 1) conjugated to crystalline bacterial cell surface layers (S-layers). Immunotechnology 1996 2:103-113.

Jancarik, J., and Kim, S. H. (1991) Sparse matrix sampling: a screening method for crystallization of proteins. *J. Appl. Crystallogr.* 24, 409-411.

Johnson-Saliba M, and Jans D A. (2001) Gene therapy: optimising DNA delivery to the nucleus. *Curr. Drug Targets* 2:371-399.

Jones D H, Corris S, McDonald S, Clegg J C, and Farrar G H. (1997) Poly(DL-lactide-co-glycolide)-encapsulated plasmid DNA elicits systemic and mucosal antibody responses to encoded protein after oral administration. Vaccine 15:814-817.

Jong, et al. Immunomodulatory Substances of Fungal Origin, J. Immunol. Immunopharmacol., Vol. XI, No. 3, 1991. pp. 115-122.

Kakuta S, Tagawa Y, Shibata S, Nanno M, and Iwakura Y. (2002) Inhibition of B16 melanoma experimental metastasis by interferon-gamma through direct inhibition of cell proliferation and activation of antitumour host mechanisms. Immunology 105:92-100.

Kamat, A. M., and Lamm, D. L. (2001) Immunotherapy for bladder cancer. *Curr. Urol. Rep.* 2, 62-69.

Kas, H. S. Chitosan: properties, preparations and application to microparticulate systems. *J. Microencapsul.* 14: 689-711, 1997.

Kino, K., Yamashita, A., Yamaoka, K., Watanabe, J., Tanaka, S., Ko, K., Shimizu, K., and Tsunoo, H. (1989) Isolation and characterization of a new immunomodulatory protein, Ling Zhi-8 (LZ-8), from *Ganoderma lucidium*. *J. Biol. Chem.* 264, 472-478.

Klaenhammer T R. (1995) Genetics of intestinal lactobacilli. Int. Dairy J. 5:1019-1058.

Ko J L, Hsu C I, Lin R H, Kao C L, Lin J Y, A new fungal immunomodulatory protein, FIP-fve isolated from the edible mushroom, *Flammulina velutipes* and its complete amino acid sequence. *Eur. J Biochem* 228(2):244-9 (1995)

Ko, J. L., Lin, S. J., Hsu, C. I., Kao, C. L & Lin, J. Y. Molecular cloning and expression of a fungal immunomodulatory protein, FIP-fve, from *flammulina velutipes*. *J Forms Med. Assoc.* 96, 517-524, (1997).

Komatsu, N., Okuto, S., Kikumoto, S., Kimura, K., Saito, G., and Sakai, S. (1969) Host mediated antitumor action of Schizophyllan, a glucan produced by Schizophyllaum commune. *Gann.* 60, 137-144.

Kong Q, Richter L, Yang Y F, Arntzen C J, Mason H S, and Thanavala Y. (2001) Oral immunization with hepatitis B surface antigen expressed in transgenic plants. Proc. Natl. Acad. Sci. USA 98:11539-11544.

Kraulis, P. J. A program to produce both detailed and schematic plots of protein. *J. Appl. Crystallogr.* 24, 946-950 (1991).

Krieg A M. (2000) The role of CpG motifs in innate immunity. Curr. Opin. Immunol. 12:35-43.

Krieg A M. (2002) A role for toll in autoimmunity. Nat. Immunol. 3: 423-424.

Kruger C, Hu Y, Pan Q, Marcotte H, Hultberg A, Delwar D, Van Dalen P J, Pouwels P H, Leer R J, Kelly C G, Van Dollenweerd C, Ma J K, and Hammarstrom L. (2002) In situ delivery of passive immunity by lactobacilli producing single-chain antibodies. Nat. Biotechnol. 20:702-706.

La Mantia, I., Grillo, C., Mattina, T., Zaccone, P., Xiang, M., Di Mauro, M., Meroni, P. L., and Nicoletti, F. (1999) Prophylaxis with the novel immunomodulator pidotimod reduces the frequency and severity of upper respiratory tract infections in children with Down's syndrome. *J. Chemother.* 11, 126-130.

Laskowski, R. A., MacArthur, M. W., Moss, D. S. & Thorton, J. M. PROCHECK: a program to check the stereochemical quality of protein structures. *J. Appl. Crystallogr.* 26, 283-290 (1993).

Leadbetter E A, Rifkin I R, Hohlbaum A M, Beaudette B C, Shlomchik M J, Marshak-Rothstein A. (2002) Chromatin-IgG complexes activate B cells by dual engagement of IgM and Toll-like receptors. Nature 416:603-607.

Leslie, A. G. W. (1992) Recent changes to the Mosflm package for processing film and image plate data. *Joint CCP4 and ESF-EACBM Newsletter on Protein Crystallography*. No. 26. SERC Daresbury Laboratory, Warrington, UK.

Liao, H. F., Chou, C. J., Wu, S. H., Khoo, K. H., Chen, C. F., and Wang, S. Y. (2001) Isolation and characterization of an active compound from black soybean [*Glycine max* (L.) Merr.] and its effect on proliferation and differentiation of human leukemic U937 cells. *Anticancer Drugs.* 12, 841-846.

Lin, W. H., Hung, C. H., Hsu, C. I., and Lin, J. Y. (1997) Dimerization of the N-terminal amphipathic α-helix domain of the fungal immunomodulatory protein from *Ganoderma tsugae* (Fip-gts) defined by a yeast two-hybrid system and site-directed mutagenesis. *J. Biol. Chem.* 272, 20044-20048.

Lu G., A WWW service system for automatic comparison of protein structures. *Protein* Data Bank Quarterly Newsletter. 78, 10-11 (1996).

Maassen C B. A rapid and safe plasmid isolation method for efficient engineering of recombinant lactobacilli expressing immunogenic or tolerogenic epitopes for oral administration. J. Immunol. Methods 223: 131-136, 1999.

MacLaughlin, F. C., Mumper, R. J., Wang, J., Tagliaferri, J. M., Gill, I., Hinchcliffe, M. & Rolland, A. P. Chitosan and depolymerized chitosan oligomers as condensing carriers for in vivo plasmid delivery. *J. Controlled Release* 56: 259-272, 1998.

Maecker H T, Hansen G, Walter D M, DeKruyff R H, Levy S, and Umetsu D T. (2001) Vaccination with allergen-IL-18 fusion DNA protects against, and reverses established, airway hyperreactivity in a murine asthma model. J. Immunol. 166:959-965.

Maeda, Y. Y. and Chihara, G. (1971) Lentinan, a new immuno-accelerator of cell-mediated responses. *Nature.* 229, 634.

Matthews, B. W. (1968) Solvent content of protein crystals. *J. Mol. Biol.* 33, 491-497.

McRee, D. E. XtalView/Xfit—A Versatile Program for Manipulating Atomic Coordinates and Electron Density. *Journal Structural Biology,* 125, 156-165 (1999)

Meneses, G., Delgado, M. A., Perez-Machado, M. A., Prieto, A., Alonso, R., Carrion, F., Lanzos, E., and Alvarez-Mon, M. (1997) Thymostimulin increases natural cytotoxic activity in patients with breast cancer. *Int. J. Immunopharmacol.* 19, 187-193.

Mercenier A, Muller-Alouf H, and Grangette C. (2000) Lactic acid bacteria as live vaccines. Curr. Issues Mol. Biol. 2:17-25.

Merrit, E. A. & Bacon, D. J. RASTER3D. *Methods Enzymol.* 277, 505-524 (1997).

Morales, A. (1984) Long term results and complications of intracavitary *bacillus* Calmette-Guerin therapy for bladder cancer. *J. Urol.* 132, 457-459.

Morris, R. J., Perrakis, A. & Lamzin, V. S. Arp/warp's model-building algorithms. i. the main chain. *Acta Crystallogr. D* 58, 968-975 (2002)

Murshudov, G. N., Lebedev, A., Vagin, A. A., Wilson, K. S. & Dodson, E. J. Efficient anisotropic refinement of Macromolecular structures using FFT *Acta Crystallogr. D* 55, 247-255 (1999)

Nakamura, K., Yamaguchi, Y., Kagota, S., Kwon, Y. M., Shinozuka, K., and Kunitomo, M. (1999) Inhibitory effect of Cordyceps sinensis on spontaneous liver metastasis of Lewis lung carcinoma and B16 melanoma cells in syngeneic mice. *Jpn. J. Pharmacol.* 79, 335-341.

Namba, K., Yamamura, E., Nitanai, H., Otani, T., and Azuma, I. (1997) Romurtide, a synthetic muramyl dipeptide derivative, promotes megakaryocytopoiesis through stimulation of cytokine production in nonhuman primates with myelosuppression. *Vaccine.* 15, 405-413.

Okamoto, M., Kaji, R., Kasetani, H., Yoshida, H., Moriya, Y., Saito, M., and Sato, M. (1993) Purification and characterization of interferon-gamma-inducing molecule of OK-432, a penicillin-killed streptococcal preparation, by monoclonal antibody neutralizing interferon-gamma-inducing activity of OK-432. *J. Immunother.* 13, 232-242.

Otwinowski, Z. M. & Minor, W. Processing of X-ray diffraction data collected in oscillation mode. *Methods Enzymol.* 276, 307-326 (1997).

Piraino, F. and Brandt, C. R. (1999) Isolation and partial characterization of an antiviral, RC-183, from the edible mushroom *Rozites caperata. Antiviral Res.* 43, 67-78.

Pochard P, Gosset P, Grangette C, Andre C, Tonnel A B, Pestel J, and Mercenier A. (2002) Lactic acid bacteria inhibit TH2 cytokine production by mononuclear cells from allergic patients. J. Allergy Clin. Immunol. 110:617-623.

Rask C, Holmgren J, Fredriksson M, Lindblad M, Nordstrom I, Sun J B, and Czerkinsky C. (2000) Prolonged oral treatment with low doses of allergen conjugated to cholera toxin B subunit suppresses immunoglobulin E antibody responses in sensitized mice. Clin. Exp. Allergy 30:1024-32.

Rost, B. (2001) Review: protein secondary structure prediction continues to rise. *J. Struct. Biol.* 134, 204-218.

Rousseau, F., Schymkowitz, J. W. H., Wilkinson, H. R., & Itzhaki, L. S. Three-dimensional domain swapping in p13suc1 occurs in the unfolded and controlled by conserved proline residues. *Proc. Natl Acad. Sci. USA.* 98, 5596-5601, (2001).

Roy, K., Mao, H. Q., Huang, S. K. & Leong, K. W. Oral gene delivery with chitosan-DNA nanoparticles generates immunologic protection in a murine model of peanut allergy. *Nat. Med.* 5: 387-391, 1999.

Scanga C B and Le Gros G. (2000) Development of an asthma vaccine: research into BCG. Drugs 59:1217-1221.

Scharf O, Agranovich I, Lee K, Eller N L, Levy L, Inman J, Scott D E, and Golding B. (2001) Ontogeny of Th1 memory responses against a *Brucella abortus* conjugate. Infect Immun 69:5417-5422.

Scheppler L, Vogel M, Zuercher A W, Zuercher M, Germond J E, Miescher S M, and Stadler B M. (2002) Recombinant *Lactobacillus johnsonii* as a mucosal vaccine delivery vehicle. Vaccine 20:2913-2920.

Shea L D, Smiley E, Bonadio J, and Mooney D J. (1999) DNA delivery from polymer matrices for tissue engineering. Nat. Biotechnol. 17:551-554.

Shimizu, Y., Hasumi, K., and Masubuchi, K. (1992) Augmenting effect of sizofuran on the immunofunction of regional lymph nodes in cervical cancer. *Cancer.* 69, 1184-1194.

Shirota H, Sano K, Kikuchi T, Tamura G, and Shirato K. (2000) Regulation of murine airway eosinophilia and Th2 cells by antigen-conjugated CpG oligodeoxynucleotides as a novel antigen-specific immunomodulator. J. Immunol. 2000 164:5575-5582.

Singh, V. K., Biswas, S., Mathur, K. B., Haq, W., Garg, S. K., and Agarwal, S. S. (1998) Thymopentin and splenopentin as immunomodulators. Current status. *Immunol Res.* 17, 345-368.

Slonim D K. (2002) From patterns to pathways: gene expression data analysis comes of age. Nat. Genet. 32 Suppl 2:502-508.

Solomon, P., Wasser & Alexander, L. W. Therapeutic effect of substance occurring in higher Basidiomycetes Mushroom: A modern perspective. Critical Review in Immunology. 19, 65-96 (1999).

Taal, B. G., Van Tinteren, H., Zoetmulder, F. A., and NACCP group. (2001) Adjuvant 5FU plus levamisole in colonic or rectal cancer: improved survival in stage 11 and III. *Br. J. Cancer.* 85, 1437-1443.

Tacket C O, Mason H S, Losonsky G, Clements J D, Levine M M, and Arntzen C J. (1998) Immunogenicity in humans of a recombinant bacterial antigen delivered in a transgenic potato. Nat. Med. 4:607-609.

Templin M F, Stoll D, Schrenk M, Traub P C, Vohringer C F, and Joos T O. (2002) Protein microarray technology. Trends Biotechnol. 20:160-166.

Terwilliger, T. C. & Berendzen, J. *Acta Crystallogr. D* 55, 849-861 (1999).

Terwilliger. Map-likelihood phasing *Acta Crysallogr. D* 57, 1763-1775 (2001)

van Berkum N L and Holstege F C. (2001) DNA microarrays: raising the profile. Curr. Opin. Biotechnol. 12:48-52.

Viland, H. and Blomgren, H. (1987) Augmentation of spontaneous cytotoxicity of human lymphocytes by RU 41.740, a glucoprotein extract of *Klebsiella pneumoniae. Anticancer Res.* 7, 17-22.

Vinuesa C G and Goodnow C C. (2002) Immunology: DNA drives autoimmunity. Nature 416:595-598.

Wasson, V. P & Wasson, R. G. Mushroom, Russia and History, Pantheon Books, New York, 433, 1957.

Wohlleben G and Erb K J. (2001) Atopic disorders: a vaccine around the corner? Trends Immunol. 22:618-626.

Yoshino, S., Tabata, T., Hazama, S., Iizuka, N., Yamamoto, K., Hirayama, M., Tangoku, A., and Oka, M. (2000) Immunoregulatory effects of the antitumor polysaccharide lentinan on Th1/Th2 balance in patients with digestive cancers. *Anticancer Res.* 20, 4707-4711.

Zhu D and Stevenson F K. (2002) DNA gene fusion vaccines against cancer. Curr. Opin. Mol. Ther. 4:41-48.

Zhu H, Bilgin M, Bangham R, Hall D, Casamayor A, Bertone P, Lan N, Jansen R, Bidlingmaier S, Houfek T, Mitchell T, Miller P, Dean R A, Gerstein M, and Snyder M. (2001) Global analysis of protein activities using proteome chips. Science 293: 2101-2105.

Zuany-Amorim C, Sawicka E, Manlius C, Le Moine A, Brunet L R, Kemeny D M, Bowen G, Rook G, and Walker C. (2002) Suppression of airway eosinophilia by killed *Mycobacterium vaccae*-induced allergen-specific regulatory T-cells. Nat. Med. 8:625-629.

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

APPENDIX A

Sequences

Fve is isolated from Golden Needle Mushroom (*Flammulina velutipes*).
ORGANISM: *Flammulina velutipes*. Eukaryota; Fungi; *Basidiomycota*; *Hymenomycetes*; *Agaricales*; *Tricholomataceae*; *Flammulina*.
Fve (Wild type)
ATGTCCGCCACGTCGCTCACCTTCCAGCTTGCCTACTTGGTGAAGAAGATCGACTTCGACTACA
CCCCCAACTGGGGCCGTGGTACCCCAAGCAGCTACATCGACAACCTTACCTTCCCCAAGGTTCT
CACCGACAAAAAATACTCGTACCGCGTCGTGGTCAATGGCTCTGACCTTGGCGTCGAGTCCAAC
TTCGCAGTGACACCGTCCGGTGGGCAGACCATCAACTTCCTCCAGTACAACAAGGGGTATGGTG
TCGCGGACACCAAAACGATTCAAGTTTTCGTTGTCATTCCAGATACCGGCAACTCGGAGGAGTA
CATCATCGCTGAGTGGAAGAAGACTTGA (SEQ ID NO: 5)

Msatsltfqlaylvkkidfdytpnwgrgtpssyidnltfpkyltdkkysyryvvngsdlgvesn
favtpsggqtinflqynkgygvadtktiqvfvvipdtgnseeyiiaewkkt (SEQ ID NO: 6)

ATG/TCC/GCC/ACG/TCG/CTC/ACC/TTC/CAG/CTT/GCC/TAC/TTG/GTG/AAG/AAG/
ATC/GAC/TTC/GAC/TAC/ACC/CCC/AAC/TGG/GGC/CGT/GGT/ACC/CCA/AGC/AGC/
TAC/ATC/GAC/AAC/CTT/ACC/TTC/CCC/AAG/GTT/CTC/ACC/GAC/AAA/AAA/TAC/
TCG/TAC/CGC/GTC/GTG/GTC/AAT/GGC/TCT/GAC/CTT/GGC/GTC/GAG/TCC/AAC/
TTC/GCA/GTG/ACA/CCG/TCC/GGT/GGG/CAG/ACC/ATC/AAC/TTC/CTC/CAG/TAC/
AAC/AAG/GGG/TAT/GGT/GTC/GCG/GAC/ACC/AAA/ACG/ATT/CAA/GTT/TTC/GTT/
GTC/ATT/CCA/GAT/ACC/GGC/AAC/TCG/GAG/GAG/TAC/ATC/ATC/GCT/GAG/TGG/
AAG/AAG/ACT/TGA (SEQ ID NO: 5)

A Fve (Wild type) sequence may also comprise a sequence as set out above, but lacking the initial methionine (M) in the amino acid sequence, or lacking the initial ATG in the nucleic acid sequence.
GST-Fve (Wild type) Nucleotide Sequence
ATGTCCCCTATACTAGGTTATTGGAAAATTAAGGGCCTTGTGCAACCCACTCGACTTCTTTTGG
AATATCTTGAAGAAAAATATGAAGAGCATTTGTATGAGCGCGATGAAGGTGATAAATGGCGAAA
CAAAAAGTTTGAATTGGGTTTGGAGTTTCCCAATCTTCCTTATTATATTGATGGTGATGTTAAA
TTAACACAGTCTATGGCCATCATACGTTATATAGCTGACAAGCACAATCATGTTGGGTGGTTGTC
CAAAAGAGCGTGCAGAGATTTCAATGCTTGAAGGAGCGGTTTTGGATATTAGATACGGTGTTTC
GAGAATTGCATATAGTAAAGACTTTGAAACTCTCAAAGTTGATTTTCTTAGCAAGCTACCTGAA
ATGCTGAAAATGTTCGAAGATCGTTTATGTCATAAAACATATTTAAATGGTGATCATGTAACCC
ATCCTGACTTCATGTTGTATGACGCTCTTGATGTTGTTTTATACATGGACCCAATGTGCCTGGA
TGCGTTCCCAAAATTAGTTTGTTTTAAAAAACGTATTGAAGCTATCCCACAAATTGATAAGTAC
TTGAAATCCAGCAAGTATATAGCATGGCCTTTGCAGGGCTGGCAAGCCACGTTTGGTGGTGGCG
ACCATCCTCCAAAATCGGATCTGGAAGTTCTGTTCCAGGGGCCCCTGGGATCCTCCGCCACGTC
GCTCACCTTCCAGCTTGCCTACTTGGTGAAGAAGATCGACTTCGACTACACCCCCAACTGGGGC
CGTGGTACCCCAAGCAGCTACATCGACAACCTTACCTTCCCCAAGGTTCTCACCGACAAAAAAT
ACTCGTACCGCGTCGTGGTCAATGGCTCTGACCTTGGCGTCGAGTCCAACTTCGCAGTGACACC
GTCCGGTGGGCAGACCATCAACTTCCTCCAGTACAACAAGGGGTATGGTGTCGCGGACACCAAA
ACGATTCAAGTTTTCGTTGTCATTCCAGATACCGGCAACTCGGAGGAGTACATCATCGCTGAGT
GGAAGAAGACTTGA
(SEQ ID NO: 7)

GST-Fve (Wild type) Amino Acid Sequence
MSPILGYWKIKGLVQPTRLLLEYLEEKYEEHLYERDEGDKWRNKKFELGLEFPNLPYYIDGDVK
LTQSMAIIRYIADKHNMLGGCPKERAEISMLEGAVLDIRYGVSRIAYSKDFETLKVDFLSKLPE
MLKMFEDRLCHKTYLNGDHVTHPDFMLYDALDVVLYMDPMCLDAFPKLVCFKKRIEAIPQIDKY
LKSSKYIAWPLQGWQATFGGGDHPPKSDLEVLFQGPLGSSATSLTFQLAYLVKKIDFDTPNWG
RGTPSSYIDNLTFPKVLTDKKYSYRVVVNGSDLGVESNFAVTPSGGQTINFLQYNKGYGVADTK
TIQVFVVIPDTGNSEEYIIAEWKKT (SEQ ID NO: 8)

FVE DELETION MUTANTS

Fve D6-18
ATG/TCC/GCC/ACG/TCGSTIC/GAC/TAC/ACC/CCC/AAC/TGG/GGC/CGT/GGT/ACC/CCA/AG
C/AGC/TAC/ATC/GAC/AAC/CTT/ACC/TTC/CCC/AAG/GTT/CTC/ACC/GAC/AAA/AAA/TAC/
TCG/TAC/CGC/GTC/GTG/GTC/AAT/GGC/TCT/GAC/CIT/GGC/GTC/GAG/TCC/AAC/TTC/GC
A/GTG/ACA/CCG/TCC/GGT/GGG/CAG/ACC/ATC/AAC/TTC/CTC/CAG/TAC/AAC/AAG/GGG/
TAT/GGT/GTC/GCG/GAC/ACC/AAA/ACG/ATT/CAA/GTT/TTC/GTT/GTC/ATT/CCA/GAT/AC
C/GGC/AAC/TCG/GAG/GAG/TAC/ATC/ATC/GCT/GAG/TGG/AAG/AAG/ACT/TGA (SEQ ID
NO: 9)

msats/fdytpnwgrgtpssyidnltfpkvltdkkysyrvvvngsdlgvesnfavtpsggqtinflqynk

APPENDIX A-continued

Sequences gygvadtktiqvfvvipdtgnseeyiiaewkkt (SEQ ID NO: 10)

Fve D19-33
ATG/TCC/GCC/ACG/TCG/CTC/ACC/TTC/CAG/CTT/GCC/TAC/TTG/GTG/AAG/AAG/ATC/GA
C/ATC/GAC/AAC/CTT/ACC/TTC/CCC/AAG/GTT/CTC/ACC/GAC/AAA/AAA/TAC/TCG/TAC/
CGC/GTC/GTG/GTC/AAT/GGC/TCT/GAC/CTT/GGC/GTC/GAG/TCC/AAC/TTC/GCA/GTG/AC
A/CCG/TCC/GGT/GGG/CAG/ACC/ATC/AAC/TTC/CTC/CAG/TAC/AAC/AAG/GGG/TAT/GGT/
GTC/GCG/GAC/ACC/AAA/ACG/ATT/CAA/GTT/TTC/GTT/GTC/ATT/CCA/GAT/ACC/GGC/AA
C/TCG/GAG/GAG/TAC/ATC/ATC/GCT/GAG/TGG/AAG/AAG/ACT/TGA (SEQ ID NO: 11)

msatsltfqlaylvkkid/idnltfpkvltdkkysyrvvvngsdlgvesnfavtpsggqtinflqynkgy
gvadtktiqvfvvipdtgnseeyiiaewkkt (SEQ ID NO: 12)

Fve D34-46
ATG/TCC/GCC/ACG/TCG/CTC/ACC/TTC/CAG/CTT/GCC/TAC/TTG/GTG/AAG/AAG/ATC/GA
C/TTC/GAC/TAC/ACC/CCC/AAC/TGG/GGC/CGT/GGT/ACC/CCA/AGC/AGC/TAC/AAA/TAC/
TCG/TAC/CGC/GTC/GTG/GTC/AAT/GGC/TCT/GAC/CTT/GGC/GTC/GAG/TCC/AAC/TTC/GC
A/GTG/ACA/CCG/TCC/GGT/GGG/CAG/ACC/ATC/AAC/TTC/CTC/CAG/TAC/AAC/AAG/GGG/
TAT/GGT/GTC/GCG/GAC/ACC/AAA/ACG/ATT/CAA/GTT/TTC/GTT/GTC/ATT/CCA/GAT/AC
C/GGC/AAC/TCG/GAG/GAG/TAC/ATC/ATC/GCT/GAG/TGG/AAG/AAG/ACT/TGA (SEQ ID
NO: 13)

msatsltfqlaylvkkidfdytpnwgrgtpssy/kysyrvvvngsdlgvesnfavtpsggqtinflqynk
gygvadtktiqvfvvipdtgnseeyiiaewkkt (SEQ ID NO: 14)

Fve D47-60
ATG/TCC/GCC/ACG/TCG/CTC/ACC/TTC/CAG/CTT/GCC/TAC/TTG/GTG/AAG/AAG/ATC/GA
C/TTC/GAC/TAC/ACC/CCC/AAC/TGG/GGC/CGT/GGT/ACC/CCA/AGC/AGC/TAC/ATC/GAC/
AAC/CTT/ACC/TTC/CCC/AAG/GTT/CTC/ACC/GAC/AAA/GTC/GAG/TCC/AAC/TTC/GCA/GT
G/ACA/CCG/TCC/GGT/GGG/CAG/ACC/ATC/AAC/TTC/CTC/CAG/TAC/AAC/AAG/GGG/TAT/
GGT/GTC/GCG/GAC/ACC/AAA/ACG/ATT/CAA/GTT/TTC/GTT/GTC/ATT/CCA/GAT/ACC/GG
C/AAC/TCG/GAG/GAG/TAC/ATC/ATC/GCT/GAG/TGG/AAG/AAG/ACT/TGA (SEQ ID NO:
15)

msatsltfqlaylvkkidfdytpnwgrgtpssyidnltfpkvltdk/vesnfavtpsggqtinflqynkg
ygvadtktiqvfvvipdtgnseeyiiaewkkt (SEQ ID NO: 16)

Fve D61-72
ATG/TCC/GCC/ACG/TCG/CTC/ACC/TTC/CAG/CTT/GCC/TAC/TTG/GTG/AAG/AAG/ATC/GA
C/TTC/GAC/TAC/ACC/CCC/AAC/TGG/GGC/CGT/GGT/ACC/CCA/AGC/AGC/TAC/ATC/GAC/
AAC/CTT/ACC/TTC/CCC/AAG/GTT/CTC/ACC/GAC/AAA/AAA/TAC/TCG/TAC/CGC/GTC/GT
G/GTC/AAT/GGC/TCT/GAC/CTT/GGC/CAG/ACC/ATC/AAC/TTC/CTC/CAG/TAC/AAC/AAG/
GGG/TAT/GGT/GTC/GCG/GAC/ACC/AAA/ACG/ATT/CAA/GTT/TTC/GTT/GTC/ATT/CCA/GA
T/ACC/GGC/AAC/TCG/GAG/GAG/TAC/ATC/ATC/GCT/GAG/TGG/AAG/AAG/ACT/TGA
(SEQ ID NO: 17)

msatsltfqlaylvkkidfdytpnwgrgtpssyidnltfpkvltdkkysyrvvvngsdlg/qtinflqyn
kgygvadtktiqvfvvipdtgnseeyiiaewkkt (SEQ ID NO: 18)

Fve D73-84
ATG/TCC/GCC/ACG/TCG/CTC/ACC/TTC/CAG/CTT/GCC/TAC/TTG/GTG/AAG/AAG/ATC/GA
C/TTC/GAC/TAC/ACC/CCC/AAC/TGG/GGC/CGT/GGT/ACC/CCA/AGC/AGC/TAC/ATC/GAC/
AAC/CTT/ACC/TTC/CCC/AAG/GTT/CTC/ACC/GAC/AAA/AAA/TAC/TCG/TAC/CGC/GTC/GT
G/GTC/AAT/GGC/TCT/GAC/CTT/GGC/GTC/GAG/TCC/AAC/TTC/GCA/GTG/ACA/CCG/TCC/
GGT/GGG/GGT/GTC/GCG/GAC/ACC/AAA/ACG/ATT/CAA/GTT/TTC/GTT/GTC/ATT/CCA/GA
T/ACC/GGC/AAC/TCG/GAG/GAG/TAC/ATC/ATC/GCT/GAG/TGG/AAG/AAG/ACT/TGA
(SEQ ID NO: 19)

msatsltfqlaylvkkidfdytpnwgrgtpssyidnltfpkvltdkkysyrvvvngsdlgvesnfavtps
gg/gvadtktiqvfvvipdtgnseeyiiaewkkt (SEQ ID NO: 20)

Fve D85-97
ATG/TCC/GCC/ACG/TCG/CTC/ACC/TTC/CAG/CTT/GCC/TAC/TTG/GTG/AAG/AAG/ATC/GA
C/TTC/GAC/TAC/ACC/CCC/AAC/TGG/GGC/CGT/GGT/ACC/CCA/AGC/AGC/TAC/ATC/GAC/
AAC/CTT/ACC/TTC/CCC/AAG/GTT/CTC/ACC/GAC/AAA/AAA/TAC/TCG/TAC/CGC/GTC/GT
G/GTC/AAT/GGC/TCT/GAC/CTT/GGC/GTC/GAG/TCC/AAC/TTC/GCA/GTG/ACA/CCG/TCC/
GGT/GGG/CAG/ACC/ATC/AAC/TTC/CTC/CAG/TAC/AAC/AAG/GGG/TAT/GTC/ATT/CCA/GA
T/ACC/GGC/AAC/TCG/GAG/GAG/TAC/ATC/ATC/GCT/GAG/TGG/AAG/AAG/ACT/TGA
(SEQ ID NO: 21)

msatsltfqlaylvkkidfdytpnwgrgtpssyidnltfpkvltdkkysyrvvvngsdlgvesnfavtps
ggqtinflqynkgy/ipdtgnseeyiiaewkkt (SEQ ID NO: 22)

Fve D98-106
ATG/TCC/GCC/ACG/TCG/CTC/ACC/TTC/CAG/CTT/GCC/TAC/TTG/GTG/AAG/AAG/ATC/GA
C/TTC/GAC/TAC/ACC/CCC/AAC/TGG/GGC/CGT/GGT/ACC/CCA/AGC/AGC/TAC/ATC/GAC/
AAC/CTT/ACC/TTC/CCC/AAG/GTT/CTC/ACC/GAC/AAA/AAA/TAC/TCG/TAC/CGC/GTC/GT
G/GTC/AAT/GGC/TCT/GAC/CTT/GGC/GTC/GAG/TCC/AAC/TTC/GCA/GTG/ACA/CCG/TCC/

APPENDIX A-continued

Sequences

GGT/GGG/CAG/ACC/ATC/AAC/TTC/CTC/CAG/TAC/AAC/AAG/GGG/TAT/GGT/GTC/GCG/GA
C/ACC/AAA/ACG/ATT/CAA/GTT/TTC/GTT/GTCSTAC/ATC/ATC/GCT/GAG/TGG/AAG/AAG/
ACT/TGA (SEQ ID NO: 23)

msatsltfqlaylvkkidfdytpnwgrgtpssyidnltfpkvltdkkysyryvvngsdlgvesnfavtps
ggqtinflqynkgygvadtktiqvfvv/yiiaewkkt (SEQ ID NO: 24)

Fve D107-115
ATG/TCC/GCC/ACG/TCG/CTC/ACC/TTC/CAG/CTT/GCC/TAC/TTG/GTG/AAG/AAG/ATC/GA
C/TTC/GAC/TAC/ACC/CCC/AAC/TGG/GGC/CGT/GGT/ACC/CCA/AGC/AGC/TAC/ATC/GAC/
AAC/CTT/ACC/TTC/CCC/AAG/GTT/CTC/ACC/GAC/AAA/AAA/TAC/TCG/TAC/CGC/GTC/GT
G/GTC/AAT/GGC/TCT/GAC/CTT/GGC/GTC/GAG/TCC/AAC/TTC/GCA/GTG/ACA/CCG/TCC/
GGT/GGG/CAG/ACC/ATC/AAC/TTC/CTC/CAG/TAC/AAC/AAG/GGG/TAT/GGT/GTC/GCG/GA
C/ACC/AAA/ACG/ATT/CAA/GTT/TTC/GTT/GTC/ATT/CCA/GAT/ACC/GGC/AAC/TCG/GAG/
GAG/TGA (SEQ ID NO: 25)

msatsltfqlaylvkkidfdytpnwgrgtpssyidnltfpkvltdkkysyryvvngsdlgvesnfavtps
ggqtinflqynkgygvadtktiqvfvvipdtgnsee/ (SEQ ID NO: 26)

Fve D61-97
ATG/TCC/GCC/ACG/TCG/CTC/ACC/TTC/CAG/CTT/GCC/TAC/TTG/GTG/AAG/AAG/ATC/GA
C/TTC/GAC/TAC/ACC/CCC/AAC/TGG/GGC/CGT/GGT/ACC/CCA/AGC/AGC/TAC/ATC/GAC/
AAC/CTT/ACC/TTC/CCC/AAG/GTT/CTC/ACC/GAC/AAA/AAA/TAC/TCG/TAC/CGC/GTC/GT
G/GTC/AAT/GGC/TCT/GAC/CTT/GGCSATT/CCA/GAT/ACC/GGC/AAC/TCG/GAG/GAG/TAC/
ATC/ATC/GCT/GAG/TGG/AAG/AAG/ACT/TGA (SEQ ID NO: 27)

msatsltfqlaylvkkidfdytpnwgrgtpssyidnltfpkvltdkkysyryvvngsdlg/ipdtgnsee
yiiaewkkt (SEQ ID NO: 28)

Fve p55-100
AAT/GGC/TCT/GAC/CTT/GGC/GTC/GAG/TCC/AAC/TTC/GCA/GTG/ACA/CCG/TCC/GGT/GG
G/CAG/ACC/ATC/AAC/TTC/CTC/CAG/TAC/AAC/AAG/GGG/TAT/GGT/GTC/GCG/GAC/ACC/
AAA/ACG/ATT/CAA/GTT/TTC/GTT/GTC/ATT/CCA/GAT/ (SEQ ID NO: 29)

Ngsdlgvesnfavtpsggqtinflqynkgygvadtktiqvfvvipd (SEQ ID NO: 30)

FVE MUTANTS WITH SINGLE AMINO ACID SUBSTITUTIONS

FveR27A
ATG/TCC/GCC/ACG/TCG/CTC/ACC/TTC/CAG/CTT/GCC/TAC/TTG/GTG/AAG/AAG/ATC/GA
C/TTC/GAC/TAC/ACC/CCC/AAC/TGG/GGC/GCA/GGT/ACC/CCA/AGC/AGC/TAC/ATC/GAC/
AAC/CTT/ACC/TTC/CCC/AAG/GTT/CTC/ACC/GAC/AAA/AAA/TAC/TCG/TAC/CGC/GTC/GT
G/GTC/AAT/GGC/TCT/GAC/CTT/GGC/GTC/GAG/TCC/AAC/TTC/GCA/GTG/ACA/CCG/TCC/
GGT/GGG/CAG/ACC/ATC/AAC/TTC/CTC/CAG/TAC/AAC/AAG/GGG/TAT/GGT/GTC/GCG/GA
C/ACC/AAA/ACG/ATT/CAA/GTT/TTC/GTT/GTC/ATT/CCA/GAT/ACC/GGC/AAC/TCG/GAG/
GAG/TAC/ATC/ATC/GCT/GAG/TGG/AAG/AAG/ACT/TGA (SEQ ID NO: 31)

Msatsltfqlaylvkkidfdytpnwgagtpssyidnltfpkvltdkkysyryvvngsdlgvesnfavtps
ggqtinflqynkgygvadtktiqvfvvipdtgnseeyiiaewkkt (SEQ ID NO: 32)

FveG28A
ATG/TCC/GCC/ACG/TCG/CTC/ACC/TTC/CAG/CTT/GCC/TAC/TTG/GTG/AAG/AAG/ATC/GA
C/TTC/GAC/TAC/ACC/CCC/AAC/TGG/GGC/CGT/GCA/ACC/CCA/AGC/AGC/TAC/ATC/GAC/
AAC/CTT/ACC/TTC/CCC/AAG/GTT/CTC/ACC/GAC/AAA/AAA/TAC/TCG/TAC/CGC/GTC/GT
G/GTC/AAT/GGC/TCT/GAC/CTT/GGC/GTC/GAG/TCC/AAC/TTC/GCA/GTG/ACA/CCG/TCC/
GGT/GGG/CAG/ACC/ATC/AAC/TTC/CTC/CAG/TAC/AAC/AAG/GGG/TAT/GGT/GTC/GCG/GA
C/ACC/AAA/ACG/ATT/CAA/GTT/TTC/GTT/GTC/ATT/CCA/GAT/ACC/GGC/AAC/TCG/GAG/
GAG/TAC/ATC/ATC/GCT/GAG/TGG/AAG/AAG/ACT/TGA (SEQ ID NO: 33)

Msatsltfqlaylvkkidfdytpnwgratpssyidnltfpkyltdkkysyryvvngsdlgvesnfavtps
ggqtinflqynkgygvadtktiqvfvvipdtgnseeyiiaewkkt (SEQ ID NO: 34)

FveT29A
ATG/TCC/GCC/ACG/TCG/CTC/ACC/TTC/CAG/CTT/GCC/TAC/TTG/GTG/AAG/AAG/ATC/GA
C/TTC/GAC/TAC/ACC/CCC/AAC/TGG/GGC/CGT/GGT/GCA/CCA/AGC/AGC/TAC/ATC/GAC/
AAC/CTT/ACC/TTC/CCC/AAG/GTT/CTC/ACC/GAC/AAA/AAA/TAC/TCG/TAC/CGC/GTC/GT
G/GTC/AAT/GGC/TCT/GAC/CTT/GGC/GTC/GAG/TCC/AAC/TTC/GCA/GTG/ACA/CCG/TCC/
GGT/GGG/CAG/ACC/ATC/AAC/TTC/CTC/CAG/TAC/AAC/AAG/GGG/TAT/GGT/GTC/GCG/GA
C/ACC/AAA/ACG/ATT/CAA/GTT/TTC/GTT/GTC/ATT/CCA/GAT/ACC/GGC/AAC/TCG/GAG/
GAG/TAC/ATC/ATC/GCT/GAG/TGG/AAG/AAG/ACT/TGA (SEQ ID NO: 35)

Msatsltfqlaylvkkidfdytpnwgrgapssyidnltfpkyltdkkysyryvvngsdlgvesnfavtps
ggqtinflqynkgygvadtktiqvfvvipdtgnseeyiiaewkkt (SEQ ID NO: 36)

FUSION PROTEINS OF MAJOR HOUSE DUST MITE ALLERGEN (BLO T 5 OR DER P 2)
AND FUNGAL IMMUNOMODULATORY PROTEIN FVE

Blo t 5-Fve (two-in-one chimeric wild type)

APPENDIX A-continued

Sequences

Caagagcacaagccaaagaaggatgatttccgaaacgaattcgatcacttgttgatcgaacaggcaaacc
atgctatcgaaaagggagaacatcaattgctttacttgcaacaccaactcgacgaattgaatgaaaacaa
gagcaaggaattgcaagagaaaatcattcgagaacttgatgttgtttgcgccatgatcgaaggagcccaa
ggagctttggaacgtgaattgaagcgaactgatcttaacattttggaacgattcaactacgaagaggctc
aaactctcagcaagatcttgcttaaggatttgaaggaaaccgaacaaaaagtgaaggatattcaaaccca
aTCCGCCACGTCGCTCACCTTCCAGCTTGCCTACTTGGTGAAGAAGATCGACTTCGACTACACCCCCAAC
TGGGGCCGTGGTACCCCAAGCAGCTACATCGACAACCTTACCTTCCCCAAGGTTCTCACCGACAAAAAAT
ACTCGTACCGCGTCGTGGTCAATGGCTCTGACCTTGGCGTCGAGTCCAACTTCGCAGTGACACCGTCCGG
TGGGCAGACCATCAACTTCCTCCAGTACAACAAGGGGTATGGTGTCGCGGACACCAAAACGATTCAAGTT
TTCGTTGTCATTCCAGATACCGGCAACTCGGAGGAGTACATCATCGCTGAGTGGAAGAAGACTTGA
(SEQ ID NO: 37)

QEHKPKKDDFRNEFDHLLIEQANHAIEKGEHQLLYLQHQLDELNENKSKELQEKIIRELDVVCAMIEGAQ
GALERELKRTDLNILERFNYEEAQTLSKILLKDLKETEQKVKDIQTQsatsltfqlaylvkkidfdytpn
wgrgtpssyidnltfpkvltdkkysyrvvvngsdlgvesnfavtpsggqtinflqynkgygvadtktiqv
fvvipdtgnseeyiiaewkkt (SEQ ID NO: 38)

Blo t 5-FveR27A (two-in-one chimeric mutant)
Caagagcacaagccaaagaaggatgatttccgaaacgaattcgatcacttgttgatcgaacaggcaaacc
atgctatcgaaaagggagaacatcaattgctttacttgcaacaccaactcgacgaattgaatgaaaacaa
gagcaaggaattgcaagagaaaatcattcgagaacttgatgttgtttgcgccatgatcgaaggagcccaa
ggagctttggaacgtgaattgaagcgaactgatcttaacattttggaacgattcaactacgaagaggctc
aaactctcagcaagatcttgcttaaggatttgaaggaaaccgaacaaaaagtgaaggatattcaaaccca
aTCCGCCACGTCGCTCACCTTCCAGCTTGCCTACTTGGTGAAGAAGATCGACTTCGACTACACCCCCAAC
TGGGGCGCAGGTACCCCAAGCAGCTACATCGACAACCTTACCTTCCCCAAGGTTCTCACCGACAAAAAAT
ACTCGTACCGCGTCGTGGTCAATGGCTCTGACCTTGGCGTCGAGTCCAACTTCGCAGTGACACCGTCCGG
TGGGCAGACCATCAACTTCCTCCAGTACAACAAGGGGTATGGTGTCGCGGACACCAAAACGATTCAAGTT
TTCGTTGTCATTCCAGATACCGGCAACTCGGAGGAGTACATCATCGCTGAGTGGAAGAAGACTTGA
(SEQ ID NO: 39)

QEHKPKKDDFRNEFDHLLIEQANHAIEKGEHQLLYLQHQLDELNENKSKELQEKIIRELDVVCAMIEGAQ
GALERELKRTDLNILERFNYEEAQTLSKILLKDLKETEQKVKDIQTQsatsltfqlaylvkkidfdytpn
wgagtpssyidnltfpkvltdkkysyrvvvngsdlgvesnfavtpsggqtinflqynkgygvadtktiqv
fvvipdtgnseeyiiaewkkt (SEQ ID NO: 40)

Blo t 5-FveT29A (two-in-one chimeric mutant)
Caagagcacaagccaaagaaggatgatttccgaaacgaattcgatcacttgttgatcgaacaggcaaacc
atgctatcgaaaagggagaacatcaattgctttacttgcaacaccaactcgacgaattgaatgaaaacaa
gagcaaggaattgcaagagaaaatcattcgagaacttgatgttgtttgcgccatgatcgaaggagcccaa
ggagctttggaacgtgaattgaagcgaactgatcttaacattttggaacgattcaactacgaagaggctc
aaactctcagcaagatcttgcttaaggatttgaaggaaaccgaacaaaaagtgaaggatattcaaaccca
aTCCGCCACGTCGCTCACCTTCCAGCTTGCCTACTTGGTGAAGAAGATCGACTTCGACTACACCCCCAAC
TGGGGCCGTGGTGCACCAAGCAGCTACATCGACAACCTTACCTTCCCCAAGGTTCTCACCGACAAAAAAT
ACTCGTACCGCGTCGTGGTCAATGGCTCTGACCTTGGCGTCGAGTCCAACTTCGCAGTGACACCGTCCGG
TGGGCAGACCATCAACTTCCTCCAGTACAACAAGGGGTATGGTGTCGCGGACACCAAAACGATTCAAGTT
TTCGTTGTCATTCCAGATACCGGCAACTCGGAGGAGTACATCATCGCTGAGTGGAAGAAGACTTGA
(SEQ ID NO: 41)

QEHKPKKDDFRNEFDHLLIEQANHAIEKGEHQLLYLQHQLDELNENKSKELQEKIIRELDVVCAMIEGAQ
GALERELKRTDLNILERFNYEEAQTLSKILLKDLKETEQKVKDIQTQsatsltfqlaylvkkidfdytpn
wgrgapssyidnltfpkvltdkkysyrvvvngsdlgvesnfavtpsggqtinflqynkgygvadtktiqv
fvvipdtgnseeyiiaewkkt (SEQ ID NO: 42)

Der p 2-FveR27A (two-in-one chimeric mutant)
Gatcaagtcgatgtcaaagattgtgccaatcatgaaatcaaaaaagttttggtaccaggatgccatggtt
cagaaccatgtatcattcatcgtggtaaaccattccaattggaagccgttttcgaagccaaccaaaacac
aaaaacggctaaaattgaaatcaaagcctcaatcgatggtttagaagttgatgttcccggtatcgatcca
aatgcatgccattacatgaaatgcccattggttaaaggacaacaatgatattaaatatacatggaatg
ttccgaaaattgcaccaaaatctgaaaatgttgtcgtcactgttaaagttatgggtgatgatggtgtttt
ggcctgtgctattgctactcatgctaaaatccgcgatTCCGCCACGTCGCTCACCTTCCAGCTTGCCTAC
TTGGTGAAGAAGATCGACTTCGACTACACCCCCAACTGGGGCGCAGGTACCCCAAGCAGCTACATCGACA
ACCTTACCTTCCCCAAGGTTCTCACCGACAAAAAATACTCGTACCGCGTCGTGGTCAATGGCTCTGACCT
TGGCGTCGAGTCCAACTTCGCAGTGACACCGTCCGGTGGGCAGACCATCAACTTCCTCCAGTACAACAAG
GGGTATGGTGTCGCGGACACCAAAACGATTCAAGTTTTCGTTGTCATTCCAGATACCGGCAACTCGGAGG
AGTACATCATCGCTGAGTGGAAGAAGACTTGA (SEQ ID NO: 43)

DQVDVKDCANHEIKKVLVPGCHGSEPCIIHRGKPFQLEAVFEANQNTKTAKIEIKASIDGLEVDVPGIDP
NACHYMKCPLVKGQQYDIKYTWNVPKIAPKSENVVVTVKVMGDDGVLACAIATHAKIRDsatsltfqlay
lvkkidfdytpnwgagtpssyidnltfpkvltdkkysyrvvvngsdlgvesnfavtpsggqtinflqynk
gygvadtktiqvfvvipdtgnseeyiiaewkkt (SEQ ID NO: 44)

Der p 2-FveT29A (two-in-one chimeric mutant)
Gatcaagtcgatgtcaaagattgtgccaatcatgaaatcaaaaaagttttggtaccaggatgccatggtt
cagaaccatgtatcattcatcgtggtaaaccattccaattggaagccgttttcgaagccaaccaaaacac
aaaaacggctaaaattgaaatcaaagcctcaatcgatggtttagaagttgatgttcccggtatcgatcca
aatgcatgccattacatgaaatgcccattggttaaaggacaacaatgatattaaatatacatggaatg
ttccgaaaattgcaccaaaatctgaaaatgttgtcgtcactgttaaagttatgggtgatgatggtgtttt
ggcctgtgctattgctactcatgctaaaatccgcgatTCCGCCACGTCGCTCACCTTCCAGCTTGCCTAC APPENDIX A-continued Sequences TTGGTGAAGAAGATCGACTTCGACTACACCCCCAACTGGGGCCGTGGTGCACCAAGCAGCTACATCGACA
ACCTTACCTTCCCCAAGGTTCTCACCGACAAAAAATACTCGTACCGCGTCGTGGTCAATGGCTCTGACCT
TGGCGTCGAGTCCAACTTCGCAGTGACACCGTCCGGTGGGCAGACCATCAACTTCCTCCAGTACAACAAG
GGGTATGGTGTCGCGGACACCAAAACGATTCAAGTTTTCGTTGTCATTCCAGATACCGGCAACTCGGAGG
AGTACATCATCGCTGAGTGGAAGAAGACTTGA (SEQ ID NO: 45)

DQVDVKDCANHEIKKVLVPGCHGSEPCIIHRGKPFQLEAVFEANQNTKTAKIEIKASIDGLEVDVPGIDP
NACHYMKCPLVKGQQYDIKYTWNVPKIAPKSENVVVTVKVMGDDGVLACAIATHAKIRDsatsltfqlay
lvkkidfdytpnwgrgapssyidnltfpkvltdkkysyrvvvngsdlgvesnfavtpsggqtinflqynk
gygvadtktipvfvvipdtgnseeyiiaewkkt (SEQ ID NO: 46)

Blo t 5-Der p 2-FveR27A (three-in-one chimeric mutant)
Caagagcacaagccaaagaaggatgatttccgaaacgaattcgatcacttgttgatcgaacaggcaaacc
atgctatcgaaaagggagaacatcaattgcttacttgcaacaccaactcgacgaattgaatgaaaacaa
gagcaaggaattgcaagagaaaatcattcgagaacttgatgttgtttgcgccatgatcgaaggagcccaa
ggagctttggaacgtgaattgaagcgaactgatcttaacattttggaacgattcaactacgaagaggctc
aaaactctcagcaagatcttgcttaaggatttgaaggaaaccgaacaaaaagtgaaggatattcaaaccca
agatcaagtcgatgtcaaagattgtgccaatcatgaaatcaaaaaagttttggtaccaggatgccatggt
tcagaaccatgtatcattcatcgtggtaaaccattccaattggaagccgttttcgaagccaaccaaaaca
caaaaacggctaaaattgaaatcaaagcctcaatcgatggtttagaagttgatgttcccggtatcgatcc
aaatgcatgccattacatgaaatgcccattggttaaaggacaacaatgatattaaatatacatggaat
gttccgaaaattgcaccaaaatctgaaaatgttgtcgtcactgttaaagttatgggtgatgatggtgttt
tggcctgtgctattgctactcatgctaaaatccgcgatTCCGCCACGTCGCTCACCTTCCAGCTTGCCTA
CTTGGTGAAGAAGATCGACTTCGACTACACCCCCAACTGGGGCGCAGGTACCCCAAGCAGCTACATCGAC
AACCTTACCTTCCCCAAGGTTCTCACCGACAAAAAATACTCGTACCGCGTCGTGGTCAATGGCTCTGACC
TTGGCGTCGAGTCCAACTTCGCAGTGACACCGTCCGGTGGGCAGACCATCAACTTCCTCCAGTACAACAA
GGGGTATGGTGTCGCGGACACCAAAACGATTCAAGTTTTCGTTGTCATTCCAGATACCGGCAACTCGGAG
GAGTACATCATCGCTGAGTGGAAGAAGACTTGA (SEQ ID NO: 47)

QEHKPKKDDFRNEFDHLLIEQANHAIEKGEHQLLYLQHQLDELNENKSKELQEKIIRELDVVCAMIEGAQ
GALERELKRTDLNILERFNYEEAQTLSKILLKDLKETEQKVKDIQTQDQVDVKDCANGEIKKVLVPGCHG
SEPCIIHRGKPFQLEAVFEANQNTKTAKIEIKASIDGLEVDVPGIDPNACHYMKCPLVKGQQYDIKYTWN
VPKIAPKSENVVVTVKVMGDDGVLACAIATHAKIRDsatsltfqlaylvkkidfdytpnwgagtpssyid
nltfpkvltdkkysyrvvvngsdlgvesnfavtpsggqtinflqynkgygvadtktiqvfvvipdtgnse
eyiiaewkkt (SEQ ID NO: 48)

FUSION PROTEINS OF VIRAL ANTIGEN AND FVE

HPV E7-FveT29A
MHGDTPTLHEYMLDLQPETTDLYCYEQLNDSSEEEDEIDGPAGQAEPDRAHYNIVTFCCKCDSTLRLCVQ
STHVDIRTLEDLLMGTLGIVCPICSQKPsatsltfqlaylvkkidfdytpnwgrgapssyidnltfpkvl
tdkkysyrvvvngsdlgvesnfavtpsggqtinflqynkgygvadtktiqvfvvipdtgnseeyiiaewk
kt (SEQ ID NO: 49)

Atgcatggagatacacctacattgcatgaatatatgttagatttgcaaccagagacaactgatctctact
gttatgagcaattaaatgacagctcagaggaggaggatgaaatagatggtccagctggacaagcagaacc
ggacagagcccattacaatattgtaaccttttgttgcaagtgtgactctacgcttcggttgtgcgtacaa
agcacacacgtagacattcgtactttggaagacctgttaatgggcaaaccTCCGCCACGTCGCTCACCTTCCAGCTTGCCTACTTGGTGAAGAAGATCGACTTCGA
CTACACCCCCAACTGGGGCCGTGGTGCACCAAGCAGCTACATCGACAACCTTACCTTCCCCAAGGTTCTC
ACCGACAAAAAATACTCGTACCGCGTCGTGGTCAATGGCTCTGACCTTGGCGTCGAGTCCAACTTCGCAG
TGACACCGTCCGGTGGGCAGACCATCAACTTCCTCCAGTACAACAAGGGGTATGGTGTCGCGGACACCAA
AACGATTCAAGTTTTCGTTGTCATTCCAGATACCGGCAACTCGGAGGAGTACATCATCGCTGAGTGGAAG
AAGACTTGA (SEQ ID NO: 50)

HCV Core23-FveT29A
Deletion of the 23 amino acids of core antigen from 141-163 amino acid
residues leads to increased protein production efficiency
MSTNPKPQRKTKRNTNRRPQDVKFPGGGQIVGGVYLLPRRGPRLGVRATRKTSERSQPRGRRQPIPKARQ
PEGRAWAQPGYPWPLYGNEGLGWAGWLLSPRGSRPSWGPTDPRRRSRNLGKVIDTLTCGFADLMGYLPLV
YATGNLPGCSFSIFLLALLSCLTIPASAsatsltfqlaylvkkidfdytpnwgrgapssyidnltfpkvl
tdkkysyrvvvngsdlgvesnfavtpsggqtinflqynkgygvadtktiqvfvvipdtgnseeyiiaewk
kt (SEQ ID NO: 51)

Atgagcacgaatcctaaacctcaaagaaaaaccaaacgtaacaccaaccgccgcccacaggacgtcaagt
tcccgggcggtggtcagatcgtcggtggagtttacctgttgccgcgcaggggccccaggttgggtgtgcg
cgcgactaggaagacttccgagcggtcgcaacctcgtggaaggcgacaacctatcccaaggctcgccag
cccgagggtagggcctgggctcagcccgggtacccctggcccctctatggcaatgagggcttgggtggg
caggatggctcctgtcaccccgtgctctcggcctagttggggccacggaccccggcgtaggtcgcg
caatttgggtaaggtcatcgataccctcacgtgcggcttcgccgatctcatggggtaccttccgctcgtc
ggcgcaacagggaatctgcccggttgctccttttctatcttcctttttggctttgctgtcctgtttgacca
tcccagcttccgcttatgaagTCCGCCACGTCGCTCACCTTCCAGCTTGCCTACTTGGTGAAGAAGATCG
ACTTCGACTACACCCCCAACTGGGGCCGTGGTGCACCAAGCAGCTACATCGACAACCTTACCTTCCCCAA
GGTTCTCACCGACAAAAAATACTCGTACCGCGTCGTGGTCAATGGCTCTGACCTTGGCGTCGAGTCCAAC
TTCGCAGTGACACCGTCCGGTGGGCAGACCATCAACTTCCTCCAGTACAACAAGGGGTATGGTGTCGCGG
ACACCAAAACGATTCAAGTTTTCGTTGTCATTCCAGATACCGGCAACTCGGAGGAGTACATCATCGCTGA
GTGGAAGAAGACTTGA (SEQ ID NO: 52)

APPENDIX A-continued

| Sequences |
|---|
| FUSION PROTEINS OF TUMOR-ASSOCIATED ANTIGEN AND FVE |

MAGE3-FveT29A
Mpleqrsqhckpeegleargealglvgaqapateeqeaasssstlvevtlgevpaaespdppqspqgass
lpttmnyplwsqsyedssnqeeegpstfpdlesefqaalsrkvaelvhflllkyrarepvtkaemlgsvv
gnwqyffpvifskassslqlvfgielmevdpighlyifatclglsydgllgdnqimpkaglliivlaiia
regdcapeekiweelsvlevfegredsilgdpkklltqhfvqenyleyrqvpgsdpacyeflwgpralve
tsyvkvlhhmvkisggphisypplhewvlregeesatsltfqlaylvkkidfdytpnwgrgapssyidnl
tfpkvltdkkysyrvvvngsdlgvesnfavtpsggqtinflqynkgygvadtktiqvfvvipdtgnseey
iiaewkkt (SEQ I DNO: 53)

atgcctcttgagcagaggagtcagcactgcaagcctgaagaaggccttgaggcccgaggagaggccctgg
gcctggtgggtcgcaggctcctgctactgaggagcaggaggctgcctcctcctcttctactctagttga
agtcaccctgggggaggtgcctgctgccgagtcaccagatcctcccagagtcctcagggagcctccagc
ctcccactaccatgaactaccctctctggagcaatcctatgaggactccagcaaccaagaagaggagg
ggccaagcaccttccctgacctggagtccgagttccaagcagcactcagtaggaaggtggccgagttggt
tcatttctgctcctcaagtatcgagccagggagccggtcacaaaggcagaaatgctggggagtgtcgtc
ggaaattggcagtatttcttcctgtgatcttcagcaaagcttccagttccttgcagctggtctttggca
tcgagctgatggaagtggacccatcggccacttgtacatcttgccacctgcctggcctctcctacga
tggcctgctgggtgacaatcagatcatgcccaaggcaggcctcctgataatcgtcctggccataatcgca
agagagggcgactgtgccctgaggagaaaatctgggaggagctgagtgtgttagaggtgtttgaggga
gggaagacagtatcttgggggatcccaagaagctgctcacccaacatttcgtgcaggaaaactacctgga
gtaccggcaggtccccggcagtgatcctgcatgttatgaattcctgtggggtccaagggcctcgttgaa
accagctatgtgaaagtcctgcaccatatggtaaagatcagtggaggacctcacatttcctacccacccc
tgcatgagtgggttttgagagaggggaagagTCCGCCACGTCGCTCACCTTCCAGCTTGCCTACTTGGT
GAAGAAGATCGACTTCGACTACACCCCCAACTGGGGCCGTGGTGCACCAAGCAGCTACATCGACAACCTT
ACCTTCCCCAAGGTTCTCACCGACAAAAAATACTCGTACCGCGTCGTGGTCAATGGCTCTGACCTTGGCG
TCGAGTCCAACTTCGCAGTGACACCGTCCGGTGGGCAGACCATCAACTTCCTCCAGTACAACAAGGGGTA
TGGTGTCGCGGACACCAAAACGATTCAAGTTTTCGTTGTCATTCCAGATACCGGCAACTCGGAGGAGTAC
ATCATCGCTGAGTGGAAGAAGACTTGA (SEQ ID NO: 54)

MART 1-FveT29A
Mpredahfiygypkkghghsyttaeeaagigiltvilgvllligcwycrrrngyralmdkslhvgtqcal
trrcpqegfdhrdskvslqekncepvvpnappayeklsaeqspppyspsatsltfqlaylvkkidfdytp
nwgrgapssyidnltfpkvltdkkysyrvvvngsdlgvesnfavtpsggqtinflqynkgygvadtktiq
vfvvipdtgnseeyiiaewkkt (SEQ ID NO: 55)

Atgccaagagaagatgctcacttcatctatggttaccccaagaagggcacggccactcttacaccacgg
ctgaagaggccgctgggatcggcatcctgacagtgatcctgggagtcttactgctcatcggctgttggta
ttgtagaagacgaaatggatacagagccttgatggataaaagtcttcatgttggcactcaatgtgcctta
acaagaagatgcccacaagaagggtttgatcatcgggacagcaaagtgtctcttcaagagaaaaactgtg
aacctgtggttcccaatgctccacctgcttatgagaaactctctgcagaacagtcaccaccaccttattc
acctTCCGCCACGTCGCTCACCTTCCAGCTTGCCTACTTGGTGAAGAAGATCGACTTCGACTACACCCCC
AACTGGGGCCGTGGTGCACCAAGCAGCTACATCGACAACCTTACCTTCCCCAAGGTTCTCACCGACAAAA
AATACTCGTACCGCGTCGTGGTCAATGGCTCTGACCTTGGCGTCGAGTCCAACTTCGCAGTGACACCGTC
CGGTGGGCAGACCATCAACTTCCTCCAGTACAACAAGGGGTATGGTGTCGCGGACACCAAAACGATTCAA
GTTTTCGTTGTCATTCCAGATACCGGCAACTCGGAGGAGTACATCATCGCTGAGTGGAAGAAGACTTGA
(SEQ ID NO: 56)

CEA-FveT29A
Kltiestpfnvaegkevllllvhnlpqhlfgyswykgervdgnrqiigyvigtqqatpgpaysgreiiypn
aslliqniiqndtgfytlhviksdlyneeatgqfrvypelpkpsissnnskpvedkdavaftcepetqda
tylwwvnnqslpvsprlqlsngnrtltlfnvtrndtasykcetqnpvsarrsdsvilnylygpdaptisp
lntsyrsgenlnlschaasnppaqyswfvngtfqqstqelfipnitvnnsgsytcqahnsdtglnrttvt
titvyaeppkpfitsnnsnpvededavaltcepeiqnttylwwvnnqslpvsprlqlsndnrtltllsvt
rndvgpyecgiqnelsvdhsdpvilnylygpddptispsytyyrpgvnlslschaasnppaqyswlidgn
iqqhtqelfisniteknsglytcqannsasghsrttyktitvsaelpkpsissnnskpvedkdavaftce
peaqnttylwwvngqslpvsprlqlsngnrtltlfnvtrndarayvcgiqnsvsanrsdpvtldvlygpd
tpiisppdssylsganlnlschsasnpspqyswringipqqhtqvlfiakitpnnngtyacfvsnlatgr
nnsivksitysasgtspglsagatvgimigvlvgvalisatsltfqlaylvkkidfdytpnwgrgapssy
idnltfpkvltdkkysyrvvvngsdlgvesnfavtpsggqtinflqynkgygvadtktiqvfvvipdtgn
seeyiiaewkkt (SEQ ID NO: 57)

aagctcactattgaatccacgccgttcaatgtcgcagaggggaaggaggtgcttctacttgtccacaatc
tgccccagcatcttttggctacagctggtacaaaggtgaaagagtggatggcaaccgtcaaattatagg
atatgtaataggaactcaacaagctaccccagggcccgcatacagtggtcgagagataatataccccaat
gcatccctgctgatccagaacatcatccagaatgacacaggattctacaccctacacgtcataaagtcag
atcttgtgaatgaagaacaactggccagttccgggtatacccggagctgcccaagccctccatctccag
caacaactccaaacccgtggaggacaaggatgctgtggccttcacctgtgaacctgagactcaggacgca
acctacctgtggtgggtaaacaatcagagcctcccggtcagtcccaggctgcagctgtccaatggcaaca
ggaccctcactctattcaatgtcacaagaaatgacacagcaagctacaaatgtgaaacccagaacccagt
gagtgccaggcgcagtgattcagtcatcctgaatgtcctctatgcccggatgccccaccatttcccct
ctaaacacatcttacagatcagggggaaaatctgaacctctcctgccatgccagtctctaacccacctgcac
agtactcttggtttgtcaatgggacttccagcaatccacccaagagctcttatccccaacatcactgt
gaataatagtggatcctatacgtgccaagccataactcagacactggcctcaataggaccacagtcacg
acgatcacagtctatgcagagccacccaaaccttcatccagcaacaactccaaccccgtggaggatg
aggatgctgtagccttaacctgtgaacctgagattcagaacacaacctacctgtggtgggtaaataatca
gagcctcccggtcagtcccaggctgcagctgtccaatgacaacaggacccctcactctactcagtgtcaca APPENDIX A-continued Sequences aggaatgatgtaggaccctatgagtgtggaatccagaacgaattaagtgttgaccacagcgacccagtca
tcctgaatgtcctctatggcccagacgaccccaccatttcccccctcatacacctattaccgtccaggggt
gaacctcagcctctcctgccatgcagcctctaacccacctgcacagtattcttggctgtcgatgggaac
atccagcaacacacacaagagctctttatctccaacatcactgagaagaacagcggactctataccgcc
aggccaataactcagccagtggccacagcaggactacagtcaagacaatcacagtctctgcggagctgcc
caagccctccatctccagcaacaactccaaacccgtggaggacaaggatgctgtggccttcacctgtgaa
cctgaggctcagaacacaacctacctgtggtgggtaaatggtcagagcctcccagtcagtcccaggctgc
agctgtccaatggcaacaggaccctcactctattcaatgtcacaagaaatgacgcaagagcctatgtatg
tggaatccagaactcagtgagtgcaaaccgcagtgacccagtcaccctggatgtcctctatgggccggac
accccatcatttcccccagactcgtcttacctttcgggagcgaacctcaacctctcctgccactcgg
cctctaacccatccccgcagtattcttggcgtatcaatgggataccgcagcaacacacacaagttctctt
tatcgccaaaatcacgccaaataataacgggacctatgctgttttgtctctaacttggctactggccgc
aataattccatagtcaagagcatcacagtctctgcatctggaacttctcctggtctctcagctggggcca
ctgtcggcatcatgattggagtgctggttggggttgctctgataTCCGCCACGTCGCTCACCTTCCAGCT
TGCCTACTTGGTGAAGAAGATCGACTTCGACTACACCCCCAACTGGGGCCGTGGTGCACCAAGCAGCTAC
ATCGACAACCTTACCTTCCCCAAGGTTCTCACCGACAAAAAATACTCGTACCGCGTCGTGGTCAATGGCT
CTGACCTTGGCGTCGAGTCCAACTTCGCAGTGACACCGTCCGGTGGGCAGACCATCAACTTCCTCCAGTA
CAACAAGGGTATGGTGTCGCGGACACCAAAACGATTCAAGTTTTCGTTGTCATTCCAGATACCGGCAAC
TCGGAGGAGTACATCATCGCTGAGTGGAAGAAGACTTGA (SEQ ID NO: 58)

PRIMERS FOR CONSTRUCTION OF FVE DELETION MUTANTS

Fd6-18F (36 mer)
5'-ggA/TCC/TCC/gCC/ACg/TCg/TTC/gAC/TAC/ACC/CCC/AAC-3' (SEQ ID NO: 59)

Fd6-18R (36 mer)
5'-gTT/ggg/ggT/gTA/gTC/gAA/CgA/CgT/ggC/ggA/gga/TCC-3' (SEQ ID NO: 60)

Fd19-33F (36 mer)
5'-TTg/gTg/AAg/AAg/ATC/gAC/ATC/gAC/AAC/CTT/ACC/TTC-3' (SEQ ID NO: 61)

Fd19-33R (36 mer)
5'-gAA/ggT/AAg/gTT/gTC/gAT/gTC/gAT/CTT/CTT/CAC/CAA-3' (SEQ ID NO: 62)

Fd34-46F (36 mer)
5'-ggT/ACC/CCA/AgC/AgC/TAC/AAA/TAC/TCg/TAC/CgC/gTC-3' (SEQ ID NO: 63)

Fd34-46R (36 mer)
5'-gAC/gCg/gTA/CgA/gTA/TTT/gTA/gCT/gCT/Tgg/ggT/ACC-3' (SEQ ID NO: 64)

Fd47-60F (36 mer)
5'-AAg/gTT/CTC/ACC/gAC/AAA/gTC/gAg/TCC/AAC/TTC/gCA-3' (SEQ ID NO: 65)

Fd47-60R (36 mer)
5'-TgC/gAA/gTT/ggA/CTC/gAC/TTT/gTC/ggT/gAg/AAC/CTT-3' (SEQ ID NO: 66)

Fd61-72F (36 mer)
5'-AAT/ggC/TCT/gAC/CTT/ggC/CAg/ACC/ATC/AAC/TTC/CTC-3' (SEQ ID NO: 67)

Fd61-72R (36 mer)
5'-gAg/gAA/gTT/gAT/ggT/CTg/gCC/AAg/gTC/AgA/gCC/ATT-3' (SEQ ID NO: 68)

Fd73-84F (36 mer)
5'-gTg/ACA/CCg/TCC/ggT/ggg/ggT/gTC/gCg/gAC/ACC/AAA-3' (SEQ ID NO: 69)

Fd73-84R (36 mer)
5'-TTT/ggT/gTC/CgC/gAC/ACC/CCC/ACC/ggA/Cgg/TgT/CAC-3' (SEQ ID NO: 70)

Fd85-97F (36 mer)
5'-CAg/TAC/AAC/AAg/ggg/TAT/ATT/CCA/gAT/ACC/ggC/AAC-3' (SEQ ID NO: 71)

Fd85-97R (36 mer)
5'-gTT/gCC/ggT/ATC/Tgg/AAT/ATA/CCC/CTT/gTT/gTA/CTg-3' (SEQ ID NO: 72)

Fd98-106F (36 mer)
5'-ATT/CAA/gTT/TTC/gTT/gTC/TAC/ATC/ATC/gCT/gAg/Tgg-3' (SEQ ID NO: 73)

Fd98-106R (36 mer)
5'-CCA/CTC/AgC/gAT/gAT/gTA/gAC/AAC/gAA/AAC/TTg/AAT-3' (SEQ ID NO: 74)

Fd107-115R (39 mer)
5'-gAT/gCA/ACT/gAA/TTC/TTA/TTA/CTC/CTC/CgA/gTT/gCC/ggT-3' (SEQ ID NO: 75)

PRIMERS FOR CONSTRUCTION OF LARGE FRAGMENT DELETION OF FVE d(61-97)-F (36 mer)

APPENDIX A-continued

Sequences

5'-/AAT/ggC/TCT/gAC/CTT/ggC/ATT/CCA/gAT/ACC/ggC/AAC/-3' (SEQ ID NO: 76)

d(61-97)-R (36 mer)
5'-/gTT/gCC/ggT/ATC/Tgg/AAT/gCC/AAg/gTC/AgA/gCC/ATT/-3' (SEQ ID NO: 77)

PRIMERS FOR CONSTRUCTION OF SMALL FRAGMENT OF FVE (FROM 55 AA TO 100 AA)

[Fv55-100]-F (48 mer)
5'-/gTT/CCg/CgT/ggA/TCC/ATC/gAA/ggT/CgT/AAT/ggC/TCT/gAC/CTT/ggC/gTC/-3' (SEQ ID NO: 78)

[Fv55-100]-R (42 mer)
5'-/gAT/gCA/ACT/gAA/TTC/TTA/TCA/ATC/Tgg/AAT/gAC/AAC/gAA/AAC/-3' (SEQ ID NO: 79)

PRIMERS FOR CONSTRUCTION OF POINT MUTANTS OF FVE

F(R27A)-F (27 mer)
5'-CCC/AAC/Tgg/ggC/gCA/ggT/ACC/CCA/AgC-3' (SEQ ID NO: 80)

F(R27A)-R (27 mer)
5'-gCT/Tgg/ggT/ACC/TgC/gCC/CCA/gTT/ggg-3' (SEQ ID NO: 81)

F(G28A)-F (27 mer)
5'-AAC/Tgg/ggC/CgT/gCA/ACC/CCA/AgC/AgC-3' (SEQ ID NO: 82)

F(G28A)-R (27 mer)
5'-gCT/gCT/Tgg/ggT/TgC/ACg/gCC/CCA/gTT-3' (SEQ ID NO: 83)

F(T29A)-F (27 mer)
5'-Tgg/ggC/CgT/ggT/gCA/CCA/AgC/AgC/TAC-3' (SEQ ID NO: 84)

F(T29A)-R (27 mer)
5'-gTA/gCT/gCT/Tgg/TgC/ACC/ACg/gCC/CCA-3' (SEQ ID NO: 85)

PRIMERS FOR BLO T 5-FVE FUSION PROTEIN

Bt5Fv-F (36 mer)
5'-/AAg/gAT/ATT/CAA/ACC/CAA/TCC/gCC/ACg/TCg/CTC/ACC/-3'
(SEQ ID NO: 86)

Bt5Fv-R (36 mer)
5'-/ggT/gAg/CgA/CgT/ggC/ggA/TTg/ggT/TTg/AAT/ATC/CTT/-3'
(SEQ ID NO: 87)

PRIMERS FOR DER P 2-FVE FUSION PROTEIN

Dp2Fv-F (36 mer)
5'-/CAT/gCT/AAA/ATC/CgC/gAT/TCC/gCC/ACg/TCg/CTC/ACC-3' (SEQ ID NO: 88)

Dp2Fv-R (36 mer)
5'-/ggT/gAg/CgA/CgT/ggC/ggA/ATC/gCg/gAT/TTT/AgC/ATg-3' (SEQ ID NO: 89)

PRIMERS FOR BLO T 5-DER P 2-FVE FUSION PROTEIN

Bt5Dp2-F (36 mer)
5'-/aag/gat/att/caa/acc/caa/gat/caa/gtc/gat/gtc/aaa/-3'
(SEQ ID NO: 90)

Bt5Dp2-R (36 mer)
5'-/ttt/gac/atc/gac/ttg/atc/ttg/ggt/ttg/aat/atc/ctt/-3'
(SEQ ID NO: 91)

APPENDIX B

FVE FRAGMENTS (RGT TRIPLET HIGHLIGHTED)

| Fragment Number | Residues | Sequence |
|---|---|---|
| 1 | 24-28 | WGRGT |
| 2 | 25-29 | GRGTP |
| 3 | 26-30 | RGTPS |

APPENDIX B-continued

FVE FRAGMENTS (RGT TRIPLET HIGHLIGHTED)

| Fragment Number | Residues | Sequence |
|---|---|---|
| 4 | 27-31 | GTPSS |
| 5 | 28-32 | TPSSY |
| 6 | 23-28 | NWGRGT |
| 7 | 24-29 | WGRGTP |
| 8 | 25-30 | GRGTPS |
| 9 | 26-31 | RGTPSS |
| 10 | 27-32 | GTPSSY |
| 11 | 28-33 | TPSSYI |
| 12 | 22-28 | PNWGRGT |
| 13 | 23-29 | NWGRGTP |
| 14 | 24-30 | WGRGTPS |
| 15 | 25-31 | GRGTPSS |
| 16 | 26-32 | RGTPSSY |
| 17 | 27-33 | GTPSSYI |
| 18 | 28-34 | TPSSYID |
| 19 | 21-28 | TPNWGRGT |
| 20 | 22-29 | PNWGRGTP |
| 21 | 23-30 | NWGRGTPS |
| 22 | 24-31 | WGRGTPSS |
| 23 | 25-32 | GRGTPSSY |
| 24 | 26-33 | RGTPSSYI |
| 25 | 27-34 | GTPSSYID |
| 26 | 28-35 | TPSSYIDN |
| 27 | 20-28 | YTPNWGRGT |
| 28 | 21-29 | TPNWGRGTP |
| 29 | 22-30 | PNWGRGTPS |
| 30 | 23-31 | NWGRGTPSS |
| 31 | 24-32 | WGRGTPSSY |
| 32 | 25-33 | GRGTPSSYI |
| 33 | 26-34 | RGTPSSYID |
| 34 | 27-35 | GTPSSYIDN |
| 35 | 28-36 | TPSSYIDNL |
| 36 | 19-28 | DYTPNWGRGT |
| 37 | 20-29 | YTPNWGRGTP |
| 38 | 21-30 | TPNWGRGTPS |
| 39 | 22-31 | PNWGRGTPSS |
| 40 | 23-32 | NWGRGTPSSY |
| 41 | 24-33 | WGRGTPSSYI |
| 42 | 25-34 | GRGTPSSYID |
| 43 | 26-35 | RGTPSSYIDN |
| 44 | 27-36 | GTPSSYIDNL |
| 45 | 28-37 | TPSSYIDNLT |
| 46 | 18-28 | FDYTPNWGRGT |
| 47 | 19-29 | DYTPNWGRGTP |
| 48 | 20-30 | YTPNWGRGTPS |
| 49 | 21-31 | TPNWGRGTPSS |
| 50 | 22-32 | PNWGRGTPSSY |
| 51 | 23-33 | NWGRGTPSSYI |
| 52 | 24-34 | WGRGTPSSYID |
| 53 | 25-35 | GRGTPSSYIDN |
| 54 | 26-36 | RGTPSSYIDNL |
| 55 | 27-37 | GTPSSYIDNLT |
| 56 | 28-38 | TPSSYIDNLTF |
| 57 | 17-28 | DFDYTPNWGRGT |
| 58 | 18-29 | FDYTPNWGRGTP |
| 59 | 19-30 | DYTPNWGRGTPS |
| 60 | 20-31 | YTPNWGRGTPSS |
| 61 | 21-32 | TPNWGRGTPSSY |
| 62 | 22-33 | PNWGRGTPSSYI |
| 63 | 23-34 | NWGRGTPSSYID |
| 64 | 24-35 | WGRGTPSSYIDN |
| 65 | 25-36 | GRGTPSSYIDNL |
| 66 | 26-37 | RGTPSSYIDNLT |
| 67 | 27-38 | GTPSSYIDNLTF |
| 68 | 28-39 | TPSSYIDNLTFP |
| 69 | 16-28 | IDFDYTPNWGRGT |
| 70 | 17-29 | DFDYTPNWGRGTP |
| 71 | 18-30 | FDYTPNWGRGTPS |
| 72 | 19-31 | DYTPNWGRGTPSS |
| 73 | 20-32 | YTPNWGRGTPSSY |
| 74 | 21-33 | TPNWGRGTPSSYI |
| 75 | 22-34 | PNWGRGTPSSYID |
| 76 | 23-35 | NWGRGTPSSYIDN |
| 77 | 24-36 | WGRGTPSSYIDNL |
| 78 | 25-37 | GRGTPSSYIDNLT |

APPENDIX B-continued

FVE FRAGMENTS (RGT TRIPLET HIGHLIGHTED)

| Fragment Number | Residues | Sequence |
|---|---|---|
| 79 | 26-38 | RGTPSSYIDNLTF |
| 80 | 27-39 | GTPSSYIDNLTFP |
| 81 | 28-40 | TPSSYIDNLTFPK |
| 82 | 15-28 | KIDFDYTPNWRGT |
| 83 | 16-29 | IDFDYTPNWRGTP |
| 84 | 17-30 | DFDYTPNWRGTPS |
| 85 | 18-31 | FDYTPNWRGTPSS |
| 86 | 19-32 | DYTPNWRGTPSSY |
| 87 | 20-33 | YTPNWRGTPSSYI |
| 88 | 21-34 | TPNWRGTPSSYID |
| 89 | 22-35 | PNWRGTPSSYIDN |
| 90 | 23-36 | NWRGTPSSYIDNL |
| 91 | 24-37 | WGRGTPSSYIDNLT |
| 92 | 25-38 | GRGTPSSYIDNLTF |
| 93 | 26-39 | RGTPSSYIDNLTFP |
| 94 | 27-40 | GTPSSYIDNLTFPK |
| 95 | 28-41 | TPSSYIDNLTFPKV |
| 96 | 14-28 | KKIDFDYTPNWRGT |
| 97 | 15-29 | KIDFDYTPNWRGTP |
| 98 | 16-30 | IDFDYTPNWRGTPS |
| 99 | 17-31 | DFDYTPNWRGTPSS |
| 100 | 18-32 | FDYTPNWRGTPSSY |
| 101 | 19-33 | DYTPNWRGTPSSYI |
| 102 | 20-34 | YTPNWRGTPSSYID |
| 103 | 21-35 | TPNWRGTPSSYIDN |
| 104 | 22-36 | PNWRGTPSSYIDNL |
| 105 | 23-37 | NWRGTPSSYIDNLT |
| 106 | 24-38 | WGRGTPSSYIDNLTF |
| 107 | 25-39 | GRGTPSSYIDNLTFP |
| 108 | 26-40 | RGTPSSYIDNLTFPK |
| 109 | 27-41 | GTPSSYIDNLTFPKV |
| 110 | 28-42 | TPSSYIDNLTFPKVL |
| 111 | 13-28 | VKKIDFDYTPNWRGT |
| 112 | 14-29 | KKIDFDYTPNWRGTP |
| 113 | 15-30 | KIDFDYTPNWRGTPS |
| 114 | 16-31 | IDFDYTPNWRGTPSS |
| 115 | 17-32 | DFDYTPNWRGTPSSY |
| 116 | 18-33 | FDYTPNWRGTPSSYI |
| 117 | 19-34 | DYTPNWRGTPSSYID |
| 118 | 20-35 | YTPNWRGTPSSYIDN |
| 119 | 21-36 | TPNWRGTPSSYIDNL |
| 120 | 22-37 | PNWRGTPSSYIDNLT |
| 121 | 23-38 | NWRGTPSSYIDNLTF |
| 122 | 24-39 | WGRGTPSSYIDNLTFP |
| 123 | 25-40 | GRGTPSSYIDNLTFPK |
| 124 | 26-41 | RGTPSSYIDNLTFPKV |
| 125 | 27-42 | GTPSSYIDNLTFPKVL |
| 126 | 28-43 | TPSSYIDNLTFPKVLT |
| 127 | 12-28 | LVKKIDFDYTPNWRGT |
| 128 | 13-29 | VKKIDFDYTPNWRGTP |
| 129 | 14-30 | KKIDFDYTPNWRGTPS |
| 130 | 15-31 | KIDFDYTPNWRGTPSS |
| 131 | 16-32 | IDFDYTPNWRGTPSSY |
| 132 | 17-33 | DFDYTPNWRGTPSSYI |
| 133 | 18-34 | FDYTPNWRGTPSSYID |
| 134 | 19-35 | DYTPNWRGTPSSYIDN |
| 135 | 20-36 | YTPNWRGTPSSYIDNL |
| 136 | 21-37 | TPNWRGTPSSYIDNLT |
| 137 | 22-38 | PNWRGTPSSYIDNLTF |
| 138 | 23-39 | NWRGTPSSYIDNLTFP |
| 139 | 24-40 | WGRGTPSSYIDNLTFPK |
| 140 | 25-41 | GRGTPSSYIDNLTFPKV |
| 141 | 26-42 | RGTPSSYIDNLTFPKVL |
| 142 | 27-43 | GTPSSYIDNLTFPKVLT |
| 143 | 28-44 | TPSSYIDNLTFPKVLTD |
| 144 | 11-28 | YLVKKIDFDYTPNWRGT |
| 145 | 12-29 | LVKKIDFDYTPNWRGTP |
| 146 | 13-30 | VKKIDFDYTPNWRGTPS |
| 147 | 14-31 | KKIDFDYTPNWRGTPSS |
| 148 | 15-32 | KIDFDYTPNWRGTPSSY |
| 149 | 16-33 | IDFDYTPNWRGTPSSYI |
| 150 | 17-34 | DFDYTPNWRGTPSSYID |
| 151 | 18-35 | FDYTPNWRGTPSSYIDN |
| 152 | 19-36 | DYTPNWRGTPSSYIDNL |
| 153 | 20-37 | YTPNWRGTPSSYIDNLT |

APPENDIX B-continued
FVE FRAGMENTS (RGT TRIPLET HIGHLIGHTED)

| Fragment Number | Residues | Sequence |
|---|---|---|
| 154 | 21-38 | TPNWGRGTPSSYIDNLTF |
| 155 | 22-39 | PNWGRGTPSSYIDNLTFP |
| 156 | 23-40 | NWGRGTPSSYIDNLTFPK |
| 157 | 24-41 | WGRGTPSSYIDNLTFPKV |
| 158 | 25-42 | GRGTPSSYIDNLTFPKVL |
| 159 | 26-43 | RGTPSSYIDNLTFPKVLT |
| 160 | 27-44 | GTPSSYIDNLTFPKVLTD |
| 161 | 28-45 | TPSSYIDNLTFPKVLTDK |
| 162 | 10-28 | AYLVKKIDFDYTPNWGRGT |
| 163 | 11-29 | YLVKKIDFDYTPNWGRGTP |
| 164 | 12-30 | LVKKIDFDYTPNWGRGTPS |
| 165 | 13-31 | VKKIDFDYTPNWGRGTPSS |
| 166 | 14-32 | KKIDFDYTPNWGRGTPSSY |
| 167 | 15-33 | KIDFDYTPNWGRGTPSSYI |
| 168 | 16-34 | IDFDYTPNWGRGTPSSYID |
| 169 | 17-35 | DFDYTPNWGRGTPSSYIDN |
| 170 | 18-36 | FDYTPNWGRGTPSSYIDNL |
| 171 | 19-37 | DYTPNWGRGTPSSYIDNLT |
| 172 | 20-38 | YTPNWGRGTPSSYIDNLTF |
| 173 | 21-39 | TPNWGRGTPSSYIDNLTFP |
| 174 | 22-40 | PNWGRGTPSSYIDNLTFPK |
| 175 | 23-41 | NWGRGTPSSYIDNLTFPKV |
| 176 | 24-42 | WGRGTPSSYIDNLTFPKVL |
| 177 | 25-43 | GRGTPSSYIDNLTFPKVLT |
| 178 | 26-44 | RGTPSSYIDNLTFPKVLTD |
| 179 | 27-45 | GTPSSYIDNLTFPKVLTDK |
| 180 | 28-46 | TPSSYIDNLTFPKVLTDKK |
| 181 | 9-28 | LAYLVKKIDFDYTPNWGRGT |
| 182 | 10-29 | AYLVKKIDFDYTPNWGRGTP |
| 183 | 11-30 | YLVKKIDFDYTPNWGRGTPS |
| 184 | 12-31 | LVKKIDFDYTPNWGRGTPSS |
| 185 | 13-32 | VKKIDFDYTPNWGRGTPSSY |
| 186 | 14-33 | KKIDFDYTPNWGRGTPSSYI |
| 187 | 15-34 | KIDFDYTPNWGRGTPSSYID |
| 188 | 16-35 | IDFDYTPNWGRGTPSSYIDN |
| 189 | 17-36 | DFDYTPNWGRGTPSSYIDNL |
| 190 | 18-37 | FDYTPNWGRGTPSSYIDNLT |
| 191 | 19-38 | DYTPNWGRGTPSSYIDNLTF |
| 192 | 20-39 | YTPNWGRGTPSSYIDNLTFP |
| 193 | 21-40 | TPNWGRGTPSSYIDNLTFPK |
| 194 | 22-41 | PNWGRGTPSSYIDNLTFPKV |
| 195 | 23-42 | NWGRGTPSSYIDNLTFPKVL |
| 196 | 24-43 | WGRGTPSSYIDNLTFPKVLT |
| 197 | 25-44 | GRGTPSSYIDNLTFPKVLTD |
| 198 | 26-45 | RGTPSSYIDNLTFPKVLTDK |
| 199 | 27-46 | GTPSSYIDNLTFPKVLTDKK |
| 200 | 28-47 | TPSSYIDNLTFPKVLTDKKY |
| 201 | 8-28 | QLAYLVKKIDFDYTPNWGRGT |
| 202 | 9-29 | LAYLVKKIDFDYTPNWGRGTP |
| 203 | 10-30 | AYLVKKIDFDYTPNWGRGTPS |
| 204 | 11-31 | YLVKKIDFDYTPNWGRGTPSS |
| 205 | 12-32 | LVKKIDFDYTPNWGRGTPSSY |
| 206 | 13-33 | VKKIDFDYTPNWGRGTPSSYI |
| 207 | 14-34 | KKIDFDYTPNWGRGTPSSYID |
| 208 | 15-35 | KIDFDYTPNWGRGTPSSYIDN |
| 209 | 16-36 | IDFDYTPNWGRGTPSSYIDNL |
| 210 | 17-37 | DFDYTPNWGRGTPSSYIDNLT |
| 211 | 18-38 | FDYTPNWGRGTPSSYIDNLTF |
| 212 | 19-39 | DYTPNWGRGTPSSYIDNLTFP |
| 213 | 20-40 | YTPNWGRGTPSSYIDNLTFPK |
| 214 | 21-41 | TPNWGRGTPSSYIDNLTFPKV |
| 215 | 22-42 | PNWGRGTPSSYIDNLTFPKVL |
| 216 | 23-43 | NWGRGTPSSYIDNLTFPKVLT |
| 217 | 24-44 | WGRGTPSSYIDNLTFPKVLTD |
| 218 | 25-45 | GRGTPSSYIDNLTFPKVLTDK |
| 219 | 26-46 | RGTPSSYIDNLTFPKVLTDKK |
| 220 | 27-47 | GTPSSYIDNLTFPKVLTDKKY |
| 221 | 28-48 | TPSSYIDNLTFPKVLTDKKYS |
| 222 | 7-28 | FQLAYLVKKIDFDYTPNWGRGT |
| 223 | 8-29 | QLAYLVKKIDFDYTPNWGRGTP |
| 224 | 9-30 | LAYLVKKIDFDYTPNWGRGTPS |
| 225 | 10-31 | AYLVKKIDFDYTPNWGRGTPSS |
| 226 | 11-32 | YLVKKIDFDYTPNWGRGTPSSY |
| 227 | 12-33 | LVKKIDFDYTPNWGRGTPSSYI |
| 228 | 13-34 | VKKIDFDYTPNWGRGTPSSYID |

APPENDIX B-continued

FVE FRAGMENTS (RGT TRIPLET HIGHLIGHTED)

| Fragment Number | Residues | Sequence |
|---|---|---|
| 229 | 14-35 | KKIDFDYTPNWGRGTPSSYIDN |
| 230 | 15-36 | KIDFDYTPNWGRGTPSSYIDNL |
| 231 | 16-37 | IDFDYTPNWGRGTPSSYIDNLT |
| 232 | 17-38 | DFDYTPNWGRGTPSSYIDNLTF |
| 233 | 18-39 | FDYTPNWGRGTPSSYIDNLTFP |
| 234 | 19-40 | DYTPNWGRGTPSSYIDNLTFPK |
| 235 | 20-41 | YTPNWGRGTPSSYIDNLTFPKV |
| 236 | 21-42 | TPNWGRGTPSSYIDNLTFPKVL |
| 237 | 22-43 | PNWGRGTPSSYIDNLTFPKVLT |
| 238 | 23-44 | NWGRGTPSSYIDNLTFPKVLTD |
| 239 | 24-45 | WGRGTPSSYIDNLTFPKVLTDK |
| 240 | 25-46 | GRGTPSSYIDNLTFPKVLTDKK |
| 241 | 26-47 | RGTPSSYIDNLTFPKVLTDKKY |
| 242 | 27-48 | GTPSSYIDNLTFPKVLTDKKYS |
| 243 | 28-49 | TPSSYIDNLTFPKVLTDKKYSY |
| 244 | 6-28 | TFQLAYLVKKIDFDYTPNWGRGT |
| 245 | 7-29 | FQLAYLVKKIDFDYTPNWGRGTP |
| 246 | 8-30 | QLAYLVKKIDFDYTPNWGRGTPS |
| 247 | 9-31 | LAYLVKKIDFDYTPNWGRGTPSS |
| 248 | 10-32 | AYLVKKIDFDYTPNWGRGTPSSY |
| 249 | 11-33 | YLVKKIDFDYTPNWGRGTPSSYI |
| 250 | 12-34 | LVKKIDFDYTPNWGRGTPSSYID |
| 251 | 13-35 | VKKIDFDYTPNWGRGTPSSYIDN |
| 252 | 14-36 | KKIDFDYTPNWGRGTPSSYIDNL |
| 253 | 15-37 | KIDFDYTPNWGRGTPSSYIDNLT |
| 254 | 16-38 | IDFDYTPNWGRGTPSSYIDNLTF |
| 255 | 17-39 | DFDYTPNWGRGTPSSYIDNLTFP |
| 256 | 18-40 | FDYTPNWGRGTPSSYIDNLTFPK |
| 257 | 19-41 | DYTPNWGRGTPSSYIDNLTFPKV |
| 258 | 20-42 | YTPNWGRGTPSSYIDNLTFPKVL |
| 259 | 21-43 | TPNWGRGTPSSYIDNLTFPKVLT |
| 260 | 22-44 | PNWGRGTPSSYIDNLTFPKVLTD |
| 261 | 23-45 | NWGRGTPSSYIDNLTFPKVLTDK |
| 262 | 24-46 | WGRGTPSSYIDNLTFPKVLTDKK |
| 263 | 25-47 | GRGTPSSYIDNLTFPKVLTDKKY |
| 264 | 26-48 | RGTPSSYIDNLTFPKVLTDKKYS |
| 265 | 27-49 | GTPSSYIDNLTFPKVLTDKKYSY |
| 266 | 28-50 | TPSSYIDNLTFPKVLTDKKYSYR |
| 267 | 5-28 | LTFQLAYLVKKIDFDYTPNWGRGT |
| 268 | 6-29 | TFQLAYLVKKIDFDYTPNWGRGTP |
| 269 | 7-30 | FQLAYLVKKIDFDYTPNWGRGTPS |
| 270 | 8-31 | QLAYLVKKIDFDYTPNWGRGTPSS |
| 271 | 9-32 | LAYLVKKIDFDYTPNWGRGTPSSY |
| 272 | 10-33 | AYLVKKIDFDYTPNWGRGTPSSYI |
| 273 | 11-34 | YLVKKIDFDYTPNWGRGTPSSYID |
| 274 | 12-35 | LVKKIDFDYTPNWGRGTPSSYIDN |
| 275 | 13-36 | VKKIDFDYTPNWGRGTPSSYIDNL |
| 276 | 14-37 | KKIDFDYTPNWGRGTPSSYIDNLT |
| 277 | 15-38 | KIDFDYTPNWGRGTPSSYIDNLTF |
| 278 | 16-39 | IDFDYTPNWGRGTPSSYIDNLTFP |
| 279 | 17-40 | DFDYTPNWGRGTPSSYIDNLTFPK |
| 280 | 18-41 | FDYTPNWGRGTPSSYIDNLTFPKV |
| 281 | 19-42 | DYTPNWGRGTPSSYIDNLTFPKVL |
| 282 | 20-43 | YTPNWGRGTPSSYIDNLTFPKVLT |
| 283 | 21-44 | TPNWGRGTPSSYIDNLTFPKVLTD |
| 284 | 22-45 | PNWGRGTPSSYIDNLTFPKVLTDK |
| 285 | 23-46 | NWGRGTPSSYIDNLTFPKVLTDKK |
| 286 | 24-47 | WGRGTPSSYIDNLTFPKVLTDKKY |
| 287 | 25-48 | GRGTPSSYIDNLTFPKVLTDKKYS |
| 288 | 26-49 | RGTPSSYIDNLTFPKVLTDKKYSY |
| 289 | 27-50 | GTPSSYIDNLTFPKVLTDKKYSYR |
| 290 | 28-51 | TPSSYIDNLTFPKVLTDKKYSYRV |
| 291 | 4-28 | SLTFQLAYLVKKIDFDYTPNWGRGT |
| 292 | 5-29 | LTFQLAYLVKKIDFDYTPNWGRGTP |
| 293 | 6-30 | TFQLAYLVKKIDFDYTPNWGRGTPS |
| 294 | 7-31 | FQLAYLVKKIDFDYTPNWGRGTPSS |
| 295 | 8-32 | QLAYLVKKIDFDYTPNWGRGTPSSY |
| 296 | 9-33 | LAYLVKKIDFDYTPNWGRGTPSSYI |
| 297 | 10-34 | AYLVKKIDFDYTPNWGRGTPSSYID |
| 298 | 11-35 | YLVKKIDFDYTPNWGRGTPSSYIDN |
| 299 | 12-36 | LVKKIDFDYTPNWGRGTPSSYIDNL |
| 300 | 13-37 | VKKIDFDYTPNWGRGTPSSYIDNLT |
| 301 | 14-38 | KKIDFDYTPNWGRGTPSSYIDNLTF |
| 302 | 15-39 | KIDFDYTPNWGRGTPSSYIDNLTFP |
| 303 | 16-40 | IDFDYTPNWGRGTPSSYIDNLTFPK |

APPENDIX B-continued

FVE FRAGMENTS (RGT TRIPLET HIGHLIGHTED)

| Fragment Number | Residues | Sequence |
|---|---|---|
| 304 | 17-41 | DFDYTPNWGRGTPSSYIDNLTFPKV |
| 305 | 18-42 | FDYTPNWGRGTPSSYIDNLTFPKVL |
| 306 | 19-43 | DYTPNWGRGTPSSYIDNLTFPKVLT |
| 307 | 20-44 | YTPNWGRGTPSSYIDNLTFPKVLTD |
| 308 | 21-45 | TPNWGRGTPSSYIDNLTFPKVLTDK |
| 309 | 22-46 | PNWGRGTPSSYIDNLTFPKVLTDKK |
| 310 | 23-47 | NWGRGTPSSYIDNLTFPKVLTDKKY |
| 311 | 24-48 | WGRGTPSSYIDNLTFPKVLTDKKYS |
| 312 | 25-49 | GRGTPSSYIDNLTFPKVLTDKKYSY |
| 313 | 26-50 | RGTPSSYIDNLTFPKVLTDKKYSYR |
| 314 | 27-51 | GTPSSYIDNLTFPKVLTDKKYSYRV |
| 315 | 28-52 | TPSSYIDNLTFPKVLTDKKYSYRVV |
| 316 | 3-28 | TSLTFQLAYLVKKIDFDYTPNWGRGT |
| 317 | 4-29 | SLTFQLAYLVKKIDFDYTPNWGRGTP |
| 318 | 5-30 | LTFQLAYLVKKIDFDYTPNWGRGTPS |
| 319 | 6-31 | TFQLAYLVKKIDFDYTPNWGRGTPSS |
| 320 | 7-32 | FQLAYLVKKIDFDYTPNWGRGTPSSY |
| 321 | 8-33 | QLAYLVKKIDFDYTPNWGRGTPSSYI |
| 322 | 9-34 | LAYLVKKIDFDYTPNWGRGTPSSYID |
| 323 | 10-35 | AYLVKKIDFDYTPNWGRGTPSSYIDN |
| 324 | 11-36 | YLVKKIDFDYTPNWGRGTPSSYIDNL |
| 325 | 12-37 | LVKKIDFDYTPNWGRGTPSSYIDNLT |
| 326 | 13-38 | VKKIDFDYTPNWGRGTPSSYIDNLTF |
| 327 | 14-39 | KKIDFDYTPNWGRGTPSSYIDNLTFP |
| 328 | 15-40 | KIDFDYTPNWGRGTPSSYIDNLTFPK |
| 329 | 16-41 | IDFDYTPNWGRGTPSSYIDNLTFPKV |
| 330 | 17-42 | DFDYTPNWGRGTPSSYIDNLTFPKVL |
| 331 | 18-43 | FDYTPNWGRGTPSSYIDNLTFPKVLT |
| 332 | 19-44 | DYTPNWGRGTPSSYIDNLTFPKVLTD |
| 333 | 20-45 | YTPNWGRGTPSSYIDNLTFPKVLTDK |
| 334 | 21-46 | TPNWGRGTPSSYIDNLTFPKVLTDKK |
| 335 | 22-47 | PNWGRGTPSSYIDNLTFPKVLTDKKY |
| 336 | 23-48 | NWGRGTPSSYIDNLTFPKVLTDKKYS |
| 337 | 24-49 | WGRGTPSSYIDNLTFPKVLTDKKYSY |
| 338 | 25-50 | GRGTPSSYIDNLTFPKVLTDKKYSYR |
| 339 | 26-51 | RGTPSSYIDNLTFPKVLTDKKYSYRV |
| 340 | 27-52 | GTPSSYIDNLTFPKVLTDKKYSYRVV |
| 341 | 28-53 | TPSSYIDNLTFPKVLTDKKYSYRVVV |
| 342 | 2-28 | ATSLTFQLAYLVKKIDFDYTPNWGRGT |
| 343 | 3-29 | TSLTFQLAYLVKKIDFDYTPNWGRGTP |
| 344 | 4-30 | SLTFQLAYLVKKIDFDYTPNWGRGTPS |
| 345 | 5-31 | LTFQLAYLVKKIDFDYTPNWGRGTPSS |
| 346 | 6-32 | TFQLAYLVKKIDFDYTPNWGRGTPSSY |
| 347 | 7-33 | FQLAYLVKKIDFDYTPNWGRGTPSSYI |
| 348 | 8-34 | QLAYLVKKIDFDYTPNWGRGTPSSYID |
| 349 | 9-35 | LAYLVKKIDFDYTPNWGRGTPSSYIDN |
| 350 | 10-36 | AYLVKKIDFDYTPNWGRGTPSSYIDNL |
| 351 | 11-37 | YLVKKIDFDYTPNWGRGTPSSYIDNLT |
| 352 | 12-38 | LVKKIDFDYTPNWGRGTPSSYIDNLTF |
| 353 | 13-39 | VKKIDFDYTPNWGRGTPSSYIDNLTFP |
| 354 | 14-40 | KKIDFDYTPNWGRGTPSSYIDNLTFPK |
| 355 | 15-41 | KIDFDYTPNWGRGTPSSYIDNLTFPKV |
| 356 | 16-42 | IDFDYTPNWGRGTPSSYIDNLTFPKVL |
| 357 | 17-43 | DFDYTPNWGRGTPSSYIDNLTFPKVLT |
| 358 | 18-44 | FDYTPNWGRGTPSSYIDNLTFPKVLTD |
| 359 | 19-45 | DYTPNWGRGTPSSYIDNLTFPKVLTDK |
| 360 | 20-46 | YTPNWGRGTPSSYIDNLTFPKVLTDKK |
| 361 | 21-47 | TPNWGRGTPSSYIDNLTFPKVLTDKKY |
| 362 | 22-48 | PNWGRGTPSSYIDNLTFPKVLTDKKYS |
| 363 | 23-49 | NWGRGTPSSYIDNLTFPKVLTDKKYSY |
| 364 | 24-50 | WGRGTPSSYIDNLTFPKVLTDKKYSYR |
| 365 | 25-51 | GRGTPSSYIDNLTFPKVLTDKKYSYRV |
| 366 | 26-52 | RGTPSSYIDNLTFPKVLTDKKYSYRVV |
| 367 | 27-53 | GTPSSYIDNLTFPKVLTDKKYSYRVVV |
| 368 | 28-54 | TPSSYIDNLTFPKVLTDKKYSYRVVVN |
| 369 | 1-28 | SATSLTFQLAYLVKKIDFDYTPNWGRGT |
| 370 | 2-29 | ATSLTFQLAYLVKKIDFDYTPNWGRGTP |
| 371 | 3-30 | TSLTFQLAYLVKKIDFDYTPNWGRGTPS |
| 372 | 4-31 | SLTFQLAYLVKKIDFDYTPNWGRGTPSS |
| 373 | 5-32 | LTFQLAYLVKKIDFDYTPNWGRGTPSSY |
| 374 | 6-33 | TFQLAYLVKKIDFDYTPNWGRGTPSSYI |
| 375 | 7-34 | FQLAYLVKKIDFDYTPNWGRGTPSSYID |
| 376 | 8-35 | QLAYLVKKIDFDYTPNWGRGTPSSYIDN |
| 377 | 9-36 | LAYLVKKIDFDYTPNWGRGTPSSYIDNL |
| 378 | 10-37 | AYLVKKIDFDYTPNWGRGTPSSYIDNLT |

APPENDIX B-continued

FVE FRAGMENTS (RGT TRIPLET HIGHLIGHTED)

| Fragment Number | Residues | Sequence |
|---|---|---|
| 379 | 11-38 | YLVKKIDFDYTPNWGRGTPSSYIDNLTF |
| 380 | 12-39 | LVKKIDFDYTPNWGRGTPSSYIDNLTFP |
| 381 | 13-40 | VKKIDFDYTPNWGRGTPSSYIDNLTFPK |
| 382 | 14-41 | KKIDFDYTPNWGRGTPSSYIDNLTFPKV |
| 383 | 15-42 | KIDFDYTPNWGRGTPSSYIDNLTFPKVL |
| 384 | 16-43 | IDFDYTPNWGRGTPSSYIDNLTFPKVLT |
| 385 | 17-44 | DFDYTPNWGRGTPSSYIDNLTFPKVLTD |
| 386 | 18-45 | FDYTPNWGRGTPSSYIDNLTFPKVLTDK |
| 387 | 19-46 | DYTPNWGRGTPSSYIDNLTFPKVLTDKK |
| 388 | 20-47 | YTPNWGRGTPSSYIDNLTFPKVLTDKKY |
| 389 | 21-48 | TPNWGRGTPSSYIDNLTFPKVLTDKKYS |
| 390 | 22-49 | PNWGRGTPSSYIDNLTFPKVLTDKKYSY |
| 391 | 23-50 | NWGRGTPSSYIDNLTFPKVLTDKKYSYR |
| 392 | 24-51 | WGRGTPSSYIDNLTFPKVLTDKKYSYRV |
| 393 | 25-52 | GRGTPSSYIDNLTFPKVLTDKKYSYRVV |
| 394 | 26-53 | RGTPSSYIDNLTFPKVLTDKKYSYRVVV |
| 395 | 27-54 | GTPSSYIDNLTFPKVLTDKKYSYRVVVN |
| 396 | 28-55 | TPSSYIDNLTFPKVLTDKKYSYRVVVNG |

(Appendix discloses SEQ ID NOS: 92-487, respectively, in order of appearance)

APPENDIX C: CRYSTAL COORDINATES OF FVE PROTEIN

```
HEADER    ---- XX-XXX-XX xxxx
COMPND    ---
REMARK    3
REMARK    3  REFINEMENT.
REMARK    3  PROGRAM: REFMAC 5.0
REMARK    3  AUTHORS: MURSHUDOV, VAGIN, DODSON
REMARK    3
REMARK    3  REFINEMENT TARGET: MAXIMUM LIKELIHOOD
REMARK    3
REMARK    3  DATA USED IN REFINEMENT.
REMARK    3  RESOLUTION RANGE HIGH (ANGSTROMS): 1.70
REMARK    3  RESOLUTION RANGE LOW (ANGSTROMS): 30.02
REMARK    3  DATA CUTOFF (SIGMA(F)): NONE
REMARK    3  COMPLETENESS FOR RANGE (%): 98.80
REMARK    3  NUMBER OF REFLECTIONS: 30783
REMARK    3
REMARK    3  FIT TO DATA USED IN REFINEMENT.
REMARK    3  CROSS-VALIDATION METHOD: THROUGHOUT
REMARK    3  FREE R VALUE TEST SET SELECTION: RANDOM
REMARK    3  R VALUE (WORKING + TEST SET): 0.18358
REMARK    3  R VALUE (WORKING SET): 0.18218
REMARK    3  FREE R VALUE: 0.21016
REMARK    3  FREE R VALUE TEST SET SIZE (%): 5.1
REMARK    3  FREE R VALUE TEST SET COUNT: 1650
REMARK    3
REMARK    3  FIT IN THE HIGHEST RESOLUTION BIN.
REMARK    3  TOTAL NUMBER OF BINS USED: 20
REMARK    3  BIN RESOLUTION RANGE HIGH: 1.701
REMARK    3  BIN RESOLUTION RANGE LOW: 1.745
REMARK    3  REFLECTION IN BIN (WORKING SET): 2183
REMARK    3  BIN R VALUE (WORKING SET): 0.160
REMARK    3  BIN FREE R VALUE SET COUNT: 114
REMARK    3  BIN FREE R VALUE: 0.197
REMARK    3
REMARK    3  NUMBER OF NON-HYDROGEN ATOMS USED IN REFINEMENT.
REMARK    3  ALL ATOMS: 1940
REMARK    3
REMARK    3  B VALUES.
REMARK    3  FROM WILSON PLOT (A**2): NULL
REMARK    3  MEAN B VALUE (OVERALL, A**2): 13.666
REMARK    3  OVERALL ANISOTROPIC B VALUE.
REMARK    3  B11 (A**2): -0.02
REMARK    3  B22 (A**2): -0.02
REMARK    3  B33 (A**2): 0.03
REMARK    3  B12 (A**2): 0.00
REMARK    3  B13 (A**2): 0.00
REMARK    3  B23 (A**2): 0.00
REMARK    3
REMARK    3  ESTIMATED OVERALL COORDINATE ERROR.
```

-continued

| APPENDIX C: CRYSTAL COORDINATES OF FVE PROTEIN | | |
|---|---|---|
| REMARK | 3 | ESU BASED ON R VALUE (A): 0.092 |
| REMARK | 3 | ESU BASED ON FREE R VALUE (A): 0.092 |
| REMARK | 3 | ESU BASED ON MAXIMUM LIKELIHOOD (A): 0.075 |
| REMARK | 3 | ESU FOR B VALUES BASED ON MAXIMUM LIKELIHOOD (A**2): 2.208 |
| REMARK | 3 | |
| REMARK | 3 | CORRELATION COEFFICIENTS. |
| REMARK | 3 | CORRELATION COEFFICIENT FO-FC: 0.947 |
| REMARK | 3 | CORRELATION COEFFICIENT FO-FC FREE: 0.933 |
| REMARK | 3 | |
| REMARK | 3 | RMS DEVIATIONS FROM IDEAL VALUES COUNT RMS WEIGHT |
| REMARK | 3 | BOND LENGTHS REFINED ATOMS (A): 1830; 0.010; 0.022 |
| REMARK | 3 | BOND LENGTHS OTHERS (A): 1593; 0.001; 0.020 |
| REMARK | 3 | BOND ANGLES REFINED ATOMS (DEGREES): 2490; 1.466; 1.941 |
| REMARK | 3 | BOND ANGLES OTHERS (DEGREES): 3724; 0.921; 3.000 |
| REMARK | 3 | TORSION ANGLES, PERIOD 1 (DEGREES): 224; 4.899; 3.000 |
| REMARK | 3 | TORSION ANGLES, PERIOD 3 (DEGREES): 311; 16.844; 15.000 |
| REMARK | 3 | CHIRAL-CENTER RESTRAINTS (A**3): 280; 0.231; 0.200 |
| REMARK | 3 | GENERAL PLANES REFINED ATOMS (A): 2026; 0.006; 0.020 |
| REMARK | 3 | GENERAL PLANES OTHERS (A): 374; 0.003; 0.020 |
| REMARK | 3 | NON-BONDED CONTACTS REFINED ATOMS (A): 327; 0.271; 0.300 |
| REMARK | 3 | NON-BONDED CONTACTS OTHERS (A): 1447; 0.212; 0.300 |
| REMARK | 3 | H-BOND (X . . . Y) REFINED ATOMS (A): 131; 0.131; 0.500 |
| REMARK | 3 | SYMMETRY VDW REFINED ATOMS (A): 8; 0.310; 0.300 |
| REMARK | 3 | SYMMETRY VDW OTHERS (A): 17; 0.291; 0.300 |
| REMARK | 3 | SYMMETRY H-BOND REFINED ATOMS (A): 14; 0.144; 0.500 |
| REMARK | 3 | |
| REMARK | 3 | ISOTROPIC THERMAL FACTOR RESTRAINTS. COUNT RMS WEIGHT |
| REMARK | 3 | MAIN-CHAIN BOND REFINED ATOMS (A**2): 1124; 0.898; 1.500 |
| REMARK | 3 | MAIN-CHAIN ANGLE REFINED ATOMS (A**2): 1827; 1.603; 2.000 |
| REMARK | 3 | SIDE-CHAIN BOND REFINED ATOMS (A**2): 706; 2.292; 3.000 |
| REMARK | 3 | SIDE-CHAIN ANGLE REFINED ATOMS (A**2): 663; 3.839; 4.500 |
| REMARK | 3 | |
| REMARK | 3 | NCS RESTRAINTS STATISTICS |
| REMARK | 3 | NUMBER OF NCS GROUPS: NULL |
| REMARK | 3 | |
| REMARK | 3 | |
| REMARK | 3 | TLS DETAILS |
| REMARK | 3 | NUMBER OF TLS GROUPS: 2 |
| REMARK | 3 | |
| REMARK | 3 | TLS GROUP: 1 |
| REMARK | 3 | NUMBER OF COMPONENTS GROUP: 1 |
| REMARK | 3 | COMPONENTS C SSSEQI TO C SSSEQI |
| REMARK | 3 | RESIDUE RANGE: A 1 A 113 |
| REMARK | 3 | ORIGIN FOR THE GROUP (A): 31.8380 34.4130 15.9540 |
| REMARK | 3 | T TENSOR |
| REMARK | 3 | T11: 0.0826 T22: 0.0528 |
| REMARK | 3 | T33: 0.0022 T12: 0.0085 |
| REMARK | 3 | T13: 0.0118 T23: 0.0066 |
| REMARK | 3 | L TENSOR |
| REMARK | 3 | L11: 0.3236 L22: 1.6346 |
| REMARK | 3 | L33: 0.0319 L12: −0.4538 |
| REMARK | 3 | L13: −0.1060 L23: −0.1134 |
| REMARK | 3 | S TENSOR |
| REMARK | 3 | S11: 0.0668 S12: 0.0317 S13: 0.0266 |
| REMARK | 3 | S21: −0.0158 S22: −0.0508 S23: −0.0656 |
| REMARK | 3 | S31: −0.0111 S32: 0.0027 S33: −0.0160 |
| REMARK | 3 | |
| REMARK | 3 | TLS GROUP: 2 |
| REMARK | 3 | NUMBER OF COMPONENTS GROUP: 1 |
| REMARK | 3 | COMPONENTS C SSSEQI TO C SSSEQI |
| REMARK | 3 | RESIDUE RANGE: B 1 B 112 |
| REMARK | 3 | ORIGIN FOR THE GROUP (A): 33.7580 2.5150 18.4210 |
| REMARK | 3 | T TENSOR |
| REMARK | 3 | T11: 0.0638 T22: 0.0608 |
| REMARK | 3 | T33: 0.0227 T12: 0.0019 |
| REMARK | 3 | T13: −0.0064 T23: −0.0055 |
| REMARK | 3 | L TENSOR |
| REMARK | 3 | L11: 0.0923 L22: 0.6926 |
| REMARK | 3 | L33: 0.1427 L12: −0.1092 |
| REMARK | 3 | L13: −0.1135 L23: −0.0160 |
| REMARK | 3 | S TENSOR |
| REMARK | 3 | S11: 0.0096 S12: 0.0276 S13: −0.0212 |
| REMARK | 3 | S21: −0.0046 S22: −0.0327 S23: 0.0279 |
| REMARK | 3 | S31: −0.0061 S32: −0.0095 S33: 0.0231 |
| REMARK | 3 | |
| REMARK | 3 | |
| REMARK | 3 | BULK SOLVENT MODELLING. |
| REMARK | 3 | METHOD USED: BABINET MODEL WITH MASK |

APPENDIX C: CRYSTAL COORDINATES OF FVE PROTEIN

```
REMARK   3  PARAMETERS FOR MASK CALCULATION
REMARK   3  VDW PROBE RADIUS: 1.40
REMARK   3  ION PROBE RADIUS: 0.80
REMARK   3  SHRINKAGE RADIUS: 0.80
REMARK   3
REMARK   3  OTHER REFINEMENT REMARKS:
REMARK   3  HYDROGENS HAVE BEEN ADDED IN THE RIDING POSITIONS
REMARK   3
CISPEP   1  THR A 28 PRO A 29 0.00
CISPEP   2  THR B 28 PRO B 29 0.00
CRYST1   97.118 97.118 61.413 90.00 90.00 90.00 P 43 21 2
SCALE1   0.010297 0.000000 0.000000 0.00000
SCALE2   0.000000 0.010297 0.000000 0.00000
SCALE3   0.000000 0.000000 0.016283 0.00000
ATOM     1    O    ACE  A  0   39.758  17.815   6.621  1.00  32.04 O
ATOM     2    C    ACE  A  0   38.470  17.959   6.297  1.00  30.44 C
ATOM     3    CA   ACE  A  0   37.841  19.332   5.940  1.00  30.13 C
ATOM     4    N    SER  A  1   37.877  16.775   5.643  1.00  19.18 N
ATOM     6    CA   SER  A  1   36.408  16.741   5.468  1.00  17.19 C
ATOM     8    CB   SER  A  1   35.991  15.421   4.841  1.00  17.15 C
ATOM    11    OG   SER  A  1   36.194  14.363   5.768  1.00  16.56 O
ATOM    13    C    SER  A  1   35.748  16.842   6.834  1.00  16.94 C
ATOM    14    O    SER  A  1   36.412  16.630   7.854  1.00  16.93 O
ATOM    17    N    ALA  A  2   34.500  17.297   6.850  1.00  17.11 N
ATOM    19    CA   ALA  A  2   33.637  17.247   8.031  1.00  16.12 C
ATOM    21    CB   ALA  A  2   32.200  17.465   7.619  1.00  16.40 C
ATOM    25    C    ALA  A  2   33.762  15.907   8.757  1.00  15.10 C
ATOM    26    O    ALA  A  2   33.901  15.848   9.975  1.00  13.93 O
ATOM    27    N    THR  A  3   33.680  14.823   8.009  1.00  14.66 N
ATOM    29    CA   THR  A  3   33.773  13.515   8.630  1.00  13.12 C
ATOM    31    CB   THR  A  3   33.497  12.440   7.599  1.00  13.38 C
ATOM    33    OG1  THR  A  3   32.154  12.599   7.122  1.00  13.50 O
ATOM    35    CG2  THR  A  3   33.517  11.067   8.238  1.00  14.13 C
ATOM    39    C    THR  A  3   35.111  13.272   9.307  1.00  12.51 C
ATOM    40    O    THR  A  3   35.141  12.780  10.440  1.00  10.83 O
ATOM    41    N    SER  A  4   36.216  13.578   8.632  1.00  11.39 N
ATOM    43    CA   SER  A  4   37.538  13.356   9.244  1.00  12.60 C
ATOM    45    CB   SER  A  4   38.694  13.609   8.266  1.00  13.31 C
ATOM    48    OG   SER  A  4   38.566  14.874   7.668  1.00  19.57 O
ATOM    50    C    SER  A  4   37.726  14.223  10.471  1.00  11.69 C
ATOM    51    O    SER  A  4   38.223  13.765  11.484  1.00  10.87 O
ATOM    52    N    LEU  A  5   37.331  15.484  10.379  1.00  11.95 N
ATOM    54    CA   LEU  A  5   37.478  16.382  11.515  1.00  11.00 C
ATOM    56    CB   LEU  A  5   37.047  17.801  11.149  1.00  11.44 C
ATOM    59    CG   LEU  A  5   37.928  18.509  10.117  1.00  13.46 C
ATOM    61    CD1  LEU  A  5   37.267  19.790   9.651  1.00  15.05 C
ATOM    65    CD2  LEU  A  5   39.270  18.807  10.731  1.00  15.52 C
ATOM    69    C    LEU  A  5   36.658  15.900  12.698  1.00  10.25 C
ATOM    70    O    LEU  A  5   37.114  15.947  13.852  1.00   9.79 O
ATOM    71    N    THR  A  6   35.440  15.446  12.417  1.00   9.51 N
ATOM    73    CA   THR  A  6   34.547  14.953  13.459  1.00   9.80 C
ATOM    75    CB   THR  A  6   33.250  14.425  12.840  1.00   9.84 C
ATOM    77    OG1  THR  A  6   32.454  15.510  12.319  1.00  10.30 O
ATOM    79    CG2  THR  A  6   32.388  13.749  13.859  1.00   9.40 C
ATOM    83    C    THR  A  6   35.186  13.816  14.236  1.00   9.72 C
ATOM    84    O    THR  A  6   35.215  13.845  15.451  1.00   9.30 O
ATOM    85    N    PHE  A  7   35.679  12.796  13.545  1.00   9.95 N
ATOM    87    CA   PHE  A  7   36.185  11.642  14.278  1.00   8.92 C
ATOM    89    CB   PHE  A  7   35.993  10.367  13.490  1.00   8.90 C
ATOM    92    CG   PHE  A  7   34.552   9.988  13.365  1.00   8.19 C
ATOM    93    CD1  PHE  A  7   33.848   9.583  14.485  1.00  10.40 C
ATOM    95    CE1  PHE  A  7   32.512   9.267  14.407  1.00  10.95 C
ATOM    97    CZ   PHE  A  7   31.848   9.370  13.217  1.00  11.35 C
ATOM    99    CE2  PHE  A  7   32.532   9.791  12.080  1.00  10.55 C
ATOM   101    CD2  PHE  A  7   33.872  10.127  12.165  1.00  10.65 C
ATOM   103    C    PHE  A  7   37.603  11.819  14.812  1.00   9.58 C
ATOM   104    O    PHE  A  7   37.970  11.203  15.811  1.00   9.17 O
ATOM   105    N    GLN  A  8   38.405  12.669  14.177  1.00   9.36 N
ATOM   107    CA   GLN  A  8   39.683  12.999  14.778  1.00  10.36 C
ATOM   109    CB   GLN  A  8   40.476  13.937  13.891  1.00  10.90 C
ATOM   112    CG   GLN  A  8   41.097  13.322  12.692  1.00  14.14 C
ATOM   115    CD   GLN  A  8   41.805  14.419  11.894  1.00  16.75 C
ATOM   116    OE1  GLN  A  8   41.409  14.742  10.787  1.00  21.77 O
ATOM   117    NE2  GLN  A  8   42.799  15.056  12.517  1.00  20.28 N
ATOM   120    C    GLN  A  8   39.409  13.716  16.116  1.00  10.53 C
ATOM   121    O    GLN  A  8   40.049  13.416  17.118  1.00  10.95 O
ATOM   122    N    LEU  A  9   38.457  14.654  16.122  1.00   9.95 N
ATOM   124    CA   LEU  A  9   38.145  15.413  17.332  1.00   9.62 C
```

-continued

| APPENDIX C: CRYSTAL COORDINATES OF FVE PROTEIN | | | | | | | | | |
|---|---|---|---|---|---|---|---|---|---|
| ATOM | 126 | CB | LEU | A | 9 | 37.162 | 16.537 | 17.057 | 1.00 | 9.66 C |
| ATOM | 129 | CG | LEU | A | 9 | 36.767 | 17.375 | 18.278 | 1.00 | 9.80 C |
| ATOM | 131 | CD1 | LEU | A | 9 | 37.974 | 18.098 | 18.862 | 1.00 | 10.08 C |
| ATOM | 135 | CD2 | LEU | A | 9 | 35.701 | 18.397 | 17.886 | 1.00 | 12.75 C |
| ATOM | 139 | C | LEU | A | 9 | 37.541 | 14.467 | 18.346 | 1.00 | 9.58 C |
| ATOM | 140 | O | LEU | A | 9 | 37.935 | 14.484 | 19.514 | 1.00 | 9.46 O |
| ATOM | 141 | N | ALA | A | 10 | 36.588 | 13.637 | 17.917 | 1.00 | 9.20 N |
| ATOM | 143 | CA | ALA | A | 10 | 35.952 | 12.701 | 18.856 | 1.00 | 9.03 C |
| ATOM | 145 | CB | ALA | A | 10 | 34.875 | 11.850 | 18.154 | 1.00 | 8.72 C |
| ATOM | 149 | C | ALA | A | 10 | 36.949 | 11.802 | 19.605 | 1.00 | 8.50 C |
| ATOM | 150 | O | ALA | A | 10 | 36.855 | 11.615 | 20.825 | 1.00 | 8.50 O |
| ATOM | 151 | N | TYR | A | 11 | 37.918 | 11.242 | 18.899 | 1.00 | 9.18 N |
| ATOM | 153 | CA | TYR | A | 11 | 38.865 | 10.359 | 19.541 | 1.00 | 8.12 C |
| ATOM | 155 | CB | TYR | A | 11 | 39.716 | 9.664 | 18.491 | 1.00 | 8.30 C |
| ATOM | 158 | CG | TYR | A | 11 | 40.642 | 8.638 | 19.075 | 1.00 | 7.61 C |
| ATOM | 159 | CD1 | TYR | A | 11 | 40.156 | 7.495 | 19.699 | 1.00 | 9.07 C |
| ATOM | 161 | CE1 | TYR | A | 11 | 41.008 | 6.560 | 20.229 | 1.00 | 10.41 C |
| ATOM | 163 | CZ | TYR | A | 11 | 42.359 | 6.768 | 20.170 | 1.00 | 13.73 C |
| ATOM | 164 | OH | TYR | A | 11 | 43.210 | 5.831 | 20.740 | 1.00 | 15.09 O |
| ATOM | 166 | CE2 | TYR | A | 11 | 42.868 | 7.898 | 19.571 | 1.00 | 10.94 C |
| ATOM | 168 | CD2 | TYR | A | 11 | 42.014 | 8.827 | 19.027 | 1.00 | 10.00 C |
| ATOM | 170 | C | TYR | A | 11 | 39.752 | 11.139 | 20.530 | 1.00 | 8.66 C |
| ATOM | 171 | O | TYR | A | 11 | 40.158 | 10.596 | 21.550 | 1.00 | 8.96 O |
| ATOM | 172 | N | LEU | A | 12 | 40.012 | 12.412 | 20.245 | 1.00 | 8.35 N |
| ATOM | 174 | CA | LEU | A | 12 | 40.899 | 13.238 | 21.081 | 1.00 | 9.68 C |
| ATOM | 176 | CB | LEU | A | 12 | 41.501 | 14.374 | 20.257 | 1.00 | 10.19 C |
| ATOM | 179 | CG | LEU | A | 12 | 42.469 | 13.943 | 19.152 | 1.00 | 15.33 C |
| ATOM | 181 | CD1 | LEU | A | 12 | 43.187 | 15.145 | 18.549 | 1.00 | 18.28 C |
| ATOM | 185 | CD2 | LEU | A | 12 | 43.464 | 12.905 | 19.653 | 1.00 | 18.55 C |
| ATOM | 189 | C | LEU | A | 12 | 40.242 | 13.812 | 22.351 | 1.00 | 9.19 C |
| ATOM | 190 | O | LEU | A | 12 | 40.851 | 13.776 | 23.445 | 1.00 | 10.13 O |
| ATOM | 191 | N | VAL | A | 13 | 39.010 | 14.301 | 22.232 | 1.00 | 8.92 N |
| ATOM | 193 | CA | VAL | A | 13 | 38.357 | 14.969 | 23.368 | 1.00 | 8.52 C |
| ATOM | 195 | CB | VAL | A | 13 | 38.013 | 16.426 | 23.050 | 1.00 | 8.78 C |
| ATOM | 197 | CG1 | VAL | A | 13 | 39.251 | 17.141 | 22.537 | 1.00 | 10.74 C |
| ATOM | 201 | CG2 | VAL | A | 13 | 36.864 | 16.560 | 22.057 | 1.00 | 9.49 C |
| ATOM | 205 | C | VAL | A | 13 | 37.131 | 14.252 | 23.904 | 1.00 | 8.44 C |
| ATOM | 206 | O | VAL | A | 13 | 36.592 | 14.631 | 24.947 | 1.00 | 8.60 O |
| ATOM | 207 | N | LYS | A | 14 | 36.709 | 13.218 | 23.178 | 1.00 | 8.48 N |
| ATOM | 209 | CA | LYS | A | 14 | 35.583 | 12.339 | 23.536 | 1.00 | 8.98 C |
| ATOM | 211 | CB | LYS | A | 14 | 35.771 | 11.687 | 24.909 | 1.00 | 8.33 C |
| ATOM | 214 | CG | LYS | A | 14 | 37.127 | 11.029 | 25.118 | 1.00 | 7.66 C |
| ATOM | 217 | CD | LYS | A | 14 | 37.513 | 10.044 | 23.992 | 1.00 | 8.44 C |
| ATOM | 220 | CE | LYS | A | 14 | 38.818 | 9.318 | 24.229 | 1.00 | 7.68 C |
| ATOM | 223 | NZ | LYS | A | 14 | 39.160 | 8.416 | 23.087 | 1.00 | 7.55 N |
| ATOM | 227 | C | LYS | A | 14 | 34.187 | 12.932 | 23.465 | 1.00 | 10.23 C |
| ATOM | 228 | O | LYS | A | 14 | 33.306 | 12.332 | 22.864 | 1.00 | 9.28 O |
| ATOM | 229 | N | LYS | A | 15 | 33.976 | 14.083 | 24.089 | 1.00 | 10.78 N |
| ATOM | 231 | CA | LYS | A | 15 | 32.636 | 14.648 | 24.202 | 1.00 | 12.04 C |
| ATOM | 233 | CB | LYS | A | 15 | 32.058 | 14.428 | 25.615 | 1.00 | 13.87 C |
| ATOM | 236 | CG | LYS | A | 15 | 30.626 | 14.970 | 25.767 | 1.00 | 18.29 C |
| ATOM | 239 | CD | LYS | A | 15 | 30.411 | 15.838 | 26.991 | 1.00 | 25.35 C |
| ATOM | 242 | CE | LYS | A | 15 | 29.648 | 17.144 | 26.648 | 1.00 | 26.80 C |
| ATOM | 245 | NZ | LYS | A | 15 | 30.479 | 18.398 | 26.848 | 1.00 | 28.04 N |
| ATOM | 249 | C | LYS | A | 15 | 32.701 | 16.124 | 23.876 | 1.00 | 11.99 C |
| ATOM | 250 | O | LYS | A | 15 | 33.603 | 16.825 | 24.333 | 1.00 | 12.92 O |
| ATOM | 251 | N | ILE | A | 16 | 31.770 | 16.587 | 23.054 | 1.00 | 11.71 N |
| ATOM | 253 | CA | ILE | A | 16 | 31.631 | 18.011 | 22.795 | 1.00 | 11.45 C |
| ATOM | 255 | CB | ILE | A | 16 | 32.644 | 18.502 | 21.769 | 1.00 | 12.21 C |
| ATOM | 257 | CG1 | ILE | A | 16 | 32.966 | 19.980 | 22.019 | 1.00 | 12.61 C |
| ATOM | 260 | CD1 | ILE | A | 16 | 34.167 | 20.459 | 21.239 | 1.00 | 16.67 C |
| ATOM | 264 | CG2 | ILE | A | 16 | 32.154 | 18.226 | 20.357 | 1.00 | 12.62 C |
| ATOM | 268 | C | ILE | A | 16 | 30.193 | 18.273 | 22.375 | 1.00 | 11.19 C |
| ATOM | 269 | O | ILE | A | 16 | 29.515 | 17.396 | 21.835 | 1.00 | 10.05 O |
| ATOM | 270 | N | ASP | A | 17 | 29.729 | 19.495 | 22.614 | 1.00 | 11.77 N |
| ATOM | 272 | CA | ASP | A | 17 | 28.357 | 19.861 | 22.315 | 1.00 | 11.36 C |
| ATOM | 274 | CB | ASP | A | 17 | 27.503 | 19.570 | 23.548 | 1.00 | 12.18 C |
| ATOM | 277 | CG | ASP | A | 17 | 26.019 | 19.854 | 23.363 | 1.00 | 13.83 C |
| ATOM | 278 | OD1 | ASP | A | 17 | 25.558 | 20.190 | 22.262 | 1.00 | 14.93 O |
| ATOM | 279 | OD2 | ASP | A | 17 | 25.207 | 19.726 | 24.327 | 1.00 | 17.34 O |
| ATOM | 280 | C | ASP | A | 17 | 28.354 | 21.342 | 22.018 | 1.00 | 10.94 C |
| ATOM | 281 | O | ASP | A | 17 | 28.505 | 22.158 | 22.930 | 1.00 | 12.08 O |
| ATOM | 282 | N | PHE | A | 18 | 28.220 | 21.709 | 20.754 | 1.00 | 9.97 N |
| ATOM | 284 | CA | PHE | A | 18 | 28.208 | 23.121 | 20.420 | 1.00 | 9.42 C |
| ATOM | 286 | CB | PHE | A | 18 | 29.621 | 23.630 | 20.070 | 1.00 | 9.10 C |
| ATOM | 289 | CG | PHE | A | 18 | 30.262 | 22.990 | 18.849 | 1.00 | 9.30 C |
| ATOM | 290 | CD1 | PHE | A | 18 | 31.457 | 22.269 | 18.966 | 1.00 | 11.84 C |
| ATOM | 292 | CE1 | PHE | A | 18 | 32.069 | 21.704 | 17.850 | 1.00 | 11.09 C |

APPENDIX C: CRYSTAL COORDINATES OF FVE PROTEIN

-continued

| ATOM | 294 | CZ | PHE | A | 18 | 31.520 | 21.860 | 16.619 | 1.00 | 10.73 | C |
|---|---|---|---|---|---|---|---|---|---|---|---|
| ATOM | 296 | CE2 | PHE | A | 18 | 30.335 | 22.573 | 16.470 | 1.00 | 11.19 | C |
| ATOM | 298 | CD2 | PHE | A | 18 | 29.725 | 23.157 | 17.586 | 1.00 | 8.90 | C |
| ATOM | 300 | C | PHE | A | 18 | 27.226 | 23.431 | 19.299 | 1.00 | 9.78 | C |
| ATOM | 301 | O | PHE | A | 18 | 26.794 | 22.537 | 18.568 | 1.00 | 9.84 | O |
| ATOM | 302 | N | ASP | A | 19 | 26.899 | 24.711 | 19.156 | 1.00 | 10.97 | N |
| ATOM | 304 | CA | ASP | A | 19 | 26.059 | 25.169 | 18.060 | 1.00 | 10.37 | C |
| ATOM | 306 | CB | ASP | A | 19 | 24.575 | 25.130 | 18.429 | 1.00 | 10.87 | C |
| ATOM | 309 | CG | ASP | A | 19 | 23.674 | 25.452 | 17.267 | 1.00 | 11.55 | C |
| ATOM | 310 | OD1 | ASP | A | 19 | 24.180 | 25.843 | 16.178 | 1.00 | 11.30 | O |
| ATOM | 311 | OD2 | ASP | A | 19 | 22.418 | 25.322 | 17.350 | 1.00 | 12.10 | O |
| ATOM | 312 | C | ASP | A | 19 | 26.497 | 26.590 | 17.705 | 1.00 | 10.71 | C |
| ATOM | 313 | O | ASP | A | 19 | 26.136 | 27.575 | 18.388 | 1.00 | 10.19 | O |
| ATOM | 314 | N | TYR | A | 20 | 27.297 | 26.678 | 16.646 | 1.00 | 10.10 | N |
| ATOM | 316 | CA | TYR | A | 20 | 27.788 | 27.942 | 16.103 | 1.00 | 9.68 | C |
| ATOM | 318 | CB | TYR | A | 20 | 29.308 | 27.879 | 15.911 | 1.00 | 9.82 | C |
| ATOM | 321 | CG | TYR | A | 20 | 30.089 | 28.043 | 17.181 | 1.00 | 8.36 | C |
| ATOM | 322 | CD1 | TYR | A | 20 | 30.459 | 26.943 | 17.934 | 1.00 | 9.01 | C |
| ATOM | 324 | CE1 | TYR | A | 20 | 31.175 | 27.087 | 19.115 | 1.00 | 9.44 | C |
| ATOM | 326 | CZ | TYR | A | 20 | 31.514 | 28.335 | 19.546 | 1.00 | 10.02 | C |
| ATOM | 327 | OH | TYR | A | 20 | 32.228 | 28.469 | 20.703 | 1.00 | 9.07 | O |
| ATOM | 329 | CE2 | TYR | A | 20 | 31.167 | 29.441 | 18.804 | 1.00 | 10.02 | C |
| ATOM | 331 | CD2 | TYR | A | 20 | 30.451 | 29.303 | 17.648 | 1.00 | 8.62 | C |
| ATOM | 333 | C | TYR | A | 20 | 27.054 | 28.282 | 14.786 | 1.00 | 10.92 | C |
| ATOM | 334 | O | TYR | A | 20 | 27.600 | 28.930 | 13.878 | 1.00 | 11.60 | O |
| ATOM | 335 | N | THR | A | 21 | 25.800 | 27.857 | 14.694 | 1.00 | 12.18 | N |
| ATOM | 337 | CA | THR | A | 21 | 24.980 | 28.261 | 13.567 | 1.00 | 12.37 | C |
| ATOM | 339 | CB | THR | A | 21 | 23.584 | 27.692 | 13.676 | 1.00 | 12.82 | C |
| ATOM | 341 | OG1 | THR | A | 21 | 23.623 | 26.259 | 13.737 | 1.00 | 12.95 | O |
| ATOM | 343 | CG2 | THR | A | 21 | 22.832 | 27.997 | 12.401 | 1.00 | 13.70 | C |
| ATOM | 347 | C | THR | A | 21 | 24.871 | 29.776 | 13.598 | 1.00 | 12.58 | C |
| ATOM | 348 | O | THR | A | 21 | 24.445 | 30.332 | 14.595 | 1.00 | 12.57 | O |
| ATOM | 349 | N | PRO | A | 22 | 25.259 | 30.460 | 12.528 | 1.00 | 12.83 | N |
| ATOM | 350 | CA | PRO | A | 22 | 25.263 | 31.917 | 12.549 | 1.00 | 12.54 | C |
| ATOM | 352 | CB | PRO | A | 22 | 26.214 | 32.276 | 11.409 | 1.00 | 12.71 | C |
| ATOM | 355 | CG | PRO | A | 22 | 26.064 | 31.150 | 10.423 | 1.00 | 12.51 | C |
| ATOM | 358 | CD | PRO | A | 22 | 25.773 | 29.925 | 11.259 | 1.00 | 12.22 | C |
| ATOM | 361 | C | PRO | A | 22 | 23.890 | 32.509 | 12.337 | 1.00 | 12.87 | C |
| ATOM | 362 | O | PRO | A | 22 | 23.281 | 32.302 | 11.282 | 1.00 | 14.33 | O |
| ATOM | 363 | N | ASN | A | 23 | 23.405 | 33.202 | 13.363 | 1.00 | 12.69 | N |
| ATOM | 365 | CA | ASN | A | 23 | 22.145 | 33.920 | 13.285 | 1.00 | 12.96 | C |
| ATOM | 367 | CB | ASN | A | 23 | 21.290 | 33.568 | 14.497 | 1.00 | 13.22 | C |
| ATOM | 370 | CG | ASN | A | 23 | 20.761 | 32.141 | 14.427 | 1.00 | 16.73 | C |
| ATOM | 371 | OD1 | ASN | A | 23 | 19.705 | 31.904 | 13.821 | 1.00 | 22.06 | O |
| ATOM | 372 | ND2 | ASN | A | 23 | 21.511 | 31.174 | 14.977 | 1.00 | 18.52 | N |
| ATOM | 375 | C | ASN | A | 23 | 22.449 | 35.415 | 13.208 | 1.00 | 12.31 | C |
| ATOM | 376 | O | ASN | A | 23 | 22.904 | 36.007 | 14.185 | 1.00 | 12.34 | O |
| ATOM | 377 | N | TRP | A | 24 | 22.216 | 36.016 | 12.048 | 1.00 | 12.92 | N |
| ATOM | 379 | CA | TRP | A | 24 | 22.554 | 37.408 | 11.814 | 1.00 | 12.37 | C |
| ATOM | 381 | CB | TRP | A | 24 | 22.990 | 37.612 | 10.367 | 1.00 | 13.22 | C |
| ATOM | 384 | CG | TRP | A | 24 | 24.130 | 36.740 | 9.944 | 1.00 | 12.12 | C |
| ATOM | 385 | CD1 | TRP | A | 24 | 24.039 | 35.556 | 9.279 | 1.00 | 11.86 | C |
| ATOM | 387 | NE1 | TRP | A | 24 | 25.292 | 35.046 | 9.042 | 1.00 | 13.92 | N |
| ATOM | 389 | CE2 | TRP | A | 24 | 26.230 | 35.904 | 9.547 | 1.00 | 11.19 | C |
| ATOM | 390 | CD2 | TRP | A | 24 | 25.536 | 36.989 | 10.123 | 1.00 | 10.96 | C |
| ATOM | 391 | CE3 | TRP | A | 24 | 26.276 | 38.003 | 10.726 | 1.00 | 11.62 | C |
| ATOM | 393 | CZ3 | TRP | A | 24 | 27.660 | 37.925 | 10.707 | 1.00 | 13.20 | C |
| ATOM | 395 | CH2 | TRP | A | 24 | 28.317 | 36.833 | 10.136 | 1.00 | 11.66 | C |
| ATOM | 397 | CZ2 | TRP | A | 24 | 27.619 | 35.814 | 9.545 | 1.00 | 10.81 | C |
| ATOM | 399 | C | TRP | A | 24 | 21.343 | 38.268 | 12.120 | 1.00 | 12.73 | C |
| ATOM | 400 | O | TRP | A | 24 | 20.282 | 38.076 | 11.532 | 1.00 | 13.03 | O |
| ATOM | 401 | N | GLY | A | 25 | 21.488 | 39.222 | 13.029 | 1.00 | 12.00 | N |
| ATOM | 403 | CA | GLY | A | 25 | 20.370 | 40.074 | 13.398 | 1.00 | 11.21 | C |
| ATOM | 406 | C | GLY | A | 25 | 20.495 | 41.423 | 12.706 | 1.00 | 11.71 | C |
| ATOM | 407 | O | GLY | A | 25 | 21.592 | 41.969 | 12.603 | 1.00 | 11.26 | O |
| ATOM | 408 | N | ARG | A | 26 | 19.375 | 41.957 | 12.233 | 1.00 | 11.79 | N |
| ATOM | 410 | CA | ARG | A | 26 | 19.388 | 43.192 | 11.486 | 1.00 | 12.49 | C |
| ATOM | 412 | CB | ARG | A | 26 | 18.460 | 43.083 | 10.267 | 1.00 | 12.94 | C |
| ATOM | 415 | CG | ARG | A | 26 | 18.999 | 42.137 | 9.202 | 1.00 | 16.01 | C |
| ATOM | 418 | CD | ARG | A | 26 | 18.019 | 41.888 | 8.062 | 1.00 | 20.32 | C |
| ATOM | 421 | NE | ARG | A | 26 | 18.565 | 41.043 | 6.998 | 1.00 | 24.78 | N |
| ATOM | 423 | CZ | ARG | A | 26 | 19.426 | 41.460 | 6.071 | 1.00 | 25.04 | C |
| ATOM | 424 | NH1 | ARG | A | 26 | 19.860 | 40.607 | 5.149 | 1.00 | 29.16 | N |
| ATOM | 427 | NH2 | ARG | A | 26 | 19.863 | 42.715 | 6.057 | 1.00 | 19.47 | N |
| ATOM | 430 | C | ARG | A | 26 | 19.010 | 44.365 | 12.357 | 1.00 | 12.60 | C |
| ATOM | 431 | O | ARG | A | 26 | 18.369 | 44.206 | 13.398 | 1.00 | 12.88 | O |
| ATOM | 432 | N | GLY | A | 27 | 19.411 | 45.549 | 11.917 | 1.00 | 12.77 | N |
| ATOM | 434 | CA | GLY | A | 27 | 19.173 | 46.761 | 12.675 | 1.00 | 12.32 | C |

APPENDIX C: CRYSTAL COORDINATES OF FVE PROTEIN

| ATOM | 437 | C | GLY | A | 27 | 18.090 | 47.628 | 12.071 | 1.00 | 13.21 | C |
|---|---|---|---|---|---|---|---|---|---|---|---|
| ATOM | 438 | O | GLY | A | 27 | 17.167 | 47.128 | 11.435 | 1.00 | 11.98 | O |
| ATOM | 439 | N | THR | A | 28 | 18.203 | 48.928 | 12.316 | 1.00 | 14.26 | N |
| ATOM | 441 | CA | THR | A | 28 | 17.261 | 49.925 | 11.819 | 1.00 | 14.60 | C |
| ATOM | 443 | CB | THR | A | 28 | 16.523 | 50.576 | 13.006 | 1.00 | 13.94 | C |
| ATOM | 445 | OG1 | THR | A | 28 | 15.801 | 49.590 | 13.761 | 1.00 | 12.38 | O |
| ATOM | 447 | CG2 | THR | A | 28 | 15.460 | 51.569 | 12.517 | 1.00 | 14.06 | C |
| ATOM | 451 | C | THR | A | 28 | 18.039 | 51.002 | 11.041 | 1.00 | 15.60 | C |
| ATOM | 452 | O | THR | A | 28 | 18.823 | 51.756 | 11.636 | 1.00 | 15.37 | O |
| ATOM | 453 | N | PRO | A | 29 | 17.874 | 51.082 | 9.718 | 1.00 | 17.62 | N |
| ATOM | 454 | CA | PRO | A | 29 | 17.025 | 50.182 | 8.928 | 1.00 | 17.21 | C |
| ATOM | 456 | CB | PRO | A | 29 | 16.956 | 50.887 | 7.570 | 1.00 | 17.70 | C |
| ATOM | 459 | CG | PRO | A | 29 | 18.211 | 51.657 | 7.483 | 1.00 | 17.48 | C |
| ATOM | 462 | CD | PRO | A | 29 | 18.513 | 52.109 | 8.878 | 1.00 | 17.56 | C |
| ATOM | 465 | C | PRO | A | 29 | 17.586 | 48.772 | 8.752 | 1.00 | 17.76 | C |
| ATOM | 466 | O | PRO | A | 29 | 18.751 | 48.525 | 9.061 | 1.00 | 16.07 | O |
| ATOM | 467 | N | SER | A | 30 | 16.742 | 47.873 | 8.242 | 1.00 | 18.81 | N |
| ATOM | 469 | CA | SER | A | 30 | 17.050 | 46.450 | 8.184 | 1.00 | 18.37 | C |
| ATOM | 471 | CB | SER | A | 30 | 15.805 | 45.644 | 7.833 | 1.00 | 18.99 | C |
| ATOM | 474 | OG | SER | A | 30 | 15.343 | 45.991 | 6.543 | 1.00 | 20.21 | O |
| ATOM | 476 | C | SER | A | 30 | 18.169 | 46.068 | 7.246 | 1.00 | 17.73 | C |
| ATOM | 477 | O | SER | A | 30 | 18.593 | 44.925 | 7.249 | 1.00 | 17.30 | O |
| ATOM | 478 | N | SER | A | 31 | 18.638 | 47.019 | 6.442 | 1.00 | 17.71 | N |
| ATOM | 480 | CA | SER | A | 31 | 19.762 | 46.788 | 5.545 | 1.00 | 16.65 | C |
| ATOM | 482 | CB | SER | A | 31 | 19.806 | 47.894 | 4.489 | 1.00 | 16.79 | C |
| ATOM | 485 | OG | SER | A | 31 | 19.921 | 49.171 | 5.094 | 1.00 | 17.30 | O |
| ATOM | 487 | C | SER | A | 31 | 21.098 | 46.709 | 6.297 | 1.00 | 16.11 | C |
| ATOM | 488 | O | SER | A | 31 | 22.127 | 46.365 | 5.704 | 1.00 | 15.78 | O |
| ATOM | 489 | N | TYR | A | 32 | 21.086 | 47.032 | 7.597 | 1.00 | 14.64 | N |
| ATOM | 491 | CA | TYR | A | 32 | 22.271 | 46.896 | 8.439 | 1.00 | 14.65 | C |
| ATOM | 493 | CB | TYR | A | 32 | 22.375 | 48.046 | 9.422 | 1.00 | 14.98 | C |
| ATOM | 496 | CG | TYR | A | 32 | 22.739 | 49.334 | 8.714 | 1.00 | 18.51 | C |
| ATOM | 497 | CD1 | TYR | A | 32 | 24.066 | 49.674 | 8.496 | 1.00 | 21.23 | C |
| ATOM | 499 | CE1 | TYR | A | 32 | 24.407 | 50.838 | 7.829 | 1.00 | 23.56 | C |
| ATOM | 501 | CZ | TYR | A | 32 | 23.413 | 51.669 | 7.369 | 1.00 | 24.54 | C |
| ATOM | 502 | OH | TYR | A | 32 | 23.739 | 52.830 | 6.706 | 1.00 | 26.67 | O |
| ATOM | 504 | CE2 | TYR | A | 32 | 22.087 | 51.341 | 7.555 | 1.00 | 23.37 | C |
| ATOM | 506 | CD2 | TYR | A | 32 | 21.758 | 50.174 | 8.225 | 1.00 | 21.68 | C |
| ATOM | 508 | C | TYR | A | 32 | 22.237 | 45.591 | 9.229 | 1.00 | 13.62 | C |
| ATOM | 509 | O | TYR | A | 32 | 21.188 | 45.198 | 9.725 | 1.00 | 13.16 | O |
| ATOM | 510 | N | ILE | A | 33 | 23.380 | 44.911 | 9.286 | 1.00 | 13.61 | N |
| ATOM | 512 | CA | ILE | A | 33 | 23.586 | 43.751 | 10.157 | 1.00 | 12.63 | C |
| ATOM | 514 | CB | ILE | A | 33 | 24.578 | 42.754 | 9.534 | 1.00 | 12.46 | C |
| ATOM | 516 | CG1 | ILE | A | 33 | 24.075 | 42.259 | 8.180 | 1.00 | 15.30 | C |
| ATOM | 519 | CD1 | ILE | A | 33 | 22.722 | 41.668 | 8.218 | 1.00 | 17.61 | C |
| ATOM | 523 | CG2 | ILE | A | 33 | 24.827 | 41.551 | 10.448 | 1.00 | 12.99 | C |
| ATOM | 527 | C | ILE | A | 33 | 24.190 | 44.290 | 11.450 | 1.00 | 12.11 | C |
| ATOM | 528 | O | ILE | A | 33 | 25.296 | 44.828 | 11.452 | 1.00 | 11.53 | O |
| ATOM | 529 | N | ASP | A | 34 | 23.471 | 44.131 | 12.551 | 1.00 | 12.39 | N |
| ATOM | 531 | CA | ASP | A | 34 | 23.884 | 44.688 | 13.831 | 1.00 | 11.42 | C |
| ATOM | 533 | CB | ASP | A | 34 | 22.658 | 45.171 | 14.607 | 1.00 | 11.00 | C |
| ATOM | 536 | CG | ASP | A | 34 | 22.217 | 46.584 | 14.234 | 1.00 | 12.48 | C |
| ATOM | 537 | OD1 | ASP | A | 34 | 22.658 | 47.096 | 13.183 | 1.00 | 13.04 | O |
| ATOM | 538 | OD2 | ASP | A | 34 | 21.399 | 47.223 | 14.951 | 1.00 | 13.34 | O |
| ATOM | 539 | C | ASP | A | 34 | 24.580 | 43.675 | 14.723 | 1.00 | 10.32 | C |
| ATOM | 540 | O | ASP | A | 34 | 25.317 | 44.056 | 15.621 | 1.00 | 10.05 | O |
| ATOM | 541 | N | ASN | A | 35 | 24.321 | 42.394 | 14.504 | 1.00 | 10.16 | N |
| ATOM | 543 | CA | ASN | A | 35 | 24.851 | 41.393 | 15.433 | 1.00 | 9.67 | C |
| ATOM | 545 | CB | ASN | A | 35 | 24.030 | 41.450 | 16.727 | 1.00 | 10.07 | C |
| ATOM | 548 | CG | ASN | A | 35 | 22.554 | 41.273 | 16.471 | 1.00 | 10.85 | C |
| ATOM | 549 | OD1 | ASN | A | 35 | 22.107 | 40.167 | 16.176 | 1.00 | 12.45 | O |
| ATOM | 550 | ND2 | ASN | A | 35 | 21.783 | 42.374 | 16.550 | 1.00 | 9.57 | N |
| ATOM | 553 | C | ASN | A | 35 | 24.840 | 39.977 | 14.875 | 1.00 | 9.80 | C |
| ATOM | 554 | O | ASN | A | 35 | 24.247 | 39.693 | 13.824 | 1.00 | 10.06 | O |
| ATOM | 555 | N | LEU | A | 36 | 25.504 | 39.087 | 15.604 | 1.00 | 9.45 | N |
| ATOM | 557 | CA | LEU | A | 36 | 25.636 | 37.689 | 15.262 | 1.00 | 9.51 | C |
| ATOM | 559 | CB | LEU | A | 36 | 27.042 | 37.442 | 14.753 | 1.00 | 9.66 | C |
| ATOM | 562 | CG | LEU | A | 36 | 27.470 | 36.000 | 14.536 | 1.00 | 9.35 | C |
| ATOM | 564 | CD1 | LEU | A | 36 | 26.605 | 35.300 | 13.482 | 1.00 | 10.39 | C |
| ATOM | 568 | CD2 | LEU | A | 36 | 28.951 | 35.986 | 14.161 | 1.00 | 10.50 | C |
| ATOM | 572 | C | LEU | A | 36 | 25.419 | 36.881 | 16.535 | 1.00 | 10.20 | C |
| ATOM | 573 | O | LEU | A | 36 | 26.105 | 37.111 | 17.539 | 1.00 | 10.03 | O |
| ATOM | 574 | N | THR | A | 37 | 24.482 | 35.941 | 16.502 | 1.00 | 10.24 | N |
| ATOM | 576 | CA | THR | A | 37 | 24.190 | 35.099 | 17.661 | 1.00 | 10.84 | C |
| ATOM | 578 | CB | THR | A | 37 | 22.716 | 35.234 | 18.063 | 1.00 | 11.04 | C |
| ATOM | 580 | OG1 | THR | A | 37 | 22.440 | 36.591 | 18.421 | 1.00 | 12.32 | O |
| ATOM | 582 | CG2 | THR | A | 37 | 22.397 | 34.382 | 19.308 | 1.00 | 11.78 | C |
| ATOM | 586 | C | THR | A | 37 | 24.484 | 33.647 | 17.365 | 1.00 | 10.36 | C |

-continued

| APPENDIX C: CRYSTAL COORDINATES OF FVE PROTEIN | | | | | | | | | |
|---|---|---|---|---|---|---|---|---|---|
| ATOM | 587 | O | THR | A | 37 | 24.103 | 33.128 | 16.314 | 1.00 | 11.69 O |
| ATOM | 588 | N | PHE | A | 38 | 25.183 | 33.002 | 18.288 | 1.00 | 10.33 N |
| ATOM | 590 | CA | PHE | A | 38 | 25.435 | 31.568 | 18.220 | 1.00 | 10.67 C |
| ATOM | 592 | CB | PHE | A | 38 | 26.892 | 31.285 | 18.520 | 1.00 | 10.97 C |
| ATOM | 595 | CG | PHE | A | 38 | 27.844 | 31.792 | 17.480 | 1.00 | 9.37 C |
| ATOM | 596 | CD1 | PHE | A | 38 | 28.952 | 32.543 | 17.835 | 1.00 | 10.78 C |
| ATOM | 598 | CE1 | PHE | A | 38 | 29.844 | 32.982 | 16.879 | 1.00 | 10.42 C |
| ATOM | 600 | CZ | PHE | A | 38 | 29.659 | 32.667 | 15.590 | 1.00 | 12.03 C |
| ATOM | 602 | CE2 | PHE | A | 38 | 28.559 | 31.898 | 15.215 | 1.00 | 10.68 C |
| ATOM | 604 | CD2 | PHE | A | 38 | 27.660 | 31.476 | 16.146 | 1.00 | 10.68 C |
| ATOM | 606 | C | PHE | A | 38 | 24.595 | 30.912 | 19.303 | 1.00 | 11.13 C |
| ATOM | 607 | O | PHE | A | 38 | 24.678 | 31.328 | 20.444 | 1.00 | 11.20 O |
| ATOM | 608 | N | PRO | A | 39 | 23.777 | 29.911 | 18.995 | 1.00 | 11.41 N |
| ATOM | 609 | CA | PRO | A | 39 | 22.920 | 29.317 | 20.033 | 1.00 | 11.03 C |
| ATOM | 611 | CB | PRO | A | 39 | 22.047 | 28.347 | 19.251 | 1.00 | 11.55 C |
| ATOM | 614 | CG | PRO | A | 39 | 22.138 | 28.792 | 17.827 | 1.00 | 11.41 C |
| ATOM | 617 | CD | PRO | A | 39 | 23.501 | 29.337 | 17.671 | 1.00 | 10.69 C |
| ATOM | 620 | C | PRO | A | 39 | 23.593 | 28.585 | 21.186 | 1.00 | 10.78 C |
| ATOM | 621 | O | PRO | A | 39 | 23.007 | 28.537 | 22.272 | 1.00 | 11.13 O |
| ATOM | 622 | N | LYS | A | 40 | 24.756 | 27.986 | 20.961 | 1.00 | 10.03 N |
| ATOM | 624 | CA | LYS | A | 40 | 25.420 | 27.246 | 22.033 | 1.00 | 11.35 C |
| ATOM | 626 | CB | LYS | A | 40 | 24.930 | 25.808 | 22.100 | 1.00 | 11.81 C |
| ATOM | 629 | CG | LYS | A | 40 | 25.329 | 25.153 | 23.413 | 1.00 | 15.47 C |
| ATOM | 632 | CD | LYS | A | 40 | 25.020 | 23.673 | 23.445 | 1.00 | 21.03 C |
| ATOM | 635 | CE | LYS | A | 40 | 25.654 | 23.024 | 24.665 | 1.00 | 26.85 C |
| ATOM | 638 | NZ | LYS | A | 40 | 24.928 | 23.362 | 25.917 | 1.00 | 35.22 N |
| ATOM | 642 | C | LYS | A | 40 | 26.939 | 27.297 | 21.877 | 1.00 | 11.13 C |
| ATOM | 643 | O | LYS | A | 40 | 27.540 | 26.454 | 21.211 | 1.00 | 11.86 O |
| ATOM | 644 | N | VAL | A | 41 | 27.549 | 28.310 | 22.479 | 1.00 | 10.84 N |
| ATOM | 646 | CA | VAL | A | 41 | 28.995 | 28.462 | 22.410 | 1.00 | 10.68 C |
| ATOM | 648 | CB | VAL | A | 41 | 29.449 | 29.903 | 22.641 | 1.00 | 10.07 C |
| ATOM | 650 | CG1 | VAL | A | 41 | 28.907 | 30.826 | 21.533 | 1.00 | 10.33 C |
| ATOM | 654 | CG2 | VAL | A | 41 | 29.040 | 30.419 | 24.007 | 1.00 | 10.45 C |
| ATOM | 658 | C | VAL | A | 41 | 29.690 | 27.564 | 23.425 | 1.00 | 11.85 C |
| ATOM | 659 | O | VAL | A | 41 | 29.093 | 27.111 | 24.425 | 1.00 | 12.38 O |
| ATOM | 660 | N | LEU | A | 42 | 30.957 | 27.305 | 23.165 | 1.00 | 13.03 N |
| ATOM | 662 | CA | LEU | A | 42 | 31.803 | 26.664 | 24.159 | 1.00 | 15.12 C |
| ATOM | 664 | CB | LEU | A | 42 | 33.126 | 26.219 | 23.556 | 1.00 | 14.97 C |
| ATOM | 667 | CG | LEU | A | 42 | 32.873 | 25.139 | 22.491 | 1.00 | 15.42 C |
| ATOM | 669 | CD1 | LEU | A | 42 | 34.128 | 24.763 | 21.705 | 1.00 | 16.85 C |
| ATOM | 673 | CD2 | LEU | A | 42 | 32.303 | 23.917 | 23.125 | 1.00 | 17.26 C |
| ATOM | 677 | C | LEU | A | 42 | 32.012 | 27.709 | 25.245 | 1.00 | 17.87 C |
| ATOM | 678 | O | LEU | A | 42 | 32.083 | 28.897 | 24.974 | 1.00 | 17.12 O |
| ATOM | 679 | N | THR | A | 43 | 32.171 | 27.279 | 26.476 | 1.00 | 21.75 N |
| ATOM | 681 | CA | THR | A | 43 | 32.188 | 28.272 | 27.549 | 1.00 | 24.61 C |
| ATOM | 683 | CB | THR | A | 43 | 30.761 | 28.365 | 28.043 | 1.00 | 24.82 C |
| ATOM | 685 | OG1 | THR | A | 43 | 29.883 | 29.292 | 27.424 | 1.00 | 27.15 O |
| ATOM | 687 | CG2 | THR | A | 43 | 30.199 | 27.229 | 28.835 | 1.00 | 24.68 C |
| ATOM | 691 | C | THR | A | 43 | 33.197 | 27.863 | 28.620 | 1.00 | 26.54 C |
| ATOM | 692 | O | THR | A | 43 | 33.185 | 28.377 | 29.738 | 1.00 | 27.45 O |
| ATOM | 693 | N | ASP | A | 44 | 34.103 | 26.963 | 28.249 | 1.00 | 28.93 N |
| ATOM | 695 | CA | ASP | A | 44 | 35.103 | 26.469 | 29.179 | 1.00 | 29.14 C |
| ATOM | 697 | CB | ASP | A | 44 | 35.855 | 25.271 | 28.602 | 1.00 | 28.74 C |
| ATOM | 700 | CG | ASP | A | 44 | 36.401 | 25.521 | 27.217 | 1.00 | 28.34 C |
| ATOM | 701 | OD1 | ASP | A | 44 | 37.572 | 25.172 | 26.990 | 1.00 | 26.28 O |
| ATOM | 702 | OD2 | ASP | A | 44 | 35.734 | 26.028 | 26.286 | 1.00 | 24.46 O |
| ATOM | 703 | C | ASP | A | 44 | 36.063 | 27.575 | 29.547 | 1.00 | 30.53 C |
| ATOM | 704 | O | ASP | A | 44 | 36.513 | 27.663 | 30.699 | 1.00 | 30.19 O |
| ATOM | 705 | N | LYS | A | 45 | 36.372 | 28.422 | 28.568 | 1.00 | 31.95 N |
| ATOM | 707 | CA | LYS | A | 45 | 37.275 | 29.547 | 28.790 | 1.00 | 31.72 C |
| ATOM | 709 | CB | LYS | A | 45 | 38.701 | 29.244 | 28.320 | 1.00 | 31.90 C |
| ATOM | 712 | CG | LYS | A | 45 | 38.971 | 29.445 | 26.860 | 1.00 | 32.28 C |
| ATOM | 715 | CD | LYS | A | 45 | 39.201 | 28.149 | 26.171 | 1.00 | 33.73 C |
| ATOM | 718 | CE | LYS | A | 45 | 40.448 | 27.462 | 26.609 | 1.00 | 33.84 C |
| ATOM | 721 | NZ | LYS | A | 45 | 40.509 | 26.190 | 25.855 | 1.00 | 36.70 N |
| ATOM | 725 | C | LYS | A | 45 | 36.715 | 30.803 | 28.140 | 1.00 | 31.38 C |
| ATOM | 726 | O | LYS | A | 45 | 35.679 | 30.756 | 27.482 | 1.00 | 31.01 O |
| ATOM | 727 | N | LYS | A | 46 | 37.399 | 31.925 | 28.352 | 1.00 | 31.71 N |
| ATOM | 729 | CA | LYS | A | 46 | 36.910 | 33.224 | 27.903 | 1.00 | 29.44 C |
| ATOM | 731 | CB | LYS | A | 46 | 37.338 | 34.330 | 28.875 | 1.00 | 30.08 C |
| ATOM | 734 | CG | LYS | A | 46 | 38.819 | 34.397 | 29.144 | 1.00 | 32.08 C |
| ATOM | 737 | CD | LYS | A | 46 | 39.083 | 34.836 | 30.591 | 1.00 | 35.03 C |
| ATOM | 740 | CE | LYS | A | 46 | 40.571 | 34.941 | 30.910 | 1.00 | 36.79 C |
| ATOM | 743 | NZ | LYS | A | 46 | 40.827 | 34.716 | 32.367 | 1.00 | 37.85 N |
| ATOM | 747 | C | LYS | A | 46 | 37.335 | 33.551 | 26.488 | 1.00 | 26.70 C |
| ATOM | 748 | O | LYS | A | 46 | 38.347 | 34.201 | 26.240 | 1.00 | 26.57 O |
| ATOM | 749 | N | TYR | A | 47 | 36.542 | 33.083 | 25.544 | 1.00 | 24.74 N |
| ATOM | 751 | CA | TYR | A | 47 | 36.802 | 33.387 | 24.144 | 1.00 | 20.86 C |

-continued

| APPENDIX C: CRYSTAL COORDINATES OF FVE PROTEIN | | | | | | | | | | |
|---|---|---|---|---|---|---|---|---|---|---|
| ATOM | 753 | CB | TYR | A | 47 | 35.966 | 32.476 | 23.252 | 1.00 | 19.97 C |
| ATOM | 756 | CG | TYR | A | 47 | 36.251 | 31.026 | 23.482 | 1.00 | 17.82 C |
| ATOM | 757 | CD1 | TYR | A | 47 | 35.393 | 30.240 | 24.244 | 1.00 | 17.29 C |
| ATOM | 759 | CE1 | TYR | A | 47 | 35.654 | 28.910 | 24.468 | 1.00 | 17.53 C |
| ATOM | 761 | CZ | TYR | A | 47 | 36.797 | 28.346 | 23.956 | 1.00 | 16.67 C |
| ATOM | 762 | OH | TYR | A | 47 | 37.076 | 27.005 | 24.174 | 1.00 | 20.90 O |
| ATOM | 764 | CE2 | TYR | A | 47 | 37.670 | 29.109 | 23.205 | 1.00 | 17.26 C |
| ATOM | 766 | CD2 | TYR | A | 47 | 37.395 | 30.446 | 22.984 | 1.00 | 16.93 C |
| ATOM | 768 | C | TYR | A | 47 | 36.482 | 34.836 | 23.806 | 1.00 | 18.65 C |
| ATOM | 769 | O | TYR | A | 47 | 35.575 | 35.432 | 24.361 | 1.00 | 19.20 O |
| ATOM | 770 | N | SER | A | 48 | 37.229 | 35.388 | 22.863 | 1.00 | 16.14 N |
| ATOM | 772 | CA | SER | A | 48 | 36.957 | 36.716 | 22.329 | 1.00 | 14.79 C |
| ATOM | 774 | CB | SER | A | 48 | 38.168 | 37.624 | 22.472 | 1.00 | 15.65 C |
| ATOM | 777 | OG | SER | A | 48 | 38.434 | 37.890 | 23.830 | 1.00 | 17.92 O |
| ATOM | 779 | C | SER | A | 48 | 36.638 | 36.586 | 20.852 | 1.00 | 12.87 C |
| ATOM | 780 | O | SER | A | 48 | 36.836 | 35.525 | 20.255 | 1.00 | 11.78 O |
| ATOM | 781 | N | TYR | A | 49 | 36.173 | 37.675 | 20.249 | 1.00 | 10.68 N |
| ATOM | 783 | CA | TYR | A | 49 | 35.870 | 37.671 | 18.822 | 1.00 | 11.65 C |
| ATOM | 785 | CB | TYR | A | 49 | 34.362 | 37.641 | 18.580 | 1.00 | 11.29 C |
| ATOM | 788 | CG | TYR | A | 49 | 33.668 | 36.471 | 19.256 | 1.00 | 10.85 C |
| ATOM | 789 | CD1 | TYR | A | 49 | 33.098 | 36.593 | 20.510 | 1.00 | 10.38 C |
| ATOM | 791 | CE1 | TYR | A | 49 | 32.475 | 35.517 | 21.131 | 1.00 | 10.61 C |
| ATOM | 793 | CZ | TYR | A | 49 | 32.404 | 34.310 | 20.480 | 1.00 | 12.03 C |
| ATOM | 794 | OH | TYR | A | 49 | 31.781 | 33.238 | 21.072 | 1.00 | 13.62 O |
| ATOM | 796 | CE2 | TYR | A | 49 | 32.980 | 34.163 | 19.239 | 1.00 | 10.96 C |
| ATOM | 798 | CD2 | TYR | A | 49 | 33.598 | 35.240 | 18.631 | 1.00 | 11.17 C |
| ATOM | 800 | C | TYR | A | 49 | 36.446 | 38.895 | 18.119 | 1.00 | 11.93 C |
| ATOM | 801 | O | TYR | A | 49 | 36.259 | 40.028 | 18.564 | 1.00 | 12.07 O |
| ATOM | 802 | N | ARG | A | 50 | 37.122 | 38.649 | 17.004 | 1.00 | 13.41 N |
| ATOM | 804 | CA | ARG | A | 50 | 37.603 | 39.714 | 16.134 | 1.00 | 13.03 C |
| ATOM | 806 | CB | ARG | A | 50 | 38.983 | 39.376 | 15.561 | 1.00 | 13.84 C |
| ATOM | 809 | CG | ARG | A | 50 | 39.542 | 40.479 | 14.661 | 1.00 | 15.89 C |
| ATOM | 812 | CD | ARG | A | 50 | 40.799 | 40.094 | 13.892 | 1.00 | 19.76 C |
| ATOM | 815 | NE | ARG | A | 50 | 41.825 | 39.658 | 14.809 | 1.00 | 22.85 N |
| ATOM | 817 | CZ | ARG | A | 50 | 42.474 | 40.468 | 15.643 | 1.00 | 29.33 C |
| ATOM | 818 | NH1 | ARG | A | 50 | 43.391 | 39.966 | 16.456 | 1.00 | 35.65 N |
| ATOM | 821 | NH2 | ARG | A | 50 | 42.224 | 41.779 | 15.666 | 1.00 | 30.97 N |
| ATOM | 824 | C | ARG | A | 50 | 36.632 | 39.865 | 14.982 | 1.00 | 12.87 C |
| ATOM | 825 | O | ARG | A | 50 | 36.175 | 38.857 | 14.420 | 1.00 | 12.78 O |
| ATOM | 826 | N | VAL | A | 51 | 36.338 | 41.108 | 14.605 | 1.00 | 12.80 N |
| ATOM | 828 | CA | VAL | A | 51 | 35.419 | 41.393 | 13.506 | 1.00 | 13.04 C |
| ATOM | 830 | CB | VAL | A | 51 | 34.206 | 42.194 | 13.983 | 1.00 | 12.62 C |
| ATOM | 832 | CG1 | VAL | A | 51 | 33.343 | 42.630 | 12.809 | 1.00 | 12.65 C |
| ATOM | 836 | CG2 | VAL | A | 51 | 33.389 | 41.356 | 14.936 | 1.00 | 12.04 C |
| ATOM | 840 | C | VAL | A | 51 | 36.167 | 42.170 | 12.438 | 1.00 | 13.60 C |
| ATOM | 841 | O | VAL | A | 51 | 36.851 | 43.153 | 12.738 | 1.00 | 13.27 O |
| ATOM | 842 | N | VAL | A | 52 | 36.074 | 41.685 | 11.206 | 1.00 | 14.90 N |
| ATOM | 844 | CA | VAL | A | 52 | 36.768 | 42.287 | 10.070 | 1.00 | 14.99 C |
| ATOM | 846 | CB | VAL | A | 52 | 37.834 | 41.307 | 9.534 | 1.00 | 15.36 C |
| ATOM | 848 | CG1 | VAL | A | 52 | 38.577 | 41.908 | 8.360 | 1.00 | 15.94 C |
| ATOM | 852 | CG2 | VAL | A | 52 | 38.819 | 40.945 | 10.636 | 1.00 | 15.62 C |
| ATOM | 856 | C | VAL | A | 52 | 35.733 | 42.590 | 8.981 | 1.00 | 15.27 C |
| ATOM | 857 | O | VAL | A | 52 | 35.001 | 41.691 | 8.577 | 1.00 | 14.98 O |
| ATOM | 858 | N | VAL | A | 53 | 35.680 | 43.840 | 8.506 | 1.00 | 15.37 N |
| ATOM | 860 | CA | VAL | A | 53 | 34.663 | 44.255 | 7.542 | 1.00 | 16.36 C |
| ATOM | 862 | CB | VAL | A | 53 | 33.805 | 45.395 | 8.090 | 1.00 | 16.50 C |
| ATOM | 864 | CG1 | VAL | A | 53 | 32.827 | 45.905 | 7.043 | 1.00 | 16.92 C |
| ATOM | 868 | CG2 | VAL | A | 53 | 33.037 | 44.923 | 9.314 | 1.00 | 16.68 C |
| ATOM | 872 | C | VAL | A | 53 | 35.366 | 44.712 | 6.284 | 1.00 | 17.90 C |
| ATOM | 873 | O | VAL | A | 53 | 36.121 | 45.670 | 6.321 | 1.00 | 17.86 O |
| ATOM | 874 | N | ASN | A | 54 | 35.099 | 44.024 | 5.182 | 1.00 | 19.87 N |
| ATOM | 876 | CA | ASN | A | 54 | 35.764 | 44.316 | 3.916 | 1.00 | 20.93 C |
| ATOM | 878 | CB | ASN | A | 54 | 35.225 | 45.606 | 3.324 | 1.00 | 20.73 C |
| ATOM | 881 | CG | ASN | A | 54 | 33.946 | 45.408 | 2.504 | 1.00 | 20.64 C |
| ATOM | 882 | OD1 | ASN | A | 54 | 33.395 | 46.382 | 1.976 | 1.00 | 22.37 O |
| ATOM | 883 | ND2 | ASN | A | 54 | 33.474 | 44.168 | 2.388 | 1.00 | 18.46 N |
| ATOM | 886 | C | ASN | A | 54 | 37.281 | 44.421 | 4.100 | 1.00 | 22.08 C |
| ATOM | 887 | O | ASN | A | 54 | 37.924 | 45.291 | 3.513 | 1.00 | 22.88 O |
| ATOM | 888 | N | GLY | A | 55 | 37.851 | 43.545 | 4.924 | 1.00 | 23.68 N |
| ATOM | 890 | CA | GLY | A | 55 | 39.288 | 43.532 | 5.134 | 1.00 | 22.59 C |
| ATOM | 893 | C | GLY | A | 55 | 39.767 | 44.478 | 6.212 | 1.00 | 22.03 C |
| ATOM | 894 | O | GLY | A | 55 | 40.936 | 44.441 | 6.586 | 1.00 | 22.03 O |
| ATOM | 895 | N | SER | A | 56 | 38.883 | 45.332 | 6.712 | 1.00 | 21.22 N |
| ATOM | 897 | CA | SER | A | 56 | 39.268 | 46.257 | 7.764 | 1.00 | 20.83 C |
| ATOM | 899 | CB | SER | A | 56 | 38.434 | 47.521 | 7.666 | 1.00 | 21.16 C |
| ATOM | 902 | OG | SER | A | 56 | 38.925 | 48.496 | 8.556 | 1.00 | 24.04 O |
| ATOM | 904 | C | SER | A | 56 | 39.068 | 45.628 | 9.138 | 1.00 | 19.96 C |
| ATOM | 905 | O | SER | A | 56 | 37.961 | 45.229 | 9.477 | 1.00 | 18.84 O |

-continued

| APPENDIX C: CRYSTAL COORDINATES OF FVE PROTEIN | | | | | | | | | |
|---|---|---|---|---|---|---|---|---|---|
| ATOM | 906 | N | ASP | A | 57 | 40.129 | 45.590 | 9.937 | 1.00 19.21 N |
| ATOM | 908 | CA | ASP | A | 57 | 40.100 | 44.953 | 11.252 | 1.00 19.05 C |
| ATOM | 910 | CB | ASP | A | 57 | 41.547 | 44.599 | 11.610 | 1.00 19.38 C |
| ATOM | 913 | CG | ASP | A | 57 | 41.704 | 43.926 | 12.947 | 1.00 20.67 C |
| ATOM | 914 | OD1 | ASP | A | 57 | 40.717 | 43.476 | 13.545 | 1.00 19.91 O |
| ATOM | 915 | OD2 | ASP | A | 57 | 42.833 | 43.786 | 13.472 | 1.00 25.20 O |
| ATOM | 916 | C | ASP | A | 57 | 39.483 | 45.908 | 12.263 | 1.00 18.66 C |
| ATOM | 917 | O | ASP | A | 57 | 40.031 | 46.992 | 12.524 | 1.00 17.62 O |
| ATOM | 918 | N | LEU | A | 58 | 38.337 | 45.517 | 12.823 | 1.00 18.14 N |
| ATOM | 920 | CA | LEU | A | 58 | 37.660 | 46.339 | 13.821 | 1.00 17.44 C |
| ATOM | 922 | CB | LEU | A | 58 | 36.140 | 46.283 | 13.638 | 1.00 17.54 C |
| ATOM | 925 | CG | LEU | A | 58 | 35.587 | 46.711 | 12.271 | 1.00 18.21 C |
| ATOM | 927 | CD1 | LEU | A | 58 | 34.067 | 46.915 | 12.314 | 1.00 18.79 C |
| ATOM | 931 | CD2 | LEU | A | 58 | 36.271 | 47.970 | 11.777 | 1.00 20.33 C |
| ATOM | 935 | C | LEU | A | 58 | 38.058 | 45.955 | 15.248 | 1.00 17.13 C |
| ATOM | 936 | O | LEU | A | 58 | 37.539 | 46.510 | 16.221 | 1.00 17.54 O |
| ATOM | 937 | N | GLY | A | 59 | 38.978 | 45.010 | 15.381 | 1.00 16.87 N |
| ATOM | 939 | CA | GLY | A | 59 | 39.503 | 44.667 | 16.686 | 1.00 16.43 C |
| ATOM | 942 | C | GLY | A | 59 | 38.781 | 43.524 | 17.361 | 1.00 16.14 C |
| ATOM | 943 | O | GLY | A | 59 | 37.953 | 42.845 | 16.768 | 1.00 13.91 O |
| ATOM | 944 | N | VAL | A | 60 | 39.070 | 43.377 | 18.641 | 1.00 16.63 N |
| ATOM | 946 | CA | VAL | A | 60 | 38.664 | 42.216 | 19.409 | 1.00 16.80 C |
| ATOM | 948 | CB | VAL | A | 60 | 39.909 | 41.452 | 19.859 | 1.00 17.07 C |
| ATOM | 950 | CG1 | VAL | A | 60 | 39.536 | 40.267 | 20.694 | 1.00 17.82 C |
| ATOM | 954 | CG2 | VAL | A | 60 | 40.719 | 40.997 | 18.636 | 1.00 17.98 C |
| ATOM | 958 | C | VAL | A | 60 | 37.883 | 42.635 | 20.638 | 1.00 17.13 C |
| ATOM | 959 | O | VAL | A | 60 | 38.254 | 43.594 | 21.331 | 1.00 17.22 O |
| ATOM | 960 | N | GLU | A | 61 | 36.806 | 41.913 | 20.913 | 1.00 16.81 N |
| ATOM | 962 | CA | GLU | A | 61 | 35.954 | 42.215 | 22.058 | 1.00 17.72 C |
| ATOM | 964 | CB | GLU | A | 61 | 34.759 | 43.060 | 21.623 | 1.00 18.26 C |
| ATOM | 967 | CG | GLU | A | 61 | 35.079 | 44.412 | 20.956 | 1.00 20.64 C |
| ATOM | 970 | CD | GLU | A | 61 | 35.548 | 45.510 | 21.912 | 1.00 24.07 C |
| ATOM | 971 | OE1 | GLU | A | 61 | 35.294 | 45.417 | 23.142 | 1.00 25.24 O |
| ATOM | 972 | OE2 | GLU | A | 61 | 36.174 | 46.484 | 21.416 | 1.00 24.17 O |
| ATOM | 973 | C | GLU | A | 61 | 35.477 | 40.897 | 22.667 | 1.00 18.17 C |
| ATOM | 974 | O | GLU | A | 61 | 35.387 | 39.870 | 21.972 | 1.00 15.50 O |
| ATOM | 975 | N | SER | A | 62 | 35.171 | 40.917 | 23.964 | 1.00 19.13 N |
| ATOM | 977 | CA | SER | A | 62 | 34.710 | 39.697 | 24.634 | 1.00 20.18 C |
| ATOM | 979 | CB | SER | A | 62 | 35.838 | 39.109 | 25.479 | 1.00 20.45 C |
| ATOM | 982 | OG | SER | A | 62 | 36.229 | 40.016 | 26.499 | 1.00 21.81 O |
| ATOM | 984 | C | SER | A | 62 | 33.488 | 39.884 | 25.537 | 1.00 20.19 C |
| ATOM | 985 | O | SER | A | 62 | 32.920 | 38.912 | 26.038 | 1.00 20.33 O |
| ATOM | 986 | N | ASN | A | 63 | 33.073 | 41.120 | 25.735 | 1.00 20.95 N |
| ATOM | 988 | CA | ASN | A | 63 | 32.043 | 41.388 | 26.729 | 1.00 21.35 C |
| ATOM | 990 | CB | ASN | A | 63 | 32.310 | 42.725 | 27.418 | 1.00 22.62 C |
| ATOM | 993 | CG | ASN | A | 63 | 31.947 | 43.893 | 26.582 | 1.00 26.10 C |
| ATOM | 994 | OD1 | ASN | A | 63 | 31.697 | 44.985 | 27.106 | 1.00 33.95 O |
| ATOM | 995 | ND2 | ASN | A | 63 | 31.936 | 43.704 | 25.268 | 1.00 38.69 N |
| ATOM | 998 | C | ASN | A | 63 | 30.655 | 41.248 | 26.135 | 1.00 19.66 C |
| ATOM | 999 | O | ASN | A | 63 | 29.954 | 42.221 | 25.801 | 1.00 20.53 O |
| ATOM | 1000 | N | PHE | A | 64 | 30.318 | 39.982 | 25.925 | 1.00 17.32 N |
| ATOM | 1002 | CA | PHE | A | 64 | 29.024 | 39.592 | 25.437 | 1.00 15.47 C |
| ATOM | 1004 | CB | PHE | A | 64 | 29.125 | 39.076 | 23.995 | 1.00 14.91 C |
| ATOM | 1007 | CG | PHE | A | 64 | 29.885 | 40.014 | 23.077 | 1.00 13.87 C |
| ATOM | 1008 | CD1 | PHE | A | 64 | 29.388 | 41.270 | 22.792 | 1.00 14.13 C |
| ATOM | 1010 | CE1 | PHE | A | 64 | 30.091 | 42.136 | 21.982 | 1.00 14.78 C |
| ATOM | 1012 | CZ | PHE | A | 64 | 31.299 | 41.748 | 21.441 | 1.00 12.67 C |
| ATOM | 1014 | CE2 | PHE | A | 64 | 31.808 | 40.511 | 21.723 | 1.00 13.44 C |
| ATOM | 1016 | CD2 | PHE | A | 64 | 31.108 | 39.644 | 22.529 | 1.00 13.11 C |
| ATOM | 1018 | C | PHE | A | 64 | 28.561 | 38.496 | 26.376 | 1.00 14.27 C |
| ATOM | 1019 | O | PHE | A | 64 | 29.242 | 37.490 | 26.585 | 1.00 12.73 O |
| ATOM | 1020 | N | ALA | A | 65 | 27.382 | 38.708 | 26.928 | 1.00 14.30 N |
| ATOM | 1022 | CA | ALA | A | 65 | 26.782 | 37.806 | 27.875 | 1.00 14.41 C |
| ATOM | 1024 | CB | ALA | A | 65 | 25.441 | 38.380 | 28.300 | 1.00 14.45 C |
| ATOM | 1028 | C | ALA | A | 65 | 26.581 | 36.424 | 27.282 | 1.00 14.66 C |
| ATOM | 1029 | O | ALA | A | 65 | 26.244 | 36.311 | 26.098 | 1.00 15.01 O |
| ATOM | 1030 | N | VAL | A | 66 | 26.796 | 35.389 | 28.086 | 1.00 15.36 N |
| ATOM | 1032 | CA | VAL | A | 66 | 26.427 | 34.049 | 27.683 | 1.00 15.61 C |
| ATOM | 1034 | CB | VAL | A | 66 | 27.484 | 32.994 | 27.972 | 1.00 15.66 C |
| ATOM | 1036 | CG1 | VAL | A | 66 | 26.958 | 31.609 | 27.592 | 1.00 17.06 C |
| ATOM | 1040 | CG2 | VAL | A | 66 | 28.754 | 33.275 | 27.215 | 1.00 16.50 C |
| ATOM | 1044 | C | VAL | A | 66 | 25.158 | 33.766 | 28.476 | 1.00 15.70 C |
| ATOM | 1045 | O | VAL | A | 66 | 25.098 | 33.936 | 29.705 | 1.00 17.12 O |
| ATOM | 1046 | N | THR | A | 67 | 24.115 | 33.379 | 27.777 | 1.00 15.06 N |
| ATOM | 1048 | CA | THR | A | 67 | 22.854 | 33.106 | 28.439 | 1.00 15.98 C |
| ATOM | 1050 | CB | THR | A | 67 | 21.681 | 33.345 | 27.491 | 1.00 15.54 C |
| ATOM | 1052 | OG1 | THR | A | 67 | 21.794 | 32.535 | 26.311 | 1.00 14.59 O |
| ATOM | 1054 | CG2 | THR | A | 67 | 21.718 | 34.774 | 26.958 | 1.00 15.99 C |

| APPENDIX C: CRYSTAL COORDINATES OF FVE PROTEIN |||||||||
|---|---|---|---|---|---|---|---|---|
| ATOM | 1058 | C    | THR | A | 67 | 22.910 | 31.687 | 29.016 | 1.00 | 16.78 | C |
| ATOM | 1059 | O    | THR | A | 67 | 23.742 | 30.885 | 28.620 | 1.00 | 16.89 | O |
| ATOM | 1060 | N    | PRO | A | 68 | 22.150 | 31.418 | 30.062 | 1.00 | 18.84 | N |
| ATOM | 1061 | CA   | PRO | A | 68 | 22.093 | 30.058 | 30.617 | 1.00 | 19.21 | C |
| ATOM | 1063 | CB   | PRO | A | 68 | 20.997 | 30.168 | 31.683 | 1.00 | 19.65 | C |
| ATOM | 1066 | CG   | PRO | A | 68 | 21.101 | 31.602 | 32.125 | 1.00 | 18.30 | C |
| ATOM | 1069 | CD   | PRO | A | 68 | 21.436 | 32.395 | 30.897 | 1.00 | 18.90 | C |
| ATOM | 1072 | C    | PRO | A | 68 | 21.826 | 28.955 | 29.582 | 1.00 | 20.21 | C |
| ATOM | 1073 | O    | PRO | A | 68 | 22.274 | 27.827 | 29.790 | 1.00 | 19.65 | O |
| ATOM | 1074 | N    | SER | A | 69 | 21.145 | 29.278 | 28.485 | 1.00 | 22.19 | N |
| ATOM | 1076 | CA   | SER | A | 69 | 20.918 | 28.325 | 27.390 | 1.00 | 21.01 | C |
| ATOM | 1078 | CB   | SER | A | 69 | 19.822 | 28.847 | 26.463 | 1.00 | 21.48 | C |
| ATOM | 1081 | OG   | SER | A | 69 | 20.198 | 30.084 | 25.869 | 1.00 | 21.75 | O |
| ATOM | 1083 | C    | SER | A | 69 | 22.189 | 28.062 | 26.582 | 1.00 | 20.29 | C |
| ATOM | 1084 | O    | SER | A | 69 | 22.276 | 27.090 | 25.825 | 1.00 | 20.29 | O |
| ATOM | 1085 | N    | GLY | A | 70 | 23.185 | 28.926 | 26.742 | 1.00 | 18.45 | N |
| ATOM | 1087 | CA   | GLY | A | 70 | 24.455 | 28.736 | 26.089 | 1.00 | 16.37 | C |
| ATOM | 1090 | C    | GLY | A | 70 | 24.635 | 29.701 | 24.941 | 1.00 | 14.59 | C |
| ATOM | 1091 | O    | GLY | A | 70 | 25.655 | 29.678 | 24.275 | 1.00 | 14.71 | O |
| ATOM | 1092 | N    | GLY | A | 71 | 23.655 | 30.564 | 24.707 | 1.00 | 12.55 | N |
| ATOM | 1094 | CA   | GLY | A | 71 | 23.758 | 31.485 | 23.587 | 1.00 | 11.79 | C |
| ATOM | 1097 | C    | GLY | A | 71 | 24.646 | 32.689 | 23.872 | 1.00 | 11.04 | C |
| ATOM | 1098 | O    | GLY | A | 71 | 24.827 | 33.109 | 25.024 | 1.00 | 11.27 | O |
| ATOM | 1099 | N    | GLN | A | 72 | 25.209 | 33.247 | 22.807 | 1.00 | 10.97 | N |
| ATOM | 1101 | CA   | GLN | A | 72 | 26.016 | 34.462 | 22.914 | 1.00 | 10.54 | C |
| ATOM | 1103 | CB   | GLN | A | 72 | 27.497 | 34.125 | 23.115 | 1.00 | 10.98 | C |
| ATOM | 1106 | CG   | GLN | A | 72 | 28.414 | 35.293 | 23.430 | 1.00 | 12.20 | C |
| ATOM | 1109 | CD   | GLN | A | 72 | 29.834 | 34.862 | 23.853 | 1.00 | 15.65 | C |
| ATOM | 1110 | OE1  | GLN | A | 72 | 30.449 | 35.487 | 24.742 | 1.00 | 17.66 | O |
| ATOM | 1111 | NE2  | GLN | A | 72 | 30.354 | 33.820 | 23.222 | 1.00 | 10.29 | N |
| ATOM | 1114 | C    | GLN | A | 72 | 25.807 | 35.312 | 21.675 | 1.00 | 11.06 | C |
| ATOM | 1115 | O    | GLN | A | 72 | 25.877 | 34.821 | 20.533 | 1.00 | 11.31 | O |
| ATOM | 1116 | N    | THR | A | 73 | 25.535 | 36.589 | 21.904 | 1.00 | 10.95 | N |
| ATOM | 1118 | CA   | THR | A | 73 | 25.337 | 37.526 | 20.830 | 1.00 | 9.80  | C |
| ATOM | 1120 | CB   | THR | A | 73 | 24.021 | 38.290 | 21.035 | 1.00 | 10.73 | C |
| ATOM | 1122 | OG1  | THR | A | 73 | 22.912 | 37.385 | 21.013 | 1.00 | 11.04 | O |
| ATOM | 1124 | CG2  | THR | A | 73 | 23.786 | 39.270 | 19.891 | 1.00 | 10.78 | C |
| ATOM | 1128 | C    | THR | A | 73 | 26.475 | 38.540 | 20.782 | 1.00 | 9.92  | C |
| ATOM | 1129 | O    | THR | A | 73 | 26.722 | 39.283 | 21.745 | 1.00 | 10.19 | O |
| ATOM | 1130 | N    | ILE | A | 74 | 27.161 | 38.554 | 19.643 | 1.00 | 9.37  | N |
| ATOM | 1132 | CA   | ILE | A | 74 | 28.232 | 39.493 | 19.364 | 1.00 | 10.19 | C |
| ATOM | 1134 | CB   | ILE | A | 74 | 29.235 | 38.855 | 18.371 | 1.00 | 10.48 | C |
| ATOM | 1136 | CG1  | ILE | A | 74 | 29.843 | 37.581 | 18.972 | 1.00 | 12.71 | C |
| ATOM | 1139 | CD1  | ILE | A | 74 | 30.471 | 36.666 | 17.946 | 1.00 | 16.05 | C |
| ATOM | 1143 | CG2  | ILE | A | 74 | 30.296 | 39.860 | 17.986 | 1.00 | 10.70 | C |
| ATOM | 1147 | C    | ILE | A | 74 | 27.609 | 40.733 | 18.756 | 1.00 | 10.18 | C |
| ATOM | 1148 | O    | ILE | A | 74 | 27.052 | 40.677 | 17.660 | 1.00 | 11.08 | O |
| ATOM | 1149 | N    | ASN | A | 75 | 27.674 | 41.851 | 19.489 | 1.00 | 9.17  | N |
| ATOM | 1151 | CA   | ASN | A | 75 | 27.079 | 43.102 | 19.040 | 1.00 | 9.50  | C |
| ATOM | 1153 | CB   | ASN | A | 75 | 26.600 | 43.849 | 20.274 | 1.00 | 9.51  | C |
| ATOM | 1156 | CG   | ASN | A | 75 | 25.994 | 45.177 | 19.950 | 1.00 | 10.45 | C |
| ATOM | 1157 | OD1  | ASN | A | 75 | 25.558 | 45.424 | 18.827 | 1.00 | 9.62  | O |
| ATOM | 1158 | ND2  | ASN | A | 75 | 25.931 | 46.046 | 20.959 | 1.00 | 12.30 | N |
| ATOM | 1161 | C    | ASN | A | 75 | 28.050 | 43.975 | 18.248 | 1.00 | 9.58  | C |
| ATOM | 1162 | O    | ASN | A | 75 | 28.992 | 44.543 | 18.807 | 1.00 | 10.09 | O |
| ATOM | 1163 | N    | PHE | A | 76 | 27.817 | 44.088 | 16.945 | 1.00 | 10.23 | N |
| ATOM | 1165 | CA   | PHE | A | 76 | 28.751 | 44.809 | 16.087 | 1.00 | 10.31 | C |
| ATOM | 1167 | CB   | PHE | A | 76 | 28.464 | 44.552 | 14.610 | 1.00 | 10.82 | C |
| ATOM | 1170 | CG   | PHE | A | 76 | 28.596 | 43.096 | 14.199 | 1.00 | 11.07 | C |
| ATOM | 1171 | CD1  | PHE | A | 76 | 29.568 | 42.277 | 14.737 | 1.00 | 13.37 | C |
| ATOM | 1173 | CE1  | PHE | A | 76 | 29.681 | 40.936 | 14.328 | 1.00 | 10.49 | C |
| ATOM | 1175 | CZ   | PHE | A | 76 | 28.820 | 40.441 | 13.411 | 1.00 | 10.42 | C |
| ATOM | 1177 | CE2  | PHE | A | 76 | 27.856 | 41.259 | 12.865 | 1.00 | 11.96 | C |
| ATOM | 1179 | CD2  | PHE | A | 76 | 27.746 | 42.568 | 13.258 | 1.00 | 12.00 | C |
| ATOM | 1181 | C    | PHE | A | 76 | 28.780 | 46.301 | 16.409 | 1.00 | 10.53 | C |
| ATOM | 1182 | O    | PHE | A | 76 | 29.743 | 46.978 | 16.059 | 1.00 | 10.34 | O |
| ATOM | 1183 | N    | LEU | A | 77 | 27.746 | 46.826 | 17.073 | 1.00 | 10.19 | N |
| ATOM | 1185 | CA   | LEU | A | 77 | 27.754 | 48.242 | 17.446 | 1.00 | 11.27 | C |
| ATOM | 1187 | CB   | LEU | A | 77 | 26.443 | 48.652 | 18.120 | 1.00 | 11.26 | C |
| ATOM | 1190 | CG   | LEU | A | 77 | 25.267 | 48.913 | 17.154 | 1.00 | 12.41 | C |
| ATOM | 1192 | CD1  | LEU | A | 77 | 24.989 | 47.774 | 16.232 | 1.00 | 12.55 | C |
| ATOM | 1196 | CD2  | LEU | A | 77 | 23.977 | 49.223 | 17.911 | 1.00 | 13.90 | C |
| ATOM | 1200 | C    | LEU | A | 77 | 28.933 | 48.577 | 18.368 | 1.00 | 12.07 | C |
| ATOM | 1201 | O    | LEU | A | 77 | 29.399 | 49.717 | 18.371 | 1.00 | 13.10 | O |
| ATOM | 1202 | N    | GLN | A | 78 | 29.416 | 47.580 | 19.112 | 1.00 | 12.87 | N |
| ATOM | 1204 | CA   | GLN | A | 78 | 30.562 | 47.741 | 20.011 | 1.00 | 13.30 | C |
| ATOM | 1206 | CB   | GLN | A | 78 | 30.588 | 46.602 | 21.048 | 1.00 | 13.42 | C |
| ATOM | 1209 | CG   | GLN | A | 78 | 29.408 | 46.690 | 22.022 | 1.00 | 14.19 | C |

APPENDIX C: CRYSTAL COORDINATES OF FVE PROTEIN

| ATOM | 1212 | CD | GLN | A | 78 | 29.251 | 45.560 | 23.009 | 1.00 | 17.92 | C |
|---|---|---|---|---|---|---|---|---|---|---|---|
| ATOM | 1213 | OE1 | GLN | A | 78 | 28.141 | 45.045 | 23.165 | 1.00 | 20.68 | O |
| ATOM | 1214 | NE2 | GLN | A | 78 | 30.316 | 45.212 | 23.726 | 1.00 | 21.02 | N |
| ATOM | 1217 | C | GLN | A | 78 | 31.892 | 47.837 | 19.231 | 1.00 | 14.14 | C |
| ATOM | 1218 | O | GLN | A | 78 | 32.905 | 48.303 | 19.774 | 1.00 | 16.34 | O |
| ATOM | 1219 | N | TYR | A | 79 | 31.896 | 47.398 | 17.979 | 1.00 | 13.44 | N |
| ATOM | 1221 | CA | TYR | A | 79 | 33.101 | 47.443 | 17.143 | 1.00 | 13.76 | C |
| ATOM | 1223 | CB | TYR | A | 79 | 33.220 | 46.165 | 16.311 | 1.00 | 13.39 | C |
| ATOM | 1226 | CG | TYR | A | 79 | 33.402 | 44.856 | 17.041 | 1.00 | 12.44 | C |
| ATOM | 1227 | CD1 | TYR | A | 79 | 34.649 | 44.249 | 17.117 | 1.00 | 11.93 | C |
| ATOM | 1229 | CE1 | TYR | A | 79 | 34.816 | 43.040 | 17.755 | 1.00 | 11.71 | C |
| ATOM | 1231 | CZ | TYR | A | 79 | 33.712 | 42.414 | 18.310 | 1.00 | 12.16 | C |
| ATOM | 1232 | OH | TYR | A | 79 | 33.873 | 41.215 | 18.929 | 1.00 | 13.43 | O |
| ATOM | 1234 | CE2 | TYR | A | 79 | 32.463 | 43.002 | 18.239 | 1.00 | 10.82 | C |
| ATOM | 1236 | CD2 | TYR | A | 79 | 32.319 | 44.204 | 17.607 | 1.00 | 11.32 | C |
| ATOM | 1238 | C | TYR | A | 79 | 33.092 | 48.571 | 16.111 | 1.00 | 14.75 | C |
| ATOM | 1239 | O | TYR | A | 79 | 34.154 | 48.964 | 15.600 | 1.00 | 14.73 | O |
| ATOM | 1240 | N | ASN | A | 80 | 31.899 | 49.072 | 15.786 | 1.00 | 15.93 | N |
| ATOM | 1242 | CA | ASN | A | 80 | 31.702 | 49.928 | 14.614 | 1.00 | 15.93 | C |
| ATOM | 1244 | CB | ASN | A | 80 | 30.814 | 49.164 | 13.619 | 1.00 | 15.91 | C |
| ATOM | 1247 | CG | ASN | A | 80 | 30.884 | 49.703 | 12.203 | 1.00 | 17.60 | C |
| ATOM | 1248 | OD1 | ASN | A | 80 | 29.863 | 49.757 | 11.507 | 1.00 | 22.84 | O |
| ATOM | 1249 | ND2 | ASN | A | 80 | 32.067 | 50.104 | 11.767 | 1.00 | 16.39 | N |
| ATOM | 1252 | C | ASN | A | 80 | 31.101 | 51.293 | 14.941 | 1.00 | 16.30 | C |
| ATOM | 1253 | O | ASN | A | 80 | 30.238 | 51.789 | 14.220 | 1.00 | 16.27 | O |
| ATOM | 1254 | N | LYS | A | 81 | 31.559 | 51.881 | 16.042 | 1.00 | 16.66 | N |
| ATOM | 1256 | CA | LYS | A | 81 | 31.166 | 53.238 | 16.448 | 1.00 | 17.75 | C |
| ATOM | 1258 | CB | LYS | A | 81 | 31.753 | 54.274 | 15.485 | 1.00 | 18.72 | C |
| ATOM | 1261 | CG | LYS | A | 81 | 33.275 | 54.164 | 15.279 | 1.00 | 22.17 | C |
| ATOM | 1264 | CD | LYS | A | 81 | 34.098 | 53.637 | 16.494 | 1.00 | 28.26 | C |
| ATOM | 1267 | CE | LYS | A | 81 | 33.999 | 54.432 | 17.816 | 1.00 | 31.88 | C |
| ATOM | 1270 | NZ | LYS | A | 81 | 34.916 | 53.895 | 18.908 | 1.00 | 34.98 | N |
| ATOM | 1274 | C | LYS | A | 81 | 29.660 | 53.445 | 16.590 | 1.00 | 17.22 | C |
| ATOM | 1275 | O | LYS | A | 81 | 29.139 | 54.507 | 16.230 | 1.00 | 16.93 | O |
| ATOM | 1276 | N | GLY | A | 82 | 28.969 | 52.429 | 17.115 | 1.00 | 16.00 | N |
| ATOM | 1278 | CA | GLY | A | 82 | 27.546 | 52.523 | 17.393 | 1.00 | 16.21 | C |
| ATOM | 1281 | C | GLY | A | 82 | 26.612 | 52.249 | 16.232 | 1.00 | 16.87 | C |
| ATOM | 1282 | O | GLY | A | 82 | 25.406 | 52.461 | 16.362 | 1.00 | 16.37 | O |
| ATOM | 1283 | N | TYR | A | 83 | 27.152 | 51.772 | 15.111 | 1.00 | 16.99 | N |
| ATOM | 1285 | CA | TYR | A | 83 | 26.342 | 51.425 | 13.958 | 1.00 | 17.84 | C |
| ATOM | 1287 | CB | TYR | A | 83 | 26.751 | 52.240 | 12.735 | 1.00 | 18.95 | C |
| ATOM | 1290 | CG | TYR | A | 83 | 26.375 | 53.678 | 12.816 | 1.00 | 24.21 | C |
| ATOM | 1291 | CD1 | TYR | A | 83 | 25.138 | 54.103 | 12.373 | 1.00 | 29.21 | C |
| ATOM | 1293 | CE1 | TYR | A | 83 | 24.775 | 55.428 | 12.440 | 1.00 | 31.15 | C |
| ATOM | 1295 | CZ | TYR | A | 83 | 25.660 | 56.351 | 12.956 | 1.00 | 32.63 | C |
| ATOM | 1296 | OH | TYR | A | 83 | 25.291 | 57.680 | 13.016 | 1.00 | 35.54 | O |
| ATOM | 1298 | CE2 | TYR | A | 83 | 26.906 | 55.954 | 13.404 | 1.00 | 31.21 | C |
| ATOM | 1300 | CD2 | TYR | A | 83 | 27.258 | 54.618 | 13.327 | 1.00 | 28.33 | C |
| ATOM | 1302 | C | TYR | A | 83 | 26.576 | 49.990 | 13.590 | 1.00 | 16.45 | C |
| ATOM | 1303 | O | TYR | A | 83 | 27.652 | 49.438 | 13.854 | 1.00 | 16.18 | O |
| ATOM | 1304 | N | GLY | A | 84 | 25.570 | 49.372 | 12.982 | 1.00 | 14.45 | N |
| ATOM | 1306 | CA | GLY | A | 84 | 25.761 | 48.049 | 12.430 | 1.00 | 14.93 | C |
| ATOM | 1309 | C | GLY | A | 84 | 26.514 | 48.187 | 11.109 | 1.00 | 15.19 | C |
| ATOM | 1310 | O | GLY | A | 84 | 27.001 | 49.273 | 10.757 | 1.00 | 15.50 | O |
| ATOM | 1311 | N | VAL | A | 85 | 26.565 | 47.099 | 10.353 | 1.00 | 15.19 | N |
| ATOM | 1313 | CA | VAL | A | 85 | 27.352 | 47.043 | 9.112 | 1.00 | 15.08 | C |
| ATOM | 1315 | CB | VAL | A | 85 | 28.332 | 45.860 | 9.143 | 1.00 | 15.27 | C |
| ATOM | 1317 | CG1 | VAL | A | 85 | 29.157 | 45.794 | 7.872 | 1.00 | 15.21 | C |
| ATOM | 1321 | CG2 | VAL | A | 85 | 29.255 | 45.956 | 10.329 | 1.00 | 15.25 | C |
| ATOM | 1325 | C | VAL | A | 85 | 26.438 | 46.873 | 7.911 | 1.00 | 15.53 | C |
| ATOM | 1326 | O | VAL | A | 85 | 25.551 | 46.025 | 7.910 | 1.00 | 14.72 | O |
| ATOM | 1327 | N | ALA | A | 86 | 26.648 | 47.673 | 6.875 | 1.00 | 15.80 | N |
| ATOM | 1329 | CA | ALA | A | 86 | 25.802 | 47.548 | 5.698 | 1.00 | 16.04 | C |
| ATOM | 1331 | CB | ALA | A | 86 | 26.250 | 48.488 | 4.631 | 1.00 | 16.32 | C |
| ATOM | 1335 | C | ALA | A | 86 | 25.861 | 46.128 | 5.186 | 1.00 | 15.57 | C |
| ATOM | 1336 | O | ALA | A | 86 | 26.941 | 45.575 | 5.059 | 1.00 | 15.01 | O |
| ATOM | 1337 | N | ASP | A | 87 | 24.708 | 45.558 | 4.842 | 1.00 | 16.64 | N |
| ATOM | 1339 | CA | ASP | A | 87 | 24.658 | 44.160 | 4.402 | 1.00 | 16.37 | C |
| ATOM | 1341 | CB | ASP | A | 87 | 23.253 | 43.550 | 4.495 | 1.00 | 16.92 | C |
| ATOM | 1344 | CG | ASP | A | 87 | 22.293 | 44.088 | 3.472 | 1.00 | 17.15 | C |
| ATOM | 1345 | OD1 | ASP | A | 87 | 21.117 | 43.677 | 3.520 | 1.00 | 17.33 | O |
| ATOM | 1346 | OD2 | ASP | A | 87 | 22.615 | 44.920 | 2.605 | 1.00 | 17.89 | O |
| ATOM | 1347 | C | ASP | A | 87 | 25.316 | 43.899 | 3.046 | 1.00 | 16.95 | C |
| ATOM | 1348 | O | ASP | A | 87 | 25.392 | 42.753 | 2.623 | 1.00 | 16.19 | O |
| ATOM | 1349 | N | THR | A | 88 | 25.812 | 44.949 | 2.398 | 1.00 | 18.29 | N |
| ATOM | 1351 | CA | THR | A | 88 | 26.566 | 44.803 | 1.146 | 1.00 | 17.50 | C |
| ATOM | 1353 | CB | THR | A | 88 | 26.427 | 46.084 | 0.327 | 1.00 | 17.73 | C |
| ATOM | 1355 | OG1 | THR | A | 88 | 26.702 | 47.225 | 1.150 | 1.00 | 16.82 | O |

-continued

| APPENDIX C: CRYSTAL COORDINATES OF FVE PROTEIN | | | | | | | | | |
|---|---|---|---|---|---|---|---|---|---|
| ATOM | 1357 | CG2 | THR | A | 88 | 25.020 | 46.269 | −0.109 | 1.00 | 18.14 C |
| ATOM | 1361 | C | THR | A | 88 | 28.052 | 44.563 | 1.361 | 1.00 | 17.57 C |
| ATOM | 1362 | O | THR | A | 88 | 28.820 | 44.404 | 0.409 | 1.00 | 16.74 O |
| ATOM | 1363 | N | LYS | A | 89 | 28.477 | 44.594 | 2.609 | 1.00 | 17.46 N |
| ATOM | 1365 | CA | LYS | A | 89 | 29.871 | 44.389 | 2.919 | 1.00 | 17.25 C |
| ATOM | 1367 | CB | LYS | A | 89 | 30.312 | 45.388 | 3.978 | 1.00 | 17.22 C |
| ATOM | 1370 | CG | LYS | A | 89 | 30.058 | 46.844 | 3.579 | 1.00 | 18.92 C |
| ATOM | 1373 | CD | LYS | A | 89 | 30.818 | 47.788 | 4.471 | 1.00 | 22.27 C |
| ATOM | 1376 | CE | LYS | A | 89 | 30.590 | 49.242 | 4.055 | 1.00 | 25.20 C |
| ATOM | 1379 | NZ | LYS | A | 89 | 31.208 | 50.160 | 5.042 | 1.00 | 29.86 N |
| ATOM | 1383 | C | LYS | A | 89 | 30.069 | 42.968 | 3.411 | 1.00 | 17.09 C |
| ATOM | 1384 | O | LYS | A | 89 | 29.122 | 42.311 | 3.818 | 1.00 | 16.84 O |
| ATOM | 1385 | N | THR | A | 90 | 31.300 | 42.493 | 3.343 | 1.00 | 17.10 N |
| ATOM | 1387 | CA | THR | A | 90 | 31.662 | 41.181 | 3.842 | 1.00 | 16.27 C |
| ATOM | 1389 | CB | THR | A | 90 | 32.860 | 40.644 | 3.086 | 1.00 | 17.13 C |
| ATOM | 1391 | OG1 | THR | A | 90 | 32.533 | 40.515 | 1.704 | 1.00 | 15.79 O |
| ATOM | 1393 | CG2 | THR | A | 90 | 33.199 | 39.226 | 3.543 | 1.00 | 17.35 C |
| ATOM | 1397 | C | THR | A | 90 | 32.068 | 41.322 | 5.296 | 1.00 | 15.60 C |
| ATOM | 1398 | O | THR | A | 90 | 32.930 | 42.137 | 5.613 | 1.00 | 14.66 O |
| ATOM | 1399 | N | ILE | A | 91 | 31.451 | 40.543 | 6.170 | 1.00 | 15.11 N |
| ATOM | 1401 | CA | ILE | A | 91 | 31.823 | 40.561 | 7.577 | 1.00 | 14.05 C |
| ATOM | 1403 | CB | ILE | A | 91 | 30.596 | 40.777 | 8.475 | 1.00 | 14.05 C |
| ATOM | 1405 | CG1 | ILE | A | 91 | 29.771 | 41.971 | 7.995 | 1.00 | 13.77 C |
| ATOM | 1408 | CD1 | ILE | A | 91 | 28.482 | 42.119 | 8.725 | 1.00 | 15.25 C |
| ATOM | 1412 | CG2 | ILE | A | 91 | 31.039 | 40.924 | 9.949 | 1.00 | 13.82 C |
| ATOM | 1416 | C | ILE | A | 91 | 32.435 | 39.221 | 7.914 | 1.00 | 14.03 C |
| ATOM | 1417 | O | ILE | A | 91 | 31.795 | 38.191 | 7.702 | 1.00 | 14.85 O |
| ATOM | 1418 | N | GLN | A | 92 | 33.679 | 39.230 | 8.382 | 1.00 | 12.86 N |
| ATOM | 1420 | CA | GLN | A | 92 | 34.298 | 38.028 | 8.919 | 1.00 | 13.25 C |
| ATOM | 1422 | CB | GLN | A | 92 | 35.678 | 37.818 | 8.338 | 1.00 | 14.29 C |
| ATOM | 1425 | CG | GLN | A | 92 | 35.645 | 37.428 | 6.904 | 1.00 | 16.51 C |
| ATOM | 1428 | CD | GLN | A | 92 | 37.020 | 37.515 | 6.275 | 1.00 | 21.30 C |
| ATOM | 1429 | OE1 | GLN | A | 92 | 37.536 | 36.517 | 5.775 | 1.00 | 25.59 O |
| ATOM | 1430 | NE2 | GLN | A | 92 | 37.627 | 38.701 | 6.319 | 1.00 | 23.68 N |
| ATOM | 1433 | C | GLN | A | 92 | 34.443 | 38.120 | 10.423 | 1.00 | 12.74 C |
| ATOM | 1434 | O | GLN | A | 92 | 34.914 | 39.127 | 10.940 | 1.00 | 12.27 O |
| ATOM | 1435 | N | VAL | A | 93 | 34.072 | 37.051 | 11.115 | 1.00 | 11.90 N |
| ATOM | 1437 | CA | VAL | A | 93 | 34.217 | 36.985 | 12.564 | 1.00 | 11.73 C |
| ATOM | 1439 | CB | VAL | A | 93 | 32.865 | 36.841 | 13.257 | 1.00 | 11.43 C |
| ATOM | 1441 | CG1 | VAL | A | 93 | 33.048 | 36.856 | 14.771 | 1.00 | 12.22 C |
| ATOM | 1445 | CG2 | VAL | A | 93 | 31.925 | 37.956 | 12.809 | 1.00 | 12.10 C |
| ATOM | 1449 | C | VAL | A | 93 | 35.118 | 35.797 | 12.912 | 1.00 | 11.97 C |
| ATOM | 1450 | O | VAL | A | 93 | 34.953 | 34.707 | 12.379 | 1.00 | 11.23 O |
| ATOM | 1451 | N | PHE | A | 94 | 36.096 | 36.055 | 13.773 | 1.00 | 11.48 N |
| ATOM | 1453 | CA | PHE | A | 94 | 37.069 | 35.064 | 14.188 | 1.00 | 12.22 C |
| ATOM | 1455 | CB | PHE | A | 94 | 38.473 | 35.563 | 13.871 | 1.00 | 12.62 C |
| ATOM | 1458 | CG | PHE | A | 94 | 38.736 | 35.743 | 12.404 | 1.00 | 12.77 C |
| ATOM | 1459 | CD1 | PHE | A | 94 | 38.345 | 36.900 | 11.763 | 1.00 | 14.64 C |
| ATOM | 1461 | CE1 | PHE | A | 94 | 38.598 | 37.083 | 10.420 | 1.00 | 16.13 C |
| ATOM | 1463 | CZ | PHE | A | 94 | 39.255 | 36.106 | 9.711 | 1.00 | 15.54 C |
| ATOM | 1465 | CE2 | PHE | A | 94 | 39.660 | 34.948 | 10.345 | 1.00 | 16.06 C |
| ATOM | 1467 | CD2 | PHE | A | 94 | 39.409 | 34.768 | 11.682 | 1.00 | 13.20 C |
| ATOM | 1469 | C | PHE | A | 94 | 36.984 | 34.837 | 15.681 | 1.00 | 12.26 C |
| ATOM | 1470 | O | PHE | A | 94 | 36.882 | 35.794 | 16.458 | 1.00 | 11.72 O |
| ATOM | 1471 | N | VAL | A | 95 | 36.998 | 33.581 | 16.097 | 1.00 | 12.66 N |
| ATOM | 1473 | CA | VAL | A | 95 | 37.063 | 33.304 | 17.530 | 1.00 | 13.63 C |
| ATOM | 1475 | CB | VAL | A | 95 | 36.390 | 31.976 | 17.924 | 1.00 | 13.74 C |
| ATOM | 1477 | CG1 | VAL | A | 95 | 37.054 | 30.809 | 17.246 | 1.00 | 15.18 C |
| ATOM | 1481 | CG2 | VAL | A | 95 | 36.397 | 31.814 | 19.473 | 1.00 | 15.16 C |
| ATOM | 1485 | C | VAL | A | 95 | 38.554 | 33.362 | 17.882 | 1.00 | 13.85 C |
| ATOM | 1486 | O | VAL | A | 95 | 39.399 | 32.777 | 17.203 | 1.00 | 13.33 O |
| ATOM | 1487 | N | VAL | A | 96 | 38.862 | 34.116 | 18.924 | 1.00 | 14.98 N |
| ATOM | 1489 | CA | VAL | A | 96 | 40.231 | 34.355 | 19.364 | 1.00 | 16.25 C |
| ATOM | 1491 | CB | VAL | A | 96 | 40.478 | 35.868 | 19.524 | 1.00 | 16.70 C |
| ATOM | 1493 | CG1 | VAL | A | 96 | 41.904 | 36.141 | 20.002 | 1.00 | 17.91 C |
| ATOM | 1497 | CG2 | VAL | A | 96 | 40.202 | 36.576 | 18.209 | 1.00 | 17.10 C |
| ATOM | 1501 | C | VAL | A | 96 | 40.466 | 33.634 | 20.691 | 1.00 | 17.27 C |
| ATOM | 1502 | O | VAL | A | 96 | 39.695 | 33.788 | 21.641 | 1.00 | 16.34 O |
| ATOM | 1503 | N | ILE | A | 97 | 41.522 | 32.830 | 20.726 | 1.00 | 18.96 N |
| ATOM | 1505 | CA | ILE | A | 97 | 41.842 | 32.001 | 21.883 | 1.00 | 20.35 C |
| ATOM | 1507 | CB | ILE | A | 97 | 42.745 | 30.808 | 21.453 | 1.00 | 20.22 C |
| ATOM | 1509 | CG1 | ILE | A | 97 | 42.107 | 30.040 | 20.289 | 1.00 | 19.14 C |
| ATOM | 1512 | CD1 | ILE | A | 97 | 40.750 | 29.510 | 20.588 | 1.00 | 18.75 C |
| ATOM | 1516 | CG2 | ILE | A | 97 | 43.031 | 29.889 | 22.639 | 1.00 | 20.66 C |
| ATOM | 1520 | C | ILE | A | 97 | 42.545 | 32.863 | 22.925 | 1.00 | 22.26 C |
| ATOM | 1521 | O | ILE | A | 97 | 43.457 | 33.599 | 22.579 | 1.00 | 22.69 O |
| ATOM | 1522 | N | PRO | A | 98 | 42.099 | 32.814 | 24.176 | 1.00 | 24.62 N |
| ATOM | 1523 | CA | PRO | A | 98 | 42.733 | 33.599 | 25.240 | 1.00 | 26.52 C |

APPENDIX C: CRYSTAL COORDINATES OF FVE PROTEIN

-continued

| ATOM | 1525 | CB | PRO | A | 98 | 41.778 | 33.441 | 26.426 | 1.00 | 25.97 | C |
|---|---|---|---|---|---|---|---|---|---|---|---|
| ATOM | 1528 | CG | PRO | A | 98 | 40.990 | 32.213 | 26.153 | 1.00 | 25.73 | C |
| ATOM | 1531 | CD | PRO | A | 98 | 40.942 | 32.054 | 24.669 | 1.00 | 24.63 | C |
| ATOM | 1534 | C | PRO | A | 98 | 44.114 | 33.108 | 25.621 | 1.00 | 28.91 | C |
| ATOM | 1535 | O | PRO | A | 98 | 44.507 | 31.975 | 25.313 | 1.00 | 28.13 | O |
| ATOM | 1536 | N | ASP | A | 99 | 44.838 | 33.999 | 26.295 | 1.00 | 32.98 | N |
| ATOM | 1538 | CA | ASP | A | 99 | 46.175 | 33.735 | 26.804 | 1.00 | 34.16 | C |
| ATOM | 1540 | CB | ASP | A | 99 | 46.090 | 32.683 | 27.897 | 1.00 | 34.51 | C |
| ATOM | 1543 | CG | ASP | A | 99 | 45.238 | 33.162 | 29.064 | 1.00 | 36.30 | C |
| ATOM | 1544 | OD1 | ASP | A | 99 | 45.547 | 34.247 | 29.608 | 1.00 | 39.17 | O |
| ATOM | 1545 | OD2 | ASP | A | 99 | 44.222 | 32.559 | 29.481 | 1.00 | 39.73 | O |
| ATOM | 1546 | C | ASP | A | 99 | 47.083 | 33.361 | 25.645 | 1.00 | 35.01 | C |
| ATOM | 1547 | O | ASP | A | 99 | 47.925 | 32.468 | 25.733 | 1.00 | 35.21 | O |
| ATOM | 1548 | N | THR | A | 100 | 46.914 | 34.118 | 24.568 | 1.00 | 36.50 | N |
| ATOM | 1550 | CA | THR | A | 100 | 47.559 | 33.836 | 23.307 | 1.00 | 35.94 | C |
| ATOM | 1552 | CB | THR | A | 100 | 46.536 | 33.051 | 22.457 | 1.00 | 36.18 | C |
| ATOM | 1554 | OG1 | THR | A | 100 | 47.151 | 31.891 | 21.882 | 1.00 | 36.31 | O |
| ATOM | 1556 | CG2 | THR | A | 100 | 46.021 | 33.845 | 21.282 | 1.00 | 35.16 | C |
| ATOM | 1560 | C | THR | A | 100 | 48.034 | 35.115 | 22.606 | 1.00 | 36.08 | C |
| ATOM | 1561 | O | THR | A | 100 | 48.650 | 35.058 | 21.542 | 1.00 | 35.70 | O |
| ATOM | 1562 | N | GLY | A | 101 | 47.776 | 36.267 | 23.220 | 1.00 | 36.43 | N |
| ATOM | 1564 | CA | GLY | A | 101 | 48.151 | 37.550 | 22.636 | 1.00 | 36.52 | C |
| ATOM | 1567 | C | GLY | A | 101 | 47.365 | 37.850 | 21.368 | 1.00 | 36.69 | C |
| ATOM | 1568 | O | GLY | A | 101 | 47.842 | 38.551 | 20.467 | 1.00 | 36.66 | O |
| ATOM | 1569 | N | ASN | A | 102 | 46.149 | 37.309 | 21.305 | 1.00 | 37.04 | N |
| ATOM | 1571 | CA | ASN | A | 102 | 45.279 | 37.436 | 20.135 | 1.00 | 35.46 | C |
| ATOM | 1573 | CB | ASN | A | 102 | 44.881 | 38.904 | 19.889 | 1.00 | 35.74 | C |
| ATOM | 1576 | CG | ASN | A | 102 | 44.070 | 39.509 | 21.044 | 1.00 | 36.19 | C |
| ATOM | 1577 | OD1 | ASN | A | 102 | 43.556 | 38.795 | 21.914 | 1.00 | 36.82 | O |
| ATOM | 1578 | ND2 | ASN | A | 102 | 43.948 | 40.836 | 21.046 | 1.00 | 38.45 | N |
| ATOM | 1581 | C | ASN | A | 102 | 45.884 | 36.813 | 18.855 | 1.00 | 34.28 | C |
| ATOM | 1582 | O | ASN | A | 102 | 45.401 | 37.081 | 17.757 | 1.00 | 34.09 | O |
| ATOM | 1583 | N | SER | A | 103 | 46.919 | 35.978 | 18.997 | 1.00 | 32.94 | N |
| ATOM | 1585 | CA | SER | A | 103 | 47.608 | 35.359 | 17.852 | 1.00 | 30.99 | C |
| ATOM | 1587 | CB | SER | A | 103 | 49.068 | 35.070 | 18.214 | 1.00 | 31.29 | C |
| ATOM | 1590 | OG | SER | A | 103 | 49.175 | 34.552 | 19.532 | 1.00 | 32.26 | O |
| ATOM | 1592 | C | SER | A | 103 | 46.981 | 34.072 | 17.315 | 1.00 | 28.93 | C |
| ATOM | 1593 | O | SER | A | 103 | 47.135 | 33.752 | 16.140 | 1.00 | 29.01 | O |
| ATOM | 1594 | N | GLU | A | 104 | 46.308 | 33.320 | 18.173 | 1.00 | 26.74 | N |
| ATOM | 1596 | CA | GLU | A | 104 | 45.648 | 32.098 | 17.739 | 1.00 | 23.55 | C |
| ATOM | 1598 | CB | GLU | A | 104 | 45.821 | 30.969 | 18.759 | 1.00 | 23.10 | C |
| ATOM | 1601 | CG | GLU | A | 104 | 45.217 | 29.652 | 18.294 | 1.00 | 22.29 | C |
| ATOM | 1604 | CD | GLU | A | 104 | 45.267 | 28.539 | 19.335 | 1.00 | 20.79 | C |
| ATOM | 1605 | OE1 | GLU | A | 104 | 44.705 | 27.459 | 19.063 | 1.00 | 18.27 | O |
| ATOM | 1606 | OE2 | GLU | A | 104 | 45.872 | 28.735 | 20.405 | 1.00 | 19.73 | O |
| ATOM | 1607 | C | GLU | A | 104 | 44.166 | 32.431 | 17.527 | 1.00 | 21.26 | C |
| ATOM | 1608 | O | GLU | A | 104 | 43.463 | 32.788 | 18.468 | 1.00 | 20.20 | O |
| ATOM | 1609 | N | GLU | A | 105 | 43.706 | 32.342 | 16.286 | 1.00 | 19.27 | N |
| ATOM | 1611 | CA | GLU | A | 105 | 42.310 | 32.652 | 15.989 | 1.00 | 17.92 | C |
| ATOM | 1613 | CB | GLU | A | 105 | 42.119 | 34.141 | 15.658 | 1.00 | 18.34 | C |
| ATOM | 1616 | CG | GLU | A | 105 | 42.614 | 34.515 | 14.283 | 1.00 | 19.41 | C |
| ATOM | 1619 | CD | GLU | A | 105 | 42.443 | 35.986 | 13.960 | 1.00 | 21.46 | C |
| ATOM | 1620 | OE1 | GLU | A | 105 | 42.657 | 36.346 | 12.779 | 1.00 | 22.55 | O |
| ATOM | 1621 | OE2 | GLU | A | 105 | 42.097 | 36.770 | 14.872 | 1.00 | 19.79 | O |
| ATOM | 1622 | C | GLU | A | 105 | 41.807 | 31.788 | 14.851 | 1.00 | 16.31 | C |
| ATOM | 1623 | O | GLU | A | 105 | 42.589 | 31.268 | 14.050 | 1.00 | 16.35 | O |
| ATOM | 1624 | N | TYR | A | 106 | 40.489 | 31.642 | 14.779 | 1.00 | 14.92 | N |
| ATOM | 1626 | CA | TYR | A | 106 | 39.856 | 30.789 | 13.784 | 1.00 | 13.70 | C |
| ATOM | 1628 | CB | TYR | A | 106 | 39.466 | 29.416 | 14.400 | 1.00 | 12.91 | C |
| ATOM | 1631 | CG | TYR | A | 106 | 40.630 | 28.705 | 15.037 | 1.00 | 13.45 | C |
| ATOM | 1632 | CD1 | TYR | A | 106 | 41.441 | 27.863 | 14.296 | 1.00 | 15.31 | C |
| ATOM | 1634 | CE1 | TYR | A | 106 | 42.517 | 27.226 | 14.869 | 1.00 | 15.32 | C |
| ATOM | 1636 | CZ | TYR | A | 106 | 42.812 | 27.428 | 16.186 | 1.00 | 15.25 | C |
| ATOM | 1637 | OH | TYR | A | 106 | 43.904 | 26.776 | 16.728 | 1.00 | 16.78 | O |
| ATOM | 1639 | CE2 | TYR | A | 106 | 42.027 | 28.251 | 16.961 | 1.00 | 15.05 | C |
| ATOM | 1641 | CD2 | TYR | A | 106 | 40.934 | 28.890 | 16.379 | 1.00 | 13.75 | C |
| ATOM | 1643 | C | TYR | A | 106 | 38.605 | 31.460 | 13.230 | 1.00 | 13.16 | C |
| ATOM | 1644 | O | TYR | A | 106 | 37.789 | 31.993 | 14.001 | 1.00 | 12.90 | O |
| ATOM | 1645 | N | ILE | A | 107 | 38.432 | 31.416 | 11.911 | 1.00 | 12.87 | N |
| ATOM | 1647 | CA | ILE | A | 107 | 37.219 | 31.954 | 11.296 | 1.00 | 13.04 | C |
| ATOM | 1649 | CB | ILE | A | 107 | 37.271 | 31.865 | 9.734 | 1.00 | 13.61 | C |
| ATOM | 1651 | CG1 | ILE | A | 107 | 36.049 | 32.531 | 9.105 | 1.00 | 16.08 | C |
| ATOM | 1654 | CD1 | ILE | A | 107 | 36.054 | 33.996 | 9.131 | 1.00 | 19.25 | C |
| ATOM | 1658 | CG2 | ILE | A | 107 | 37.277 | 30.431 | 9.234 | 1.00 | 14.39 | C |
| ATOM | 1662 | C | ILE | A | 107 | 36.026 | 31.203 | 11.890 | 1.00 | 12.69 | C |
| ATOM | 1663 | O | ILE | A | 107 | 36.050 | 29.967 | 11.991 | 1.00 | 12.26 | O |
| ATOM | 1664 | N | ILE | A | 108 | 34.994 | 31.931 | 12.314 | 1.00 | 10.96 | N |
| ATOM | 1666 | CA | ILE | A | 108 | 33.831 | 31.283 | 12.892 | 1.00 | 11.58 | C |

-continued

| APPENDIX C: CRYSTAL COORDINATES OF FVE PROTEIN | | | | | | | | | |
|---|---|---|---|---|---|---|---|---|---|
| ATOM | 1668 | CB | ILE | A | 108 | 33.823 | 31.470 | 14.438 | 1.00 | 11.47 | C |
| ATOM | 1670 | CG1 | ILE | A | 108 | 32.825 | 30.527 | 15.117 | 1.00 | 12.45 | C |
| ATOM | 1673 | CD1 | ILE | A | 108 | 33.138 | 29.042 | 14.913 | 1.00 | 14.07 | C |
| ATOM | 1677 | CG2 | ILE | A | 108 | 33.541 | 32.903 | 14.825 | 1.00 | 11.20 | C |
| ATOM | 1681 | C | ILE | A | 108 | 32.516 | 31.695 | 12.234 | 1.00 | 11.67 | C |
| ATOM | 1682 | O | ILE | A | 108 | 31.510 | 31.041 | 12.437 | 1.00 | 13.19 | O |
| ATOM | 1683 | N | ALA | A | 109 | 32.512 | 32.756 | 11.438 | 1.00 | 11.35 | N |
| ATOM | 1685 | CA | ALA | A | 109 | 31.319 | 33.139 | 10.675 | 1.00 | 12.23 | C |
| ATOM | 1687 | CB | ALA | A | 109 | 30.290 | 33.798 | 11.582 | 1.00 | 12.13 | C |
| ATOM | 1691 | C | ALA | A | 109 | 31.699 | 34.113 | 9.557 | 1.00 | 12.08 | C |
| ATOM | 1692 | O | ALA | A | 109 | 32.648 | 34.879 | 9.714 | 1.00 | 12.05 | O |
| ATOM | 1693 | N | GLU | A | 110 | 30.956 | 34.090 | 8.448 | 1.00 | 13.59 | N |
| ATOM | 1695 | CA | GLU | A | 110 | 31.147 | 35.085 | 7.399 | 1.00 | 13.30 | C |
| ATOM | 1697 | CB | GLU | A | 110 | 32.149 | 34.594 | 6.336 | 1.00 | 14.11 | C |
| ATOM | 1700 | CG | GLU | A | 110 | 32.258 | 35.509 | 5.123 | 1.00 | 15.16 | C |
| ATOM | 1703 | CD | GLU | A | 110 | 33.187 | 34.947 | 4.059 | 1.00 | 18.76 | C |
| ATOM | 1704 | OE1 | GLU | A | 110 | 34.393 | 35.270 | 4.085 | 1.00 | 20.47 | O |
| ATOM | 1705 | OE2 | GLU | A | 110 | 32.706 | 34.165 | 3.204 | 1.00 | 21.90 | O |
| ATOM | 1706 | C | GLU | A | 110 | 29.814 | 35.470 | 6.762 | 1.00 | 13.12 | C |
| ATOM | 1707 | O | GLU | A | 110 | 29.028 | 34.608 | 6.372 | 1.00 | 13.60 | O |
| ATOM | 1708 | N | TRP | A | 111 | 29.559 | 36.772 | 6.709 | 1.00 | 12.93 | N |
| ATOM | 1710 | CA | TRP | A | 111 | 28.420 | 37.335 | 6.032 | 1.00 | 14.60 | C |
| ATOM | 1712 | CB | TRP | A | 111 | 27.809 | 38.507 | 6.808 | 1.00 | 15.14 | C |
| ATOM | 1715 | CG | TRP | A | 111 | 26.726 | 39.127 | 5.988 | 1.00 | 15.69 | C |
| ATOM | 1716 | CD1 | TRP | A | 111 | 26.858 | 40.164 | 5.110 | 1.00 | 16.10 | C |
| ATOM | 1718 | NE1 | TRP | A | 111 | 25.661 | 40.419 | 4.489 | 1.00 | 16.03 | N |
| ATOM | 1720 | CE2 | TRP | A | 111 | 24.727 | 39.530 | 4.949 | 1.00 | 18.16 | C |
| ATOM | 1721 | CD2 | TRP | A | 111 | 25.367 | 38.695 | 5.891 | 1.00 | 18.12 | C |
| ATOM | 1722 | CE3 | TRP | A | 111 | 24.618 | 37.689 | 6.510 | 1.00 | 19.20 | C |
| ATOM | 1724 | CZ3 | TRP | A | 111 | 23.277 | 37.560 | 6.189 | 1.00 | 21.05 | C |
| ATOM | 1726 | CH2 | TRP | A | 111 | 22.673 | 38.410 | 5.255 | 1.00 | 20.77 | C |
| ATOM | 1728 | CZ2 | TRP | A | 111 | 23.382 | 39.397 | 4.626 | 1.00 | 19.73 | C |
| ATOM | 1730 | C | TRP | A | 111 | 28.912 | 37.854 | 4.684 | 1.00 | 16.60 | C |
| ATOM | 1731 | O | TRP | A | 111 | 29.813 | 38.692 | 4.621 | 1.00 | 15.60 | O |
| ATOM | 1732 | N | LYS | A | 112 | 28.344 | 37.323 | 3.618 | 1.00 | 18.75 | N |
| ATOM | 1734 | CA | LYS | A | 112 | 28.630 | 37.843 | 2.288 | 1.00 | 21.69 | C |
| ATOM | 1736 | CB | LYS | A | 112 | 29.829 | 37.176 | 1.651 | 1.00 | 21.83 | C |
| ATOM | 1739 | CG | LYS | A | 112 | 30.317 | 37.972 | 0.444 | 1.00 | 24.07 | C |
| ATOM | 1742 | CD | LYS | A | 112 | 31.330 | 37.217 | −0.360 | 1.00 | 26.81 | C |
| ATOM | 1745 | CE | LYS | A | 112 | 32.648 | 37.120 | 0.351 | 1.00 | 28.67 | C |
| ATOM | 1748 | NZ | LYS | A | 112 | 33.684 | 36.627 | −0.601 | 1.00 | 31.60 | N |
| ATOM | 1752 | C | LYS | A | 112 | 27.394 | 37.622 | 1.452 | 1.00 | 23.68 | C |
| ATOM | 1753 | O | LYS | A | 112 | 27.097 | 36.495 | 1.042 | 1.00 | 24.51 | O |
| ATOM | 1754 | N | LYS | A | 113 | 26.678 | 38.708 | 1.226 | 1.00 | 26.48 | N |
| ATOM | 1756 | CA | LYS | A | 113 | 25.423 | 38.686 | 0.536 | 1.00 | 29.15 | C |
| ATOM | 1758 | CB | LYS | A | 113 | 24.840 | 40.091 | 0.501 | 1.00 | 29.56 | C |
| ATOM | 1761 | CG | LYS | A | 113 | 23.349 | 40.115 | 0.396 | 1.00 | 31.24 | C |
| ATOM | 1764 | CD | LYS | A | 113 | 22.790 | 41.488 | 0.542 | 1.00 | 33.22 | C |
| ATOM | 1767 | CE | LYS | A | 113 | 21.264 | 41.332 | 0.752 | 1.00 | 34.56 | C |
| ATOM | 1770 | NZ | LYS | A | 113 | 20.811 | 40.425 | 1.911 | 1.00 | 34.61 | N |
| ATOM | 1774 | C | LYS | A | 113 | 25.589 | 38.215 | −0.870 | 1.00 | 30.92 | C |
| ATOM | 1775 | O | LYS | A | 113 | 26.581 | 38.511 | −1.536 | 1.00 | 31.06 | O |
| ATOM | 1776 | N | ALA | A | 114 | 24.575 | 37.490 | −1.308 | 1.00 | 33.51 | N |
| ATOM | 1778 | CA | ALA | A | 114 | 24.484 | 37.015 | −2.669 | 1.00 | 34.75 | C |
| ATOM | 1780 | CB | ALA | A | 114 | 25.336 | 35.792 | −2.859 | 1.00 | 35.33 | C |
| ATOM | 1784 | C | ALA | A | 114 | 23.016 | 36.693 | −2.918 | 1.00 | 35.91 | C |
| ATOM | 1785 | O | ALA | A | 114 | 22.275 | 36.373 | −1.973 | 1.00 | 37.33 | O |
| ATOM | 1786 | O | ACE | B | 0 | 45.942 | 19.784 | 14.579 | 1.00 | 39.31 | O |
| ATOM | 1787 | C | ACE | B | 0 | 45.727 | 19.383 | 15.830 | 1.00 | 38.58 | C |
| ATOM | 1788 | CA | ACE | B | 0 | 44.966 | 18.078 | 16.167 | 1.00 | 38.68 | C |
| ATOM | 1789 | N | SER | B | 1 | 45.689 | 20.569 | 16.659 | 1.00 | 19.77 | N |
| ATOM | 1791 | CA | SER | B | 1 | 45.431 | 20.583 | 18.122 | 1.00 | 17.98 | C |
| ATOM | 1793 | CB | SER | B | 1 | 45.842 | 21.915 | 18.761 | 1.00 | 18.61 | C |
| ATOM | 1796 | OG | SER | B | 1 | 44.965 | 22.977 | 18.387 | 1.00 | 16.99 | O |
| ATOM | 1798 | C | SER | B | 1 | 43.950 | 20.368 | 18.350 | 1.00 | 17.78 | C |
| ATOM | 1799 | O | SER | B | 1 | 43.169 | 20.531 | 17.414 | 1.00 | 17.20 | O |
| ATOM | 1802 | N | ALA | B | 2 | 43.575 | 19.905 | 19.539 | 1.00 | 16.87 | N |
| ATOM | 1804 | CA | ALA | B | 2 | 42.161 | 19.821 | 19.902 | 1.00 | 16.13 | C |
| ATOM | 1806 | CB | ALA | B | 2 | 41.991 | 19.439 | 21.370 | 1.00 | 16.68 | C |
| ATOM | 1810 | C | ALA | B | 2 | 41.405 | 21.112 | 19.611 | 1.00 | 15.41 | C |
| ATOM | 1811 | O | ALA | B | 2 | 40.278 | 21.088 | 19.118 | 1.00 | 14.56 | O |
| ATOM | 1812 | N | THR | B | 3 | 42.018 | 22.234 | 19.952 | 1.00 | 15.22 | N |
| ATOM | 1814 | CA | THR | B | 3 | 41.391 | 23.526 | 19.766 | 1.00 | 14.31 | C |
| ATOM | 1816 | CB | THR | B | 3 | 42.264 | 24.598 | 20.403 | 1.00 | 14.74 | C |
| ATOM | 1818 | OG1 | THR | B | 3 | 42.272 | 24.402 | 21.826 | 1.00 | 16.14 | O |
| ATOM | 1820 | CG2 | THR | B | 3 | 41.660 | 25.961 | 20.217 | 1.00 | 14.49 | C |
| ATOM | 1824 | C | THR | B | 3 | 41.194 | 23.813 | 18.295 | 1.00 | 13.68 | C |
| ATOM | 1825 | O | THR | B | 3 | 40.111 | 24.227 | 17.861 | 1.00 | 13.01 | O |

-continued

APPENDIX C: CRYSTAL COORDINATES OF FVE PROTEIN

| ATOM | 1826 | N | SER | B | 4 | 42.231 | 23.568 | 17.505 | 1.00 | 12.92 | N |
|------|------|------|-----|---|----|--------|--------|--------|------|-------|---|
| ATOM | 1828 | CA | SER | B | 4 | 42.114 | 23.823 | 16.074 | 1.00 | 12.63 | C |
| ATOM | 1830 | CB | SER | B | 4 | 43.466 | 23.637 | 15.389 | 1.00 | 13.31 | C |
| ATOM | 1833 | OG | SER | B | 4 | 43.349 | 23.779 | 13.980 | 1.00 | 15.34 | O |
| ATOM | 1835 | C | SER | B | 4 | 41.042 | 22.939 | 15.427 | 1.00 | 11.99 | C |
| ATOM | 1836 | O | SER | B | 4 | 40.232 | 23.408 | 14.613 | 1.00 | 11.15 | O |
| ATOM | 1837 | N | LEU | B | 5 | 41.045 | 21.652 | 15.755 | 1.00 | 11.62 | N |
| ATOM | 1839 | CA | LEU | B | 5 | 40.036 | 20.744 | 15.224 | 1.00 | 10.95 | C |
| ATOM | 1841 | CB | LEU | B | 5 | 40.253 | 19.326 | 15.755 | 1.00 | 11.58 | C |
| ATOM | 1844 | CG | LEU | B | 5 | 41.493 | 18.602 | 15.191 | 1.00 | 13.26 | C |
| ATOM | 1846 | CD1 | LEU | B | 5 | 41.671 | 17.274 | 15.878 | 1.00 | 14.30 | C |
| ATOM | 1850 | CD2 | LEU | B | 5 | 41.430 | 18.388 | 13.679 | 1.00 | 16.20 | C |
| ATOM | 1854 | C | LEU | B | 5 | 38.633 | 21.207 | 15.621 | 1.00 | 10.05 | C |
| ATOM | 1855 | O | LEU | B | 5 | 37.713 | 21.115 | 14.830 | 1.00 | 9.60 | O |
| ATOM | 1856 | N | THR | B | 6 | 38.482 | 21.669 | 16.858 | 1.00 | 9.83 | N |
| ATOM | 1858 | CA | THR | B | 6 | 37.187 | 22.108 | 17.359 | 1.00 | 10.01 | C |
| ATOM | 1860 | CB | THR | B | 6 | 37.300 | 22.622 | 18.794 | 1.00 | 9.92 | C |
| ATOM | 1862 | OG1 | THR | B | 6 | 37.622 | 21.536 | 19.681 | 1.00 | 10.43 | O |
| ATOM | 1864 | CG2 | THR | B | 6 | 35.965 | 23.168 | 19.289 | 1.00 | 9.67 | C |
| ATOM | 1868 | C | THR | B | 6 | 36.616 | 23.197 | 16.490 | 1.00 | 10.19 | C |
| ATOM | 1869 | O | THR | B | 6 | 35.478 | 23.121 | 16.047 | 1.00 | 10.13 | O |
| ATOM | 1870 | N | PHE | B | 7 | 37.416 | 24.217 | 16.232 | 1.00 | 10.95 | N |
| ATOM | 1872 | CA | PHE | B | 7 | 36.898 | 25.372 | 15.532 | 1.00 | 10.37 | C |
| ATOM | 1874 | CB | PHE | B | 7 | 37.576 | 26.643 | 16.024 | 1.00 | 10.33 | C |
| ATOM | 1877 | CG | PHE | B | 7 | 37.149 | 27.021 | 17.415 | 1.00 | 10.12 | C |
| ATOM | 1878 | CD1 | PHE | B | 7 | 35.833 | 27.366 | 17.673 | 1.00 | 10.88 | C |
| ATOM | 1880 | CE1 | PHE | B | 7 | 35.417 | 27.659 | 18.945 | 1.00 | 11.19 | C |
| ATOM | 1882 | CZ | PHE | B | 7 | 36.296 | 27.605 | 19.969 | 1.00 | 11.18 | C |
| ATOM | 1884 | CE2 | PHE | B | 7 | 37.605 | 27.245 | 19.734 | 1.00 | 12.59 | C |
| ATOM | 1886 | CD2 | PHE | B | 7 | 38.021 | 26.936 | 18.466 | 1.00 | 11.83 | C |
| ATOM | 1888 | C | PHE | B | 7 | 36.909 | 25.194 | 14.025 | 1.00 | 10.94 | C |
| ATOM | 1889 | O | PHE | B | 7 | 36.103 | 25.820 | 13.353 | 1.00 | 11.93 | O |
| ATOM | 1890 | N | GLN | B | 8 | 37.767 | 24.329 | 13.489 | 1.00 | 11.93 | N |
| ATOM | 1892 | CA | GLN | B | 8 | 37.647 | 24.010 | 12.067 | 1.00 | 11.34 | C |
| ATOM | 1894 | CB | GLN | B | 8 | 38.761 | 23.087 | 11.621 | 1.00 | 12.48 | C |
| ATOM | 1897 | CG | GLN | B | 8 | 40.113 | 23.720 | 11.528 | 1.00 | 14.22 | C |
| ATOM | 1900 | CD | GLN | B | 8 | 41.117 | 22.698 | 11.051 | 1.00 | 15.81 | C |
| ATOM | 1901 | OE1 | GLN | B | 8 | 42.036 | 22.331 | 11.781 | 1.00 | 19.91 | O |
| ATOM | 1902 | NE2 | GLN | B | 8 | 40.902 | 22.184 | 9.843 | 1.00 | 17.92 | N |
| ATOM | 1905 | C | GLN | B | 8 | 36.316 | 23.286 | 11.855 | 1.00 | 10.37 | C |
| ATOM | 1906 | O | GLN | B | 8 | 35.580 | 23.546 | 10.908 | 1.00 | 10.98 | O |
| ATOM | 1907 | N | LEU | B | 9 | 36.006 | 22.360 | 12.758 | 1.00 | 10.06 | N |
| ATOM | 1909 | CA | LEU | B | 9 | 34.757 | 21.608 | 12.648 | 1.00 | 9.71 | C |
| ATOM | 1911 | CB | LEU | B | 9 | 34.726 | 20.455 | 13.634 | 1.00 | 9.51 | C |
| ATOM | 1914 | CG | LEU | B | 9 | 33.493 | 19.574 | 13.606 | 1.00 | 10.41 | C |
| ATOM | 1916 | CD1 | LEU | B | 9 | 33.447 | 18.825 | 12.265 | 1.00 | 11.23 | C |
| ATOM | 1920 | CD2 | LEU | B | 9 | 33.561 | 18.587 | 14.753 | 1.00 | 9.36 | C |
| ATOM | 1924 | C | LEU | B | 9 | 33.552 | 22.498 | 12.880 | 1.00 | 9.33 | C |
| ATOM | 1925 | O | LEU | B | 9 | 32.566 | 22.409 | 12.160 | 1.00 | 10.21 | O |
| ATOM | 1926 | N | ALA | B | 10 | 33.618 | 23.376 | 13.874 | 1.00 | 9.78 | N |
| ATOM | 1928 | CA | ALA | B | 10 | 32.476 | 24.246 | 14.138 | 1.00 | 9.75 | C |
| ATOM | 1930 | CB | ALA | B | 10 | 32.727 | 25.091 | 15.353 | 1.00 | 10.03 | C |
| ATOM | 1934 | C | ALA | B | 10 | 32.145 | 25.126 | 12.919 | 1.00 | 9.57 | C |
| ATOM | 1935 | O | ALA | B | 10 | 30.982 | 25.275 | 12.554 | 1.00 | 8.63 | O |
| ATOM | 1936 | N | TYR | B | 11 | 33.155 | 25.688 | 12.269 | 1.00 | 9.75 | N |
| ATOM | 1938 | CA | TYR | B | 11 | 32.885 | 26.566 | 11.136 | 1.00 | 10.72 | C |
| ATOM | 1940 | CB | TYR | B | 11 | 34.159 | 27.237 | 10.688 | 1.00 | 10.48 | C |
| ATOM | 1943 | CG | TYR | B | 11 | 33.979 | 28.188 | 9.535 | 1.00 | 11.27 | C |
| ATOM | 1944 | CD1 | TYR | B | 11 | 34.664 | 27.988 | 8.352 | 1.00 | 11.30 | C |
| ATOM | 1946 | CE1 | TYR | B | 11 | 34.534 | 28.867 | 7.292 | 1.00 | 13.85 | C |
| ATOM | 1948 | CZ | TYR | B | 11 | 33.706 | 29.949 | 7.409 | 1.00 | 14.97 | C |
| ATOM | 1949 | OH | TYR | B | 11 | 33.579 | 30.827 | 6.350 | 1.00 | 16.32 | O |
| ATOM | 1951 | CE2 | TYR | B | 11 | 33.022 | 30.183 | 8.582 | 1.00 | 14.29 | C |
| ATOM | 1953 | CD2 | TYR | B | 11 | 33.159 | 29.300 | 9.640 | 1.00 | 12.05 | C |
| ATOM | 1955 | C | TYR | B | 11 | 32.250 | 25.801 | 9.987 | 1.00 | 11.09 | C |
| ATOM | 1956 | O | TYR | B | 11 | 31.380 | 26.310 | 9.272 | 1.00 | 11.19 | O |
| ATOM | 1957 | N | LEU | B | 12 | 32.672 | 24.556 | 9.823 | 1.00 | 12.21 | N |
| ATOM | 1959 | CA | LEU | B | 12 | 32.179 | 23.730 | 8.742 | 1.00 | 12.45 | C |
| ATOM | 1961 | CB | LEU | B | 12 | 33.187 | 22.614 | 8.470 | 1.00 | 12.95 | C |
| ATOM | 1964 | CG | LEU | B | 12 | 33.011 | 21.779 | 7.209 | 1.00 | 16.64 | C |
| ATOM | 1966 | CD1 | LEU | B | 12 | 32.907 | 22.662 | 5.962 | 1.00 | 17.27 | C |
| ATOM | 1970 | CD2 | LEU | B | 12 | 34.193 | 20.804 | 7.093 | 1.00 | 18.06 | C |
| ATOM | 1974 | C | LEU | B | 12 | 30.767 | 23.156 | 8.956 | 1.00 | 12.37 | C |
| ATOM | 1975 | O | LEU | B | 12 | 29.914 | 23.302 | 8.071 | 1.00 | 13.09 | O |
| ATOM | 1976 | N | VAL | B | 13 | 30.514 | 22.525 | 10.103 | 1.00 | 12.47 | N |
| ATOM | 1978 | CA | VAL | B | 13 | 29.256 | 21.805 | 10.335 | 1.00 | 12.51 | C |
| ATOM | 1980 | CB | VAL | B | 13 | 29.485 | 20.381 | 10.894 | 1.00 | 13.37 | C |
| ATOM | 1982 | CG1 | VAL | B | 13 | 30.492 | 19.620 | 10.042 | 1.00 | 15.30 | C |

-continued

| APPENDIX C: CRYSTAL COORDINATES OF FVE PROTEIN | | | | | | | | | |
|---|---|---|---|---|---|---|---|---|---|
| ATOM | 1986 | CG2 | VAL | B | 13 | 29.922 | 20.398 | 12.336 | 1.00 14.08 C |
| ATOM | 1990 | C | VAL | B | 13 | 28.273 | 22.541 | 11.237 | 1.00 12.00 C |
| ATOM | 1991 | O | VAL | B | 13 | 27.106 | 22.172 | 11.319 | 1.00 11.68 O |
| ATOM | 1992 | N | LYS | B | 14 | 28.775 | 23.558 | 11.917 | 1.00 11.40 N |
| ATOM | 1994 | CA | LYS | B | 14 | 27.991 | 24.459 | 12.764 | 1.00 11.19 C |
| ATOM | 1996 | CB | LYS | B | 14 | 26.759 | 25.042 | 12.035 | 1.00 11.48 C |
| ATOM | 1999 | CG | LYS | B | 14 | 27.039 | 25.761 | 10.731 | 1.00 11.14 C |
| ATOM | 2002 | CD | LYS | B | 14 | 28.190 | 26.750 | 10.824 | 1.00 9.92 C |
| ATOM | 2005 | CE | LYS | B | 14 | 28.422 | 27.540 | 9.526 | 1.00 10.31 C |
| ATOM | 2008 | NZ | LYS | B | 14 | 29.602 | 28.448 | 9.653 | 1.00 12.24 N |
| ATOM | 2012 | C | LYS | B | 14 | 27.549 | 23.850 | 14.104 | 1.00 10.98 C |
| ATOM | 2013 | O | LYS | B | 14 | 27.795 | 24.432 | 15.165 | 1.00 10.55 O |
| ATOM | 2014 | N | LYS | B | 15 | 26.914 | 22.684 | 14.069 | 1.00 10.86 N |
| ATOM | 2016 | CA | LYS | B | 15 | 26.282 | 22.127 | 15.256 | 1.00 12.66 C |
| ATOM | 2018 | CB | LYS | B | 15 | 24.753 | 22.337 | 15.149 | 1.00 13.78 C |
| ATOM | 2021 | CG | LYS | B | 15 | 23.878 | 21.739 | 16.237 | 1.00 18.00 C |
| ATOM | 2024 | CD | LYS | B | 15 | 22.382 | 22.146 | 16.068 | 1.00 23.19 C |
| ATOM | 2027 | CE | LYS | B | 15 | 21.671 | 21.394 | 14.921 | 1.00 27.17 C |
| ATOM | 2030 | NZ | LYS | B | 15 | 20.279 | 21.902 | 14.547 | 1.00 34.39 N |
| ATOM | 2034 | C | LYS | B | 15 | 26.637 | 20.640 | 15.355 | 1.00 12.47 C |
| ATOM | 2035 | O | LYS | B | 15 | 26.526 | 19.913 | 14.363 | 1.00 13.03 O |
| ATOM | 2036 | N | ILE | B | 16 | 27.094 | 20.207 | 16.526 | 1.00 13.16 N |
| ATOM | 2038 | CA | ILE | B | 16 | 27.368 | 18.784 | 16.760 | 1.00 12.11 C |
| ATOM | 2040 | CB | ILE | B | 16 | 28.707 | 18.380 | 16.149 | 1.00 12.61 C |
| ATOM | 2042 | CG1 | ILE | B | 16 | 28.660 | 16.894 | 15.756 | 1.00 13.09 C |
| ATOM | 2045 | CD1 | ILE | B | 16 | 29.822 | 16.447 | 14.941 | 1.00 14.91 C |
| ATOM | 2049 | CG2 | ILE | B | 16 | 29.831 | 18.704 | 17.105 | 1.00 12.04 C |
| ATOM | 2053 | C | ILE | B | 16 | 27.276 | 18.487 | 18.258 | 1.00 12.09 C |
| ATOM | 2054 | O | ILE | B | 16 | 27.516 | 19.360 | 19.098 | 1.00 11.30 O |
| ATOM | 2055 | N | ASP | B | 17 | 26.903 | 17.257 | 18.587 | 1.00 11.37 N |
| ATOM | 2057 | CA | ASP | B | 17 | 26.701 | 16.850 | 19.977 | 1.00 11.97 C |
| ATOM | 2059 | CB | ASP | B | 17 | 25.238 | 17.060 | 20.347 | 1.00 12.19 C |
| ATOM | 2062 | CG | ASP | B | 17 | 24.929 | 16.770 | 21.795 | 1.00 15.47 C |
| ATOM | 2063 | OD1 | ASP | B | 17 | 25.834 | 16.488 | 22.602 | 1.00 15.71 O |
| ATOM | 2064 | OD2 | ASP | B | 17 | 23.746 | 16.838 | 22.212 | 1.00 21.94 O |
| ATOM | 2065 | C | ASP | B | 17 | 27.026 | 15.373 | 20.040 | 1.00 11.79 C |
| ATOM | 2066 | O | ASP | B | 17 | 26.246 | 14.552 | 19.554 | 1.00 12.85 O |
| ATOM | 2067 | N | PHE | B | 18 | 28.190 | 15.029 | 20.566 | 1.00 10.57 N |
| ATOM | 2069 | CA | PHE | B | 18 | 28.552 | 13.620 | 20.686 | 1.00 10.47 C |
| ATOM | 2071 | CB | PHE | B | 18 | 29.385 | 13.115 | 19.479 | 1.00 9.71 C |
| ATOM | 2074 | CG | PHE | B | 18 | 30.728 | 13.797 | 19.316 | 1.00 9.88 C |
| ATOM | 2075 | CD1 | PHE | B | 18 | 31.732 | 13.663 | 20.275 | 1.00 7.77 C |
| ATOM | 2077 | CE1 | PHE | B | 18 | 32.936 | 14.318 | 20.131 | 1.00 9.85 C |
| ATOM | 2079 | CZ | PHE | B | 18 | 33.172 | 15.094 | 19.013 | 1.00 10.47 C |
| ATOM | 2081 | CE2 | PHE | B | 18 | 32.194 | 15.226 | 18.062 | 1.00 9.60 C |
| ATOM | 2083 | CD2 | PHE | B | 18 | 30.979 | 14.584 | 18.211 | 1.00 9.21 C |
| ATOM | 2085 | C | PHE | B | 18 | 29.281 | 13.324 | 21.983 | 1.00 9.72 C |
| ATOM | 2086 | O | PHE | B | 18 | 29.760 | 14.220 | 22.691 | 1.00 10.09 O |
| ATOM | 2087 | N | ASP | B | 19 | 29.326 | 12.041 | 22.306 | 1.00 9.08 N |
| ATOM | 2089 | CA | ASP | B | 19 | 30.050 | 11.562 | 23.459 | 1.00 9.72 C |
| ATOM | 2091 | CB | ASP | B | 19 | 29.193 | 11.549 | 24.716 | 1.00 9.54 C |
| ATOM | 2094 | CG | ASP | B | 19 | 29.999 | 11.225 | 25.937 | 1.00 11.36 C |
| ATOM | 2095 | OD1 | ASP | B | 19 | 29.498 | 11.408 | 27.093 | 1.00 13.80 O |
| ATOM | 2096 | OD2 | ASP | B | 19 | 31.149 | 10.767 | 25.834 | 1.00 10.64 O |
| ATOM | 2097 | C | ASP | B | 19 | 30.543 | 10.155 | 23.160 | 1.00 9.57 C |
| ATOM | 2098 | O | ASP | B | 19 | 29.765 | 9.177 | 23.218 | 1.00 10.53 O |
| ATOM | 2099 | N | TYR | B | 20 | 31.830 | 10.085 | 22.813 | 1.00 9.01 N |
| ATOM | 2101 | CA | TYR | B | 20 | 32.505 | 8.831 | 22.518 | 1.00 8.11 C |
| ATOM | 2103 | CB | TYR | B | 20 | 33.232 | 8.896 | 21.163 | 1.00 7.80 C |
| ATOM | 2106 | CG | TYR | B | 20 | 32.292 | 8.800 | 19.966 | 1.00 7.18 C |
| ATOM | 2107 | CD1 | TYR | B | 20 | 31.765 | 9.933 | 19.381 | 1.00 8.23 C |
| ATOM | 2109 | CE1 | TYR | B | 20 | 30.897 | 9.849 | 18.286 | 1.00 8.63 C |
| ATOM | 2111 | CZ | TYR | B | 20 | 30.570 | 8.623 | 17.777 | 1.00 8.76 C |
| ATOM | 2112 | OH | TYR | B | 20 | 29.690 | 8.504 | 16.698 | 1.00 7.11 O |
| ATOM | 2114 | CE2 | TYR | B | 20 | 31.081 | 7.492 | 18.358 | 1.00 7.59 C |
| ATOM | 2116 | CD2 | TYR | B | 20 | 31.929 | 7.580 | 19.435 | 1.00 8.21 C |
| ATOM | 2118 | C | TYR | B | 20 | 33.453 | 8.446 | 23.657 | 1.00 7.82 C |
| ATOM | 2119 | O | TYR | B | 20 | 34.453 | 7.777 | 23.416 | 1.00 8.72 O |
| ATOM | 2120 | N | THR | B | 21 | 33.128 | 8.834 | 24.892 | 1.00 8.34 N |
| ATOM | 2122 | CA | THR | B | 21 | 33.897 | 8.365 | 26.046 | 1.00 8.81 C |
| ATOM | 2124 | CB | THR | B | 21 | 33.320 | 8.922 | 27.334 | 1.00 9.96 C |
| ATOM | 2126 | OG1 | THR | B | 21 | 33.372 | 10.363 | 27.299 | 1.00 10.43 O |
| ATOM | 2128 | CG2 | THR | B | 21 | 34.222 | 8.512 | 28.491 | 1.00 9.86 C |
| ATOM | 2132 | C | THR | B | 21 | 33.804 | 6.831 | 26.040 | 1.00 9.35 C |
| ATOM | 2133 | O | THR | B | 21 | 32.692 | 6.291 | 26.011 | 1.00 9.22 O |
| ATOM | 2134 | N | PRO | B | 22 | 34.922 | 6.111 | 26.025 | 1.00 9.19 N |
| ATOM | 2135 | CA | PRO | B | 22 | 34.844 | 4.647 | 25.905 | 1.00 9.50 C |
| ATOM | 2137 | CB | PRO | B | 22 | 36.209 | 4.280 | 25.352 | 1.00 9.82 C |

APPENDIX C: CRYSTAL COORDINATES OF FVE PROTEIN

| ATOM | 2140 | CG | PRO | B | 22 | 37.138 | 5.334 | 25.941 | 1.00 | 9.26 | C |
|---|---|---|---|---|---|---|---|---|---|---|---|
| ATOM | 2143 | CD | PRO | B | 22 | 36.320 | 6.589 | 26.015 | 1.00 | 9.34 | C |
| ATOM | 2146 | C | PRO | B | 22 | 34.616 | 3.930 | 27.227 | 1.00 | 10.16 | C |
| ATOM | 2147 | O | PRO | B | 22 | 35.520 | 3.898 | 28.070 | 1.00 | 10.91 | O |
| ATOM | 2148 | N | ASN | B | 23 | 33.413 | 3.394 | 27.413 | 1.00 | 10.40 | N |
| ATOM | 2150 | CA | ASN | B | 23 | 33.082 | 2.645 | 28.614 | 1.00 | 10.53 | C |
| ATOM | 2152 | CB | ASN | B | 23 | 31.680 | 3.014 | 29.089 | 1.00 | 11.14 | C |
| ATOM | 2155 | CG | ASN | B | 23 | 31.595 | 4.472 | 29.590 | 1.00 | 13.44 | C |
| ATOM | 2156 | OD1 | ASN | B | 23 | 31.816 | 4.721 | 30.763 | 1.00 | 19.39 | O |
| ATOM | 2157 | ND2 | ASN | B | 23 | 31.342 | 5.441 | 28.685 | 1.00 | 14.28 | N |
| ATOM | 2160 | C | ASN | B | 23 | 33.228 | 1.143 | 28.312 | 1.00 | 9.85 | C |
| ATOM | 2161 | O | ASN | B | 23 | 32.489 | 0.595 | 27.483 | 1.00 | 10.11 | O |
| ATOM | 2162 | N | TRP | B | 24 | 34.208 | 0.502 | 28.942 | 1.00 | 8.96 | N |
| ATOM | 2164 | CA | TRP | B | 24 | 34.524 | −0.899 | 28.684 | 1.00 | 8.99 | C |
| ATOM | 2166 | CB | TRP | B | 24 | 36.032 | −1.117 | 28.760 | 1.00 | 8.98 | C |
| ATOM | 2169 | CG | TRP | B | 24 | 36.799 | −0.256 | 27.823 | 1.00 | 8.22 | C |
| ATOM | 2170 | CD1 | TRP | B | 24 | 37.375 | 0.965 | 28.116 | 1.00 | 9.52 | C |
| ATOM | 2172 | NE1 | TRP | B | 24 | 38.003 | 1.469 | 27.000 | 1.00 | 9.37 | N |
| ATOM | 2174 | CE2 | TRP | B | 24 | 37.860 | 0.574 | 25.967 | 1.00 | 9.60 | C |
| ATOM | 2175 | CD2 | TRP | B | 24 | 37.099 | −0.517 | 26.446 | 1.00 | 9.21 | C |
| ATOM | 2176 | CE3 | TRP | B | 24 | 36.824 | −1.577 | 25.560 | 1.00 | 9.09 | C |
| ATOM | 2178 | CZ3 | TRP | B | 24 | 37.292 | −1.502 | 24.264 | 1.00 | 9.03 | C |
| ATOM | 2180 | CH2 | TRP | B | 24 | 38.045 | −0.414 | 23.829 | 1.00 | 7.76 | C |
| ATOM | 2182 | CZ2 | TRP | B | 24 | 38.337 | 0.636 | 24.661 | 1.00 | 8.73 | C |
| ATOM | 2184 | C | TRP | B | 24 | 33.806 | −1.771 | 29.715 | 1.00 | 10.09 | C |
| ATOM | 2185 | O | TRP | B | 24 | 34.024 | −1.610 | 30.922 | 1.00 | 11.35 | O |
| ATOM | 2186 | N | GLY | B | 25 | 32.931 | −2.655 | 29.234 | 1.00 | 10.43 | N |
| ATOM | 2188 | CA | GLY | B | 25 | 32.143 | −3.516 | 30.098 | 1.00 | 9.95 | C |
| ATOM | 2191 | C | GLY | B | 25 | 32.749 | −4.894 | 30.176 | 1.00 | 10.10 | C |
| ATOM | 2192 | O | GLY | B | 25 | 33.220 | −5.444 | 29.184 | 1.00 | 10.44 | O |
| ATOM | 2193 | N | ARG | B | 26 | 32.721 | −5.470 | 31.372 | 1.00 | 9.91 | N |
| ATOM | 2195 | CA | ARG | B | 26 | 33.393 | −6.738 | 31.594 | 1.00 | 10.74 | C |
| ATOM | 2197 | CB | ARG | B | 26 | 34.185 | −6.692 | 32.897 | 1.00 | 11.28 | C |
| ATOM | 2200 | CG | ARG | B | 26 | 35.418 | −5.792 | 32.764 | 1.00 | 14.61 | C |
| ATOM | 2203 | CD | ARG | B | 26 | 36.168 | −5.505 | 34.025 | 1.00 | 18.47 | C |
| ATOM | 2206 | NE | ARG | B | 26 | 37.353 | −4.694 | 33.713 | 1.00 | 22.81 | N |
| ATOM | 2208 | CZ | ARG | B | 26 | 38.526 | −5.167 | 33.274 | 1.00 | 20.92 | C |
| ATOM | 2209 | NH1 | ARG | B | 26 | 38.730 | −6.471 | 33.093 | 1.00 | 16.47 | N |
| ATOM | 2212 | NH2 | ARG | B | 26 | 39.522 | −4.318 | 33.028 | 1.00 | 21.83 | N |
| ATOM | 2215 | C | ARG | B | 26 | 32.431 | −7.898 | 31.604 | 1.00 | 11.12 | C |
| ATOM | 2216 | O | ARG | B | 26 | 31.227 | −7.721 | 31.802 | 1.00 | 11.55 | O |
| ATOM | 2217 | N | GLY | B | 27 | 32.990 | −9.082 | 31.405 | 1.00 | 10.76 | N |
| ATOM | 2219 | CA | GLY | B | 27 | 32.203 | −10.305 | 31.337 | 1.00 | 11.53 | C |
| ATOM | 2222 | C | GLY | B | 27 | 32.382 | −11.170 | 32.553 | 1.00 | 12.49 | C |
| ATOM | 2223 | O | GLY | B | 27 | 32.588 | −10.677 | 33.664 | 1.00 | 11.38 | O |
| ATOM | 2224 | N | THR | B | 28 | 32.285 | −12.468 | 32.308 | 1.00 | 14.02 | N |
| ATOM | 2226 | CA | THR | B | 28 | 32.361 | −13.494 | 33.325 | 1.00 | 14.82 | C |
| ATOM | 2228 | CB | THR | B | 28 | 30.965 | −14.118 | 33.495 | 1.00 | 14.80 | C |
| ATOM | 2230 | OG1 | THR | B | 28 | 30.052 | −13.151 | 34.032 | 1.00 | 15.92 | O |
| ATOM | 2232 | CG2 | THR | B | 28 | 30.974 | −15.235 | 34.519 | 1.00 | 16.05 | C |
| ATOM | 2236 | C | THR | B | 28 | 33.327 | −14.552 | 32.828 | 1.00 | 15.01 | C |
| ATOM | 2237 | O | THR | B | 28 | 33.037 | −15.215 | 31.838 | 1.00 | 15.21 | O |
| ATOM | 2238 | N | PRO | B | 29 | 34.490 | −14.700 | 33.454 | 1.00 | 16.30 | N |
| ATOM | 2239 | CA | PRO | B | 29 | 34.948 | −13.877 | 34.569 | 1.00 | 16.04 | C |
| ATOM | 2241 | CB | PRO | B | 29 | 36.219 | −14.575 | 35.028 | 1.00 | 16.47 | C |
| ATOM | 2244 | CG | PRO | B | 29 | 36.636 | −15.376 | 33.917 | 1.00 | 16.57 | C |
| ATOM | 2247 | CD | PRO | B | 29 | 35.467 | −15.724 | 33.083 | 1.00 | 16.58 | C |
| ATOM | 2250 | C | PRO | B | 29 | 35.286 | −12.472 | 34.156 | 1.00 | 15.67 | C |
| ATOM | 2251 | O | PRO | B | 29 | 35.396 | −12.161 | 32.977 | 1.00 | 14.52 | O |
| ATOM | 2252 | N | SER | B | 30 | 35.477 | −11.643 | 35.164 | 1.00 | 15.56 | N |
| ATOM | 2254 | CA | SER | B | 30 | 35.592 | −10.188 | 34.990 | 1.00 | 15.79 | C |
| ATOM | 2256 | CB | SER | B | 30 | 35.368 | −9.479 | 36.338 | 1.00 | 16.72 | C |
| ATOM | 2259 | OG | SER | B | 30 | 36.454 | −9.647 | 37.224 | 1.00 | 19.27 | O |
| ATOM | 2261 | C | SER | B | 30 | 36.886 | −9.718 | 34.319 | 1.00 | 15.13 | C |
| ATOM | 2262 | O | SER | B | 30 | 37.028 | −8.535 | 33.981 | 1.00 | 14.89 | O |
| ATOM | 2263 | N | SER | B | 31 | 37.813 | −10.644 | 34.117 | 1.00 | 15.18 | N |
| ATOM | 2265 | CA | SER | B | 31 | 39.073 | −10.365 | 33.451 | 1.00 | 14.92 | C |
| ATOM | 2267 | CB | SER | B | 31 | 40.078 | −11.489 | 33.743 | 1.00 | 15.53 | C |
| ATOM | 2270 | OG | SER | B | 31 | 39.588 | −12.751 | 33.330 | 1.00 | 16.71 | O |
| ATOM | 2272 | C | SER | B | 31 | 38.833 | −10.220 | 31.958 | 1.00 | 14.13 | C |
| ATOM | 2273 | O | SER | B | 31 | 39.704 | −9.755 | 31.247 | 1.00 | 14.11 | O |
| ATOM | 2274 | N | TYR | B | 32 | 37.655 | −10.629 | 31.492 | 1.00 | 13.25 | N |
| ATOM | 2276 | CA | TYR | B | 32 | 37.263 | −10.430 | 30.088 | 1.00 | 12.84 | C |
| ATOM | 2278 | CB | TYR | B | 32 | 36.386 | −11.579 | 29.595 | 1.00 | 13.42 | C |
| ATOM | 2281 | CG | TYR | B | 32 | 37.194 | −12.849 | 29.494 | 1.00 | 17.98 | C |
| ATOM | 2282 | CD1 | TYR | B | 32 | 37.301 | −13.710 | 30.586 | 1.00 | 22.94 | C |
| ATOM | 2284 | CE1 | TYR | B | 32 | 38.065 | −14.852 | 30.521 | 1.00 | 23.98 | C |
| ATOM | 2286 | CZ | TYR | B | 32 | 38.746 | −15.143 | 29.354 | 1.00 | 25.27 | C |

-continued

| | | | | APPENDIX C: CRYSTAL COORDINATES OF FVE PROTEIN | | | | | |
|---|---|---|---|---|---|---|---|---|---|
| ATOM | 2287 | OH | TYR | B | 32 | 39.505 | −16.288 | 29.289 | 1.00 | 27.54 O |
| ATOM | 2289 | CE2 | TYR | B | 32 | 38.663 | −14.298 | 28.266 | 1.00 | 23.63 C |
| ATOM | 2291 | CD2 | TYR | B | 32 | 37.895 | −13.159 | 28.344 | 1.00 | 21.29 C |
| ATOM | 2293 | C | TYR | B | 32 | 36.533 | −9.112 | 29.846 | 1.00 | 11.60 C |
| ATOM | 2294 | O | TYR | B | 32 | 35.685 | −8.695 | 30.647 | 1.00 | 10.60 O |
| ATOM | 2295 | N | ILE | B | 33 | 36.880 | −8.444 | 28.745 | 1.00 | 10.45 N |
| ATOM | 2297 | CA | ILE | B | 33 | 36.165 | −7.242 | 28.298 | 1.00 | 10.39 C |
| ATOM | 2299 | CB | ILE | B | 33 | 37.144 | −6.198 | 27.724 | 1.00 | 10.57 C |
| ATOM | 2301 | CG1 | ILE | B | 33 | 38.031 | −5.676 | 28.860 | 1.00 | 13.06 C |
| ATOM | 2304 | CD1 | ILE | B | 33 | 39.008 | −4.662 | 28.440 | 1.00 | 16.01 C |
| ATOM | 2308 | CG2 | ILE | B | 33 | 36.395 | −5.062 | 26.975 | 1.00 | 10.92 C |
| ATOM | 2312 | C | ILE | B | 33 | 35.178 | −7.715 | 27.237 | 1.00 | 9.65 C |
| ATOM | 2313 | O | ILE | B | 33 | 35.595 | −8.249 | 26.202 | 1.00 | 8.88 O |
| ATOM | 2314 | N | ASP | B | 34 | 33.883 | −7.580 | 27.498 | 1.00 | 9.91 N |
| ATOM | 2316 | CA | ASP | B | 34 | 32.857 | −8.063 | 26.583 | 1.00 | 9.11 C |
| ATOM | 2318 | CB | ASP | B | 34 | 31.665 | −8.615 | 27.367 | 1.00 | 9.19 C |
| ATOM | 2321 | CG | ASP | B | 34 | 31.881 | −10.030 | 27.892 | 1.00 | 11.22 C |
| ATOM | 2322 | OD1 | ASP | B | 34 | 33.013 | −10.576 | 27.882 | 1.00 | 10.96 O |
| ATOM | 2323 | OD2 | ASP | B | 34 | 30.916 | −10.660 | 28.362 | 1.00 | 11.64 O |
| ATOM | 2324 | C | ASP | B | 34 | 32.306 | −7.017 | 25.640 | 1.00 | 9.26 C |
| ATOM | 2325 | O | ASP | B | 34 | 31.726 | −7.362 | 24.616 | 1.00 | 8.27 O |
| ATOM | 2326 | N | ASN | B | 35 | 32.465 | −5.740 | 25.959 | 1.00 | 9.55 N |
| ATOM | 2328 | CA | ASN | B | 35 | 31.791 | −4.730 | 25.152 | 1.00 | 8.99 C |
| ATOM | 2330 | CB | ASN | B | 35 | 30.278 | −4.762 | 25.446 | 1.00 | 9.72 C |
| ATOM | 2333 | CG | ASN | B | 35 | 29.970 | −4.723 | 26.949 | 1.00 | 11.37 C |
| ATOM | 2334 | OD1 | ASN | B | 35 | 29.559 | −5.741 | 27.574 | 1.00 | 14.30 O |
| ATOM | 2335 | ND2 | ASN | B | 35 | 30.186 | −3.573 | 27.551 | 1.00 | 7.97 N |
| ATOM | 2338 | C | ASN | B | 35 | 32.351 | −3.341 | 25.400 | 1.00 | 9.17 C |
| ATOM | 2339 | O | ASN | B | 35 | 33.129 | −3.115 | 26.332 | 1.00 | 9.29 O |
| ATOM | 2340 | N | LEU | B | 36 | 31.917 | −2.413 | 24.552 | 1.00 | 9.41 N |
| ATOM | 2342 | CA | LEU | B | 36 | 32.345 | −1.026 | 24.581 | 1.00 | 9.12 C |
| ATOM | 2344 | CB | LEU | B | 36 | 33.308 | −0.779 | 23.414 | 1.00 | 8.17 C |
| ATOM | 2347 | CG | LEU | B | 36 | 33.652 | 0.670 | 23.053 | 1.00 | 9.08 C |
| ATOM | 2349 | CD1 | LEU | B | 36 | 34.294 | 1.387 | 24.199 | 1.00 | 9.44 C |
| ATOM | 2353 | CD2 | LEU | B | 36 | 34.560 | 0.729 | 21.837 | 1.00 | 10.64 C |
| ATOM | 2357 | C | LEU | B | 36 | 31.099 | −0.186 | 24.369 | 1.00 | 9.10 C |
| ATOM | 2358 | O | LEU | B | 36 | 30.382 | −0.391 | 23.385 | 1.00 | 8.92 O |
| ATOM | 2359 | N | THR | B | 37 | 30.824 | 0.737 | 25.279 | 1.00 | 9.13 N |
| ATOM | 2361 | CA | THR | B | 37 | 29.653 | 1.596 | 25.151 | 1.00 | 8.93 C |
| ATOM | 2363 | CB | THR | B | 37 | 28.725 | 1.447 | 26.372 | 1.00 | 9.51 C |
| ATOM | 2365 | OG1 | THR | B | 37 | 28.238 | 0.095 | 26.458 | 1.00 | 10.29 O |
| ATOM | 2367 | CG2 | THR | B | 37 | 27.474 | 2.316 | 26.234 | 1.00 | 10.22 C |
| ATOM | 2371 | C | THR | B | 37 | 30.041 | 3.056 | 25.034 | 1.00 | 8.89 C |
| ATOM | 2372 | O | THR | B | 37 | 30.857 | 3.557 | 25.814 | 1.00 | 8.97 O |
| ATOM | 2373 | N | PHE | B | 38 | 29.450 | 3.724 | 24.042 | 1.00 | 7.97 N |
| ATOM | 2375 | CA | PHE | B | 38 | 29.584 | 5.161 | 23.853 | 1.00 | 8.58 C |
| ATOM | 2377 | CB | PHE | B | 38 | 29.827 | 5.456 | 22.386 | 1.00 | 8.85 C |
| ATOM | 2380 | CG | PHE | B | 38 | 31.134 | 4.951 | 21.847 | 1.00 | 7.28 C |
| ATOM | 2381 | CD1 | PHE | B | 38 | 32.340 | 5.237 | 22.482 | 1.00 | 7.91 C |
| ATOM | 2383 | CE1 | PHE | B | 38 | 33.544 | 4.811 | 21.942 | 1.00 | 8.72 C |
| ATOM | 2385 | CZ | PHE | B | 38 | 33.555 | 4.102 | 20.756 | 1.00 | 11.58 C |
| ATOM | 2387 | CE2 | PHE | B | 38 | 32.366 | 3.817 | 20.120 | 1.00 | 9.53 C |
| ATOM | 2389 | CD2 | PHE | B | 38 | 31.163 | 4.243 | 20.661 | 1.00 | 7.95 C |
| ATOM | 2391 | C | PHE | B | 38 | 28.269 | 5.844 | 24.273 | 1.00 | 8.73 C |
| ATOM | 2392 | O | PHE | B | 38 | 27.216 | 5.431 | 23.811 | 1.00 | 9.98 O |
| ATOM | 2393 | N | PRO | B | 39 | 28.293 | 6.842 | 25.163 | 1.00 | 8.76 N |
| ATOM | 2394 | CA | PRO | B | 39 | 27.036 | 7.460 | 25.636 | 1.00 | 8.86 C |
| ATOM | 2396 | CB | PRO | B | 39 | 27.497 | 8.386 | 26.780 | 1.00 | 9.34 C |
| ATOM | 2399 | CG | PRO | B | 39 | 28.785 | 7.866 | 27.199 | 1.00 | 9.35 C |
| ATOM | 2402 | CD | PRO | B | 39 | 29.448 | 7.348 | 25.916 | 1.00 | 9.58 C |
| ATOM | 2405 | C | PRO | B | 39 | 26.209 | 8.230 | 24.627 | 1.00 | 9.13 C |
| ATOM | 2406 | O | PRO | B | 39 | 24.991 | 8.328 | 24.796 | 1.00 | 8.44 O |
| ATOM | 2407 | N | LYS | B | 40 | 26.834 | 8.794 | 23.602 | 1.00 | 9.49 N |
| ATOM | 2409 | CA | LYS | B | 40 | 26.061 | 9.548 | 22.618 | 1.00 | 9.43 C |
| ATOM | 2411 | CB | LYS | B | 40 | 25.784 | 10.967 | 23.094 | 1.00 | 10.36 C |
| ATOM | 2414 | CG | LYS | B | 40 | 24.760 | 11.685 | 22.232 | 1.00 | 12.43 C |
| ATOM | 2417 | CD | LYS | B | 40 | 24.661 | 13.182 | 22.550 | 1.00 | 16.76 C |
| ATOM | 2420 | CE | LYS | B | 40 | 24.030 | 13.456 | 23.916 | 1.00 | 22.56 C |
| ATOM | 2423 | NZ | LYS | B | 40 | 24.148 | 14.904 | 24.336 | 1.00 | 28.45 N |
| ATOM | 2427 | C | LYS | B | 40 | 26.748 | 9.529 | 21.265 | 1.00 | 9.14 C |
| ATOM | 2428 | O | LYS | B | 40 | 27.597 | 10.355 | 20.962 | 1.00 | 9.57 O |
| ATOM | 2429 | N | VAL | B | 41 | 26.393 | 8.544 | 20.458 | 1.00 | 9.12 N |
| ATOM | 2431 | CA | VAL | B | 41 | 26.969 | 8.438 | 19.131 | 1.00 | 9.08 C |
| ATOM | 2433 | CB | VAL | B | 41 | 26.967 | 6.970 | 18.603 | 1.00 | 9.12 C |
| ATOM | 2435 | CG1 | VAL | B | 41 | 27.769 | 6.059 | 19.553 | 1.00 | 8.74 C |
| ATOM | 2439 | CG2 | VAL | B | 41 | 25.556 | 6.453 | 18.410 | 1.00 | 8.61 C |
| ATOM | 2443 | C | VAL | B | 41 | 26.243 | 9.323 | 18.136 | 1.00 | 9.87 C |
| ATOM | 2444 | O | VAL | B | 41 | 25.107 | 9.759 | 18.350 | 1.00 | 9.30 O |

-continued

| APPENDIX C: CRYSTAL COORDINATES OF FVE PROTEIN | | | | | | | | | |
|---|---|---|---|---|---|---|---|---|---|
| ATOM | 2445 | N | LEU | B | 42 | 26.907 | 9.582 | 17.022 | 1.00 | 10.23 N |
| ATOM | 2447 | CA | LEU | B | 42 | 26.261 | 10.288 | 15.932 | 1.00 | 11.90 C |
| ATOM | 2449 | CB | LEU | B | 42 | 27.303 | 10.820 | 14.948 | 1.00 | 11.82 C |
| ATOM | 2452 | CG | LEU | B | 42 | 28.246 | 11.835 | 15.604 | 1.00 | 13.37 C |
| ATOM | 2454 | CD1 | LEU | B | 42 | 29.484 | 12.076 | 14.765 | 1.00 | 17.49 C |
| ATOM | 2458 | CD2 | LEU | B | 42 | 27.504 | 13.150 | 15.923 | 1.00 | 13.74 C |
| ATOM | 2462 | C | LEU | B | 42 | 25.303 | 9.312 | 15.257 | 1.00 | 13.53 C |
| ATOM | 2463 | O | LEU | B | 42 | 25.559 | 8.103 | 15.208 | 1.00 | 13.30 O |
| ATOM | 2464 | N | THR | B | 43 | 24.203 | 9.824 | 14.717 | 1.00 | 16.10 N |
| ATOM | 2466 | CA | THR | B | 43 | 23.223 | 8.949 | 14.082 | 1.00 | 17.45 C |
| ATOM | 2468 | CB | THR | B | 43 | 21.953 | 8.828 | 14.935 | 1.00 | 17.82 C |
| ATOM | 2470 | OG1 | THR | B | 43 | 21.431 | 10.123 | 15.252 | 1.00 | 20.64 O |
| ATOM | 2472 | CG2 | THR | B | 43 | 22.241 | 8.193 | 16.296 | 1.00 | 18.56 C |
| ATOM | 2476 | C | THR | B | 43 | 22.842 | 9.433 | 12.691 | 1.00 | 18.34 C |
| ATOM | 2477 | O | THR | B | 43 | 21.866 | 8.947 | 12.117 | 1.00 | 18.70 O |
| ATOM | 2478 | N | ASP | B | 44 | 23.614 | 10.367 | 12.148 | 1.00 | 18.36 N |
| ATOM | 2480 | CA | ASP | B | 44 | 23.349 | 10.867 | 10.776 | 1.00 | 19.37 C |
| ATOM | 2482 | CB | ASP | B | 44 | 24.158 | 12.130 | 10.514 | 1.00 | 18.75 C |
| ATOM | 2485 | CG | ASP | B | 44 | 25.649 | 11.906 | 10.660 | 1.00 | 20.65 C |
| ATOM | 2486 | OD1 | ASP | B | 44 | 26.435 | 12.599 | 9.975 | 1.00 | 22.24 O |
| ATOM | 2487 | OD2 | ASP | B | 44 | 26.119 | 11.081 | 11.464 | 1.00 | 18.51 O |
| ATOM | 2488 | C | ASP | B | 44 | 23.632 | 9.875 | 9.640 | 1.00 | 20.76 C |
| ATOM | 2489 | O | ASP | B | 44 | 23.120 | 10.045 | 8.516 | 1.00 | 20.73 O |
| ATOM | 2490 | N | LYS | B | 45 | 24.451 | 8.858 | 9.910 | 1.00 | 22.30 N |
| ATOM | 2492 | CA | LYS | B | 45 | 24.845 | 7.850 | 8.930 | 1.00 | 22.65 C |
| ATOM | 2494 | CB | LYS | B | 45 | 26.271 | 8.089 | 8.416 | 1.00 | 23.02 C |
| ATOM | 2497 | CG | LYS | B | 45 | 26.515 | 9.467 | 7.807 | 1.00 | 25.19 C |
| ATOM | 2500 | CD | LYS | B | 45 | 27.968 | 9.681 | 7.419 | 1.00 | 29.05 C |
| ATOM | 2503 | CE | LYS | B | 45 | 28.158 | 10.993 | 6.672 | 1.00 | 32.51 C |
| ATOM | 2506 | NZ | LYS | B | 45 | 29.514 | 11.592 | 6.878 | 1.00 | 36.79 N |
| ATOM | 2510 | C | LYS | B | 45 | 24.790 | 6.500 | 9.640 | 1.00 | 23.32 C |
| ATOM | 2511 | O | LYS | B | 45 | 24.775 | 6.441 | 10.878 | 1.00 | 23.05 O |
| ATOM | 2512 | N | LYS | B | 46 | 24.771 | 5.425 | 8.856 | 1.00 | 24.20 N |
| ATOM | 2514 | CA | LYS | B | 46 | 24.712 | 4.075 | 9.398 | 1.00 | 23.77 C |
| ATOM | 2516 | CB | LYS | B | 46 | 24.033 | 3.132 | 8.406 | 1.00 | 23.95 C |
| ATOM | 2519 | CG | LYS | B | 46 | 22.685 | 3.632 | 7.903 | 1.00 | 24.89 C |
| ATOM | 2522 | CD | LYS | B | 46 | 22.803 | 4.957 | 7.139 | 1.00 | 24.88 C |
| ATOM | 2525 | CE | LYS | B | 46 | 23.693 | 4.858 | 5.919 | 1.00 | 24.51 C |
| ATOM | 2528 | NZ | LYS | B | 46 | 24.316 | 6.162 | 5.572 | 1.00 | 20.23 N |
| ATOM | 2532 | C | LYS | B | 46 | 26.127 | 3.598 | 9.655 | 1.00 | 22.13 C |
| ATOM | 2533 | O | LYS | B | 46 | 26.717 | 2.916 | 8.828 | 1.00 | 23.19 O |
| ATOM | 2534 | N | TYR | B | 47 | 26.678 | 3.932 | 10.814 | 1.00 | 21.82 N |
| ATOM | 2536 | CA | TYR | B | 47 | 28.065 | 3.580 | 11.084 | 1.00 | 17.30 C |
| ATOM | 2538 | CB | TYR | B | 47 | 28.630 | 4.461 | 12.199 | 1.00 | 16.73 C |
| ATOM | 2541 | CG | TYR | B | 47 | 28.584 | 5.926 | 11.880 | 1.00 | 14.44 C |
| ATOM | 2542 | CD1 | TYR | B | 47 | 29.504 | 6.494 | 11.022 | 1.00 | 14.82 C |
| ATOM | 2544 | CE1 | TYR | B | 47 | 29.475 | 7.842 | 10.736 | 1.00 | 15.44 C |
| ATOM | 2546 | CZ | TYR | B | 47 | 28.502 | 8.629 | 11.305 | 1.00 | 14.96 C |
| ATOM | 2547 | OH | TYR | B | 47 | 28.457 | 9.966 | 11.010 | 1.00 | 16.74 O |
| ATOM | 2549 | CE2 | TYR | B | 47 | 27.572 | 8.078 | 12.165 | 1.00 | 15.51 C |
| ATOM | 2551 | CD2 | TYR | B | 47 | 27.616 | 6.748 | 12.446 | 1.00 | 15.33 C |
| ATOM | 2553 | C | TYR | B | 47 | 28.239 | 2.119 | 11.467 | 1.00 | 15.49 C |
| ATOM | 2554 | O | TYR | B | 47 | 27.349 | 1.501 | 12.055 | 1.00 | 15.48 O |
| ATOM | 2555 | N | SER | B | 48 | 29.376 | 1.550 | 11.086 | 1.00 | 12.97 N |
| ATOM | 2557 | CA | SER | B | 48 | 29.731 | 0.219 | 11.553 | 1.00 | 12.31 C |
| ATOM | 2559 | CB | SER | B | 48 | 29.852 | −0.787 | 10.419 | 1.00 | 13.21 C |
| ATOM | 2562 | OG | SER | B | 48 | 30.688 | −0.272 | 9.425 | 1.00 | 17.27 O |
| ATOM | 2564 | C | SER | B | 48 | 31.064 | 0.343 | 12.277 | 1.00 | 10.66 C |
| ATOM | 2565 | O | SER | B | 48 | 31.687 | 1.401 | 12.295 | 1.00 | 9.38 O |
| ATOM | 2566 | N | TYR | B | 49 | 31.478 | −0.754 | 12.890 | 1.00 | 9.05 N |
| ATOM | 2568 | CA | TYR | B | 49 | 32.700 | −0.772 | 13.663 | 1.00 | 8.64 C |
| ATOM | 2570 | CB | TYR | B | 49 | 32.345 | −0.790 | 15.142 | 1.00 | 8.24 C |
| ATOM | 2573 | CG | TYR | B | 49 | 31.547 | 0.419 | 15.574 | 1.00 | 7.93 C |
| ATOM | 2574 | CD1 | TYR | B | 49 | 30.173 | 0.348 | 15.704 | 1.00 | 9.31 C |
| ATOM | 2576 | CE1 | TYR | B | 49 | 29.444 | 1.443 | 16.089 | 1.00 | 10.10 C |
| ATOM | 2578 | CZ | TYR | B | 49 | 30.076 | 2.635 | 16.361 | 1.00 | 9.43 C |
| ATOM | 2579 | OH | TYR | B | 49 | 29.321 | 3.726 | 16.755 | 1.00 | 11.22 O |
| ATOM | 2581 | CE2 | TYR | B | 49 | 31.442 | 2.741 | 16.222 | 1.00 | 7.22 C |
| ATOM | 2583 | CD2 | TYR | B | 49 | 32.169 | 1.629 | 15.833 | 1.00 | 7.22 C |
| ATOM | 2585 | C | TYR | B | 49 | 33.542 | −1.997 | 13.338 | 1.00 | 8.84 C |
| ATOM | 2586 | O | TYR | B | 49 | 33.035 | −3.120 | 13.301 | 1.00 | 8.75 O |
| ATOM | 2587 | N | ARG | B | 50 | 34.838 | −1.764 | 13.149 | 1.00 | 8.80 N |
| ATOM | 2589 | CA | ARG | B | 50 | 35.811 | −2.821 | 12.915 | 1.00 | 8.50 C |
| ATOM | 2591 | CB | ARG | B | 50 | 36.725 | −2.427 | 11.771 | 1.00 | 8.52 C |
| ATOM | 2594 | CG | ARG | B | 50 | 37.615 | −3.545 | 11.308 | 1.00 | 9.29 C |
| ATOM | 2597 | CD | ARG | B | 50 | 38.349 | −3.220 | 10.048 | 1.00 | 9.53 C |
| ATOM | 2600 | NE | ARG | B | 50 | 39.382 | −2.205 | 10.191 | 1.00 | 8.80 N |
| ATOM | 2602 | CZ | ARG | B | 50 | 40.631 | −2.476 | 10.566 | 1.00 | 11.23 C |

-continued

| APPENDIX C: CRYSTAL COORDINATES OF FVE PROTEIN | | | | | | | | | |
|---|---|---|---|---|---|---|---|---|---|
| ATOM | 2603 | NH1 | ARG | B | 50 | 40.986 | −3.721 | 10.901 | 1.00 | 11.51 N |
| ATOM | 2606 | NH2 | ARG | B | 50 | 41.533 | −1.506 | 10.650 | 1.00 | 13.88 N |
| ATOM | 2609 | C | ARG | B | 50 | 36.627 | −2.987 | 14.186 | 1.00 | 8.77 C |
| ATOM | 2610 | O | ARG | B | 50 | 37.063 | −2.001 | 14.787 | 1.00 | 8.89 O |
| ATOM | 2611 | N | VAL | B | 51 | 36.797 | −4.230 | 14.609 | 1.00 | 9.25 N |
| ATOM | 2613 | CA | VAL | B | 51 | 37.467 | −4.543 | 15.860 | 1.00 | 9.05 C |
| ATOM | 2615 | CB | VAL | B | 51 | 36.503 | −5.312 | 16.778 | 1.00 | 9.51 C |
| ATOM | 2617 | CG1 | VAL | B | 51 | 37.193 | −5.808 | 18.029 | 1.00 | 10.94 C |
| ATOM | 2621 | CG2 | VAL | B | 51 | 35.356 | −4.425 | 17.179 | 1.00 | 9.48 C |
| ATOM | 2625 | C | VAL | B | 51 | 38.729 | −5.378 | 15.614 | 1.00 | 9.31 C |
| ATOM | 2626 | O | VAL | B | 51 | 38.692 | −6.344 | 14.865 | 1.00 | 9.58 O |
| ATOM | 2627 | N | VAL | B | 52 | 39.827 | −5.004 | 16.274 | 1.00 | 8.69 N |
| ATOM | 2629 | CA | VAL | B | 52 | 41.136 | −5.638 | 16.112 | 1.00 | 8.61 C |
| ATOM | 2631 | CB | VAL | B | 52 | 42.132 | −4.664 | 15.406 | 1.00 | 8.82 C |
| ATOM | 2633 | CG1 | VAL | B | 52 | 43.432 | −5.350 | 15.057 | 1.00 | 8.22 C |
| ATOM | 2637 | CG2 | VAL | B | 52 | 41.503 | −4.031 | 14.166 | 1.00 | 8.20 C |
| ATOM | 2641 | C | VAL | B | 52 | 41.680 | −6.010 | 17.490 | 1.00 | 8.96 C |
| ATOM | 2642 | O | VAL | B | 52 | 41.759 | −5.166 | 18.367 | 1.00 | 9.37 O |
| ATOM | 2643 | N | VAL | B | 53 | 42.050 | −7.276 | 17.677 | 1.00 | 8.28 N |
| ATOM | 2645 | CA | VAL | B | 53 | 42.521 | −7.758 | 18.973 | 1.00 | 9.11 C |
| ATOM | 2647 | CB | VAL | B | 53 | 41.645 | −8.918 | 19.482 | 1.00 | 9.88 C |
| ATOM | 2649 | CG1 | VAL | B | 53 | 42.248 | −9.531 | 20.746 | 1.00 | 10.11 C |
| ATOM | 2653 | CG2 | VAL | B | 53 | 40.207 | −8.420 | 19.731 | 1.00 | 10.75 C |
| ATOM | 2657 | C | VAL | B | 53 | 43.965 | −8.214 | 18.850 | 1.00 | 9.11 C |
| ATOM | 2658 | O | VAL | B | 53 | 44.254 | −9.170 | 18.105 | 1.00 | 9.06 O |
| ATOM | 2659 | N | ASN | B | 54 | 44.873 | −7.543 | 19.563 | 1.00 | 8.85 N |
| ATOM | 2661 | CA | ASN | B | 54 | 46.310 | −7.827 | 19.435 | 1.00 | 9.61 C |
| ATOM | 2663 | CB | ASN | B | 54 | 46.676 | −9.140 | 20.109 | 1.00 | 10.03 C |
| ATOM | 2666 | CG | ASN | B | 54 | 47.031 | −8.996 | 21.586 | 1.00 | 11.16 C |
| ATOM | 2667 | OD1 | ASN | B | 54 | 47.247 | −10.014 | 22.267 | 1.00 | 16.89 O |
| ATOM | 2668 | ND2 | ASN | B | 54 | 47.126 | −7.781 | 22.076 | 1.00 | 9.72 N |
| ATOM | 2671 | C | ASN | B | 54 | 46.747 | −7.870 | 17.956 | 1.00 | 10.26 C |
| ATOM | 2672 | O | ASN | B | 54 | 47.522 | −8.745 | 17.548 | 1.00 | 11.02 O |
| ATOM | 2673 | N | GLY | B | 55 | 46.238 | −6.928 | 17.168 | 1.00 | 10.54 N |
| ATOM | 2675 | CA | GLY | B | 55 | 46.575 | −6.793 | 15.760 | 1.00 | 9.95 C |
| ATOM | 2678 | C | GLY | B | 55 | 45.844 | −7.707 | 14.792 | 1.00 | 9.84 C |
| ATOM | 2679 | O | GLY | B | 55 | 45.998 | −7.522 | 13.579 | 1.00 | 9.89 O |
| ATOM | 2680 | N | SER | B | 56 | 45.036 | −8.629 | 15.310 | 1.00 | 9.14 N |
| ATOM | 2682 | CA | SER | B | 56 | 44.226 | −9.538 | 14.506 | 1.00 | 9.52 C |
| ATOM | 2684 | CB | SER | B | 56 | 44.022 | −10.867 | 15.235 | 1.00 | 10.16 C |
| ATOM | 2687 | OG | SER | B | 56 | 43.162 | −11.730 | 14.503 | 1.00 | 10.98 O |
| ATOM | 2689 | C | SER | B | 56 | 42.858 | −8.888 | 14.232 | 1.00 | 9.17 C |
| ATOM | 2690 | O | SER | B | 56 | 42.065 | −8.653 | 15.148 | 1.00 | 8.64 O |
| ATOM | 2691 | N | ASP | B | 57 | 42.613 | −8.558 | 12.976 | 1.00 | 9.04 N |
| ATOM | 2693 | CA | ASP | B | 57 | 41.358 | −7.950 | 12.530 | 1.00 | 8.46 C |
| ATOM | 2695 | CB | ASP | B | 57 | 41.559 | −7.526 | 11.067 | 1.00 | 8.57 C |
| ATOM | 2698 | CG | ASP | B | 57 | 40.364 | −6.842 | 10.457 | 1.00 | 9.39 C |
| ATOM | 2699 | OD1 | ASP | B | 57 | 40.383 | −6.708 | 9.193 | 1.00 | 9.52 O |
| ATOM | 2700 | OD2 | ASP | B | 57 | 39.385 | −6.414 | 11.106 | 1.00 | 9.56 O |
| ATOM | 2701 | C | ASP | B | 57 | 40.201 | −8.950 | 12.628 | 1.00 | 8.72 C |
| ATOM | 2702 | O | ASP | B | 57 | 40.218 | −10.003 | 11.966 | 1.00 | 8.92 O |
| ATOM | 2703 | N | LEU | B | 58 | 39.217 | −8.665 | 13.478 | 1.00 | 9.29 N |
| ATOM | 2705 | CA | LEU | B | 58 | 38.021 | −9.508 | 13.542 | 1.00 | 9.33 C |
| ATOM | 2707 | CB | LEU | B | 58 | 37.508 | −9.582 | 14.977 | 1.00 | 9.53 C |
| ATOM | 2710 | CG | LEU | B | 58 | 38.564 | −9.973 | 16.005 | 1.00 | 9.47 C |
| ATOM | 2712 | CD1 | LEU | B | 58 | 37.925 | −10.156 | 17.379 | 1.00 | 11.17 C |
| ATOM | 2716 | CD2 | LEU | B | 58 | 39.325 | −11.242 | 15.604 | 1.00 | 11.86 C |
| ATOM | 2720 | C | LEU | B | 58 | 36.897 | −9.037 | 12.608 | 1.00 | 9.41 C |
| ATOM | 2721 | O | LEU | B | 58 | 35.797 | −9.607 | 12.608 | 1.00 | 10.79 O |
| ATOM | 2722 | N | GLY | B | 59 | 37.166 | −8.006 | 11.826 | 1.00 | 9.53 N |
| ATOM | 2724 | CA | GLY | B | 59 | 36.245 | −7.517 | 10.815 | 1.00 | 9.73 C |
| ATOM | 2727 | C | GLY | B | 59 | 35.209 | −6.570 | 11.375 | 1.00 | 9.94 C |
| ATOM | 2728 | O | GLY | B | 59 | 35.355 | −6.046 | 12.482 | 1.00 | 9.32 O |
| ATOM | 2729 | N | VAL | B | 60 | 34.133 | −6.407 | 10.614 | 1.00 | 10.86 N |
| ATOM | 2731 | CA | VAL | B | 60 | 33.165 | −5.356 | 10.840 | 1.00 | 11.57 C |
| ATOM | 2733 | CB | VAL | B | 60 | 33.048 | −4.476 | 9.571 | 1.00 | 11.80 C |
| ATOM | 2735 | CG1 | VAL | B | 60 | 32.330 | −3.170 | 9.845 | 1.00 | 13.91 C |
| ATOM | 2739 | CG2 | VAL | B | 60 | 32.361 | −5.227 | 8.443 | 1.00 | 13.46 C |
| ATOM | 2743 | C | VAL | B | 60 | 31.806 | −5.894 | 11.230 | 1.00 | 11.41 C |
| ATOM | 2744 | O | VAL | B | 60 | 31.409 | −7.016 | 10.849 | 1.00 | 11.80 O |
| ATOM | 2745 | N | GLU | B | 61 | 31.090 | −5.084 | 11.998 | 1.00 | 10.41 N |
| ATOM | 2747 | CA | GLU | B | 61 | 29.728 | −5.416 | 12.391 | 1.00 | 11.68 C |
| ATOM | 2749 | CB | GLU | B | 61 | 29.701 | −6.352 | 13.600 | 1.00 | 11.99 C |
| ATOM | 2752 | CG | GLU | B | 61 | 28.316 | −6.803 | 14.051 | 1.00 | 16.37 C |
| ATOM | 2755 | CD | GLU | B | 61 | 27.469 | −7.353 | 12.931 | 1.00 | 18.62 C |
| ATOM | 2756 | OE1 | GLU | B | 61 | 26.499 | −6.673 | 12.533 | 1.00 | 19.03 O |
| ATOM | 2757 | OE2 | GLU | B | 61 | 27.791 | −8.452 | 12.418 | 1.00 | 20.11 O |
| ATOM | 2758 | C | GLU | B | 61 | 28.994 | −4.105 | 12.643 | 1.00 | 12.02 C |

-continued

APPENDIX C: CRYSTAL COORDINATES OF FVE PROTEIN

| ATOM | 2759 | O   | GLU | B | 61 | 29.616 | -3.087 | 12.944 | 1.00 | 10.24 | O |
|------|------|-----|-----|---|----|--------|--------|--------|------|-------|---|
| ATOM | 2760 | N   | SER | B | 62 | 27.673 | -4.129 | 12.540 | 1.00 | 13.34 | N |
| ATOM | 2762 | CA  | SER | B | 62 | 26.908 | -2.919 | 12.741 | 1.00 | 13.52 | C |
| ATOM | 2764 | CB  | SER | B | 62 | 26.526 | -2.289 | 11.407 | 1.00 | 14.00 | C |
| ATOM | 2767 | OG  | SER | B | 62 | 25.717 | -3.176 | 10.647 | 1.00 | 13.96 | O |
| ATOM | 2769 | C   | SER | B | 62 | 25.631 | -3.142 | 13.513 | 1.00 | 13.46 | C |
| ATOM | 2770 | O   | SER | B | 62 | 24.940 | -2.159 | 13.807 | 1.00 | 14.34 | O |
| ATOM | 2771 | N   | ASN | B | 63 | 25.333 | -4.389 | 13.869 | 1.00 | 12.74 | N |
| ATOM | 2773 | CA  | ASN | B | 63 | 24.037 | -4.692 | 14.474 | 1.00 | 14.23 | C |
| ATOM | 2775 | CB  | ASN | B | 63 | 23.557 | -6.123 | 14.156 | 1.00 | 15.00 | C |
| ATOM | 2778 | CG  | ASN | B | 63 | 22.193 | -6.441 | 14.798 | 1.00 | 16.84 | C |
| ATOM | 2779 | OD1 | ASN | B | 63 | 21.441 | -5.531 | 15.129 | 1.00 | 21.06 | O |
| ATOM | 2780 | ND2 | ASN | B | 63 | 21.895 | -7.727 | 15.010 | 1.00 | 21.14 | N |
| ATOM | 2783 | C   | ASN | B | 63 | 24.089 | -4.438 | 15.971 | 1.00 | 13.99 | C |
| ATOM | 2784 | O   | ASN | B | 63 | 24.093 | -5.385 | 16.770 | 1.00 | 13.96 | O |
| ATOM | 2785 | N   | PHE | B | 64 | 24.126 | -3.143 | 16.308 | 1.00 | 13.92 | N |
| ATOM | 2787 | CA  | PHE | B | 64 | 24.126 | -2.622 | 17.673 | 1.00 | 12.95 | C |
| ATOM | 2789 | CB  | PHE | B | 64 | 25.518 | -2.121 | 18.080 | 1.00 | 12.24 | C |
| ATOM | 2792 | CG  | PHE | B | 64 | 26.621 | -3.056 | 17.698 | 1.00 | 10.08 | C |
| ATOM | 2793 | CD1 | PHE | B | 64 | 26.707 | -4.313 | 18.267 | 1.00 | 9.82  | C |
| ATOM | 2795 | CE1 | PHE | B | 64 | 27.717 | -5.176 | 17.900 | 1.00 | 10.20 | C |
| ATOM | 2797 | CZ  | PHE | B | 64 | 28.622 | -4.784 | 16.947 | 1.00 | 10.37 | C |
| ATOM | 2799 | CE2 | PHE | B | 64 | 28.533 | -3.542 | 16.383 | 1.00 | 10.15 | C |
| ATOM | 2801 | CD2 | PHE | B | 64 | 27.547 | -2.689 | 16.752 | 1.00 | 9.91  | C |
| ATOM | 2803 | C   | PHE | B | 64 | 23.135 | -1.462 | 17.777 | 1.00 | 12.85 | C |
| ATOM | 2804 | O   | PHE | B | 64 | 23.282 | -0.433 | 17.128 | 1.00 | 12.07 | O |
| ATOM | 2805 | N   | ALA | B | 65 | 22.124 | -1.637 | 18.613 | 1.00 | 13.52 | N |
| ATOM | 2807 | CA  | ALA | B | 65 | 21.038 | -0.677 | 18.719 | 1.00 | 13.11 | C |
| ATOM | 2809 | CB  | ALA | B | 65 | 19.990 | -1.165 | 19.701 | 1.00 | 13.88 | C |
| ATOM | 2813 | C   | ALA | B | 65 | 21.554 | 0.641  | 19.215 | 1.00 | 13.59 | C |
| ATOM | 2814 | O   | ALA | B | 65 | 22.471 | 0.668  | 20.026 | 1.00 | 13.52 | O |
| ATOM | 2815 | N   | VAL | B | 66 | 20.985 | 1.727  | 18.716 | 1.00 | 13.44 | N |
| ATOM | 2817 | CA  | VAL | B | 66 | 21.223 | 3.015  | 19.337 | 1.00 | 13.23 | C |
| ATOM | 2819 | CB  | VAL | B | 66 | 21.412 | 4.126  | 18.322 | 1.00 | 13.46 | C |
| ATOM | 2821 | CG1 | VAL | B | 66 | 21.554 | 5.453  | 19.053 | 1.00 | 14.25 | C |
| ATOM | 2825 | CG2 | VAL | B | 66 | 22.634 | 3.839  | 17.457 | 1.00 | 12.99 | C |
| ATOM | 2829 | C   | VAL | B | 66 | 20.007 | 3.276  | 20.232 | 1.00 | 13.98 | C |
| ATOM | 2830 | O   | VAL | B | 66 | 18.860 | 3.239  | 19.765 | 1.00 | 14.47 | O |
| ATOM | 2831 | N   | THR | B | 67 | 20.241 | 3.517  | 21.512 | 1.00 | 13.83 | N |
| ATOM | 2833 | CA  | THR | B | 67 | 19.134 | 3.762  | 22.438 | 1.00 | 15.29 | C |
| ATOM | 2835 | CB  | THR | B | 67 | 19.577 | 3.436  | 23.873 | 1.00 | 15.38 | C |
| ATOM | 2837 | OG1 | THR | B | 67 | 20.710 | 4.246  | 24.225 | 1.00 | 13.23 | O |
| ATOM | 2839 | CG2 | THR | B | 67 | 20.111 | 2.014  | 23.990 | 1.00 | 15.32 | C |
| ATOM | 2843 | C   | THR | B | 67 | 18.644 | 5.220  | 22.269 | 1.00 | 16.76 | C |
| ATOM | 2844 | O   | THR | B | 67 | 19.300 | 6.037  | 21.642 | 1.00 | 16.95 | O |
| ATOM | 2845 | N   | PRO | B | 68 | 17.459 | 5.547  | 22.766 | 1.00 | 20.60 | N |
| ATOM | 2846 | CA  | PRO | B | 68 | 16.921 | 6.907  | 22.635 | 1.00 | 20.58 | C |
| ATOM | 2848 | CB  | PRO | B | 68 | 15.605 | 6.822  | 23.400 | 1.00 | 21.01 | C |
| ATOM | 2851 | CG  | PRO | B | 68 | 15.218 | 5.414  | 23.278 | 1.00 | 21.24 | C |
| ATOM | 2854 | CD  | PRO | B | 68 | 16.507 | 4.646  | 23.423 | 1.00 | 19.89 | C |
| ATOM | 2857 | C   | PRO | B | 68 | 17.814 | 8.029  | 23.188 | 1.00 | 21.33 | C |
| ATOM | 2858 | O   | PRO | B | 68 | 17.759 | 9.162  | 22.687 | 1.00 | 21.25 | O |
| ATOM | 2859 | N   | SER | B | 69 | 18.616 | 7.701  | 24.199 | 1.00 | 22.75 | N |
| ATOM | 2861 | CA  | SER | B | 69 | 19.587 | 8.608  | 24.826 | 1.00 | 21.20 | C |
| ATOM | 2863 | CB  | SER | B | 69 | 20.082 | 7.995  | 26.138 | 1.00 | 21.30 | C |
| ATOM | 2866 | OG  | SER | B | 69 | 20.644 | 6.705  | 25.953 | 1.00 | 22.43 | O |
| ATOM | 2868 | C   | SER | B | 69 | 20.769 | 8.877  | 23.909 | 1.00 | 20.23 | C |
| ATOM | 2869 | O   | SER | B | 69 | 21.553 | 9.820  | 24.111 | 1.00 | 20.71 | O |
| ATOM | 2870 | N   | GLY | B | 70 | 20.897 | 8.016  | 22.908 | 1.00 | 18.48 | N |
| ATOM | 2872 | CA  | GLY | B | 70 | 21.923 | 8.132  | 21.904 | 1.00 | 15.60 | C |
| ATOM | 2875 | C   | GLY | B | 70 | 23.049 | 7.151  | 22.179 | 1.00 | 13.15 | C |
| ATOM | 2876 | O   | GLY | B | 70 | 24.061 | 7.186  | 21.524 | 1.00 | 12.69 | O |
| ATOM | 2877 | N   | GLY | B | 71 | 22.876 | 6.276  | 23.162 | 1.00 | 10.24 | N |
| ATOM | 2879 | CA  | GLY | B | 71 | 23.942 | 5.354  | 23.525 | 1.00 | 10.32 | C |
| ATOM | 2882 | C   | GLY | B | 71 | 24.044 | 4.180  | 22.570 | 1.00 | 10.01 | C |
| ATOM | 2883 | O   | GLY | B | 71 | 23.067 | 3.830  | 21.893 | 1.00 | 9.06  | O |
| ATOM | 2884 | N   | GLN | B | 72 | 25.221 | 3.567  | 22.513 | 1.00 | 9.21  | N |
| ATOM | 2886 | CA  | GLN | B | 72 | 25.427 | 2.402  | 21.654 | 1.00 | 9.07  | C |
| ATOM | 2888 | CB  | GLN | B | 72 | 25.841 | 2.818  | 20.242 | 1.00 | 9.26  | C |
| ATOM | 2891 | CG  | GLN | B | 72 | 25.762 | 1.671  | 19.241 | 1.00 | 10.65 | C |
| ATOM | 2894 | CD  | GLN | B | 72 | 25.989 | 2.078  | 17.779 | 1.00 | 11.82 | C |
| ATOM | 2895 | OE1 | GLN | B | 72 | 25.420 | 1.465  | 16.838 | 1.00 | 14.64 | O |
| ATOM | 2896 | NE2 | GLN | B | 72 | 26.832 | 3.043  | 17.578 | 1.00 | 8.39  | N |
| ATOM | 2899 | C   | GLN | B | 72 | 26.482 | 1.500  | 22.251 | 1.00 | 8.92  | C |
| ATOM | 2900 | O   | GLN | B | 72 | 27.562 | 1.958  | 22.606 | 1.00 | 9.57  | O |
| ATOM | 2901 | N   | THR | B | 73 | 26.154 | 0.216  | 22.363 | 1.00 | 8.86  | N |
| ATOM | 2903 | CA  | THR | B | 73 | 27.059 | -0.781 | 22.906 | 1.00 | 9.09  | C |
| ATOM | 2905 | CB  | THR | B | 73 | 26.344 | -1.572 | 24.005 | 1.00 | 9.39  | C |

-continued

| APPENDIX C: CRYSTAL COORDINATES OF FVE PROTEIN |
|---|

| ATOM | 2907 | OG1 | THR | B | 73 | 25.995 | −0.692 | 25.072 | 1.00 | 9.52 | O |
|---|---|---|---|---|---|---|---|---|---|---|---|
| ATOM | 2909 | CG2 | THR | B | 73 | 27.270 | −2.612 | 24.627 | 1.00 | 10.72 | C |
| ATOM | 2913 | C | THR | B | 73 | 27.509 | −1.748 | 21.809 | 1.00 | 9.41 | C |
| ATOM | 2914 | O | THR | B | 73 | 26.680 | −2.437 | 21.200 | 1.00 | 10.31 | O |
| ATOM | 2915 | N | ILE | B | 74 | 28.812 | −1.757 | 21.563 | 1.00 | 9.66 | N |
| ATOM | 2917 | CA | ILE | B | 74 | 29.458 | −2.662 | 20.630 | 1.00 | 9.26 | C |
| ATOM | 2919 | CB | ILE | B | 74 | 30.716 | −2.000 | 20.065 | 1.00 | 9.30 | C |
| ATOM | 2921 | CG1 | ILE | B | 74 | 30.322 | −0.764 | 19.234 | 1.00 | 10.63 | C |
| ATOM | 2924 | CD1 | ILE | B | 74 | 31.405 | 0.279 | 19.094 | 1.00 | 13.52 | C |
| ATOM | 2928 | CG2 | ILE | B | 74 | 31.494 | −2.996 | 19.212 | 1.00 | 9.71 | C |
| ATOM | 2932 | C | ILE | B | 74 | 29.779 | −3.915 | 21.441 | 1.00 | 8.04 | C |
| ATOM | 2933 | O | ILE | B | 74 | 30.553 | −3.873 | 22.389 | 1.00 | 8.84 | O |
| ATOM | 2934 | N | ASN | B | 75 | 29.117 | −5.012 | 21.103 | 1.00 | 8.10 | N |
| ATOM | 2936 | CA | ASN | B | 75 | 29.257 | −6.266 | 21.819 | 1.00 | 7.89 | C |
| ATOM | 2938 | CB | ASN | B | 75 | 27.908 | −6.975 | 21.781 | 1.00 | 8.13 | C |
| ATOM | 2941 | CG | ASN | B | 75 | 27.942 | −8.323 | 22.426 | 1.00 | 8.20 | C |
| ATOM | 2942 | OD1 | ASN | B | 75 | 28.856 | −8.662 | 23.195 | 1.00 | 7.74 | O |
| ATOM | 2943 | ND2 | ASN | B | 75 | 26.946 | −9.120 | 22.108 | 1.00 | 11.67 | N |
| ATOM | 2946 | C | ASN | B | 75 | 30.324 | −7.129 | 21.149 | 1.00 | 8.35 | C |
| ATOM | 2947 | O | ASN | B | 75 | 30.128 | −7.635 | 20.029 | 1.00 | 7.57 | O |
| ATOM | 2948 | N | PHE | B | 76 | 31.449 | −7.309 | 21.831 | 1.00 | 8.93 | N |
| ATOM | 2950 | CA | PHE | B | 76 | 32.572 | −8.022 | 21.228 | 1.00 | 9.24 | C |
| ATOM | 2952 | CB | PHE | B | 76 | 33.846 | −7.826 | 22.054 | 1.00 | 9.38 | C |
| ATOM | 2955 | CG | PHE | B | 76 | 34.319 | −6.391 | 22.076 | 1.00 | 9.36 | C |
| ATOM | 2956 | CD1 | PHE | B | 76 | 34.307 | −5.628 | 20.921 | 1.00 | 10.05 | C |
| ATOM | 2958 | CE1 | PHE | B | 76 | 34.715 | −4.318 | 20.939 | 1.00 | 9.26 | C |
| ATOM | 2960 | CZ | PHE | B | 76 | 35.131 | −3.763 | 22.112 | 1.00 | 8.99 | C |
| ATOM | 2962 | CE2 | PHE | B | 76 | 35.143 | −4.500 | 23.259 | 1.00 | 10.57 | C |
| ATOM | 2964 | CD2 | PHE | B | 76 | 34.745 | −5.806 | 23.246 | 1.00 | 10.62 | C |
| ATOM | 2966 | C | PHE | B | 76 | 32.260 | −9.502 | 20.999 | 1.00 | 9.01 | C |
| ATOM | 2967 | O | PHE | B | 76 | 32.893 | −10.149 | 20.169 | 1.00 | 9.14 | O |
| ATOM | 2968 | N | LEU | B | 77 | 31.268 | −10.038 | 21.708 | 1.00 | 9.74 | N |
| ATOM | 2970 | CA | LEU | B | 77 | 30.894 | −11.444 | 21.525 | 1.00 | 9.62 | C |
| ATOM | 2972 | CB | LEU | B | 77 | 29.844 | −11.840 | 22.565 | 1.00 | 9.60 | C |
| ATOM | 2975 | CG | LEU | B | 77 | 30.361 | −12.157 | 23.981 | 1.00 | 11.85 | C |
| ATOM | 2977 | CD1 | LEU | B | 77 | 31.102 | −11.029 | 24.640 | 1.00 | 13.22 | C |
| ATOM | 2981 | CD2 | LEU | B | 77 | 29.174 | −12.593 | 24.854 | 1.00 | 12.68 | C |
| ATOM | 2985 | C | LEU | B | 77 | 30.400 | −11.713 | 20.077 | 1.00 | 9.32 | C |
| ATOM | 2986 | O | LEU | B | 77 | 30.481 | −12.843 | 19.574 | 1.00 | 10.46 | O |
| ATOM | 2987 | N | GLN | B | 78 | 29.907 | −10.671 | 19.415 | 1.00 | 9.10 | N |
| ATOM | 2989 | CA | GLN | B | 78 | 29.450 | −10.748 | 18.032 | 1.00 | 10.10 | C |
| ATOM | 2991 | CB | GLN | B | 78 | 28.517 | −9.569 | 17.697 | 1.00 | 10.43 | C |
| ATOM | 2994 | CG | GLN | B | 78 | 27.143 | −9.734 | 18.379 | 1.00 | 9.66 | C |
| ATOM | 2997 | CD | GLN | B | 78 | 26.224 | −8.538 | 18.295 | 1.00 | 11.71 | C |
| ATOM | 2998 | OE1 | GLN | B | 78 | 25.803 | −8.019 | 19.329 | 1.00 | 11.16 | O |
| ATOM | 2999 | NE2 | GLN | B | 78 | 25.871 | −8.113 | 17.071 | 1.00 | 13.17 | N |
| ATOM | 3002 | C | GLN | B | 78 | 30.612 | −10.816 | 17.042 | 1.00 | 11.05 | C |
| ATOM | 3003 | O | GLN | B | 78 | 30.379 | −11.128 | 15.859 | 1.00 | 13.23 | O |
| ATOM | 3004 | N | TYR | B | 79 | 31.826 | −10.506 | 17.500 | 1.00 | 10.96 | N |
| ATOM | 3006 | CA | TYR | B | 79 | 33.026 | −10.570 | 16.654 | 1.00 | 12.02 | C |
| ATOM | 3008 | CB | TYR | B | 79 | 33.915 | −9.339 | 16.842 | 1.00 | 11.81 | C |
| ATOM | 3011 | CG | TYR | B | 79 | 33.345 | −8.005 | 16.481 | 1.00 | 10.03 | C |
| ATOM | 3012 | CD1 | TYR | B | 79 | 33.681 | −7.372 | 15.280 | 1.00 | 8.25 | C |
| ATOM | 3014 | CE1 | TYR | B | 79 | 33.169 | −6.116 | 14.965 | 1.00 | 8.39 | C |
| ATOM | 3016 | CZ | TYR | B | 79 | 32.322 | −5.483 | 15.842 | 1.00 | 8.21 | C |
| ATOM | 3017 | OH | TYR | B | 79 | 31.827 | −4.250 | 15.505 | 1.00 | 8.87 | O |
| ATOM | 3019 | CE2 | TYR | B | 79 | 31.972 | −6.104 | 17.033 | 1.00 | 10.02 | C |
| ATOM | 3021 | CD2 | TYR | B | 79 | 32.487 | −7.347 | 17.345 | 1.00 | 9.93 | C |
| ATOM | 3023 | C | TYR | B | 79 | 33.940 | −11.728 | 16.985 | 1.00 | 13.56 | C |
| ATOM | 3024 | O | TYR | B | 79 | 34.689 | −12.190 | 16.120 | 1.00 | 13.49 | O |
| ATOM | 3025 | N | ASN | B | 80 | 33.919 | −12.162 | 18.242 | 1.00 | 15.17 | N |
| ATOM | 3027 | CA | ASN | B | 80 | 34.925 | −13.076 | 18.751 | 1.00 | 14.48 | C |
| ATOM | 3029 | CB | ASN | B | 80 | 35.582 | −12.444 | 19.978 | 1.00 | 14.14 | C |
| ATOM | 3032 | CG | ASN | B | 80 | 36.890 | −13.105 | 20.361 | 1.00 | 14.62 | C |
| ATOM | 3033 | OD1 | ASN | B | 80 | 37.651 | −13.558 | 19.509 | 1.00 | 16.67 | O |
| ATOM | 3034 | ND2 | ASN | B | 80 | 37.153 | −13.163 | 21.664 | 1.00 | 13.88 | N |
| ATOM | 3037 | C | ASN | B | 80 | 34.352 | −14.437 | 19.084 | 1.00 | 14.66 | C |
| ATOM | 3038 | O | ASN | B | 80 | 34.712 | −15.056 | 20.083 | 1.00 | 13.88 | O |
| ATOM | 3039 | N | LYS | B | 81 | 33.412 | −14.879 | 18.257 | 1.00 | 15.51 | N |
| ATOM | 3041 | CA | LYS | B | 81 | 32.859 | −16.233 | 18.368 | 1.00 | 16.46 | C |
| ATOM | 3043 | CB | LYS | B | 81 | 33.943 | −17.263 | 17.992 | 1.00 | 16.91 | C |
| ATOM | 3046 | CG | LYS | B | 81 | 34.644 | −16.962 | 16.663 | 1.00 | 20.41 | C |
| ATOM | 3049 | CD | LYS | B | 81 | 35.616 | −18.076 | 16.175 | 1.00 | 26.52 | C |
| ATOM | 3052 | CE | LYS | B | 81 | 36.392 | −18.798 | 17.293 | 1.00 | 31.18 | C |
| ATOM | 3055 | NZ | LYS | B | 81 | 37.525 | −19.720 | 16.822 | 1.00 | 38.55 | N |
| ATOM | 3059 | C | LYS | B | 81 | 32.216 | −16.559 | 19.735 | 1.00 | 15.91 | C |
| ATOM | 3060 | O | LYS | B | 81 | 32.322 | −17.678 | 20.227 | 1.00 | 16.16 | O |
| ATOM | 3061 | N | GLY | B | 82 | 31.522 | −15.575 | 20.307 | 1.00 | 15.03 | N |

-continued

APPENDIX C: CRYSTAL COORDINATES OF FVE PROTEIN

| ATOM | 3063 | CA | GLY | B | 82 | 30.735 | −15.736 | 21.512 | 1.00 | 15.26 | C |
|---|---|---|---|---|---|---|---|---|---|---|---|
| ATOM | 3066 | C | GLY | B | 82 | 31.492 | −15.553 | 22.800 | 1.00 | 15.69 | C |
| ATOM | 3067 | O | GLY | B | 82 | 30.960 | −15.833 | 23.857 | 1.00 | 15.34 | O |
| ATOM | 3068 | N | TYR | B | 83 | 32.721 | −15.052 | 22.708 | 1.00 | 16.90 | N |
| ATOM | 3070 | CA | TYR | B | 83 | 33.550 | −14.806 | 23.873 | 1.00 | 17.19 | C |
| ATOM | 3072 | CB | TYR | B | 83 | 34.815 | −15.667 | 23.808 | 1.00 | 18.20 | C |
| ATOM | 3075 | CG | TYR | B | 83 | 34.583 | −17.155 | 23.934 | 1.00 | 23.38 | C |
| ATOM | 3076 | CD1 | TYR | B | 83 | 34.448 | −17.745 | 25.181 | 1.00 | 28.89 | C |
| ATOM | 3078 | CE1 | TYR | B | 83 | 34.239 | −19.105 | 25.310 | 1.00 | 31.05 | C |
| ATOM | 3080 | CZ | TYR | B | 83 | 34.170 | −19.896 | 24.184 | 1.00 | 32.68 | C |
| ATOM | 3081 | OH | TYR | B | 83 | 33.962 | −21.259 | 24.329 | 1.00 | 36.36 | O |
| ATOM | 3083 | CE2 | TYR | B | 83 | 34.305 | −19.340 | 22.930 | 1.00 | 30.78 | C |
| ATOM | 3085 | CD2 | TYR | B | 83 | 34.506 | −17.972 | 22.810 | 1.00 | 28.62 | C |
| ATOM | 3087 | C | TYR | B | 83 | 34.006 | −13.355 | 23.925 | 1.00 | 16.15 | C |
| ATOM | 3088 | O | TYR | B | 83 | 34.169 | −12.715 | 22.894 | 1.00 | 15.94 | O |
| ATOM | 3089 | N | GLY | B | 84 | 34.190 | −12.828 | 25.134 | 1.00 | 15.91 | N |
| ATOM | 3091 | CA | GLY | B | 84 | 34.842 | −11.539 | 25.278 | 1.00 | 14.80 | C |
| ATOM | 3094 | C | GLY | B | 84 | 36.359 | −11.675 | 25.047 | 1.00 | 13.96 | C |
| ATOM | 3095 | O | GLY | B | 84 | 36.882 | −12.737 | 24.675 | 1.00 | 14.24 | O |
| ATOM | 3096 | N | VAL | B | 85 | 37.071 | −10.586 | 25.311 | 1.00 | 11.64 | N |
| ATOM | 3098 | CA | VAL | B | 85 | 38.497 | −10.478 | 25.027 | 1.00 | 12.19 | C |
| ATOM | 3100 | CB | VAL | B | 85 | 38.761 | −9.214 | 24.159 | 1.00 | 11.76 | C |
| ATOM | 3102 | CG1 | VAL | B | 85 | 40.254 | −9.019 | 23.892 | 1.00 | 12.27 | C |
| ATOM | 3106 | CG2 | VAL | B | 85 | 37.970 | −9.236 | 22.852 | 1.00 | 12.61 | C |
| ATOM | 3110 | C | VAL | B | 85 | 39.258 | −10.315 | 26.329 | 1.00 | 12.06 | C |
| ATOM | 3111 | O | VAL | B | 85 | 38.954 | −9.435 | 27.133 | 1.00 | 11.39 | O |
| ATOM | 3112 | N | ALA | B | 86 | 40.263 | −11.154 | 26.554 | 1.00 | 11.94 | N |
| ATOM | 3114 | CA | ALA | B | 86 | 41.077 | −11.026 | 27.752 | 1.00 | 12.43 | C |
| ATOM | 3116 | CB | ALA | B | 86 | 42.221 | −12.031 | 27.709 | 1.00 | 12.46 | C |
| ATOM | 3120 | C | ALA | B | 86 | 41.630 | −9.606 | 27.895 | 1.00 | 12.58 | C |
| ATOM | 3121 | O | ALA | B | 86 | 42.145 | −9.034 | 26.921 | 1.00 | 11.12 | O |
| ATOM | 3122 | N | ASP | B | 87 | 41.542 | −9.046 | 29.101 | 1.00 | 12.96 | N |
| ATOM | 3124 | CA | ASP | B | 87 | 41.977 | −7.664 | 29.319 | 1.00 | 13.26 | C |
| ATOM | 3126 | CB | ASP | B | 87 | 41.413 | −7.038 | 30.599 | 1.00 | 12.94 | C |
| ATOM | 3129 | CG | ASP | B | 87 | 41.973 | −7.621 | 31.863 | 1.00 | 15.55 | C |
| ATOM | 3130 | OD1 | ASP | B | 87 | 42.925 | −8.435 | 31.811 | 1.00 | 16.54 | O |
| ATOM | 3131 | OD2 | ASP | B | 87 | 41.478 | −7.304 | 32.971 | 1.00 | 17.64 | O |
| ATOM | 3132 | C | ASP | B | 87 | 43.473 | −7.446 | 29.177 | 1.00 | 13.14 | C |
| ATOM | 3133 | O | ASP | B | 87 | 43.923 | −6.303 | 29.211 | 1.00 | 13.88 | O |
| ATOM | 3134 | N | THR | B | 88 | 44.222 | −8.529 | 28.986 | 1.00 | 13.35 | N |
| ATOM | 3136 | CA | THR | B | 88 | 45.648 | −8.426 | 28.770 | 1.00 | 13.89 | C |
| ATOM | 3138 | CB | THR | B | 88 | 46.376 | −9.702 | 29.223 | 1.00 | 13.97 | C |
| ATOM | 3140 | OG1 | THR | B | 88 | 45.720 | −10.853 | 28.692 | 1.00 | 14.23 | O |
| ATOM | 3142 | CG2 | THR | B | 88 | 46.312 | −9.865 | 30.728 | 1.00 | 15.70 | C |
| ATOM | 3146 | C | THR | B | 88 | 45.972 | −8.179 | 27.308 | 1.00 | 14.14 | C |
| ATOM | 3147 | O | THR | B | 88 | 47.138 | −7.960 | 26.978 | 1.00 | 16.23 | O |
| ATOM | 3148 | N | LYS | B | 89 | 44.961 | −8.217 | 26.444 | 1.00 | 13.28 | N |
| ATOM | 3150 | CA | LYS | B | 89 | 45.163 | −7.962 | 25.021 | 1.00 | 13.04 | C |
| ATOM | 3152 | CB | LYS | B | 89 | 44.317 | −8.922 | 24.185 | 1.00 | 13.74 | C |
| ATOM | 3155 | CG | LYS | B | 89 | 44.531 | −10.371 | 24.562 | 1.00 | 15.15 | C |
| ATOM | 3158 | CD | LYS | B | 89 | 43.821 | −11.309 | 23.612 | 1.00 | 18.37 | C |
| ATOM | 3161 | CE | LYS | B | 89 | 43.980 | −12.771 | 24.006 | 1.00 | 20.95 | C |
| ATOM | 3164 | NZ | LYS | B | 89 | 43.412 | −13.640 | 22.933 | 1.00 | 24.82 | N |
| ATOM | 3168 | C | LYS | B | 89 | 44.798 | −6.531 | 24.667 | 1.00 | 12.47 | C |
| ATOM | 3169 | O | LYS | B | 89 | 44.022 | −5.884 | 25.369 | 1.00 | 12.82 | O |
| ATOM | 3170 | N | THR | B | 90 | 45.377 | −6.023 | 23.589 | 1.00 | 11.85 | N |
| ATOM | 3172 | CA | THR | B | 90 | 45.017 | −4.714 | 23.072 | 1.00 | 11.57 | C |
| ATOM | 3174 | CB | THR | B | 90 | 46.177 | −4.184 | 22.273 | 1.00 | 11.83 | C |
| ATOM | 3176 | OG1 | THR | B | 90 | 47.280 | −3.912 | 23.164 | 1.00 | 14.04 | O |
| ATOM | 3178 | CG2 | THR | B | 90 | 45.838 | −2.872 | 21.626 | 1.00 | 13.14 | C |
| ATOM | 3182 | C | THR | B | 90 | 43.780 | −4.827 | 22.180 | 1.00 | 11.03 | C |
| ATOM | 3183 | O | THR | B | 90 | 43.684 | −5.748 | 21.355 | 1.00 | 10.60 | O |
| ATOM | 3184 | N | ILE | B | 91 | 42.839 | −3.893 | 22.344 | 1.00 | 10.28 | N |
| ATOM | 3186 | CA | ILE | B | 91 | 41.640 | −3.871 | 21.530 | 1.00 | 10.28 | C |
| ATOM | 3188 | CB | ILE | B | 91 | 40.361 | −4.011 | 22.361 | 1.00 | 10.29 | C |
| ATOM | 3190 | CG1 | ILE | B | 91 | 40.407 | −5.261 | 23.238 | 1.00 | 11.66 | C |
| ATOM | 3193 | CD1 | ILE | B | 91 | 39.298 | −5.354 | 24.285 | 1.00 | 13.60 | C |
| ATOM | 3197 | CG2 | ILE | B | 91 | 39.141 | −4.060 | 21.408 | 1.00 | 10.59 | C |
| ATOM | 3201 | C | ILE | B | 91 | 41.597 | −2.536 | 20.815 | 1.00 | 10.62 | C |
| ATOM | 3202 | O | ILE | B | 91 | 41.700 | −1.489 | 21.442 | 1.00 | 10.66 | O |
| ATOM | 3203 | N | GLN | B | 92 | 41.490 | −2.563 | 19.497 | 1.00 | 10.49 | N |
| ATOM | 3205 | CA | GLN | B | 92 | 41.313 | −1.326 | 18.764 | 1.00 | 10.71 | C |
| ATOM | 3207 | CB | GLN | B | 92 | 42.410 | −1.146 | 17.719 | 1.00 | 11.65 | C |
| ATOM | 3210 | CG | GLN | B | 92 | 43.778 | −0.942 | 18.282 | 1.00 | 15.30 | C |
| ATOM | 3213 | CD | GLN | B | 92 | 44.809 | −1.227 | 17.215 | 1.00 | 21.75 | C |
| ATOM | 3214 | OE1 | GLN | B | 92 | 45.030 | −2.382 | 16.855 | 1.00 | 23.06 | O |
| ATOM | 3215 | NE2 | GLN | B | 92 | 45.388 | −0.176 | 16.654 | 1.00 | 29.53 | N |
| ATOM | 3218 | C | GLN | B | 92 | 39.964 | −1.384 | 18.063 | 1.00 | 9.76 | C |

-continued

| APPENDIX C: CRYSTAL COORDINATES OF FVE PROTEIN | | | | | | | | | |
|---|---|---|---|---|---|---|---|---|---|
| ATOM | 3219 | O | GLN | B | 92 | 39.599 | −2.416 | 17.499 | 1.00 | 9.52 O |
| ATOM | 3220 | N | VAL | B | 93 | 39.225 | −0.286 | 18.109 | 1.00 | 8.49 N |
| ATOM | 3222 | CA | VAL | B | 93 | 37.922 | −0.204 | 17.447 | 1.00 | 8.46 C |
| ATOM | 3224 | CB | VAL | B | 93 | 36.754 | −0.031 | 18.452 | 1.00 | 8.40 C |
| ATOM | 3226 | CG1 | VAL | B | 93 | 35.408 | −0.068 | 17.715 | 1.00 | 8.33 C |
| ATOM | 3230 | CG2 | VAL | B | 93 | 36.818 | −1.110 | 19.565 | 1.00 | 9.21 C |
| ATOM | 3234 | C | VAL | B | 93 | 37.954 | 0.979 | 16.498 | 1.00 | 8.80 C |
| ATOM | 3235 | O | VAL | B | 93 | 38.313 | 2.100 | 16.913 | 1.00 | 9.38 O |
| ATOM | 3236 | N | PHE | B | 94 | 37.585 | 0.735 | 15.235 | 1.00 | 7.89 N |
| ATOM | 3238 | CA | PHE | B | 94 | 37.514 | 1.756 | 14.207 | 1.00 | 8.32 C |
| ATOM | 3240 | CB | PHE | B | 94 | 38.303 | 1.336 | 12.954 | 1.00 | 8.53 C |
| ATOM | 3243 | CG | PHE | B | 94 | 39.774 | 1.165 | 13.207 | 1.00 | 8.61 C |
| ATOM | 3244 | CD1 | PHE | B | 94 | 40.658 | 2.188 | 12.898 | 1.00 | 10.93 C |
| ATOM | 3246 | CE1 | PHE | B | 94 | 42.001 | 2.046 | 13.153 | 1.00 | 11.25 C |
| ATOM | 3248 | CZ | PHE | B | 94 | 42.482 | 0.899 | 13.732 | 1.00 | 10.46 C |
| ATOM | 3250 | CE2 | PHE | B | 94 | 41.644 | −0.131 | 14.027 | 1.00 | 10.75 C |
| ATOM | 3252 | CD2 | PHE | B | 94 | 40.273 | 0.003 | 13.776 | 1.00 | 10.71 C |
| ATOM | 3254 | C | PHE | B | 94 | 36.070 | 1.974 | 13.819 | 1.00 | 8.61 C |
| ATOM | 3255 | O | PHE | B | 94 | 35.314 | 1.013 | 13.648 | 1.00 | 9.56 O |
| ATOM | 3256 | N | VAL | B | 95 | 35.687 | 3.231 | 13.647 | 1.00 | 8.45 N |
| ATOM | 3258 | CA | VAL | B | 95 | 34.370 | 3.546 | 13.104 | 1.00 | 9.19 C |
| ATOM | 3260 | CB | VAL | B | 95 | 33.767 | 4.834 | 13.699 | 1.00 | 9.11 C |
| ATOM | 3262 | CG1 | VAL | B | 95 | 34.614 | 6.052 | 13.439 | 1.00 | 11.33 C |
| ATOM | 3266 | CG2 | VAL | B | 95 | 32.342 | 5.013 | 13.203 | 1.00 | 10.43 C |
| ATOM | 3270 | C | VAL | B | 95 | 34.535 | 3.607 | 11.594 | 1.00 | 9.06 C |
| ATOM | 3271 | O | VAL | B | 95 | 35.480 | 4.251 | 11.094 | 1.00 | 9.36 O |
| ATOM | 3272 | N | VAL | B | 96 | 33.660 | 2.896 | 10.888 | 1.00 | 10.07 N |
| ATOM | 3274 | CA | VAL | B | 96 | 33.731 | 2.760 | 9.435 | 1.00 | 10.75 C |
| ATOM | 3276 | CB | VAL | B | 96 | 33.633 | 1.287 | 9.027 | 1.00 | 11.31 C |
| ATOM | 3278 | CG1 | VAL | B | 96 | 33.699 | 1.117 | 7.507 | 1.00 | 12.23 C |
| ATOM | 3282 | CG2 | VAL | B | 96 | 34.726 | 0.475 | 9.716 | 1.00 | 11.29 C |
| ATOM | 3286 | C | VAL | B | 96 | 32.598 | 3.544 | 8.811 | 1.00 | 11.08 C |
| ATOM | 3287 | O | VAL | B | 96 | 31.425 | 3.388 | 9.170 | 1.00 | 11.36 O |
| ATOM | 3288 | N | ILE | B | 97 | 32.948 | 4.403 | 7.866 | 1.00 | 11.39 N |
| ATOM | 3290 | CA | ILE | B | 97 | 31.959 | 5.265 | 7.236 | 1.00 | 12.42 C |
| ATOM | 3292 | CB | ILE | B | 97 | 32.677 | 6.496 | 6.644 | 1.00 | 12.48 C |
| ATOM | 3294 | CG1 | ILE | B | 97 | 33.614 | 7.145 | 7.677 | 1.00 | 12.52 C |
| ATOM | 3297 | CD1 | ILE | B | 97 | 32.936 | 7.612 | 8.958 | 1.00 | 14.19 C |
| ATOM | 3301 | CG2 | ILE | B | 97 | 31.669 | 7.488 | 6.082 | 1.00 | 12.90 C |
| ATOM | 3305 | C | ILE | B | 97 | 31.234 | 4.501 | 6.130 | 1.00 | 13.56 C |
| ATOM | 3306 | O | ILE | B | 97 | 31.898 | 3.883 | 5.308 | 1.00 | 13.06 O |
| ATOM | 3307 | N | PRO | B | 98 | 29.898 | 4.524 | 6.113 | 1.00 | 15.09 N |
| ATOM | 3308 | CA | PRO | B | 98 | 29.132 | 3.809 | 5.086 | 1.00 | 16.07 C |
| ATOM | 3310 | CB | PRO | B | 98 | 27.696 | 3.899 | 5.600 | 1.00 | 15.86 C |
| ATOM | 3313 | CG | PRO | B | 98 | 27.661 | 5.122 | 6.370 | 1.00 | 16.80 C |
| ATOM | 3316 | CD | PRO | B | 98 | 29.007 | 5.184 | 7.076 | 1.00 | 14.97 C |
| ATOM | 3319 | C | PRO | B | 98 | 29.267 | 4.451 | 3.718 | 1.00 | 17.70 C |
| ATOM | 3320 | O | PRO | B | 98 | 29.605 | 5.631 | 3.592 | 1.00 | 17.04 O |
| ATOM | 3321 | N | ASP | B | 99 | 29.014 | 3.649 | 2.696 | 1.00 | 20.10 N |
| ATOM | 3323 | CA | ASP | B | 99 | 29.082 | 4.091 | 1.303 | 1.00 | 20.04 C |
| ATOM | 3325 | CB | ASP | B | 99 | 28.029 | 5.172 | 1.061 | 1.00 | 21.12 C |
| ATOM | 3328 | CG | ASP | B | 99 | 26.612 | 4.657 | 1.337 | 1.00 | 23.44 C |
| ATOM | 3329 | OD1 | ASP | B | 99 | 26.291 | 3.537 | 0.874 | 1.00 | 27.92 O |
| ATOM | 3330 | OD2 | ASP | B | 99 | 25.761 | 5.269 | 2.020 | 1.00 | 28.30 O |
| ATOM | 3331 | C | ASP | B | 99 | 30.494 | 4.496 | 0.860 | 1.00 | 19.38 C |
| ATOM | 3332 | O | ASP | B | 99 | 30.646 | 5.358 | −0.015 | 1.00 | 19.12 O |
| ATOM | 3333 | N | THR | B | 100 | 31.521 | 3.879 | 1.460 | 1.00 | 17.96 N |
| ATOM | 3335 | CA | THR | B | 100 | 32.917 | 4.061 | 1.030 | 1.00 | 18.27 C |
| ATOM | 3337 | CB | THR | B | 100 | 33.757 | 4.812 | 2.091 | 1.00 | 18.29 C |
| ATOM | 3339 | OG1 | THR | B | 100 | 33.964 | 3.969 | 3.249 | 1.00 | 16.21 O |
| ATOM | 3341 | CG2 | THR | B | 100 | 33.041 | 6.065 | 2.595 | 1.00 | 18.22 C |
| ATOM | 3345 | C | THR | B | 100 | 33.606 | 2.725 | 0.744 | 1.00 | 18.55 C |
| ATOM | 3346 | O | THR | B | 100 | 34.839 | 2.644 | 0.724 | 1.00 | 18.17 O |
| ATOM | 3347 | N | GLY | B | 101 | 32.813 | 1.676 | 0.537 | 1.00 | 19.93 N |
| ATOM | 3349 | CA | GLY | B | 101 | 33.346 | 0.341 | 0.306 | 1.00 | 19.59 C |
| ATOM | 3352 | C | GLY | B | 101 | 34.217 | −0.119 | 1.467 | 1.00 | 19.66 C |
| ATOM | 3353 | O | GLY | B | 101 | 35.181 | −0.861 | 1.285 | 1.00 | 19.57 O |
| ATOM | 3354 | N | ASN | B | 102 | 33.856 | 0.343 | 2.661 | 1.00 | 19.84 N |
| ATOM | 3356 | CA | ASN | B | 102 | 34.580 | 0.071 | 3.906 | 1.00 | 19.99 C |
| ATOM | 3358 | CB | ASN | B | 102 | 34.517 | −1.406 | 4.266 | 1.00 | 20.27 C |
| ATOM | 3361 | CG | ASN | B | 102 | 33.148 | −1.823 | 4.683 | 1.00 | 22.54 C |
| ATOM | 3362 | OD1 | ASN | B | 102 | 32.856 | −1.970 | 5.871 | 1.00 | 26.86 O |
| ATOM | 3363 | ND2 | ASN | B | 102 | 32.293 | −2.035 | 3.709 | 1.00 | 25.85 N |
| ATOM | 3366 | C | ASN | B | 102 | 36.016 | 0.557 | 3.943 | 1.00 | 19.98 C |
| ATOM | 3367 | O | ASN | B | 102 | 36.805 | 0.124 | 4.782 | 1.00 | 19.09 O |
| ATOM | 3368 | N | SER | B | 103 | 36.343 | 1.504 | 3.076 | 1.00 | 20.60 N |
| ATOM | 3370 | CA | SER | B | 103 | 37.707 | 1.990 | 2.986 | 1.00 | 19.63 C |
| ATOM | 3372 | CB | SER | B | 103 | 38.016 | 2.353 | 1.541 | 1.00 | 20.16 C |

-continued

| APPENDIX C: CRYSTAL COORDINATES OF FVE PROTEIN | | | | | | | | | |
|---|---|---|---|---|---|---|---|---|---|
| ATOM | 3375 | OG | SER | B | 103 | 37.253 | 3.481 | 1.156 | 1.00 22.36 O |
| ATOM | 3377 | C | SER | B | 103 | 37.979 | 3.214 | 3.870 | 1.00 18.01 C |
| ATOM | 3378 | O | SER | B | 103 | 39.137 | 3.525 | 4.144 | 1.00 18.98 O |
| ATOM | 3379 | N | GLU | B | 104 | 36.936 | 3.918 | 4.294 | 1.00 15.67 N |
| ATOM | 3381 | CA | GLU | B | 104 | 37.135 | 5.116 | 5.120 | 1.00 13.43 C |
| ATOM | 3383 | CB | GLU | B | 104 | 36.265 | 6.297 | 4.656 | 1.00 12.81 C |
| ATOM | 3386 | CG | GLU | B | 104 | 36.679 | 7.618 | 5.313 | 1.00 13.27 C |
| ATOM | 3389 | CD | GLU | B | 104 | 35.732 | 8.776 | 5.029 | 1.00 14.64 C |
| ATOM | 3390 | OE1 | GLU | B | 104 | 34.919 | 8.679 | 4.069 | 1.00 15.08 O |
| ATOM | 3391 | OE2 | GLU | B | 104 | 35.814 | 9.803 | 5.742 | 1.00 14.12 O |
| ATOM | 3392 | C | GLU | B | 104 | 36.797 | 4.780 | 6.558 | 1.00 12.23 C |
| ATOM | 3393 | O | GLU | B | 104 | 35.659 | 4.435 | 6.855 | 1.00 11.79 O |
| ATOM | 3394 | N | GLU | B | 105 | 37.793 | 4.856 | 7.439 | 1.00 11.65 N |
| ATOM | 3396 | CA | GLU | B | 105 | 37.573 | 4.534 | 8.845 | 1.00 10.60 C |
| ATOM | 3398 | CB | GLU | B | 105 | 37.830 | 3.047 | 9.102 | 1.00 10.23 C |
| ATOM | 3401 | CG | GLU | B | 105 | 39.288 | 2.653 | 8.998 | 1.00 11.51 C |
| ATOM | 3404 | CD | GLU | B | 105 | 39.569 | 1.177 | 9.250 | 1.00 13.25 C |
| ATOM | 3405 | OE1 | GLU | B | 105 | 40.772 | 0.827 | 9.367 | 1.00 14.63 O |
| ATOM | 3406 | OE2 | GLU | B | 105 | 38.617 | 0.366 | 9.341 | 1.00 11.87 O |
| ATOM | 3407 | C | GLU | B | 105 | 38.476 | 5.381 | 9.732 | 1.00 9.65 C |
| ATOM | 3408 | O | GLU | B | 105 | 39.492 | 5.931 | 9.272 | 1.00 10.58 O |
| ATOM | 3409 | N | TYR | B | 106 | 38.112 | 5.465 | 11.014 | 1.00 9.46 N |
| ATOM | 3411 | CA | TYR | B | 106 | 38.842 | 6.260 | 12.004 | 1.00 9.17 C |
| ATOM | 3413 | CB | TYR | B | 106 | 38.119 | 7.593 | 12.258 | 1.00 9.00 C |
| ATOM | 3416 | CG | TYR | B | 106 | 37.989 | 8.388 | 10.990 | 1.00 9.70 C |
| ATOM | 3417 | CD1 | TYR | B | 106 | 39.000 | 9.227 | 10.565 | 1.00 10.02 C |
| ATOM | 3419 | CE1 | TYR | B | 106 | 38.900 | 9.908 | 9.378 | 1.00 11.83 C |
| ATOM | 3421 | CZ | TYR | B | 106 | 37.797 | 9.755 | 8.584 | 1.00 10.67 C |
| ATOM | 3422 | OH | TYR | B | 106 | 37.719 | 10.438 | 7.368 | 1.00 13.02 O |
| ATOM | 3424 | CE2 | TYR | B | 106 | 36.784 | 8.909 | 8.958 | 1.00 10.26 C |
| ATOM | 3426 | CD2 | TYR | B | 106 | 36.887 | 8.224 | 10.166 | 1.00 9.29 C |
| ATOM | 3428 | C | TYR | B | 106 | 38.949 | 5.516 | 13.318 | 1.00 9.17 C |
| ATOM | 3429 | O | TYR | B | 106 | 37.963 | 4.945 | 13.774 | 1.00 8.39 O |
| ATOM | 3430 | N | ILE | B | 107 | 40.116 | 5.546 | 13.955 | 1.00 8.89 N |
| ATOM | 3432 | CA | ILE | B | 107 | 40.211 | 4.966 | 15.288 | 1.00 8.90 C |
| ATOM | 3434 | CB | ILE | B | 107 | 41.652 | 5.037 | 15.848 | 1.00 9.24 C |
| ATOM | 3436 | CG1 | ILE | B | 107 | 41.770 | 4.245 | 17.155 | 1.00 10.76 C |
| ATOM | 3439 | CD1 | ILE | B | 107 | 41.571 | 2.765 | 16.979 | 1.00 12.64 C |
| ATOM | 3443 | CG2 | ILE | B | 107 | 42.088 | 6.484 | 16.051 | 1.00 9.73 C |
| ATOM | 3447 | C | ILE | B | 107 | 39.211 | 5.679 | 16.194 | 1.00 9.06 C |
| ATOM | 3448 | O | ILE | B | 107 | 39.102 | 6.912 | 16.171 | 1.00 9.11 O |
| ATOM | 3449 | N | ILE | B | 108 | 38.448 | 4.908 | 16.958 | 1.00 8.10 N |
| ATOM | 3451 | CA | ILE | B | 108 | 37.466 | 5.505 | 17.858 | 1.00 8.46 C |
| ATOM | 3453 | CB | ILE | B | 108 | 36.038 | 5.362 | 17.263 | 1.00 7.92 C |
| ATOM | 3455 | CG1 | ILE | B | 108 | 35.058 | 6.318 | 17.933 | 1.00 8.44 C |
| ATOM | 3458 | CD1 | ILE | B | 108 | 35.451 | 7.735 | 17.791 | 1.00 10.51 C |
| ATOM | 3462 | CG2 | ILE | B | 108 | 35.548 | 3.943 | 17.367 | 1.00 7.73 C |
| ATOM | 3466 | C | ILE | B | 108 | 37.577 | 5.032 | 19.315 | 1.00 9.21 C |
| ATOM | 3467 | O | ILE | B | 108 | 37.028 | 5.675 | 20.206 | 1.00 9.94 O |
| ATOM | 3468 | N | ALA | B | 109 | 38.295 | 3.939 | 19.566 | 1.00 8.98 N |
| ATOM | 3470 | CA | ALA | B | 109 | 38.565 | 3.467 | 20.929 | 1.00 8.87 C |
| ATOM | 3472 | CB | ALA | B | 109 | 37.358 | 2.771 | 21.525 | 1.00 9.01 C |
| ATOM | 3476 | C | ALA | B | 109 | 39.744 | 2.507 | 20.935 | 1.00 8.73 C |
| ATOM | 3477 | O | ALA | B | 109 | 39.957 | 1.757 | 19.994 | 1.00 9.76 O |
| ATOM | 3478 | N | GLU | B | 110 | 40.533 | 2.576 | 21.998 | 1.00 9.54 N |
| ATOM | 3480 | CA | GLU | B | 110 | 41.607 | 1.634 | 22.215 | 1.00 9.46 C |
| ATOM | 3482 | CB | GLU | B | 110 | 42.946 | 2.257 | 21.824 | 1.00 10.74 C |
| ATOM | 3485 | CG | GLU | B | 110 | 44.120 | 1.290 | 21.888 | 1.00 14.55 C |
| ATOM | 3488 | CD | GLU | B | 110 | 45.414 | 1.938 | 21.419 | 1.00 21.68 C |
| ATOM | 3489 | OE1 | GLU | B | 110 | 45.950 | 2.812 | 22.134 | 1.00 25.49 O |
| ATOM | 3490 | OE2 | GLU | B | 110 | 45.877 | 1.587 | 20.321 | 1.00 27.22 O |
| ATOM | 3491 | C | GLU | B | 110 | 41.678 | 1.209 | 23.680 | 1.00 9.73 C |
| ATOM | 3492 | O | GLU | B | 110 | 41.720 | 2.056 | 24.582 | 1.00 10.15 O |
| ATOM | 3493 | N | TRP | B | 111 | 41.703 | −0.098 | 23.894 | 1.00 9.39 N |
| ATOM | 3495 | CA | TRP | B | 111 | 41.990 | −0.671 | 25.187 | 1.00 10.20 C |
| ATOM | 3497 | CB | TRP | B | 111 | 41.076 | −1.840 | 25.491 | 1.00 9.67 C |
| ATOM | 3500 | CG | TRP | B | 111 | 41.470 | −2.528 | 26.787 | 1.00 8.52 C |
| ATOM | 3501 | CD1 | TRP | B | 111 | 42.308 | −3.581 | 26.928 | 1.00 9.95 C |
| ATOM | 3503 | NE1 | TRP | B | 111 | 42.456 | −3.906 | 28.256 | 1.00 13.10 N |
| ATOM | 3505 | CE2 | TRP | B | 111 | 41.728 | −3.017 | 29.010 | 1.00 10.98 C |
| ATOM | 3506 | CD2 | TRP | B | 111 | 41.102 | −2.128 | 28.116 | 1.00 9.50 C |
| ATOM | 3507 | CE3 | TRP | B | 111 | 40.282 | −1.123 | 28.636 | 1.00 10.62 C |
| ATOM | 3509 | CZ3 | TRP | B | 111 | 40.114 | −1.040 | 30.002 | 1.00 12.26 C |
| ATOM | 3511 | CH2 | TRP | B | 111 | 40.756 | −1.929 | 30.857 | 1.00 9.96 C |
| ATOM | 3513 | CZ2 | TRP | B | 111 | 41.561 | −2.926 | 30.385 | 1.00 12.41 C |
| ATOM | 3515 | C | TRP | B | 111 | 43.423 | −1.193 | 25.169 | 1.00 13.35 C |
| ATOM | 3516 | O | TRP | B | 111 | 43.775 | −2.031 | 24.344 | 1.00 11.63 O |
| ATOM | 3517 | N | LYS | B | 112 | 44.263 | −0.666 | 26.056 | 1.00 16.48 N |

-continued

| \multicolumn{9}{c|}{APPENDIX C: CRYSTAL COORDINATES OF FVE PROTEIN} | | | | | | | | |
|---|---|---|---|---|---|---|---|---|
| ATOM | 3519 | CA | LYS | B | 112 | 45.593 | −1.223 | 26.244 | 1.00 | 20.35 C |
| ATOM | 3521 | CB | LYS | B | 112 | 46.627 | −0.459 | 25.436 | 1.00 | 22.00 C |
| ATOM | 3524 | CG | LYS | B | 112 | 47.926 | −1.228 | 25.265 | 1.00 | 26.13 C |
| ATOM | 3527 | CD | LYS | B | 112 | 49.024 | −0.337 | 24.701 | 1.00 | 31.80 C |
| ATOM | 3530 | CE | LYS | B | 112 | 48.724 | 0.098 | 23.278 | 1.00 | 34.89 C |
| ATOM | 3533 | NZ | LYS | B | 112 | 49.811 | 0.945 | 22.716 | 1.00 | 40.47 N |
| ATOM | 3537 | C | LYS | B | 112 | 45.946 | −1.177 | 27.725 | 1.00 | 22.27 C |
| ATOM | 3538 | O | LYS | B | 112 | 46.204 | −0.081 | 28.253 | 1.00 | 23.96 O |
| ATOM | 3539 | BR | BR1 | C | 1 | 32.421 | 56.008 | 18.617 | 1.00 | 7.69 B |
| ATOM | 3540 | BR | BR1 | C | 2 | 29.535 | 49.785 | 7.652 | 1.00 | 7.89 B |
| ATOM | 3541 | BR | BR1 | C | 3 | 14.888 | 42.517 | 9.414 | 1.00 | 6.57 B |
| ATOM | 3542 | BR | BR1 | C | 4 | 25.062 | 15.958 | 16.407 | 1.00 | 10.90 B |
| ATOM | 3543 | BR | BR1 | C | 5 | 33.144 | 18.262 | 4.026 | 1.00 | 20.03 B |
| ATOM | 3544 | BR | BR1 | C | 6 | 40.800 | 30.559 | 10.185 | 1.00 | 12.36 B |
| ATOM | 3545 | BR | BR1 | C | 7 | 30.248 | 54.190 | 19.852 | 1.00 | 14.74 B |
| ATOM | 3546 | BR | BR1 | C | 8 | 38.772 | 41.003 | 24.687 | 1.00 | 22.37 B |
| ATOM | 3547 | BR | BR1 | C | 9 | 26.990 | 5.115 | 28.326 | 1.00 | 15.47 B |
| ATOM | 3548 | BR | BR1 | C | 10 | 40.148 | 5.267 | 23.548 | 1.00 | 2.00 B |
| ATOM | 3549 | BR | BR1 | C | 11 | 40.494 | −13.035 | 23.333 | 1.00 | 14.97 B |
| ATOM | 3550 | BR | BR1 | C | 12 | 26.318 | −12.293 | 15.448 | 1.00 | 14.38 B |
| ATOM | 3551 | BR | BR1 | C | 13 | 31.199 | −18.188 | 15.135 | 1.00 | 9.41 B |
| ATOM | 3552 | BR | BR1 | C | 14 | 32.035 | −14.040 | 15.742 | 1.00 | 12.63 B |
| ATOM | 3553 | BR | BR1 | C | 15 | 29.171 | 31.139 | 8.101 | 1.00 | 2.00 B |
| ATOM | 3554 | BR | BR1 | C | 16 | 28.318 | −4.326 | 9.061 | 1.00 | 2.00 B |
| ATOM | 3555 | O | HOH | D | 1 | 45.016 | −8.481 | 11.093 | 1.00 | 14.02 O |
| ATOM | 3558 | O | HOH | D | 2 | 39.945 | 9.187 | 15.069 | 1.00 | 13.06 O |
| ATOM | 3561 | O | HOH | D | 3 | 37.478 | 27.672 | 11.707 | 1.00 | 16.80 O |
| ATOM | 3564 | O | HOH | D | 4 | 44.772 | −4.577 | 18.363 | 1.00 | 14.26 O |
| ATOM | 3567 | O | HOH | D | 5 | 28.336 | −7.855 | 25.862 | 1.00 | 13.43 O |
| ATOM | 3570 | O | HOH | D | 6 | 23.544 | 0.467 | 24.663 | 1.00 | 16.56 O |
| ATOM | 3573 | O | HOH | D | 7 | 29.531 | −5.991 | 30.538 | 1.00 | 15.82 O |
| ATOM | 3576 | O | HOH | D | 8 | 24.673 | 37.622 | 24.477 | 1.00 | 15.51 O |
| ATOM | 3579 | O | HOH | D | 9 | 33.907 | 51.248 | 18.235 | 1.00 | 18.02 O |
| ATOM | 3582 | O | HOH | D | 10 | 29.468 | 6.207 | 15.500 | 1.00 | 14.54 O |
| ATOM | 3585 | O | HOH | D | 11 | 33.083 | 30.830 | 21.409 | 1.00 | 17.28 O |
| ATOM | 3588 | O | HOH | D | 12 | 22.901 | 44.556 | 18.335 | 1.00 | 14.73 O |
| ATOM | 3591 | O | HOH | D | 13 | 31.027 | 20.428 | 25.544 | 1.00 | 16.68 O |
| ATOM | 3594 | O | HOH | D | 14 | 30.995 | 8.205 | 30.208 | 1.00 | 19.66 O |
| ATOM | 3597 | O | HOH | D | 15 | 28.108 | −13.792 | 35.951 | 1.00 | 20.73 O |
| ATOM | 3600 | O | HOH | D | 16 | 42.527 | 6.434 | 12.302 | 1.00 | 18.94 O |
| ATOM | 3603 | O | HOH | D | 17 | 32.508 | 14.749 | 4.982 | 1.00 | 23.91 O |
| ATOM | 3606 | O | HOH | D | 18 | 23.468 | 6.955 | 26.616 | 1.00 | 18.06 O |
| ATOM | 3609 | O | HOH | D | 19 | 22.712 | 2.972 | 25.766 | 1.00 | 20.00 O |
| ATOM | 3612 | O | HOH | D | 20 | 13.244 | 50.277 | 14.738 | 1.00 | 18.37 O |
| ATOM | 3615 | O | HOH | D | 21 | 36.790 | 15.994 | 26.963 | 1.00 | 17.85 O |
| ATOM | 3618 | O | HOH | D | 22 | 22.367 | 36.375 | 23.529 | 1.00 | 17.11 O |
| ATOM | 3621 | O | HOH | D | 23 | 18.911 | 31.260 | 28.272 | 1.00 | 26.39 O |
| ATOM | 3624 | O | HOH | D | 24 | 31.505 | 1.688 | 3.641 | 1.00 | 20.97 O |
| ATOM | 3627 | O | HOH | D | 25 | 21.210 | 33.851 | 24.000 | 1.00 | 21.28 O |
| ATOM | 3630 | O | HOH | D | 26 | 23.386 | −0.715 | 22.103 | 1.00 | 15.14 O |
| ATOM | 3633 | O | HOH | D | 27 | 29.074 | −11.945 | 31.532 | 1.00 | 24.32 O |
| ATOM | 3636 | O | HOH | D | 28 | 25.268 | 40.455 | 23.574 | 1.00 | 23.95 O |
| ATOM | 3639 | O | HOH | D | 29 | 33.156 | −9.344 | 11.616 | 1.00 | 20.79 O |
| ATOM | 3642 | O | HOH | D | 30 | 38.478 | −5.911 | 7.639 | 1.00 | 21.26 O |
| ATOM | 3645 | O | HOH | D | 31 | 24.308 | 53.095 | 18.780 | 1.00 | 19.70 O |
| ATOM | 3648 | O | HOH | D | 32 | 17.754 | 48.477 | 15.499 | 1.00 | 20.76 O |
| ATOM | 3651 | O | HOH | D | 33 | 42.790 | 5.854 | 23.394 | 1.00 | 23.30 O |
| ATOM | 3654 | O | HOH | D | 34 | 27.861 | 15.691 | 24.120 | 1.00 | 23.40 O |
| ATOM | 3657 | O | HOH | D | 35 | 35.797 | 12.184 | 4.416 | 1.00 | 21.31 O |
| ATOM | 3660 | O | HOH | D | 36 | 30.360 | −0.992 | 28.013 | 1.00 | 16.72 O |
| ATOM | 3663 | O | HOH | D | 37 | 28.276 | −16.367 | 24.146 | 1.00 | 20.65 O |
| ATOM | 3666 | O | HOH | D | 38 | 32.226 | 24.366 | 27.005 | 1.00 | 23.68 O |
| ATOM | 3669 | O | HOH | D | 39 | 20.858 | 29.760 | 23.162 | 1.00 | 21.99 O |
| ATOM | 3672 | O | HOH | D | 40 | 49.235 | 18.819 | 15.583 | 1.00 | 25.35 O |
| ATOM | 3675 | O | HOH | D | 41 | 24.467 | −3.793 | 21.863 | 1.00 | 22.04 O |
| ATOM | 3678 | O | HOH | D | 42 | 26.332 | −5.940 | 25.774 | 1.00 | 16.62 O |
| ATOM | 3681 | O | HOH | D | 43 | 40.578 | 4.994 | 6.108 | 1.00 | 25.58 O |
| ATOM | 3684 | O | HOH | D | 44 | 20.863 | 46.163 | 17.522 | 1.00 | 25.28 O |
| ATOM | 3687 | O | HOH | D | 45 | 42.794 | 2.619 | 9.388 | 1.00 | 23.00 O |
| ATOM | 3690 | O | HOH | D | 46 | 20.611 | 25.977 | 15.514 | 1.00 | 25.08 O |
| ATOM | 3693 | O | HOH | D | 47 | 24.778 | 21.030 | 19.875 | 1.00 | 21.37 O |
| ATOM | 3696 | O | HOH | D | 48 | 24.759 | −5.920 | 23.503 | 1.00 | 16.11 O |
| ATOM | 3699 | O | HOH | D | 49 | 36.889 | 24.475 | 8.631 | 1.00 | 23.03 O |
| ATOM | 3702 | O | HOH | D | 50 | 20.215 | 49.361 | 14.399 | 1.00 | 22.50 O |
| ATOM | 3705 | O | HOH | D | 51 | 47.164 | −5.215 | 12.615 | 1.00 | 22.87 O |
| ATOM | 3708 | O | HOH | D | 52 | 46.004 | 25.078 | 19.448 | 1.00 | 25.71 O |
| ATOM | 3711 | O | HOH | D | 53 | 20.097 | 31.594 | 19.238 | 1.00 | 27.29 O |
| ATOM | 3714 | O | HOH | D | 54 | 19.046 | 1.435 | 16.404 | 1.00 | 27.34 O |

-continued

| APPENDIX C: CRYSTAL COORDINATES OF FVE PROTEIN | | | | | | | | | |
|---|---|---|---|---|---|---|---|---|---|
| ATOM | 3717 | O | HOH | D | 55 | 39.089 | 23.057 | 7.816 | 1.00 28.18 O |
| ATOM | 3720 | O | HOH | D | 56 | 22.799 | 49.789 | 12.926 | 1.00 27.76 O |
| ATOM | 3723 | O | HOH | D | 57 | 21.681 | 37.631 | 15.807 | 1.00 23.46 O |
| ATOM | 3726 | O | HOH | D | 58 | 44.307 | 22.404 | 22.181 | 1.00 23.37 O |
| ATOM | 3729 | O | HOH | D | 59 | 46.170 | −13.085 | 20.941 | 1.00 17.48 O |
| ATOM | 3732 | O | HOH | D | 60 | 36.365 | 41.071 | 5.729 | 1.00 27.02 O |
| ATOM | 3735 | O | HOH | D | 61 | 36.990 | 7.023 | 22.512 | 1.00 22.71 O |
| ATOM | 3738 | O | HOH | D | 62 | 19.169 | −8.584 | 16.372 | 1.00 23.92 O |
| ATOM | 3741 | O | HOH | D | 63 | 20.055 | 28.469 | 14.698 | 1.00 26.12 O |
| ATOM | 3744 | O | HOH | D | 64 | 30.998 | −12.907 | 29.623 | 1.00 25.28 O |
| ATOM | 3747 | O | HOH | D | 65 | 37.347 | −1.150 | 7.121 | 1.00 22.93 O |
| ATOM | 3750 | O | HOH | D | 66 | 33.031 | −13.258 | 27.775 | 1.00 32.50 O |
| ATOM | 3753 | O | HOH | D | 67 | 22.945 | −4.003 | 11.274 | 1.00 30.88 O |
| ATOM | 3756 | O | HOH | D | 68 | 27.701 | 41.270 | 1.720 | 1.00 29.57 O |
| ATOM | 3759 | O | HOH | D | 69 | 25.980 | −9.896 | 14.868 | 1.00 27.31 O |
| ATOM | 3762 | O | HOH | D | 70 | 23.821 | 12.814 | 14.658 | 1.00 24.54 O |
| ATOM | 3765 | O | HOH | D | 71 | 35.006 | 43.534 | 25.083 | 1.00 28.85 O |
| ATOM | 3768 | O | HOH | D | 72 | 35.312 | 36.253 | 1.522 | 1.00 29.21 O |
| ATOM | 3771 | O | HOH | D | 73 | 48.598 | −9.901 | 24.935 | 1.00 25.55 O |
| ATOM | 3774 | O | HOH | D | 74 | 42.294 | −13.685 | 16.218 | 1.00 25.18 O |
| ATOM | 3777 | O | HOH | D | 75 | 42.607 | 12.387 | 16.515 | 1.00 31.10 O |
| ATOM | 3780 | O | HOH | D | 76 | 26.330 | 35.006 | 4.050 | 1.00 31.74 O |
| ATOM | 3783 | O | HOH | D | 77 | 32.850 | 10.209 | 3.504 | 1.00 27.19 O |
| ATOM | 3786 | O | HOH | D | 78 | 30.508 | 10.747 | 29.512 | 1.00 25.87 O |
| ATOM | 3789 | O | HOH | D | 79 | 45.693 | 19.098 | 22.237 | 1.00 30.36 O |
| ATOM | 3792 | O | HOH | D | 80 | 15.634 | 44.761 | 11.710 | 1.00 26.02 O |
| ATOM | 3795 | O | HOH | D | 81 | 18.085 | 50.959 | 3.872 | 1.00 35.51 O |
| ATOM | 3798 | O | HOH | D | 82 | 29.549 | 1.503 | 7.572 | 1.00 29.19 O |
| ATOM | 3801 | O | HOH | D | 83 | 39.725 | 31.841 | 30.695 | 1.00 40.77 O |
| ATOM | 3804 | O | HOH | D | 84 | 20.283 | 36.188 | −4.205 | 1.00 39.38 O |
| ATOM | 3807 | O | HOH | D | 85 | 34.763 | −11.883 | 13.146 | 1.00 21.47 O |
| ATOM | 3810 | O | HOH | D | 26 | 26.410 | 32.901 | 7.289 | 1.00 24.64 O |
| ATOM | 3813 | O | HOH | D | 87 | 44.314 | −2.758 | 11.932 | 1.00 23.95 O |
| ATOM | 3816 | O | HOH | D | 88 | 30.034 | −14.313 | 17.413 | 1.00 29.20 O |
| ATOM | 3819 | O | HOH | D | 89 | 26.961 | 12.263 | 27.391 | 1.00 30.17 O |
| ATOM | 3822 | O | HOH | D | 90 | 28.249 | 0.678 | 3.312 | 1.00 28.11 O |
| ATOM | 3825 | O | HOH | D | 91 | 45.718 | 32.030 | 14.220 | 1.00 34.46 O |
| ATOM | 3828 | O | HOH | D | 92 | 28.299 | −9.696 | 27.995 | 1.00 24.79 O |
| ATOM | 3831 | O | HOH | D | 93 | 13.832 | 48.982 | 7.768 | 1.00 33.46 O |
| ATOM | 3834 | O | HOH | D | 94 | 43.000 | −11.174 | 31.241 | 1.00 28.43 O |
| ATOM | 3837 | O | HOH | D | 95 | 35.944 | 8.335 | 1.385 | 1.00 29.40 O |
| ATOM | 3840 | O | HOH | D | 96 | 29.165 | 29.895 | 11.877 | 1.00 24.28 O |
| ATOM | 3843 | O | HOH | D | 97 | 32.349 | 31.864 | 24.473 | 1.00 30.09 O |
| ATOM | 3846 | O | HOH | D | 98 | 22.954 | 24.601 | 11.686 | 1.00 28.72 O |
| ATOM | 3849 | O | HOH | D | 99 | 31.154 | 51.462 | 19.574 | 1.00 25.81 O |
| ATOM | 3852 | O | HOH | D | 100 | 43.443 | 12.360 | 23.615 | 1.00 24.55 O |
| ATOM | 3855 | O | HOH | D | 101 | 15.670 | 52.252 | 4.362 | 1.00 34.13 O |
| ATOM | 3858 | O | HOH | D | 102 | 25.701 | 41.081 | 26.231 | 1.00 27.56 O |
| ATOM | 3861 | O | HOH | D | 103 | 37.527 | 21.694 | 22.195 | 1.00 32.29 O |
| ATOM | 3864 | O | HOH | D | 104 | 33.325 | −12.660 | 37.738 | 1.00 35.18 O |
| ATOM | 3867 | O | HOH | D | 105 | 26.319 | 5.217 | 15.262 | 1.00 26.13 O |
| ATOM | 3870 | O | HOH | D | 106 | 33.848 | 22.140 | 26.173 | 1.00 31.07 O |
| ATOM | 3873 | O | HOH | D | 107 | 35.489 | 18.857 | 24.618 | 1.00 27.43 O |
| ATOM | 3876 | O | HOH | D | 108 | 42.855 | 46.462 | 8.947 | 1.00 33.41 O |
| ATOM | 3879 | O | HOH | D | 109 | 42.188 | 5.317 | 9.853 | 1.00 30.90 O |
| ATOM | 3882 | O | HOH | D | 110 | 41.401 | 45.084 | 19.630 | 1.00 35.22 O |
| ATOM | 3885 | O | HOH | D | 111 | 45.990 | −4.685 | 27.447 | 1.00 36.33 O |
| ATOM | 3888 | O | HOH | D | 112 | 44.969 | 4.979 | 13.641 | 1.00 30.89 O |
| ATOM | 3891 | O | HOH | D | 113 | 21.231 | 24.488 | 19.771 | 1.00 29.91 O |
| ATOM | 3894 | O | HOH | D | 114 | 28.991 | 22.460 | 25.768 | 1.00 32.28 O |
| ATOM | 3897 | O | HOH | D | 115 | 30.182 | 42.704 | 28.664 | 1.00 34.73 O |
| ATOM | 3900 | O | HOH | D | 116 | 38.457 | 26.788 | 9.301 | 1.00 28.25 O |
| ATOM | 3903 | O | HOH | D | 117 | 33.010 | 8.247 | 32.080 | 1.00 30.38 O |
| ATOM | 3906 | O | HOH | D | 118 | 40.296 | −12.388 | 19.763 | 1.00 29.43 O |
| ATOM | 3909 | O | HOH | D | 119 | 26.522 | 44.371 | 25.621 | 1.00 29.51 O |
| ATOM | 3912 | O | HOH | D | 120 | 43.804 | −4.826 | 10.570 | 1.00 33.46 O |
| ATOM | 3915 | O | HOH | D | 121 | 47.448 | −11.680 | 26.748 | 1.00 37.40 O |
| ATOM | 3918 | O | HOH | D | 122 | 40.716 | −13.572 | 24.920 | 1.00 24.40 O |
| ATOM | 3921 | O | HOH | D | 123 | 41.998 | −1.274 | 34.849 | 1.00 32.74 O |
| ATOM | 3924 | O | HOH | D | 124 | 45.154 | 42.318 | 18.028 | 1.00 36.95 O |
| ATOM | 3927 | O | HOH | D | 125 | 30.324 | −11.134 | 10.862 | 1.00 29.46 O |
| ATOM | 3930 | O | HOH | D | 126 | 42.517 | 10.179 | 15.159 | 1.00 30.78 O |
| ATOM | 3933 | O | HOH | D | 127 | 48.214 | −11.222 | 16.932 | 1.00 31.45 O |
| ATOM | 3936 | O | HOH | D | 128 | 23.815 | −9.373 | 14.042 | 1.00 33.96 O |
| ATOM | 3939 | O | HOH | D | 129 | 31.988 | 24.965 | 29.884 | 1.00 32.47 O |
| ATOM | 3942 | O | HOH | D | 130 | 35.266 | 30.662 | 4.339 | 1.00 37.13 O |
| ATOM | 3945 | O | HOH | D | 131 | 42.057 | 38.530 | 10.976 | 1.00 38.75 O |
| ATOM | 3948 | O | HOH | D | 132 | 24.900 | 3.888 | 13.671 | 1.00 41.30 O |

-continued

| APPENDIX C: CRYSTAL COORDINATES OF FVE PROTEIN | | | | | | | | | |
|---|---|---|---|---|---|---|---|---|---|
| ATOM | 3951 | O | HOH | D | 133 | 44.797 | −11.819 | 18.372 | 1.00 31.27 O |
| ATOM | 3954 | O | HOH | D | 134 | 31.380 | 27.561 | 6.462 | 1.00 38.93 O |
| ATOM | 3957 | O | HOH | D | 135 | 24.585 | −2.131 | 6.886 | 1.00 36.52 O |
| ATOM | 3960 | O | HOH | D | 136 | 44.178 | 14.598 | 21.666 | 1.00 49.82 O |

The invention claimed is:

1. A polypeptide having the sequence of MAGE3-FveT29A (SEQ ID NO: 53), MART1-FveT29A (SEQ ID NO: 55) or CEA-FveT29A (SEQ ID NO: 57).

2. A pharmaceutical composition comprising a polypeptide of claim 1, together with a pharmaceutically acceptable carrier or diluent.

* * * * *

SEQUENCE LISTING

<160> NUMBER OF SEQ ID NOS: 487

<210> SEQ ID NO 1
<211> LENGTH: 13
<212> TYPE: DNA
<213> ORGANISM: Artificial
<220> FEATURE:
<223> OTHER INFORMATION: Low complexity filter
<220> FEATURE:
<221> NAME/KEY: misc_feature
<222> LOCATION: (1)..(13)
<223> OTHER INFORMATION: N is any amono acid

<400> SEQUENCE: 1
nnnnnnnnnn nnn                                                        13

<210> SEQ ID NO 2
<211> LENGTH: 9
<212> TYPE: PRT
<213> ORGANISM: Artificial
<220> FEATURE:
<223> OTHER INFORMATION: Low complexity filter
<220> FEATURE:
<221> NAME/KEY: UNSURE
<222> LOCATION: (1)..(9)
<223> OTHER INFORMATION: X is any amino acid

<400> SEQUENCE: 2

Xaa Xaa Xaa Xaa Xaa Xaa Xaa Xaa Xaa
1               5

<210> SEQ ID NO 3
<211> LENGTH: 32
<212> TYPE: DNA
<213> ORGANISM: Artificial
<220> FEATURE:
<223> OTHER INFORMATION: PCR primer

<400> SEQUENCE: 3
ttgttggatc ccatggagat acacctacat tg                                   32

<210> SEQ ID NO 4
<211> LENGTH: 33
<212> TYPE: DNA
<213> ORGANISM: Artificial
<220> FEATURE:
<223> OTHER INFORMATION: PCR primer

<400> SEQUENCE: 4
ttactgaatt cttatggttt ctgagaacag atg                                  33

<210> SEQ ID NO 5
<211> LENGTH: 348
<212> TYPE: DNA
<213> ORGANISM: Flammulina velutipes

<400> SEQUENCE: 5

```
atgtccgcca cgtcgctcac cttccagctt gcctacttgg tgaagaagat cgacttcgac    60 tacacccca  actggggccg tggtacccca agcagctaca tcgacaacct taccttcccc   120
aaggttctca ccgacaaaaa atactcgtac cgcgtcgtgg tcaatggctc tgaccttggc   180
gtcgagtcca acttcgcagt gacaccgtcc ggtgggcaga ccatcaactt cctccagtac   240 aacaagggt  atggtgtcgc ggacaccaaa acgattcaag ttttcgttgt cattccagat   300
accggcaact cggaggagta catcatcgct gagtggaaga agacttga                348
```

<210> SEQ ID NO 6
<211> LENGTH: 115
<212> TYPE: PRT
<213> ORGANISM: Flammulina velutipes

<400> SEQUENCE: 6

Met Ser Ala Thr Ser Leu Thr Phe Gln Leu Ala Tyr Leu Val Lys Lys
1               5                   10                  15

Ile Asp Phe Asp Tyr Thr Pro Asn Trp Gly Arg Gly Thr Pro Ser Ser
            20                  25                  30

Tyr Ile Asp Asn Leu Thr Phe Pro Lys Val Leu Thr Asp Lys Lys Tyr
        35                  40                  45

Ser Tyr Arg Val Val Asn Gly Ser Asp Leu Gly Val Glu Ser Asn
    50                  55                  60

Phe Ala Val Thr Pro Ser Gly Gly Gln Thr Ile Asn Phe Leu Gln Tyr
65                  70                  75                  80

Asn Lys Gly Tyr Gly Val Ala Asp Thr Lys Thr Ile Gln Val Phe Val
                85                  90                  95

Val Ile Pro Asp Thr Gly Asn Ser Glu Glu Tyr Ile Ile Ala Glu Trp
            100                 105                 110

Lys Lys Thr
        115

<210> SEQ ID NO 7
<211> LENGTH: 1038
<212> TYPE: DNA
<213> ORGANISM: Flammulina velutipes
<220> FEATURE:
<221> NAME/KEY: misc_feature
<222> LOCATION: (1)..(694)
<223> OTHER INFORMATION: GST-FVE sequence

<400> SEQUENCE: 7

```
atgtcccta  tactaggtta ttggaaaatt aagggccttg tgcaacccac tcgacttctt    60
ttggaatatc ttgaagaaaa atatgaagag catttgtatg agcgcgatga aggtgataaa   120
tggcgaaaca aaaagtttga attgggtttg gagtttccca atcttcctta ttatattgat   180
ggtgatgtta aattaacaca gtctatggcc atcatacgtt atatagctga caagcacaac   240
atgttgggtg gttgtccaaa agagcgtgca gagatttcaa tgcttgaagg agcggttttg   300 gatattgat  acggtgtttc gagaattgca tatagtaaag actttgaaac tctcaaagtt   360
gattttctta gcaagctacc tgaaatgctg aaaatgttcg aagatcgttt atgtcataaa   420
acatatttaa atggtgatca tgtaacccat cctgacttca tgttgtatga cgctcttgat   480
gttgttttat acatggaccc aatgtgcctg gatgcgttcc caaaattagt ttgttttaaa   540
aaacgtattg aagctatccc acaaattgat aagtacttga atccagcaa  gtatatagca   600 tggccttgc  agggctggca agccacgttt ggtggtggca accatcctcc aaaatcggat   660
ctggaagttc tgttccaggg gcccctggga tcctccgcca cgtcgctcac cttccagctt   720
```

-continued

```
gcctacttgg tgaagaagat cgacttcgac tacacccca actggggccg tggtacccca      780
agcagctaca tcgacaacct taccttcccc aaggttctca ccgacaaaaa atactcgtac      840
cgcgtcgtgg tcaatggctc tgaccttggc gtcgagtcca acttcgcagt gacaccgtcc      900
ggtgggcaga ccatcaactt cctccagtac aacaagggt atggtgtcgc ggacaccaaa       960
acgattcaag ttttcgttgt cattccagat accggcaact cggaggagta catcatcgct     1020
gagtggaaga agacttga                                                   1038

<210> SEQ ID NO 8
<211> LENGTH: 345
<212> TYPE: PRT
<213> ORGANISM: Flammulina velutipes
<220> FEATURE:
<221> NAME/KEY: UNSURE
<222> LOCATION: (1)..(232)
<223> OTHER INFORMATION: GST domain

<400> SEQUENCE: 8

Met Ser Pro Ile Leu Gly Tyr Trp Lys Ile Lys Gly Leu Val Gln Pro
1               5                   10                  15

Thr Arg Leu Leu Leu Glu Tyr Leu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Glu Val Leu
    210                 215                 220

Phe Gln Gly Pro Leu Gly Ser Ser Ala Thr Ser Leu Thr Phe Gln Leu
225                 230                 235                 240

Ala Tyr Leu Val Lys Lys Ile Asp Phe Asp Tyr Thr Pro Asn Trp Gly
                245                 250                 255

Arg Gly Thr Pro Ser Ser Tyr Ile Asp Asn Leu Thr Phe Pro Lys Val
            260                 265                 270

Leu Thr Asp Lys Lys Tyr Ser Tyr Arg Val Val Val Asn Gly Ser Asp
        275                 280                 285

Leu Gly Val Glu Ser Asn Phe Ala Val Thr Pro Ser Gly Gly Gln Thr
```

```
                    290               295               300
Ile Asn Phe Leu Gln Tyr Asn Lys Gly Tyr Gly Val Ala Asp Thr Lys
305                 310               315               320

Thr Ile Gln Val Phe Val Ile Pro Asp Thr Gly Asn Ser Glu Glu
                325               330               335

Tyr Ile Ile Ala Glu Trp Lys Lys Thr
                340               345

<210> SEQ ID NO 9
<211> LENGTH: 309
<212> TYPE: DNA
<213> ORGANISM: Artificial
<220> FEATURE:
<223> OTHER INFORMATION: Deletion mutant

<400> SEQUENCE: 9
atgtccgcca cgtcgttcga ctacaccccc aactggggcc gtggtacccc aagcagctac      60
atcgacaacc ttaccttccc caaggttctc accgacaaaa aatactcgta ccgcgtcgtg     120
gtcaatggct ctgaccttgg cgtcgagtcc aacttcgcag tgacaccgtc cggtgggcag     180
accatcaact tcctccagta caacaagggg tatggtgtcg cggacaccaa aacgattcaa     240
gttttcgttg tcattccaga taccggcaac tcggaggagt acatcatcgc tgagtggaag     300
aagacttga                                                             309

<210> SEQ ID NO 10
<211> LENGTH: 102
<212> TYPE: PRT
<213> ORGANISM: Artificial
<220> FEATURE:
<223> OTHER INFORMATION: Deletion protein

<400> SEQUENCE: 10

Met Ser Ala Thr Ser Phe Asp Tyr Thr Pro Asn Trp Gly Arg Gly Thr
1               5                   10                  15

Pro Ser Ser Tyr Ile Asp Asn Leu Thr Phe Pro Lys Val Leu Thr Asp
                20                  25                  30

Lys Lys Tyr Ser Tyr Arg Val Val Asn Gly Ser Asp Leu Gly Val
            35                  40                  45

Glu Ser Asn Phe Ala Val Thr Pro Ser Gly Gly Gln Thr Ile Asn Phe
    50                  55                  60

Leu Gln Tyr Asn Lys Gly Tyr Gly Val Ala Asp Thr Lys Thr Ile Gln
65                  70                  75                  80

Val Phe Val Val Ile Pro Asp Thr Gly Asn Ser Glu Glu Tyr Ile Ile
                85                  90                  95

Ala Glu Trp Lys Lys Thr
            100

<210> SEQ ID NO 11
<211> LENGTH: 303
<212> TYPE: DNA
<213> ORGANISM: Artificial
<220> FEATURE:
<223> OTHER INFORMATION: Deletion mutant

<400> SEQUENCE: 11
atgtccgcca cgtcgctcac cttccagctt gcctacttgg tgaagaagat cgacatcgac      60
aaccttacct tccccaaggt tctcaccgac aaaaaatact cgtaccgcgt cgtggtcaat     120
ggctctgacc ttggcgtcga gtccaacttc gcagtgacac cgtccggtgg gcagaccatc     180
```

-continued

```
aacttcctcc agtacaacaa ggggtatggt gtcgcggaca ccaaaacgat tcaagttttc    240
gttgtcattc cagataccgg caactcggag gagtacatca tcgctgagtg gaagaagact    300
tga                                                                  303
```

<210> SEQ ID NO 12
<211> LENGTH: 100
<212> TYPE: PRT
<213> ORGANISM: Artificial
<220> FEATURE:
<223> OTHER INFORMATION: Deletion mutant

<400> SEQUENCE: 12

```
Met Ser Ala Thr Ser Leu Thr Phe Gln Leu Ala Tyr Leu Val Lys Lys
1               5                   10                  15

Ile Asp Ile Asp Asn Leu Thr Phe Pro Lys Val Leu Thr Asp Lys Lys
            20                  25                  30

Tyr Ser Tyr Arg Val Val Asn Gly Ser Asp Leu Gly Val Glu Ser
        35                  40                  45

Asn Phe Ala Val Thr Pro Ser Gly Gly Gln Thr Ile Asn Phe Leu Gln
    50                  55                  60

Tyr Asn Lys Gly Tyr Gly Val Ala Asp Thr Lys Thr Ile Gln Val Phe
65                  70                  75                  80

Val Val Ile Pro Asp Thr Gly Asn Ser Glu Glu Tyr Ile Ile Ala Glu
                85                  90                  95

Trp Lys Lys Thr
            100
```

<210> SEQ ID NO 13
<211> LENGTH: 309
<212> TYPE: DNA
<213> ORGANISM: Artificial
<220> FEATURE:
<223> OTHER INFORMATION: Deletion mutant

<400> SEQUENCE: 13

```
atgtccgcca cgtcgctcac cttccagctt gcctacttgg tgaagaagat cgacttcgac    60 tacacccca actggggccg tggtaccca agcagctaca atactcgta ccgcgtcgtg      120 gtcaatggct ctgaccttgg cgtcgagtcc aacttcgcag tgacaccgtc cggtgggcag    180
accatcaact tcctccagta caacaagggg tatggtgtcg cggacaccaa aacgattcaa    240
gttttcgttg tcattccaga taccggcaac tcggaggagt acatcatcgc tgagtggaag    300
aagacttga                                                            309
```

<210> SEQ ID NO 14
<211> LENGTH: 102
<212> TYPE: PRT
<213> ORGANISM: Artificial
<220> FEATURE:
<223> OTHER INFORMATION: Deletion mutant

<400> SEQUENCE: 14

```
Met Ser Ala Thr Ser Leu Thr Phe Gln Leu Ala Tyr Leu Val Lys Lys
1               5                   10                  15

Ile Asp Phe Asp Tyr Thr Pro Asn Trp Gly Arg Gly Thr Pro Ser Ser
            20                  25                  30

Tyr Lys Tyr Ser Tyr Arg Val Val Asn Gly Ser Asp Leu Gly Val
        35                  40                  45

Glu Ser Asn Phe Ala Val Thr Pro Ser Gly Gly Gln Thr Ile Asn Phe
    50                  55                  60
```

```
Leu Gln Tyr Asn Lys Gly Tyr Gly Val Ala Asp Thr Lys Thr Ile Gln
 65                  70                  75                  80

Val Phe Val Val Ile Pro Asp Thr Gly Asn Ser Glu Glu Tyr Ile Ile
                 85                  90                  95

Ala Glu Trp Lys Lys Thr
            100
```

```
<210> SEQ ID NO 15
<211> LENGTH: 306
<212> TYPE: DNA
<213> ORGANISM: Artificial
<220> FEATURE:
<223> OTHER INFORMATION: Deletion mutant

<400> SEQUENCE: 15
atgtccgcca cgtcgctcac cttccagctt gcctacttgg tgaagaagat cgacttcgac     60 tacacccca actggggccg tggtacccca agcagctaca tcgacaacct taccttcccc    120
aaggttctca ccgacaaagt cgagtccaac ttcgcagtga caccgtccgg tgggcagacc   180
atcaacttcc tccagtacaa caaggggtat ggtgtcgcgg acaccaaaac gattcaagtt   240
ttcgttgtca ttccagatac cggcaactcg gaggagtaca tcatcgctga gtggaagaag   300
acttga                                                              306
```

```
<210> SEQ ID NO 16
<211> LENGTH: 101
<212> TYPE: PRT
<213> ORGANISM: Artificial
<220> FEATURE:
<223> OTHER INFORMATION: Deletion mutant

<400> SEQUENCE: 16

Met Ser Ala Thr Ser Leu Thr Phe Gln Leu Ala Tyr Leu Val Lys Lys
  1               5                  10                  15

Ile Asp Phe Asp Tyr Thr Pro Asn Trp Gly Arg Gly Thr Pro Ser Ser
                 20                  25                  30

Tyr Ile Asp Asn Leu Thr Phe Pro Lys Val Leu Thr Asp Lys Val Glu
             35                  40                  45

Ser Asn Phe Ala Val Thr Pro Ser Gly Gly Gln Thr Ile Asn Phe Leu
 50                  55                  60

Gln Tyr Asn Lys Gly Tyr Gly Val Ala Asp Thr Lys Thr Ile Gln Val
 65                  70                  75                  80

Phe Val Val Ile Pro Asp Thr Gly Asn Ser Glu Glu Tyr Ile Ile Ala
                 85                  90                  95

Glu Trp Lys Lys Thr
            100
```

```
<210> SEQ ID NO 17
<211> LENGTH: 312
<212> TYPE: DNA
<213> ORGANISM: Artificial
<220> FEATURE:
<223> OTHER INFORMATION: Deletion mutant

<400> SEQUENCE: 17
atgtccgcca cgtcgctcac cttccagctt gcctacttgg tgaagaagat cgacttcgac     60 tacacccca actggggccg tggtacccca agcagctaca tcgacaacct taccttcccc    120
aaggttctca ccgacaaaaa atactcgtac cgcgtcgtgt caatggctc tgaccttggc    180 cagaccatca acttcctcca gtacaacaag gggtatggtg tcgcggacac caaaacgatt  240
```

```
caagttttcg ttgtcattcc agataccggc aactcggagg agtacatcat cgctgagtgg    300
aagaagactt ga                                                        312
```

<210> SEQ ID NO 18
<211> LENGTH: 103
<212> TYPE: PRT
<213> ORGANISM: Artificial
<220> FEATURE:
<223> OTHER INFORMATION: Deletion mutant

<400> SEQUENCE: 18

```
Met Ser Ala Thr Ser Leu Thr Phe Gln Leu Ala Tyr Leu Val Lys Lys
1               5                   10                  15

Ile Asp Phe Asp Tyr Thr Pro Asn Trp Gly Arg Gly Thr Pro Ser Ser
                20                  25                  30

Tyr Ile Asp Asn Leu Thr Phe Pro Lys Val Leu Thr Asp Lys Lys Tyr
            35                  40                  45

Ser Tyr Arg Val Val Val Asn Gly Ser Asp Leu Gly Gln Thr Ile Asn
        50                  55                  60

Phe Leu Gln Tyr Asn Lys Gly Tyr Gly Val Ala Asp Thr Lys Thr Ile
65                  70                  75                  80

Gln Val Phe Val Val Ile Pro Asp Thr Gly Asn Ser Glu Glu Tyr Ile
                85                  90                  95

Ile Ala Glu Trp Lys Lys Thr
            100
```

<210> SEQ ID NO 19
<211> LENGTH: 312
<212> TYPE: DNA
<213> ORGANISM: Artificial
<220> FEATURE:
<223> OTHER INFORMATION: Deletion mutants

<400> SEQUENCE: 19

```
atgtccgcca cgtcgctcac cttccagctt gcctacttgg tgaagaagat cgacttcgac    60
tacaccccca actggggccg tggtacccca agcagctaca tcgacaacct taccttcccc   120
aaggttctca ccgacaaaaa atactcgtac cgcgtcgtgg tcaatggctc tgaccttggc   180
gtcgagtcca acttcgcagt gacaccgtcc ggtgggggtg tcgcggacac caaaacgatt   240
caagttttcg ttgtcattcc agataccggc aactcggagg agtacatcat cgctgagtgg   300
aagaagactt ga                                                       312
```

<210> SEQ ID NO 20
<211> LENGTH: 103
<212> TYPE: PRT
<213> ORGANISM: Artificial
<220> FEATURE:
<223> OTHER INFORMATION: Deletion mutants

<400> SEQUENCE: 20

```
Met Ser Ala Thr Ser Leu Thr Phe Gln Leu Ala Tyr Leu Val Lys Lys
1               5                   10                  15

Ile Asp Phe Asp Tyr Thr Pro Asn Trp Gly Arg Gly Thr Pro Ser Ser
                20                  25                  30

Tyr Ile Asp Asn Leu Thr Phe Pro Lys Val Leu Thr Asp Lys Lys Tyr
            35                  40                  45

Ser Tyr Arg Val Val Val Asn Gly Ser Asp Leu Gly Val Glu Ser Asn
        50                  55                  60
```

```
Phe Ala Val Thr Pro Ser Gly Gly Val Ala Asp Thr Lys Thr Ile
65                  70                  75                  80

Gln Val Phe Val Val Ile Pro Asp Thr Gly Asn Ser Glu Glu Tyr Ile
                85                  90                  95

Ile Ala Glu Trp Lys Lys Thr
            100

<210> SEQ ID NO 21
<211> LENGTH: 312
<212> TYPE: DNA
<213> ORGANISM: Artificial
<220> FEATURE:
<223> OTHER INFORMATION: Deletion mutants

<400> SEQUENCE: 21
atgtccgcca cgtcgctcac cttccagctt gcctacttgg tgaagaagat cgacttcgac      60
tacacccccc actggggccg tggtaccccc agcagctaca tcgacaacct taccttcccc    120
aaggttctca ccgacaaaaa atactcgtac cgcgtcgtgg tcaatggctc tgaccttggc    180
gtcgagtcca acttcgcagt gacaccgtcc ggtgggcaga ccatcaactt cctccagtac    240
aacaaggggt atgtcattcc agataccggc aactcggagg agtacatcat cgctgagtgg    300
aagaagactt ga                                                        312

<210> SEQ ID NO 22
<211> LENGTH: 102
<212> TYPE: PRT
<213> ORGANISM: Artificial
<220> FEATURE:
<223> OTHER INFORMATION: Deletion mutants

<400> SEQUENCE: 22

Met Ser Ala Thr Ser Leu Thr Phe Gln Leu Ala Tyr Leu Val Lys Lys
1               5                   10                  15

Ile Asp Phe Asp Tyr Thr Pro Asn Trp Gly Arg Gly Thr Pro Ser Ser
            20                  25                  30

Tyr Ile Asp Asn Leu Thr Phe Pro Lys Val Leu Thr Asp Lys Lys Tyr
        35                  40                  45

Ser Tyr Arg Val Val Val Asn Gly Ser Asp Leu Gly Val Glu Ser Asn
    50                  55                  60

Phe Ala Val Thr Pro Ser Gly Gly Gln Thr Ile Asn Phe Leu Gln Tyr
65                  70                  75                  80

Asn Lys Gly Tyr Ile Pro Asp Thr Gly Asn Ser Glu Glu Tyr Ile Ile
                85                  90                  95

Ala Glu Trp Lys Lys Thr
            100

<210> SEQ ID NO 23
<211> LENGTH: 321
<212> TYPE: DNA
<213> ORGANISM: Artificial
<220> FEATURE:
<223> OTHER INFORMATION: Deletion mutant

<400> SEQUENCE: 23
atgtccgcca cgtcgctcac cttccagctt gcctacttgg tgaagaagat cgacttcgac      60
tacacccccc actggggccg tggtaccccc agcagctaca tcgacaacct taccttcccc    120
aaggttctca ccgacaaaaa atactcgtac cgcgtcgtgg tcaatggctc tgaccttggc    180
gtcgagtcca acttcgcagt gacaccgtcc ggtgggcaga ccatcaactt cctccagtac    240
```

```
aacaaggggt atggtgtcgc ggacaccaaa acgattcaag ttttcgttgt ctacatcatc    300
gctgagtgga agaagacttg a                                              321
```

<210> SEQ ID NO 24
<211> LENGTH: 106
<212> TYPE: PRT
<213> ORGANISM: Artificial
<220> FEATURE:
<223> OTHER INFORMATION: Deletion mutant

<400> SEQUENCE: 24

```
Met Ser Ala Thr Ser Leu Thr Phe Gln Leu Ala Tyr Leu Val Lys Lys
1               5                   10                  15

Ile Asp Phe Asp Tyr Thr Pro Asn Trp Gly Arg Gly Thr Pro Ser Ser
            20                  25                  30

Tyr Ile Asp Asn Leu Thr Phe Pro Lys Val Leu Thr Asp Lys Lys Tyr
        35                  40                  45

Ser Tyr Arg Val Val Asn Gly Ser Asp Leu Gly Val Glu Ser Asn
    50                  55                  60

Phe Ala Val Thr Pro Ser Gly Gly Gln Thr Ile Asn Phe Leu Gln Tyr
65                  70                  75                  80

Asn Lys Gly Tyr Gly Val Ala Asp Thr Lys Thr Ile Gln Val Phe Val
                85                  90                  95

Val Tyr Ile Ile Ala Glu Trp Lys Lys Thr
            100                 105
```

<210> SEQ ID NO 25
<211> LENGTH: 321
<212> TYPE: DNA
<213> ORGANISM: Artificial
<220> FEATURE:
<223> OTHER INFORMATION: Deletion mutant

<400> SEQUENCE: 25

```
atgtccgcca cgtcgctcac cttccagctt gcctacttgg tgaagaagat cgacttcgac    60
tacaccccca actggggccg tggtacccca agcagctaca tcgacaacct taccttcccc   120
aaggttctca ccgacaaaaa atactcgtac cgcgtcgtgg tcaatggctc tgaccttggc   180
gtcgagtcca acttcgcagt gacaccgtcc ggtgggcaga ccatcaactt cctccagtac   240
aacaaggggt atggtgtcgc ggacaccaaa acgattcaag ttttcgttgt cattccagat   300
accggcaact cggaggagtg a                                              321
```

<210> SEQ ID NO 26
<211> LENGTH: 106
<212> TYPE: PRT
<213> ORGANISM: Artificial
<220> FEATURE:
<223> OTHER INFORMATION: Deletion mutant

<400> SEQUENCE: 26

```
Met Ser Ala Thr Ser Leu Thr Phe Gln Leu Ala Tyr Leu Val Lys Lys
1               5                   10                  15

Ile Asp Phe Asp Tyr Thr Pro Asn Trp Gly Arg Gly Thr Pro Ser Ser
            20                  25                  30

Tyr Ile Asp Asn Leu Thr Phe Pro Lys Val Leu Thr Asp Lys Lys Tyr
        35                  40                  45

Ser Tyr Arg Val Val Asn Gly Ser Asp Leu Gly Val Glu Ser Asn
    50                  55                  60

Phe Ala Val Thr Pro Ser Gly Gly Gln Thr Ile Asn Phe Leu Gln Tyr
```

```
                65                  70                  75                  80
Asn Lys Gly Tyr Gly Val Ala Asp Thr Lys Thr Ile Gln Val Phe Val
                    85                  90                  95

Val Ile Pro Asp Thr Gly Asn Ser Glu Glu
                100                 105

<210> SEQ ID NO 27
<211> LENGTH: 237
<212> TYPE: DNA
<213> ORGANISM: Artificial
<220> FEATURE:
<223> OTHER INFORMATION: Deletion mutant

<400> SEQUENCE: 27
atgtccgcca cgtcgctcac cttccagctt gcctacttgg tgaagaagat cgacttcgac      60
tacaccccca actggggccg tggtacccca agcagctaca tcgacaacct taccttcccc     120
aaggttctca ccgacaaaaa atactcgtac cgcgtcgtgg tcaatggctc tgaccttggc     180
attccagata ccggcaactc ggaggagtac atcatcgctg agtggaagaa gacttga        237

<210> SEQ ID NO 28
<211> LENGTH: 78
<212> TYPE: PRT
<213> ORGANISM: Artificial
<220> FEATURE:
<223> OTHER INFORMATION: Deletion mutant

<400> SEQUENCE: 28

Met Ser Ala Thr Ser Leu Thr Phe Gln Leu Ala Tyr Leu Val Lys Lys
1               5                   10                  15

Ile Asp Phe Asp Tyr Thr Pro Asn Trp Gly Arg Gly Thr Pro Ser Ser
                20                  25                  30

Tyr Ile Asp Asn Leu Thr Phe Pro Lys Val Leu Thr Asp Lys Lys Tyr
            35                  40                  45

Ser Tyr Arg Val Val Val Asn Gly Ser Asp Leu Gly Ile Pro Asp Thr
        50                  55                  60

Gly Asn Ser Glu Glu Tyr Ile Ile Ala Glu Trp Lys Lys Thr
65                  70                  75

<210> SEQ ID NO 29
<211> LENGTH: 138
<212> TYPE: DNA
<213> ORGANISM: Artificial
<220> FEATURE:
<223> OTHER INFORMATION: Deletion mutant

<400> SEQUENCE: 29
aatggctctg accttggcgt cgagtccaac ttcgcagtga caccgtccgg tgggcagacc      60
atcaacttcc tccagtacaa caagggtat ggtgtcgcgg acaccaaaac gattcaagtt      120
ttcgttgtca ttccagat                                                    138

<210> SEQ ID NO 30
<211> LENGTH: 46
<212> TYPE: PRT
<213> ORGANISM: Artificial
<220> FEATURE:
<223> OTHER INFORMATION: Deletion mutant

<400> SEQUENCE: 30

Asn Gly Ser Asp Leu Gly Val Glu Ser Asn Phe Ala Val Thr Pro Ser
1               5                   10                  15
```

```
Gly Gly Gln Thr Ile Asn Phe Leu Gln Tyr Asn Lys Gly Tyr Gly Val
            20                  25                  30

Ala Asp Thr Lys Thr Ile Gln Val Phe Val Val Ile Pro Asp
        35                  40                  45
```

<210> SEQ ID NO 31
<211> LENGTH: 348
<212> TYPE: DNA
<213> ORGANISM: Artificial
<220> FEATURE:
<223> OTHER INFORMATION: Deletion mutant

<400> SEQUENCE: 31

```
atgtccgcca cgtcgctcac cttccagctt gcctacttgg tgaagaagat cgacttcgac      60
tacacccca actggggcgc aggtacccca agcagctaca tcgacaacct taccttcccc     120
aaggttctca ccgacaaaaa atactcgtac cgcgtcgtgg tcaatggctc tgaccttggc     180
gtcgagtcca acttcgcagt gacaccgtcc ggtgggcaga ccatcaactt cctccagtac     240
aacaagggt atggtgtcgc ggacaccaaa acgattcaag ttttcgttgt cattccagat     300
accggcaact cggaggagta catcatcgct gagtggaaga agacttga                  348
```

<210> SEQ ID NO 32
<211> LENGTH: 115
<212> TYPE: PRT
<213> ORGANISM: Artificial
<220> FEATURE:
<223> OTHER INFORMATION: Deletion mutant

<400> SEQUENCE: 32

```
Met Ser Ala Thr Ser Leu Thr Phe Gln Leu Ala Tyr Leu Val Lys Lys
1               5                   10                  15

Ile Asp Phe Asp Tyr Thr Pro Asn Trp Gly Ala Gly Thr Pro Ser Ser
            20                  25                  30

Tyr Ile Asp Asn Leu Thr Phe Pro Lys Val Leu Thr Asp Lys Lys Tyr
        35                  40                  45

Ser Tyr Arg Val Val Val Asn Gly Ser Asp Leu Gly Val Glu Ser Asn
    50                  55                  60

Phe Ala Val Thr Pro Ser Gly Gly Gln Thr Ile Asn Phe Leu Gln Tyr
65                  70                  75                  80

Asn Lys Gly Tyr Gly Val Ala Asp Thr Lys Thr Ile Gln Val Phe Val
                85                  90                  95

Val Ile Pro Asp Thr Gly Asn Ser Glu Glu Tyr Ile Ile Ala Glu Trp
            100                 105                 110

Lys Lys Thr
        115
```

<210> SEQ ID NO 33
<211> LENGTH: 348
<212> TYPE: DNA
<213> ORGANISM: Artificial
<220> FEATURE:
<223> OTHER INFORMATION: Deletion mutant

<400> SEQUENCE: 33

```
atgtccgcca cgtcgctcac cttccagctt gcctacttgg tgaagaagat cgacttcgac      60
tacacccca actggggccg tgcaacccca agcagctaca tcgacaacct taccttcccc     120
aaggttctca ccgacaaaaa atactcgtac cgcgtcgtgg tcaatggctc tgaccttggc     180
gtcgagtcca acttcgcagt gacaccgtcc ggtgggcaga ccatcaactt cctccagtac     240
```

```
aacaaggggt atggtgtcgc ggacaccaaa acgattcaag ttttcgttgt cattccagat    300
accggcaact cggaggagta catcatcgct gagtggaaga agacttga                 348
```

<210> SEQ ID NO 34
<211> LENGTH: 115
<212> TYPE: PRT
<213> ORGANISM: Artificial
<220> FEATURE:
<223> OTHER INFORMATION: Deletion mutant

<400> SEQUENCE: 34

```
Met Ser Ala Thr Ser Leu Thr Phe Gln Leu Ala Tyr Leu Val Lys Lys
1               5                   10                  15

Ile Asp Phe Asp Tyr Thr Pro Asn Trp Gly Arg Ala Thr Pro Ser Ser
            20                  25                  30

Tyr Ile Asp Asn Leu Thr Phe Pro Lys Val Leu Thr Asp Lys Lys Tyr
        35                  40                  45

Ser Tyr Arg Val Val Val Asn Gly Ser Asp Leu Gly Val Glu Ser Asn
    50                  55                  60

Phe Ala Val Thr Pro Ser Gly Gly Gln Thr Ile Asn Phe Leu Gln Tyr
65                  70                  75                  80

Asn Lys Gly Tyr Gly Val Ala Asp Thr Lys Thr Ile Gln Val Phe Val
                85                  90                  95

Val Ile Pro Asp Thr Gly Asn Ser Glu Glu Tyr Ile Ile Ala Glu Trp
            100                 105                 110

Lys Lys Thr
        115
```

<210> SEQ ID NO 35
<211> LENGTH: 348
<212> TYPE: DNA
<213> ORGANISM: Artificial
<220> FEATURE:
<223> OTHER INFORMATION: Deletion mutant

<400> SEQUENCE: 35

```
atgtccgcca cgtcgctcac cttccagctt gcctacttgg tgaagaagat cgacttcgac    60 tacacccca actggggccg tggtgcacca agcagctaca tcgacaacct taccttcccc    120
aaggttctca ccgacaaaaa atactcgtac cgcgtcgtgg tcaatggctc tgaccttggc    180
gtcgagtcca acttcgcagt gacaccgtcc ggtgggcaga ccatcaactt cctccagtac    240
aacaaggggt atggtgtcgc ggacaccaaa acgattcaag ttttcgttgt cattccagat    300
accggcaact cggaggagta catcatcgct gagtggaaga agacttga                 348
```

<210> SEQ ID NO 36
<211> LENGTH: 115
<212> TYPE: PRT
<213> ORGANISM: Artificial
<220> FEATURE:
<223> OTHER INFORMATION: Deletion mutant

<400> SEQUENCE: 36

```
Met Ser Ala Thr Ser Leu Thr Phe Gln Leu Ala Tyr Leu Val Lys Lys
1               5                   10                  15

Ile Asp Phe Asp Tyr Thr Pro Asn Trp Gly Arg Gly Ala Pro Ser Ser
            20                  25                  30

Tyr Ile Asp Asn Leu Thr Phe Pro Lys Val Leu Thr Asp Lys Lys Tyr
        35                  40                  45

Ser Tyr Arg Val Val Val Asn Gly Ser Asp Leu Gly Val Glu Ser Asn
```

```
                50                  55                  60
Phe Ala Val Thr Pro Ser Gly Gly Gln Thr Ile Asn Phe Leu Gln Tyr
 65                  70                  75                  80

Asn Lys Gly Tyr Gly Val Ala Asp Thr Lys Thr Ile Gln Val Phe Val
                 85                  90                  95

Val Ile Pro Asp Thr Gly Asn Ser Glu Glu Tyr Ile Ile Ala Glu Trp
            100                 105                 110

Lys Lys Thr
        115

<210> SEQ ID NO 37
<211> LENGTH: 696
<212> TYPE: DNA
<213> ORGANISM: Artificial
<220> FEATURE:
<223> OTHER INFORMATION: chimeric mutant
<220> FEATURE:
<221> NAME/KEY: misc_feature
<222> LOCATION: (352)..(696)
<223> OTHER INFORMATION: Wild type sequence

<400> SEQUENCE: 37
caagagcaca agccaaagaa ggatgatttc cgaaacgaat tcgatcactt gttgatcgaa      60
caggcaaacc atgctatcga aagggagaa catcaattgc tttacttgca acaccaactc     120
gacgaattga atgaaaacaa gagcaaggaa ttgcaagaga aaatcattcg agaacttgat     180
gttgtttgcg ccatgatcga aggagcccaa ggagctttgg aacgtgaatt gaagcgaact     240
gatcttaaca ttttggaacg attcaactac gaagaggctc aaactctcag caagatcttg     300
cttaaggatt tgaaggaaac cgaacaaaaa gtgaaggata ttcaaaccca atccgccacg     360
tcgctcacct tccagcttgc ctacttggtg aagaagatcg acttcgacta cacccccaac     420 tgggccgtg gtaccccaag cagctacatc gacaacctta ccttcccaa ggttctcacc      480 gacaaaaaat actcgtaccg cgtcgtggtc aatggctctg accttggcgt cgagtccaac     540
ttcgcagtga caccgtccgg tgggcagacc atcaacttcc tccagtacaa caaggggtat     600
ggtgtcgcgg acaccaaaac gattcaagtt ttcgttgtca ttccagatac cggcaactcg     660
gaggagtaca tcatcgctga gtggaagaag acttga                              696

<210> SEQ ID NO 38
<211> LENGTH: 231
<212> TYPE: PRT
<213> ORGANISM: Artificial
<220> FEATURE:
<223> OTHER INFORMATION: Chimeric mutant
<220> FEATURE:
<221> NAME/KEY: UNSURE
<222> LOCATION: (118)..(231)
<223> OTHER INFORMATION: wildtype sequence

<400> SEQUENCE: 38

Gln Glu His Lys Pro Lys Lys Asp Asp Phe Arg Asn Glu Phe Asp His
  1               5                  10                  15

Leu Leu Ile Glu Gln Ala Asn His Ala Ile Glu Lys Gly Glu His Gln
             20                  25                  30

Leu Leu Tyr Leu Gln His Gln Leu Asp Glu Leu Asn Glu Asn Lys Ser
         35                  40                  45

Lys Glu Leu Gln Glu Lys Ile Ile Arg Glu Leu Asp Val Val Cys Ala
     50                  55                  60

Met Ile Glu Gly Ala Gln Gly Ala Leu Glu Arg Glu Leu Lys Arg Thr
 65                  70                  75                  80
```

```
Asp Leu Asn Ile Leu Glu Arg Phe Asn Tyr Glu Glu Ala Gln Thr Leu
                85                  90                  95

Ser Lys Ile Leu Leu Lys Asp Leu Lys Glu Thr Glu Gln Lys Val Lys
            100                 105                 110

Asp Ile Gln Thr Gln Ser Ala Thr Ser Leu Thr Phe Gln Leu Ala Tyr
        115                 120                 125

Leu Val Lys Lys Ile Asp Phe Asp Tyr Thr Pro Asn Trp Gly Arg Gly
    130                 135                 140

Thr Pro Ser Ser Tyr Ile Asp Asn Leu Thr Phe Pro Lys Val Leu Thr
145                 150                 155                 160

Asp Lys Lys Tyr Ser Tyr Arg Val Val Asn Gly Ser Asp Leu Gly
                165                 170                 175

Val Glu Ser Asn Phe Ala Val Thr Pro Ser Gly Gly Gln Thr Ile Asn
            180                 185                 190

Phe Leu Gln Tyr Asn Lys Gly Tyr Gly Val Ala Asp Thr Lys Thr Ile
        195                 200                 205

Gln Val Phe Val Val Ile Pro Asp Thr Gly Asn Ser Glu Glu Tyr Ile
    210                 215                 220

Ile Ala Glu Trp Lys Lys Thr
225                 230
```

<210> SEQ ID NO 39
<211> LENGTH: 696
<212> TYPE: DNA
<213> ORGANISM: Artificial
<220> FEATURE:
<223> OTHER INFORMATION: Chimeric mutant

<400> SEQUENCE: 39

```
caagagcaca agccaaagaa ggatgatttc cgaaacgaat tcgatcactt gttgatcgaa      60
caggcaaacc atgctatcga aaagggagaa catcaattgc tttacttgca acaccaactc     120
gacgaattga atgaaaacaa gagcaaggaa ttgcaagaga aaatcattcg agaacttgat     180
gttgtttgcg ccatgatcga aggagcccaa ggagctttgg aacgtgaatt gaagcgaact     240
gatcttaaca ttttggaacg attcaactac gaagaggctc aaactctcag caagatcttg     300
cttaaggatt tgaaggaaac cgaacaaaaa gtgaaggata ttcaaaccca atccgccacg     360
tcgctcacct tccagcttgc ctacttggtg aagaagatcg acttcgacta caccccaac      420
tggggcgcag gtaccccaag cagctacatc gacaacctta ccttcccaa ggttctcacc       480
gacaaaaaat actcgtaccg cgtcgtggtc aatggctctg accttggcgt cgagtccaac     540
ttcgcagtga caccgtccgg tgggcagacc atcaacttcc tccagtacaa caaggggtat     600
ggtgtcgcgg acaccaaaac gattcaagtt ttcgttgtca ttccagatac cggcaactcg     660
gaggagtaca tcatcgctga gtggaagaag acttga                              696
```

<210> SEQ ID NO 40
<211> LENGTH: 231
<212> TYPE: PRT
<213> ORGANISM: Artificial
<220> FEATURE:
<223> OTHER INFORMATION: Chimeric mutant
<220> FEATURE:
<221> NAME/KEY: UNSURE
<222> LOCATION: (118)..(231)
<223> OTHER INFORMATION: wild type sequence

<400> SEQUENCE: 40

Gln Glu His Lys Pro Lys Lys Asp Asp Phe Arg Asn Glu Phe Asp His

```
              1               5              10              15
Leu Leu Ile Glu Gln Ala Asn His Ala Ile Glu Lys Gly Glu His Gln
                20                  25                  30
Leu Leu Tyr Leu Gln His Gln Leu Asp Glu Leu Asn Glu Asn Lys Ser
            35                  40                  45
Lys Glu Leu Gln Glu Lys Ile Ile Arg Glu Leu Asp Val Val Cys Ala
        50                  55                  60
Met Ile Glu Gly Ala Gln Gly Ala Leu Glu Arg Glu Leu Lys Arg Thr
65                  70                  75                  80
Asp Leu Asn Ile Leu Glu Arg Phe Asn Tyr Glu Glu Ala Gln Thr Leu
                85                  90                  95
Ser Lys Ile Leu Leu Lys Asp Leu Lys Glu Thr Glu Gln Lys Val Lys
            100                 105                 110
Asp Ile Gln Thr Gln Ser Ala Thr Ser Leu Thr Phe Gln Leu Ala Tyr
        115                 120                 125
Leu Val Lys Lys Ile Asp Phe Asp Tyr Thr Pro Asn Trp Gly Ala Gly
    130                 135                 140
Thr Pro Ser Ser Tyr Ile Asp Asn Leu Thr Phe Pro Lys Val Leu Thr
145                 150                 155                 160
Asp Lys Lys Tyr Ser Tyr Arg Val Val Asn Gly Ser Asp Leu Gly
                165                 170                 175
Val Glu Ser Asn Phe Ala Val Thr Pro Ser Gly Gln Thr Ile Asn
            180                 185                 190
Phe Leu Gln Tyr Asn Lys Gly Tyr Gly Val Ala Asp Thr Lys Thr Ile
        195                 200                 205
Gln Val Phe Val Val Ile Pro Asp Thr Gly Asn Ser Glu Glu Tyr Ile
    210                 215                 220
Ile Ala Glu Trp Lys Lys Thr
225                 230

<210> SEQ ID NO 41
<211> LENGTH: 696
<212> TYPE: DNA
<213> ORGANISM: Artificial
<220> FEATURE:
<223> OTHER INFORMATION: Chimeric mutant
<220> FEATURE:
<221> NAME/KEY: misc_feature
<222> LOCATION: (352)..(696)
<223> OTHER INFORMATION: Wildtype sequence

<400> SEQUENCE: 41
caagagcaca agccaaagaa ggatgatttc cgaaacgaat tcgatcactt gttgatcgaa     60
caggcaaacc atgctatcga aaagggagaa catcaattgc tttacttgca acaccaactc    120
gacgaattga atgaaaacaa gagcaaggaa ttgcaagaga aaatcattcg agaacttgat    180
gttgtttgcg ccatgatcga aggagcccaa ggagctttgg aacgtgaatt gaagcgaact    240
gatcttaaca ttttggaacg attcaactac gaagaggctc aaactctcag caagatcttg    300
cttaaggatt tgaaggaaac cgaacaaaaa gtgaaggata ttcaaaccca atccgccacg    360
tcgctcacct tccagcttgc ctacttggtg aagaagatcg acttcgacta cccccccaac    420
tggggccgtg gtgcaccaag cagctacatc gacaacctta ccttccccaa ggttctcacc    480
gacaaaaaat actcgtaccg cgtcgtggtc aatggctctg accttggcgt cgagtccaac    540
ttcgcagtga caccgtccgg tgggcagacc atcaacttcc tccagtacaa caagggtat    600
ggtgtcgcgg acaccaaaac gattcaagtt ttcgttgtca ttccagatac cggcaactcg    660
```
gaggagtaca tcatcgctga gtggaagaag acttga                                    696

<210> SEQ ID NO 42
<211> LENGTH: 231
<212> TYPE: PRT
<213> ORGANISM: Artificial
<220> FEATURE:
<223> OTHER INFORMATION: Chimeric mutant
<220> FEATURE:
<221> NAME/KEY: UNSURE
<222> LOCATION: (118)..(231)
<223> OTHER INFORMATION: Wildtype sequence

<400> SEQUENCE: 42

```
Gln Glu His Lys Pro Lys Lys Asp Asp Phe Arg Asn Glu Phe Asp His
1               5                   10                  15

Leu Leu Ile Glu Gln Ala Asn His Ala Ile Glu Lys Gly Glu His Gln
            20                  25                  30

Leu Leu Tyr Leu Gln His Gln Leu Asp Glu Leu Asn Glu Asn Lys Ser
        35                  40                  45

Lys Glu Leu Gln Glu Lys Ile Ile Arg Glu Leu Asp Val Val Cys Ala
    50                  55                  60

Met Ile Glu Gly Ala Gln Gly Ala Leu Glu Arg Glu Leu Lys Arg Thr
65                  70                  75                  80

Asp Leu Asn Ile Leu Glu Arg Phe Asn Tyr Glu Glu Ala Gln Thr Leu
                85                  90                  95

Ser Lys Ile Leu Leu Lys Asp Leu Lys Glu Thr Glu Gln Lys Val Lys
            100                 105                 110

Asp Ile Gln Thr Gln Ser Ala Thr Ser Leu Thr Phe Gln Leu Ala Tyr
        115                 120                 125

Leu Val Lys Lys Ile Asp Phe Asp Tyr Thr Pro Asn Trp Gly Arg Gly
    130                 135                 140

Ala Pro Ser Ser Tyr Ile Asp Asn Leu Thr Phe Pro Lys Val Leu Thr
145                 150                 155                 160

Asp Lys Lys Tyr Ser Tyr Arg Val Val Asn Gly Ser Asp Leu Gly
                165                 170                 175

Val Glu Ser Asn Phe Ala Val Thr Pro Ser Gly Gly Gln Thr Ile Asn
            180                 185                 190

Phe Leu Gln Tyr Asn Lys Gly Tyr Gly Val Ala Asp Thr Lys Thr Ile
        195                 200                 205

Gln Val Phe Val Val Ile Pro Asp Thr Gly Asn Ser Glu Glu Tyr Ile
    210                 215                 220

Ile Ala Glu Trp Lys Lys Thr
225                 230
```

<210> SEQ ID NO 43
<211> LENGTH: 732
<212> TYPE: DNA
<213> ORGANISM: Artificial
<220> FEATURE:
<223> OTHER INFORMATION: Chimeric mutant
<220> FEATURE:
<221> NAME/KEY: misc_feature
<222> LOCATION: (388)..(732)
<223> OTHER INFORMATION: wildtype sequence

<400> SEQUENCE: 43
gatcaagtcg atgtcaaaga ttgtgccaat catgaaatca aaaagttttt ggtaccagga      60
tgccatggtt cagaaccatg tatcattcat cgtggtaaac cattccaatt ggaagccgtt     120
ttcgaagcca accaaaacac aaaaacggct aaaattgaaa tcaaagcctc aatcgatggt     180

-continued

```
ttagaagttg atgttcccgg tatcgatcca aatgcatgcc attacatgaa atgcccattg    240
gttaaaggac aacaatatga tattaaatat acatggaatg ttccgaaaat tgcaccaaaa    300
tctgaaaatg ttgtcgtcac tgttaaagtt atgggtgatg atggtgtttt ggcctgtgct    360
attgctactc atgctaaaat ccgcgattcc gccacgtcgc tcaccttcca gcttgcctac    420
ttggtgaaga agatcgactt cgactacacc cccaactggg gcgcaggtac cccaagcagc    480
tacatcgaca accttacctt ccccaaggtt ctcaccgaca aaaatactc gtaccgcgtc     540 gtggtcaatg gctctgacct tggcgtcgag tccaacttcg cagtgacacc gtccggtggg    600
cagaccatca acttcctcca gtacaacaag gggtatggtg tcgcggacac caaaacgatt    660
caagttttcg ttgtcattcc agataccggc aactcggagg agtacatcat cgctgagtgg    720
aagaagactt ga                                                        732
```

```
<210> SEQ ID NO 44
<211> LENGTH: 243
<212> TYPE: PRT
<213> ORGANISM: Artificial
<220> FEATURE:
<223> OTHER INFORMATION: Chimeric mutant
<220> FEATURE:
<221> NAME/KEY: misc_feature
<222> LOCATION: (130)..(243)
<223> OTHER INFORMATION: wildtype sequence

<400> SEQUENCE: 44
```

Asp Gln Val Asp Val Lys Asp Cys Ala Asn His Glu Ile Lys Lys Val
1               5                   10                  15

Leu Val Pro Gly Cys His Gly Ser Glu Pro Cys Ile Ile His Arg Gly
            20                  25                  30

Lys Pro Phe Gln Leu Glu Ala Val Phe Glu Ala Asn Gln Asn Thr Lys
        35                  40                  45

Thr Ala Lys Ile Glu Ile Lys Ala Ser Ile Asp Gly Leu Glu Val Asp
    50                  55                  60

Val Pro Gly Ile Asp Pro Asn Ala Cys His Tyr Met Lys Cys Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Val Lys Val Met Gly
            100                 105                 110

Asp Asp Gly Val Leu Ala Cys Ala Ile Ala Thr His Ala Lys Ile Arg
        115                 120                 125

Asp Ser Ala Thr Ser Leu Thr Phe Gln Leu Ala Tyr Leu Val Lys Lys
    130                 135                 140

Ile Asp Phe Asp Tyr Thr Pro Asn Trp Gly Ala Gly Thr Pro Ser Ser
145                 150                 155                 160

Tyr Ile Asp Asn Leu Thr Phe Pro Lys Val Leu Thr Asp Lys Lys Tyr
                165                 170                 175

Ser Tyr Arg Val Val Val Asn Gly Ser Asp Leu Gly Val Glu Ser Asn
            180                 185                 190

Phe Ala Val Thr Pro Ser Gly Gly Gln Thr Ile Asn Phe Leu Gln Tyr
        195                 200                 205

Asn Lys Gly Tyr Gly Val Ala Asp Thr Lys Thr Ile Gln Val Phe Val
    210                 215                 220

Val Ile Pro Asp Thr Gly Asn Ser Glu Glu Tyr Ile Ile Ala Glu Trp
225                 230                 235                 240

Lys Lys Thr

<210> SEQ ID NO 45
<211> LENGTH: 732
<212> TYPE: DNA
<213> ORGANISM: Artificial
<220> FEATURE:
<223> OTHER INFORMATION: Chimeric mutant
<220> FEATURE:
<221> NAME/KEY: misc_feature
<222> LOCATION: (388)..(732)
<223> OTHER INFORMATION: wildtype sequence

<400> SEQUENCE: 45

```
gatcaagtcg atgtcaaaga ttgtgccaat catgaaatca aaaagttttt ggtaccagga     60
tgccatggtt cagaaccatg tatcattcat cgtggtaaac cattccaatt ggaagccgtt    120
ttcgaagcca accaaaacac aaaaacggct aaaattgaaa tcaaagcctc aatcgatggt    180
ttagaagttg atgttcccgg tatcgatcca aatgcatgcc attacatgaa atgcccattg    240
gttaaaggac aacaatatga tattaaatat acatggaatg ttccgaaaat tgcaccaaaa    300
tctgaaaatg ttgtcgtcac tgttaaagtt atgggtgatg atggtgtttt ggcctgtgct    360
attgctactc atgctaaaat ccgcgattcc gccacgtcgc tcaccttcca gcttgcctac    420
ttggtgaaga gatcgactt cgactacacc cccaactggg gccgtggtgc accaagcagc    480
tacatcgaca accttacctt ccccaaggtt ctcaccgaca aaaatactc gtaccgcgtc    540 gtggtcaatg gctctgacct tggcgtcgag tccaacttcg cagtgacacc gtccggtggg    600
cagaccatca acttcctcca gtacaacaag gggtatggtg tcgcggacac caaaacgatt    660
caagttttcg ttgtcattcc agataccggc aactcggagg agtacatcat cgctgagtgg    720
aagaagactt ga                                                        732
```

<210> SEQ ID NO 46
<211> LENGTH: 243
<212> TYPE: PRT
<213> ORGANISM: Artificial
<220> FEATURE:
<223> OTHER INFORMATION: Chimeric mutant
<220> FEATURE:
<221> NAME/KEY: UNSURE
<222> LOCATION: (130)..(243)
<223> OTHER INFORMATION: Wildtype sequence

<400> SEQUENCE: 46

Asp Gln Val Asp Val Lys Asp Cys Ala Asn His Glu Ile Lys Lys Val
1               5                   10                  15

Leu Val Pro Gly Cys His Gly Ser Glu Pro Cys Ile Ile His Arg Gly
            20                  25                  30

Lys Pro Phe Gln Leu Glu Ala Val Phe Glu Ala Asn Gln Asn Thr Lys
        35                  40                  45

Thr Ala Lys Ile Glu Ile Lys Ala Ser Ile Asp Gly Leu Glu Val Asp
    50                  55                  60

Val Pro Gly Ile Asp Pro Asn Ala Cys His Tyr Met Lys Cys Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Thr Val Lys Val Met Gly
            100                 105                 110

Asp Asp Gly Val Leu Ala Cys Ala Ile Ala Thr His Ala Lys Ile Arg
        115                 120                 125

```
Asp Ser Ala Thr Ser Leu Thr Phe Gln Leu Ala Tyr Leu Val Lys Lys
        130                 135                 140

Ile Asp Phe Asp Tyr Thr Pro Asn Trp Gly Arg Gly Ala Pro Ser Ser
145                 150                 155                 160

Tyr Ile Asp Asn Leu Thr Phe Pro Lys Val Leu Thr Asp Lys Lys Tyr
                165                 170                 175

Ser Tyr Arg Val Val Val Asn Gly Ser Asp Leu Gly Val Glu Ser Asn
            180                 185                 190

Phe Ala Val Thr Pro Ser Gly Gln Thr Ile Asn Phe Leu Gln Tyr
        195                 200                 205

Asn Lys Gly Tyr Gly Val Ala Asp Thr Lys Thr Ile Gln Val Phe Val
        210                 215                 220

Val Ile Pro Asp Thr Gly Asn Ser Glu Glu Tyr Ile Ile Ala Glu Trp
225                 230                 235                 240

Lys Lys Thr

<210> SEQ ID NO 47
<211> LENGTH: 1083
<212> TYPE: DNA
<213> ORGANISM: Artificial
<220> FEATURE:
<223> OTHER INFORMATION: Chimeric mutant
<220> FEATURE:
<221> NAME/KEY: misc_feature
<222> LOCATION: (1)..(351)
<223> OTHER INFORMATION: Domain
<220> FEATURE:
<221> NAME/KEY: misc_feature
<222> LOCATION: (352)..(738)
<223> OTHER INFORMATION: Domain

<400> SEQUENCE: 47
caagagcaca agccaaagaa ggatgatttc cgaaacgaat tcgatcactt gttgatcgaa      60
caggcaaacc atgctatcga aagggagaa catcaattgc tttacttgca acaccaactc     120
gacgaattga atgaaaacaa gagcaaggaa ttgcaagaga aaatcattcg agaacttgat     180
gttgtttgcg ccatgatcga aggagcccaa ggagctttgg aacgtgaatt gaagcgaact     240
gatcttaaca ttttggaacg attcaactac gaagaggctc aaactctcag caagatcttg     300
cttaaggatt tgaaggaaac cgaacaaaaa gtgaaggata ttcaaaccca agatcaagtc     360
gatgtcaaag attgtgccaa tcatgaaatc aaaaaagttt tggtaccagg atgccatggt     420
tcagaaccat gtatcattca tcgtggtaaa ccattccaat ggaagccgt tttcgaagcc     480
aaccaaaaca caaaaacggc taaaattgaa atcaaagcct caatcgatgg tttagaagtt     540
gatgttcccg gtatcgatcc aaatgcatgc cattacatga atgcccatt ggttaaagga     600
caacaatatg atattaaata tacatggaat gttccgaaaa ttgcaccaaa atctgaaaat     660
gttgtcgtca ctgttaaagt tatgggtgat gatggtgttt tggcctgtgc tattgctact     720
catgctaaaa tccgcgattc cgccacgtcg ctcaccttcc agcttgccta cttggtgaag     780
aagatcgact cgactacac ccccaactgg ggcgcaggta ccccaagcag ctacatcgac     840
aaccttacct tccccaaggt tctcaccgac aaaaatact cgtaccgcgt cgtggtcaat     900
ggctctgacc ttggcgtcga gtccaacttc gcagtgacac cgtccggtgg cagaccatc     960
aacttcctcc agtacaacaa ggggtatggt gtcgcggaca ccaaaacgat tcaagttttc    1020
gttgtcattc cagataccgg caactcggag gagtacatca tcgctgagtg gaagaagact    1080
tga                                                                 1083
```

-continued

```
<210> SEQ ID NO 48
<211> LENGTH: 360
<212> TYPE: PRT
<213> ORGANISM: Artificial
<220> FEATURE:
<223> OTHER INFORMATION: Chimeric mutant
<220> FEATURE:
<221> NAME/KEY: UNSURE
<222> LOCATION: (1)..(117)
<223> OTHER INFORMATION: domain
<220> FEATURE:
<221> NAME/KEY: UNSURE
<222> LOCATION: (118)..(247)
<223> OTHER INFORMATION: domain

<400> SEQUENCE: 48

Gln Glu His Lys Pro Lys Lys Asp Asp Phe Arg Asn Glu Phe Asp His
1               5                   10                  15

Leu Leu Ile Glu Gln Ala Asn His Ala Ile Glu Lys Gly Glu His Gln
            20                  25                  30

Leu Leu Tyr Leu Gln His Gln Leu Asp Glu Leu Asn Glu Asn Lys Ser
        35                  40                  45

Lys Glu Leu Gln Glu Lys Ile Ile Arg Glu Leu Asp Val Val Cys Ala
    50                  55                  60

Met Ile Glu Gly Ala Gln Gly Ala Leu Glu Arg Glu Leu Lys Arg Thr
65                  70                  75                  80

Asp Leu Asn Ile Leu Glu Arg Phe Asn Tyr Glu Ala Gln Thr Leu
                85                  90                  95

Ser Lys Ile Leu Leu Lys Asp Leu Lys Glu Thr Glu Gln Lys Val Lys
            100                 105                 110

Asp Ile Gln Thr Gln Asp Gln Val Asp Val Lys Asp Cys Ala Asn His
        115                 120                 125

Glu Ile Lys Lys Val Leu Val Pro Gly Cys His Gly Ser Glu Pro Cys
    130                 135                 140

Ile Ile His Arg Gly Lys Pro Phe Gln Leu Glu Ala Val Phe Glu Ala
145                 150                 155                 160

Asn Gln Asn Thr Lys Thr Ala Lys Ile Glu Ile Lys Ala Ser Ile Asp
                165                 170                 175

Gly Leu Glu Val Asp Val Pro Gly Ile Asp Pro Asn Ala Cys His Tyr
            180                 185                 190

Met Lys Cys Pro Leu Val Lys Gly Gln Gln Tyr Asp Ile Lys Tyr Thr
        195                 200                 205

Trp Asn Val Pro Lys Ile Ala Pro Lys Ser Glu Asn Val Val Val Thr
    210                 215                 220

Val Lys Val Met Gly Asp Asp Gly Val Leu Ala Cys Ala Ile Ala Thr
225                 230                 235                 240

His Ala Lys Ile Arg Asp Ser Ala Thr Ser Leu Thr Phe Gln Leu Ala
                245                 250                 255

Tyr Leu Val Lys Lys Ile Asp Phe Asp Tyr Thr Pro Asn Trp Gly Ala
            260                 265                 270

Gly Thr Pro Ser Ser Tyr Ile Asp Asn Leu Thr Phe Pro Lys Val Leu
        275                 280                 285

Thr Asp Lys Lys Tyr Ser Tyr Arg Val Val Asn Gly Ser Asp Leu
    290                 295                 300

Gly Val Glu Ser Asn Phe Ala Val Thr Pro Ser Gly Gly Gln Thr Ile
305                 310                 315                 320

Asn Phe Leu Gln Tyr Asn Lys Gly Tyr Gly Val Ala Asp Thr Lys Thr
                325                 330                 335
```

```
Ile Gln Val Phe Val Val Ile Pro Asp Thr Gly Asn Ser Glu Glu Tyr
             340                 345                 350

Ile Ile Ala Glu Trp Lys Lys Thr
        355                 360
```

<210> SEQ ID NO 49
<211> LENGTH: 212
<212> TYPE: PRT
<213> ORGANISM: Artificial
<220> FEATURE:
<223> OTHER INFORMATION: Fusion protien
<220> FEATURE:
<221> NAME/KEY: UNSURE
<222> LOCATION: (99)..(212)
<223> OTHER INFORMATION: FVE

<400> SEQUENCE: 49

```
Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro Ser Ala Thr Ser Leu Thr Phe Gln Leu Ala Tyr Leu Val Lys
            100                 105                 110

Lys Ile Asp Phe Asp Tyr Thr Pro Asn Trp Gly Arg Gly Ala Pro Ser
        115                 120                 125

Ser Tyr Ile Asp Asn Leu Thr Phe Pro Lys Val Leu Thr Asp Lys Lys
    130                 135                 140

Tyr Ser Tyr Arg Val Val Val Asn Gly Ser Asp Leu Gly Val Glu Ser
145                 150                 155                 160

Asn Phe Ala Val Thr Pro Ser Gly Gly Gln Thr Ile Asn Phe Leu Gln
                165                 170                 175

Tyr Asn Lys Gly Tyr Gly Val Ala Asp Thr Lys Thr Ile Gln Val Phe
            180                 185                 190

Val Val Ile Pro Asp Thr Gly Asn Ser Glu Glu Tyr Ile Ile Ala Glu
        195                 200                 205

Trp Lys Lys Thr
    210
```

<210> SEQ ID NO 50
<211> LENGTH: 639
<212> TYPE: DNA
<213> ORGANISM: Artificial
<220> FEATURE:
<223> OTHER INFORMATION: Fusion protein
<220> FEATURE:
<221> NAME/KEY: misc_feature
<222> LOCATION: (295)..(639)
<223> OTHER INFORMATION: FVE

<400> SEQUENCE: 50

```
atgcatggag atacacctac attgcatgaa tatatgttag atttgcaacc agagacaact      60
gatctctact gttatgagca attaaatgac agctcagagg aggaggatga aatagatggt     120
```

```
ccagctggac aagcagaacc ggacagagcc cattacaata ttgtaacctt ttgttgcaag    180
tgtgactcta cgcttcggtt gtgcgtacaa agcacacacg tagacattcg tactttggaa    240
gacctgttaa tgggcacact aggaattgtg tgccccatct gttctcagaa accatccgcc    300
acgtcgctca ccttccagct tgcctacttg gtgaagaaga tcgacttcga ctacaccccc    360
aactggggcc gtggtgcacc aagcagctac atcgacaacc ttaccttccc caaggttctc    420
accgacaaaa aatactcgta ccgcgtcgtg gtcaatggct ctgaccttgg cgtcgagtcc    480
aacttcgcag tgacaccgtc cggtgggcag accatcaact tcctccagta caacaagggg    540
tatggtgtcg cggacaccaa aacgattcaa gttttcgttg tcattccaga taccggcaac    600
tcggaggagt acatcatcgc tgagtggaag aagacttga                           639
```

<210> SEQ ID NO 51
<211> LENGTH: 282
<212> TYPE: PRT
<213> ORGANISM: Artificial
<220> FEATURE:
<223> OTHER INFORMATION: Fusion protein
<220> FEATURE:
<221> NAME/KEY: UNSURE
<222> LOCATION: (169)..(282)
<223> OTHER INFORMATION: FVE

<400> SEQUENCE: 51

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Gln Pro Glu Gly Arg Ala Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Leu Pro Leu Val Tyr Ala Thr Gly
        130                 135                 140

Asn Leu Pro Gly Cys Ser Phe Ser Ile Phe Leu Leu Ala Leu Leu Ser
145                 150                 155                 160

Cys Leu Thr Ile Pro Ala Ser Ala Ser Ala Thr Ser Leu Thr Phe Gln
                165                 170                 175

Leu Ala Tyr Leu Val Lys Lys Ile Asp Phe Asp Tyr Thr Pro Asn Trp
                180                 185                 190

Gly Arg Gly Ala Pro Ser Ser Tyr Ile Asp Asn Leu Thr Phe Pro Lys
            195                 200                 205

Val Leu Thr Asp Lys Lys Tyr Ser Tyr Arg Val Val Val Asn Gly Ser
        210                 215                 220

Asp Leu Gly Val Glu Ser Asn Phe Ala Val Thr Pro Ser Gly Gly Gln
225                 230                 235                 240

Thr Ile Asn Phe Leu Gln Tyr Asn Lys Gly Tyr Gly Val Ala Asp Thr
                245                 250                 255
```

Lys Thr Ile Gln Val Phe Val Val Ile Pro Asp Thr Gly Asn Ser Glu
                260                 265                 270

Glu Tyr Ile Ile Ala Glu Trp Lys Lys Thr
            275                 280

<210> SEQ ID NO 52
<211> LENGTH: 856
<212> TYPE: DNA
<213> ORGANISM: Artificial
<220> FEATURE:
<223> OTHER INFORMATION: Fusion protein
<220> FEATURE:
<221> NAME/KEY: misc_feature
<222> LOCATION: (512)..(856)
<223> OTHER INFORMATION: FVE

<400> SEQUENCE: 52

| | | | | | | |
|---|---|---|---|---|---|---|
| atgagcacga | atcctaaacc | tcaaagaaaa | accaaacgta | acaccaaccg | ccgcccacag | 60 |
| gacgtcaagt | tcccgggcgg | tggtcagatc | gtcggtggag | tttacctgtt | gccgcgcagg | 120 |
| ggccccaggt | tgggtgtgcg | cgcgactagg | aagacttccg | agcggtcgca | acctcgtgga | 180 |
| aggcgacaac | ctatcccaa | ggctcgccag | cccgagggta | gggcctgggc | tcagcccggg | 240 |
| taccctggc | ccctctatgg | caatgagggc | ttggggtggg | caggatggct | cctgtcaccc | 300 |
| cgtggctctc | ggcctagttg | gggccccacg | daccccggc | gtaggtcgcg | caatttgggt | 360 |
| aaggtcatcg | ataccctcac | gtgcggcttc | gccgatctca | tggggtacct | tccgctcgtc | 420 |
| ggcgcaacag | ggaatctgcc | cggttgctcc | ttttctatct | tccttttggc | tttgctgtcc | 480 |
| tgtttgacca | tcccagcttc | cgcttatgaa | gtccgccacg | tcgctcacct | tccagcttgc | 540 |
| ctacttggtg | aagaagatcg | acttcgacta | caccccaac | tggggccgtg | gtgcaccaag | 600 |
| cagctacatc | gacaacctta | ccttccccaa | ggttctcacc | gacaaaaaat | actcgtaccg | 660 |
| cgtcgtggtc | aatggctctg | accttggcgt | cgagtccaac | ttcgcagtga | caccgtccgg | 720 |
| tgggcagacc | atcaacttcc | tccagtacaa | caagggggtat | ggtgtcgcgg | acaccaaaac | 780 |
| gattcaagtt | ttcgttgtca | ttccagatac | cggcaactcg | gaggagtaca | tcatcgctga | 840 |
| gtggaagaag | acttga | | | | | 856 |

<210> SEQ ID NO 53
<211> LENGTH: 428
<212> TYPE: PRT
<213> ORGANISM: Artificial
<220> FEATURE:
<223> OTHER INFORMATION: Fusion protein
<220> FEATURE:
<221> NAME/KEY: UNSURE
<222> LOCATION: (315)..(428)
<223> OTHER INFORMATION: FVE

<400> SEQUENCE: 53

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Glu Ala Ala Ser Ser Ser Thr Leu Val Glu Val
        35                  40                  45

Thr Leu Gly Glu Val Pro Ala Ala Glu Ser Pro Asp Pro Gln Ser
    50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser

|     |     |     | 85  |     |     |     |     | 90  |     |     |     |     | 95  |     |
| --- | --- | --- | --- | --- | --- | --- | --- | --- | --- | --- | --- | --- | --- | --- |
| Thr | Phe | Pro | Asp | Leu | Glu | Ser | Glu | Phe | Gln | Ala | Ala | Leu | Ser | Arg | Lys |
|     |     |     | 100 |     |     |     |     | 105 |     |     |     |     | 110 |     |

Val Ala Glu Leu Val His Phe Leu Leu Lys Tyr Arg Ala Arg Glu
                115                     120                 125

Pro Val Thr Lys Ala Glu Met Leu Gly Ser Val Val Gly Asn Trp Gln
            130                 135                 140

Tyr Phe Phe Pro Val Ile Phe Ser Lys Ala Ser Ser Leu Gln Leu
145                 150                 155                 160

Val Phe Gly Ile Glu Leu Met Glu Val Asp Pro Ile Gly His Leu Tyr
                165                 170                 175

Ile Phe Ala Thr Cys Leu Gly Leu Ser Tyr Asp Gly Leu Leu Gly Asp
            180                 185                 190

Asn Gln Ile Met Pro Lys Ala Gly Leu Leu Ile Ile Val Leu Ala Ile
                195                 200                 205

Ile Ala Arg Glu Gly Asp Cys Ala Pro Glu Glu Lys Ile Trp Glu Glu
            210                 215                 220

Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
            275                 280                 285

His Met Val Lys Ile Ser Gly Gly Pro His Ile Ser Tyr Pro Pro Leu
290                 295                 300

His Glu Trp Val Leu Arg Glu Gly Glu Glu Ser Ala Thr Ser Leu Thr
305                 310                 315                 320

Phe Gln Leu Ala Tyr Leu Val Lys Lys Ile Asp Phe Asp Tyr Thr Pro
                325                 330                 335

Asn Trp Gly Arg Gly Ala Pro Ser Ser Tyr Ile Asp Asn Leu Thr Phe
            340                 345                 350

Pro Lys Val Leu Thr Asp Lys Lys Tyr Ser Tyr Arg Val Val Asn
            355                 360                 365

Gly Ser Asp Leu Gly Val Glu Ser Asn Phe Ala Val Thr Pro Ser Gly
            370                 375                 380

Gly Gln Thr Ile Asn Phe Leu Gln Tyr Asn Lys Gly Tyr Gly Val Ala
385                 390                 395                 400

Asp Thr Lys Thr Ile Gln Val Phe Val Val Ile Pro Asp Thr Gly Asn
                405                 410                 415

Ser Glu Glu Tyr Ile Ile Ala Glu Trp Lys Lys Thr
            420                 425

<210> SEQ ID NO 54
<211> LENGTH: 1287
<212> TYPE: DNA
<213> ORGANISM: Artificial
<220> FEATURE:
<223> OTHER INFORMATION: Fusion protein
<220> FEATURE:
<221> NAME/KEY: misc_feature
<222> LOCATION: (943)..(1287)
<223> OTHER INFORMATION: FVE

<400> SEQUENCE: 54
atgcctcttg agcagaggag tcagcactgc aagcctgaag aaggccttga ggcccgagga    60

```
gaggccctgg gcctggtggg tgcgcaggct cctgctactg aggagcagga ggctgcctcc    120
tcctcttcta ctctagttga agtcaccctg ggggaggtgc ctgctgccga gtcaccagat    180
cctcccagac gtcctcaggg agcctccagc ctccccacta ccatgaacta ccctctctgg    240
agccaatcct atgaggactc cagcaaccaa gaagaggagg ggccaagcac cttccctgac    300
ctggagtccg agttccaagc agcactcagt aggaaggtgg ccgagttggt tcattttctg    360
ctcctcaagt atcgagccag ggagccggtc acaaaggcag aaatgctggg gagtgtcgtc    420
ggaaattggc agtatttctt tcctgtgatc ttcagcaaag cttccagttc cttgcagctg    480
gtctttggca tcgagctgat ggaagtggac cccatcggcc acttgtacat ctttgccacc    540
tgcctgggcc tctcctacga tggcctgctg ggtgacaatc agatcatgcc caaggcaggc    600
ctcctgataa tcgtcctggc cataatcgca agagagggcg actgtgcccc tgaggagaaa    660
atctgggagg agctgagtgt gttagaggtg tttgagggga gggaagacag tatcttgggg    720
gatcccaaga agctgctcac ccaacatttc gtgcaggaaa actacctgga gtaccggcag    780
gtccccggca gtgatcctgc atgttatgaa ttcctgtggg gtccaagggc cctcgttgaa    840
accagctatg tgaaagtcct gcaccatatg gtaaagatca gtggaggacc tcacatttcc    900
tacccacccc tgcatgagtg ggttttgaga gagggggaag agtccgccac gtcgctcacc    960
ttccagcttg cctacttggt gaagaagatc gacttcgact acaccccaa ctggggccgt   1020
ggtgcaccaa gcagctacat cgacaacctt accttcccca aggttctcac cgacaaaaaa   1080
tactcgtacc gcgtcgtggt caatggctct gaccttggcg tcgagtccaa cttcgcagtg   1140
acaccgtccg gtgggcagac catcaacttc ctccagtaca caaggggta tggtgtcgcg   1200
gacaccaaaa cgattcaagt tttcgttgtc attccagata ccggcaactc ggaggagtac   1260
atcatcgctg agtggaagaa gacttga                                      1287
```

<210> SEQ ID NO 55
<211> LENGTH: 232
<212> TYPE: PRT
<213> ORGANISM: Artificial
<220> FEATURE:
<223> OTHER INFORMATION: Fusion protein
<220> FEATURE:
<221> NAME/KEY: UNSURE
<222> LOCATION: (119)..(232)
<223> OTHER INFORMATION: FVE

<400> SEQUENCE: 55

```
Met Pro Arg Glu Asp Ala His Phe Ile Tyr Gly Tyr Pro Lys Lys Gly
1               5                   10                  15

His Gly His Ser Tyr Thr Thr Ala Glu Glu Ala Ala Gly Ile Gly Ile
                20                  25                  30

Leu Thr Val Ile Leu Gly Val Leu Leu Leu Ile Gly Cys Trp Tyr Cys
            35                  40                  45

Arg Arg Arg Asn Gly Tyr Arg Ala Leu Met Asp Lys Ser Leu His Val
        50                  55                  60

Gly Thr Gln Cys Ala Leu Thr Arg Arg Cys Pro Gln Glu Gly Phe Asp
65                  70                  75                  80

His Arg Asp Ser Lys Val Ser Leu Gln Glu Lys Asn Cys Glu Pro Val
                85                  90                  95

Val Pro Asn Ala Pro Pro Ala Tyr Glu Lys Leu Ser Ala Glu Gln Ser
                100                 105                 110

Pro Pro Pro Tyr Ser Pro Ser Ala Thr Ser Leu Thr Phe Gln Leu Ala
            115                 120                 125
```

Tyr Leu Val Lys Lys Ile Asp Phe Asp Tyr Thr Pro Asn Trp Gly Arg
        130                 135                 140

Gly Ala Pro Ser Ser Tyr Ile Asp Asn Leu Thr Phe Pro Lys Val Leu
145                 150                 155                 160

Thr Asp Lys Lys Tyr Ser Tyr Arg Val Val Asn Gly Ser Asp Leu
                165                 170                 175

Gly Val Glu Ser Asn Phe Ala Val Thr Pro Ser Gly Gln Thr Ile
            180                 185                 190

Asn Phe Leu Gln Tyr Asn Lys Gly Tyr Gly Val Ala Asp Thr Lys Thr
            195                 200                 205

Ile Gln Val Phe Val Val Ile Pro Asp Thr Gly Asn Ser Glu Glu Tyr
        210                 215                 220

Ile Ile Ala Glu Trp Lys Lys Thr
225                 230

<210> SEQ ID NO 56
<211> LENGTH: 699
<212> TYPE: DNA
<213> ORGANISM: Artificial
<220> FEATURE:
<223> OTHER INFORMATION: Fusion protein
<220> FEATURE:
<221> NAME/KEY: misc_feature
<222> LOCATION: (355)..(699)
<223> OTHER INFORMATION: FVE

<400> SEQUENCE: 56
atgccaagag aagatgctca cttcatctat ggttacccca agaaggggca cggccactct    60
tacaccacgg ctgaagaggc cgctgggatc ggcatcctga cagtgatcct gggagtctta   120
ctgctcatcg gctgttggta ttgtagaaga cgaaatggat acagagcctt gatggataaa   180
agtcttcatg ttggcactca atgtgcctta acaagaagat gcccacaaga agggtttgat   240
catcgggaca gcaaagtgtc tcttcaagag aaaaactgtg aacctgtggt tcccaatgct   300
ccacctgctt atgagaaact ctctgcagaa cagtcaccac acccttattc accttccgcc   360
acgtcgctca ccttccagct tgcctacttg gtgaagaaga tcgacttcga ctacaccccc   420 aactgggggcc gtggtgcacc aagcagctac atcgacaacc ttaccttccc caaggttctc   480
accgacaaaa aatactcgta ccgcgtcgtg gtcaatggct ctgaccttgg cgtcgagtcc   540
aacttcgcag tgacaccgtc cggtgggcag accatcaact cctccagta caacaagggg   600 tatggtgtcg cggacaccaa aacgattcaa gttttcgttg tcattccaga taccggcaac   660
tcggaggagt acatcatcgc tgagtggaag aagacttga                          699

<210> SEQ ID NO 57
<211> LENGTH: 782
<212> TYPE: PRT
<213> ORGANISM: Artificial
<220> FEATURE:
<223> OTHER INFORMATION: Fusion protein
<220> FEATURE:
<221> NAME/KEY: UNSURE
<222> LOCATION: (669)..(782)
<223> OTHER INFORMATION: FVE

<400> SEQUENCE: 57

Lys Leu Thr Ile Glu Ser Thr Pro Phe Asn Val Ala Glu Gly Lys Glu
1               5                   10                  15

Val Leu Leu Leu Val His Asn Leu Pro Gln His Leu Phe Gly Tyr Ser
            20                  25                  30

```
Trp Tyr Lys Gly Glu Arg Val Asp Gly Asn Arg Gln Ile Ile Gly Tyr
             35                  40                  45

Val Ile Gly Thr Gln Gln Ala Thr Pro Gly Pro Ala Tyr Ser Gly Arg
 50                  55                  60

Glu Ile Ile Tyr Pro Asn Ala Ser Leu Leu Ile Gln Asn Ile Ile Gln
 65                  70                  75                  80

Asn Asp Thr Gly Phe Tyr Thr Leu His Val Ile Lys Ser Asp Leu Val
                 85                  90                  95

Asn Glu Glu Ala Thr Gly Gln Phe Arg Val Tyr Pro Glu Leu Pro Lys
                100                 105                 110

Pro Ser Ile Ser Ser Asn Ser Lys Pro Val Glu Asp Lys Asp Ala
                115                 120                 125

Val Ala Phe Thr Cys Glu Pro Glu Thr Gln Asp Ala Thr Tyr Leu Trp
            130                 135                 140

Trp Val Asn Asn Gln Ser Leu Pro Val Ser Pro Arg Leu Gln Leu Ser
145                 150                 155                 160

Asn Gly Asn Arg Thr Leu Thr Leu Phe Asn Val Thr Arg Asn Asp Thr
                165                 170                 175

Ala Ser Tyr Lys Cys Glu Thr Gln Asn Pro Val Ser Ala Arg Arg Ser
            180                 185                 190

Asp Ser Val Ile Leu Asn Val Leu Tyr Gly Pro Asp Ala Pro Thr Ile
        195                 200                 205

Ser Pro Leu Asn Thr Ser Tyr Arg Ser Gly Glu Asn Leu Asn Leu Ser
    210                 215                 220

Cys His Ala Ala Ser Asn Pro Pro Ala Gln Tyr Ser Trp Phe Val Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Thr Cys Gln Ala His Asn Ser Asp Thr
            260                 265                 270

Gly Leu Asn Arg Thr Thr Val Thr Thr Ile Thr Val Tyr Ala Glu Pro
        275                 280                 285

Pro Lys Pro Phe Ile Thr Ser Asn Asn Ser Asn Pro Val Glu Asp Glu
    290                 295                 300

Asp Ala Val Ala Leu Thr Cys Glu Pro Glu Ile Gln Asn Thr Thr Tyr
305                 310                 315                 320

Leu Trp Trp Val Asn Asn Gln Ser Leu Pro Val Ser Pro Arg Leu Gln
                325                 330                 335

Leu Ser Asn Asp Asn Arg Thr Leu Thr Leu Leu Ser Val Thr Arg Asn
            340                 345                 350

Asp Val Gly Pro Tyr Glu Cys Gly Ile Gln Asn Glu Leu Ser Val Asp
        355                 360                 365

His Ser Asp Pro Val Ile Leu Asn Val Leu Tyr Gly Pro Asp Asp Pro
    370                 375                 380

Thr Ile Ser Pro Ser Tyr Thr Tyr Tyr Arg Pro Gly Val Asn Leu Ser
385                 390                 395                 400

Leu Ser Cys His Ala Ala Ser Asn Pro Pro Ala Gln Tyr Ser Trp Leu
                405                 410                 415

Ile Asp Gly Asn Ile Gln Gln His Thr Gln Glu Leu Phe Ile Ser Asn
            420                 425                 430

Ile Thr Glu Lys Asn Ser Gly Leu Tyr Thr Cys Gln Ala Asn Asn Ser
        435                 440                 445

Ala Ser Gly His Ser Arg Thr Thr Val Lys Thr Ile Thr Val Ser Ala
    450                 455                 460
```

Glu Leu Pro Lys Pro Ser Ile Ser Ser Asn Asn Ser Lys Pro Val Glu
465                 470                 475                 480

Asp Lys Asp Ala Val Ala Phe Thr Cys Glu Pro Glu Ala Gln Asn Thr
            485                 490                 495

Thr Tyr Leu Trp Trp Val Asn Gly Gln Ser Leu Pro Val Ser Pro Arg
                500                 505                 510

Leu Gln Leu Ser Asn Gly Asn Arg Thr Leu Thr Leu Phe Asn Val Thr
            515                 520                 525

Arg Asn Asp Ala Arg Ala Tyr Val Cys Gly Ile Gln Asn Ser Val Ser
    530                 535                 540

Ala Asn Arg Ser Asp Pro Val Thr Leu Asp Val Leu Tyr Gly Pro Asp
545                 550                 555                 560

Thr Pro Ile Ile Ser Pro Pro Asp Ser Ser Tyr Leu Ser Gly Ala Asn
                565                 570                 575

Leu Asn Leu Ser Cys His Ser Ala Ser Asn Pro Ser Pro Gln Tyr Ser
            580                 585                 590

Trp Arg Ile Asn Gly Ile Pro Gln Gln His Thr Gln Val Leu Phe Ile
    595                 600                 605

Ala Lys Ile Thr Pro Asn Asn Asn Gly Thr Tyr Ala Cys Phe Val Ser
610                 615                 620

Asn Leu Ala Thr Gly Arg Asn Asn Ser Ile Val Lys Ser Ile Thr Val
625                 630                 635                 640

Ser Ala Ser Gly Thr Ser Pro Gly Leu Ser Ala Gly Ala Thr Val Gly
                645                 650                 655

Ile Met Ile Gly Val Leu Val Gly Val Ala Leu Ile Ser Ala Thr Ser
            660                 665                 670

Leu Thr Phe Gln Leu Ala Tyr Leu Val Lys Lys Ile Asp Phe Asp Tyr
    675                 680                 685

Thr Pro Asn Trp Gly Arg Gly Ala Pro Ser Ser Tyr Ile Asp Asn Leu
690                 695                 700

Thr Phe Pro Lys Val Leu Thr Asp Lys Lys Tyr Ser Tyr Arg Val Val
705                 710                 715                 720

Val Asn Gly Ser Asp Leu Gly Val Glu Ser Asn Phe Ala Val Thr Pro
                725                 730                 735

Ser Gly Gly Gln Thr Ile Asn Phe Leu Gln Tyr Asn Lys Gly Tyr Gly
            740                 745                 750

Val Ala Asp Thr Lys Thr Ile Gln Val Phe Val Ile Pro Asp Thr
    755                 760                 765

Gly Asn Ser Glu Glu Tyr Ile Ile Ala Glu Trp Lys Lys Thr
770                 775                 780

<210> SEQ ID NO 58
<211> LENGTH: 2349
<212> TYPE: DNA
<213> ORGANISM: Artificial
<220> FEATURE:
<223> OTHER INFORMATION: Fusion protein
<220> FEATURE:
<221> NAME/KEY: misc_feature
<222> LOCATION: (2005)..(2349)
<223> OTHER INFORMATION: FVE

<400> SEQUENCE: 58
aagctcacta ttgaatccac gccgttcaat gtcgcagagg ggaaggaggt gcttctactt    60
gtccacaatc tgccccagca tcttttttggc tacagctggt acaaaggtga agagtggat    120 ggcaaccgtc aaattatagg atatgtaata ggaactcaac aagctacccc agggcccgca    180

```
tacagtggtc gagagataat ataccccaat gcatccctgc tgatccgaaa catcatccag    240
aatgacacag gattctacac cctacacgtc ataaagtcag atcttgtgaa tgaagaagca    300
actggccagt tccgggtata cccggagctg cccaagccct ccatctccag caacaactcc    360
aaacccgtgg aggacaagga tgctgtggcc ttcacctgtg aacctgagac tcaggacgca    420
acctacctgt ggtgggtaaa caatcagagc ctcccggtca gtcccaggct gcagctgtcc    480
aatggcaaca ggaccctcac tctattcaat gtcacaagaa atgacacagc aagctacaaa    540
tgtgaaaccc agaacccagt gagtgccagg cgcagtgatt cagtcatcct gaatgtcctc    600
tatggcccgg atgcccccac catttcccct ctaaacacat cttacagatc aggggaaaat    660
ctgaacctct cctgccatgc agcctctaac ccacctgcac agtactcttg gtttgtcaat    720
gggactttcc agcaatccac ccaagagctc tttatcccca acatcactgt gaataatagt    780
ggatcctata cgtgccaagc ccataactca gacactggcc tcaataggac cacagtcacg    840
acgatcacag tctatgcaga gccacccaaa cccttcatca ccagcaacaa ctccaacccc    900
gtggaggatg aggatgctgt agccttaacc tgtgaacctg agattcagaa cacaacctac    960
ctgtggtggg taaataatca gagcctcccg gtcagtccca ggctgcagct gtccaatgac    1020
aacaggaccc tcactctact cagtgtcaca aggaatgatg taggacccta tgagtgtgga    1080
atccagaacg aattaagtgt tgaccacagc gacccagtca tcctgaatgt cctctatggc    1140
ccagacgacc ccaccatttc ccctcatac acctattacc gtccaggggt gaacctcagc    1200
ctctcctgcc atgcagcctc taacccacct gcacagtatt cttggctgat tgatgggaac    1260
atccagcaac acacacaaga gctctttatc tccaacatca ctgagaagaa cagcggactc    1320
tatacctgcc aggccaataa ctcagccagt ggccacagca ggactacagt caagacaatc    1380
acagtctctg cggagctgcc caagccctcc atctccagca caactccaa acccgtggag    1440 gacaaggatg ctgtggcctt cacctgtgaa cctgaggctc agaacacaac ctacctgtgg    1500
tgggtaaatg gtcagagcct cccagtcagt cccaggctgc agctgtccaa tggcaacagg    1560
accctcactc tattcaatgt cacaagaaat gacgcaagag cctatgtatg tggaatccag    1620
aactcagtga gtgcaaaccg cagtgaccca gtcaccctgg atgtcctcta ggggccggac    1680
acccccatca tttccccccc agactcgtct tacctttcgg gagcgaacct caacctctcc    1740
tgccactcgg cctctaaccc atcccgcag tattcttggc gtatcaatgg gatacccag    1800 caacacacac aagttctctt tatcgccaaa atcacgccaa ataataacgg gacctatgcc    1860
tgttttgtct ctaacttggc tactggccgc aataattcca tagtcaagag catcacagtc    1920
tctgcatctg gaacttctcc tggtctctca gctggggcca ctgtcggcat catgattgga    1980
gtgctggttg gggttgctct gatatccgcc acgtcgctca ccttccagct tgcctacttg    2040
gtgaagaaga tcgacttcga ctacaccccc aactggggcc gtggtgcacc aagcagctac    2100
atcgacaacc ttaccttccc caaggttctc accgacaaaa aatactcgta ccgcgtcgtg    2160
gtcaatggct ctgaccttgg cgtcgagtcc aacttcgcag tgacaccgtc cggtgggcag    2220
accatcaact tcctccagta caacaagggg tatggtgtcg cggacaccaa aacgattcaa    2280
gttttcgttg tcattccaga taccggcaac tcggaggagt acatcatcgc tgagtggaag    2340
aagacttga                                                           2349
```

<210> SEQ ID NO 59
<211> LENGTH: 36
<212> TYPE: DNA
<213> ORGANISM: Artificial

```
<220> FEATURE:
<223> OTHER INFORMATION: Primer

<400> SEQUENCE: 59
ggatcctccg ccacgtcgtt cgactacacc cccaac                                    36

<210> SEQ ID NO 60
<211> LENGTH: 36
<212> TYPE: DNA
<213> ORGANISM: Artificial
<220> FEATURE:
<223> OTHER INFORMATION: Primer

<400> SEQUENCE: 60 gttggggtg tagtcgaacg acgtggcgga ggatcc                                     36

<210> SEQ ID NO 61
<211> LENGTH: 36
<212> TYPE: DNA
<213> ORGANISM: Artificial
<220> FEATURE:
<223> OTHER INFORMATION: Primer

<400> SEQUENCE: 61
ttggtgaaga agatcgacat cgacaacctt accttc                                    36

<210> SEQ ID NO 62
<211> LENGTH: 36
<212> TYPE: DNA
<213> ORGANISM: Artificial
<220> FEATURE:
<223> OTHER INFORMATION: Primer

<400> SEQUENCE: 62
gaaggtaagg ttgtcgatgt cgatcttctt caccaa                                    36

<210> SEQ ID NO 63
<211> LENGTH: 36
<212> TYPE: DNA
<213> ORGANISM: Artificial
<220> FEATURE:
<223> OTHER INFORMATION: Primer

<400> SEQUENCE: 63
ggtaccccaa gcagctacaa atactcgtac cgcgtc                                    36

<210> SEQ ID NO 64
<211> LENGTH: 36
<212> TYPE: DNA
<213> ORGANISM: Artificial
<220> FEATURE:
<223> OTHER INFORMATION: primer

<400> SEQUENCE: 64
gacgcggtac gagtatttgt agctgcttgg ggtacc                                    36

<210> SEQ ID NO 65
<211> LENGTH: 36
<212> TYPE: DNA
<213> ORGANISM: Artificial
<220> FEATURE:
<223> OTHER INFORMATION: Primer

<400> SEQUENCE: 65
aaggttctca ccgacaaagt cgagtccaac ttcgca                                    36
```

```
<210> SEQ ID NO 66
<211> LENGTH: 36
<212> TYPE: DNA
<213> ORGANISM: Artificial
<220> FEATURE:
<223> OTHER INFORMATION: Primer

<400> SEQUENCE: 66
tgcgaagttg gactcgactt tgtcggtgag aacctt                              36

<210> SEQ ID NO 67
<211> LENGTH: 36
<212> TYPE: DNA
<213> ORGANISM: Artificial
<220> FEATURE:
<223> OTHER INFORMATION: Primer

<400> SEQUENCE: 67
aatggctctg accttggcca gaccatcaac ttcctc                              36

<210> SEQ ID NO 68
<211> LENGTH: 36
<212> TYPE: DNA
<213> ORGANISM: Artificial
<220> FEATURE:
<223> OTHER INFORMATION: Primer

<400> SEQUENCE: 68
gaggaagttg atggtctggc caaggtcaga gccatt                              36

<210> SEQ ID NO 69
<211> LENGTH: 36
<212> TYPE: DNA
<213> ORGANISM: Artificial
<220> FEATURE:
<223> OTHER INFORMATION: Primer

<400> SEQUENCE: 69
gtgacaccgt ccggtggggg tgtcgcggac accaaa                              36

<210> SEQ ID NO 70
<211> LENGTH: 36
<212> TYPE: DNA
<213> ORGANISM: Artificial
<220> FEATURE:
<223> OTHER INFORMATION: Primer

<400> SEQUENCE: 70
tttggtgtcc gcgacacccc caccggacgg tgtcac                              36

<210> SEQ ID NO 71
<211> LENGTH: 36
<212> TYPE: DNA
<213> ORGANISM: Artificial
<220> FEATURE:
<223> OTHER INFORMATION: Primer

<400> SEQUENCE: 71
cagtacaaca aggggtatat tccagatacc ggcaac                              36

<210> SEQ ID NO 72
<211> LENGTH: 36
<212> TYPE: DNA
<213> ORGANISM: Artificial
<220> FEATURE:
<223> OTHER INFORMATION: Primer

<400> SEQUENCE: 72
```

```
gttgccggta tctggaatat acccctttgtt gtactg                                    36

<210> SEQ ID NO 73
<211> LENGTH: 36
<212> TYPE: DNA
<213> ORGANISM: Artificial
<220> FEATURE:
<223> OTHER INFORMATION: Primer

<400> SEQUENCE: 73
attcaagttt tcgttgtcta catcatcgct gagtgg                                     36

<210> SEQ ID NO 74
<211> LENGTH: 36
<212> TYPE: DNA
<213> ORGANISM: Artificial
<220> FEATURE:
<223> OTHER INFORMATION: Primer

<400> SEQUENCE: 74
ccactcagcg atgatgtaga caacgaaaac ttgaat                                     36

<210> SEQ ID NO 75
<211> LENGTH: 39
<212> TYPE: DNA
<213> ORGANISM: Artificial
<220> FEATURE:
<223> OTHER INFORMATION: Primer

<400> SEQUENCE: 75
gatgcaactg aattcttatt actcctccga gttgccggt                                  39

<210> SEQ ID NO 76
<211> LENGTH: 36
<212> TYPE: DNA
<213> ORGANISM: Artificial
<220> FEATURE:
<223> OTHER INFORMATION: Primer

<400> SEQUENCE: 76
aatggctctg accttggcat tccagatacc ggcaac                                     36

<210> SEQ ID NO 77
<211> LENGTH: 36
<212> TYPE: DNA
<213> ORGANISM: Artificial
<220> FEATURE:
<223> OTHER INFORMATION: Primer

<400> SEQUENCE: 77
gttgccggta tctggaatgc caaggtcaga gccatt                                     36

<210> SEQ ID NO 78
<211> LENGTH: 48
<212> TYPE: DNA
<213> ORGANISM: Artificial
<220> FEATURE:
<223> OTHER INFORMATION: Primer

<400> SEQUENCE: 78
gttccgcgtg gatccatcga aggtcgtaat ggctctgacc ttggcgtc                        48

<210> SEQ ID NO 79
<211> LENGTH: 42
<212> TYPE: DNA
<213> ORGANISM: Artificial
```

```
<220> FEATURE:
<223> OTHER INFORMATION: Primer

<400> SEQUENCE: 79
gatgcaactg aattcttatc aatctggaat gacaacgaaa ac                            42

<210> SEQ ID NO 80
<211> LENGTH: 27
<212> TYPE: DNA
<213> ORGANISM: Artificial
<220> FEATURE:
<223> OTHER INFORMATION: Primer

<400> SEQUENCE: 80
cccaactggg gcgcaggtac cccaagc                                             27

<210> SEQ ID NO 81
<211> LENGTH: 27
<212> TYPE: DNA
<213> ORGANISM: Artificial
<220> FEATURE:
<223> OTHER INFORMATION: Primer

<400> SEQUENCE: 81
gcttggggta cctgcgcccc agttggg                                             27

<210> SEQ ID NO 82
<211> LENGTH: 27
<212> TYPE: DNA
<213> ORGANISM: Artificial
<220> FEATURE:
<223> OTHER INFORMATION: Primer

<400> SEQUENCE: 82
aactggggcc gtgcaacccc aagcagc                                             27

<210> SEQ ID NO 83
<211> LENGTH: 27
<212> TYPE: DNA
<213> ORGANISM: Artificial
<220> FEATURE:
<223> OTHER INFORMATION: Primer

<400> SEQUENCE: 83
gctgcttggg gttgcacggc cccagtt                                             27

<210> SEQ ID NO 84
<211> LENGTH: 27
<212> TYPE: DNA
<213> ORGANISM: Artificial
<220> FEATURE:
<223> OTHER INFORMATION: Primer

<400> SEQUENCE: 84
tggggccgtg gtgcaccaag cagctac                                             27

<210> SEQ ID NO 85
<211> LENGTH: 27
<212> TYPE: DNA
<213> ORGANISM: Artificial
<220> FEATURE:
<223> OTHER INFORMATION: Primer

<400> SEQUENCE: 85
gtagctgctt ggtgcaccac ggcccca                                             27
```

```
<210> SEQ ID NO 86
<211> LENGTH: 36
<212> TYPE: DNA
<213> ORGANISM: Artificial
<220> FEATURE:
<223> OTHER INFORMATION: Primer

<400> SEQUENCE: 86
aaggatattc aaacccaatc cgccacgtcg ctcacc                        36

<210> SEQ ID NO 87
<211> LENGTH: 36
<212> TYPE: DNA
<213> ORGANISM: Artificial
<220> FEATURE:
<223> OTHER INFORMATION: Primer

<400> SEQUENCE: 87
ggtgagcgac gtggcggatt gggtttgaat atcctt                        36

<210> SEQ ID NO 88
<211> LENGTH: 36
<212> TYPE: DNA
<213> ORGANISM: Artificial
<220> FEATURE:
<223> OTHER INFORMATION: Primer

<400> SEQUENCE: 88
catgctaaaa tccgcgattc cgccacgtcg ctcacc                        36

<210> SEQ ID NO 89
<211> LENGTH: 36
<212> TYPE: DNA
<213> ORGANISM: Artificial
<220> FEATURE:
<223> OTHER INFORMATION: Primer

<400> SEQUENCE: 89
ggtgagcgac gtggcggaat cgcggatttt agcatg                        36

<210> SEQ ID NO 90
<211> LENGTH: 36
<212> TYPE: DNA
<213> ORGANISM: Artificial
<220> FEATURE:
<223> OTHER INFORMATION: Primer

<400> SEQUENCE: 90
aaggatattc aaacccaaga tcaagtcgat gtcaaa                        36

<210> SEQ ID NO 91
<211> LENGTH: 36
<212> TYPE: DNA
<213> ORGANISM: Artificial
<220> FEATURE:
<223> OTHER INFORMATION: Primer

<400> SEQUENCE: 91
tttgacatcg acttgatctt gggtttgaat atcctt                        36

<210> SEQ ID NO 92
<211> LENGTH: 5
<212> TYPE: PRT
<213> ORGANISM: Artificial
<220> FEATURE:
<223> OTHER INFORMATION: FVE fragments

<400> SEQUENCE: 92
```

```
Trp Gly Arg Gly Thr
1               5

<210> SEQ ID NO 93
<211> LENGTH: 5
<212> TYPE: PRT
<213> ORGANISM: Artificial
<220> FEATURE:
<223> OTHER INFORMATION: FVE fragment

<400> SEQUENCE: 93

Gly Arg Gly Thr Pro
1               5

<210> SEQ ID NO 94
<211> LENGTH: 5
<212> TYPE: PRT
<213> ORGANISM: Artificial
<220> FEATURE:
<223> OTHER INFORMATION: FVE fragment

<400> SEQUENCE: 94

Arg Gly Thr Pro Ser
1               5

<210> SEQ ID NO 95
<211> LENGTH: 5
<212> TYPE: PRT
<213> ORGANISM: Artificial
<220> FEATURE:
<223> OTHER INFORMATION: FVE fragment

<400> SEQUENCE: 95

Gly Thr Pro Ser Ser
1               5

<210> SEQ ID NO 96
<211> LENGTH: 5
<212> TYPE: PRT
<213> ORGANISM: Artificial
<220> FEATURE:
<223> OTHER INFORMATION: FVE fragment

<400> SEQUENCE: 96

Thr Pro Ser Ser Tyr
1               5

<210> SEQ ID NO 97
<211> LENGTH: 6
<212> TYPE: PRT
<213> ORGANISM: Artificial
<220> FEATURE:
<223> OTHER INFORMATION: FVE fragment

<400> SEQUENCE: 97

Asn Trp Gly Arg Gly Thr
1               5

<210> SEQ ID NO 98
<211> LENGTH: 6
<212> TYPE: PRT
<213> ORGANISM: Artificial
<220> FEATURE:
<223> OTHER INFORMATION: FVE fragment

<400> SEQUENCE: 98

Trp Gly Arg Gly Thr Pro
```

<210> SEQ ID NO 99
<211> LENGTH: 6
<212> TYPE: PRT
<213> ORGANISM: Artificial
<220> FEATURE:
<223> OTHER INFORMATION: FVE fragment

<400> SEQUENCE: 99

Gly Arg Gly Thr Pro Ser
1               5

<210> SEQ ID NO 100
<211> LENGTH: 6
<212> TYPE: PRT
<213> ORGANISM: Artificial
<220> FEATURE:
<223> OTHER INFORMATION: FVE fragment

<400> SEQUENCE: 100

Arg Gly Thr Pro Ser Ser
1               5

<210> SEQ ID NO 101
<211> LENGTH: 6
<212> TYPE: PRT
<213> ORGANISM: Artificial
<220> FEATURE:
<223> OTHER INFORMATION: FVE fragment

<400> SEQUENCE: 101

Gly Thr Pro Ser Ser Tyr
1               5

<210> SEQ ID NO 102
<211> LENGTH: 6
<212> TYPE: PRT
<213> ORGANISM: Artificial
<220> FEATURE:
<223> OTHER INFORMATION: FVE fragment

<400> SEQUENCE: 102

Thr Pro Ser Ser Tyr Ile
1               5

<210> SEQ ID NO 103
<211> LENGTH: 7
<212> TYPE: PRT
<213> ORGANISM: Artificial
<220> FEATURE:
<223> OTHER INFORMATION: FVE fragment

<400> SEQUENCE: 103

Pro Asn Trp Gly Arg Gly Thr
1               5

<210> SEQ ID NO 104
<211> LENGTH: 7
<212> TYPE: PRT
<213> ORGANISM: Artificial
<220> FEATURE:
<223> OTHER INFORMATION: FVE fragment

<400> SEQUENCE: 104

Asn Trp Gly Arg Gly Thr Pro
1               5

```
<210> SEQ ID NO 105
<211> LENGTH: 7
<212> TYPE: PRT
<213> ORGANISM: Artificial
<220> FEATURE:
<223> OTHER INFORMATION: FVE fragment

<400> SEQUENCE: 105

Trp Gly Arg Gly Thr Pro Ser
1               5

<210> SEQ ID NO 106
<211> LENGTH: 7
<212> TYPE: PRT
<213> ORGANISM: Artificial
<220> FEATURE:
<223> OTHER INFORMATION: FVE fragment

<400> SEQUENCE: 106

Gly Arg Gly Thr Pro Ser Ser
1               5

<210> SEQ ID NO 107
<211> LENGTH: 7
<212> TYPE: PRT
<213> ORGANISM: Artificial
<220> FEATURE:
<223> OTHER INFORMATION: FVE fragment

<400> SEQUENCE: 107

Arg Gly Thr Pro Ser Ser Tyr
1               5

<210> SEQ ID NO 108
<211> LENGTH: 7
<212> TYPE: PRT
<213> ORGANISM: Artificial
<220> FEATURE:
<223> OTHER INFORMATION: FVE fragment

<400> SEQUENCE: 108

Gly Thr Pro Ser Ser Tyr Ile
1               5

<210> SEQ ID NO 109
<211> LENGTH: 7
<212> TYPE: PRT
<213> ORGANISM: Artificial
<220> FEATURE:
<223> OTHER INFORMATION: FVE fragment

<400> SEQUENCE: 109

Thr Pro Ser Ser Tyr Ile Asp
1               5

<210> SEQ ID NO 110
<211> LENGTH: 8
<212> TYPE: PRT
<213> ORGANISM: Artificial
<220> FEATURE:
<223> OTHER INFORMATION: FVE fragment

<400> SEQUENCE: 110

Thr Pro Asn Trp Gly Arg Gly Thr
1               5

<210> SEQ ID NO 111
```

```
<211> LENGTH: 8
<212> TYPE: PRT
<213> ORGANISM: Artificial
<220> FEATURE:
<223> OTHER INFORMATION: FVE fragment

<400> SEQUENCE: 111

Pro Asn Trp Gly Arg Gly Thr Pro
1               5

<210> SEQ ID NO 112
<211> LENGTH: 8
<212> TYPE: PRT
<213> ORGANISM: Artificial
<220> FEATURE:
<223> OTHER INFORMATION: FVE fragment

<400> SEQUENCE: 112

Asn Trp Gly Arg Gly Thr Pro Ser
1               5

<210> SEQ ID NO 113
<211> LENGTH: 8
<212> TYPE: PRT
<213> ORGANISM: Artificial
<220> FEATURE:
<223> OTHER INFORMATION: FVE fragment

<400> SEQUENCE: 113

Trp Gly Arg Gly Thr Pro Ser Ser
1               5

<210> SEQ ID NO 114
<211> LENGTH: 8
<212> TYPE: PRT
<213> ORGANISM: Artificial
<220> FEATURE:
<223> OTHER INFORMATION: FVE fragment

<400> SEQUENCE: 114

Gly Arg Gly Thr Pro Ser Ser Tyr
1               5

<210> SEQ ID NO 115
<211> LENGTH: 8
<212> TYPE: PRT
<213> ORGANISM: Artificial
<220> FEATURE:
<223> OTHER INFORMATION: FVE fragment

<400> SEQUENCE: 115

Arg Gly Thr Pro Ser Ser Tyr Ile
1               5

<210> SEQ ID NO 116
<211> LENGTH: 8
<212> TYPE: PRT
<213> ORGANISM: Artificial
<220> FEATURE:
<223> OTHER INFORMATION: FVE fragment

<400> SEQUENCE: 116

Gly Thr Pro Ser Ser Tyr Ile Asp
1               5

<210> SEQ ID NO 117
<211> LENGTH: 8
<212> TYPE: PRT
```

<213> ORGANISM: Artificial
<220> FEATURE:
<223> OTHER INFORMATION: FVE fragment

<400> SEQUENCE: 117

Thr Pro Ser Ser Tyr Ile Asp Asn
1               5

<210> SEQ ID NO 118
<211> LENGTH: 9
<212> TYPE: PRT
<213> ORGANISM: Artificial
<220> FEATURE:
<223> OTHER INFORMATION: FVE fragment

<400> SEQUENCE: 118

Tyr Thr Pro Asn Trp Gly Arg Gly Thr
1               5

<210> SEQ ID NO 119
<211> LENGTH: 9
<212> TYPE: PRT
<213> ORGANISM: Artificial
<220> FEATURE:
<223> OTHER INFORMATION: FVE Fragment

<400> SEQUENCE: 119

Thr Pro Asn Trp Gly Arg Gly Thr Pro
1               5

<210> SEQ ID NO 120
<211> LENGTH: 9
<212> TYPE: PRT
<213> ORGANISM: Artificial
<220> FEATURE:
<223> OTHER INFORMATION: FVE fragment

<400> SEQUENCE: 120

Pro Asn Trp Gly Arg Gly Thr Pro Ser
1               5

<210> SEQ ID NO 121
<211> LENGTH: 9
<212> TYPE: PRT
<213> ORGANISM: Artificial
<220> FEATURE:
<223> OTHER INFORMATION: FVE fragment

<400> SEQUENCE: 121

Asn Trp Gly Arg Gly Thr Pro Ser Ser
1               5

<210> SEQ ID NO 122
<211> LENGTH: 9
<212> TYPE: PRT
<213> ORGANISM: Artificial
<220> FEATURE:
<223> OTHER INFORMATION: FVE fragment

<400> SEQUENCE: 122

Trp Gly Arg Gly Thr Pro Ser Ser Tyr
1               5

<210> SEQ ID NO 123
<211> LENGTH: 9
<212> TYPE: PRT
<213> ORGANISM: Artificial
<220> FEATURE:

<223> OTHER INFORMATION: FVE fragment

<400> SEQUENCE: 123

Gly Arg Gly Thr Pro Ser Ser Tyr Ile
1               5

<210> SEQ ID NO 124
<211> LENGTH: 9
<212> TYPE: PRT
<213> ORGANISM: Artificial
<220> FEATURE:
<223> OTHER INFORMATION: FVE fragment

<400> SEQUENCE: 124

Arg Gly Thr Pro Ser Ser Tyr Ile Asp
1               5

<210> SEQ ID NO 125
<211> LENGTH: 9
<212> TYPE: PRT
<213> ORGANISM: Artificial
<220> FEATURE:
<223> OTHER INFORMATION: FVE fragment

<400> SEQUENCE: 125

Gly Thr Pro Ser Ser Tyr Ile Asp Asn
1               5

<210> SEQ ID NO 126
<211> LENGTH: 9
<212> TYPE: PRT
<213> ORGANISM: Artificial
<220> FEATURE:
<223> OTHER INFORMATION: FVE fragment

<400> SEQUENCE: 126

Thr Pro Ser Ser Tyr Ile Asp Asn Leu
1               5

<210> SEQ ID NO 127
<211> LENGTH: 10
<212> TYPE: PRT
<213> ORGANISM: Artificial
<220> FEATURE:
<223> OTHER INFORMATION: FVE fragment

<400> SEQUENCE: 127

Asp Tyr Thr Pro Asn Trp Gly Arg Gly Thr
1               5                   10

<210> SEQ ID NO 128
<211> LENGTH: 10
<212> TYPE: PRT
<213> ORGANISM: Artificial
<220> FEATURE:
<223> OTHER INFORMATION: FVE fragment

<400> SEQUENCE: 128

Tyr Thr Pro Asn Trp Gly Arg Gly Thr Pro
1               5                   10

<210> SEQ ID NO 129
<211> LENGTH: 10
<212> TYPE: PRT
<213> ORGANISM: Artificial
<220> FEATURE:
<223> OTHER INFORMATION: FVE fragment

```
<400> SEQUENCE: 129

Thr Pro Asn Trp Gly Arg Gly Thr Pro Ser
1               5                   10

<210> SEQ ID NO 130
<211> LENGTH: 10
<212> TYPE: PRT
<213> ORGANISM: Artificial
<220> FEATURE:
<223> OTHER INFORMATION: FVE fragment

<400> SEQUENCE: 130

Pro Asn Trp Gly Arg Gly Thr Pro Ser Ser
1               5                   10

<210> SEQ ID NO 131
<211> LENGTH: 10
<212> TYPE: PRT
<213> ORGANISM: Artificial
<220> FEATURE:
<223> OTHER INFORMATION: FVE fragment

<400> SEQUENCE: 131

Asn Trp Gly Arg Gly Thr Pro Ser Ser Tyr
1               5                   10

<210> SEQ ID NO 132
<211> LENGTH: 10
<212> TYPE: PRT
<213> ORGANISM: Artificial
<220> FEATURE:
<223> OTHER INFORMATION: FVE fragment

<400> SEQUENCE: 132

Trp Gly Arg Gly Thr Pro Ser Ser Tyr Ile
1               5                   10

<210> SEQ ID NO 133
<211> LENGTH: 10
<212> TYPE: PRT
<213> ORGANISM: Artificial
<220> FEATURE:
<223> OTHER INFORMATION: FVE fragment

<400> SEQUENCE: 133

Gly Arg Gly Thr Pro Ser Ser Tyr Ile Asp
1               5                   10

<210> SEQ ID NO 134
<211> LENGTH: 10
<212> TYPE: PRT
<213> ORGANISM: Artificial
<220> FEATURE:
<223> OTHER INFORMATION: FVE fragment

<400> SEQUENCE: 134

Arg Gly Thr Pro Ser Ser Tyr Ile Asp Asn
1               5                   10

<210> SEQ ID NO 135
<211> LENGTH: 10
<212> TYPE: PRT
<213> ORGANISM: Artificial
<220> FEATURE:
<223> OTHER INFORMATION: FVE fragment

<400> SEQUENCE: 135
```

```
Gly Thr Pro Ser Ser Tyr Ile Asp Asn Leu
1               5                   10
```

<210> SEQ ID NO 136
<211> LENGTH: 10
<212> TYPE: PRT
<213> ORGANISM: Artificial
<220> FEATURE:
<223> OTHER INFORMATION: FVE fragment

<400> SEQUENCE: 136

```
Thr Pro Ser Ser Tyr Ile Asp Asn Leu Thr
1               5                   10
```

<210> SEQ ID NO 137
<211> LENGTH: 11
<212> TYPE: PRT
<213> ORGANISM: Artificial
<220> FEATURE:
<223> OTHER INFORMATION: FVE fragment

<400> SEQUENCE: 137

```
Phe Asp Tyr Thr Pro Asn Trp Gly Arg Gly Thr
1               5                   10
```

<210> SEQ ID NO 138
<211> LENGTH: 11
<212> TYPE: PRT
<213> ORGANISM: Artificial
<220> FEATURE:
<223> OTHER INFORMATION: FVE fragment

<400> SEQUENCE: 138

```
Asp Tyr Thr Pro Asn Trp Gly Arg Gly Thr Pro
1               5                   10
```

<210> SEQ ID NO 139
<211> LENGTH: 11
<212> TYPE: PRT
<213> ORGANISM: Artificial
<220> FEATURE:
<223> OTHER INFORMATION: FVE fragment

<400> SEQUENCE: 139

```
Tyr Thr Pro Asn Trp Gly Arg Gly Thr Pro Ser
1               5                   10
```

<210> SEQ ID NO 140
<211> LENGTH: 11
<212> TYPE: PRT
<213> ORGANISM: Artificial
<220> FEATURE:
<223> OTHER INFORMATION: FVe fragment

<400> SEQUENCE: 140

```
Thr Pro Asn Trp Gly Arg Gly Thr Pro Ser Ser
1               5                   10
```

<210> SEQ ID NO 141
<211> LENGTH: 11
<212> TYPE: PRT
<213> ORGANISM: Artificial
<220> FEATURE:
<223> OTHER INFORMATION: FVE fragment

<400> SEQUENCE: 141

```
Pro Asn Trp Gly Arg Gly Thr Pro Ser Ser Tyr
1               5                   10
```

<210> SEQ ID NO 142
<211> LENGTH: 11
<212> TYPE: PRT
<213> ORGANISM: Artificial
<220> FEATURE:
<223> OTHER INFORMATION: FVE fragment

<400> SEQUENCE: 142

Asn Trp Gly Arg Gly Thr Pro Ser Ser Tyr Ile
1               5                   10

<210> SEQ ID NO 143
<211> LENGTH: 11
<212> TYPE: PRT
<213> ORGANISM: Artificial
<220> FEATURE:
<223> OTHER INFORMATION: FVE fragment

<400> SEQUENCE: 143

Trp Gly Arg Gly Thr Pro Ser Ser Tyr Ile Asp
1               5                   10

<210> SEQ ID NO 144
<211> LENGTH: 11
<212> TYPE: PRT
<213> ORGANISM: Artificial
<220> FEATURE:
<223> OTHER INFORMATION: FVE fragment

<400> SEQUENCE: 144

Gly Arg Gly Thr Pro Ser Ser Tyr Ile Asp Asn
1               5                   10

<210> SEQ ID NO 145
<211> LENGTH: 11
<212> TYPE: PRT
<213> ORGANISM: Artificial
<220> FEATURE:
<223> OTHER INFORMATION: FVE fragment

<400> SEQUENCE: 145

Arg Gly Thr Pro Ser Ser Tyr Ile Asp Asn Leu
1               5                   10

<210> SEQ ID NO 146
<211> LENGTH: 11
<212> TYPE: PRT
<213> ORGANISM: Artificial
<220> FEATURE:
<223> OTHER INFORMATION: FVE fragment

<400> SEQUENCE: 146

Gly Thr Pro Ser Ser Tyr Ile Asp Asn Leu Thr
1               5                   10

<210> SEQ ID NO 147
<211> LENGTH: 11
<212> TYPE: PRT
<213> ORGANISM: Artificial
<220> FEATURE:
<223> OTHER INFORMATION: FVE fragment

<400> SEQUENCE: 147

Thr Pro Ser Ser Tyr Ile Asp Asn Leu Thr Phe
1               5                   10

```
<210> SEQ ID NO 148
<211> LENGTH: 12
<212> TYPE: PRT
<213> ORGANISM: Artificial
<220> FEATURE:
<223> OTHER INFORMATION: FVE fragment

<400> SEQUENCE: 148

Asp Phe Asp Tyr Thr Pro Asn Trp Gly Arg Gly Thr
1               5                   10

<210> SEQ ID NO 149
<211> LENGTH: 12
<212> TYPE: PRT
<213> ORGANISM: Artificial
<220> FEATURE:
<223> OTHER INFORMATION: FVE fragment

<400> SEQUENCE: 149

Phe Asp Tyr Thr Pro Asn Trp Gly Arg Gly Thr Pro
1               5                   10

<210> SEQ ID NO 150
<211> LENGTH: 12
<212> TYPE: PRT
<213> ORGANISM: Artificial
<220> FEATURE:
<223> OTHER INFORMATION: FVE fragment

<400> SEQUENCE: 150

Asp Tyr Thr Pro Asn Trp Gly Arg Gly Thr Pro Ser
1               5                   10

<210> SEQ ID NO 151
<211> LENGTH: 12
<212> TYPE: PRT
<213> ORGANISM: Artificial
<220> FEATURE:
<223> OTHER INFORMATION: FVE fragment

<400> SEQUENCE: 151

Tyr Thr Pro Asn Trp Gly Arg Gly Thr Pro Ser Ser
1               5                   10

<210> SEQ ID NO 152
<211> LENGTH: 12
<212> TYPE: PRT
<213> ORGANISM: Artificial
<220> FEATURE:
<223> OTHER INFORMATION: FVE fragment

<400> SEQUENCE: 152

Thr Pro Asn Trp Gly Arg Gly Thr Pro Ser Ser Tyr
1               5                   10

<210> SEQ ID NO 153
<211> LENGTH: 12
<212> TYPE: PRT
<213> ORGANISM: Artificial
<220> FEATURE:
<223> OTHER INFORMATION: FVE fragment

<400> SEQUENCE: 153

Pro Asn Trp Gly Arg Gly Thr Pro Ser Ser Tyr Ile
1               5                   10

<210> SEQ ID NO 154
<211> LENGTH: 12
```

```
<212> TYPE: PRT
<213> ORGANISM: Artificial
<220> FEATURE:
<223> OTHER INFORMATION: FVE fragment

<400> SEQUENCE: 154

Asn Trp Gly Arg Gly Thr Pro Ser Ser Tyr Ile Asp
1               5                   10

<210> SEQ ID NO 155
<211> LENGTH: 12
<212> TYPE: PRT
<213> ORGANISM: Artificial
<220> FEATURE:
<223> OTHER INFORMATION: FVE fragment

<400> SEQUENCE: 155

Trp Gly Arg Gly Thr Pro Ser Ser Tyr Ile Asp Asn
1               5                   10

<210> SEQ ID NO 156
<211> LENGTH: 12
<212> TYPE: PRT
<213> ORGANISM: Artificial
<220> FEATURE:
<223> OTHER INFORMATION: FVE fragment

<400> SEQUENCE: 156

Gly Arg Gly Thr Pro Ser Ser Tyr Ile Asp Asn Leu
1               5                   10

<210> SEQ ID NO 157
<211> LENGTH: 12
<212> TYPE: PRT
<213> ORGANISM: Artificial
<220> FEATURE:
<223> OTHER INFORMATION: FVE fragment

<400> SEQUENCE: 157

Arg Gly Thr Pro Ser Ser Tyr Ile Asp Asn Leu Thr
1               5                   10

<210> SEQ ID NO 158
<211> LENGTH: 12
<212> TYPE: PRT
<213> ORGANISM: Artificial
<220> FEATURE:
<223> OTHER INFORMATION: FVE fragment

<400> SEQUENCE: 158

Gly Thr Pro Ser Ser Tyr Ile Asp Asn Leu Thr Phe
1               5                   10

<210> SEQ ID NO 159
<211> LENGTH: 12
<212> TYPE: PRT
<213> ORGANISM: Artificial
<220> FEATURE:
<223> OTHER INFORMATION: FVE fragment

<400> SEQUENCE: 159

Thr Pro Ser Ser Tyr Ile Asp Asn Leu Thr Phe Pro
1               5                   10

<210> SEQ ID NO 160
<211> LENGTH: 13
<212> TYPE: PRT
<213> ORGANISM: Artificial
```

<220> FEATURE:
<223> OTHER INFORMATION: FVE fragment

<400> SEQUENCE: 160

Ile Asp Phe Asp Tyr Thr Pro Asn Trp Gly Arg Gly Thr
1               5                   10

<210> SEQ ID NO 161
<211> LENGTH: 13
<212> TYPE: PRT
<213> ORGANISM: Artificial
<220> FEATURE:
<223> OTHER INFORMATION: FVE fragment

<400> SEQUENCE: 161

Asp Phe Asp Tyr Thr Pro Asn Trp Gly Arg Gly Thr Pro
1               5                   10

<210> SEQ ID NO 162
<211> LENGTH: 13
<212> TYPE: PRT
<213> ORGANISM: Artificial
<220> FEATURE:
<223> OTHER INFORMATION: FVE fragment

<400> SEQUENCE: 162

Phe Asp Tyr Thr Pro Asn Trp Gly Arg Gly Thr Pro Ser
1               5                   10

<210> SEQ ID NO 163
<211> LENGTH: 13
<212> TYPE: PRT
<213> ORGANISM: Artificial
<220> FEATURE:
<223> OTHER INFORMATION: FVE fragment

<400> SEQUENCE: 163

Asp Tyr Thr Pro Asn Trp Gly Arg Gly Thr Pro Ser Ser
1               5                   10

<210> SEQ ID NO 164
<211> LENGTH: 13
<212> TYPE: PRT
<213> ORGANISM: Artificial
<220> FEATURE:
<223> OTHER INFORMATION: FVe fragment

<400> SEQUENCE: 164

Tyr Thr Pro Asn Trp Gly Arg Gly Thr Pro Ser Ser Tyr
1               5                   10

<210> SEQ ID NO 165
<211> LENGTH: 13
<212> TYPE: PRT
<213> ORGANISM: Artificial
<220> FEATURE:
<223> OTHER INFORMATION: FVE fragment

<400> SEQUENCE: 165

Thr Pro Asn Trp Gly Arg Gly Thr Pro Ser Ser Tyr Ile
1               5                   10

<210> SEQ ID NO 166
<211> LENGTH: 13
<212> TYPE: PRT
<213> ORGANISM: Artificial
<220> FEATURE:
<223> OTHER INFORMATION: FVE fragment

<400> SEQUENCE: 166

Pro Asn Trp Gly Arg Gly Thr Pro Ser Ser Tyr Ile Asp
1               5                   10

<210> SEQ ID NO 167
<211> LENGTH: 13
<212> TYPE: PRT
<213> ORGANISM: Artificial
<220> FEATURE:
<223> OTHER INFORMATION: FVE fragment

<400> SEQUENCE: 167

Asn Trp Gly Arg Gly Thr Pro Ser Ser Tyr Ile Asp Asn
1               5                   10

<210> SEQ ID NO 168
<211> LENGTH: 13
<212> TYPE: PRT
<213> ORGANISM: Artificial
<220> FEATURE:
<223> OTHER INFORMATION: FVE fragment

<400> SEQUENCE: 168

Trp Gly Arg Gly Thr Pro Ser Ser Tyr Ile Asp Asn Leu
1               5                   10

<210> SEQ ID NO 169
<211> LENGTH: 13
<212> TYPE: PRT
<213> ORGANISM: Artificial
<220> FEATURE:
<223> OTHER INFORMATION: FVE Fragment

<400> SEQUENCE: 169

Gly Arg Gly Thr Pro Ser Ser Tyr Ile Asp Asn Leu Thr
1               5                   10

<210> SEQ ID NO 170
<211> LENGTH: 13
<212> TYPE: PRT
<213> ORGANISM: Artificial
<220> FEATURE:
<223> OTHER INFORMATION: FVE fragment

<400> SEQUENCE: 170

Arg Gly Thr Pro Ser Ser Tyr Ile Asp Asn Leu Thr Phe
1               5                   10

<210> SEQ ID NO 171
<211> LENGTH: 13
<212> TYPE: PRT
<213> ORGANISM: Artificial
<220> FEATURE:
<223> OTHER INFORMATION: FVE fragment

<400> SEQUENCE: 171

Gly Thr Pro Ser Ser Tyr Ile Asp Asn Leu Thr Phe Pro
1               5                   10

<210> SEQ ID NO 172
<211> LENGTH: 13
<212> TYPE: PRT
<213> ORGANISM: Artificial
<220> FEATURE:
<223> OTHER INFORMATION: FVE fragment

<400> SEQUENCE: 172

```
Thr Pro Ser Ser Tyr Ile Asp Asn Leu Thr Phe Pro Lys
1               5                   10
```

<210> SEQ ID NO 173
<211> LENGTH: 14
<212> TYPE: PRT
<213> ORGANISM: Artificial
<220> FEATURE:
<223> OTHER INFORMATION: FVE fragment

<400> SEQUENCE: 173

```
Lys Ile Asp Phe Asp Tyr Thr Pro Asn Trp Gly Arg Gly Thr
1               5                   10
```

<210> SEQ ID NO 174
<211> LENGTH: 14
<212> TYPE: PRT
<213> ORGANISM: Artificial
<220> FEATURE:
<223> OTHER INFORMATION: FVE fragment

<400> SEQUENCE: 174

```
Ile Asp Phe Asp Tyr Thr Pro Asn Trp Gly Arg Gly Thr Pro
1               5                   10
```

<210> SEQ ID NO 175
<211> LENGTH: 14
<212> TYPE: PRT
<213> ORGANISM: Artificial
<220> FEATURE:
<223> OTHER INFORMATION: FVE Fragment

<400> SEQUENCE: 175

```
Asp Phe Asp Tyr Thr Pro Asn Trp Gly Arg Gly Thr Pro Ser
1               5                   10
```

<210> SEQ ID NO 176
<211> LENGTH: 14
<212> TYPE: PRT
<213> ORGANISM: Artificial
<220> FEATURE:
<223> OTHER INFORMATION: FVE fragment

<400> SEQUENCE: 176

```
Phe Asp Tyr Thr Pro Asn Trp Gly Arg Gly Thr Pro Ser Ser
1               5                   10
```

<210> SEQ ID NO 177
<211> LENGTH: 14
<212> TYPE: PRT
<213> ORGANISM: Artificial
<220> FEATURE:
<223> OTHER INFORMATION: FVE Fragment

<400> SEQUENCE: 177

```
Asp Tyr Thr Pro Asn Trp Gly Arg Gly Thr Pro Ser Ser Tyr
1               5                   10
```

<210> SEQ ID NO 178
<211> LENGTH: 14
<212> TYPE: PRT
<213> ORGANISM: Artificial
<220> FEATURE:
<223> OTHER INFORMATION: FVE Fragment

<400> SEQUENCE: 178

```
Tyr Thr Pro Asn Trp Gly Arg Gly Thr Pro Ser Ser Tyr Ile
```

```
1               5                   10
```

<210> SEQ ID NO 179
<211> LENGTH: 14
<212> TYPE: PRT
<213> ORGANISM: Artificial
<220> FEATURE:
<223> OTHER INFORMATION: FVE Fragment

<400> SEQUENCE: 179

```
Thr Pro Asn Trp Gly Arg Gly Thr Pro Ser Ser Tyr Ile Asp
1               5                   10
```

<210> SEQ ID NO 180
<211> LENGTH: 14
<212> TYPE: PRT
<213> ORGANISM: Artificial
<220> FEATURE:
<223> OTHER INFORMATION: FVE Fragment

<400> SEQUENCE: 180

```
Pro Asn Trp Gly Arg Gly Thr Pro Ser Ser Tyr Ile Asp Asn
1               5                   10
```

<210> SEQ ID NO 181
<211> LENGTH: 14
<212> TYPE: PRT
<213> ORGANISM: Artificial
<220> FEATURE:
<223> OTHER INFORMATION: FVE Fragment

<400> SEQUENCE: 181

```
Asn Trp Gly Arg Gly Thr Pro Ser Ser Tyr Ile Asp Asn Leu
1               5                   10
```

<210> SEQ ID NO 182
<211> LENGTH: 14
<212> TYPE: PRT
<213> ORGANISM: Artificial
<220> FEATURE:
<223> OTHER INFORMATION: FVE Fragment

<400> SEQUENCE: 182

```
Trp Gly Arg Gly Thr Pro Ser Ser Tyr Ile Asp Asn Leu Thr
1               5                   10
```

<210> SEQ ID NO 183
<211> LENGTH: 14
<212> TYPE: PRT
<213> ORGANISM: Artificial
<220> FEATURE:
<223> OTHER INFORMATION: FVE Fragment

<400> SEQUENCE: 183

```
Gly Arg Gly Thr Pro Ser Ser Tyr Ile Asp Asn Leu Thr Phe
1               5                   10
```

<210> SEQ ID NO 184
<211> LENGTH: 14
<212> TYPE: PRT
<213> ORGANISM: Artificial
<220> FEATURE:
<223> OTHER INFORMATION: FVE Fragment

<400> SEQUENCE: 184

```
Arg Gly Thr Pro Ser Ser Tyr Ile Asp Asn Leu Thr Phe Pro
1               5                   10
```

```
<210> SEQ ID NO 185
<211> LENGTH: 14
<212> TYPE: PRT
<213> ORGANISM: Artificial
<220> FEATURE:
<223> OTHER INFORMATION: FVE Fragment

<400> SEQUENCE: 185

Gly Thr Pro Ser Ser Tyr Ile Asp Asn Leu Thr Phe Pro Lys
1               5                  10

<210> SEQ ID NO 186
<211> LENGTH: 14
<212> TYPE: PRT
<213> ORGANISM: Artificial
<220> FEATURE:
<223> OTHER INFORMATION: FVE Fragment

<400> SEQUENCE: 186

Thr Pro Ser Ser Tyr Ile Asp Asn Leu Thr Phe Pro Lys Val
1               5                  10

<210> SEQ ID NO 187
<211> LENGTH: 15
<212> TYPE: PRT
<213> ORGANISM: Artificial
<220> FEATURE:
<223> OTHER INFORMATION: FVE Fragment

<400> SEQUENCE: 187

Lys Lys Ile Asp Phe Asp Tyr Thr Pro Asn Trp Gly Arg Gly Thr
1               5                  10                  15

<210> SEQ ID NO 188
<211> LENGTH: 15
<212> TYPE: PRT
<213> ORGANISM: Artificial
<220> FEATURE:
<223> OTHER INFORMATION: FVE Fragment

<400> SEQUENCE: 188

Lys Ile Asp Phe Asp Tyr Thr Pro Asn Trp Gly Arg Gly Thr Pro
1               5                  10                  15

<210> SEQ ID NO 189
<211> LENGTH: 15
<212> TYPE: PRT
<213> ORGANISM: Artificial
<220> FEATURE:
<223> OTHER INFORMATION: FVE Fragment

<400> SEQUENCE: 189

Ile Asp Phe Asp Tyr Thr Pro Asn Trp Gly Arg Gly Thr Pro Ser
1               5                  10                  15

<210> SEQ ID NO 190
<211> LENGTH: 15
<212> TYPE: PRT
<213> ORGANISM: Artificial
<220> FEATURE:
<223> OTHER INFORMATION: FVE Fragment

<400> SEQUENCE: 190

Asp Phe Asp Tyr Thr Pro Asn Trp Gly Arg Gly Thr Pro Ser Ser
1               5                  10                  15

<210> SEQ ID NO 191
```

```
<211> LENGTH: 15
<212> TYPE: PRT
<213> ORGANISM: Artificial
<220> FEATURE:
<223> OTHER INFORMATION: FVE Fragment

<400> SEQUENCE: 191

Phe Asp Tyr Thr Pro Asn Trp Gly Arg Gly Thr Pro Ser Ser Tyr
1               5                   10                  15

<210> SEQ ID NO 192
<211> LENGTH: 15
<212> TYPE: PRT
<213> ORGANISM: Artificial
<220> FEATURE:
<223> OTHER INFORMATION: FVE Fragment

<400> SEQUENCE: 192

Asp Tyr Thr Pro Asn Trp Gly Arg Gly Thr Pro Ser Ser Tyr Ile
1               5                   10                  15

<210> SEQ ID NO 193
<211> LENGTH: 15
<212> TYPE: PRT
<213> ORGANISM: Artificial
<220> FEATURE:
<223> OTHER INFORMATION: FVE Fragment

<400> SEQUENCE: 193

Tyr Thr Pro Asn Trp Gly Arg Gly Thr Pro Ser Ser Tyr Ile Asp
1               5                   10                  15

<210> SEQ ID NO 194
<211> LENGTH: 15
<212> TYPE: PRT
<213> ORGANISM: Artificial
<220> FEATURE:
<223> OTHER INFORMATION: FVE Fragment

<400> SEQUENCE: 194

Thr Pro Asn Trp Gly Arg Gly Thr Pro Ser Ser Tyr Ile Asp Asn
1               5                   10                  15

<210> SEQ ID NO 195
<211> LENGTH: 15
<212> TYPE: PRT
<213> ORGANISM: Artificial
<220> FEATURE:
<223> OTHER INFORMATION: FVE Fragment

<400> SEQUENCE: 195

Pro Asn Trp Gly Arg Gly Thr Pro Ser Ser Tyr Ile Asp Asn Leu
1               5                   10                  15

<210> SEQ ID NO 196
<211> LENGTH: 15
<212> TYPE: PRT
<213> ORGANISM: Artificial
<220> FEATURE:
<223> OTHER INFORMATION: FVE Fragment

<400> SEQUENCE: 196

Asn Trp Gly Arg Gly Thr Pro Ser Ser Tyr Ile Asp Asn Leu Thr
1               5                   10                  15

<210> SEQ ID NO 197
<211> LENGTH: 15
<212> TYPE: PRT
```

```
<213> ORGANISM: Artificial
<220> FEATURE:
<223> OTHER INFORMATION: FVE Fragment

<400> SEQUENCE: 197

Trp Gly Arg Gly Thr Pro Ser Ser Tyr Ile Asp Asn Leu Thr Phe
1               5                   10                  15

<210> SEQ ID NO 198
<211> LENGTH: 15
<212> TYPE: PRT
<213> ORGANISM: Artificial
<220> FEATURE:
<223> OTHER INFORMATION: FVE Fragment

<400> SEQUENCE: 198

Gly Arg Gly Thr Pro Ser Ser Tyr Ile Asp Asn Leu Thr Phe Pro
1               5                   10                  15

<210> SEQ ID NO 199
<211> LENGTH: 15
<212> TYPE: PRT
<213> ORGANISM: Artificial
<220> FEATURE:
<223> OTHER INFORMATION: FVE Fragment

<400> SEQUENCE: 199

Arg Gly Thr Pro Ser Ser Tyr Ile Asp Asn Leu Thr Phe Pro Lys
1               5                   10                  15

<210> SEQ ID NO 200
<211> LENGTH: 15
<212> TYPE: PRT
<213> ORGANISM: Artificial
<220> FEATURE:
<223> OTHER INFORMATION: FVE Fragment

<400> SEQUENCE: 200

Gly Thr Pro Ser Ser Tyr Ile Asp Asn Leu Thr Phe Pro Lys Val
1               5                   10                  15

<210> SEQ ID NO 201
<211> LENGTH: 15
<212> TYPE: PRT
<213> ORGANISM: Artificial
<220> FEATURE:
<223> OTHER INFORMATION: FVE Fragment

<400> SEQUENCE: 201

Thr Pro Ser Ser Tyr Ile Asp Asn Leu Thr Phe Pro Lys Val Leu
1               5                   10                  15

<210> SEQ ID NO 202
<211> LENGTH: 16
<212> TYPE: PRT
<213> ORGANISM: Artificial
<220> FEATURE:
<223> OTHER INFORMATION: FVE Fragment

<400> SEQUENCE: 202

Val Lys Lys Ile Asp Phe Asp Tyr Thr Pro Asn Trp Gly Arg Gly Thr
1               5                   10                  15

<210> SEQ ID NO 203
<211> LENGTH: 16
<212> TYPE: PRT
<213> ORGANISM: Artificial
<220> FEATURE:
```

<223> OTHER INFORMATION: FVE Fragment

<400> SEQUENCE: 203

Lys Lys Ile Asp Phe Asp Tyr Thr Pro Asn Trp Gly Arg Gly Thr Pro
1               5                   10                  15

<210> SEQ ID NO 204
<211> LENGTH: 16
<212> TYPE: PRT
<213> ORGANISM: Artificial
<220> FEATURE:
<223> OTHER INFORMATION: FVE Fragment

<400> SEQUENCE: 204

Lys Ile Asp Phe Asp Tyr Thr Pro Asn Trp Gly Arg Gly Thr Pro Ser
1               5                   10                  15

<210> SEQ ID NO 205
<211> LENGTH: 16
<212> TYPE: PRT
<213> ORGANISM: Artificial
<220> FEATURE:
<223> OTHER INFORMATION: FVE Fragment

<400> SEQUENCE: 205

Ile Asp Phe Asp Tyr Thr Pro Asn Trp Gly Arg Gly Thr Pro Ser Ser
1               5                   10                  15

<210> SEQ ID NO 206
<211> LENGTH: 16
<212> TYPE: PRT
<213> ORGANISM: Artificial
<220> FEATURE:
<223> OTHER INFORMATION: FVE Fragment

<400> SEQUENCE: 206

Asp Phe Asp Tyr Thr Pro Asn Trp Gly Arg Gly Thr Pro Ser Ser Tyr
1               5                   10                  15

<210> SEQ ID NO 207
<211> LENGTH: 16
<212> TYPE: PRT
<213> ORGANISM: Artificial
<220> FEATURE:
<223> OTHER INFORMATION: FVE Fragment

<400> SEQUENCE: 207

Phe Asp Tyr Thr Pro Asn Trp Gly Arg Gly Thr Pro Ser Ser Tyr Ile
1               5                   10                  15

<210> SEQ ID NO 208
<211> LENGTH: 16
<212> TYPE: PRT
<213> ORGANISM: Artificial
<220> FEATURE:
<223> OTHER INFORMATION: FVE Fragment

<400> SEQUENCE: 208

Asp Tyr Thr Pro Asn Trp Gly Arg Gly Thr Pro Ser Ser Tyr Ile Asp
1               5                   10                  15

<210> SEQ ID NO 209
<211> LENGTH: 16
<212> TYPE: PRT
<213> ORGANISM: Artificial
<220> FEATURE:
<223> OTHER INFORMATION: FVe Fragment

```
<400> SEQUENCE: 209

Tyr Thr Pro Asn Trp Gly Arg Gly Thr Pro Ser Ser Tyr Ile Asp Asn
1               5                   10                  15

<210> SEQ ID NO 210
<211> LENGTH: 16
<212> TYPE: PRT
<213> ORGANISM: Artificial
<220> FEATURE:
<223> OTHER INFORMATION: FVE fragment

<400> SEQUENCE: 210

Thr Pro Asn Trp Gly Arg Gly Thr Pro Ser Ser Tyr Ile Asp Asn Leu
1               5                   10                  15

<210> SEQ ID NO 211
<211> LENGTH: 16
<212> TYPE: PRT
<213> ORGANISM: Artificial
<220> FEATURE:
<223> OTHER INFORMATION: FVE Fragment

<400> SEQUENCE: 211

Pro Asn Trp Gly Arg Gly Thr Pro Ser Ser Tyr Ile Asp Asn Leu Thr
1               5                   10                  15

<210> SEQ ID NO 212
<211> LENGTH: 16
<212> TYPE: PRT
<213> ORGANISM: Artificial
<220> FEATURE:
<223> OTHER INFORMATION: FVE Fragment

<400> SEQUENCE: 212

Asn Trp Gly Arg Gly Thr Pro Ser Ser Tyr Ile Asp Asn Leu Thr Phe
1               5                   10                  15

<210> SEQ ID NO 213
<211> LENGTH: 16
<212> TYPE: PRT
<213> ORGANISM: Artificial
<220> FEATURE:
<223> OTHER INFORMATION: FVE Fragment

<400> SEQUENCE: 213

Trp Gly Arg Gly Thr Pro Ser Ser Tyr Ile Asp Asn Leu Thr Phe Pro
1               5                   10                  15

<210> SEQ ID NO 214
<211> LENGTH: 16
<212> TYPE: PRT
<213> ORGANISM: Artificial
<220> FEATURE:
<223> OTHER INFORMATION: FVE fragment

<400> SEQUENCE: 214

Gly Arg Gly Thr Pro Ser Ser Tyr Ile Asp Asn Leu Thr Phe Pro Lys
1               5                   10                  15

<210> SEQ ID NO 215
<211> LENGTH: 16
<212> TYPE: PRT
<213> ORGANISM: Artificial
<220> FEATURE:
<223> OTHER INFORMATION: FVE Fragment

<400> SEQUENCE: 215
```

Arg Gly Thr Pro Ser Ser Tyr Ile Asp Asn Leu Thr Phe Pro Lys Val
1               5                   10                  15

<210> SEQ ID NO 216
<211> LENGTH: 16
<212> TYPE: PRT
<213> ORGANISM: Artificial
<220> FEATURE:
<223> OTHER INFORMATION: FVE Fragment

<400> SEQUENCE: 216

Gly Thr Pro Ser Ser Tyr Ile Asp Asn Leu Thr Phe Pro Lys Val Leu
1               5                   10                  15

<210> SEQ ID NO 217
<211> LENGTH: 16
<212> TYPE: PRT
<213> ORGANISM: Artificial
<220> FEATURE:
<223> OTHER INFORMATION: FVE fragment

<400> SEQUENCE: 217

Thr Pro Ser Ser Tyr Ile Asp Asn Leu Thr Phe Pro Lys Val Leu Thr
1               5                   10                  15

<210> SEQ ID NO 218
<211> LENGTH: 17
<212> TYPE: PRT
<213> ORGANISM: Artificial
<220> FEATURE:
<223> OTHER INFORMATION: FVE Fragment

<400> SEQUENCE: 218

Leu Val Lys Lys Ile Asp Phe Asp Tyr Thr Pro Asn Trp Gly Arg Gly
1               5                   10                  15

Thr

<210> SEQ ID NO 219
<211> LENGTH: 17
<212> TYPE: PRT
<213> ORGANISM: Artificial
<220> FEATURE:
<223> OTHER INFORMATION: FVE Fragment

<400> SEQUENCE: 219

Val Lys Lys Ile Asp Phe Asp Tyr Thr Pro Asn Trp Gly Arg Gly Thr
1               5                   10                  15

Pro

<210> SEQ ID NO 220
<211> LENGTH: 17
<212> TYPE: PRT
<213> ORGANISM: Artificial
<220> FEATURE:
<223> OTHER INFORMATION: FVE Fragment

<400> SEQUENCE: 220

Lys Lys Ile Asp Phe Asp Tyr Thr Pro Asn Trp Gly Arg Gly Thr Pro
1               5                   10                  15

Ser

<210> SEQ ID NO 221
<211> LENGTH: 17
<212> TYPE: PRT
<213> ORGANISM: Artificial
<220> FEATURE:

<223> OTHER INFORMATION: FVE Fragment

<400> SEQUENCE: 221

Lys Ile Asp Phe Asp Tyr Thr Pro Asn Trp Gly Arg Gly Thr Pro Ser
1               5                   10                  15
Ser

<210> SEQ ID NO 222
<211> LENGTH: 17
<212> TYPE: PRT
<213> ORGANISM: Artificial
<220> FEATURE:
<223> OTHER INFORMATION: FVE Fragment

<400> SEQUENCE: 222

Ile Asp Phe Asp Tyr Thr Pro Asn Trp Gly Arg Gly Thr Pro Ser Ser
1               5                   10                  15
Tyr

<210> SEQ ID NO 223
<211> LENGTH: 17
<212> TYPE: PRT
<213> ORGANISM: Artificial
<220> FEATURE:
<223> OTHER INFORMATION: FVE Fragment

<400> SEQUENCE: 223

Asp Phe Asp Tyr Thr Pro Asn Trp Gly Arg Gly Thr Pro Ser Ser Tyr
1               5                   10                  15
Ile

<210> SEQ ID NO 224
<211> LENGTH: 17
<212> TYPE: PRT
<213> ORGANISM: Artificial
<220> FEATURE:
<223> OTHER INFORMATION: FVE Fragment

<400> SEQUENCE: 224

Phe Asp Tyr Thr Pro Asn Trp Gly Arg Gly Thr Pro Ser Ser Tyr Ile
1               5                   10                  15
Asp

<210> SEQ ID NO 225
<211> LENGTH: 17
<212> TYPE: PRT
<213> ORGANISM: Artificial
<220> FEATURE:
<223> OTHER INFORMATION: FVE Fragment

<400> SEQUENCE: 225

Asp Tyr Thr Pro Asn Trp Gly Arg Gly Thr Pro Ser Ser Tyr Ile Asp
1               5                   10                  15
Asn

<210> SEQ ID NO 226
<211> LENGTH: 17
<212> TYPE: PRT
<213> ORGANISM: Artificial
<220> FEATURE:
<223> OTHER INFORMATION: FVE Fragment

<400> SEQUENCE: 226

Tyr Thr Pro Asn Trp Gly Arg Gly Thr Pro Ser Ser Tyr Ile Asp Asn

```
                1               5                  10                 15
Leu

<210> SEQ ID NO 227
<211> LENGTH: 17
<212> TYPE: PRT
<213> ORGANISM: Artificial
<220> FEATURE:
<223> OTHER INFORMATION: FVE Fragment

<400> SEQUENCE: 227

Thr Pro Asn Trp Gly Arg Gly Thr Pro Ser Ser Tyr Ile Asp Asn Leu
1               5                   10                  15
Thr

<210> SEQ ID NO 228
<211> LENGTH: 17
<212> TYPE: PRT
<213> ORGANISM: Artificial
<220> FEATURE:
<223> OTHER INFORMATION: FVE Fragment

<400> SEQUENCE: 228

Pro Asn Trp Gly Arg Gly Thr Pro Ser Ser Tyr Ile Asp Asn Leu Thr
1               5                   10                  15
Phe

<210> SEQ ID NO 229
<211> LENGTH: 17
<212> TYPE: PRT
<213> ORGANISM: Artificial
<220> FEATURE:
<223> OTHER INFORMATION: FVE Fragment

<400> SEQUENCE: 229

Asn Trp Gly Arg Gly Thr Pro Ser Ser Tyr Ile Asp Asn Leu Thr Phe
1               5                   10                  15
Pro

<210> SEQ ID NO 230
<211> LENGTH: 17
<212> TYPE: PRT
<213> ORGANISM: Artificial
<220> FEATURE:
<223> OTHER INFORMATION: FVE Fragment

<400> SEQUENCE: 230

Trp Gly Arg Gly Thr Pro Ser Ser Tyr Ile Asp Asn Leu Thr Phe Pro
1               5                   10                  15
Lys

<210> SEQ ID NO 231
<211> LENGTH: 17
<212> TYPE: PRT
<213> ORGANISM: Artificial
<220> FEATURE:
<223> OTHER INFORMATION: FVE Fragment

<400> SEQUENCE: 231

Gly Arg Gly Thr Pro Ser Ser Tyr Ile Asp Asn Leu Thr Phe Pro Lys
1               5                   10                  15
Val
```

```
<210> SEQ ID NO 232
<211> LENGTH: 17
<212> TYPE: PRT
<213> ORGANISM: Artificial
<220> FEATURE:
<223> OTHER INFORMATION: FVE Fragment

<400> SEQUENCE: 232

Arg Gly Thr Pro Ser Ser Tyr Ile Asp Asn Leu Thr Phe Pro Lys Val
1               5                   10                  15

Leu

<210> SEQ ID NO 233
<211> LENGTH: 17
<212> TYPE: PRT
<213> ORGANISM: Artificial
<220> FEATURE:
<223> OTHER INFORMATION: FVE Fragment

<400> SEQUENCE: 233

Gly Thr Pro Ser Ser Tyr Ile Asp Asn Leu Thr Phe Pro Lys Val Leu
1               5                   10                  15

Thr

<210> SEQ ID NO 234
<211> LENGTH: 17
<212> TYPE: PRT
<213> ORGANISM: Artificial
<220> FEATURE:
<223> OTHER INFORMATION: FVE Fragment

<400> SEQUENCE: 234

Thr Pro Ser Ser Tyr Ile Asp Asn Leu Thr Phe Pro Lys Val Leu Thr
1               5                   10                  15

Asp

<210> SEQ ID NO 235
<211> LENGTH: 18
<212> TYPE: PRT
<213> ORGANISM: Artificial
<220> FEATURE:
<223> OTHER INFORMATION: FVE Fragment

<400> SEQUENCE: 235

Tyr Leu Val Lys Lys Ile Asp Phe Asp Tyr Thr Pro Asn Trp Gly Arg
1               5                   10                  15

Gly Thr

<210> SEQ ID NO 236
<211> LENGTH: 18
<212> TYPE: PRT
<213> ORGANISM: Artificial
<220> FEATURE:
<223> OTHER INFORMATION: FVE Fragment

<400> SEQUENCE: 236

Leu Val Lys Lys Ile Asp Phe Asp Tyr Thr Pro Asn Trp Gly Arg Gly
1               5                   10                  15

Thr Pro

<210> SEQ ID NO 237
<211> LENGTH: 18
<212> TYPE: PRT
<213> ORGANISM: Artificial
<220> FEATURE:
```

<223> OTHER INFORMATION: FVE Fragment

<400> SEQUENCE: 237

Val Lys Lys Ile Asp Phe Asp Tyr Thr Pro Asn Trp Gly Arg Gly Thr
1               5                   10                  15

Pro Ser

<210> SEQ ID NO 238
<211> LENGTH: 18
<212> TYPE: PRT
<213> ORGANISM: Artificial
<220> FEATURE:
<223> OTHER INFORMATION: FVE Fragment

<400> SEQUENCE: 238

Lys Lys Ile Asp Phe Asp Tyr Thr Pro Asn Trp Gly Arg Gly Thr Pro
1               5                   10                  15

Ser Ser

<210> SEQ ID NO 239
<211> LENGTH: 18
<212> TYPE: PRT
<213> ORGANISM: Artificial
<220> FEATURE:
<223> OTHER INFORMATION: FVE Fragment

<400> SEQUENCE: 239

Lys Ile Asp Phe Asp Tyr Thr Pro Asn Trp Gly Arg Gly Thr Pro Ser
1               5                   10                  15

Ser Tyr

<210> SEQ ID NO 240
<211> LENGTH: 18
<212> TYPE: PRT
<213> ORGANISM: Artificial
<220> FEATURE:
<223> OTHER INFORMATION: FVE Fragment

<400> SEQUENCE: 240

Ile Asp Phe Asp Tyr Thr Pro Asn Trp Gly Arg Gly Thr Pro Ser Ser
1               5                   10                  15

Tyr Ile

<210> SEQ ID NO 241
<211> LENGTH: 18
<212> TYPE: PRT
<213> ORGANISM: Artificial
<220> FEATURE:
<223> OTHER INFORMATION: FVE Fragment

<400> SEQUENCE: 241

Asp Phe Asp Tyr Thr Pro Asn Trp Gly Arg Gly Thr Pro Ser Ser Tyr
1               5                   10                  15

Ile Asp

<210> SEQ ID NO 242
<211> LENGTH: 18
<212> TYPE: PRT
<213> ORGANISM: Artificial
<220> FEATURE:
<223> OTHER INFORMATION: FVE Fragment

<400> SEQUENCE: 242

Phe Asp Tyr Thr Pro Asn Trp Gly Arg Gly Thr Pro Ser Ser Tyr Ile

```
                1               5                  10                  15
Asp Asn

<210> SEQ ID NO 243
<211> LENGTH: 18
<212> TYPE: PRT
<213> ORGANISM: Artificial
<220> FEATURE:
<223> OTHER INFORMATION: FVE Fragment

<400> SEQUENCE: 243

Asp Tyr Thr Pro Asn Trp Gly Arg Gly Thr Pro Ser Ser Tyr Ile Asp
1               5                   10                  15

Asn Leu

<210> SEQ ID NO 244
<211> LENGTH: 18
<212> TYPE: PRT
<213> ORGANISM: Artificial
<220> FEATURE:
<223> OTHER INFORMATION: FVE Fragment

<400> SEQUENCE: 244

Tyr Thr Pro Asn Trp Gly Arg Gly Thr Pro Ser Ser Tyr Ile Asp Asn
1               5                   10                  15

Leu Thr

<210> SEQ ID NO 245
<211> LENGTH: 18
<212> TYPE: PRT
<213> ORGANISM: Artificial
<220> FEATURE:
<223> OTHER INFORMATION: FVE Fragment

<400> SEQUENCE: 245

Thr Pro Asn Trp Gly Arg Gly Thr Pro Ser Ser Tyr Ile Asp Asn Leu
1               5                   10                  15

Thr Phe

<210> SEQ ID NO 246
<211> LENGTH: 18
<212> TYPE: PRT
<213> ORGANISM: Artificial
<220> FEATURE:
<223> OTHER INFORMATION: FVE Fragment

<400> SEQUENCE: 246

Pro Asn Trp Gly Arg Gly Thr Pro Ser Ser Tyr Ile Asp Asn Leu Thr
1               5                   10                  15

Phe Pro

<210> SEQ ID NO 247
<211> LENGTH: 18
<212> TYPE: PRT
<213> ORGANISM: Artificial
<220> FEATURE:
<223> OTHER INFORMATION: FVE Fragment

<400> SEQUENCE: 247

Asn Trp Gly Arg Gly Thr Pro Ser Ser Tyr Ile Asp Asn Leu Thr Phe
1               5                   10                  15

Pro Lys
```

-continued

```
<210> SEQ ID NO 248
<211> LENGTH: 18
<212> TYPE: PRT
<213> ORGANISM: Artificial
<220> FEATURE:
<223> OTHER INFORMATION: FVE Fragment

<400> SEQUENCE: 248

Trp Gly Arg Gly Thr Pro Ser Ser Tyr Ile Asp Asn Leu Thr Phe Pro
1               5                   10                  15

Lys Val

<210> SEQ ID NO 249
<211> LENGTH: 18
<212> TYPE: PRT
<213> ORGANISM: Artificial
<220> FEATURE:
<223> OTHER INFORMATION: FVE Fragment

<400> SEQUENCE: 249

Gly Arg Gly Thr Pro Ser Ser Tyr Ile Asp Asn Leu Thr Phe Pro Lys
1               5                   10                  15

Val Leu

<210> SEQ ID NO 250
<211> LENGTH: 18
<212> TYPE: PRT
<213> ORGANISM: Artificial
<220> FEATURE:
<223> OTHER INFORMATION: FVE Fragment

<400> SEQUENCE: 250

Arg Gly Thr Pro Ser Ser Tyr Ile Asp Asn Leu Thr Phe Pro Lys Val
1               5                   10                  15

Leu Thr

<210> SEQ ID NO 251
<211> LENGTH: 18
<212> TYPE: PRT
<213> ORGANISM: Artificial
<220> FEATURE:
<223> OTHER INFORMATION: FVE Fragment

<400> SEQUENCE: 251

Gly Thr Pro Ser Ser Tyr Ile Asp Asn Leu Thr Phe Pro Lys Val Leu
1               5                   10                  15

Thr Asp

<210> SEQ ID NO 252
<211> LENGTH: 18
<212> TYPE: PRT
<213> ORGANISM: Artificial
<220> FEATURE:
<223> OTHER INFORMATION: FVE Fragment

<400> SEQUENCE: 252

Thr Pro Ser Ser Tyr Ile Asp Asn Leu Thr Phe Pro Lys Val Leu Thr
1               5                   10                  15

Asp Lys

<210> SEQ ID NO 253
<211> LENGTH: 19
<212> TYPE: PRT
<213> ORGANISM: Artificial
<220> FEATURE:
```

<223> OTHER INFORMATION: FVE Fragment

<400> SEQUENCE: 253

Ala Tyr Leu Val Lys Lys Ile Asp Phe Asp Tyr Thr Pro Asn Trp Gly
1               5                   10                  15

Arg Gly Thr

<210> SEQ ID NO 254
<211> LENGTH: 19
<212> TYPE: PRT
<213> ORGANISM: Artificial
<220> FEATURE:
<223> OTHER INFORMATION: FVE Fragment

<400> SEQUENCE: 254

Tyr Leu Val Lys Lys Ile Asp Phe Asp Tyr Thr Pro Asn Trp Gly Arg
1               5                   10                  15

Gly Thr Pro

<210> SEQ ID NO 255
<211> LENGTH: 19
<212> TYPE: PRT
<213> ORGANISM: Artificial
<220> FEATURE:
<223> OTHER INFORMATION: FVE Fragment

<400> SEQUENCE: 255

Leu Val Lys Lys Ile Asp Phe Asp Tyr Thr Pro Asn Trp Gly Arg Gly
1               5                   10                  15

Thr Pro Ser

<210> SEQ ID NO 256
<211> LENGTH: 19
<212> TYPE: PRT
<213> ORGANISM: Artificial
<220> FEATURE:
<223> OTHER INFORMATION: FVE Fragment

<400> SEQUENCE: 256

Val Lys Lys Ile Asp Phe Asp Tyr Thr Pro Asn Trp Gly Arg Gly Thr
1               5                   10                  15

Pro Ser Ser

<210> SEQ ID NO 257
<211> LENGTH: 19
<212> TYPE: PRT
<213> ORGANISM: Artificial
<220> FEATURE:
<223> OTHER INFORMATION: FVE Fragment

<400> SEQUENCE: 257

Lys Lys Ile Asp Phe Asp Tyr Thr Pro Asn Trp Gly Arg Gly Thr Pro
1               5                   10                  15

Ser Ser Tyr

<210> SEQ ID NO 258
<211> LENGTH: 19
<212> TYPE: PRT
<213> ORGANISM: Artificial
<220> FEATURE:
<223> OTHER INFORMATION: FVE Fragment

<400> SEQUENCE: 258

Lys Ile Asp Phe Asp Tyr Thr Pro Asn Trp Gly Arg Gly Thr Pro Ser

```
                1               5                   10                  15
Ser Tyr Ile

<210> SEQ ID NO 259
<211> LENGTH: 19
<212> TYPE: PRT
<213> ORGANISM: Artificial
<220> FEATURE:
<223> OTHER INFORMATION: FVE Fragment

<400> SEQUENCE: 259

Ile Asp Phe Asp Tyr Thr Pro Asn Trp Gly Arg Gly Thr Pro Ser Ser
1               5                   10                  15

Tyr Ile Asp

<210> SEQ ID NO 260
<211> LENGTH: 19
<212> TYPE: PRT
<213> ORGANISM: Artificial
<220> FEATURE:
<223> OTHER INFORMATION: FVE Fragment

<400> SEQUENCE: 260

Asp Phe Asp Tyr Thr Pro Asn Trp Gly Arg Gly Thr Pro Ser Ser Tyr
1               5                   10                  15

Ile Asp Asn

<210> SEQ ID NO 261
<211> LENGTH: 19
<212> TYPE: PRT
<213> ORGANISM: Artificial
<220> FEATURE:
<223> OTHER INFORMATION: FVE Fragment

<400> SEQUENCE: 261

Phe Asp Tyr Thr Pro Asn Trp Gly Arg Gly Thr Pro Ser Ser Tyr Ile
1               5                   10                  15

Asp Asn Leu

<210> SEQ ID NO 262
<211> LENGTH: 19
<212> TYPE: PRT
<213> ORGANISM: Artificial
<220> FEATURE:
<223> OTHER INFORMATION: FVE Fragment

<400> SEQUENCE: 262

Asp Tyr Thr Pro Asn Trp Gly Arg Gly Thr Pro Ser Ser Tyr Ile Asp
1               5                   10                  15

Asn Leu Thr

<210> SEQ ID NO 263
<211> LENGTH: 19
<212> TYPE: PRT
<213> ORGANISM: Artificial
<220> FEATURE:
<223> OTHER INFORMATION: FVE Fragment

<400> SEQUENCE: 263

Tyr Thr Pro Asn Trp Gly Arg Gly Thr Pro Ser Ser Tyr Ile Asp Asn
1               5                   10                  15

Leu Thr Phe
```

```
<210> SEQ ID NO 264
<211> LENGTH: 19
<212> TYPE: PRT
<213> ORGANISM: Artificial
<220> FEATURE:
<223> OTHER INFORMATION: FVE Fragment

<400> SEQUENCE: 264

Thr Pro Asn Trp Gly Arg Gly Thr Pro Ser Ser Tyr Ile Asp Asn Leu
1               5                   10                  15

Thr Phe Pro

<210> SEQ ID NO 265
<211> LENGTH: 19
<212> TYPE: PRT
<213> ORGANISM: Artificial
<220> FEATURE:
<223> OTHER INFORMATION: FVE Fragment

<400> SEQUENCE: 265

Pro Asn Trp Gly Arg Gly Thr Pro Ser Ser Tyr Ile Asp Asn Leu Thr
1               5                   10                  15

Phe Pro Lys

<210> SEQ ID NO 266
<211> LENGTH: 19
<212> TYPE: PRT
<213> ORGANISM: Artificial
<220> FEATURE:
<223> OTHER INFORMATION: FVE Fragment

<400> SEQUENCE: 266

Asn Trp Gly Arg Gly Thr Pro Ser Ser Tyr Ile Asp Asn Leu Thr Phe
1               5                   10                  15

Pro Lys Val

<210> SEQ ID NO 267
<211> LENGTH: 19
<212> TYPE: PRT
<213> ORGANISM: Artificial
<220> FEATURE:
<223> OTHER INFORMATION: FVE Fragment

<400> SEQUENCE: 267

Trp Gly Arg Gly Thr Pro Ser Ser Tyr Ile Asp Asn Leu Thr Phe Pro
1               5                   10                  15

Lys Val Leu

<210> SEQ ID NO 268
<211> LENGTH: 19
<212> TYPE: PRT
<213> ORGANISM: Artificial
<220> FEATURE:
<223> OTHER INFORMATION: FVE Fragment

<400> SEQUENCE: 268

Gly Arg Gly Thr Pro Ser Ser Tyr Ile Asp Asn Leu Thr Phe Pro Lys
1               5                   10                  15

Val Leu Thr

<210> SEQ ID NO 269
<211> LENGTH: 19
<212> TYPE: PRT
<213> ORGANISM: Artificial
<220> FEATURE:
```

<223> OTHER INFORMATION: FVE Fragment

<400> SEQUENCE: 269

Arg Gly Thr Pro Ser Ser Tyr Ile Asp Asn Leu Thr Phe Pro Lys Val
1               5                   10                  15

Leu Thr Asp

<210> SEQ ID NO 270
<211> LENGTH: 19
<212> TYPE: PRT
<213> ORGANISM: Artificial
<220> FEATURE:
<223> OTHER INFORMATION: FVE Fragment

<400> SEQUENCE: 270

Gly Thr Pro Ser Ser Tyr Ile Asp Asn Leu Thr Phe Pro Lys Val Leu
1               5                   10                  15

Thr Asp Lys

<210> SEQ ID NO 271
<211> LENGTH: 19
<212> TYPE: PRT
<213> ORGANISM: Artificial
<220> FEATURE:
<223> OTHER INFORMATION: FVE Fragment

<400> SEQUENCE: 271

Thr Pro Ser Ser Tyr Ile Asp Asn Leu Thr Phe Pro Lys Val Leu Thr
1               5                   10                  15

Asp Lys Lys

<210> SEQ ID NO 272
<211> LENGTH: 20
<212> TYPE: PRT
<213> ORGANISM: Artificial
<220> FEATURE:
<223> OTHER INFORMATION: FVE Fragment

<400> SEQUENCE: 272

Leu Ala Tyr Leu Val Lys Lys Ile Asp Phe Asp Tyr Thr Pro Asn Trp
1               5                   10                  15

Gly Arg Gly Thr
            20

<210> SEQ ID NO 273
<211> LENGTH: 20
<212> TYPE: PRT
<213> ORGANISM: Artificial
<220> FEATURE:
<223> OTHER INFORMATION: FVE Fragment

<400> SEQUENCE: 273

Ala Tyr Leu Val Lys Lys Ile Asp Phe Asp Tyr Thr Pro Asn Trp Gly
1               5                   10                  15

Arg Gly Thr Pro
            20

<210> SEQ ID NO 274
<211> LENGTH: 20
<212> TYPE: PRT
<213> ORGANISM: Artificial
<220> FEATURE:
<223> OTHER INFORMATION: FVE Fragment

<400> SEQUENCE: 274

-continued

Tyr Leu Val Lys Ile Asp Phe Asp Tyr Thr Pro Asn Trp Gly Arg
1               5                   10                  15

Gly Thr Pro Ser
            20

<210> SEQ ID NO 275
<211> LENGTH: 20
<212> TYPE: PRT
<213> ORGANISM: Artificial
<220> FEATURE:
<223> OTHER INFORMATION: FVE Fragment

<400> SEQUENCE: 275

Leu Val Lys Lys Ile Asp Phe Asp Tyr Thr Pro Asn Trp Gly Arg Gly
1               5                   10                  15

Thr Pro Ser Ser
            20

<210> SEQ ID NO 276
<211> LENGTH: 20
<212> TYPE: PRT
<213> ORGANISM: Artificial
<220> FEATURE:
<223> OTHER INFORMATION: FVE Fragment

<400> SEQUENCE: 276

Val Lys Lys Ile Asp Phe Asp Tyr Thr Pro Asn Trp Gly Arg Gly Thr
1               5                   10                  15

Pro Ser Ser Tyr
            20

<210> SEQ ID NO 277
<211> LENGTH: 20
<212> TYPE: PRT
<213> ORGANISM: Artificial
<220> FEATURE:
<223> OTHER INFORMATION: FVE Fragment

<400> SEQUENCE: 277

Lys Lys Ile Asp Phe Asp Tyr Thr Pro Asn Trp Gly Arg Gly Thr Pro
1               5                   10                  15

Ser Ser Tyr Ile
            20

<210> SEQ ID NO 278
<211> LENGTH: 20
<212> TYPE: PRT
<213> ORGANISM: Artificial
<220> FEATURE:
<223> OTHER INFORMATION: FVE Fragment

<400> SEQUENCE: 278

Lys Ile Asp Phe Asp Tyr Thr Pro Asn Trp Gly Arg Gly Thr Pro Ser
1               5                   10                  15

Ser Tyr Ile Asp
            20

<210> SEQ ID NO 279
<211> LENGTH: 20
<212> TYPE: PRT
<213> ORGANISM: Artificial
<220> FEATURE:
<223> OTHER INFORMATION: FVE Fragment

<400> SEQUENCE: 279

Ile Asp Phe Asp Tyr Thr Pro Asn Trp Gly Arg Gly Thr Pro Ser Ser
1               5                   10                  15

Tyr Ile Asp Asn
            20

<210> SEQ ID NO 280
<211> LENGTH: 20
<212> TYPE: PRT
<213> ORGANISM: Artificial
<220> FEATURE:
<223> OTHER INFORMATION: FVE Fragment

<400> SEQUENCE: 280

Asp Phe Asp Tyr Thr Pro Asn Trp Gly Arg Gly Thr Pro Ser Ser Tyr
1               5                   10                  15

Ile Asp Asn Leu
            20

<210> SEQ ID NO 281
<211> LENGTH: 20
<212> TYPE: PRT
<213> ORGANISM: Artificial
<220> FEATURE:
<223> OTHER INFORMATION: FVE Fragment

<400> SEQUENCE: 281

Phe Asp Tyr Thr Pro Asn Trp Gly Arg Gly Thr Pro Ser Ser Tyr Ile
1               5                   10                  15

Asp Asn Leu Thr
            20

<210> SEQ ID NO 282
<211> LENGTH: 20
<212> TYPE: PRT
<213> ORGANISM: Artificial
<220> FEATURE:
<223> OTHER INFORMATION: FVE Fragment

<400> SEQUENCE: 282

Asp Tyr Thr Pro Asn Trp Gly Arg Gly Thr Pro Ser Ser Tyr Ile Asp
1               5                   10                  15

Asn Leu Thr Phe
            20

<210> SEQ ID NO 283
<211> LENGTH: 20
<212> TYPE: PRT
<213> ORGANISM: Artificial
<220> FEATURE:
<223> OTHER INFORMATION: FVE Fragment

<400> SEQUENCE: 283

Tyr Thr Pro Asn Trp Gly Arg Gly Thr Pro Ser Ser Tyr Ile Asp Asn
1               5                   10                  15

Leu Thr Phe Pro
            20

<210> SEQ ID NO 284
<211> LENGTH: 20
<212> TYPE: PRT
<213> ORGANISM: Artificial
<220> FEATURE:
<223> OTHER INFORMATION: FVE Fragment

<400> SEQUENCE: 284

Thr Pro Asn Trp Gly Arg Gly Thr Pro Ser Ser Tyr Ile Asp Asn Leu
1               5                   10                  15

Thr Phe Pro Lys
            20

<210> SEQ ID NO 285
<211> LENGTH: 20
<212> TYPE: PRT
<213> ORGANISM: Artificial
<220> FEATURE:
<223> OTHER INFORMATION: FVE Fragment

<400> SEQUENCE: 285

Pro Asn Trp Gly Arg Gly Thr Pro Ser Ser Tyr Ile Asp Asn Leu Thr
1               5                   10                  15

Phe Pro Lys Val
            20

<210> SEQ ID NO 286
<211> LENGTH: 20
<212> TYPE: PRT
<213> ORGANISM: Artificial
<220> FEATURE:
<223> OTHER INFORMATION: FVE Fragment

<400> SEQUENCE: 286

Asn Trp Gly Arg Gly Thr Pro Ser Ser Tyr Ile Asp Asn Leu Thr Phe
1               5                   10                  15

Pro Lys Val Leu
            20

<210> SEQ ID NO 287
<211> LENGTH: 20
<212> TYPE: PRT
<213> ORGANISM: Artificial
<220> FEATURE:
<223> OTHER INFORMATION: FVE Fragment

<400> SEQUENCE: 287

Trp Gly Arg Gly Thr Pro Ser Ser Tyr Ile Asp Asn Leu Thr Phe Pro
1               5                   10                  15

Lys Val Leu Thr
            20

<210> SEQ ID NO 288
<211> LENGTH: 20
<212> TYPE: PRT
<213> ORGANISM: Artificial
<220> FEATURE:
<223> OTHER INFORMATION: FVE Fragment

<400> SEQUENCE: 288

Gly Arg Gly Thr Pro Ser Ser Tyr Ile Asp Asn Leu Thr Phe Pro Lys
1               5                   10                  15

Val Leu Thr Asp
            20

<210> SEQ ID NO 289
<211> LENGTH: 20
<212> TYPE: PRT
<213> ORGANISM: Artificial
<220> FEATURE:
<223> OTHER INFORMATION: FVE Fragment

<400> SEQUENCE: 289

-continued

```
Arg Gly Thr Pro Ser Ser Tyr Ile Asp Asn Leu Thr Phe Pro Lys Val
1               5                   10                  15

Leu Thr Asp Lys
            20

<210> SEQ ID NO 290
<211> LENGTH: 20
<212> TYPE: PRT
<213> ORGANISM: Artificial
<220> FEATURE:
<223> OTHER INFORMATION: FVE Fragment

<400> SEQUENCE: 290

Gly Thr Pro Ser Ser Tyr Ile Asp Asn Leu Thr Phe Pro Lys Val Leu
1               5                   10                  15

Thr Asp Lys Lys
            20

<210> SEQ ID NO 291
<211> LENGTH: 20
<212> TYPE: PRT
<213> ORGANISM: Artificial
<220> FEATURE:
<223> OTHER INFORMATION: FVE Fragment

<400> SEQUENCE: 291

Thr Pro Ser Ser Tyr Ile Asp Asn Leu Thr Phe Pro Lys Val Leu Thr
1               5                   10                  15

Asp Lys Lys Tyr
            20

<210> SEQ ID NO 292
<211> LENGTH: 21
<212> TYPE: PRT
<213> ORGANISM: Artificial
<220> FEATURE:
<223> OTHER INFORMATION: FVE Fragment

<400> SEQUENCE: 292

Gln Leu Ala Tyr Leu Val Lys Lys Ile Asp Phe Asp Tyr Thr Pro Asn
1               5                   10                  15

Trp Gly Arg Gly Thr
            20

<210> SEQ ID NO 293
<211> LENGTH: 21
<212> TYPE: PRT
<213> ORGANISM: Artificial
<220> FEATURE:
<223> OTHER INFORMATION: FVE Fragment

<400> SEQUENCE: 293

Leu Ala Tyr Leu Val Lys Lys Ile Asp Phe Asp Tyr Thr Pro Asn Trp
1               5                   10                  15

Gly Arg Gly Thr Pro
            20

<210> SEQ ID NO 294
<211> LENGTH: 21
<212> TYPE: PRT
<213> ORGANISM: Artificial
<220> FEATURE:
<223> OTHER INFORMATION: FVE Fragment

<400> SEQUENCE: 294
```

Ala Tyr Leu Val Lys Lys Ile Asp Phe Asp Tyr Thr Pro Asn Trp Gly
1               5                   10                  15

Arg Gly Thr Pro Ser
            20

<210> SEQ ID NO 295
<211> LENGTH: 21
<212> TYPE: PRT
<213> ORGANISM: Artificial
<220> FEATURE:
<223> OTHER INFORMATION: FVE Fragment

<400> SEQUENCE: 295

Tyr Leu Val Lys Lys Ile Asp Phe Asp Tyr Thr Pro Asn Trp Gly Arg
1               5                   10                  15

Gly Thr Pro Ser Ser
            20

<210> SEQ ID NO 296
<211> LENGTH: 21
<212> TYPE: PRT
<213> ORGANISM: Artificial
<220> FEATURE:
<223> OTHER INFORMATION: FVE Fragment

<400> SEQUENCE: 296

Leu Val Lys Lys Ile Asp Phe Asp Tyr Thr Pro Asn Trp Gly Arg Gly
1               5                   10                  15

Thr Pro Ser Ser Tyr
            20

<210> SEQ ID NO 297
<211> LENGTH: 21
<212> TYPE: PRT
<213> ORGANISM: Artificial
<220> FEATURE:
<223> OTHER INFORMATION: FVE Fragment

<400> SEQUENCE: 297

Val Lys Lys Ile Asp Phe Asp Tyr Thr Pro Asn Trp Gly Arg Gly Thr
1               5                   10                  15

Pro Ser Ser Tyr Ile
            20

<210> SEQ ID NO 298
<211> LENGTH: 21
<212> TYPE: PRT
<213> ORGANISM: Artificial
<220> FEATURE:
<223> OTHER INFORMATION: FVE Fragment

<400> SEQUENCE: 298

Lys Lys Ile Asp Phe Asp Tyr Thr Pro Asn Trp Gly Arg Gly Thr Pro
1               5                   10                  15

Ser Ser Tyr Ile Asp
            20

<210> SEQ ID NO 299
<211> LENGTH: 21
<212> TYPE: PRT
<213> ORGANISM: Artificial
<220> FEATURE:
<223> OTHER INFORMATION: FVE Fragment

<400> SEQUENCE: 299

```
Lys Ile Asp Phe Asp Tyr Thr Pro Asn Trp Gly Arg Gly Thr Pro Ser
1               5                   10                  15

Ser Tyr Ile Asp Asn
            20

<210> SEQ ID NO 300
<211> LENGTH: 21
<212> TYPE: PRT
<213> ORGANISM: Artificial
<220> FEATURE:
<223> OTHER INFORMATION: FVE Fragment

<400> SEQUENCE: 300

Ile Asp Phe Asp Tyr Thr Pro Asn Trp Gly Arg Gly Thr Pro Ser Ser
1               5                   10                  15

Tyr Ile Asp Asn Leu
            20

<210> SEQ ID NO 301
<211> LENGTH: 21
<212> TYPE: PRT
<213> ORGANISM: Artificial
<220> FEATURE:
<223> OTHER INFORMATION: FVE Fragment

<400> SEQUENCE: 301

Asp Phe Asp Tyr Thr Pro Asn Trp Gly Arg Gly Thr Pro Ser Ser Tyr
1               5                   10                  15

Ile Asp Asn Leu Thr
            20

<210> SEQ ID NO 302
<211> LENGTH: 21
<212> TYPE: PRT
<213> ORGANISM: Artificial
<220> FEATURE:
<223> OTHER INFORMATION: FVE Fragment

<400> SEQUENCE: 302

Phe Asp Tyr Thr Pro Asn Trp Gly Arg Gly Thr Pro Ser Ser Tyr Ile
1               5                   10                  15

Asp Asn Leu Thr Phe
            20

<210> SEQ ID NO 303
<211> LENGTH: 21
<212> TYPE: PRT
<213> ORGANISM: Artificial
<220> FEATURE:
<223> OTHER INFORMATION: FVE Fragment

<400> SEQUENCE: 303

Asp Tyr Thr Pro Asn Trp Gly Arg Gly Thr Pro Ser Ser Tyr Ile Asp
1               5                   10                  15

Asn Leu Thr Phe Pro
            20

<210> SEQ ID NO 304
<211> LENGTH: 21
<212> TYPE: PRT
<213> ORGANISM: Artificial
<220> FEATURE:
<223> OTHER INFORMATION: FVE Fragment

<400> SEQUENCE: 304
```

-continued

```
Tyr Thr Pro Asn Trp Gly Arg Gly Thr Pro Ser Ser Tyr Ile Asp Asn
1               5                   10                  15

Leu Thr Phe Pro Lys
            20

<210> SEQ ID NO 305
<211> LENGTH: 21
<212> TYPE: PRT
<213> ORGANISM: Artificial
<220> FEATURE:
<223> OTHER INFORMATION: FVE Fragment

<400> SEQUENCE: 305

Thr Pro Asn Trp Gly Arg Gly Thr Pro Ser Ser Tyr Ile Asp Asn Leu
1               5                   10                  15

Thr Phe Pro Lys Val
            20

<210> SEQ ID NO 306
<211> LENGTH: 21
<212> TYPE: PRT
<213> ORGANISM: Artificial
<220> FEATURE:
<223> OTHER INFORMATION: FVE Fragment

<400> SEQUENCE: 306

Pro Asn Trp Gly Arg Gly Thr Pro Ser Ser Tyr Ile Asp Asn Leu Thr
1               5                   10                  15

Phe Pro Lys Val Leu
            20

<210> SEQ ID NO 307
<211> LENGTH: 21
<212> TYPE: PRT
<213> ORGANISM: Artificial
<220> FEATURE:
<223> OTHER INFORMATION: FVE Fragment

<400> SEQUENCE: 307

Asn Trp Gly Arg Gly Thr Pro Ser Ser Tyr Ile Asp Asn Leu Thr Phe
1               5                   10                  15

Pro Lys Val Leu Thr
            20

<210> SEQ ID NO 308
<211> LENGTH: 21
<212> TYPE: PRT
<213> ORGANISM: Artificial
<220> FEATURE:
<223> OTHER INFORMATION: FVE Fragment

<400> SEQUENCE: 308

Trp Gly Arg Gly Thr Pro Ser Ser Tyr Ile Asp Asn Leu Thr Phe Pro
1               5                   10                  15

Lys Val Leu Thr Asp
            20

<210> SEQ ID NO 309
<211> LENGTH: 21
<212> TYPE: PRT
<213> ORGANISM: Artificial
<220> FEATURE:
<223> OTHER INFORMATION: FVE Fragment

<400> SEQUENCE: 309
```

```
Gly Arg Gly Thr Pro Ser Ser Tyr Ile Asp Asn Leu Thr Phe Pro Lys
1               5                   10                  15

Val Leu Thr Asp Lys
            20

<210> SEQ ID NO 310
<211> LENGTH: 21
<212> TYPE: PRT
<213> ORGANISM: Artificial
<220> FEATURE:
<223> OTHER INFORMATION: FVE Fragment

<400> SEQUENCE: 310

Arg Gly Thr Pro Ser Ser Tyr Ile Asp Asn Leu Thr Phe Pro Lys Val
1               5                   10                  15

Leu Thr Asp Lys Lys
            20

<210> SEQ ID NO 311
<211> LENGTH: 21
<212> TYPE: PRT
<213> ORGANISM: Artificial
<220> FEATURE:
<223> OTHER INFORMATION: FVE Fragment

<400> SEQUENCE: 311

Gly Thr Pro Ser Ser Tyr Ile Asp Asn Leu Thr Phe Pro Lys Val Leu
1               5                   10                  15

Thr Asp Lys Lys Tyr
            20

<210> SEQ ID NO 312
<211> LENGTH: 21
<212> TYPE: PRT
<213> ORGANISM: Artificial
<220> FEATURE:
<223> OTHER INFORMATION: FVE Fragment

<400> SEQUENCE: 312

Thr Pro Ser Ser Tyr Ile Asp Asn Leu Thr Phe Pro Lys Val Leu Thr
1               5                   10                  15

Asp Lys Lys Tyr Ser
            20

<210> SEQ ID NO 313
<211> LENGTH: 22
<212> TYPE: PRT
<213> ORGANISM: Artificial
<220> FEATURE:
<223> OTHER INFORMATION: FVE Fragment

<400> SEQUENCE: 313

Phe Gln Leu Ala Tyr Leu Val Lys Lys Ile Asp Phe Asp Tyr Thr Pro
1               5                   10                  15

Asn Trp Gly Arg Gly Thr
            20

<210> SEQ ID NO 314
<211> LENGTH: 22
<212> TYPE: PRT
<213> ORGANISM: Artificial
<220> FEATURE:
<223> OTHER INFORMATION: FVE Fragment

<400> SEQUENCE: 314
```

-continued

```
Gln Leu Ala Tyr Leu Val Lys Lys Ile Asp Phe Asp Tyr Thr Pro Asn
1               5                   10                  15

Trp Gly Arg Gly Thr Pro
            20

<210> SEQ ID NO 315
<211> LENGTH: 22
<212> TYPE: PRT
<213> ORGANISM: Artificial
<220> FEATURE:
<223> OTHER INFORMATION: FVE Fragment

<400> SEQUENCE: 315

Leu Ala Tyr Leu Val Lys Lys Ile Asp Phe Asp Tyr Thr Pro Asn Trp
1               5                   10                  15

Gly Arg Gly Thr Pro Ser
            20

<210> SEQ ID NO 316
<211> LENGTH: 22
<212> TYPE: PRT
<213> ORGANISM: Artificial
<220> FEATURE:
<223> OTHER INFORMATION: FVE Fragment

<400> SEQUENCE: 316

Ala Tyr Leu Val Lys Lys Ile Asp Phe Asp Tyr Thr Pro Asn Trp Gly
1               5                   10                  15

Arg Gly Thr Pro Ser Ser
            20

<210> SEQ ID NO 317
<211> LENGTH: 22
<212> TYPE: PRT
<213> ORGANISM: Artificial
<220> FEATURE:
<223> OTHER INFORMATION: FVE Fragment

<400> SEQUENCE: 317

Tyr Leu Val Lys Lys Ile Asp Phe Asp Tyr Thr Pro Asn Trp Gly Arg
1               5                   10                  15

Gly Thr Pro Ser Ser Tyr
            20

<210> SEQ ID NO 318
<211> LENGTH: 22
<212> TYPE: PRT
<213> ORGANISM: Artificial
<220> FEATURE:
<223> OTHER INFORMATION: FVE Fragment

<400> SEQUENCE: 318

Leu Val Lys Lys Ile Asp Phe Asp Tyr Thr Pro Asn Trp Gly Arg Gly
1               5                   10                  15

Thr Pro Ser Ser Tyr Ile
            20

<210> SEQ ID NO 319
<211> LENGTH: 22
<212> TYPE: PRT
<213> ORGANISM: Artificial
<220> FEATURE:
<223> OTHER INFORMATION: FVE Fragment

<400> SEQUENCE: 319
```

Val Lys Lys Ile Asp Phe Asp Tyr Thr Pro Asn Trp Gly Arg Gly Thr
1               5                   10                  15

Pro Ser Ser Tyr Ile Asp
            20

<210> SEQ ID NO 320
<211> LENGTH: 22
<212> TYPE: PRT
<213> ORGANISM: Artificial
<220> FEATURE:
<223> OTHER INFORMATION: FVE Fragment

<400> SEQUENCE: 320

Lys Lys Ile Asp Phe Asp Tyr Thr Pro Asn Trp Gly Arg Gly Thr Pro
1               5                   10                  15

Ser Ser Tyr Ile Asp Asn
            20

<210> SEQ ID NO 321
<211> LENGTH: 22
<212> TYPE: PRT
<213> ORGANISM: Artificial
<220> FEATURE:
<223> OTHER INFORMATION: FVE Fragment

<400> SEQUENCE: 321

Lys Ile Asp Phe Asp Tyr Thr Pro Asn Trp Gly Arg Gly Thr Pro Ser
1               5                   10                  15

Ser Tyr Ile Asp Asn Leu
            20

<210> SEQ ID NO 322
<211> LENGTH: 22
<212> TYPE: PRT
<213> ORGANISM: Artificial
<220> FEATURE:
<223> OTHER INFORMATION: FVE Fragment

<400> SEQUENCE: 322

Ile Asp Phe Asp Tyr Thr Pro Asn Trp Gly Arg Gly Thr Pro Ser Ser
1               5                   10                  15

Tyr Ile Asp Asn Leu Thr
            20

<210> SEQ ID NO 323
<211> LENGTH: 22
<212> TYPE: PRT
<213> ORGANISM: Artificial
<220> FEATURE:
<223> OTHER INFORMATION: FVE Fragment

<400> SEQUENCE: 323

Asp Phe Asp Tyr Thr Pro Asn Trp Gly Arg Gly Thr Pro Ser Ser Tyr
1               5                   10                  15

Ile Asp Asn Leu Thr Phe
            20

<210> SEQ ID NO 324
<211> LENGTH: 22
<212> TYPE: PRT
<213> ORGANISM: Artificial
<220> FEATURE:
<223> OTHER INFORMATION: FVE Fragment

<400> SEQUENCE: 324

-continued

Phe Asp Tyr Thr Pro Asn Trp Gly Arg Gly Thr Pro Ser Ser Tyr Ile
1               5                   10                  15

Asp Asn Leu Thr Phe Pro
            20

<210> SEQ ID NO 325
<211> LENGTH: 22
<212> TYPE: PRT
<213> ORGANISM: Artificial
<220> FEATURE:
<223> OTHER INFORMATION: FVE Fragment

<400> SEQUENCE: 325

Asp Tyr Thr Pro Asn Trp Gly Arg Gly Thr Pro Ser Ser Tyr Ile Asp
1               5                   10                  15

Asn Leu Thr Phe Pro Lys
            20

<210> SEQ ID NO 326
<211> LENGTH: 22
<212> TYPE: PRT
<213> ORGANISM: Artificial
<220> FEATURE:
<223> OTHER INFORMATION: FVE Fragment

<400> SEQUENCE: 326

Tyr Thr Pro Asn Trp Gly Arg Gly Thr Pro Ser Ser Tyr Ile Asp Asn
1               5                   10                  15

Leu Thr Phe Pro Lys Val
            20

<210> SEQ ID NO 327
<211> LENGTH: 22
<212> TYPE: PRT
<213> ORGANISM: Artificial
<220> FEATURE:
<223> OTHER INFORMATION: FVE Fragment

<400> SEQUENCE: 327

Thr Pro Asn Trp Gly Arg Gly Thr Pro Ser Ser Tyr Ile Asp Asn Leu
1               5                   10                  15

Thr Phe Pro Lys Val Leu
            20

<210> SEQ ID NO 328
<211> LENGTH: 22
<212> TYPE: PRT
<213> ORGANISM: Artificial
<220> FEATURE:
<223> OTHER INFORMATION: FVE Fragment

<400> SEQUENCE: 328

Pro Asn Trp Gly Arg Gly Thr Pro Ser Ser Tyr Ile Asp Asn Leu Thr
1               5                   10                  15

Phe Pro Lys Val Leu Thr
            20

<210> SEQ ID NO 329
<211> LENGTH: 22
<212> TYPE: PRT
<213> ORGANISM: Artificial
<220> FEATURE:
<223> OTHER INFORMATION: FVE Fragment

<400> SEQUENCE: 329

```
Asn Trp Gly Arg Gly Thr Pro Ser Ser Tyr Ile Asp Asn Leu Thr Phe
1               5                   10                  15

Pro Lys Val Leu Thr Asp
            20
```

<210> SEQ ID NO 330
<211> LENGTH: 22
<212> TYPE: PRT
<213> ORGANISM: Artificial
<220> FEATURE:
<223> OTHER INFORMATION: FVE Fragment

<400> SEQUENCE: 330

```
Trp Gly Arg Gly Thr Pro Ser Ser Tyr Ile Asp Asn Leu Thr Phe Pro
1               5                   10                  15

Lys Val Leu Thr Asp Lys
            20
```

<210> SEQ ID NO 331
<211> LENGTH: 22
<212> TYPE: PRT
<213> ORGANISM: Artificial
<220> FEATURE:
<223> OTHER INFORMATION: FVE Fragment

<400> SEQUENCE: 331

```
Gly Arg Gly Thr Pro Ser Ser Tyr Ile Asp Asn Leu Thr Phe Pro Lys
1               5                   10                  15

Val Leu Thr Asp Lys Lys
            20
```

<210> SEQ ID NO 332
<211> LENGTH: 22
<212> TYPE: PRT
<213> ORGANISM: Artificial
<220> FEATURE:
<223> OTHER INFORMATION: FVE Fragment

<400> SEQUENCE: 332

```
Arg Gly Thr Pro Ser Ser Tyr Ile Asp Asn Leu Thr Phe Pro Lys Val
1               5                   10                  15

Leu Thr Asp Lys Lys Tyr
            20
```

<210> SEQ ID NO 333
<211> LENGTH: 22
<212> TYPE: PRT
<213> ORGANISM: Artificial
<220> FEATURE:
<223> OTHER INFORMATION: FVE Fragment

<400> SEQUENCE: 333

```
Gly Thr Pro Ser Ser Tyr Ile Asp Asn Leu Thr Phe Pro Lys Val Leu
1               5                   10                  15

Thr Asp Lys Lys Tyr Ser
            20
```

<210> SEQ ID NO 334
<211> LENGTH: 22
<212> TYPE: PRT
<213> ORGANISM: Artificial
<220> FEATURE:
<223> OTHER INFORMATION: FVE Fragment

<400> SEQUENCE: 334

```
Thr Pro Ser Ser Tyr Ile Asp Asn Leu Thr Phe Pro Lys Val Leu Thr
1               5                   10                  15

Asp Lys Lys Tyr Ser Tyr
            20

<210> SEQ ID NO 335
<211> LENGTH: 23
<212> TYPE: PRT
<213> ORGANISM: Artificial
<220> FEATURE:
<223> OTHER INFORMATION: FVE Fragment

<400> SEQUENCE: 335

Thr Phe Gln Leu Ala Tyr Leu Val Lys Lys Ile Asp Phe Asp Tyr Thr
1               5                   10                  15

Pro Asn Trp Gly Arg Gly Thr
            20

<210> SEQ ID NO 336
<211> LENGTH: 23
<212> TYPE: PRT
<213> ORGANISM: Artificial
<220> FEATURE:
<223> OTHER INFORMATION: FVE Fragment

<400> SEQUENCE: 336

Phe Gln Leu Ala Tyr Leu Val Lys Lys Ile Asp Phe Asp Tyr Thr Pro
1               5                   10                  15

Asn Trp Gly Arg Gly Thr Pro
            20

<210> SEQ ID NO 337
<211> LENGTH: 23
<212> TYPE: PRT
<213> ORGANISM: Artificial
<220> FEATURE:
<223> OTHER INFORMATION: FVE Fragment

<400> SEQUENCE: 337

Gln Leu Ala Tyr Leu Val Lys Lys Ile Asp Phe Asp Tyr Thr Pro Asn
1               5                   10                  15

Trp Gly Arg Gly Thr Pro Ser
            20

<210> SEQ ID NO 338
<211> LENGTH: 23
<212> TYPE: PRT
<213> ORGANISM: Artificial
<220> FEATURE:
<223> OTHER INFORMATION: FVE Fragment

<400> SEQUENCE: 338

Leu Ala Tyr Leu Val Lys Lys Ile Asp Phe Asp Tyr Thr Pro Asn Trp
1               5                   10                  15

Gly Arg Gly Thr Pro Ser Ser
            20

<210> SEQ ID NO 339
<211> LENGTH: 23
<212> TYPE: PRT
<213> ORGANISM: Artificial
<220> FEATURE:
<223> OTHER INFORMATION: FVE Fragment

<400> SEQUENCE: 339
```

```
Ala Tyr Leu Val Lys Lys Ile Asp Phe Asp Tyr Thr Pro Asn Trp Gly
1               5                   10                  15

Arg Gly Thr Pro Ser Ser Tyr
            20

<210> SEQ ID NO 340
<211> LENGTH: 23
<212> TYPE: PRT
<213> ORGANISM: Artificial
<220> FEATURE:
<223> OTHER INFORMATION: FVE Fragment

<400> SEQUENCE: 340

Tyr Leu Val Lys Lys Ile Asp Phe Asp Tyr Thr Pro Asn Trp Gly Arg
1               5                   10                  15

Gly Thr Pro Ser Ser Tyr Ile
            20

<210> SEQ ID NO 341
<211> LENGTH: 23
<212> TYPE: PRT
<213> ORGANISM: Artificial
<220> FEATURE:
<223> OTHER INFORMATION: FVE Fragment

<400> SEQUENCE: 341

Leu Val Lys Lys Ile Asp Phe Asp Tyr Thr Pro Asn Trp Gly Arg Gly
1               5                   10                  15

Thr Pro Ser Ser Tyr Ile Asp
            20

<210> SEQ ID NO 342
<211> LENGTH: 23
<212> TYPE: PRT
<213> ORGANISM: Artificial
<220> FEATURE:
<223> OTHER INFORMATION: FVE Fragment

<400> SEQUENCE: 342

Val Lys Lys Ile Asp Phe Asp Tyr Thr Pro Asn Trp Gly Arg Gly Thr
1               5                   10                  15

Pro Ser Ser Tyr Ile Asp Asn
            20

<210> SEQ ID NO 343
<211> LENGTH: 23
<212> TYPE: PRT
<213> ORGANISM: Artificial
<220> FEATURE:
<223> OTHER INFORMATION: FVE Fragment

<400> SEQUENCE: 343

Lys Lys Ile Asp Phe Asp Tyr Thr Pro Asn Trp Gly Arg Gly Thr Pro
1               5                   10                  15

Ser Ser Tyr Ile Asp Asn Leu
            20

<210> SEQ ID NO 344
<211> LENGTH: 23
<212> TYPE: PRT
<213> ORGANISM: Artificial
<220> FEATURE:
<223> OTHER INFORMATION: FVE Fragment

<400> SEQUENCE: 344
```

Lys Ile Asp Phe Asp Tyr Thr Pro Asn Trp Gly Arg Gly Thr Pro Ser
1               5                   10                  15

Ser Tyr Ile Asp Asn Leu Thr
            20

<210> SEQ ID NO 345
<211> LENGTH: 23
<212> TYPE: PRT
<213> ORGANISM: Artificial
<220> FEATURE:
<223> OTHER INFORMATION: FVE Fragment

<400> SEQUENCE: 345

Ile Asp Phe Asp Tyr Thr Pro Asn Trp Gly Arg Gly Thr Pro Ser Ser
1               5                   10                  15

Tyr Ile Asp Asn Leu Thr Phe
            20

<210> SEQ ID NO 346
<211> LENGTH: 23
<212> TYPE: PRT
<213> ORGANISM: Artificial
<220> FEATURE:
<223> OTHER INFORMATION: FVE Fragment

<400> SEQUENCE: 346

Asp Phe Asp Tyr Thr Pro Asn Trp Gly Arg Gly Thr Pro Ser Ser Tyr
1               5                   10                  15

Ile Asp Asn Leu Thr Phe Pro
            20

<210> SEQ ID NO 347
<211> LENGTH: 23
<212> TYPE: PRT
<213> ORGANISM: Artificial
<220> FEATURE:
<223> OTHER INFORMATION: FVE Fragment

<400> SEQUENCE: 347

Phe Asp Tyr Thr Pro Asn Trp Gly Arg Gly Thr Pro Ser Ser Tyr Ile
1               5                   10                  15

Asp Asn Leu Thr Phe Pro Lys
            20

<210> SEQ ID NO 348
<211> LENGTH: 23
<212> TYPE: PRT
<213> ORGANISM: Artificial
<220> FEATURE:
<223> OTHER INFORMATION: FVE Fragment

<400> SEQUENCE: 348

Asp Tyr Thr Pro Asn Trp Gly Arg Gly Thr Pro Ser Ser Tyr Ile Asp
1               5                   10                  15

Asn Leu Thr Phe Pro Lys Val
            20

<210> SEQ ID NO 349
<211> LENGTH: 23
<212> TYPE: PRT
<213> ORGANISM: Artificial
<220> FEATURE:
<223> OTHER INFORMATION: FVE Fragment

<400> SEQUENCE: 349

Tyr Thr Pro Asn Trp Gly Arg Gly Thr Pro Ser Ser Tyr Ile Asp Asn
1               5                   10                  15

Leu Thr Phe Pro Lys Val Leu
            20

<210> SEQ ID NO 350
<211> LENGTH: 23
<212> TYPE: PRT
<213> ORGANISM: Artificial
<220> FEATURE:
<223> OTHER INFORMATION: FVE Fragment

<400> SEQUENCE: 350

Thr Pro Asn Trp Gly Arg Gly Thr Pro Ser Ser Tyr Ile Asp Asn Leu
1               5                   10                  15

Thr Phe Pro Lys Val Leu Thr
            20

<210> SEQ ID NO 351
<211> LENGTH: 23
<212> TYPE: PRT
<213> ORGANISM: Artificial
<220> FEATURE:
<223> OTHER INFORMATION: FVE Fragment

<400> SEQUENCE: 351

Pro Asn Trp Gly Arg Gly Thr Pro Ser Ser Tyr Ile Asp Asn Leu Thr
1               5                   10                  15

Phe Pro Lys Val Leu Thr Asp
            20

<210> SEQ ID NO 352
<211> LENGTH: 23
<212> TYPE: PRT
<213> ORGANISM: Artificial
<220> FEATURE:
<223> OTHER INFORMATION: FVE Fragment

<400> SEQUENCE: 352

Asn Trp Gly Arg Gly Thr Pro Ser Ser Tyr Ile Asp Asn Leu Thr Phe
1               5                   10                  15

Pro Lys Val Leu Thr Asp Lys
            20

<210> SEQ ID NO 353
<211> LENGTH: 23
<212> TYPE: PRT
<213> ORGANISM: Artificial
<220> FEATURE:
<223> OTHER INFORMATION: FVE Fragment

<400> SEQUENCE: 353

Trp Gly Arg Gly Thr Pro Ser Ser Tyr Ile Asp Asn Leu Thr Phe Pro
1               5                   10                  15

Lys Val Leu Thr Asp Lys Lys
            20

<210> SEQ ID NO 354
<211> LENGTH: 23
<212> TYPE: PRT
<213> ORGANISM: Artificial
<220> FEATURE:
<223> OTHER INFORMATION: FVE Fragment

<400> SEQUENCE: 354

-continued

Gly Arg Gly Thr Pro Ser Ser Tyr Ile Asp Asn Leu Thr Phe Pro Lys
1               5                   10                  15

Val Leu Thr Asp Lys Lys Tyr
            20

<210> SEQ ID NO 355
<211> LENGTH: 23
<212> TYPE: PRT
<213> ORGANISM: Artificial
<220> FEATURE:
<223> OTHER INFORMATION: FVE Fragment

<400> SEQUENCE: 355

Arg Gly Thr Pro Ser Ser Tyr Ile Asp Asn Leu Thr Phe Pro Lys Val
1               5                   10                  15

Leu Thr Asp Lys Lys Tyr Ser
            20

<210> SEQ ID NO 356
<211> LENGTH: 23
<212> TYPE: PRT
<213> ORGANISM: Artificial
<220> FEATURE:
<223> OTHER INFORMATION: FVE Fragment

<400> SEQUENCE: 356

Gly Thr Pro Ser Ser Tyr Ile Asp Asn Leu Thr Phe Pro Lys Val Leu
1               5                   10                  15

Thr Asp Lys Lys Tyr Ser Tyr
            20

<210> SEQ ID NO 357
<211> LENGTH: 23
<212> TYPE: PRT
<213> ORGANISM: Artificial
<220> FEATURE:
<223> OTHER INFORMATION: FVE Fragment

<400> SEQUENCE: 357

Thr Pro Ser Ser Tyr Ile Asp Asn Leu Thr Phe Pro Lys Val Leu Thr
1               5                   10                  15

Asp Lys Lys Tyr Ser Tyr Arg
            20

<210> SEQ ID NO 358
<211> LENGTH: 24
<212> TYPE: PRT
<213> ORGANISM: Artificial
<220> FEATURE:
<223> OTHER INFORMATION: FVE Fragment

<400> SEQUENCE: 358

Leu Thr Phe Gln Leu Ala Tyr Leu Val Lys Lys Ile Asp Phe Asp Tyr
1               5                   10                  15

Thr Pro Asn Trp Gly Arg Gly Thr
            20

<210> SEQ ID NO 359
<211> LENGTH: 24
<212> TYPE: PRT
<213> ORGANISM: Artificial
<220> FEATURE:
<223> OTHER INFORMATION: FVE Fragment

<400> SEQUENCE: 359

Thr Phe Gln Leu Ala Tyr Leu Val Lys Lys Ile Asp Phe Asp Tyr Thr
1               5                   10                  15

Pro Asn Trp Gly Arg Gly Thr Pro
            20

<210> SEQ ID NO 360
<211> LENGTH: 24
<212> TYPE: PRT
<213> ORGANISM: Artificial
<220> FEATURE:
<223> OTHER INFORMATION: FVE Fragment

<400> SEQUENCE: 360

Phe Gln Leu Ala Tyr Leu Val Lys Lys Ile Asp Phe Asp Tyr Thr Pro
1               5                   10                  15

Asn Trp Gly Arg Gly Thr Pro Ser
            20

<210> SEQ ID NO 361
<211> LENGTH: 24
<212> TYPE: PRT
<213> ORGANISM: Artificial
<220> FEATURE:
<223> OTHER INFORMATION: FVE Fragment

<400> SEQUENCE: 361

Gln Leu Ala Tyr Leu Val Lys Lys Ile Asp Phe Asp Tyr Thr Pro Asn
1               5                   10                  15

Trp Gly Arg Gly Thr Pro Ser Ser
            20

<210> SEQ ID NO 362
<211> LENGTH: 24
<212> TYPE: PRT
<213> ORGANISM: Artificial
<220> FEATURE:
<223> OTHER INFORMATION: FVE Fragment

<400> SEQUENCE: 362

Leu Ala Tyr Leu Val Lys Lys Ile Asp Phe Asp Tyr Thr Pro Asn Trp
1               5                   10                  15

Gly Arg Gly Thr Pro Ser Ser Tyr
            20

<210> SEQ ID NO 363
<211> LENGTH: 24
<212> TYPE: PRT
<213> ORGANISM: Artificial
<220> FEATURE:
<223> OTHER INFORMATION: FVE Fragment

<400> SEQUENCE: 363

Ala Tyr Leu Val Lys Lys Ile Asp Phe Asp Tyr Thr Pro Asn Trp Gly
1               5                   10                  15

Arg Gly Thr Pro Ser Ser Tyr Ile
            20

<210> SEQ ID NO 364
<211> LENGTH: 24
<212> TYPE: PRT
<213> ORGANISM: Artificial
<220> FEATURE:
<223> OTHER INFORMATION: FVE Fragment

<400> SEQUENCE: 364

```
Tyr Leu Val Lys Lys Ile Asp Phe Asp Tyr Thr Pro Asn Trp Gly Arg
1               5                   10                  15

Gly Thr Pro Ser Ser Tyr Ile Asp
            20

<210> SEQ ID NO 365
<211> LENGTH: 24
<212> TYPE: PRT
<213> ORGANISM: Artificial
<220> FEATURE:
<223> OTHER INFORMATION: FVE Fragment

<400> SEQUENCE: 365

Leu Val Lys Lys Ile Asp Phe Asp Tyr Thr Pro Asn Trp Gly Arg Gly
1               5                   10                  15

Thr Pro Ser Ser Tyr Ile Asp Asn
            20

<210> SEQ ID NO 366
<211> LENGTH: 24
<212> TYPE: PRT
<213> ORGANISM: Artificial
<220> FEATURE:
<223> OTHER INFORMATION: FVE Fragment

<400> SEQUENCE: 366

Val Lys Lys Ile Asp Phe Asp Tyr Thr Pro Asn Trp Gly Arg Gly Thr
1               5                   10                  15

Pro Ser Ser Tyr Ile Asp Asn Leu
            20

<210> SEQ ID NO 367
<211> LENGTH: 24
<212> TYPE: PRT
<213> ORGANISM: Artificial
<220> FEATURE:
<223> OTHER INFORMATION: FVE Fragment

<400> SEQUENCE: 367

Lys Lys Ile Asp Phe Asp Tyr Thr Pro Asn Trp Gly Arg Gly Thr Pro
1               5                   10                  15

Ser Ser Tyr Ile Asp Asn Leu Thr
            20

<210> SEQ ID NO 368
<211> LENGTH: 24
<212> TYPE: PRT
<213> ORGANISM: Artificial
<220> FEATURE:
<223> OTHER INFORMATION: FVE Fragment

<400> SEQUENCE: 368

Lys Ile Asp Phe Asp Tyr Thr Pro Asn Trp Gly Arg Gly Thr Pro Ser
1               5                   10                  15

Ser Tyr Ile Asp Asn Leu Thr Phe
            20

<210> SEQ ID NO 369
<211> LENGTH: 24
<212> TYPE: PRT
<213> ORGANISM: Artificial
<220> FEATURE:
<223> OTHER INFORMATION: FVE Fragment

<400> SEQUENCE: 369
```

-continued

Ile Asp Phe Asp Tyr Thr Pro Asn Trp Gly Arg Gly Thr Pro Ser Ser
1               5                   10                  15

Tyr Ile Asp Asn Leu Thr Phe Pro
            20

<210> SEQ ID NO 370
<211> LENGTH: 24
<212> TYPE: PRT
<213> ORGANISM: Artificial
<220> FEATURE:
<223> OTHER INFORMATION: FVE Fragment

<400> SEQUENCE: 370

Asp Phe Asp Tyr Thr Pro Asn Trp Gly Arg Gly Thr Pro Ser Ser Tyr
1               5                   10                  15

Ile Asp Asn Leu Thr Phe Pro Lys
            20

<210> SEQ ID NO 371
<211> LENGTH: 24
<212> TYPE: PRT
<213> ORGANISM: Artificial
<220> FEATURE:
<223> OTHER INFORMATION: FVE Fragment

<400> SEQUENCE: 371

Phe Asp Tyr Thr Pro Asn Trp Gly Arg Gly Thr Pro Ser Ser Tyr Ile
1               5                   10                  15

Asp Asn Leu Thr Phe Pro Lys Val
            20

<210> SEQ ID NO 372
<211> LENGTH: 24
<212> TYPE: PRT
<213> ORGANISM: Artificial
<220> FEATURE:
<223> OTHER INFORMATION: FVE Fragment

<400> SEQUENCE: 372

Asp Tyr Thr Pro Asn Trp Gly Arg Gly Thr Pro Ser Ser Tyr Ile Asp
1               5                   10                  15

Asn Leu Thr Phe Pro Lys Val Leu
            20

<210> SEQ ID NO 373
<211> LENGTH: 24
<212> TYPE: PRT
<213> ORGANISM: Artificial
<220> FEATURE:
<223> OTHER INFORMATION: FVE Fragment

<400> SEQUENCE: 373

Tyr Thr Pro Asn Trp Gly Arg Gly Thr Pro Ser Ser Tyr Ile Asp Asn
1               5                   10                  15

Leu Thr Phe Pro Lys Val Leu Thr
            20

<210> SEQ ID NO 374
<211> LENGTH: 24
<212> TYPE: PRT
<213> ORGANISM: Artificial
<220> FEATURE:
<223> OTHER INFORMATION: FVE Fragment

<400> SEQUENCE: 374

```
Thr Pro Asn Trp Gly Arg Gly Thr Pro Ser Ser Tyr Ile Asp Asn Leu
1               5                   10                  15

Thr Phe Pro Lys Val Leu Thr Asp
            20
```

<210> SEQ ID NO 375
<211> LENGTH: 24
<212> TYPE: PRT
<213> ORGANISM: Artificial
<220> FEATURE:
<223> OTHER INFORMATION: FVE Fragment

<400> SEQUENCE: 375

```
Pro Asn Trp Gly Arg Gly Thr Pro Ser Ser Tyr Ile Asp Asn Leu Thr
1               5                   10                  15

Phe Pro Lys Val Leu Thr Asp Lys
            20
```

<210> SEQ ID NO 376
<211> LENGTH: 24
<212> TYPE: PRT
<213> ORGANISM: Artificial
<220> FEATURE:
<223> OTHER INFORMATION: FVE Fragment

<400> SEQUENCE: 376

```
Asn Trp Gly Arg Gly Thr Pro Ser Ser Tyr Ile Asp Asn Leu Thr Phe
1               5                   10                  15

Pro Lys Val Leu Thr Asp Lys Lys
            20
```

<210> SEQ ID NO 377
<211> LENGTH: 24
<212> TYPE: PRT
<213> ORGANISM: Artificial
<220> FEATURE:
<223> OTHER INFORMATION: FVE Fragment

<400> SEQUENCE: 377

```
Trp Gly Arg Gly Thr Pro Ser Ser Tyr Ile Asp Asn Leu Thr Phe Pro
1               5                   10                  15

Lys Val Leu Thr Asp Lys Lys Tyr
            20
```

<210> SEQ ID NO 378
<211> LENGTH: 24
<212> TYPE: PRT
<213> ORGANISM: Artificial
<220> FEATURE:
<223> OTHER INFORMATION: FVE Fragment

<400> SEQUENCE: 378

```
Gly Arg Gly Thr Pro Ser Ser Tyr Ile Asp Asn Leu Thr Phe Pro Lys
1               5                   10                  15

Val Leu Thr Asp Lys Lys Tyr Ser
            20
```

<210> SEQ ID NO 379
<211> LENGTH: 24
<212> TYPE: PRT
<213> ORGANISM: Artificial
<220> FEATURE:
<223> OTHER INFORMATION: FVE Fragment

<400> SEQUENCE: 379

-continued

```
Arg Gly Thr Pro Ser Ser Tyr Ile Asp Asn Leu Thr Phe Pro Lys Val
1               5                   10                  15

Leu Thr Asp Lys Lys Tyr Ser Tyr
            20

<210> SEQ ID NO 380
<211> LENGTH: 24
<212> TYPE: PRT
<213> ORGANISM: Artificial
<220> FEATURE:
<223> OTHER INFORMATION: FVE Fragment

<400> SEQUENCE: 380

Gly Thr Pro Ser Ser Tyr Ile Asp Asn Leu Thr Phe Pro Lys Val Leu
1               5                   10                  15

Thr Asp Lys Lys Tyr Ser Tyr Arg
            20

<210> SEQ ID NO 381
<211> LENGTH: 24
<212> TYPE: PRT
<213> ORGANISM: Artificial
<220> FEATURE:
<223> OTHER INFORMATION: FVE Fragment

<400> SEQUENCE: 381

Thr Pro Ser Ser Tyr Ile Asp Asn Leu Thr Phe Pro Lys Val Leu Thr
1               5                   10                  15

Asp Lys Lys Tyr Ser Tyr Arg Val
            20

<210> SEQ ID NO 382
<211> LENGTH: 25
<212> TYPE: PRT
<213> ORGANISM: Artificial
<220> FEATURE:
<223> OTHER INFORMATION: FVE Fragment

<400> SEQUENCE: 382

Ser Leu Thr Phe Gln Leu Ala Tyr Leu Val Lys Lys Ile Asp Phe Asp
1               5                   10                  15

Tyr Thr Pro Asn Trp Gly Arg Gly Thr
            20                  25

<210> SEQ ID NO 383
<211> LENGTH: 25
<212> TYPE: PRT
<213> ORGANISM: Artificial
<220> FEATURE:
<223> OTHER INFORMATION: FVE Fragment

<400> SEQUENCE: 383

Leu Thr Phe Gln Leu Ala Tyr Leu Val Lys Lys Ile Asp Phe Asp Tyr
1               5                   10                  15

Thr Pro Asn Trp Gly Arg Gly Thr Pro
            20                  25

<210> SEQ ID NO 384
<211> LENGTH: 25
<212> TYPE: PRT
<213> ORGANISM: Artificial
<220> FEATURE:
<223> OTHER INFORMATION: FVE Fragment

<400> SEQUENCE: 384
```

-continued

```
Thr Phe Gln Leu Ala Tyr Leu Val Lys Lys Ile Asp Phe Asp Tyr Thr
1               5                   10                  15

Pro Asn Trp Gly Arg Gly Thr Pro Ser
            20                  25

<210> SEQ ID NO 385
<211> LENGTH: 25
<212> TYPE: PRT
<213> ORGANISM: Artificial
<220> FEATURE:
<223> OTHER INFORMATION: FVE Fragment

<400> SEQUENCE: 385

Phe Gln Leu Ala Tyr Leu Val Lys Lys Ile Asp Phe Asp Tyr Thr Pro
1               5                   10                  15

Asn Trp Gly Arg Gly Thr Pro Ser Ser
            20                  25

<210> SEQ ID NO 386
<211> LENGTH: 25
<212> TYPE: PRT
<213> ORGANISM: Artificial
<220> FEATURE:
<223> OTHER INFORMATION: FVE Fragment

<400> SEQUENCE: 386

Gln Leu Ala Tyr Leu Val Lys Lys Ile Asp Phe Asp Tyr Thr Pro Asn
1               5                   10                  15

Trp Gly Arg Gly Thr Pro Ser Ser Tyr
            20                  25

<210> SEQ ID NO 387
<211> LENGTH: 25
<212> TYPE: PRT
<213> ORGANISM: Artificial
<220> FEATURE:
<223> OTHER INFORMATION: FVE Fragment

<400> SEQUENCE: 387

Leu Ala Tyr Leu Val Lys Lys Ile Asp Phe Asp Tyr Thr Pro Asn Trp
1               5                   10                  15

Gly Arg Gly Thr Pro Ser Ser Tyr Ile
            20                  25

<210> SEQ ID NO 388
<211> LENGTH: 25
<212> TYPE: PRT
<213> ORGANISM: Artificial
<220> FEATURE:
<223> OTHER INFORMATION: FVE Fragment

<400> SEQUENCE: 388

Ala Tyr Leu Val Lys Lys Ile Asp Phe Asp Tyr Thr Pro Asn Trp Gly
1               5                   10                  15

Arg Gly Thr Pro Ser Ser Tyr Ile Asp
            20                  25

<210> SEQ ID NO 389
<211> LENGTH: 25
<212> TYPE: PRT
<213> ORGANISM: Artificial
<220> FEATURE:
<223> OTHER INFORMATION: FVE Fragment

<400> SEQUENCE: 389
```

Tyr Leu Val Lys Lys Ile Asp Phe Asp Tyr Thr Pro Asn Trp Gly Arg
1               5                   10                  15

Gly Thr Pro Ser Ser Tyr Ile Asp Asn
            20                  25

<210> SEQ ID NO 390
<211> LENGTH: 25
<212> TYPE: PRT
<213> ORGANISM: Artificial
<220> FEATURE:
<223> OTHER INFORMATION: FVE Fragment

<400> SEQUENCE: 390

Leu Val Lys Lys Ile Asp Phe Asp Tyr Thr Pro Asn Trp Gly Arg Gly
1               5                   10                  15

Thr Pro Ser Ser Tyr Ile Asp Asn Leu
            20                  25

<210> SEQ ID NO 391
<211> LENGTH: 25
<212> TYPE: PRT
<213> ORGANISM: Artificial
<220> FEATURE:
<223> OTHER INFORMATION: FVE Fragment

<400> SEQUENCE: 391

Val Lys Lys Ile Asp Phe Asp Tyr Thr Pro Asn Trp Gly Arg Gly Thr
1               5                   10                  15

Pro Ser Ser Tyr Ile Asp Asn Leu Thr
            20                  25

<210> SEQ ID NO 392
<211> LENGTH: 25
<212> TYPE: PRT
<213> ORGANISM: Artificial
<220> FEATURE:
<223> OTHER INFORMATION: FVE Fragment

<400> SEQUENCE: 392

Lys Lys Ile Asp Phe Asp Tyr Thr Pro Asn Trp Gly Arg Gly Thr Pro
1               5                   10                  15

Ser Ser Tyr Ile Asp Asn Leu Thr Phe
            20                  25

<210> SEQ ID NO 393
<211> LENGTH: 25
<212> TYPE: PRT
<213> ORGANISM: Artificial
<220> FEATURE:
<223> OTHER INFORMATION: FVE Fragment

<400> SEQUENCE: 393

Lys Ile Asp Phe Asp Tyr Thr Pro Asn Trp Gly Arg Gly Thr Pro Ser
1               5                   10                  15

Ser Tyr Ile Asp Asn Leu Thr Phe Pro
            20                  25

<210> SEQ ID NO 394
<211> LENGTH: 25
<212> TYPE: PRT
<213> ORGANISM: Artificial
<220> FEATURE:
<223> OTHER INFORMATION: FVE Fragment

<400> SEQUENCE: 394

Ile Asp Phe Asp Tyr Thr Pro Asn Trp Gly Arg Gly Thr Pro Ser Ser
1               5                   10                  15

Tyr Ile Asp Asn Leu Thr Phe Pro Lys
                20                  25

<210> SEQ ID NO 395
<211> LENGTH: 25
<212> TYPE: PRT
<213> ORGANISM: Artificial
<220> FEATURE:
<223> OTHER INFORMATION: FVE Fragment

<400> SEQUENCE: 395

Asp Phe Asp Tyr Thr Pro Asn Trp Gly Arg Gly Thr Pro Ser Ser Tyr
1               5                   10                  15

Ile Asp Asn Leu Thr Phe Pro Lys Val
                20                  25

<210> SEQ ID NO 396
<211> LENGTH: 25
<212> TYPE: PRT
<213> ORGANISM: Artificial
<220> FEATURE:
<223> OTHER INFORMATION: FVE Fragment

<400> SEQUENCE: 396

Phe Asp Tyr Thr Pro Asn Trp Gly Arg Gly Thr Pro Ser Ser Tyr Ile
1               5                   10                  15

Asp Asn Leu Thr Phe Pro Lys Val Leu
                20                  25

<210> SEQ ID NO 397
<211> LENGTH: 25
<212> TYPE: PRT
<213> ORGANISM: Artificial
<220> FEATURE:
<223> OTHER INFORMATION: FVE Fragment

<400> SEQUENCE: 397

Asp Tyr Thr Pro Asn Trp Gly Arg Gly Thr Pro Ser Ser Tyr Ile Asp
1               5                   10                  15

Asn Leu Thr Phe Pro Lys Val Leu Thr
                20                  25

<210> SEQ ID NO 398
<211> LENGTH: 25
<212> TYPE: PRT
<213> ORGANISM: Artificial
<220> FEATURE:
<223> OTHER INFORMATION: FVE Fragment

<400> SEQUENCE: 398

Tyr Thr Pro Asn Trp Gly Arg Gly Thr Pro Ser Ser Tyr Ile Asp Asn
1               5                   10                  15

Leu Thr Phe Pro Lys Val Leu Thr Asp
                20                  25

<210> SEQ ID NO 399
<211> LENGTH: 25
<212> TYPE: PRT
<213> ORGANISM: Artificial
<220> FEATURE:
<223> OTHER INFORMATION: FVE Fragment

<400> SEQUENCE: 399

Thr Pro Asn Trp Gly Arg Gly Thr Pro Ser Ser Tyr Ile Asp Asn Leu
1               5                   10                  15

Thr Phe Pro Lys Val Leu Thr Asp Lys
            20                  25

<210> SEQ ID NO 400
<211> LENGTH: 25
<212> TYPE: PRT
<213> ORGANISM: Artificial
<220> FEATURE:
<223> OTHER INFORMATION: FVE Fragment

<400> SEQUENCE: 400

Pro Asn Trp Gly Arg Gly Thr Pro Ser Ser Tyr Ile Asp Asn Leu Thr
1               5                   10                  15

Phe Pro Lys Val Leu Thr Asp Lys Lys
            20                  25

<210> SEQ ID NO 401
<211> LENGTH: 25
<212> TYPE: PRT
<213> ORGANISM: Artificial
<220> FEATURE:
<223> OTHER INFORMATION: FVE Fragment

<400> SEQUENCE: 401

Asn Trp Gly Arg Gly Thr Pro Ser Ser Tyr Ile Asp Asn Leu Thr Phe
1               5                   10                  15

Pro Lys Val Leu Thr Asp Lys Lys Tyr
            20                  25

<210> SEQ ID NO 402
<211> LENGTH: 25
<212> TYPE: PRT
<213> ORGANISM: Artificial
<220> FEATURE:
<223> OTHER INFORMATION: FVE Fragment

<400> SEQUENCE: 402

Trp Gly Arg Gly Thr Pro Ser Ser Tyr Ile Asp Asn Leu Thr Phe Pro
1               5                   10                  15

Lys Val Leu Thr Asp Lys Lys Tyr Ser
            20                  25

<210> SEQ ID NO 403
<211> LENGTH: 25
<212> TYPE: PRT
<213> ORGANISM: Artificial
<220> FEATURE:
<223> OTHER INFORMATION: FVE Fragment

<400> SEQUENCE: 403

Gly Arg Gly Thr Pro Ser Ser Tyr Ile Asp Asn Leu Thr Phe Pro Lys
1               5                   10                  15

Val Leu Thr Asp Lys Lys Tyr Ser Tyr
            20                  25

<210> SEQ ID NO 404
<211> LENGTH: 25
<212> TYPE: PRT
<213> ORGANISM: Artificial
<220> FEATURE:
<223> OTHER INFORMATION: FVE Fragment

<400> SEQUENCE: 404

```
Arg Gly Thr Pro Ser Ser Tyr Ile Asp Asn Leu Thr Phe Pro Lys Val
1               5                   10                  15

Leu Thr Asp Lys Lys Tyr Ser Tyr Arg
            20                  25
```

<210> SEQ ID NO 405
<211> LENGTH: 25
<212> TYPE: PRT
<213> ORGANISM: Artificial
<220> FEATURE:
<223> OTHER INFORMATION: FVE Fragment

<400> SEQUENCE: 405

```
Gly Thr Pro Ser Ser Tyr Ile Asp Asn Leu Thr Phe Pro Lys Val Leu
1               5                   10                  15

Thr Asp Lys Lys Tyr Ser Tyr Arg Val
            20                  25
```

<210> SEQ ID NO 406
<211> LENGTH: 25
<212> TYPE: PRT
<213> ORGANISM: Artificial
<220> FEATURE:
<223> OTHER INFORMATION: FVE Fragment

<400> SEQUENCE: 406

```
Thr Pro Ser Ser Tyr Ile Asp Asn Leu Thr Phe Pro Lys Val Leu Thr
1               5                   10                  15

Asp Lys Lys Tyr Ser Tyr Arg Val Val
            20                  25
```

<210> SEQ ID NO 407
<211> LENGTH: 26
<212> TYPE: PRT
<213> ORGANISM: Artificial
<220> FEATURE:
<223> OTHER INFORMATION: FVE Fragment

<400> SEQUENCE: 407

```
Thr Ser Leu Thr Phe Gln Leu Ala Tyr Leu Val Lys Lys Ile Asp Phe
1               5                   10                  15

Asp Tyr Thr Pro Asn Trp Gly Arg Gly Thr
            20                  25
```

<210> SEQ ID NO 408
<211> LENGTH: 26
<212> TYPE: PRT
<213> ORGANISM: Artificial
<220> FEATURE:
<223> OTHER INFORMATION: FVE Fragment

<400> SEQUENCE: 408

```
Ser Leu Thr Phe Gln Leu Ala Tyr Leu Val Lys Lys Ile Asp Phe Asp
1               5                   10                  15

Tyr Thr Pro Asn Trp Gly Arg Gly Thr Pro
            20                  25
```

<210> SEQ ID NO 409
<211> LENGTH: 26
<212> TYPE: PRT
<213> ORGANISM: Artificial
<220> FEATURE:
<223> OTHER INFORMATION: FVE Fragment

<400> SEQUENCE: 409

Leu Thr Phe Gln Leu Ala Tyr Leu Val Lys Lys Ile Asp Phe Asp Tyr
1               5                   10                  15

Thr Pro Asn Trp Gly Arg Gly Thr Pro Ser
            20                  25

<210> SEQ ID NO 410
<211> LENGTH: 26
<212> TYPE: PRT
<213> ORGANISM: Artificial
<220> FEATURE:
<223> OTHER INFORMATION: FVE Fragment

<400> SEQUENCE: 410

Thr Phe Gln Leu Ala Tyr Leu Val Lys Lys Ile Asp Phe Asp Tyr Thr
1               5                   10                  15

Pro Asn Trp Gly Arg Gly Thr Pro Ser Ser
            20                  25

<210> SEQ ID NO 411
<211> LENGTH: 26
<212> TYPE: PRT
<213> ORGANISM: Artificial
<220> FEATURE:
<223> OTHER INFORMATION: FVE Fragment

<400> SEQUENCE: 411

Phe Gln Leu Ala Tyr Leu Val Lys Lys Ile Asp Phe Asp Tyr Thr Pro
1               5                   10                  15

Asn Trp Gly Arg Gly Thr Pro Ser Ser Tyr
            20                  25

<210> SEQ ID NO 412
<211> LENGTH: 26
<212> TYPE: PRT
<213> ORGANISM: Artificial
<220> FEATURE:
<223> OTHER INFORMATION: FVE Fragment

<400> SEQUENCE: 412

Gln Leu Ala Tyr Leu Val Lys Lys Ile Asp Phe Asp Tyr Thr Pro Asn
1               5                   10                  15

Trp Gly Arg Gly Thr Pro Ser Ser Tyr Ile
            20                  25

<210> SEQ ID NO 413
<211> LENGTH: 26
<212> TYPE: PRT
<213> ORGANISM: Artificial
<220> FEATURE:
<223> OTHER INFORMATION: FVE Fragment

<400> SEQUENCE: 413

Leu Ala Tyr Leu Val Lys Lys Ile Asp Phe Asp Tyr Thr Pro Asn Trp
1               5                   10                  15

Gly Arg Gly Thr Pro Ser Ser Tyr Ile Asp
            20                  25

<210> SEQ ID NO 414
<211> LENGTH: 26
<212> TYPE: PRT
<213> ORGANISM: Artificial
<220> FEATURE:
<223> OTHER INFORMATION: FVE Fragment

<400> SEQUENCE: 414

```
Ala Tyr Leu Val Lys Lys Ile Asp Phe Asp Tyr Thr Pro Asn Trp Gly
1               5                   10                  15

Arg Gly Thr Pro Ser Ser Tyr Ile Asp Asn
                20                  25

<210> SEQ ID NO 415
<211> LENGTH: 26
<212> TYPE: PRT
<213> ORGANISM: Artificial
<220> FEATURE:
<223> OTHER INFORMATION: FVE Fragment

<400> SEQUENCE: 415

Tyr Leu Val Lys Lys Ile Asp Phe Asp Tyr Thr Pro Asn Trp Gly Arg
1               5                   10                  15

Gly Thr Pro Ser Ser Tyr Ile Asp Asn Leu
                20                  25

<210> SEQ ID NO 416
<211> LENGTH: 26
<212> TYPE: PRT
<213> ORGANISM: Artificial
<220> FEATURE:
<223> OTHER INFORMATION: FVE Fragment

<400> SEQUENCE: 416

Leu Val Lys Lys Ile Asp Phe Asp Tyr Thr Pro Asn Trp Gly Arg Gly
1               5                   10                  15

Thr Pro Ser Ser Tyr Ile Asp Asn Leu Thr
                20                  25

<210> SEQ ID NO 417
<211> LENGTH: 26
<212> TYPE: PRT
<213> ORGANISM: Artificial
<220> FEATURE:
<223> OTHER INFORMATION: FVE Fragment

<400> SEQUENCE: 417

Val Lys Lys Ile Asp Phe Asp Tyr Thr Pro Asn Trp Gly Arg Gly Thr
1               5                   10                  15

Pro Ser Ser Tyr Ile Asp Asn Leu Thr Phe
                20                  25

<210> SEQ ID NO 418
<211> LENGTH: 26
<212> TYPE: PRT
<213> ORGANISM: Artificial
<220> FEATURE:
<223> OTHER INFORMATION: FVE Fragment

<400> SEQUENCE: 418

Lys Lys Ile Asp Phe Asp Tyr Thr Pro Asn Trp Gly Arg Gly Thr Pro
1               5                   10                  15

Ser Ser Tyr Ile Asp Asn Leu Thr Phe Pro
                20                  25

<210> SEQ ID NO 419
<211> LENGTH: 26
<212> TYPE: PRT
<213> ORGANISM: Artificial
<220> FEATURE:
<223> OTHER INFORMATION: FVE Fragment

<400> SEQUENCE: 419
```

```
Lys Ile Asp Phe Asp Tyr Thr Pro Asn Trp Gly Arg Gly Thr Pro Ser
1               5                   10                  15

Ser Tyr Ile Asp Asn Leu Thr Phe Pro Lys
            20                  25
```

<210> SEQ ID NO 420
<211> LENGTH: 26
<212> TYPE: PRT
<213> ORGANISM: Artificial
<220> FEATURE:
<223> OTHER INFORMATION: FVE Fragment

<400> SEQUENCE: 420

```
Ile Asp Phe Asp Tyr Thr Pro Asn Trp Gly Arg Gly Thr Pro Ser Ser
1               5                   10                  15

Tyr Ile Asp Asn Leu Thr Phe Pro Lys Val
            20                  25
```

<210> SEQ ID NO 421
<211> LENGTH: 26
<212> TYPE: PRT
<213> ORGANISM: Artificial
<220> FEATURE:
<223> OTHER INFORMATION: FVE Fragment

<400> SEQUENCE: 421

```
Asp Phe Asp Tyr Thr Pro Asn Trp Gly Arg Gly Thr Pro Ser Ser Tyr
1               5                   10                  15

Ile Asp Asn Leu Thr Phe Pro Lys Val Leu
            20                  25
```

<210> SEQ ID NO 422
<211> LENGTH: 26
<212> TYPE: PRT
<213> ORGANISM: Artificial
<220> FEATURE:
<223> OTHER INFORMATION: FVE Fragment

<400> SEQUENCE: 422

```
Phe Asp Tyr Thr Pro Asn Trp Gly Arg Gly Thr Pro Ser Ser Tyr Ile
1               5                   10                  15

Asp Asn Leu Thr Phe Pro Lys Val Leu Thr
            20                  25
```

<210> SEQ ID NO 423
<211> LENGTH: 26
<212> TYPE: PRT
<213> ORGANISM: Artificial
<220> FEATURE:
<223> OTHER INFORMATION: FVE Fragment

<400> SEQUENCE: 423

```
Asp Tyr Thr Pro Asn Trp Gly Arg Gly Thr Pro Ser Ser Tyr Ile Asp
1               5                   10                  15

Asn Leu Thr Phe Pro Lys Val Leu Thr Asp
            20                  25
```

<210> SEQ ID NO 424
<211> LENGTH: 26
<212> TYPE: PRT
<213> ORGANISM: Artificial
<220> FEATURE:
<223> OTHER INFORMATION: FVE Fragment

<400> SEQUENCE: 424

Tyr Thr Pro Asn Trp Gly Arg Gly Thr Pro Ser Ser Tyr Ile Asp Asn
1               5                   10                  15

Leu Thr Phe Pro Lys Val Leu Thr Asp Lys
            20                  25

<210> SEQ ID NO 425
<211> LENGTH: 26
<212> TYPE: PRT
<213> ORGANISM: Artificial
<220> FEATURE:
<223> OTHER INFORMATION: FVE Fragment

<400> SEQUENCE: 425

Thr Pro Asn Trp Gly Arg Gly Thr Pro Ser Ser Tyr Ile Asp Asn Leu
1               5                   10                  15

Thr Phe Pro Lys Val Leu Thr Asp Lys Lys
            20                  25

<210> SEQ ID NO 426
<211> LENGTH: 26
<212> TYPE: PRT
<213> ORGANISM: Artificial
<220> FEATURE:
<223> OTHER INFORMATION: FVE Fragment

<400> SEQUENCE: 426

Pro Asn Trp Gly Arg Gly Thr Pro Ser Ser Tyr Ile Asp Asn Leu Thr
1               5                   10                  15

Phe Pro Lys Val Leu Thr Asp Lys Lys Tyr
            20                  25

<210> SEQ ID NO 427
<211> LENGTH: 26
<212> TYPE: PRT
<213> ORGANISM: Artificial
<220> FEATURE:
<223> OTHER INFORMATION: FVE Fragment

<400> SEQUENCE: 427

Asn Trp Gly Arg Gly Thr Pro Ser Ser Tyr Ile Asp Asn Leu Thr Phe
1               5                   10                  15

Pro Lys Val Leu Thr Asp Lys Lys Tyr Ser
            20                  25

<210> SEQ ID NO 428
<211> LENGTH: 26
<212> TYPE: PRT
<213> ORGANISM: Artificial
<220> FEATURE:
<223> OTHER INFORMATION: FVE Fragment

<400> SEQUENCE: 428

Trp Gly Arg Gly Thr Pro Ser Ser Tyr Ile Asp Asn Leu Thr Phe Pro
1               5                   10                  15

Lys Val Leu Thr Asp Lys Lys Tyr Ser Tyr
            20                  25

<210> SEQ ID NO 429
<211> LENGTH: 26
<212> TYPE: PRT
<213> ORGANISM: Artificial
<220> FEATURE:
<223> OTHER INFORMATION: FVE Fragment

<400> SEQUENCE: 429

```
Gly Arg Gly Thr Pro Ser Ser Tyr Ile Asp Asn Leu Thr Phe Pro Lys
1               5                   10                  15

Val Leu Thr Asp Lys Lys Tyr Ser Tyr Arg
            20                  25

<210> SEQ ID NO 430
<211> LENGTH: 26
<212> TYPE: PRT
<213> ORGANISM: Artificial
<220> FEATURE:
<223> OTHER INFORMATION: FVE Fragment

<400> SEQUENCE: 430

Arg Gly Thr Pro Ser Ser Tyr Ile Asp Asn Leu Thr Phe Pro Lys Val
1               5                   10                  15

Leu Thr Asp Lys Lys Tyr Ser Tyr Arg Val
            20                  25

<210> SEQ ID NO 431
<211> LENGTH: 26
<212> TYPE: PRT
<213> ORGANISM: Artificial
<220> FEATURE:
<223> OTHER INFORMATION: FVE Fragment

<400> SEQUENCE: 431

Gly Thr Pro Ser Ser Tyr Ile Asp Asn Leu Thr Phe Pro Lys Val Leu
1               5                   10                  15

Thr Asp Lys Lys Tyr Ser Tyr Arg Val Val
            20                  25

<210> SEQ ID NO 432
<211> LENGTH: 26
<212> TYPE: PRT
<213> ORGANISM: Artificial
<220> FEATURE:
<223> OTHER INFORMATION: FVE Fragment

<400> SEQUENCE: 432

Thr Pro Ser Ser Tyr Ile Asp Asn Leu Thr Phe Pro Lys Val Leu Thr
1               5                   10                  15

Asp Lys Lys Tyr Ser Tyr Arg Val Val Val
            20                  25

<210> SEQ ID NO 433
<211> LENGTH: 27
<212> TYPE: PRT
<213> ORGANISM: Artificial
<220> FEATURE:
<223> OTHER INFORMATION: FVE Fragment

<400> SEQUENCE: 433

Ala Thr Ser Leu Thr Phe Gln Leu Ala Tyr Leu Val Lys Lys Ile Asp
1               5                   10                  15

Phe Asp Tyr Thr Pro Asn Trp Gly Arg Gly Thr
            20                  25

<210> SEQ ID NO 434
<211> LENGTH: 27
<212> TYPE: PRT
<213> ORGANISM: Artificial
<220> FEATURE:
<223> OTHER INFORMATION: FVE Fragment

<400> SEQUENCE: 434
```

-continued

```
Thr Ser Leu Thr Phe Gln Leu Ala Tyr Leu Val Lys Lys Ile Asp Phe
1               5                   10                  15

Asp Tyr Thr Pro Asn Trp Gly Arg Gly Thr Pro
            20                  25
```

<210> SEQ ID NO 435
<211> LENGTH: 27
<212> TYPE: PRT
<213> ORGANISM: Artificial
<220> FEATURE:
<223> OTHER INFORMATION: FVE Fragment

<400> SEQUENCE: 435

```
Ser Leu Thr Phe Gln Leu Ala Tyr Leu Val Lys Lys Ile Asp Phe Asp
1               5                   10                  15

Tyr Thr Pro Asn Trp Gly Arg Gly Thr Pro Ser
            20                  25
```

<210> SEQ ID NO 436
<211> LENGTH: 27
<212> TYPE: PRT
<213> ORGANISM: Artificial
<220> FEATURE:
<223> OTHER INFORMATION: FVE Fragment

<400> SEQUENCE: 436

```
Leu Thr Phe Gln Leu Ala Tyr Leu Val Lys Lys Ile Asp Phe Asp Tyr
1               5                   10                  15

Thr Pro Asn Trp Gly Arg Gly Thr Pro Ser Ser
            20                  25
```

<210> SEQ ID NO 437
<211> LENGTH: 27
<212> TYPE: PRT
<213> ORGANISM: Artificial
<220> FEATURE:
<223> OTHER INFORMATION: FVE Fragment

<400> SEQUENCE: 437

```
Thr Phe Gln Leu Ala Tyr Leu Val Lys Lys Ile Asp Phe Asp Tyr Thr
1               5                   10                  15

Pro Asn Trp Gly Arg Gly Thr Pro Ser Ser Tyr
            20                  25
```

<210> SEQ ID NO 438
<211> LENGTH: 27
<212> TYPE: PRT
<213> ORGANISM: Artificial
<220> FEATURE:
<223> OTHER INFORMATION: FVE Fragment

<400> SEQUENCE: 438

```
Phe Gln Leu Ala Tyr Leu Val Lys Lys Ile Asp Phe Asp Tyr Thr Pro
1               5                   10                  15

Asn Trp Gly Arg Gly Thr Pro Ser Ser Tyr Ile
            20                  25
```

<210> SEQ ID NO 439
<211> LENGTH: 27
<212> TYPE: PRT
<213> ORGANISM: Artificial
<220> FEATURE:
<223> OTHER INFORMATION: FVE Fragment

<400> SEQUENCE: 439

Gln Leu Ala Tyr Leu Val Lys Lys Ile Asp Phe Asp Tyr Thr Pro Asn
1               5                   10                  15

Trp Gly Arg Gly Thr Pro Ser Ser Tyr Ile Asp
            20                  25

<210> SEQ ID NO 440
<211> LENGTH: 27
<212> TYPE: PRT
<213> ORGANISM: Artificial
<220> FEATURE:
<223> OTHER INFORMATION: FVE Fragment

<400> SEQUENCE: 440

Leu Ala Tyr Leu Val Lys Lys Ile Asp Phe Asp Tyr Thr Pro Asn Trp
1               5                   10                  15

Gly Arg Gly Thr Pro Ser Ser Tyr Ile Asp Asn
            20                  25

<210> SEQ ID NO 441
<211> LENGTH: 27
<212> TYPE: PRT
<213> ORGANISM: Artificial
<220> FEATURE:
<223> OTHER INFORMATION: FVE Fragment

<400> SEQUENCE: 441

Ala Tyr Leu Val Lys Lys Ile Asp Phe Asp Tyr Thr Pro Asn Trp Gly
1               5                   10                  15

Arg Gly Thr Pro Ser Ser Tyr Ile Asp Asn Leu
            20                  25

<210> SEQ ID NO 442
<211> LENGTH: 27
<212> TYPE: PRT
<213> ORGANISM: Artificial
<220> FEATURE:
<223> OTHER INFORMATION: FVE Fragment

<400> SEQUENCE: 442

Tyr Leu Val Lys Lys Ile Asp Phe Asp Tyr Thr Pro Asn Trp Gly Arg
1               5                   10                  15

Gly Thr Pro Ser Ser Tyr Ile Asp Asn Leu Thr
            20                  25

<210> SEQ ID NO 443
<211> LENGTH: 27
<212> TYPE: PRT
<213> ORGANISM: Artificial
<220> FEATURE:
<223> OTHER INFORMATION: FVE Fragment

<400> SEQUENCE: 443

Leu Val Lys Lys Ile Asp Phe Asp Tyr Thr Pro Asn Trp Gly Arg Gly
1               5                   10                  15

Thr Pro Ser Ser Tyr Ile Asp Asn Leu Thr Phe
            20                  25

<210> SEQ ID NO 444
<211> LENGTH: 27
<212> TYPE: PRT
<213> ORGANISM: Artificial
<220> FEATURE:
<223> OTHER INFORMATION: FVE Fragment

<400> SEQUENCE: 444

Val Lys Lys Ile Asp Phe Asp Tyr Thr Pro Asn Trp Gly Arg Gly Thr
1               5                   10                  15

Pro Ser Ser Tyr Ile Asp Asn Leu Thr Phe Pro
                20                  25

<210> SEQ ID NO 445
<211> LENGTH: 27
<212> TYPE: PRT
<213> ORGANISM: Artificial
<220> FEATURE:
<223> OTHER INFORMATION: FVE Fragment

<400> SEQUENCE: 445

Lys Lys Ile Asp Phe Asp Tyr Thr Pro Asn Trp Gly Arg Gly Thr Pro
1               5                   10                  15

Ser Ser Tyr Ile Asp Asn Leu Thr Phe Pro Lys
                20                  25

<210> SEQ ID NO 446
<211> LENGTH: 27
<212> TYPE: PRT
<213> ORGANISM: Artificial
<220> FEATURE:
<223> OTHER INFORMATION: FVE Fragment

<400> SEQUENCE: 446

Lys Ile Asp Phe Asp Tyr Thr Pro Asn Trp Gly Arg Gly Thr Pro Ser
1               5                   10                  15

Ser Tyr Ile Asp Asn Leu Thr Phe Pro Lys Val
                20                  25

<210> SEQ ID NO 447
<211> LENGTH: 27
<212> TYPE: PRT
<213> ORGANISM: Artificial
<220> FEATURE:
<223> OTHER INFORMATION: FVE Fragment

<400> SEQUENCE: 447

Ile Asp Phe Asp Tyr Thr Pro Asn Trp Gly Arg Gly Thr Pro Ser Ser
1               5                   10                  15

Tyr Ile Asp Asn Leu Thr Phe Pro Lys Val Leu
                20                  25

<210> SEQ ID NO 448
<211> LENGTH: 27
<212> TYPE: PRT
<213> ORGANISM: Artificial
<220> FEATURE:
<223> OTHER INFORMATION: FVE Fragment

<400> SEQUENCE: 448

Asp Phe Asp Tyr Thr Pro Asn Trp Gly Arg Gly Thr Pro Ser Ser Tyr
1               5                   10                  15

Ile Asp Asn Leu Thr Phe Pro Lys Val Leu Thr
                20                  25

<210> SEQ ID NO 449
<211> LENGTH: 27
<212> TYPE: PRT
<213> ORGANISM: Artificial
<220> FEATURE:
<223> OTHER INFORMATION: FVE Fragment

<400> SEQUENCE: 449

```
Phe Asp Tyr Thr Pro Asn Trp Gly Arg Gly Thr Pro Ser Ser Tyr Ile
1               5                   10                  15

Asp Asn Leu Thr Phe Pro Lys Val Leu Thr Asp
            20                  25
```

<210> SEQ ID NO 450
<211> LENGTH: 27
<212> TYPE: PRT
<213> ORGANISM: Artificial
<220> FEATURE:
<223> OTHER INFORMATION: FVE Fragment

<400> SEQUENCE: 450

```
Asp Tyr Thr Pro Asn Trp Gly Arg Gly Thr Pro Ser Ser Tyr Ile Asp
1               5                   10                  15

Asn Leu Thr Phe Pro Lys Val Leu Thr Asp Lys
            20                  25
```

<210> SEQ ID NO 451
<211> LENGTH: 27
<212> TYPE: PRT
<213> ORGANISM: Artificial
<220> FEATURE:
<223> OTHER INFORMATION: FVE Fragment

<400> SEQUENCE: 451

```
Tyr Thr Pro Asn Trp Gly Arg Gly Thr Pro Ser Ser Tyr Ile Asp Asn
1               5                   10                  15

Leu Thr Phe Pro Lys Val Leu Thr Asp Lys Lys
            20                  25
```

<210> SEQ ID NO 452
<211> LENGTH: 27
<212> TYPE: PRT
<213> ORGANISM: Artificial
<220> FEATURE:
<223> OTHER INFORMATION: FVE Fragment

<400> SEQUENCE: 452

```
Thr Pro Asn Trp Gly Arg Gly Thr Pro Ser Ser Tyr Ile Asp Asn Leu
1               5                   10                  15

Thr Phe Pro Lys Val Leu Thr Asp Lys Lys Tyr
            20                  25
```

<210> SEQ ID NO 453
<211> LENGTH: 27
<212> TYPE: PRT
<213> ORGANISM: Artificial
<220> FEATURE:
<223> OTHER INFORMATION: FVE Fragment

<400> SEQUENCE: 453

```
Pro Asn Trp Gly Arg Gly Thr Pro Ser Ser Tyr Ile Asp Asn Leu Thr
1               5                   10                  15

Phe Pro Lys Val Leu Thr Asp Lys Lys Tyr Ser
            20                  25
```

<210> SEQ ID NO 454
<211> LENGTH: 27
<212> TYPE: PRT
<213> ORGANISM: Artificial
<220> FEATURE:
<223> OTHER INFORMATION: FVE Fragment

<400> SEQUENCE: 454

-continued

Asn Trp Gly Arg Gly Thr Pro Ser Ser Tyr Ile Asp Asn Leu Thr Phe
1               5                   10                  15

Pro Lys Val Leu Thr Asp Lys Lys Tyr Ser Tyr
            20                  25

<210> SEQ ID NO 455
<211> LENGTH: 27
<212> TYPE: PRT
<213> ORGANISM: Artificial
<220> FEATURE:
<223> OTHER INFORMATION: FVE Fragment

<400> SEQUENCE: 455

Trp Gly Arg Gly Thr Pro Ser Ser Tyr Ile Asp Asn Leu Thr Phe Pro
1               5                   10                  15

Lys Val Leu Thr Asp Lys Lys Tyr Ser Tyr Arg
            20                  25

<210> SEQ ID NO 456
<211> LENGTH: 27
<212> TYPE: PRT
<213> ORGANISM: Artificial
<220> FEATURE:
<223> OTHER INFORMATION: FVE Fragment

<400> SEQUENCE: 456

Gly Arg Gly Thr Pro Ser Ser Tyr Ile Asp Asn Leu Thr Phe Pro Lys
1               5                   10                  15

Val Leu Thr Asp Lys Lys Tyr Ser Tyr Arg Val
            20                  25

<210> SEQ ID NO 457
<211> LENGTH: 27
<212> TYPE: PRT
<213> ORGANISM: Artificial
<220> FEATURE:
<223> OTHER INFORMATION: FVE Fragment

<400> SEQUENCE: 457

Arg Gly Thr Pro Ser Ser Tyr Ile Asp Asn Leu Thr Phe Pro Lys Val
1               5                   10                  15

Leu Thr Asp Lys Lys Tyr Ser Tyr Arg Val Val
            20                  25

<210> SEQ ID NO 458
<211> LENGTH: 27
<212> TYPE: PRT
<213> ORGANISM: Artificial
<220> FEATURE:
<223> OTHER INFORMATION: FVE Fragment

<400> SEQUENCE: 458

Gly Thr Pro Ser Ser Tyr Ile Asp Asn Leu Thr Phe Pro Lys Val Leu
1               5                   10                  15

Thr Asp Lys Lys Tyr Ser Tyr Arg Val Val Val
            20                  25

<210> SEQ ID NO 459
<211> LENGTH: 27
<212> TYPE: PRT
<213> ORGANISM: Artificial
<220> FEATURE:
<223> OTHER INFORMATION: FVE Fragment

<400> SEQUENCE: 459

Thr Pro Ser Ser Tyr Ile Asp Asn Leu Thr Phe Pro Lys Val Leu Thr
1               5                   10                  15

Asp Lys Lys Tyr Ser Tyr Arg Val Val Val Asn
            20                  25

<210> SEQ ID NO 460
<211> LENGTH: 28
<212> TYPE: PRT
<213> ORGANISM: Artificial
<220> FEATURE:
<223> OTHER INFORMATION: FVE Fragment

<400> SEQUENCE: 460

Ser Ala Thr Ser Leu Thr Phe Gln Leu Ala Tyr Leu Val Lys Lys Ile
1               5                   10                  15

Asp Phe Asp Tyr Thr Pro Asn Trp Gly Arg Gly Thr
            20                  25

<210> SEQ ID NO 461
<211> LENGTH: 28
<212> TYPE: PRT
<213> ORGANISM: Artificial
<220> FEATURE:
<223> OTHER INFORMATION: FVE Fragment

<400> SEQUENCE: 461

Ala Thr Ser Leu Thr Phe Gln Leu Ala Tyr Leu Val Lys Lys Ile Asp
1               5                   10                  15

Phe Asp Tyr Thr Pro Asn Trp Gly Arg Gly Thr Pro
            20                  25

<210> SEQ ID NO 462
<211> LENGTH: 28
<212> TYPE: PRT
<213> ORGANISM: Artificial
<220> FEATURE:
<223> OTHER INFORMATION: FVE Fragment

<400> SEQUENCE: 462

Thr Ser Leu Thr Phe Gln Leu Ala Tyr Leu Val Lys Lys Ile Asp Phe
1               5                   10                  15

Asp Tyr Thr Pro Asn Trp Gly Arg Gly Thr Pro Ser
            20                  25

<210> SEQ ID NO 463
<211> LENGTH: 28
<212> TYPE: PRT
<213> ORGANISM: Artificial
<220> FEATURE:
<223> OTHER INFORMATION: FVE Fragment

<400> SEQUENCE: 463

Ser Leu Thr Phe Gln Leu Ala Tyr Leu Val Lys Lys Ile Asp Phe Asp
1               5                   10                  15

Tyr Thr Pro Asn Trp Gly Arg Gly Thr Pro Ser Ser
            20                  25

<210> SEQ ID NO 464
<211> LENGTH: 28
<212> TYPE: PRT
<213> ORGANISM: Artificial
<220> FEATURE:
<223> OTHER INFORMATION: FVE Fragment

<400> SEQUENCE: 464

Leu Thr Phe Gln Leu Ala Tyr Leu Val Lys Lys Ile Asp Phe Asp Tyr
1               5                   10                  15

Thr Pro Asn Trp Gly Arg Gly Thr Pro Ser Ser Tyr
            20                  25

<210> SEQ ID NO 465
<211> LENGTH: 28
<212> TYPE: PRT
<213> ORGANISM: Artificial
<220> FEATURE:
<223> OTHER INFORMATION: FVE Fragment

<400> SEQUENCE: 465

Thr Phe Gln Leu Ala Tyr Leu Val Lys Lys Ile Asp Phe Asp Tyr Thr
1               5                   10                  15

Pro Asn Trp Gly Arg Gly Thr Pro Ser Ser Tyr Ile
            20                  25

<210> SEQ ID NO 466
<211> LENGTH: 28
<212> TYPE: PRT
<213> ORGANISM: Artificial
<220> FEATURE:
<223> OTHER INFORMATION: FVE Fragment

<400> SEQUENCE: 466

Phe Gln Leu Ala Tyr Leu Val Lys Lys Ile Asp Phe Asp Tyr Thr Pro
1               5                   10                  15

Asn Trp Gly Arg Gly Thr Pro Ser Ser Tyr Ile Asp
            20                  25

<210> SEQ ID NO 467
<211> LENGTH: 28
<212> TYPE: PRT
<213> ORGANISM: Artificial
<220> FEATURE:
<223> OTHER INFORMATION: FVE Fragment

<400> SEQUENCE: 467

Gln Leu Ala Tyr Leu Val Lys Lys Ile Asp Phe Asp Tyr Thr Pro Asn
1               5                   10                  15

Trp Gly Arg Gly Thr Pro Ser Ser Tyr Ile Asp Asn
            20                  25

<210> SEQ ID NO 468
<211> LENGTH: 28
<212> TYPE: PRT
<213> ORGANISM: Artificial
<220> FEATURE:
<223> OTHER INFORMATION: FVE Fragment

<400> SEQUENCE: 468

Leu Ala Tyr Leu Val Lys Lys Ile Asp Phe Asp Tyr Thr Pro Asn Trp
1               5                   10                  15

Gly Arg Gly Thr Pro Ser Ser Tyr Ile Asp Asn Leu
            20                  25

<210> SEQ ID NO 469
<211> LENGTH: 28
<212> TYPE: PRT
<213> ORGANISM: Artificial
<220> FEATURE:
<223> OTHER INFORMATION: FVE Fragment

<400> SEQUENCE: 469

Ala Tyr Leu Val Lys Lys Ile Asp Phe Asp Tyr Thr Pro Asn Trp Gly
1               5                   10                  15

Arg Gly Thr Pro Ser Ser Tyr Ile Asp Asn Leu Thr
            20                  25

<210> SEQ ID NO 470
<211> LENGTH: 28
<212> TYPE: PRT
<213> ORGANISM: Artificial
<220> FEATURE:
<223> OTHER INFORMATION: FVE Fragment

<400> SEQUENCE: 470

Tyr Leu Val Lys Lys Ile Asp Phe Asp Tyr Thr Pro Asn Trp Gly Arg
1               5                   10                  15

Gly Thr Pro Ser Ser Tyr Ile Asp Asn Leu Thr Phe
            20                  25

<210> SEQ ID NO 471
<211> LENGTH: 28
<212> TYPE: PRT
<213> ORGANISM: Artificial
<220> FEATURE:
<223> OTHER INFORMATION: FVE Fragment

<400> SEQUENCE: 471

Leu Val Lys Lys Ile Asp Phe Asp Tyr Thr Pro Asn Trp Gly Arg Gly
1               5                   10                  15

Thr Pro Ser Ser Tyr Ile Asp Asn Leu Thr Phe Pro
            20                  25

<210> SEQ ID NO 472
<211> LENGTH: 28
<212> TYPE: PRT
<213> ORGANISM: Artificial
<220> FEATURE:
<223> OTHER INFORMATION: FVE Fragment

<400> SEQUENCE: 472

Val Lys Lys Ile Asp Phe Asp Tyr Thr Pro Asn Trp Gly Arg Gly Thr
1               5                   10                  15

Pro Ser Ser Tyr Ile Asp Asn Leu Thr Phe Pro Lys
            20                  25

<210> SEQ ID NO 473
<211> LENGTH: 28
<212> TYPE: PRT
<213> ORGANISM: Artificial
<220> FEATURE:
<223> OTHER INFORMATION: FVE Fragment

<400> SEQUENCE: 473

Lys Lys Ile Asp Phe Asp Tyr Thr Pro Asn Trp Gly Arg Gly Thr Pro
1               5                   10                  15

Ser Ser Tyr Ile Asp Asn Leu Thr Phe Pro Lys Val
            20                  25

<210> SEQ ID NO 474
<211> LENGTH: 28
<212> TYPE: PRT
<213> ORGANISM: Artificial
<220> FEATURE:
<223> OTHER INFORMATION: FVE Fragment

<400> SEQUENCE: 474

```
Lys Ile Asp Phe Asp Tyr Thr Pro Asn Trp Gly Arg Gly Thr Pro Ser
1               5                   10                  15

Ser Tyr Ile Asp Asn Leu Thr Phe Pro Lys Val Leu
            20                  25
```

<210> SEQ ID NO 475
<211> LENGTH: 28
<212> TYPE: PRT
<213> ORGANISM: Artificial
<220> FEATURE:
<223> OTHER INFORMATION: FVE Fragment

<400> SEQUENCE: 475

```
Ile Asp Phe Asp Tyr Thr Pro Asn Trp Gly Arg Gly Thr Pro Ser Ser
1               5                   10                  15

Tyr Ile Asp Asn Leu Thr Phe Pro Lys Val Leu Thr
            20                  25
```

<210> SEQ ID NO 476
<211> LENGTH: 28
<212> TYPE: PRT
<213> ORGANISM: Artificial
<220> FEATURE:
<223> OTHER INFORMATION: FVE Fragment

<400> SEQUENCE: 476

```
Asp Phe Asp Tyr Thr Pro Asn Trp Gly Arg Gly Thr Pro Ser Ser Tyr
1               5                   10                  15

Ile Asp Asn Leu Thr Phe Pro Lys Val Leu Thr Asp
            20                  25
```

<210> SEQ ID NO 477
<211> LENGTH: 28
<212> TYPE: PRT
<213> ORGANISM: Artificial
<220> FEATURE:
<223> OTHER INFORMATION: FVE Fragment

<400> SEQUENCE: 477

```
Phe Asp Tyr Thr Pro Asn Trp Gly Arg Gly Thr Pro Ser Ser Tyr Ile
1               5                   10                  15

Asp Asn Leu Thr Phe Pro Lys Val Leu Thr Asp Lys
            20                  25
```

<210> SEQ ID NO 478
<211> LENGTH: 28
<212> TYPE: PRT
<213> ORGANISM: Artificial
<220> FEATURE:
<223> OTHER INFORMATION: FVE Fragment

<400> SEQUENCE: 478

```
Asp Tyr Thr Pro Asn Trp Gly Arg Gly Thr Pro Ser Ser Tyr Ile Asp
1               5                   10                  15

Asn Leu Thr Phe Pro Lys Val Leu Thr Asp Lys Lys
            20                  25
```

<210> SEQ ID NO 479
<211> LENGTH: 28
<212> TYPE: PRT
<213> ORGANISM: Artificial
<220> FEATURE:
<223> OTHER INFORMATION: FVE Fragment

<400> SEQUENCE: 479

Tyr Thr Pro Asn Trp Gly Arg Gly Thr Pro Ser Ser Tyr Ile Asp Asn
1               5                   10                  15

Leu Thr Phe Pro Lys Val Leu Thr Asp Lys Lys Tyr
            20                  25

<210> SEQ ID NO 480
<211> LENGTH: 28
<212> TYPE: PRT
<213> ORGANISM: Artificial
<220> FEATURE:
<223> OTHER INFORMATION: FVE Fragment

<400> SEQUENCE: 480

Thr Pro Asn Trp Gly Arg Gly Thr Pro Ser Ser Tyr Ile Asp Asn Leu
1               5                   10                  15

Thr Phe Pro Lys Val Leu Thr Asp Lys Lys Tyr Ser
            20                  25

<210> SEQ ID NO 481
<211> LENGTH: 28
<212> TYPE: PRT
<213> ORGANISM: Artificial
<220> FEATURE:
<223> OTHER INFORMATION: FVE Fragment

<400> SEQUENCE: 481

Pro Asn Trp Gly Arg Gly Thr Pro Ser Ser Tyr Ile Asp Asn Leu Thr
1               5                   10                  15

Phe Pro Lys Val Leu Thr Asp Lys Lys Tyr Ser Tyr
            20                  25

<210> SEQ ID NO 482
<211> LENGTH: 28
<212> TYPE: PRT
<213> ORGANISM: Artificial
<220> FEATURE:
<223> OTHER INFORMATION: FVE Fragment

<400> SEQUENCE: 482

Asn Trp Gly Arg Gly Thr Pro Ser Ser Tyr Ile Asp Asn Leu Thr Phe
1               5                   10                  15

Pro Lys Val Leu Thr Asp Lys Lys Tyr Ser Tyr Arg
            20                  25

<210> SEQ ID NO 483
<211> LENGTH: 28
<212> TYPE: PRT
<213> ORGANISM: Artificial
<220> FEATURE:
<223> OTHER INFORMATION: FVE Fragment

<400> SEQUENCE: 483

Trp Gly Arg Gly Thr Pro Ser Ser Tyr Ile Asp Asn Leu Thr Phe Pro
1               5                   10                  15

Lys Val Leu Thr Asp Lys Lys Tyr Ser Tyr Arg Val
            20                  25

<210> SEQ ID NO 484
<211> LENGTH: 28
<212> TYPE: PRT
<213> ORGANISM: Artificial
<220> FEATURE:
<223> OTHER INFORMATION: FVE Fragment

<400> SEQUENCE: 484

-continued

```
Gly Arg Gly Thr Pro Ser Ser Tyr Ile Asp Asn Leu Thr Phe Pro Lys
1               5                   10                  15

Val Leu Thr Asp Lys Lys Tyr Ser Tyr Arg Val Val
            20                  25

<210> SEQ ID NO 485
<211> LENGTH: 28
<212> TYPE: PRT
<213> ORGANISM: Artificial
<220> FEATURE:
<223> OTHER INFORMATION: FVE Fragment

<400> SEQUENCE: 485

Arg Gly Thr Pro Ser Ser Tyr Ile Asp Asn Leu Thr Phe Pro Lys Val
1               5                   10                  15

Leu Thr Asp Lys Lys Tyr Ser Tyr Arg Val Val Val
            20                  25

<210> SEQ ID NO 486
<211> LENGTH: 28
<212> TYPE: PRT
<213> ORGANISM: Artificial
<220> FEATURE:
<223> OTHER INFORMATION: FVE Fragment

<400> SEQUENCE: 486

Gly Thr Pro Ser Ser Tyr Ile Asp Asn Leu Thr Phe Pro Lys Val Leu
1               5                   10                  15

Thr Asp Lys Lys Tyr Ser Tyr Arg Val Val Val Asn
            20                  25

<210> SEQ ID NO 487
<211> LENGTH: 28
<212> TYPE: PRT
<213> ORGANISM: Artificial
<220> FEATURE:
<223> OTHER INFORMATION: FVE Fragment

<400> SEQUENCE: 487

Thr Pro Ser Ser Tyr Ile Asp Asn Leu Thr Phe Pro Lys Val Leu Thr
1               5                   10                  15

Asp Lys Lys Tyr Ser Tyr Arg Val Val Val Asn Gly
            20                  25
```